US012440558B2

(12) United States Patent
Matsunaga et al.

(10) Patent No.: US 12,440,558 B2

(45) Date of Patent: Oct. 14, 2025

(54) SOYBEAN ALLERGY ANTIGEN

(71) Applicant: HOYU CO., LTD., Aichi (JP)

(72) Inventors: Kayoko Matsunaga, Aichi (JP); Akiko Yagami, Aichi (JP); Naoshi Shimojo, Aichi (JP); Masashi Nakamura, Aichi (JP); Nayu Sato, Aichi (JP)

(73) Assignee: HOYU CO., LTD., Aichi (JP)

( * ) Notice: Subject to any disclaimer, the term of this patent is extended or adjusted under 35 U.S.C. 154(b) by 0 days.

(21) Appl. No.: 18/462,987

(22) Filed: Sep. 7, 2023

(65) Prior Publication Data

US 2024/0123063 A1 Apr. 18, 2024

Related U.S. Application Data

(62) Division of application No. 16/081,032, filed as application No. PCT/JP2017/008593 on Mar. 3, 2017, now abandoned.

(30) Foreign Application Priority Data

Mar. 3, 2016 (JP) ................................ 2016-041547

(51) Int. Cl.

| | |
|---|---|
| ***A61K 39/35*** | (2006.01) |
| ***A23L 11/30*** | (2016.01) |
| ***A61K 49/00*** | (2006.01) |
| ***A61P 37/08*** | (2006.01) |
| ***C07K 4/10*** | (2006.01) |
| ***C07K 14/415*** | (2006.01) |
| ***C07K 14/47*** | (2006.01) |
| ***G01N 33/53*** | (2006.01) |
| *A61K 38/00* | (2006.01) |

(52) U.S. Cl.

CPC .............. *A61K 39/35* (2013.01); *A23L 11/30* (2016.08); *A61K 49/00* (2013.01); *A61K 49/0006* (2013.01); *A61P 37/08* (2018.01); *C07K 4/10* (2013.01); *C07K 14/415* (2013.01); *C07K 14/47* (2013.01); *G01N 33/53* (2013.01); *A61K 38/00* (2013.01); *G01N 2800/24* (2013.01)

(58) Field of Classification Search

None

See application file for complete search history.

(56) References Cited

U.S. PATENT DOCUMENTS

| | | | |
|---|---|---|---|
| 5,597,607 | A | 1/1997 | Samoto et al. |
| 5,792,506 | A | 8/1998 | Buchanan et al. |
| 6,607,731 | B1 | 8/2003 | Reed et al. |
| 2003/0166518 | A1 | 9/2003 | Beardslee et al. |
| 2004/0031072 | A1 | 2/2004 | La Rosa et al. |
| 2006/0123505 | A1 | 6/2006 | Kikuchi et al. |
| 2010/0158933 | A1 | 6/2010 | Brown et al. |
| 2014/0357512 | A1 | 12/2014 | Yang et al. |
| 2016/0137725 | A1 | 5/2016 | Gu et al. |
| 2016/0219910 | A1 | 8/2016 | Silver et al. |
| 2019/0076521 | A1 | 3/2019 | Matsunaga et al. |
| 2021/0292383 | A1 | 9/2021 | Matsunaga et al. |

FOREIGN PATENT DOCUMENTS

| | | | |
|---|---|---|---|
| JP | S63-051335 | A | 3/1988 |
| JP | 5-184308 | A | 7/1993 |
| JP | 9-136897 | A | 5/1997 |
| JP | H10-510244 | A | 10/1998 |
| JP | 2002-286716 | A | 10/2002 |
| JP | 2005-185101 | A | 7/2005 |
| JP | 2011-033544 | A | 2/2011 |
| JP | 2011-033546 | A | 2/2011 |
| JP | 2011-033547 | A | 2/2011 |
| JP | 2011-033548 | A | 2/2011 |
| WO | 2004/069863 | A2 | 8/2004 |
| WO | 2010/037402 | A1 | 4/2010 |
| WO | 2013/040142 | A2 | 3/2013 |
| WO | 2013/148329 | A1 | 10/2013 |
| WO | 2015/048334 | A2 | 4/2015 |
| WO | 2015/048342 | A2 | 4/2015 |
| WO | 2015/101435 | A1 | 7/2015 |
| WO | 2015/153151 | A1 | 10/2015 |
| WO | 2016/172722 | A1 | 10/2016 |
| WO | 2017/150724 | A1 | 9/2017 |

OTHER PUBLICATIONS

Kim et al., Identification of Novel IgE-binding Soybean Allergens Using Serological Analysis of a Recombinant cDNA Expression Library (SEREX). Food Sci Biotechnol. 2014;23(4):1037-1042.

Ogawa et al., Soybean allergens and hypoallergenic soybean products. J Nutr Sci Vitaminol (Tokyo). Dec. 2000;46 (6):271-9.

Abaza et al., Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.

Baek et al., Nucleotide sequence homology of cDNAs encoding soybean Bowman-Birk type proteinase inhibitor and its isoinhibitors. Biosci Biotechnol Biochem. May 1994;58(5):843-6.

Beezhold et al., Mutational analysis of the IgE epitopes in the latex allergen Hev b 5. J Allergy Clin Immunol. 2001;107:1069-76.

Blumenthal et al., Definition of an allergen (immunobiology). Clin Allergy Immunol. 2004;18:37-50.

Brandon et al., Immunoassays of soy proteins. J Agric Food Chem. Oct. 23, 2002;50(22):6635-42.

(Continued)

*Primary Examiner* — Nora M Rooney

(74) *Attorney, Agent, or Firm* — McCarter & English, LLP; Yu Lu

(57) ABSTRACT

The present invention provides novel antigens of an allergy to soybean, methods and kits for diagnosing an allergy to soybean, pharmaceutical compositions comprising such an antigen, soybeans or processed products of soybean in which such an antigen is eliminated, and a tester for determining the presence or absence of a soybean antigen in an object of interest.

5 Claims, 15 Drawing Sheets

Specification includes a Sequence Listing.

(56) References Cited

OTHER PUBLICATIONS

Bratthauer et al., The Avidin-Biotin Complex (ABC) Method and Other Avidin-Biotin Methods. Immunocytochemical Methods and Protocols, vol. 588, Third Edition. Humana Press. Chapter 26, pp. 257-270, (2010).
Colman, Effects of amino acid sequence changes on antibody-antigen interactions. Res Immunol. Jan. 1994; 145 (1):33-6.
Cong et al., Identification of the critical amino acid residues of immunoglobulin E and immunoglobulin G epitopes on as1-casein by alanine scanning analysis. J Dairy Sci. 2013;96(11):6870-6876.
Deshimaru et al., Multigene family for Bowman-Birk type proteinase inhibitors of wild soja and soybean: the presence of two BBI-A genes and pseudogenes. Biosci Biotechnol Biochem. Jun. 2004;68(6):1279-86.
Friedman et al., Nutritional and Health Benefits of Soy Proteins. Journal of Agricultural and Food Chemistry. Mar. 2001;49(3):1069-1086.
GenBank Accession No. ACU21482.1, unknown [Glycine max]. 1 page, Aug. 1, 2009.
Hwang et al., Purification, partial characterization, and immunological relationships of multiple low molecular weight protease inhibitors of soybean. Biochim Biophys Acta. Dec. 20, 1977;495(2):369-82.
Jiao et al., Effect of Thioredoxin-Linked Reduction on the Activity and Stability of the Kunitz and Bowman-Birk Soybean Trypsin Inhibitor Proteins. J Agric Food Chem. 1992;40:2333-2336.
Lederman et al., A single amino acid substitution in a common African allele of the CD4 molecule ablates binding of the monoclonal antibody, OKT4. Mol Immunol. Nov. 1991;28(11):1171-81.
Maki et al., Studies related to the potential antigenicity of the Bowman-Birk inhibitor, an anticarcinogenic protease inhibitor isolated from soybeans. Nutr Cancer. 1994;22(2):185-93.
Mao et al., Conjugation of Fluorochromes to Antibodies. Immunocytochemical Methods and Protocols, vol. 588, Third Edition. Humana Press. Chapter 6, pp. 43-48, (2010).
Matsuo et al., Identification of the IgE-binding epitope in omega-5 gliadin, a major allergen in wheat-dependent exercise-induced anaphylaxis. J Biol Chem. Mar. 26, 2004;279(13):12135-40.
Moroz et al., Kunitz soybean trypsin inhibitor: a specific allergen in food anaphylaxis. N Engl J Med. May 15, 1980;302(20):1126-8.
Muroshita et al., Summarized Proceedings of the Japan Society of Nutrition and Food Science Conference. Apr. 1, 2004;58:293.
Odani et al., Studies on soybean trypsin inhibitors, XII. Linear sequences of two soybean double-headed trypsin inhibitors, D-II and E-I. J Biochem. Mar. 1978;83(3):737-45.
Ogawa et al., Investigation of the IgE-binding proteins in soybeans by immunoblotting with the sera of the soybean-sensitive patients with atopic dermatitis. J Nutr Sci Vitaminol (Tokyo). Dec. 1991;37(6):555-65.
Panda, Soybean Allergy: Effect of Genetic Modification (GM), Heat and Enzymatic Treatment on Overall Allergenicity. Dissertation. Presented to the Faculty of The Graduate College at the University of Nebraska in Partial Fulfillment of Requirements for the Degree of Doctor of Philosophy. 233 pages, Dec. 2012.
Riascos, A Genomic-Based Search for Novel Soybean (*Glycine max* L.) Allergens. A thesis submitted to the Graduate Faculty of North CArolina State University in partial fulfillment of the Requirements for the Degree of Doctor of Philosophy. 224 pages, (2009).
Sun et al., Prediction and characterization of the linear IgE epitopes for the major soybean allergen ß-conglycinin using immunoinformatics tools. Food Chem Toxicol. Jun. 2013;56:254-60.
UniProtKB/TrEMBL, I1MC33_*Glycine max* (Soybean) (*Glycine hispida*). 3 pages, Oct. 7, 2020. Version 66.
UniProtKB/TrEMBL, K7MP24, *Glycine max* (Soybean) (*Glycine hispida*). 3 pages, Oct. 7, 2020. Version 63.
Wan et al., Detection of Bowman-Birk inhibitor and anti-Bowman-Birk inhibitor antibodies in sera of humans and animals treated with Bowman-Birk inhibitor concentrate. Nutr Cancer. 2002;43(2):167-73.
Xiang et al., C-Terminal 23 kDa polypeptide of soybean Gly m Bd 28 K is a potential allergen. Planta. Nov. 2004;220 (1):56-63.
Xiang et al., Identification and analysis of a conserved immunoglobulin E-binding epitope in soybean G1a and G2a and peanut Ara h 3 glycinins. Arch Biochem Biophys. Dec. 1, 2002;408(1):51-7.
Zhao et al., Identification of a common Ara h 3 epitope recognized by both the capture and the detection monoclonal antibodies in an ELISA detection kit. PLOS One. Aug. 11, 2017;12(8):e0182935, 12 pages.
European Office Action for Application No. 17898509.9, dated Nov. 30, 2020, 19 pages.
International Search Report for Application No. PCT/2017/032005, dated Nov. 28, 2017, 3 pages.
International Search Report for Application No. PCT/JP2017/008593, dated May 30, 2017. 2 pages.
Supplementary Partial European Search Report for Application No. 17760186.1, dated Sep. 27, 2019, 16 pages.
GenPept Accession No. XP_003886492, uncharacterized protein, partial [Leishmania mexicana MHOM/GT/2001/U1103]. 3 pages, Jun. 29, 2015.
Vanegas et al., Enolase as a plasminogen binding protein in Leishmania mexicana. Parasitol Res. Nov. 2007;101 (6):1511-6.
U.S. Appl. No. 16/081,032, filed Aug. 30, 2018, 2019-0076521, Published.
U.S. Appl. No. 16/490,092, filed Aug. 30, 2019, 2021-0292383, Published.

PATIENT 1

PATIENT 2

PATIENT 3

PATIENT 4

HEALTHY

PATIENT 1α

PATIENT 2α

PATIENT 3α

PATIENT 4α

PATIENT 5α

PATIENT 6α

PATIENT 7α

PATIENT 8α

PATIENT 9α

SEQUENCE LISTING

```
Sequence total quantity: 649
SEQ ID NO: 1           moltype = DNA  length = 249
FEATURE                Location/Qualifiers
source                 1..249
                       mol_type = other DNA
                       organism = Glycine max
CDS                    1..249
SEQUENCE: 1
atgtgtattc tgagcttcct caaaagtgat cagtcatcaa gttatgatga tgatgagtat  60
tcaaaaccat gctgtgatct ctgcatgtgc acacgctcaa tgcctcctca atgcagctgt  120
gaagatatta ggctgaattc atgccactca gattgtaaga gctgtatgtg cacacgctca  180
cagccaggac agtgtcgttg tcttgacacc aacgacttct gctacaaacc ttgcaagtcc  240
agagatgac                                                          249

SEQ ID NO: 2           moltype = AA  length = 83
FEATURE                Location/Qualifiers
source                 1..83
                       mol_type = protein
                       organism = Glycine max
SEQUENCE: 2
MCILSFLKSD QSSSYDDDEY SKPCCDLCMC TRSMPPQCSC EDIRLNSCHS DCKSCMCTRS  60
QPGQCRCLDT NDFCYKPCKS RDD                                          83

SEQ ID NO: 3           moltype = DNA  length = 1425
FEATURE                Location/Qualifiers
source                 1..1425
                       mol_type = other DNA
                       organism = Glycine max
CDS                    1..1425
SEQUENCE: 3
atgtcaccac aaacagagac taaagcaagt gttgggttca aagctggtgt taaagattat  60
aaattgactt attatactcc tgactatgaa accaaagata ctgatatctt ggcagcattc  120
cgagtaactc ctcaaccagg agttccgcct gaagaagcag gtgccgcggt agccgccgaa  180
tcttctactg gtacatggac aactgtgtgg accgatgggc ttaccagtct tgatcgttac  240
aaagggcgat gctacggcct tgaacctgtt gctggggaag aaaatcaata tattgcttat  300
gtagcttatc ccttagacct tttgaagaa ggttctgtta ctaacatgtt tacttccatt  360
gtcggtaatg tatttgggtt caaggccctg cgtgctctac gtctggagga tttgcgaatc  420
cctactgctt atattaaaac tttccaaggt ccgcctcatg gcatccaagt tgagagagat  480
aaattgaaca agtatggtcg tcccctatta ggatgtacta ttaaacctaa attggggtta  540
tccgctaaga attatggtag agctgtttat gaatgtcttc gtgggggact tgattttacc  600
aaagatgatg aaaatgtgaa ttcccaacca tttatgcgtt ggagagaccg tttcttattt  660
tgtgccgaag ccatttttaa atcacaggct gaaacaggtg aaatcaaagg gcattacttg  720
aatgcaactg cgggtacatg cgaagaaatg atgaaaagag ctgtatttgc cagagaatta  780
ggcgttccta tcgtaatgca tgattattta acggggggat tcactgcaaa tactagcttg  840
gctcattatt gccgagataa tggtctactt cttcatatac accgtgcaat gcatgcagtt  900
atcgacagac aaaagaatca tggtatgcac tttcgtgtac tagctaaagc attacgtttg  960
tctggtggag atcatgttca cgccggtacc gtagtaggta aacttgaagg ggaaagagaa  1020
atcactttag gttttgttga tttactacgt gatgattttg ttgaaaaaga tcgaagtcgc  1080
ggtatttatt tcactcagga ttgggtttct ctaccaggtg ttttgcctgt agcttcggga  1140
ggtattcacg tttggcatat gcctgctctg accgagatct ttggggatga ttctgtactc  1200
caatttggcg gaggaacttt aggacaccct tggggaaatg caccaggtgc tgtagctaat  1260
cgagtagctc ttgaagcatg tgtgcaggct cgaaatgaag gacgcgatct tgctcgtgaa  1320
ggtaatgaaa ttatccgtga ggctagcaaa tggagtcctg aattagctgc tgcttgtgaa  1380
gtatggaagg agatcaaatt tgaattcgaa gcaatggata ctttg                  1425

SEQ ID NO: 4           moltype = AA  length = 475
FEATURE                Location/Qualifiers
source                 1..475
                       mol_type = protein
                       organism = Glycine max
```

```
SEQUENCE: 4
MSPQTETKAS VGFKAGVKDY KLTYYTPDYE TKDTDILAAF RVTPQPGVPP EEAGAAVAAE  60
SSTGTWTTVW TDGLTSLDRY KGRCYGLEPV AGEENQYIAY VAYPLDLFEE GSVTNMFTSI  120
VGNVFGFKAL RALRLEDLRI PTAYIKTFQG PPHGIQVERD KLNKYGRPLL GCTIKPKLGL  180
SAKNYGRAVY ECLRGGLDFT KDDENVNSQP FMRWRDRFLF CAEAIFKSQA ETGEIKGHYL  240
NATAGTCEEM MKRAVFAREL GVPIVMHDYL TGGFTANTSL AHYCRDNGLL LHIHRAMHAV  300
IDRQKNHGMH FRVLAKALRL SGGDHVHAGT VVGKLEGERE ITLGFVDLLR DDFVEKDRSR  360
GIYFTQDWVS LPGVLPVASG GIHVWHMPAL TEIFGDDSVL QFGGGTLGHP WGNAPGAVAN  420
RVALEACVQA RNEGRDLARE GNEIIREASK WSPELAAACE VWKEIKFEFE AMDTL       475

SEQ ID NO: 5            moltype = DNA  length = 1026
FEATURE                 Location/Qualifiers
source                  1..1026
                        mol_type = other DNA
                        organism = Glycine max
CDS                     1..1026
SEQUENCE: 5
atgccaaacg acagcgttct gagtcttttc ttcttcgtta ccctcttcac atgccttctc  60
tctgctactt cccacgatga ccatattttc ctaccgagtc aactccatga cgatgactca  120
gtgagttgca ctgcaaccga cccaagcctt aactacaagc cggtgatcgg aatcctgacc  180
caccccggcg acggtgcctc tggccggctc agcaacgcca ccggggtttc ttacatcgcc  240
gcctcctacg ttaaattcgt ggagtccggt ggtgctagag ttattcccct tatctacaat  300
gagtcacctg agaaccttaa caagaagctc gatttggtca atggagtgct cttcactggt  360
gggtgggctg tttctggtcc atatttggat actcttggaa acatttttaa gaaagcttta  420
gagagaaatg atgctggaga ccatttccca gtaattgcct tcaacttagg tggaaacctc  480
gtaataagga tcgtaagcga gcaaactgat attcttgaac catttactgc gtcgagtttg  540
ccaagttctc ttgtattgtg gaacgaagca aatgctaaag gaagtctatt tcaaagattt  600
ccttcagatt tgttgacaca gctgaagaca gattgtctcg tcctgcacaa tcatcgttat  660
gccatatccc cacgcaagct tcaatataat accaagttat ctgacttttt tgagattctg  720
gcaacatctg gggatagaga tggaaagact ttcgtttcca cagcacgtgg taggaaatat  780
cccgtgactg tcaacctatg gcaaccagag aaaaatgcgt ttgagtgggc tacatctttg  840
aaagcccctc acacagagga tgcaattcgg gttactcagt ccacagcaaa ctttttcata  900
agtgaagcta ggaaatccac aaacacacct gatgctcaaa aagtgcgaga tagtctcatc  960
tacaattaca aacctacttt tggtggaacg gctgggaaag gatatgatca agtgtatctc  1020
tttgaa                                                             1026

SEQ ID NO: 6            moltype = AA  length = 342
FEATURE                 Location/Qualifiers
source                  1..342
                        mol_type = protein
                        organism = Glycine max
SEQUENCE: 6
MPNDSVLSLF FFVTLFTCLL SATSHDDHIF LPSQLHDDDS VSCTATDPSL NYKPVIGILT  60
HPGDGASGRL SNATGVSYIA ASYVKFVESG GARVIPLIYN ESPENLNKKL DLVNGVLFTG  120
GWAVSGPYLD TLGNIFKKAL ERNDAGDHFP VIAFNLGGNL VIRIVSEQTD ILEPFTASSL  180
PSSLVLWNEA NAKGSLFQRF PSDLLTQLKT DCLVLHNHRY AISPRKLQYN TKLSDFFEIL  240
ATSGDRDGKT FVSTARGRKY PVTVNLWQPE KNAFEWATSL KAPHTEDAIR VTQSTANFFI  300
SEARKSTNTP DAQKVRDSLI YNYKPTFGGT AGKGYDQVYL FE                     342

SEQ ID NO: 7            moltype = DNA  length = 975
FEATURE                 Location/Qualifiers
source                  1..975
                        mol_type = other DNA
                        organism = Glycine max
CDS                     1..975
SEQUENCE: 7
atggcggaag gactcgtcct gaagggaacc atgcgcgccc acaccgacgt cgtgacggcg  60
attgccactc ccatcgacaa ctccgacatg atcgtgacgg cgtcgcgcga cagatccatc  120
attctctggc acctcaccaa ggaggacaag acctacggtg tcccccgccg ccgcctcacc  180
ggacattctc acttcgtcca ggacgtcgtc ctctcatccg acggtcagtt cgccctctcc  240
ggctcctggg acggcgagct ccgcctctgg gacctcgcgg ctggcacctc tgcccgccgc  300
ttcgttggcc acaccaagga cgtgctctcc gtggcgttct ccatcgacaa ccgtcagatc  360
gtgtcggcct ctcgtgaccg cacgatcaag ctgtggaaca ccctgggtga gtgcaagtac  420
acaatccaag atggcgatgc gcattcggat tgggtaagtt gcgtccgttt cagccctagc  480
actcttcagc caaccattgt ttctgcttca tgggacagga ccgttaaggt ttggaacctg  540
accaactgca agctgaggaa caccctttgct ggacacaatg ggtatgtgaa tactgttgct  600
gtttcccctg atggctctct ctgtgccagt ggtggcaaag atggggttat tcttctgtgg  660
gatttggctg agggtaagcg tctttactct ctcgatgctg gctcaatcat ccatgcactc  720
tgcttcagcc ccagcaggta ctggctctgc gccgccaccg agcagagcat caagatctgg  780
gatttggaga gcaagagtat cgttgaggat ttgaaggttg acctcaagac tgaggctgat  840
gccacctccg gtggtggtaa cgccaacaag aagaaggtta tttattgcac aagtttgaac  900
tggagtgcgg atggaagcac tttgtttagt ggctataccg atggtgtggc cagagtttgg  960
gctattggac gttat                                                   975

SEQ ID NO: 8            moltype = AA  length = 325
FEATURE                 Location/Qualifiers
source                  1..325
                        mol_type = protein
                        organism = Glycine max
```

```
SEQUENCE: 8
MAEGLVLKGT MRAHTDVVTA IATPIDNSDM IVTASRDRSI ILWHLTKEDK TYGVPRRRLT  60
GHSHFVQDVV LSSDGQFALS GSWDGELRLW DLAAGTSARR FVGHTKDVLS VAFSIDNRQI  120
VSASRDRTIK LWNTLGECKY TIQDGDAHSD WVSCVRFSPS TLQPTIVSAS WDRTVKVWNL  180
TNCKLRNTLA GHNGYVNTVA VSPDGSLCAS GGKDGVILLW DLAEGKRLYS LDAGSIIHAL  240
CFSPSRYWLC AATEQSIKIW DLESKSIVED LKVDLKTEAD ATSGGGNANK KKVIYCTSLN  300
WSADGSTLFS GYTDGVARVW AIGRY                                      325

SEQ ID NO: 9           moltype = DNA  length = 303
FEATURE                Location/Qualifiers
source                 1..303
                       mol_type = other DNA
                       organism = Glycine max
CDS                    1..303
SEQUENCE: 9
atggcatctc atcaacaaaa caagcaagag cttgatgaaa gggcaaggca aggagagact  60
gttgttccgg gtggcactgg tggcaagagc cttgaggctc agcaacatct tgctgaagga  120
aggagcaggg gagggaaaac aaggaaggag cagctgggga cagaagggta ccatgaaatg  180
ggacgcaaag gtgggttgag cactatggac aagtcaggag aagaacgtgc tcaagaggaa  240
gccattgaca tcgatgagtc caagttcagg actggtaata accaagacaa gaaccagaac  300
aag                                                              303

SEQ ID NO: 10          moltype = AA  length = 101
FEATURE                Location/Qualifiers
source                 1..101
                       mol_type = protein
                       organism = Glycine max
SEQUENCE: 10
MASHQQNKQE LDERARQGET VVPGGTGGKS LEAQQHLAEG RSRGGKTRKE QLGTEGYHEM  60
GRKGGLSTMD KSGEERAQEE AIDIDESKFR TGNNQDKNQN K                    101

SEQ ID NO: 11          moltype = DNA  length = 1929
FEATURE                Location/Qualifiers
source                 1..1929
                       mol_type = other DNA
                       organism = Glycine max
CDS                    1..1929
SEQUENCE: 11
atggcgtctg aacaattggc tcgcagagag aacaccacca ccgagaagga gattcacgtt  60
gagaaacaca gggttcccaa gatggccacc cacttcgagc accttgcgga gcaagctaaa  120
gaatctgaca tcaccgctgg gaaggatact ccgcagggta gcatagaagc cttgcaagct  180
ggagagaggg tcaaagatca tgcaggaaaa gccatgggag atattggtgg acgtgggaaa  240
gccagagaga ctcacgagct gggtgcacac tttgaatccc tggctgacaa agtaactgac  300
catgcagcag ccaatgtagt tggaaacaaa gagagtcaaa gagaagctcg tggtggtgtt  360
cgtgatgttg ggaagttcga aatgagaact gaagggggag aaaaaggaaa caaggataga  420
ccagaactga aaacacgaac cagagaggta ataggaagaa cggagaaaga aagaggaaga  480
gaaagtggag gacaagtagt ggcagagaaa ggaagagaaa cagaaactgc aaggggaagg  540
gttggtgctg aaaatgaagg tgcaagaaca accgctgtta taacttgcac gttggaaaaa  600
ggtggtggta ctcagaaacc aataagagaa gaagagagag agagtgaaag tgaaagatca  660
gcgtgggaac agatttccaa ctacagtgat caagccacac aaggtgtgaa ggaaaagtac  720
gagagagcaa agcaagcagc aagcgagaca ctgaacacca caacacaaac cgcacaagag  780
aaaagcgcac aggcaaagaa tcttgcagca caagcaaagg acgcaacgtt agagaagggt  840
cagcaaggct atgctgtgac aaaggacacc atttcaagtg cagcgaaaac cgcttcggag  900
aaaactgcgc cagtggcaga gaaggccaaa gactacactc ttcaggctgc ggagaaggcc  960
aagagtgcgg gtggcacaac ggcgagttac gtcggagaga aagcggtgca ggccaaggat  1020
gtcgccgtgg agagtgggaa gagtgcggct gggtatgctg ccaaggtggc tgctgatttg  1080
agggacaagg ccaccgcggt ggggtgggcc gcggcccatt tttcggcgga aaagacggtg  1140
gaagggacca aggccgccgc ccatgttgtc gagggagcgg ccgggtatgc cggacataag  1200
gccgcggagc ttgcttcgat gtcggccggt gctgttaaag ggctggctgc ttctgctggt  1260
gagactgcta aggaatacac cgcaaagaag aaagaggagg cacagcggga attggaggcc  1320
aaaaaaccat ctcaacctca ggaagctgaa gagaggccat cagaaggaat tggcgaaact  1380
gtgaggcagt atgcacaaaa accaaagcca agtgaaggaa accctcagaa ggagggaacc  1440
ggaagcatcg tgtttacagc aataggcgaa acagtaagca gtgccggtga gaaggtaaag  1500
aaaccgttta aaaacactat gggaggagaa agtgaaggag gaggagggaa agaagaggga  1560
aagagtgtca ttggtaaaag tttgaccagc attggtgaga agctgggtga tgcaaaacag  1620
agagaggagc tgttagacaa cgtcactggc aacatcaccg agggaggagg cgaggtgttg  1680
ggagcagtag gtgaaaccgt tgctgagatt ggacagaaca tgatgaagcc agcggagata  1740
gttcaggaac gcgctcacgt tcgacaagcg ggtggggtct tggatgccat tggtgaaacc  1800
attgctgaga ttgctgaaac gactcgagtc atggtttctg gagaggacga gagagtgctg  1860
aggcagagcg tggtgttgga gactcgcgta actggtcgtg ccaagcatga agaagggtcg  1920
cacggtgct                                                        1929

SEQ ID NO: 12          moltype = AA  length = 643
FEATURE                Location/Qualifiers
source                 1..643
                       mol_type = protein
                       organism = Glycine max
SEQUENCE: 12
MASEQLARRE NTTTEKEIHV EKHRVPKMAT HFEHLAEQAK ESDITAGKDT PQGSIEALQA  60
```

```
GERVKDHAGK AMGDIGGRGK ARETHELGAH FESLADKVTD HAAANVVGNK ESQREARGGV  120
RDVGKFEMRT EGGEKGNKDR PELKTRTREV IGRTEKERGR ESGGQVVAEK GRETETARGR  180
VGAENEGART TAVITCTLEK GGGTQKPIRE EERESESERS AWEQISNYSD QATQGVKEKY  240
ERAKQAASET LNTTTQTAQE KSAQAKNLAA QAKDATLEKG QQGYAVTKDT ISSAAKTASE  300
KTAPVAEKAK DYTLQAAEKA KSAGGTTASY VGEKAVQAKD VAVESGKSAA GYAAKVAADL  360
RDKATAVGWA AAHFSAEKTV EGTKAAAHVV EGAAGYAGHK AAELASMSAG AVKGLAASAG  420
ETAKEYTAKK KEEAQRELEA KKPSQPQEAE ERPSEGIGET VRQYAQKPKP SEGNPQKEGT  480
GSIVFTAIGE TVSSAGEKVK KPFKNTMGGE SEGGGGKEEG KSVIGKSLTS IGEKLGDAKQ  540
REELLDNVTG NITEGGGEVL GAVGETVAEI GQNMMKPAEI VQERAHVRQA GGVLDAIGET  600
IAEIAETTRV MVSGEDERVL RQSVVLETRV TGRAKHEEGS HGA                    643

SEQ ID NO: 13           moltype = DNA  length = 771
FEATURE                 Location/Qualifiers
misc_feature            242
                        note = n is a, c, g, or t
source                  1..771
                        mol_type = other DNA
                        organism = Glycine max
CDS                     1..771
SEQUENCE: 13
atggcccttt cttgctccaa agttttaagc ttttatctct cgcccgttgt gggtggtggt  60
gatgttccga aaaagctcac tttttcttct tttttgggtc tttctaaggg tgttggtgga  120
agcaggagct cgagggtgtg tgctgcttca aatgcacccg caccactcgc tggggtcata  180
tttgaaccat ttcaagagct caagaaggat tatcttgctg ttccgattgc acacaatgtt  240
tncttggctc gtcagaacta tgcagatgac tctgaatctg caatcaacga gcagatcaat  300
gtggaataca acgtttccta tgtgtaccac gccttgtttg cgtacttcga cagagacaac  360
atagctctca aaggacttgc aaagttcttc aaggaatcaa gtgaagaaga aagagagcat  420
gccgagcagc ttataaagta tcagaacatt cgtggtggac gagtggtgct gcacccaatc  480
acaagtcctc cctcggaatt tgagcattcg gaaaaagggg atgccttgta tgccatggaa  540
ctagctttgt ctttggagaa gttgacgaat gagaaacttc tgcacgttca cagtgtggca  600
gaacgtaaca atgatcctca aytdgcagac ttcattgaga gcgagttctt gtatgagcag  660
gttaaatcga ttaaaaagat tgcagagtat gtggctcaac tgagattagt tggaaagggt  720
catggtgtgt ggcactttga tcaaaagctt cttcacgatg aagatcatgt a           771

SEQ ID NO: 14           moltype = AA  length = 257
FEATURE                 Location/Qualifiers
SITE                    81
                        note = misc_feature - The 'Xaa' at location 81 stands for
                         Tyr, Cys, Ser, or Phe.
SITE                    208
                        note = misc_feature - The 'Xaa' at location 208 stands for
                         Leu, or Phe.
source                  1..257
                        mol_type = protein
                        organism = Glycine max
SEQUENCE: 14
MALSCSKVLS FYLSPVVGGG DVPKKLTFSS FLGLSKGVGG SRSSRVCAAS NAPAPLAGVI  60
FEPFQELKKD YLAVPIAHNV XLARQNYADD SESAINEQIN VEYNVSYVYH ALFAYFDRDN  120
IALKGLAKFF KESSEEEREH AEQLIKYQNI RGGRVVLHPI TSPPSEFEHS EKGDALYAME  180
LALSLEKLTN EKLLHVHSVA ERNNDPQXAD FIESEFLYEQ VKSIKKIAEY VAQLRLVGKG  240
HGVWHFDQKL LHDEDHV                                                 257

SEQ ID NO: 15           moltype = DNA  length = 2421
FEATURE                 Location/Qualifiers
source                  1..2421
                        mol_type = other DNA
                        organism = Glycine max
CDS                     1..2421
SEQUENCE: 15
atgtctcagc aaggcgaatc atcggacccg aaatcgggga agaaggactt ctcaaccgcg  60
attctggaac gcaaaaagtc gccgaaccgg cttgtcgtgg atgaggctgt caacgacgac  120
aactccgtgg tcaccatgca tccccaaacc atggaaaagc ttcagctttt ccgaggggac  180
actatcctca tcaagggtaa gaaacggaag gataccattt gcatagctct tgctgatgag  240
aactgtgagg agccgaagat caggatgaat aaagttgtga ggtcaaattt gcgggttcgg  300
cttggagatg ttgtgtctgt gcaccagtgc ccggatgtta aatatgggaa acgtgtgcac  360
attctgccta ttgatgatac cattgaaggt gtcactggca atctgtttga tgctttcttg  420
aaaccctatt tcttggaagc ttaccgtcct gtcagaaaag gagatctatt tcttgtccgg  480
ggagggatga gaagtgtaga gttcaaggtg gttgaaaccg atcctggaga atattgtgtt  540
gttgctccag acactgaaat tttctgtgag gggagagcctt tgaaaagaga agatgaagag  600
agactggatg aagtcgggta tgatgatgtg ggtggtgtca ggaaacaaat ggctcagatt  660
cgtgagttgg ttgagcttcc attgaggcat ccacagcttt ttaaatcaat tggtgtgaaa  720
ccacccaaag gaattttact ttatggaccc ccaggttctg ggaagacatt aatagcaaga  780
gctgtagcta atgaaactgg agcttttttc ttttgtatta acggaccaga gattatgtcc  840
aaacttgctg gagagagtga aagcaatctc aggaaagcgt ttgaagaagc agaaaagaat  900
gcaccatcca ttatcttcat tgatgaaatt gattccattg cccccaagcg ggagaagaca  960
catggtgaag ttgaaaggag gattgtttca caacttttga ctcttatgga tggattaaaa  1020
tctcgtgctc atgttattgt tattggagct actaatcgtc caaatagcat tgacccagca  1080
ttgagaaggt ttggtagatt tgatagggaa attgatattg gtgttcccga tgaagttggg  1140
agacttgaag tccttcgcat acatactaaa aacatgaagc tatctgatga tgttgattta  1200
```

```
gagagaattg caaaagatac tcatgggtat gttggtgctg accttgctgc cctttgcact  1260
gaagctgctt tgcaatgcat tagggagaag atggatgtaa ttgacttgga ggatgagact  1320
attgatgcag aagtactgaa ttccatggca gttacaaatg agcatttcca gactgccctt  1380
ggaacaagca acccatcagc tttacgtgaa actgttgttg aagtgcctaa tgtcagctgg  1440
gaagacattg gaggccttga aaatgtcaag cgtgaactgc aagagactgt acaatatcca  1500
gttgagcacc cagaaaagtt tgagaagttt ggtatgtctc catctaaagg agtacttttc  1560
tatggtcctc caggatgtgg gaaaactttg ttagccaaag caattgctaa tgaatgtcaa  1620
gctaacttca tcagtgtgaa aggtccagaa ttgcttacaa tgtggtttgg tgaaagtgaa  1680
gctaatgtta gagaaatttt tgacaaggcc agacaatcgg ctccatgtgt cctcttcttt  1740
gatgagcttg actctattgc cactcagaga ggaagcagtg ttggggatgc tggtggtgcg  1800
gctgatagag ttctaaatca acttttgact gaaatggatg gcatgtctgc caaaaagact  1860
gtgttcataa ttggggcaac taacagacct gacatcattg acccagcact tcttcgacca  1920
ggccgtctgg atcaattgat ctatattcct ctccctgatg aggattcccg gcatcaaatc  1980
tttaaagcct gcttgaggaa gtcacctatc gcaaaaaatg ttgatttgag agcattggct  2040
aggcacactc aagggttcag tggtgctgat attacagaaa tatgccagcg agcatgcaaa  2100
tatgccataa gagaaaacat agagaaggac attgagcgag agaggaagag tagggaaaac  2160
cctgaggcca tggatgaaga taccgtcgac gacgaagttg cggagatcaa ggctgctcat  2220
tttgaggagt caatgaagtt tgcacggagg agtgttagtg atgctgatat tcgcaagtat  2280
caggcatttg ctcagacctt acagcaatca agagggtttg gaagtgaatt taggtttcca  2340
gagtctggag ataggactac tactggatct gacccctttg cagcttctgc tggtggggct  2400
gacgaagatg atctatatag t                                            2421

SEQ ID NO: 16          moltype = AA  length = 807
FEATURE                Location/Qualifiers
source                 1..807
                       mol_type = protein
                       organism = Glycine max
SEQUENCE: 16
MSQQGESSDP KSGKKDFSTA ILERKKSPNR LVVDEAVNDD NSVVTMHPQT MEKLQLFRGD  60
TILIKGKKRK DTICIALADE NCEEPKIRMN KVVRSNLRVR LGDVVSVHQC PDVKYGKRVH  120
ILPIDDTIEG VTGNLFDAFL KPYFLEAYRP VRKGDLFLVR GGMRSVEFKV VETDPGEYCV  180
VAPDTEIFCE GEPLKREDEE RLDEVGYDDV GGVRKQMAQI RELVELPLRH PQLFKSIGVK  240
PPKGILLYGP PGSGKTLIAR AVANETGAFF FCINGPEIMS KLAGESESNL RKAFEEAEKN  300
APSIIFIDEI DSIAPKREKT HGEVERRIVS QLLTLMDGLK SRAHVIVIGA TNRPNSIDPA  360
LRRFGRFDRE IDIGVPDEVG RLEVLRIHTK NMKLSDDVDL ERIAKDTHGY VGADLAALCT  420
EAALQCIREK MDVIDLEDET IDAEVLNSMA VTNEHFQTAL GTSNPSALRE TVVEVPNVSW  480
EDIGGLENVK RELQETVQYP VEHPEKFEKF GMSPSKGVLF YGPPGCGKTL LAKAIANECQ  540
ANFISVKGPE LLTMWFGESE ANVREIFDKA RQSAPCVLFF DELDSIATQR GSSVGDAGGA  600
ADRVLNQLLT EMDGMSAKKT VFIIGATNRP DIIDPALLRP GRLDQLIYIP LPDEDSRHQI  660
FKACLRKSPI AKNVDLRALA RHTQGFSGAD ITEICQRACK YAIRENIEKD IERERKSREN  720
PEAMDEDTVD DEVAEIKAAH FEESMKFARR SVSDADIRKY QAFAQTLQQS RGFGSEFRFP  780
ESGDRTTTGS DPFAASAGGA DEDDLYS                                      807

SEQ ID NO: 17          moltype = AA  length = 13
FEATURE                Location/Qualifiers
source                 1..13
                       mol_type = protein
                       organism = Glycine max
SEQUENCE: 17
DQSSSYDDDE YSK                                                     13

SEQ ID NO: 18          moltype = AA  length = 15
FEATURE                Location/Qualifiers
source                 1..15
                       mol_type = protein
                       organism = Glycine max
SEQUENCE: 18
KSDQSSSYDD DEYSK                                                   15

SEQ ID NO: 19          moltype = AA  length = 14
FEATURE                Location/Qualifiers
source                 1..14
                       mol_type = protein
                       organism = Glycine max
SEQUENCE: 19
SDQSSSYDDD EYSK                                                    14

SEQ ID NO: 20          moltype = AA  length = 9
FEATURE                Location/Qualifiers
source                 1..9
                       mol_type = protein
                       organism = Glycine max
SEQUENCE: 20
SYDDDEYSK                                                          9

SEQ ID NO: 21          moltype = AA  length = 18
FEATURE                Location/Qualifiers
source                 1..18
                       mol_type = protein
```

```
                      organism = Glycine max
SEQUENCE: 21
ALRALRLEDL RIPTAYIK                                            18

SEQ ID NO: 22         moltype = AA  length = 18
FEATURE               Location/Qualifiers
source                1..18
                      mol_type = protein
                      organism = Glycine max
SEQUENCE: 22
ALRLSGGDHV HAGTVVGK                                            18

SEQ ID NO: 23         moltype = AA  length = 22
FEATURE               Location/Qualifiers
source                1..22
                      mol_type = protein
                      organism = Glycine max
SEQUENCE: 23
LEGEREITLG FVDLLRDDFV EK                                       22

SEQ ID NO: 24         moltype = AA  length = 14
FEATURE               Location/Qualifiers
source                1..14
                      mol_type = protein
                      organism = Glycine max
SEQUENCE: 24
LRLEDLRIPT AYIK                                                14

SEQ ID NO: 25         moltype = AA  length = 11
FEATURE               Location/Qualifiers
source                1..11
                      mol_type = protein
                      organism = Glycine max
SEQUENCE: 25
LTYYTPDYET K                                                   11

SEQ ID NO: 26         moltype = AA  length = 11
FEATURE               Location/Qualifiers
source                1..11
                      mol_type = protein
                      organism = Glycine max
SEQUENCE: 26
TDGLTSLDRY K                                                   11

SEQ ID NO: 27         moltype = AA  length = 14
FEATURE               Location/Qualifiers
source                1..14
                      mol_type = protein
                      organism = Glycine max
SEQUENCE: 27
TFQGPPHGIQ VERD                                                14

SEQ ID NO: 28         moltype = AA  length = 15
FEATURE               Location/Qualifiers
source                1..15
                      mol_type = protein
                      organism = Glycine max
SEQUENCE: 28
TFQGPPHGIQ VERDK                                               15

SEQ ID NO: 29         moltype = AA  length = 24
FEATURE               Location/Qualifiers
source                1..24
                      mol_type = protein
                      organism = Glycine max
SEQUENCE: 29
APHTEDAIRV TQSTANFFIS EARK                                     24

SEQ ID NO: 30         moltype = AA  length = 23
FEATURE               Location/Qualifiers
source                1..23
                      mol_type = protein
                      organism = Glycine max
SEQUENCE: 30
FVESGGARVI PLIYNESPEN LNK                                      23

SEQ ID NO: 31         moltype = AA  length = 7
FEATURE               Location/Qualifiers
source                1..7
```

```
                        mol_type = protein
                        organism = Glycine max
SEQUENCE: 31
IWDLESK                                                                      7

SEQ ID NO: 32           moltype = AA  length = 7
FEATURE                 Location/Qualifiers
source                  1..7
                        mol_type = protein
                        organism = Glycine max
SEQUENCE: 32
SIVEDLK                                                                      7

SEQ ID NO: 33           moltype = AA  length = 21
FEATURE                 Location/Qualifiers
source                  1..21
                        mol_type = protein
                        organism = Glycine max
SEQUENCE: 33
QELDERARQG ETVVPGGTGG K                                                      21

SEQ ID NO: 34           moltype = AA  length = 17
FEATURE                 Location/Qualifiers
source                  1..17
                        mol_type = protein
                        organism = Glycine max
SEQUENCE: 34
SGEERAQEEA IDIDESK                                                           17

SEQ ID NO: 35           moltype = AA  length = 16
FEATURE                 Location/Qualifiers
source                  1..16
                        mol_type = protein
                        organism = Glycine max
SEQUENCE: 35
AAAHVVEGAA GYAGHK                                                            16

SEQ ID NO: 36           moltype = AA  length = 11
FEATURE                 Location/Qualifiers
source                  1..11
                        mol_type = protein
                        organism = Glycine max
SEQUENCE: 36
AKDYTLQAAE K                                                                 11

SEQ ID NO: 37           moltype = AA  length = 17
FEATURE                 Location/Qualifiers
source                  1..17
                        mol_type = protein
                        organism = Glycine max
SEQUENCE: 37
ARETHELGAH FESLADK                                                           17

SEQ ID NO: 38           moltype = AA  length = 15
FEATURE                 Location/Qualifiers
source                  1..15
                        mol_type = protein
                        organism = Glycine max
SEQUENCE: 38
ATAVGWAAAH FSAEK                                                             15

SEQ ID NO: 39           moltype = AA  length = 17
FEATURE                 Location/Qualifiers
source                  1..17
                        mol_type = protein
                        organism = Glycine max
SEQUENCE: 39
DTPQGSIEAL QAGERVK                                                           17

SEQ ID NO: 40           moltype = AA  length = 9
FEATURE                 Location/Qualifiers
source                  1..9
                        mol_type = protein
                        organism = Glycine max
SEQUENCE: 40
DYTLQAAEK                                                                    9

SEQ ID NO: 41           moltype = AA  length = 10
FEATURE                 Location/Qualifiers
```

```
source                  1..10
                        mol_type = protein
                        organism = Glycine max
SEQUENCE: 41
EEAQRELEAK                                                                   10

SEQ ID NO: 42           moltype = AA  length = 21
FEATURE                 Location/Qualifiers
source                  1..21
                        mol_type = protein
                        organism = Glycine max
SEQUENCE: 42
EGTGSIVFTA IGETVSSAGE K                                                      21

SEQ ID NO: 43           moltype = AA  length = 14
FEATURE                 Location/Qualifiers
source                  1..14
                        mol_type = protein
                        organism = Glycine max
SEQUENCE: 43
ERGRESGGQV VAEK                                                              14

SEQ ID NO: 44           moltype = AA  length = 11
FEATURE                 Location/Qualifiers
source                  1..11
                        mol_type = protein
                        organism = Glycine max
SEQUENCE: 44
GLAASAGETA K                                                                 11

SEQ ID NO: 45           moltype = AA  length = 9
FEATURE                 Location/Qualifiers
source                  1..9
                        mol_type = protein
                        organism = Glycine max
SEQUENCE: 45
GQQGYAVTK                                                                    9

SEQ ID NO: 46           moltype = AA  length = 26
FEATURE                 Location/Qualifiers
source                  1..26
                        mol_type = protein
                        organism = Glycine max
SEQUENCE: 46
KPSQPQEAEE RPSEGIGETV RQYAQK                                                 26

SEQ ID NO: 47           moltype = AA  length = 8
FEATURE                 Location/Qualifiers
source                  1..8
                        mol_type = protein
                        organism = Glycine max
SEQUENCE: 47
PAEIVQER                                                                     8

SEQ ID NO: 48           moltype = AA  length = 15
FEATURE                 Location/Qualifiers
source                  1..15
                        mol_type = protein
                        organism = Glycine max
SEQUENCE: 48
PQGSIEALQA GERVK                                                             15

SEQ ID NO: 49           moltype = AA  length = 17
FEATURE                 Location/Qualifiers
source                  1..17
                        mol_type = protein
                        organism = Glycine max
SEQUENCE: 49
QAASETLNTT TQTAQEK                                                           17

SEQ ID NO: 50           moltype = AA  length = 13
FEATURE                 Location/Qualifiers
source                  1..13
                        mol_type = protein
                        organism = Glycine max
SEQUENCE: 50
SAGGTTASYV GEK                                                               13

SEQ ID NO: 51           moltype = AA  length = 8
```

```
FEATURE                 Location/Qualifiers
source                  1..8
                        mol_type = protein
                        organism = Glycine max
SEQUENCE: 51
SLTSIGEK                                                               8

SEQ ID NO: 52           moltype = AA  length = 16
FEATURE                 Location/Qualifiers
source                  1..16
                        mol_type = protein
                        organism = Glycine max
SEQUENCE: 52
TPQGSIEALQ AGERVK                                                      16

SEQ ID NO: 53           moltype = AA  length = 13
FEATURE                 Location/Qualifiers
source                  1..13
                        mol_type = protein
                        organism = Glycine max
SEQUENCE: 53
VTDHAAANVV GNK                                                         13

SEQ ID NO: 54           moltype = AA  length = 22
FEATURE                 Location/Qualifiers
source                  1..22
                        mol_type = protein
                        organism = Glycine max
SEQUENCE: 54
AASNAPAPLA GVIFEPFQEL KK                                               22

SEQ ID NO: 55           moltype = AA  length = 21
FEATURE                 Location/Qualifiers
source                  1..21
                        mol_type = protein
                        organism = Glycine max
SEQUENCE: 55
ASNAPAPLAG VIFEPFQELK K                                                21

SEQ ID NO: 56           moltype = AA  length = 18
FEATURE                 Location/Qualifiers
source                  1..18
                        mol_type = protein
                        organism = Glycine max
SEQUENCE: 56
FFKESSEEER EHAEQLIK                                                    18

SEQ ID NO: 57           moltype = AA  length = 10
FEATURE                 Location/Qualifiers
source                  1..10
                        mol_type = protein
                        organism = Glycine max
SEQUENCE: 57
GHGVWHFDQK                                                             10

SEQ ID NO: 58           moltype = AA  length = 13
FEATURE                 Location/Qualifiers
source                  1..13
                        mol_type = protein
                        organism = Glycine max
SEQUENCE: 58
IAEYVAQLRL VGK                                                         13

SEQ ID NO: 59           moltype = AA  length = 14
FEATURE                 Location/Qualifiers
source                  1..14
                        mol_type = protein
                        organism = Glycine max
SEQUENCE: 59
KIAEYVAQLR LVGK                                                        14

SEQ ID NO: 60           moltype = AA  length = 8
FEATURE                 Location/Qualifiers
source                  1..8
                        mol_type = protein
                        organism = Glycine max
SEQUENCE: 60
LLHDEDHV                                                               8
```

```
SEQ ID NO: 61          moltype = AA  length = 20
FEATURE                Location/Qualifiers
source                 1..20
                       mol_type = protein
                       organism = Glycine max
SEQUENCE: 61
SNAPAPLAGV IFEPFQELKK                                              20

SEQ ID NO: 62          moltype = AA  length = 10
FEATURE                Location/Qualifiers
source                 1..10
                       mol_type = protein
                       organism = Glycine max
SEQUENCE: 62
AGESESNLRK                                                         10

SEQ ID NO: 63          moltype = AA  length = 13
FEATURE                Location/Qualifiers
source                 1..13
                       mol_type = protein
                       organism = Glycine max
SEQUENCE: 63
GESEANVREI FDK                                                     13

SEQ ID NO: 64          moltype = AA  length = 12
FEATURE                Location/Qualifiers
source                 1..12
                       mol_type = protein
                       organism = Glycine max
SEQUENCE: 64
GILLYGPPGS GK                                                      12

SEQ ID NO: 65          moltype = AA  length = 11
FEATURE                Location/Qualifiers
source                 1..11
                       mol_type = protein
                       organism = Glycine max
SEQUENCE: 65
LAGESESNLR K                                                       11

SEQ ID NO: 66          moltype = AA  length = 12
FEATURE                Location/Qualifiers
source                 1..12
                       mol_type = protein
                       organism = Glycine max
SEQUENCE: 66
LSDDVDLERI AK                                                      12

SEQ ID NO: 67          moltype = AA  length = 16
FEATURE                Location/Qualifiers
source                 1..16
                       mol_type = protein
                       organism = Glycine max
SEQUENCE: 67
RELQETVQYP VEHPEK                                                  16

SEQ ID NO: 68          moltype = AA  length = 15
FEATURE                Location/Qualifiers
source                 1..15
                       mol_type = protein
                       organism = Glycine max
SEQUENCE: 68
TVFIIGATNR PDIID                                                   15

SEQ ID NO: 69          moltype = DNA  length = 2448
FEATURE                Location/Qualifiers
source                 1..2448
                       mol_type = other DNA
                       organism = Glycine max
CDS                    1..2448
SEQUENCE: 69
atgaggaagt ggacggttgc ttccgctctc cttcttctct ctctcctctt tctctttgca  60
gatcaaggtc gaaagtttca ggcgaatgcc gagggagatt ccgacgagct tgtagatcca  120
cccaaggtgg aggacaagat cggtgctgtg cctcatggcc tttcaaccga ttcagatgtc  180
gtcaagaggg aggcggagtc gatctcgaag agatctctcc ggagcaacgc ggagaagttt  240
gagttccaag cggaagtgtc gcggcttatg gatatcatca tcaattctct ctacagtaac  300
aaggatatct tcctcagaga gttgatttcc aatgcttctg atgctttgga caagattagg  360
ttcctctccc tcacggataa ggaggtgttg ggagaaggtg ataacaccaa gcttgatatt  420
cagattaagt tggacaagga aaagaaaatt ctctcaattc gagacagagg tatcggtatg  480
```

```
acgaaggagg atttgataaa gaatttgggg acaatagcga aatctggaac ttctgcattt  540
gttgagaaga tgcaaacaag tggagatctc aatctgattg ggcagtttgg agtcggcttc  600
tactctgttt atcttgtggc cgactatgtc gaagttatta gcaagaataa cgatgataag  660
cagtatgtat gggaatcaaa agctgatgga gcattcgcta tttcagaaga tacatggaat  720
gaaccacttg gacgaggaac tgagattaga ttacacctca aggaagaggc tggggaatac  780
ttggaggagt ctaaactgaa agaattggtg aagagatact ctgaatttat taacttccct  840
atctatattt gggcaagcaa agaagttgat gtggaggttc ccgctgatga agatgattcc  900
agtgatgaag aggattcatc tgaaagcagc tccaaggagg aaagcgaaga tgaagatgct  960
gataaaagtg aagatgaaga aaaaaagcct aagacaaaga cagtgaagga aacaacttat  1020
gagtgggaac ttttaaatga tgtgaaagct atatggctga ggaatccaaa agaggttaca  1080
gaagaagaat acaccaaatt ctaccactct cttgccaagg atttcagtga tgagaaacct  1140
ttagcatgga gtcatttcac tgctgagggt gatgttgagt tcaaggcagt cctgtttgta  1200
ccacctaagg cacctcaaga tttatatgag agctattata acgcaaacaa atcgaacctg  1260
aagttgtatg ttagacgtgt gttcatttca gatgaattta atgaactgtt gcccaagtac  1320
ctaaactttt tgctgggtct tgttgattct gacactttgc cacttaatgt atcacgagaa  1380
atgcttcaac aacatagtag tctgaagaca atcaagaaga aacttattag gaaagccctt  1440
gatatgatcc gcaggattgc tgatgaggat cctgacgagt caactgacaa agaaaagaaa  1500
gatgcatcct ctgacaatga tgagaagaaa ggtcaatatt ctaagttctg gaatgagttt  1560
ggtaaatcca ttaaacttgg tatcatcgag gatgccacca acagaaatcg tttggcaaaa  1620
ctgctcagat ttgagagcac caagtctgag ggtaaattga catctctgga tcagtacata  1680
tctagaatga aaactgggca gaaggatatc ttttacataa ctggaaccag caaagaacaa  1740
ctggaaaact ctcccttcct tgagcggctt aagaagaaaa attttgaggt tattttcttc  1800
acggatccag ttgatgagta cttgatgcaa tacctgatgg attatgaaga caagaagttc  1860
caaaatgtgt ccaaggaggg tttgaaactt gggaaagatt caaaagacaa ggaactgaag  1920
gaatctttta aggatcttac caagtggtgg aaaactgctc tttccaaaga caatgttgat  1980
gatgtgaaga tttccaaccg attagataac actccttgtg tagtggtgac atcaaaattt  2040
ggttggagtg ctaacatgga gagaatcatg cagtctcaaa ctttgtcaga tgctagcaag  2100
caagcataca tgcgcggcaa gagggttctt gagatcaatc ctaggcaccc tattatcaag  2160
gagctccgag agagagtagt aaagaaccct gaggatgagg gtgtgaagca tacagcacag  2220
ctgatgtacc agactgcact ctttgaaagc ggcttcctgc ttgatgatcc caaggatttt  2280
gcttcccgga tttatgattc agtgaagact agcctggaca tcagtcctga agcaacagtt  2340
gaggaggaag atgacactga agtagaggct gaaagtgacg cgaaagaaga ttcaaagcct  2400
gaaactgatg ctgttaacga tgataatgat gtcaaggacg agttgtag               2448

SEQ ID NO: 70          moltype = AA  length = 815
FEATURE                Location/Qualifiers
source                 1..815
                       mol_type = protein
                       organism = Glycine max
SEQUENCE: 70
MRKWTVASAL LLLSLLFLFA DQGRKFQANA EGDSDELVDP PKVEDKIGAV PHGLSTDSDV  60
VKREAESISK RSLRSNAEKF EFQAEVSRLM DIIINSLYSN KDIFLRELIS NASDALDKIR  120
FLSLTDKEVL GEGDNTKLDI QIKLDKEKKI LSIRDRGIGM TKEDLIKNLG TIAKSGTSAF  180
VEKMQTSGDL NLIGQFGVGF YSVYLVADYV EVISKNNDDK QYVWESKADG AFAISEDTWN  240
EPLGRGTEIR LHLKEEAGEY LEESKLKELV KRYSEFINFP IYIWASKEVD VEVPADEDDS  300
SDEEDSSESS SKEESEDEDA DKSEDEEKKP KTKTVKETTY EWELLNDVKA IWLRNPKEVT  360
EEEYTKFYHS LAKDFSDEKP LAWSHFTAEG DVEFKAVLFV PPKAPQDLYE SYYNANKSNL  420
KLYVRRVFIS DEFNELLPKY LNFLLGLVDS DTLPLNVSRE MLQQHSSLKT IKKKLIRKAL  480
DMIRRIADED PDESTDKEKK DASSDNDEKK GQYSKFWNEF GKSIKLGIIE DATNRNRLAK  540
LLRFESTKSE GKLTSLDQYI SRMKTGQKDI FYITGTSKEQ LENSPFLERL KKKNFEVIFF  600
TDPVDEYLMQ YLMDYEDKKF QNVSKEGLKL GKDSKDKELK ESFKDLTKWW KTALSKDNVD  660
DVKISNRLDN TPCVVVTSKF GWSANMERIM QSQTLSDASK QAYMRGKRVL EINPRHPIIK  720
ELRERVVKNP EDEGVKHTAQ LMYQTALFES GFLLDDPKDF ASRIYDSVKT SLDISPEATV  780
EEEDDTEVEA ESDAKEDSKP ETDAVNDDND VKDEL                            815

SEQ ID NO: 71          moltype = AA  length = 14
FEATURE                Location/Qualifiers
source                 1..14
                       mol_type = protein
                       organism = Glycine max
SEQUENCE: 71
APQDLYESYY NANK                                                   14

SEQ ID NO: 72          moltype = AA  length = 8
FEATURE                Location/Qualifiers
source                 1..8
                       mol_type = protein
                       organism = Glycine max
SEQUENCE: 72
AVLFVPPK                                                          8

SEQ ID NO: 73          moltype = AA  length = 11
FEATURE                Location/Qualifiers
source                 1..11
                       mol_type = protein
                       organism = Glycine max
SEQUENCE: 73
DFASRIYDSV K                                                      11
```

```
SEQ ID NO: 74           moltype = AA  length = 17
FEATURE                 Location/Qualifiers
source                  1..17
                        mol_type = protein
                        organism = Glycine max
SEQUENCE: 74
DIFLRELISN ASDALDK                                                    17

SEQ ID NO: 75           moltype = AA  length = 10
FEATURE                 Location/Qualifiers
source                  1..10
                        mol_type = protein
                        organism = Glycine max
SEQUENCE: 75
DIFYITGTSK                                                            10

SEQ ID NO: 76           moltype = AA  length = 7
FEATURE                 Location/Qualifiers
source                  1..7
                        mol_type = protein
                        organism = Glycine max
SEQUENCE: 76
DNVDDVK                                                               7

SEQ ID NO: 77           moltype = AA  length = 17
FEATURE                 Location/Qualifiers
source                  1..17
                        mol_type = protein
                        organism = Glycine max
SEQUENCE: 77
EDSKPETDAV NDDNDVK                                                    17

SEQ ID NO: 78           moltype = AA  length = 11
FEATURE                 Location/Qualifiers
source                  1..11
                        mol_type = protein
                        organism = Glycine max
SEQUENCE: 78
EEAGEYLEES K                                                          11

SEQ ID NO: 79           moltype = AA  length = 13
FEATURE                 Location/Qualifiers
source                  1..13
                        mol_type = protein
                        organism = Glycine max
SEQUENCE: 79
EQLENSPFLE RLK                                                        13

SEQ ID NO: 80           moltype = AA  length = 10
FEATURE                 Location/Qualifiers
source                  1..10
                        mol_type = protein
                        organism = Glycine max
SEQUENCE: 80
EVLGEGDNTK                                                            10

SEQ ID NO: 81           moltype = AA  length = 9
FEATURE                 Location/Qualifiers
source                  1..9
                        mol_type = protein
                        organism = Glycine max
SEQUENCE: 81
EVTEEEYTK                                                             9

SEQ ID NO: 82           moltype = AA  length = 7
FEATURE                 Location/Qualifiers
source                  1..7
                        mol_type = protein
                        organism = Glycine max
SEQUENCE: 82
FYHSLAK                                                               7

SEQ ID NO: 83           moltype = AA  length = 16
FEATURE                 Location/Qualifiers
source                  1..16
                        mol_type = protein
                        organism = Glycine max
SEQUENCE: 83
IGAVPHGLST DSDVVK                                                     16
```

```
SEQ ID NO: 84          moltype = AA  length = 15
FEATURE                Location/Qualifiers
source                 1..15
                       mol_type = protein
                       organism = Glycine max
SEQUENCE: 84
LGIIEDATNR NRLAK                                                   15

SEQ ID NO: 85          moltype = AA  length = 8
FEATURE                Location/Qualifiers
source                 1..8
                       mol_type = protein
                       organism = Glycine max
SEQUENCE: 85
NPEDEGVK                                                           8

SEQ ID NO: 86          moltype = AA  length = 9
FEATURE                Location/Qualifiers
source                 1..9
                       mol_type = protein
                       organism = Glycine max
SEQUENCE: 86
SGTSAFVEK                                                          9

SEQ ID NO: 87          moltype = AA  length = 26
FEATURE                Location/Qualifiers
source                 1..26
                       mol_type = protein
                       organism = Glycine max
SEQUENCE: 87
TSLDISPEAT VEEEDDTEVE AESDAK                                       26

SEQ ID NO: 88          moltype = DNA  length = 2442
FEATURE                Location/Qualifiers
source                 1..2442
                       mol_type = other DNA
                       organism = Glycine max
CDS                    1..2442
SEQUENCE: 88
atgaggaagt ggacggttgc ttccgctctc cttcttctct ctctcctctt tctctttgca  60
gatcaaggtc gaaagtttca ggcgaatgcc gagggagatt ccgacgagct tgtagatcct  120
ccgaaggtgg aggacaagat cggtgctgtg cctcatggcc tttccaccga ttcagatgtc  180
gtcaagaggg agtcggagtc gatctcgaag agatctctcc ggagcaatgc ggagaagttt  240
gagttccaag cggaagtgtc acggcttatg gatattatca tcaattctct ctacagtaac  300
aaggatatct tcctcagaga gttgatttcc aatgcttctg atgctttgga caagattagg  360
ttcctttccc tcacggataa ggacgttttg ggagaaggtg ataacaccaa gcttgatatt  420
cagattaagt tggacaagga aaagaaaatt ctctcaattc gagacagagg tattggtatg  480
acgaaggagg atttgataaa gaatttgggg acaatagcaa aatctggaac ttctgcattt  540
gttgagaaga tgcaaacaag tggagatctc aatctgattg ggcagtttgg agtcggcttc  600
tactctgttt atctcgtggc tgactatgtc gaagtcatta gcaagaataa tgatgataaa  660
cagtatgtat gggaatcaaa agctgatgga gcatttgcaa tttcagaaga tacatggaat  720
gaacctctag ggcgtggaac tgagattaga ttacacctca aggaagaggc tggggagtac  780
ttgcaggagt ctaaactgaa agaattggtg aagagatact ctgaatttat taacttccct  840
atctatattt gggcaagcaa agaggttgat gtggaggttc ccgctgatga agatgattcc  900
agtgatgaag aggattcatc tgaaagcagc tccaaggagg aaagcgaaga tgaagatgct  960
gataaaagtg aagacgaaga aaaaaagccc aagacaaaga cggtgaagga aacaacttat  1020
gaatgggaac ttttaaatga tgtgaaagct atatggctga ggaatccaaa ggaggttaca  1080
gaagaagaat acaccaaatt ctaccactct cttgccaagg atttcagtga tgagaaacct  1140
ttagcatgga gtcatttcac tgctgagggc gatgtcgagt tcaaggcagt cctgtttgta  1200
ccacctaagg cacctcaaga tttatacgag agctattata acgcaaacaa atccaacctg  1260
aagttgtatg ttagacgtgt gttcatttca gatgaattta atgaactgtt gcctaagtac  1320
ctaaactttt tgctgggtct tgttgattct gacacattgc cacttaatgt atcgcgagaa  1380
atgcttcagc aacatagtag tctaaagaca atcaagaaga aacttattag gaaagccctt  1440
gatatgatcc gtaggattgc tgatgaggat cctgatgagt ccactgacaa agaaaagaaa  1500
gatacgtcat ctgacaataa tgagaagaaa ggtcaatatt ccaagttctg gaatgagttt  1560
ggtaaatcca ttaaacttgg tatcatcgag gatgccacca acagaaatcg tttggcaaaa  1620
ctgctcagat ttgagagcac caagtctgag ggtaaattga catctctgga tcagtacata  1680
tctagaatga aagctgggca gaaggatatc ttttacataa ctggaaccag caaagaacaa  1740
ctggaaaact ctccattcct tgagcggctt aagaagaaaa attttgaggt tattttcttc  1800
acggatccag ttgatgaata cttgatgcaa tacctgatgg attatgaaga caagaagttc  1860
caaaatgtgt ccaaggaggg tttgaaactc gggaaagatt caaaagacaa ggaactgaag  1920
gaatccttca aggaccttac caagtggtgg aaaactgctc tttccaaaga caatgttgat  1980
gatgtgaaga tttccaaccg attggacaac actccttgtg tagtggtaac atcaaaattt  2040
ggttggagtg ctaacatgga gagaatcatg cagtctcaaa ctttgtctga tgctagcaag  2100
caagcataca tgcgcggcaa gagggttctt gaggtcaatc ctaggcaccc tattatcaag  2160
gagctccgag agagagtagt aaagaaccct gaggatgagg gtgtgaaaca tacagcacag  2220
ttgatgtacc agaccgcact cttcgaaagt ggcttcctgc ttgatgatcc caaggatttt  2280
gcttcccgta tttatgattc agttaagacc agcttggaca tcagtcctga agcaacagtt  2340
```

```
gaggaggaag atgacaccga agtagaggct gaaagtgatt caaagcctga agctgatgcg  2400
gttcatgatg gtgatgttga tgatgccaag gacgagttgt ag                     2442

SEQ ID NO: 89          moltype = AA  length = 813
FEATURE                Location/Qualifiers
source                 1..813
                       mol_type = protein
                       organism = Glycine max
SEQUENCE: 89
MRKWTVASAL LLLSLLFLFA DQGRKFQANA EGDSDELVDP PKVEDKIGAV PHGLSTDSDV  60
VKRESESISK RSLRSNAEKF EFQAEVSRLM DIIINSLYSN KDIFLRELIS NASDALDKIR  120
FLSLTDKDVL GEGDNTKLDI QIKLDKEKKI LSIRDRGIGM TKEDLIKNLG TIAKSGTSAF  180
VEKMQTSGDL NLIGQFGVGF YSVYLVADYV EVISKNNDDK QYVWESKADG AFAISEDTWN  240
EPLGRGTEIR LHLKEEAGEY LQESKLKELV KRYSEFINFP IYIWASKEVD VEVPADEDDS  300
SDEEDSSESS SKEESEDEDA DKSEDEEKKP KTKTVKETTY EWELLNDVKA IWLRNPKEVT  360
EEEYTKFYHS LAKDFSDEKP LAWSHFTAEG DVEFKAVLFV PPKAPQDLYE SYYNANKSNL  420
KLYVRRVFIS DEFNELLPKY LNFLLGLVDS DTLPLNVSRE MLQQHSSLKT IKKKLIRKAL  480
DMIRRIADED PDESTDKEKK DTSSDNNEKK GQYSKFWNEF GKSIKLGIIE DATNRNRLAK  540
LLRFESTKSE GKLTSLDQYI SRMKAGQKDI FYITGTSKEQ LENSPFLERL KKKNFEVIFF  600
TDPVDEYLMQ YLMDYEDKKF QNVSKEGLKL GKDSKDKELK ESFKDLTKWW KTALSKDNVD  660
DVKISNRLDN TPCVVVTSKF GWSANMERIM QSQTLSDASK QAYMRGKRVL EVNPRHPIIK  720
ELRERVVKNP EDEGVKHTAQ LMYQTALFES GFLLDDPKDF ASRIYDSVKT SLDISPEATV  780
EEEDDTEVEA ESDSKPEADA VHDGDVDDAK DEL                                813

SEQ ID NO: 90          moltype = AA  length = 14
FEATURE                Location/Qualifiers
source                 1..14
                       mol_type = protein
                       organism = Glycine max
SEQUENCE: 90
APQDLYESYY NANK                                                     14

SEQ ID NO: 91          moltype = AA  length = 8
FEATURE                Location/Qualifiers
source                 1..8
                       mol_type = protein
                       organism = Glycine max
SEQUENCE: 91
AVLFVPPK                                                            8

SEQ ID NO: 92          moltype = AA  length = 11
FEATURE                Location/Qualifiers
source                 1..11
                       mol_type = protein
                       organism = Glycine max
SEQUENCE: 92
DFASRIYDSV K                                                        11

SEQ ID NO: 93          moltype = AA  length = 17
FEATURE                Location/Qualifiers
source                 1..17
                       mol_type = protein
                       organism = Glycine max
SEQUENCE: 93
DIFLRELISN ASDALDK                                                  17

SEQ ID NO: 94          moltype = AA  length = 10
FEATURE                Location/Qualifiers
source                 1..10
                       mol_type = protein
                       organism = Glycine max
SEQUENCE: 94
DIFYITGTSK                                                          10

SEQ ID NO: 95          moltype = AA  length = 7
FEATURE                Location/Qualifiers
source                 1..7
                       mol_type = protein
                       organism = Glycine max
SEQUENCE: 95
DNVDDVK                                                             7

SEQ ID NO: 96          moltype = AA  length = 10
FEATURE                Location/Qualifiers
source                 1..10
                       mol_type = protein
                       organism = Glycine max
SEQUENCE: 96
DVLGEGDNTK                                                          10
```

```
SEQ ID NO: 97           moltype = AA  length = 11
FEATURE                 Location/Qualifiers
source                  1..11
                        mol_type = protein
                        organism = Glycine max
SEQUENCE: 97
EEAGEYLQES K                                                         11

SEQ ID NO: 98           moltype = AA  length = 13
FEATURE                 Location/Qualifiers
source                  1..13
                        mol_type = protein
                        organism = Glycine max
SEQUENCE: 98
EQLENSPFLE RLK                                                       13

SEQ ID NO: 99           moltype = AA  length = 9
FEATURE                 Location/Qualifiers
source                  1..9
                        mol_type = protein
                        organism = Glycine max
SEQUENCE: 99
EVTEEEYTK                                                            9

SEQ ID NO: 100          moltype = AA  length = 7
FEATURE                 Location/Qualifiers
source                  1..7
                        mol_type = protein
                        organism = Glycine max
SEQUENCE: 100
FYHSLAK                                                              7

SEQ ID NO: 101          moltype = AA  length = 16
FEATURE                 Location/Qualifiers
source                  1..16
                        mol_type = protein
                        organism = Glycine max
SEQUENCE: 101
IGAVPHGLST DSDVVK                                                    16

SEQ ID NO: 102          moltype = AA  length = 15
FEATURE                 Location/Qualifiers
source                  1..15
                        mol_type = protein
                        organism = Glycine max
SEQUENCE: 102
LGIIEDATNR NRLAK                                                     15

SEQ ID NO: 103          moltype = AA  length = 8
FEATURE                 Location/Qualifiers
source                  1..8
                        mol_type = protein
                        organism = Glycine max
SEQUENCE: 103
NPEDEGVK                                                             8

SEQ ID NO: 104          moltype = AA  length = 9
FEATURE                 Location/Qualifiers
source                  1..9
                        mol_type = protein
                        organism = Glycine max
SEQUENCE: 104
SGTSAFVEK                                                            9

SEQ ID NO: 105          moltype = DNA  length = 2103
FEATURE                 Location/Qualifiers
source                  1..2103
                        mol_type = other DNA
                        organism = Glycine max
CDS                     1..2103
SEQUENCE: 105
atggcttcgg agactgagac gttcgctttt caggccgaga tcaaccagct cctcagtcta  60
ataatcaaca ccttctacag caacaaggag atctttcttc gtgagctcat cagcaatgcc  120
tctgacgctt tggacaagat tcgatttgag agtcttacag acaagagcaa gcttgatgct  180
cagccagagt tgttcattca cattattcct gacaagacca acaacacatt gtctatcatt  240
gacagtggta ttggcatgac taaggctgat ttggtgaata acctcggtac tattgcaagg  300
tctgggacca aggaattcat ggaagccctg gctgctggtg ctgacgtgag catgattggg  360
cagttcggtg ttggtttcta ctcggcttat cttgtagctg ataaggttat tgttaccaca  420
```

```
aagcacaatg atgatgaaca gtatgtctgg gagtcccatg ccggtggctc atttactgtg  480
acaagagata catctggtga gaaccttggt aggggaacaa agataacttt gtttcttaag  540
gaagatcaac ttgagtatct tgaggaacgc cgtctgaagg atttgataaa gaagcattct  600
gaattcatta gctatccaat ttctctctgg attgagaaga ctactgaaaa ggagatttct  660
gatgatgagg atgaggaaga gaagaaggat gaggagggta aagttgaaga tgtggatgaa  720
gataaggaga aggaggagaa gaaaaagaag accattaagg aggtatctca cgagtggtca  780
ttggtgaaca agcagaagcc tatttggatg aggaaacctg aagagattac gaaagaagaa  840
tatgctgctt tctacaagag tcttaccaat gattgggaag agcatttggc tgttaagcac  900
ttttctgttg agggtcagct ggagtttaag gctgtcctct ttatccccaa gagggcacct  960
tttgatctct ttgacaccag gaagaagcct aacaacatca aactgtatgt ccgccgtgtc  1020
ttcatcatgg acaactgtga ggagttgatg cctgaatatc ttagctttgt taagggtatt  1080
gtggattctg aggatcttcc tctcaacatt tctagagaaa tgctgcagca gaacaagatc  1140
ctgaaagtca tcaggaagaa cttggtcaag aagtgcattg agatgttctt tgaaattgct  1200
gaaaacaagg aagactataa caagttttat gaagccttct ctaagaacct gaaacttggt  1260
attcatgagg attctcagaa caagacaaag ctagctgaat tgctcaggta tcactccact  1320
aagagtggtg atgagatgac cagcctcaag gactatgtta ccaggatgaa ggaaggacag  1380
aatgacatct actacattac tggtgaaagc aagaaagctg tcgagaattc cccttccctt  1440
gaaaagctta agaagaaggg atacgaggtt ctctacatgg ttgatgctat tgatgagtat  1500
gctgttggcc agcttaagga atttgaggga aagaagttgg tctctgctac caaggaaggc  1560
ctaaaacttg atgagagcga agacgagaag aaaaagaagg aagaactaaa ggataaattt  1620
gagggtcttt gccatgtgat caaggatgtg ttgggtgaca aggtggagaa agttgtggtg  1680
tctgatcgtg ttgtggattc tccttgctgt ctggtgacag gtgaatatgg gtggacagcc  1740
aacatggaaa ggattatgaa agcacaggca ttgagggaca gcagcatggc tggatacatg  1800
tcaagcaaga agacgatgga gattaaccct gagaacccca tcatggagga gctgaggaag  1860
cgagcagatg ctgataagaa tgacaagtct gtgaaggatc tcgtgctctt gctctttgag  1920
actgctcttc taacttctgg gttcagcctt gatgatccca acactttcgg taacaggatt  1980
cacaggatgc tgaagcttgg actgagcatt gatgaagatg ctggtgaagc agatgctgac  2040
atgcctcctc ttgaggacgc tgatgcagat gctgagggta gcaagatgga agaagttgat  2100
taa                                                                2103

SEQ ID NO: 106          moltype = AA  length = 700
FEATURE                 Location/Qualifiers
source                  1..700
                        mol_type = protein
                        organism = Glycine max
SEQUENCE: 106
MASETETFAF QAEINQLLSL IINTFYSNKE IFLRELISNA SDALDKIRFE SLTDKSKLDA  60
QPELFIHIIP DKTNNTLSII DSGIGMTKAD LVNNLGTIAR SGTKEFMEAL AAGADVSMIG  120
QFGVGFYSAY LVADKVIVTT KHNDDEQYVW ESHAGGSFTV TRDTSGENLG RGTKITLFLK  180
EDQLEYLEER RLKDLIKKHS EFISYPISLW IEKTTEKEIS DDEDEEEKKD EEGKVEDVDE  240
DKEKEEKKKK TIKEVSHEWS LVNKQKPIWM RKPEEITKEE YAAFYKSLTN DWEEHLAVKH  300
FSVEGQLEFK AVLFIPKRAP FDLFDTRKKP NNIKLYVRRV FIMDNCEELM PEYLSFVKGI  360
VDSEDLPLNI SREMLQQNKI LKVIRKNLVK KCIEMFFEIA ENKEDYNKFY EAFSKNLKLG  420
IHEDSQNKTK LAELLRYHST KSGDEMTSLK DYVTRMKEGQ NDIYYITGES KKAVENSPFL  480
EKLKKKGYEV LYMVDAIDEY AVGQLKEFEG KKLVSATKEG LKLDESEDEK KKKEELKDKF  540
EGLCHVIKDV LGDKVEKVVV SDRVVDSPCC LVTGEYGWTA NMERIMKAQA LRDSSMAGYM  600
SSKKTMEINP ENPIMEELRK RADADKNDKS VKDLVLLLFE TALLTSGFSL DDPNTFGNRI  660
HRMLKLGLSI DEDAGEADAD MPPLEDADAD AEGSKMEEVD                        700

SEQ ID NO: 107          moltype = AA  length = 16
FEATURE                 Location/Qualifiers
source                  1..16
                        mol_type = protein
                        organism = Glycine max
SEQUENCE: 107
ADLVNNLGTI ARSGTK                                                  16

SEQ ID NO: 108          moltype = AA  length = 10
FEATURE                 Location/Qualifiers
source                  1..10
                        mol_type = protein
                        organism = Glycine max
SEQUENCE: 108
AVENSPFLEK                                                         10

SEQ ID NO: 109          moltype = AA  length = 13
FEATURE                 Location/Qualifiers
source                  1..13
                        mol_type = protein
                        organism = Glycine max
SEQUENCE: 109
EDQLEYLEER RLK                                                     13

SEQ ID NO: 110          moltype = AA  length = 8
FEATURE                 Location/Qualifiers
source                  1..8
                        mol_type = protein
                        organism = Glycine max
SEQUENCE: 110
```

```
EEYAAFYK                                                        8

SEQ ID NO: 111          moltype = AA  length = 14
FEATURE                 Location/Qualifiers
source                  1..14
                        mol_type = protein
                        organism = Glycine max
SEQUENCE: 111
EGQNDIYYIT GESK                                                 14

SEQ ID NO: 112          moltype = AA  length = 17
FEATURE                 Location/Qualifiers
source                  1..17
                        mol_type = protein
                        organism = Glycine max
SEQUENCE: 112
EIFLRELISN ASDALDK                                              17

SEQ ID NO: 113          moltype = AA  length = 7
FEATURE                 Location/Qualifiers
source                  1..7
                        mol_type = protein
                        organism = Glycine max
SEQUENCE: 113
FYEAFSK                                                         7

SEQ ID NO: 114          moltype = AA  length = 11
FEATURE                 Location/Qualifiers
source                  1..11
                        mol_type = protein
                        organism = Glycine max
SEQUENCE: 114
HFSVEGQLEF K                                                    11

SEQ ID NO: 115          moltype = AA  length = 9
FEATURE                 Location/Qualifiers
source                  1..9
                        mol_type = protein
                        organism = Glycine max
SEQUENCE: 115
IRFESLTDK                                                       9

SEQ ID NO: 116          moltype = AA  length = 11
FEATURE                 Location/Qualifiers
source                  1..11
                        mol_type = protein
                        organism = Glycine max
SEQUENCE: 116
LAELLRYHST K                                                    11

SEQ ID NO: 117          moltype = AA  length = 8
FEATURE                 Location/Qualifiers
source                  1..8
                        mol_type = protein
                        organism = Glycine max
SEQUENCE: 117
LDESEDEK                                                        8

SEQ ID NO: 118          moltype = AA  length = 10
FEATURE                 Location/Qualifiers
source                  1..10
                        mol_type = protein
                        organism = Glycine max
SEQUENCE: 118
LGIHEDSQNK                                                      10

SEQ ID NO: 119          moltype = AA  length = 11
FEATURE                 Location/Qualifiers
source                  1..11
                        mol_type = protein
                        organism = Glycine max
SEQUENCE: 119
RAPFDLFDTR K                                                    11

SEQ ID NO: 120          moltype = AA  length = 8
FEATURE                 Location/Qualifiers
source                  1..8
                        mol_type = protein
                        organism = Glycine max
```

```
SEQUENCE: 120
VEDVDEDK                                                    8

SEQ ID NO: 121         moltype = DNA  length = 2109
FEATURE                Location/Qualifiers
source                 1..2109
                       mol_type = other DNA
                       organism = Glycine max
CDS                    1..2109
SEQUENCE: 121
atggcggaga cagagacgtt cgcattccaa gcagagatca accagctcct cagtctcatc  60
atcaacacct tctactccaa caaggagatt ttccttcgtg aactcatcag caacgcctcc  120
gatgctttgg acaagattcg atttgagagt ttgacagata agagcaagct cgatgctcag  180
ccagagttgt tcattcatat tattccagac aagactaaca atacactgac cattgttgac  240
agtggtattg gcatgaccaa agctgatttg gtgaacaact tgggtacaat tgctagatct  300
ggtaccaagg aattcatgga agccttggct gctggtgctg atgttagtat gattggacag  360
tttggtgtgg ggttctactc tgcatatctt gttgctgaga aggtcattgt tacaaccaaa  420
cacaatgatg atgaacagta tgtttgggag tctcaagctg gaggttcttt cactgtcacc  480
agggataaca ctggtgaggt tcttggcagg ggtactaaga tcactctcta cctcaaggaa  540
gatcagcttg agtaccttga ggagcgtcgc ttgaaggatc tgatcaagaa gcattctgag  600
ttcattagct acccaatttc tctttggatt gagaagacta ctgagaagga gatctctgac  660
gatgaggatg aggaagagaa gaaggatgag gagggtaagg tggaggatgt tgacgaagag  720
aaggagaagg aagaaaaaaa gaaaaagaag atcaaggaag tgtcacatga atggtccttg  780
gtgaacaagc agaagcccat ttggatgagg aagcctgagg agatcacaaa agaggagtat  840
tctgctttct acaagagtct taccaatgac tgggaagagc atttggctgt caagcacttc  900
tctgttgagg gtcagttgga gtttaaggct atactctttg ttcccaagag ggcacctttt  960
gacctctttg acacaaggaa gaagcctaac aacattaagc tctatgtccg ccgtgtcttt  1020
attatggaca actgtgagga gttgattcct gagtatttgg gctttgtcaa gggtattgtt  1080
gattctgaag atctcccact caacatttca agagaaatgt tgcaacagaa caagatcttg  1140
aaggtcatcc gtaagaactt ggtcaagaag tgccttgagc tcttctttga aattgcagag  1200
aacaaggagg attacaacaa gttctatgag gctttctcta agaacttaaa gcttggtatc  1260
catgaggatt cccagaacaa gggaaagatt gctgaattgc tcaggtacca ctccaccaag  1320
agtggtgatg agctgacaag cctcaaggat tatgtgacca ggatgaagga aggtcagagt  1380
gacatctact acatcaccgg tgaaagcaag aaggctgttg agaactcccc attcttggag  1440
aagttgaaga agaaagggta tgaggttctt ttcatggttg atgccattga tgaatatgct  1500
gttggccagc tcaaggaatt tgagggcaag aagcttgtct ctgccaccaa ggagggtctc  1560
aaacttgacg agagtgaaga tgagaagaag aagcaagagg agttgaagga gaagtttgac  1620
aacctatgca aggtgatcaa ggatgttttg ggtgacaagg ttgagaaggt tgtagtctct  1680
gaccgtgttg ttgattcacc atgctgtctg gtgactggag aatacggttg gactgcaaac  1740
atggaaagga tcatgaaagc tcaagcccta agggacaaca gcatggcagg atacatgtca  1800
agcaagaaga caatggagat caaccctgag aacccaatca tggaggagct caggaagcgt  1860
gcggatgctg acaagaacga caaatccgtg aaggaccttg ttctgttgct gttcgagact  1920
gctcttctca cttctggttt cagccttgac gaacccaaca cttttggaaa caggatccac  1980
agaatgttga agcttggact gagcatcgac gaggatgcag ctgaagctga tgctgatgct  2040
gatatgcccc cactggagga ggaggctgaa gctgatgctg agggcagcaa aatggaggag  2100
gttgattaa                                                   2109

SEQ ID NO: 122         moltype = AA  length = 702
FEATURE                Location/Qualifiers
source                 1..702
                       mol_type = protein
                       organism = Glycine max
SEQUENCE: 122
MAETETFAFQ AEINQLLSLI INTFYSNKEI FLRELISNAS DALDKIRFES LTDKSKLDAQ  60
PELFIHIIPD KTNNTLTIVD SGIGMTKADL VNNLGTIARS GTKEFMEALA AGADVSMIGQ  120
FGVGFYSAYL VAEKVIVTTK HNDDEQYVWE SQAGGSFTVT RDNTGEVLGR GTKITLYLKE  180
DQLEYLEERR LKDLIKKHSE FISYPISLWI EKTTEKEISD DEDEEEKKDE EGKVEDVDEE  240
KEKEEKKKKK IKEVSHEWSL VNKQKPIWMR KPEEITKEEY SAFYKSLTND WEEHLAVKHF  300
SVEGQLEFKA ILFVPKRAPF DLFDTRKKPN NIKLYVRRVF IMDNCEELIP EYLGFVKGIV  360
DSEDLPLNIS REMLQQNKIL KVIRKNLVKK CLELFFEIAE NKEDYNKFYE AFSKNLKLGI  420
HEDSQNKGKI AELLRYHSTK SGDELTSLKD YVTRMKEGQS DIYYITGESK KAVENSPFLE  480
KLKKKGYEVL FMVDAIDEYA VGQLKEFEGK KLVSATKEGL KLDESEDEKK KQEELKEKFD  540
NLCKVIKDVL GDKVEKVVVS DRVVDSPCCL VTGEYGWTAN MERIMKAQAL RDNSMAGYMS  600
SKKTMEINPE NPIMEELRKR ADADKNDKSV KDLVLLLFET ALLTSGFSLD EPNTFGNRIH  660
RMLKLGLSID EDAAEADADA DMPPLEEEAE ADAEGSKMEE VD                702

SEQ ID NO: 123         moltype = AA  length = 16
FEATURE                Location/Qualifiers
source                 1..16
                       mol_type = protein
                       organism = Glycine max
SEQUENCE: 123
ADLVNNLGTI ARSGTK                                           16

SEQ ID NO: 124         moltype = AA  length = 10
FEATURE                Location/Qualifiers
source                 1..10
                       mol_type = protein
                       organism = Glycine max
```

```
SEQUENCE: 124
AVENSPFLEK                                                          10

SEQ ID NO: 125          moltype = AA  length = 13
FEATURE                 Location/Qualifiers
source                  1..13
                        mol_type = protein
                        organism = Glycine max
SEQUENCE: 125
EDQLEYLEER RLK                                                      13

SEQ ID NO: 126          moltype = AA  length = 8
FEATURE                 Location/Qualifiers
source                  1..8
                        mol_type = protein
                        organism = Glycine max
SEQUENCE: 126
EEYSAFYK                                                            8

SEQ ID NO: 127          moltype = AA  length = 14
FEATURE                 Location/Qualifiers
source                  1..14
                        mol_type = protein
                        organism = Glycine max
SEQUENCE: 127
EGQSDIYYIT GESK                                                     14

SEQ ID NO: 128          moltype = AA  length = 17
FEATURE                 Location/Qualifiers
source                  1..17
                        mol_type = protein
                        organism = Glycine max
SEQUENCE: 128
EIFLRELISN ASDALDK                                                  17

SEQ ID NO: 129          moltype = AA  length = 7
FEATURE                 Location/Qualifiers
source                  1..7
                        mol_type = protein
                        organism = Glycine max
SEQUENCE: 129
FYEAFSK                                                             7

SEQ ID NO: 130          moltype = AA  length = 11
FEATURE                 Location/Qualifiers
source                  1..11
                        mol_type = protein
                        organism = Glycine max
SEQUENCE: 130
HFSVEGQLEF K                                                        11

SEQ ID NO: 131          moltype = AA  length = 11
FEATURE                 Location/Qualifiers
source                  1..11
                        mol_type = protein
                        organism = Glycine max
SEQUENCE: 131
IAELLRYHST K                                                        11

SEQ ID NO: 132          moltype = AA  length = 9
FEATURE                 Location/Qualifiers
source                  1..9
                        mol_type = protein
                        organism = Glycine max
SEQUENCE: 132
IRFESLTDK                                                           9

SEQ ID NO: 133          moltype = AA  length = 8
FEATURE                 Location/Qualifiers
source                  1..8
                        mol_type = protein
                        organism = Glycine max
SEQUENCE: 133
LDESEDEK                                                            8

SEQ ID NO: 134          moltype = AA  length = 10
FEATURE                 Location/Qualifiers
source                  1..10
                        mol_type = protein
```

```
                        organism = Glycine max
SEQUENCE: 134
LGIHEDSQNK                                                  10

SEQ ID NO: 135          moltype = AA  length = 11
FEATURE                 Location/Qualifiers
source                  1..11
                        mol_type = protein
                        organism = Glycine max
SEQUENCE: 135
RAPFDLFDTR K                                                11

SEQ ID NO: 136          moltype = AA  length = 9
FEATURE                 Location/Qualifiers
source                  1..9
                        mol_type = protein
                        organism = Glycine max
SEQUENCE: 136
SGDELTSLK                                                   9

SEQ ID NO: 137          moltype = AA  length = 8
FEATURE                 Location/Qualifiers
source                  1..8
                        mol_type = protein
                        organism = Glycine max
SEQUENCE: 137
VEDVDEEK                                                    8

SEQ ID NO: 138          moltype = DNA  length = 2109
FEATURE                 Location/Qualifiers
source                  1..2109
                        mol_type = other DNA
                        organism = Glycine max
CDS                     1..2109
SEQUENCE: 138
atggcttcgg agactgagac gtttgctttt caggccgaga tcaaccagct cctcagtcta  60
atcatcaaca ccttctacag caacaaggag atctttcttc gtgagctcat cagcaatgcc  120
tctgatgctt tggacaagat tcgatttgag agtcttacag acaagagcaa gcttgatgct  180
cagccagagt tgttcattca cattattcct gacaagacca acaacacatt gtctatcatt  240
gacagtggta ttggcatgac taaggccgat ttggtgaata acctcggtac tattgcaagg  300
tctgggacca aggaattcat ggaagccctg gctgctggtg ctgatgtgag catgattgga  360
cagtttggtg ttggtttcta ctcggcttat cttgtagctg acaaggttat tgttaccaca  420
aagcacaatg atgatgagca gtatgtctgg gagtcccatg ctggtggctc atttactgtg  480
acaagggata catctggtga gaaccttggt aggggaacaa agataacttt gtttctcaag  540
gaagatcaac ttgagtatct tgaggaacgc cgtctgaagg atttgataaa gaagcattct  600
gaattcatta gctatccaat ttctctttgg attgagaaga ccactgaaaa ggagatttct  660
gatgatgagg acgaggaaga gaagaaggat gaggagggta aagttgaaga tgtggatgaa  720
gataaggaga aggaggagaa gaaaaagaag accattaagg aggtatctca tgagtggtca  780
ttggtgaaca agcagaagcc tatttggatg aggaaacctg aagagatcac aaaagaagaa  840
tatgctgctt tctacaagag tcttaccaat gattgggaag agcatttggc tgttaagcac  900
ttttctgttg agggtcagct ggagtttaag gctgtcctct ttatccccaa gagggcacct  960
tttgatcttt ttgacactaa gaagaagcct aacaacatca aactgtatgt ccgccgtgtt  1020
ttcatcatgg acaactgtga ggagttgatg ccagaatatc ttagctttgt taagggtatt  1080
gtggattctg aggatcttcc tctcaacatt tctagagaaa tgctgcagca gaacaagatc  1140
ctgaaagtca tcaggaagaa cttggtcaag aagtgcattg agatgttctt tgaaattgct  1200
gagaacaagg aagactataa caagttttat gaagccttct ctaagaatct gaaacttggt  1260
attcatgagg attctcagaa caagacaaaa cttgctgaat tgctcaggta tcactccacc  1320
aagagtggtg atgagatgac cagcctcaag gactatgtta ccaggatgaa ggaagggcag  1380
aatgacatct actacattac tggtgaaagc aagaaagctg ttgagaattc cccttttcctt  1440
gaaaagctta agaagaaggg gttcgaggtt ctctacatgg ttgatgctat tgacgagtat  1500
gctgttggtc agcttaagga atttgaggga aagaagttgg tctctgctac taaggaaggc  1560
ctgaaacttg acgagagcga agacgaaaag aaaaagaagg aagaattgaa ggagaaattt  1620
gagggtctct gccatgtgat caaggatgtg ttgggtgaca aggtggagaa agttgtggtg  1680
tctgatcgtg ttgtggattc tccttgctgt ctcgtgactg gtgaatatgg gtggacagcc  1740
aacatggaaa ggattatgaa agcacaggca ttgagggaca gcagcatggc tggatacatg  1800
tcgagcaaga agaccatgga gattaaccct gagaacccca tcatggatga actgaggaag  1860
cgagctgatg ctgacaagaa tgacaaatct gtgaaggatc tcgttctcct actctttgag  1920
actgctcttc taacttctgg gttcagcctt gatgatccca acactttcgg taacaggatt  1980
cacaggatgc tgaagcttgg actgagcatt gatgaagatg ctggtgaagc agatgctgac  2040
atgcctcctc tcgaggacgc cgatgctgat gccgatgctg agggtagcaa gatggaagaa  2100
gttgattaa                                                   2109

SEQ ID NO: 139          moltype = AA  length = 702
FEATURE                 Location/Qualifiers
source                  1..702
                        mol_type = protein
                        organism = Glycine max
SEQUENCE: 139
MASETETFAF QAEINQLLSL IINTFYSNKE IFLRELISNA SDALDKIRFE SLTDKSKLDA  60
```

-continued

```
QPELFIHIIP DKTNNTLSII DSGIGMTKAD LVNNLGTIAR SGTKEFMEAL AAGADVSMIG  120
QFGVGFYSAY LVADKVIVTT KHNDDEQYVW ESHAGGSFTV TRDTSGENLG RGTKITLFLK  180
EDQLEYLEER RLKDLIKKHS EFISYPISLW IEKTTEKEIS DDEDEEEKKD EEGKVEDVDE  240
DKEKEEKKKK TIKEVSHEWS LVNKQKPIWM RKPEEITKEE YAAFYKSLTN DWEEHLAVKH  300
FSVEGQLEFK AVLFIPKRAP FDLFDTKKKP NNIKLYVRRV FIMDNCEELM PEYLSFVKGI  360
VDSEDLPLNI SREMLQQNKI LKVIRKNLVK KCIEMFFEIA ENKEDYNKFY EAFSKNLKLG  420
IHEDSQNKTK LAELLRYHST KSGDEMTSLK DYVTRMKEGQ NDIYYITGES KKAVENSPFL  480
EKLKKKGFEV LYMVDAIDEY AVGQLKEFEG KKLVSATKEG LKLDESEDEK KKKEELKEKF  540
EGLCHVIKDV LGDKVEKVVV SDRVVDSPCC LVTGEYGWTA NMERIMKAQA LRDSSMAGYM  600
SSKKTMEINP ENPIMDELRK RADADKNDKS VKDLVLLLFE TALLTSGFSL DDPNTFGNRI  660
HRMLKLGLSI DEDAGEADAD MPPLEDADAD ADAEGSKMEE VD                    702

SEQ ID NO: 140          moltype = AA  length = 16
FEATURE                 Location/Qualifiers
source                  1..16
                        mol_type = protein
                        organism = Glycine max
SEQUENCE: 140
ADLVNNLGTI ARSGTK                                                 16

SEQ ID NO: 141          moltype = AA  length = 10
FEATURE                 Location/Qualifiers
source                  1..10
                        mol_type = protein
                        organism = Glycine max
SEQUENCE: 141
AVENSPFLEK                                                        10

SEQ ID NO: 142          moltype = AA  length = 13
FEATURE                 Location/Qualifiers
source                  1..13
                        mol_type = protein
                        organism = Glycine max
SEQUENCE: 142
EDQLEYLEER RLK                                                    13

SEQ ID NO: 143          moltype = AA  length = 8
FEATURE                 Location/Qualifiers
source                  1..8
                        mol_type = protein
                        organism = Glycine max
SEQUENCE: 143
EEYAAFYK                                                          8

SEQ ID NO: 144          moltype = AA  length = 14
FEATURE                 Location/Qualifiers
source                  1..14
                        mol_type = protein
                        organism = Glycine max
SEQUENCE: 144
EGQNDIYYIT GESK                                                   14

SEQ ID NO: 145          moltype = AA  length = 17
FEATURE                 Location/Qualifiers
source                  1..17
                        mol_type = protein
                        organism = Glycine max
SEQUENCE: 145
EIFLRELISN ASDALDK                                                17

SEQ ID NO: 146          moltype = AA  length = 7
FEATURE                 Location/Qualifiers
source                  1..7
                        mol_type = protein
                        organism = Glycine max
SEQUENCE: 146
FYEAFSK                                                           7

SEQ ID NO: 147          moltype = AA  length = 11
FEATURE                 Location/Qualifiers
source                  1..11
                        mol_type = protein
                        organism = Glycine max
SEQUENCE: 147
HFSVEGQLEF K                                                      11

SEQ ID NO: 148          moltype = AA  length = 9
FEATURE                 Location/Qualifiers
source                  1..9
```

```
                        mol_type = protein
                        organism = Glycine max
SEQUENCE: 148
IRFESLTDK                                                          9

SEQ ID NO: 149          moltype = AA  length = 11
FEATURE                 Location/Qualifiers
source                  1..11
                        mol_type = protein
                        organism = Glycine max
SEQUENCE: 149
LAELLRYHST K                                                       11

SEQ ID NO: 150          moltype = AA  length = 8
FEATURE                 Location/Qualifiers
source                  1..8
                        mol_type = protein
                        organism = Glycine max
SEQUENCE: 150
LDESEDEK                                                           8

SEQ ID NO: 151          moltype = AA  length = 10
FEATURE                 Location/Qualifiers
source                  1..10
                        mol_type = protein
                        organism = Glycine max
SEQUENCE: 151
LGIHEDSQNK                                                         10

SEQ ID NO: 152          moltype = AA  length = 10
FEATURE                 Location/Qualifiers
source                  1..10
                        mol_type = protein
                        organism = Glycine max
SEQUENCE: 152
RAPFDLFDTK                                                         10

SEQ ID NO: 153          moltype = AA  length = 8
FEATURE                 Location/Qualifiers
source                  1..8
                        mol_type = protein
                        organism = Glycine max
SEQUENCE: 153
VEDVDEDK                                                           8

SEQ ID NO: 154          moltype = DNA  length = 2109
FEATURE                 Location/Qualifiers
source                  1..2109
                        mol_type = other DNA
                        organism = Glycine max
CDS                     1..2109
SEQUENCE: 154
atggcttcgg agactgagac gtttgctttt caggccgaga tcaaccagct cctcagtcta  60
atcatcaaca ccttctacag caacaaggag atctttcttc gtgagctcat cagcaatgcc  120
tctgatgctt tggacaagat tcgatttgag agtcttacag acaagagcaa gcttgatgct  180
cagccagagt tgttcattca cattattcct gacaagacca acaacacatt gtctatcatt  240
gacagtggta ttggcatgac taaggccgat ttggtgaata acctcggtac tattgcaagg  300
tctgggacca aggaattcat ggaagccctg gctgctggtg ctgatgtgag catgattgga  360
cagtttggtg ttggtttcta ctcggcttat cttgtagctg acaaggttat tgttaccaca  420
aagcacaatg atgatgagca gtatgtctgg gagtcccatg ctggtggctc atttactgtg  480
acaagggata catctggtga gaaccttggt aggggaacaa agataacttt gtttctcaag  540
gaagatcaac ttgagtatct tgaggaacgc cgtctgaagg atttgataaa gaagcattct  600
gaattcatta gctatccaat ttctctttgg attgagaaga ccactgaaaa ggagatttct  660
gatgatgagg acgaggaaga gaagaaggat gaggagggta aagttgaaga tgtggatgaa  720
gataaggaga aggaggagaa gaaaaagaag accattaagg aggtatctca tgagtggtca  780
ttggtgaaca agcagaagcc tatttggatg aggaaacctg aagagatcac aaaagaagaa  840
tatgctgctt tctacaagag tcttaccaat gattgggaag agcatttggc tgttaagcac  900
ttttctgttg agggtcagct ggagtttaag gctgtcctct ttatccccaa gagggcacct  960
tttgatcttt ttgacactaa gaagaagcct aacaacatca aactgtatgt ccgccgtgtt  1020
ttcatcatgg acaactgtga ggagttgatg ccagaatatc ttagctttgt taagggtatt  1080
gtggattctg aggatcttcc tctcaacatt tctagagaaa tgctgcagca gaacaagatc  1140
ctgaaagtca tcaggaagaa cttggtcaag aagtgcattg agatgttctt tgaaattgct  1200
gagaacaagg aagactataa caagttttat gaagccttct ctaagaatct gaaacttggt  1260
attcatgagg attctcagaa caagacaaaa cttgctgaat tgctcaggta tcactccacc  1320
aagagtggtg atgagatgac cagcctcaag gactatgtta ccaggatgaa ggaagggcag  1380
aatgacatct actacattac tggtgaaagc aagaaagctg ttgagaattc ccctttcctt  1440
gaaaagctta agaagaaggg gttcgaggtt ctctacatgg ttgatgctat tgacgagtat  1500
gctgttggtc agcttaagga atttgaggga aagaagttgg tctctgctac taaggaaggc  1560
ctgaaacttg acgagagcga agacgaaaag aaaaagaagg aagaattgaa ggagaaattt  1620
```

```
gagggtctct gccatgtgat caaggatgtg ttgggtgaca aggtggagaa agttgtggtg  1680
tctgatcgtg ttgtggattc tccttgctgt ctcgtgactg gtgaatatgg gtggacagcc  1740
aacatggaaa ggattatgaa agcacaggca ttgagggaca gcagcatggc tggatacatg  1800
tcgagcaaga agaccatgga gattaaccct gagaacccca tcatggatga actgaggaag  1860
cgagctgatg ctgacaagaa tgacaaatct gtgaaggatc tcgttctcct actctttgag  1920
actgctcttc taacttctgg gttcagcctt gatgatccca acactttcgg taacaggatt  1980
cacaggatgc tgaagcttgg actgagcatt gatgaagatg ctggtgaagc agatgctgac  2040
atgcctcctc tcgaggacgc cgatgctgat gccgatgctg agggtagcaa gatggaagaa  2100
gttgattaa                                                          2109
```

```
SEQ ID NO: 155          moltype = AA  length = 702
FEATURE                 Location/Qualifiers
source                  1..702
                        mol_type = protein
                        organism = Glycine max
SEQUENCE: 155
MASETETFAF QAEINQLLSL IINTFYSNKE IFLRELISNA SDALDKIRFE SLTDKSKLDA  60
QPELFIHIIP DKTNNTLSII DSGIGMTKAD LVNNLGTIAR SGTKEFMEAL AAGADVSMIG  120
QFGVGFYSAY LVADKVIVTT KHNDDEQYVW ESHAGGSFTV TRDTSGENLG RGTKITLFLK  180
EDQLEYLEER RLKDLIKKHS EFISYPISLW IEKTTEKEIS DDEDEEEKKD EEGKVEDVDE  240
DKEKEEKKKK TIKEVSHEWS LVNKQKPIWM RKPEEITKEE YAAFYKSLTN DWEEHLAVKH  300
FSVEGQLEFK AVLFIPKRAP FDLFDTKKKP NNIKLYVRRV FIMDNCEELM PEYLSFVKGI  360
VDSEDLPLNI SREMLQQNKI LKVIRKNLVK KCIEMFFEIA ENKEDYNKFY EAFSKNLKLG  420
IHEDSQNKTK LAELLRYHST KSGDEMTSLK DYVTRMKEGQ NDIYYITGES KKAVENSPFL  480
EKLKKKGFEV LYMVDAIDEY AVGQLKEFEG KKLVSATKEG LKLDESEDEK KKKEELKEKF  540
EGLCHVIKDV LGDKVEKVVV SDRVVDSPCC LVTGEYGWTA NMERIMKAQA LRDSSMAGYM  600
SSKKTMEINP ENPIMDELRK RADADKNDKS VKDLVLLLFE TALLTSGFSL DDPNTFGNRI  660
HRMLKLGLSI DEDAGEADAD MPPLEDADAD ADAEGSKMEE VD                    702
```

```
SEQ ID NO: 156          moltype = AA  length = 12
FEATURE                 Location/Qualifiers
source                  1..12
                        mol_type = protein
                        organism = Glycine max
SEQUENCE: 156
AGGALSIAFV SK                                                     12
```

```
SEQ ID NO: 157          moltype = AA  length = 9
FEATURE                 Location/Qualifiers
source                  1..9
                        mol_type = protein
                        organism = Glycine max
SEQUENCE: 157
DGLIVSIGK                                                         9
```

```
SEQ ID NO: 158          moltype = DNA  length = 2946
FEATURE                 Location/Qualifiers
source                  1..2946
                        mol_type = other DNA
                        organism = Glycine max
CDS                     1..2946
SEQUENCE: 158
atggcttctt cttccacgac aatgcggttc tccgcggcct ccaccggcgc cgcggcggcg  60
cttcctcgcc ggagctccgt cgccggattc atcggcgtcg cggccagatc ctccgccaaa  120
tcgaggctcc gcttcatcgg aaggaacgcg aacttgagcc tccggatgag gaggatgagc  180
tctttctccg tcgtgaagtg cgtctccgga agcgaggcca aggtgcagga taccgtggcc  240
aaacaacaag aagctacaac ctctctcagc tccttcacgc cagatgcttc atctattgcc  300
tcaagtatta aataccatgc agagttcact ccattgtttt ctccagagaa ttttgatcta  360
ccacaggctt ttcttgcaac tgcacaaagt gttcgagatt ctctcattat aaactggaat  420
gctacctatg attactatga gaaactgaat gttaagcagg catattacct ttcgatggaa  480
tttttgcagg gtagagcatt attaaatgca ataggcaatc tggagctaac tggtccctat  540
gctgaggctt tgagcaagct cggcataaa ttagaaaatg tggcatacca ggagccagat  600
gctgcacttg gaaatggtgg tcttgggcgt cttgcttcat gtttcttgga ctctttggca  660
accttgaact atccagcttg gggttatgga ttgagatata agtatggttt atttaaacag  720
cgaataacca aagatgggca ggaggaagtt gctgaagatt ggcttgagat gggcaatccc  780
tgggagatta ttagaaatga tgtttcatat cctgtaaagt tctatggcaa ggttgtttca  840
gggtcagatg gtaaaaaaca ttggattgga ggagaagata taaaagctgt tgcacatgat  900
gttcccatac caggatataa aactaagact acaatcaact tgagactttg gtctacaaaa  960
gctgcatcag aagaatttga tttatctgct tttaatgctg gaaggcacac tgaagcatct  1020
gaggctctag caaatgctga aaagatatgc tatatactct accctgggga tgaaccaata  1080
gagggcaaga tccttcgcct caagcaacaa tatactttat gttctgcttc tcttcaagac  1140
atcattgctc gttttgagag aagatcagga gcaaatgtta attgggaaga gtttcccgag  1200
aaggttgcag tgcagatgaa tgatactcac ccaacgttgt gcatcccaga gctcatgaga  1260
attttaatag atgtaaaggg cttaaattgg aaggatgctt ggaatattac acaaaggact  1320
gtagcatata caaaccacac tgttcttcca gaggcattag agaaatggag cttggatctt  1380
atgcagaaac tgcttccacg ccatattgag ataatagaaa tgattgacga ggagctggtt  1440
cggaccataa ttgcagaata tggcacagaa aattcagact tgctggagaa aaaattgaag  1500
gaaatgagaa tactagaaaa tgtcgaattg actgcagaat ttgcagatat actggttaag  1560
tccaaagagg ccattgatat tcctagtgag gagctgcaaa gttctgaaca agcagaagca  1620
```

```
gaagacgaaa aagatgatga tgaagtggaa gcagttgcta aaaagaatgg aacagatgaa  1680
agttccattg aggatgagaa agaagagttg cctgagccag taccagaacc accaaaattg  1740
gttcgtatgg caaatttgtg tgttgtgggt ggtcatgcag tgaatggggt tgcagagata  1800
catagtgaaa ttgtaaaaga tgatgttttc aatgcatttt ataagttgtg gcccgagaag  1860
ttccaaaaca aaacaaatgg tgtgacacca aggagatgga tcaggttctg caatccagat  1920
ctgagtaaaa taataaccga gtggataggt actgaggatt gggtcctaaa tactggaaaa  1980
ttggccgagc tacggaagtt tgtagacaat gaggatctac aagtgcagtg gagggaagca  2040
aagaggagta acaaagttaa agttgcagca ttcatcagag aaaaaacagg gtattctgtc  2100
agtcctgatg caatgtttga catccaggtg aagagaatcc atgaatataa gcgacaatta  2160
atgaacatat ttggaattgt ttaccgatac aagaagatga aagaaatgag tgcggcagaa  2220
agggaagcaa attttgttcc tagagtttgt atatttgggg gaaaagcatt tgctacatat  2280
gtgcaagcca agagaattgt gaaatttatt acagatgttg gggctacagt aaatcatgac  2340
cctgaaatag gagatctact taaggttgtt tttgtccctg attataatgt cagtgttgcc  2400
gagatgctta ttccagcaag tgaattgtca caacatatca gtactgctgg aatggaggca  2460
agtggaacta gcaatatgaa atttgcaatg aatggctgca tattgattgg aactttagat  2520
ggggccaatg ttgaaataag ggaagaggtt ggtgcagaca acttcttcct ctttggtgcc  2580
aaggctcatg aaattgctgg gctgaggaaa gaaagagcag agggaaagtt tgtgcctgat  2640
ccacgatttg aagaagttaa agaatttgtc agaagtggca tttttggatc ttacaactat  2700
gacgaattga tgggatcctt agaaggaaat gaaggttttg gtcgagcaga ttatttcctt  2760
gtagggaaag actttcccag ctacatagaa tgccaagaga aggttgatga agcataccgt  2820
gaccaaacta aatggacaag aatgtcaata ttgaacacag caggttcata caagtttagc  2880
agtgaccgca cgattcatga atatgcccga gagatatgga acattgaacc agtccaattg  2940
ccatag                                                             2946

SEQ ID NO: 159          moltype = AA  length = 981
FEATURE                 Location/Qualifiers
source                  1..981
                        mol_type = protein
                        organism = Glycine max
SEQUENCE: 159
MASSSTTMRF SAASTGAAAA LPRRSSVAGF IGVAARSSAK SRLRFIGRNA NLSLRMRRMS  60
SFSVVKCVSG SEAKVQDTVA KQQEATTSLS SFTPDASSIA SSIKYHAEFT PLFSPENFDL  120
PQAFLATAQS VRDSLIINWN ATYDYYEKLN VKQAYYLSME FLQGRALLNA IGNLELTGPY  180
AEALSKLGHK LENVAYQEPD AALGNGGLGR LASCFLDSLA TLNYPAWGYG LRYKYGLFKQ  240
RITKDGQEEV AEDWLEMGNP WEIIRNDVSY PVKFYGKVVS GSDGKKHWIG GEDIKAVAHD  300
VPIPGYKTKT TINLRLWSTK AASEEFDLSA FNAGRHTEAS EALANAEKIC YILYPGDEPI  360
EGKILRLKQQ YTLCSASLQD IIARFERRSG ANVNWEEFPE KVAVQMNDTH PTLCIPELMR  420
ILIDVKGLNW KDAWNITQRT VAYTNHTVLP EALEKWSLDL MQKLLPRHIE IIEMIDEELV  480
RTIIAEYGTE NSDLLEKKLK EMRILENVEL TAEFADILVK SKEAIDIPSE ELQSSEQAEA  540
EDEKDDDEVE AVAKKNGTDE SSIEDEKEEL PEPVPEPPKL VRMANLCVVG GHAVNGVAEI  600
HSEIVKDDVF NAFYKLWPEK FQNKTNGVTP RRWIRFCNPD LSKIITEWIG TEDWVLNTGK  660
LAELRKFVDN EDLQVQWREA KRSNKVKVAA FIREKTGYSV SPDAMFDIQV KRIHEYKRQL  720
MNIFGIVYRY KKMKEMSAAE REANFVPRVC IFGGKAFATY VQAKRIVKFI TDVGATVNHD  780
PEIGDLLKVV FVPDYNVSVA EMLIPASELS QHISTAGMEA SGTSNMKFAM NGCILIGTLD  840
GANVEIREEV GADNFFLFGA KAHEIAGLRK ERAEGKFVPD PRFEEVKEFV RSGIFGSYNY  900
DELMGSLEGN EGFGRADYFL VGKDFPSYIE CQEKVDEAYR DQTKWTRMSI LNTAGSYKFS  960
SDRTIHEYAR EIWNIEPVQL P                                            981

SEQ ID NO: 160          moltype = AA  length = 9
FEATURE                 Location/Qualifiers
source                  1..9
                        mol_type = protein
                        organism = Glycine max
SEQUENCE: 160
AFATYVQAK                                                          9

SEQ ID NO: 161          moltype = AA  length = 23
FEATURE                 Location/Qualifiers
source                  1..23
                        mol_type = protein
                        organism = Glycine max
SEQUENCE: 161
QQEATTSLSS FTPDASSIAS SIK                                          23

SEQ ID NO: 162          moltype = DNA  length = 2706
FEATURE                 Location/Qualifiers
source                  1..2706
                        mol_type = other DNA
                        organism = Glycine max
CDS                     1..2706
SEQUENCE: 162
atggcgactg agaatccttt caatagcatt ttgacgacgc tcgaaaagcc cggtggtgct  60
ggcgagtttg gaaagtactt tagcttgcct gctctcaacg atcgtagaat cgatagactt  120
ccttactctg tgaggatact tttggaatct gcaatccgga actgtgatga gtttcaagtt  180
aagagtaacg acgttgaaaa aattattgat tgggagaata cctctccgaa gctggtggag  240
attccattca agccagctag agtgcttctc caggatttta ctggcgtgcc tgctgttgtc  300
gatcttgctt gcatgcgaga tgccatgaac aaacttggtg gtgattctaa taaaattaat  360
cccttggtac cagttgatct tgtcattgat cactctgttc aagttgatgt ggcaagatca  420
gaaaatgctg tccaggcaaa tatggaactt gaattccaaa gaaacaagga aagatttggt  480
```

```
ttcctcaaat ggggttctaa tgcattcaat aatatgcttg tcgttcctcc tggatcaggg  540
atagttcacc aggttaattt agaatacctt ggtagagttg tgttcaacac aaatggtgtg  600
ctttatcctg acagcgttgt tggaactgat tcacacacaa ctatgattga tggcctgggt  660
gttgctggat ggggagttgg tggaatagaa gcagaagctg caatgcttgg ccaacccatg  720
agcatggtcc taccgggtgt cgttgggttc aaattattag gcaaactacg agatggtgtc  780
acagctactg acttggtgtt gactgttaca caaatgctaa gaaagcatgg ggttgttggc  840
aagtttgtag agttttatgg ggaaggcatg agtgaactgt ctttggcaga tcgtgccacc  900
atagcaaaca tgtctcctga gtatggtgca accatgggct tctttcctgt ggatcatgtc  960
actttgcaat atttgagact gactggcaga agtgatgaga ctgtttctat gatagaatcg  1020
tacttacgag caaataagat gtttgtggat tacagcgagc cccaagtgga gagagtgtac  1080
tcatcgtatt tggaactcaa tcttgaggat gtagaaccct gtgtctcagg tccaaaaagg  1140
cctcatgacc gtgtcccttt gagagaaatg aaggtagact ggcatgcctg cctcaacaat  1200
aaagttggat tcaagggttt tgctgtacca aaagaatctc agaataaggt tgcagagttc  1260
acattccaag ggacaccagc acatcttagg cacggtgatg ttgttatagc tgctatcacc  1320
agttgtacaa atacttcaaa tcctagcgta atgcttggag ctgcattggt tgcaaagaaa  1380
gcatgtgaat tgggattgca ggtgaagcca tggattaaaa caagccttgc cccaggttct  1440
ggtgttgtga ctaagtattt gcagaggagt ggcttgcaga agtatttgaa tgagctaggg  1500
tttaatatag ttgggtatgg atgcaccaca tgcattggaa attcagggga tattaatgaa  1560
gctgttgcat ctgcaattac tgaaaatgat atagtagctg cagctgtact gtctggaaat  1620
aggaactttg agggccgagt tcacccatta acaagagcta attatcttgc ttctcctcct  1680
cttgttgttg cctatgccct tgctggcaca gtggacattg actttgacac tgaacccatt  1740
gggataggga aggatggcac aaagatcttc ttcagggata tttggccatc cagtgaagaa  1800
atagcaaatg ttgtacaatc aagtgtgctg cctgctatgt ttagggacac atataatgcg  1860
atcacccaag ggaatcccat gtggaataat ttatctgttc caactggcac tctttatgct  1920
tgggacccta catcaactta tattcatgag ccaccttatt ttagagatat gagcatgtct  1980
cccccaggct ctcatggagt gaaagatgct tactgtttgc tcaactttgg agacagtatc  2040
acaactgacc acatctctcc agctggcagc atacataagg acagtcctgc agccagatac  2100
cttatagaac gtggggttga tagacgggac ttcaactcct atggaagtcg ccgtggtaat  2160
gatgaggtga tggcccgagg aactttgcc aatattcgca ttgtcaacaa atttttgaat  2220
ggagaagttg gacctaaaac tattcatatt ccttctgggg agaagttatc agtctttgat  2280
gctgcagaga aatacaagag tgaggggcat gatatgatta tcttggctgg tgctgagtat  2340
gggagtggaa gctctcgtga ttgggctgca aaggggccaa tgctactggg cgtgaaagct  2400
gtcatagcaa aagttttga aaggattcac cgaagtaatt tggtgggaat gggtatcatt  2460
ccattgtgtt ttaagcccgg ggatgatgct gattctcttg gattaactgg ccatgaacgt  2520
tacaccattg atctaccaag caatgtgaat gaaatacgac ccggccaaga tgtcacagtg  2580
gtgacagatg ccgggaaatc atttgtatct acactgagat ttgatacaga ggttgaacta  2640
gcttacttca accatggagg catcttacaa tatgtcatca gaaacatggt caatgctaaa  2700
cattga                                                             2706

SEQ ID NO: 163         moltype = AA  length = 901
FEATURE                Location/Qualifiers
source                 1..901
                       mol_type = protein
                       organism = Glycine max
SEQUENCE: 163
MATENPFNSI LTTLEKPGGA GEFGKYFSLP ALNDRRIDRL PYSVRILLES AIRNCDEFQV  60
KSNDVEKIID WENTSPKLVE IPFKPARVLL QDFTGVPAVV DLACMRDAMN KLGGDSNKIN  120
PLVPVDLVID HSVQVDVARS ENAVQANMEL EFQRNKERFG FLKWGSNAFN NMLVVPPGSG  180
IVHQVNLEYL GRVVFNTNGV LYPDSVVGTD SHTTMIDGLG VAGWGVGGIE AEAAMLGQPM  240
SMVLPGVVGF KLLGKLRDGV TATDLVLTVT QMLRKHGVVG KFVEFYGEGM SELSLADRAT  300
IANMSPEYGA TMGFFPVDHV TLQYLRLTGR SDETVSMIES YLRANKMFVD YSEPQVERVY  360
SSYLELNLED VEPCVSGPKR PHDRVPLREM KVDWHACLNN KVGFKGFAVP KESQNKVAEF  420
TFQGTPAHLR HGDVVIAAIT SCTNTSNPSV MLGAALVAKK ACELGLQVKP WIKTSLAPGS  480
GVVTKYLQRS GLQKYLNELG FNIVGYGCTT CIGNSGDINE AVASAITEND IVAAAVLSGN  540
RNFEGRVHPL TRANYLASPP LVVAYALAGT VDIDFDTEPI GIGKDGTKIF FRDIWPSSEE  600
IANVVQSSVL PAMFRDTYNA ITQGNPMWNN LSVPTGTLYA WDPTSTYIHE PPYFRDMSMS  660
PPGSHGVKDA YCLLNFGDSI TTDHISPAGS IHKDSPAARY LIERGVDRRD FNSYGSRRGN  720
DEVMARGTFA NIRIVNKFLN GEVGPKTIHI PSGEKLSVFD AAEKYKSEGH DMIILAGAEY  780
GSGSSRDWAA KGPMLLGVKA VIAKSFERIH RSNLVGMGII PLCFKPGDDA DSLGLTGHER  840
YTIDLPSNVN EIRPGQDVTV VTDAGKSFVS TLRFDTEVEL AYFNHGGILQ YVIRNMVNAK  900
H                                                                  901

SEQ ID NO: 164         moltype = AA  length = 9
FEATURE                Location/Qualifiers
source                 1..9
                       mol_type = protein
                       organism = Glycine max
SEQUENCE: 164
FLNGEVGPK                                                          9

SEQ ID NO: 165         moltype = AA  length = 9
FEATURE                Location/Qualifiers
source                 1..9
                       mol_type = protein
                       organism = Glycine max
SEQUENCE: 165
LSVFDAAEK                                                          9

SEQ ID NO: 166         moltype = AA  length = 9
```

```
FEATURE                Location/Qualifiers
source                 1..9
                       mol_type = protein
                       organism = Glycine max
SEQUENCE: 166
LSVFDVAEK                                                          9

SEQ ID NO: 167         moltype = AA  length = 12
FEATURE                Location/Qualifiers
source                 1..12
                       mol_type = protein
                       organism = Glycine max
SEQUENCE: 167
TSLAPGSGVV TK                                                      12

SEQ ID NO: 168         moltype = DNA  length = 2706
FEATURE                Location/Qualifiers
source                 1..2706
                       mol_type = other DNA
                       organism = Glycine max
CDS                    1..2706
SEQUENCE: 168
atggcgactg agaacccttt caatagcatt ttgaggacgc tcgagaagcc cggcggcgct  60
ggcgagtttg gaaagtactt tagcttgccc gctctcaacg atcctagaat cgatagactt  120
ccttactctg tgaggatact tttggaatct gcaatccgta actgtgatga gtttcaagtt  180
aagagtaacg acattgaaaa aattattgat tgggagaata cctctcccaa gctggtggag  240
attccattca agccagctag agtgcttctg caggacttta ctggggtgcc tgctgtggtt  300
gatcttgctt gcatgcgaga tgcaatgaac aaacttggtg gtgattctaa taaaattaac  360
cccttggtac cagttgatct tgtcattgat cactctgttc aagttgatgt ggcaagatca  420
gaaaatgctg tccaggcaaa tatggaactt gaattccaaa gaaacaagga aagatttggt  480
ttcctcaaat ggggttctaa tgcattcaat aatatgcttg tcgttcctcc tggatcaggg  540
atagttcatc aggttaattt agaatacctt ggtagagttg tgttcaacac aaatggtgtg  600
ctttatccag acagcgttgt cggaactgat tcacacacta ctatgataga tggcctgggt  660
gttgctggat ggggagttgg tggaatagaa gcagaagctg caatgcttgg ccagcccatg  720
agcatggtcc taccgggtgt tgttgggttc aaattattag gcaaactacg agatggtgtc  780
acagctactg acttggtgtt gactgttact caaatgctaa gaaagcatgg ggttgttggc  840
aagtttgtag agttttatgg ggaaggcatg agtgaactgt ctttggcaga tcgtgccact  900
atagcaaaca tgtctcctga gtatggtgca accatgggct tctttcctgt ggatcatgtc  960
actttgcaat atttgagact gactggcaga agtgatgaga ctgtttctat gatagaatcc  1020
tatttacgag caaataagat gtttgtggat tatagcgagc cccaagtgga gagagtgtac  1080
tcatcctatt tggaactcaa tcttgaggat gtagagccct gtgtctcagg tccaaaaagg  1140
cctcacgacc gtgtcccttt gagagaaatg aaggtagact ggcatgcctg cctcaacaat  1200
aaagttggat ttaagggttt tgctgtatca aaagaatctc agaataaggt tgcagagttc  1260
acattccaag ggacaccagc acatcttagg catggtgatg ttgttatagc tgctatcacc  1320
agttgtacaa atacttcaaa tcctagcgta atgcttggag ctgcattggt tgcaaagaaa  1380
gcatgtgaat tgggattgca ggtgaagcca tggattaaaa caagtcttgc cccaggttct  1440
ggtgttgtaa ctaagtattt gcagaggagt ggcttgcaga agtatttgaa tgagctaggg  1500
tttaatatag ttgggtatgg atgcaccaca tgcattggaa attcagggga tattaatgaa  1560
gctgttgcat ctgcgattac cgaaaatgat atagtagctg cagctgtatt gtctggaaat  1620
aggaactttg agggccgagt tcacccatta acaagagcta attatcttgc ttctcctcct  1680
cttgttgttg cctatgccct tgctggcaca gtggacattg actttgacac tgaacccatt  1740
gggataggga aggatggaac agagatcttc ttcaaggata tttggccatc cagtgaagaa  1800
atagcaaatg ttgtacaatc aagtgtgctg cctgatatgt ttagggacac atataatgca  1860
atcacccaag ggaatcccat gtggaataat ttatctgttc caacgggcac tctttatgct  1920
tgggacccta catcgactta tattcatgag ccaccttatt ttagagatat gagcatgtct  1980
cccccaggct ctcatggagt gaaggatgct tactgtttgc tcaactttgg agacagtatc  2040
acaactgacc acatctctcc agctggcagc atacataagg acagtcctgc ggccagatac  2100
cttatagaac gtggggttga tagacgggac ttcaactcct atggaagtcg ccgtggtaat  2160
gatgaggtga tggcccgagg aacgtttgcc aatattcgca ttgtcaacaa atttttgaat  2220
ggagaagttg gacctaaaac tattcatatt ccttctgggg agaagttgtc agtctttgac  2280
gttgcagaga aatacaagag tgaagggcat gatatgatta tcttggctgg tgctgagtat  2340
gggagtggaa gctctcgtga ttgggctgca aaggggccaa tgctactggg cgtgaaagct  2400
gtcatagcaa aaagttttga aaggattcac cgaagtaatt tggtgggaat gggtatcatt  2460
cctttgtgtt ttaagcccgg ggaggatgct gattctcttg gattaactgg tcaagaacgt  2520
tacaccattg atctaccaag caatgtgaat gaaatacgac ccggtcaaga tgtcacagtg  2580
gtgacagaca ccgggaaatc atttgtatct acattgagat ttgatactga ggttgaacta  2640
gcttacttca accatggagg tatcttacaa tatgtcatca gaaacttgat caatgctaaa  2700
cattga                                                             2706

SEQ ID NO: 169         moltype = AA  length = 901
FEATURE                Location/Qualifiers
source                 1..901
                       mol_type = protein
                       organism = Glycine max
SEQUENCE: 169
MATENPFNSI LRTLEKPGGA GEFGKYFSLP ALNDPRIDRL PYSVRILLES AIRNCDEFQV  60
KSNDIEKIID WENTSPKLVE IPFKPARVLL QDFTGVPAVV DLACMRDAMN KLGGDSNKIN  120
PLVPVDLVID HSVQVDVARS ENAVQANMEL EFQRNKERFG FLKWGSNAFN NMLVVPPGSG  180
IVHQVNLEYL GRVVFNTNGV LYPDSVVGTD SHTTMIDGLG VAGWGVGGIE AEAAMLGQPM  240
```

```
SMVLPGVVGF KLLGKLRDGV TATDLVLTVT QMLRKHGVVG KFVEFYGEGM SELSLADRAT  300
IANMSPEYGA TMGFFPVDHV TLQYLRLTGR SDETVSMIES YLRANKMFVD YSEPQVERVY  360
SSYLELNLED VEPCVSGPKR PHDRVPLREM KVDWHACLNN KVGFKGFAVS KESQNKVAEF  420
TFQGTPAHLR HGDVVIAAIT SCTNTSNPSV MLGAALVAKK ACELGLQVKP WIKTSLAPGS  480
GVVTKYLQRS GLQKYLNELG FNIVGYGCTT CIGNSGDINE AVASAITEND IVAAAVLSGN  540
RNFEGRVHPL TRANYLASPP LVVAYALAGT VDIDFDTEPI GIGKDGTEIF FKDIWPSSEE  600
IANVVQSSVL PDMFRDTYNA ITQGNPMWNN LSVPTGTLYA WDPTSTYIHE PPYFRDMSMS  660
PPGSHGVKDA YCLLNFGDSI TTDHISPAGS IHKDSPAARY LIERGVDRRD FNSYGSRRGN  720
DEVMARGTFA NIRIVNKFLN GEVGPKTIHI PSGEKLSVFD VAEKYKSEGH DMIILAGAEY  780
GSGSSRDWAA KGPMLLGVKA VIAKSFERIH RSNLVGMGII PLCFKPGEDA DSLGLTGQER  840
YTIDLPSNVN EIRPGQDVTV VTDTGKSFVS TLRFDTEVEL AYFNHGGILQ YVIRNLINAK  900
H                                                                 901

SEQ ID NO: 170         moltype = AA  length = 9
FEATURE                Location/Qualifiers
source                 1..9
                       mol_type = protein
                       organism = Glycine max
SEQUENCE: 170
FLNGEVGPK                                                         9

SEQ ID NO: 171         moltype = AA  length = 9
FEATURE                Location/Qualifiers
source                 1..9
                       mol_type = protein
                       organism = Glycine max
SEQUENCE: 171
LSVFDVAEK                                                         9

SEQ ID NO: 172         moltype = AA  length = 12
FEATURE                Location/Qualifiers
source                 1..12
                       mol_type = protein
                       organism = Glycine max
SEQUENCE: 172
TSLAPGSGVV TK                                                     12

SEQ ID NO: 173         moltype = DNA  length = 2292
FEATURE                Location/Qualifiers
source                 1..2292
                       mol_type = other DNA
                       organism = Glycine max
CDS                    1..2292
SEQUENCE: 173
atggcatctc acatcgttgg ataccccgt atgggtccca agagagagct caagttcgct  60
ctcgagtctt tctgggatgg caagagcagc gccgaggatt tgcagaaggt gtcttctgat  120
ctcagggcat ccatctggaa gcagatggct gatgctggga tcaagtacat ccccagcaac  180
actttctctc actatgacca ggttctcgac gccaccgcca ccctcggtgc cgttccacca  240
aggtacggct ggaccggcgg cgagattggg tttgatacct acttctccat ggccagaggt  300
aatgctaccg tgccagctat ggagatgacc aagtggttcg acaccaacta ccactttatt  360
gtccctgaat tgggccctga tgtgaacttc acctatgctt ctcacaaggc tgttgatgaa  420
tacaaggagg ccaaggcgct tggagtggat accgttccgg tcctcgttgg ccctgttaca  480
tacctgttgc tctccaagcc tgccaaggga gttgagaaat ccttttctct cctctctctc  540
cttcccaagg ttcttgctgt ctacaaggaa gttattgctg accttaaggc agctggtgct  600
tcatggattc agtttgatga gcctaccctt gtcttggacc ttgagtctca caagttgcaa  660
gcattcactg acgcatatgc agaacttgcg cctgctttgt ctggtttgaa tgttcttgtt  720
gagacctact ttgctgacat ccctgctgag gcatacaaga ccctcacatc tctgaatggc  780
gtcactgcat atggatttga tttggtccgt ggaaccaaca ctcttgattt gatcaagggt  840
ggatttccca gcggaaaata cctctttgct ggagtggttg atggaaggaa catctgggcc  900
aatgaccttg ctgcttctct cactaccttg cagggtcttg agggcattgt gggcaaagat  960
aagcttgttg tgtccacctc ctcctccctt cttcacactg ctgttgatct agttaacgag  1020
accaagttgg atgatgagat caagtcatgg ctagcttttg ctgcccaaaa aattgttgaa  1080
gttaacgcat tggctaaagc attgtctggc cacaaggatg aggccttctt ctctggtaat  1140
gctgctgctc tggcttcaag gaagtcttct ccaagagtga ccaacgaggc tgttcagaag  1200
gctgctgctg cattgaaggg ttcagatcat cgccgtgcaa caaatgtcag tgccagactg  1260
gattctcaac aaaagaagct caaccttcca atcctgccaa ccaccactat tggatccttc  1320
cctcagactg tagaactgag gagggtacgc cgtgaattca aggctaacaa gatctccgag  1380
gaagagtatg taaagtcaat taaggaggaa attcgcaaag ttgttgagct tcaagaagag  1440
cttgatattg atgttcttgt tcatggagaa ccagagagaa atgatatggt tgagtacttc  1500
ggtgaacaat tgtcaggctt tgccttcacc gttaatgggt gggtgcaatc ctatggttcc  1560
cgttgcgtga agccaccgat catctatggt gatgtgagcc gcccaaagcc aatgaccgtc  1620
ttctggtcat ctctggctca gagctttacc aagcgcccaa tgaagggaat gcttaccggt  1680
cctgttacca ttctcaactg gtcctttgtt agaaatgacc aacctagatc tgagaccacc  1740
taccagattg ctttgtctat caaggacgaa gtggaagacc ttgaaaaggc tggcatcact  1800
gttatccaaa ttgatgaagc tgctttgaga gagggtcttc cactgaggaa atcagagcaa  1860
gctcactact tggactgggc tgtccatgcc ttcagaatca ccaatgttgg tgtccaggat  1920
accacccaga tccacactca catgtgctac tcgaatttca acgacatcat ccactccatc  1980
atcgacatgg acgccgatgt tatcaccatt gagaactctc gctccgacga gaagcttctg  2040
tcagtcttcc gcgaaggtgt gaagtatggt gctggaattg gccctggtgt ctatgacatc  2100
```

```
cactccccaa gaataccacc aactgaagaa attgctgaca gaatcaacaa gatgctggca  2160
gtgctcgaga agaacatctt gtgggtgaac cctgactgtg ggctcaagac ccgtaagtac  2220
actgaggtga agccagccct cacaaacatg gttgccgcag caaaactcat ccgcaacgaa  2280
cttgccaagt ga                                                      2292

SEQ ID NO: 174          moltype = AA  length = 763
FEATURE                 Location/Qualifiers
source                  1..763
                        mol_type = protein
                        organism = Glycine max
SEQUENCE: 174
MASHIVGYPR MGPKRELKFA LESFWDGKSS AEDLQKVSSD LRASIWKQMA DAGIKYIPSN  60
TFSHYDQVLD ATATLGAVPP RYGWTGGEIG FDTYFSMARG NATVPAMEMT KWFDTNYHFI  120
VPELGPDVNF TYASHKAVDE YKEAKALGVD TVPVLVGPVT YLLLSKPAKG VEKSFSLLSL  180
LPKVLAVYKE VIADLKAAGA SWIQFDEPTL VLDLESHKLQ AFTDAYAELA PALSGLNVLV  240
ETYFADIPAE AYKTLTSLNG VTAYGFDLVR GTNTLDLIKG GFPSGKYLFA GVVDGRNIWA  300
NDLAASLTTL QGLEGIVGKD KLVVSTSSSL LHTAVDLVNE TKLDDEIKSW LAFAAQKIVE  360
VNALAKALSG HKDEAFFSGN AAALASRKSS PRVTNEAVQK AAAALKGSDH RRATNVSARL  420
DSQQKKLNLP ILPTTTIGSF PQTVELRRVR REFKANKISE EEYVKSIKEE IRKVVELQEE  480
LDIDVLVHGE PERNDMVEYF GEQLSGFAFT VNGWVQSYGS RCVKPPIIYG DVSRPKPMTV  540
FWSSLAQSFT KRPMKGMLTG PVTILNWSFV RNDQPRSETT YQIALSIKDE VEDLEKAGIT  600
VIQIDEAALR EGLPLRKSEQ AHYLDWAVHA FRITNVGVQD TTQIHTHMCY SNFNDIIHSI  660
IDMDADVITI ENSRSDEKLL SVFREGVKYG AGIGPGVYDI HSPRIPPTEE IADRINKMLA  720
VLEKNILWVN PDCGLKTRKY TEVKPALTNM VAAAKLIRNE LAK                    763

SEQ ID NO: 175          moltype = AA  length = 21
FEATURE                 Location/Qualifiers
source                  1..21
                        mol_type = protein
                        organism = Glycine max
SEQUENCE: 175
AGITVIQIDE AALREGLPLR K                                            21

SEQ ID NO: 176          moltype = AA  length = 24
FEATURE                 Location/Qualifiers
source                  1..24
                        mol_type = protein
                        organism = Glycine max
SEQUENCE: 176
ALGVDTVPVL VGPVTYLLLS KPAK                                         24

SEQ ID NO: 177          moltype = AA  length = 16
FEATURE                 Location/Qualifiers
source                  1..16
                        mol_type = protein
                        organism = Glycine max
SEQUENCE: 177
DEAFFSGNAA ALASRK                                                  16

SEQ ID NO: 178          moltype = AA  length = 8
FEATURE                 Location/Qualifiers
source                  1..8
                        mol_type = protein
                        organism = Glycine max
SEQUENCE: 178
DEVEDLEK                                                           8

SEQ ID NO: 179          moltype = AA  length = 8
FEATURE                 Location/Qualifiers
source                  1..8
                        mol_type = protein
                        organism = Glycine max
SEQUENCE: 179
ISEEEYVK                                                           8

SEQ ID NO: 180          moltype = AA  length = 9
FEATURE                 Location/Qualifiers
source                  1..9
                        mol_type = protein
                        organism = Glycine max
SEQUENCE: 180
IVEVNALAK                                                          9

SEQ ID NO: 181          moltype = AA  length = 8
FEATURE                 Location/Qualifiers
source                  1..8
                        mol_type = protein
                        organism = Glycine max
SEQUENCE: 181
```

```
LIRNELAK                                                    8

SEQ ID NO: 182          moltype = AA  length = 10
FEATURE                 Location/Qualifiers
source                  1..10
                        mol_type = protein
                        organism = Glycine max
SEQUENCE: 182
LLSVFREGVK                                                  10

SEQ ID NO: 183          moltype = AA  length = 21
FEATURE                 Location/Qualifiers
source                  1..21
                        mol_type = protein
                        organism = Glycine max
SEQUENCE: 183
LVVSTSSSLL HTAVDLVNET K                                     21

SEQ ID NO: 184          moltype = AA  length = 10
FEATURE                 Location/Qualifiers
source                  1..10
                        mol_type = protein
                        organism = Glycine max
SEQUENCE: 184
SFSLLSLLPK                                                  10

SEQ ID NO: 185          moltype = AA  length = 12
FEATURE                 Location/Qualifiers
source                  1..12
                        mol_type = protein
                        organism = Glycine max
SEQUENCE: 185
SSPRVTNEAV QK                                               12

SEQ ID NO: 186          moltype = AA  length = 26
FEATURE                 Location/Qualifiers
source                  1..26
                        mol_type = protein
                        organism = Glycine max
SEQUENCE: 186
TLTSLNGVTA YGFDLVRGTN TLDLIK                                26

SEQ ID NO: 187          moltype = AA  length = 29
FEATURE                 Location/Qualifiers
source                  1..29
                        mol_type = protein
                        organism = Glycine max
SEQUENCE: 187
YGAGIGPGVY DIHSPRIPPT EEIADRINK                             29

SEQ ID NO: 188          moltype = DNA  length = 2196
FEATURE                 Location/Qualifiers
source                  1..2196
                        mol_type = other DNA
                        organism = Glycine max
CDS                     1..2196
SEQUENCE: 188
atggcttctt ccacttcctc tatctctctc tcccaagccc tcctccgccc caccaccacc  60
tctctcccct cctcctcctc ctccctccgc ctcaccccca ctctccgccc taccccaccc  120
gccctctccc tccgccgccg cctcaccacc tccatccgcg ccgccgcctc cgtcaaaacc  180
gtcgagaagg caaccgcgga cgccgcgctg gtcgaaaaat ccgtcaacac gatccgcttc  240
ctcgccatcg acgccgtcga gaaggcgaat tcgggtcacc cggggctccc catgggatgc  300
gctccgatgg gtcacgtgct atatgatgaa accatgaagt ataaccctaa gaaccctttc  360
tggttcaacc gcgatcgctt cgttctctcc gctgggcacg ggtgcatgct tcagtacgcg  420
cttctgcacc tcgctgggtt cgatagcgtc aaggaagagg atttgaggga atttcgccaa  480
tgggggagca gaactccggg acaccctgag aattttgaga ctccgggaat tgaagttaca  540
acaggtcctc ttggtcaggg gattgccaat gctgttggtt tggcccttgc agagaagcac  600
ttggctgcaa gatacaacaa gcctgacaat gagattgttg accattacac gtatgctatt  660
ctgggtgatg gttgtcaaat ggagggaatt gcaaatgaag catgctcact tgctggccac  720
tggggactgg ggaagctgat agcattttat gatgacaatc atatttctat tgatggtaac  780
acagagattg cgttcaccga gagtgttgat agtcgttttg agggacttgg gtggcatgtt  840
atttgggtaa agaatggaaa taatggctat gatgatattc gtgctgccat taaggaagca  900
aaagctgtca aagacaaacc cacattaatc aaggtcacaa caaccattgg ttatggttct  960
cctaacaagg ctaactccta cagtgtgcat ggaagtgcac tgggtgccaa agaagttgat  1020
gccaccaggc agaaccttgg atggtcacat gagccattcc acgtgcctga ggatgtcaaa  1080
aagcattgga gtcgccacac ccctgagggt gctgcacttg aagctgagtg gaatgctaag  1140
tttgctgagt atgaaaagaa atacaaggag gaggctgcag aattgaaatc tattatcaat  1200
ggtgaattcc ctgctggttg ggagaaagca cttccgacat acactccaga gagcccagcg  1260
gatgccacca gaaacctgtc tcaaacaaac cttaatgccc ttgcaaaggt tcttcccggt  1320
```

```
ctgcttggtg gcagtgcaga tcttgcttct tccaacatga ccttgctcaa aatgttcggg  1380
gacttccaaa aggatactcc agcagagcgt aatgttagat tcggtgttag agaacacgga  1440
atgggagcta tctgcaacgg cattgctctt cacagccctg gactgattcc atattgtgca  1500
accttctttg tattcactga ctacatgaga ggtgccataa ggctttctgc gctgtctgag  1560
gctggggtta tttatgtcat gacccatgat tcaataggac ttggagaaga tgggccaacc  1620
caccagccaa ttgagcacct agcaagcttc cgggcaatgc caaacatttt gatgcttcgt  1680
cccgccgacg gtaacgaaac agccggagca tacaaagtgg ccgtgctcaa caggaagaga  1740
ccctccattc ttgccctatc caggcaaaaa ctgccccagc ttcccggaac ttccattgaa  1800
ggagttgaaa agggtggtta caccatttcg gacaactcca ctggcaacaa gcctgatgtc  1860
attttgatcg gaactggttc ggaattggaa atcgctgcca aagctgctga tgacctaagg  1920
aaggaaggga aggctgttag agttgtttcc cttgtttctt gggaactttt tgatgagcaa  1980
tcagaagcct acaaggagag tgttttccct gctgctgttt cagccagagt tagcattgag  2040
gcaggatcaa catttgggtg ggagaaaatt gttggagcaa agggaaaagc aataggcatt  2100
gatcgttttg gagctagtgc tccagctgga agaatataca aagaatttgg tatcactaag  2160
gaagctgttg ttgctgcagc taaagagctt atctag                           2196

SEQ ID NO: 189         moltype = AA  length = 731
FEATURE                Location/Qualifiers
source                 1..731
                       mol_type = protein
                       organism = Glycine max
SEQUENCE: 189
MASSTSSISL SQALLRPTTT SLPSSSSSLR LTPTLRPTPP ALSLRRRLTT SIRAAASVKT  60
VEKATADAAL VEKSVNTIRF LAIDAVEKAN SGHPGLPMGC APMGHVLYDE TMKYNPKNPF  120
WFNRDRFVLS AGHGCMLQYA LLHLAGFDSV KEEDLREFRQ WGSRTPGHPE NFETPGIEVT  180
TGPLGQGIAN AVGLALAEKH LAARYNKPDN EIVDHYTYAI LGDGCQMEGI ANEACSLAGH  240
WGLGKLIAFY DDNHISIDGN TEIAFTESVD SRFEGLGWHV IWVKNGNNGY DDIRAAIKEA  300
KAVKDKPTLI KVTTTIGYGS PNKANSYSVH GSALGAKEVD ATRQNLGWSH EPFHVPEDVK  360
KHWSRHTPEG AALEAEWNAK FAEYEKKYKE EAAELKSIIN GEFPAGWEKA LPTYTPESPA  420
DATRNLSQTN LNALAKVLPG LLGGSADLAS SNMTLLKMFG DFQKDTPAER NVRFGVREHG  480
MGAICNGIAL HSPGLIPYCA TFFVFTDYMR GAIRLSALSE AGVIYVMTHD SIGLGEDGPT  540
HQPIEHLASF RAMPNILMLR PADGNETAGA YKVAVLNRKR PSILALSRQK LPQLPGTSIE  600
GVEKGGYTIS DNSTGNKPDV ILIGTGSELE IAAKAADDLR KEGKAVRVVS LVSWELFDEQ  660
SEAYKESVFP AAVSARVSIE AGSTFGWEKI VGAKGKAIGI DRFGASAPAG RIYKEFGITK  720
EAVVAAAKEL I                                                      731

SEQ ID NO: 190         moltype = AA  length = 18
FEATURE                Location/Qualifiers
source                 1..18
                       mol_type = protein
                       organism = Glycine max
SEQUENCE: 190
AIGIDRFGAS APAGRIYK                                               18

SEQ ID NO: 191         moltype = AA  length = 27
FEATURE                Location/Qualifiers
source                 1..27
                       mol_type = protein
                       organism = Glycine max
SEQUENCE: 191
ALPTYTPESP ADATRNLSQT NLNALAK                                     27

SEQ ID NO: 192         moltype = AA  length = 14
FEATURE                Location/Qualifiers
source                 1..14
                       mol_type = protein
                       organism = Glycine max
SEQUENCE: 192
ANSYSVHGSA LGAK                                                   14

SEQ ID NO: 193         moltype = AA  length = 10
FEATURE                Location/Qualifiers
source                 1..10
                       mol_type = protein
                       organism = Glycine max
SEQUENCE: 193
ATADAALVEK                                                        10

SEQ ID NO: 194         moltype = AA  length = 7
FEATURE                Location/Qualifiers
source                 1..7
                       mol_type = protein
                       organism = Glycine max
SEQUENCE: 194
DKPTLIK                                                           7

SEQ ID NO: 195         moltype = AA  length = 30
FEATURE                Location/Qualifiers
source                 1..30
```

```
                         mol_type = protein
                         organism = Glycine max
SEQUENCE: 195
GGYTISDNST GNKPDVILIG TGSELEIAAK                                  30

SEQ ID NO: 196           moltype = AA  length = 14
FEATURE                  Location/Qualifiers
source                   1..14
                         mol_type = protein
                         organism = Glycine max
SEQUENCE: 196
LPQLPGTSIE GVEK                                                   14

SEQ ID NO: 197           moltype = AA  length = 14
FEATURE                  Location/Qualifiers
source                   1..14
                         mol_type = protein
                         organism = Glycine max
SEQUENCE: 197
NGNNGYDDIR AAIK                                                   14

SEQ ID NO: 198           moltype = AA  length = 15
FEATURE                  Location/Qualifiers
source                   1..15
                         mol_type = protein
                         organism = Glycine max
SEQUENCE: 198
SVNTIRFLAI DAVEK                                                  15

SEQ ID NO: 199           moltype = AA  length = 12
FEATURE                  Location/Qualifiers
source                   1..12
                         mol_type = protein
                         organism = Glycine max
SEQUENCE: 199
VTTTIGYGSP NK                                                     12

SEQ ID NO: 200           moltype = DNA  length = 1797
FEATURE                  Location/Qualifiers
source                   1..1797
                         mol_type = other DNA
                         organism = Glycine max
CDS                      1..1797
SEQUENCE: 200
atggaagttc cttcggaggt accatctact gacactggca ccagcaccgg caccggcgaa  60
accatgagca agaatgcgtt gaagcgggag ctgaagaaca aacagagaga agaagaaagg  120
aagcgcaagg atgaggagaa ggccaaaaag gcagctgaag cacaacaggc aaaggataac  180
aaatctgcac cagctgatga tgaggatatg gatccaactc aataccttga gaacaggcta  240
aagtatcttg cagttcaaaa gacagaaggg aagaacccgt atcctcataa attctttgtc  300
actatgtcta ttgatcaata catcaaggaa tatggaggtt taagcaacgg gcaacacatt  360
gaggatgtct ctgtgtcttt ggctggccgg atcatgcaca aacgcacctc tggttctaag  420
cttgtctttt atgacctgca cggtggtggt tgcaaggtcc aggttatggc tgatgctagt  480
aaatcagact tggatgaggc tggattttcc aaattccatt ctaatgtgaa gcgcggtgac  540
atagttggtg tcactgggtt cccaggcaaa agtaagaagg gcgaacttag tatttttccc  600
aagaatttg tgtcgctgtc tcattgtttg cacatgatgc caaggcaaaa gtctgctgct  660
gctgctattg ataatagaaa tccatggata ccgggaagta ctaggaatcc tgaaacatat  720
attttgaagg atcaggaaac tagatatcgg ttacgccatt tggatttgat gcttaatcca  780
gaggttcgag acatattcaa gaccaggtct aaaatcattt cttacattag gaggttcctt  840
gatgaccttg atttcttgga ggttgaaaca cctatgatga atatgattgc tggtggagct  900
gcagcccgtc catttgtaac acatcacaat gatcttaaca tgaggttatt catgaggatt  960
gctccagaac tgtatcttaa ggagttggtt gttggtggac tggatcgtgt ttatgaaatt  1020
ggtaaacaat ttaggaatga gggcatagat ttgactcata atcctgagtt tactacctgt  1080
gagttctata tggcttataa ggactacaat gacttaatgg atctaacaga gcaaatgttg  1140
agtggtatgg ttaaggagct tacgaaaggc agctataaaa tcaagtatca tgcagatggg  1200
attgataagg aacctattga aattgacttt actacacctt ttagaaggat tgacatgatt  1260
gaagagttag agaagatggc aggtctaagt attcccaaag acttgtcaag tgaggaagcc  1320
aatcaatatt tgaaggatgc atgcgtgaag tatgagatca aatgtcctcc ccctgagaca  1380
actgctcgtt tgttggataa acttgtgggt cactttttgg aagaaacgtg tgtaaatcct  1440
acattcatca aaaaccatcc tgagatcatg agtcctctag caaagtggca cagatcaaaa  1500
ccaggcctga ctgaacgttt tgaattgttt gttaataaac gtgaactttg caatgcatat  1560
actgaattga atgaccctgt agtacaacga cagagatttg ctgaacaact caaggatcgg  1620
caatctggcg atgatgaagc aatggcctta gatgaaacat tttgtacggc tctagaatat  1680
ggtttaccac ctactggtgg ttggggtttg ggcattgatc ggttgaccat gttactgact  1740
gattcacaga atattaagga ggttcttctc ttccctgcca tgaaacctca agactga     1797

SEQ ID NO: 201           moltype = AA  length = 598
FEATURE                  Location/Qualifiers
source                   1..598
                         mol_type = protein
```

```
                         organism = Glycine max
SEQUENCE: 201
MEVPSEVPST DTGTSTGTGE TMSKNALKRE LKNKQREEER KRKDEEKAKK AAEAQQAKDN  60
KSAPADDEDM DPTQYLENRL KYLAVQKTEG KNPYPHKFFV TMSIDQYIKE YGGLSNGQHI  120
EDVSVSLAGR IMHKRTSGSK LVFYDLHGGG CKVQVMADAS KSDLDEAGFS KFHSNVKRGD  180
IVGVTGFPGK SKKGELSIFP KNFVSLSHCL HMMPRQKSAA AAIDNRNPWI PGSTRNPETY  240
ILKDQETRYR LRHLDLMLNP EVRDIFKTRS KIISYIRRFL DDLDFLEVET PMMNMIAGGA  300
AARPFVTHHN DLNMRLFMRI APELYLKELV VGGLDRVYEI GKQFRNEGID LTHNPEFTTC  360
EFYMAYKDYN DLMDLTEQML SGMVKELTKG SYKIKYHADG IDKEPIEIDF TTPFRRIDMI  420
EELEKMAGLS IPKDLSSEEA NQYLKDACVK YEIKCPPPET TARLLDKLVG HFLEETCVNP  480
TFIKNHPEIM SPLAKWHRSK PGLTERFELF VNKRELCNAY TELNDPVVQR QRFAEQLKDR  540
QSGDDEAMAL DETFCTALEY GLPPTGGWGL GIDRLTMLLT DSQNIKEVLL FPAMKPQD    598

SEQ ID NO: 202           moltype = AA  length = 12
FEATURE                  Location/Qualifiers
source                   1..12
                         mol_type = protein
                         organism = Glycine max
SEQUENCE: 202
DLSSEEANQY LK                                                     12

SEQ ID NO: 203           moltype = DNA  length = 1728
FEATURE                  Location/Qualifiers
source                   1..1728
                         mol_type = other DNA
                         organism = Glycine max
CDS                      1..1728
SEQUENCE: 203
atgtaccgct ttgcaacctc cctcgcctcc aaagctagaa ttgccaggag cagcactcaa  60
cagattggaa gtagggtcac ttggaacagg aattatgcgg ccaaagacat taagtttggt  120
gtggaggctc gggctctgat gcttaagggt gtcgaagagc tcgctgatgc cgttaaagta  180
acaatgggcc ctaaggggcg taatgtggtt attgagcaaa gttttggagc acctaaagtg  240
acgaaagatg gagtaaccgt tgctaagagc attgaattca aggacaaagt caagaatatc  300
ggtgccagtc ttgtaaagca ggttgctaat gctactaatg acgtggctgg tgatggaacc  360
acttgtgcta caattcttac taaagcaata tttacggaag gatgtaaatc agttgcagct  420
ggaatgaatg cgatggacct gagacgaggt ataaatatgg ctgttgatgc tgtggtgaca  480
aatctgaaaa gcagagcacg tatgattagc acttctgaag aaattgccca ggttggaaca  540
atatctgcca atggggagag ggaaattggt gagttaattg caaaagctat ggagaaagtt  600
ggcaaagagg gtgtcatcac aatctcagat ggcaagacat tgtacaatga gttggaagtc  660
gttgaaggaa tgaagctcga caggggatac atttctccat atttcataac aaaccagaag  720
aaccagaaat gtgaacttga ggatcctctc attataatcc atgaaaagaa aatctcaagc  780
ataaatgcta tcgttaaagt attagagtta gctttgaaga gacaaagatc tttattgatt  840
gtcgccgagg atgtggaaag tgatgccctt gcaactctta ttctaaataa acttcgtgct  900
ggaatcaagg tatgtgccat caaagctcct ggttttggtg aaaaccgtaa atctggtctc  960
caggatcttg ctgttcttac aggaggtcaa cttatcaccg aagagcttgg tttgaatctt  1020
gaaaaagtag acctggactt atttggctct tgcaagaaga taacaatttc taaagatgac  1080
actgtcatcc ttgatggagc tggtgataag aaagcaattg aggaaagatg tgagcagatt  1140
agatcagcaa ttgaaaatag cacttcagat tatgacaagg aaaagttaca ggaaagatta  1200
gccaagcttt ctgggggtgt tgcagtactg aagattggag gagccagtga ggctgaagtt  1260
ggtgagaaga aggatagagt gacagatgcc ttaaatgcaa ccaaggcagc tgtagaggag  1320
ggcatagtac ctggtggtgg tgttgctctt ctttatgcat cgagtgagtt ggataagctt  1380
caaactgcca actttgatca aaagataggt gtccagatca tccaaaatgc tttgaagact  1440
cctgtgcaca caattgcttc aaatgcagga gttgagggtg ctgttgttgt tggcaaacta  1500
ttggaacaga atgatcctga tcttggatat gatgcagcca aaggtgaata tgttgatatg  1560
gttaaaactg gaattattga tccattgaag gttattagga ccgccttggt tgatgcagcc  1620
agtgtgtcat ctttgatgac aacaactgaa gctgttgtgt ctgaactccc gaaggacgat  1680
aaagatgttc ctgccatggg tggtggcatg ggtggcatgg attattaa              1728

SEQ ID NO: 204           moltype = AA  length = 575
FEATURE                  Location/Qualifiers
source                   1..575
                         mol_type = protein
                         organism = Glycine max
SEQUENCE: 204
MYRFATSLAS KARIARSSTQ QIGSRVTWNR NYAAKDIKFG VEARALMLKG VEELADAVKV  60
TMGPKGRNVV IEQSFGAPKV TKDGVTVAKS IEFKDKVKNI GASLVKQVAN ATNDVAGDGT  120
TCATILTKAI FTEGCKSVAA GMNAMDLRRG INMAVDAVVT NLKSRARMIS TSEEIAQVGT  180
ISANGEREIG ELIAKAMEKV GKEGVITISD GKTLYNELEV VEGMKLDRGY ISPYFITNQK  240
NQKCELEDPL IIIHEKKISS INAIVKVLEL ALKRQRSLLI VAEDVESDAL ATLILNKLRA  300
GIKVCAIKAP GFGENRKSGL QDLAVLTGGQ LITEELGLNL EKVDLDLFGS CKKITISKDD  360
TVILDGAGDK KAIEERCEQI RSAIENSTSD YDKEKLQERL AKLSGGVAVL KIGGASEAEV  420
GEKKDRVTDA LNATKAAVEE GIVPGGGVAL LYASSELDKL QTANFDQKIG VQIIQNALKT  480
PVHTIASNAG VEGAVVVGKL LEQNDPDLGY DAAKGEYVDM VKTGIIDPLK VIRTALVDAA  540
SVSSLMTTTE AVVSELPKDD KDVPAMGGGM GGMDY                            575

SEQ ID NO: 205           moltype = AA  length = 24
FEATURE                  Location/Qualifiers
source                   1..24
                         mol_type = protein
```

```
                        organism = Glycine max
SEQUENCE: 205
AAVEEGIVPG GGVALLYASS ELDK                                        24

SEQ ID NO: 206          moltype = AA  length = 11
FEATURE                 Location/Qualifiers
source                  1..11
                        mol_type = protein
                        organism = Glycine max
SEQUENCE: 206
DRVTDALNAT K                                                      11

SEQ ID NO: 207          moltype = AA  length = 10
FEATURE                 Location/Qualifiers
source                  1..10
                        mol_type = protein
                        organism = Glycine max
SEQUENCE: 207
EGVITISDGK                                                        10

SEQ ID NO: 208          moltype = AA  length = 14
FEATURE                 Location/Qualifiers
source                  1..14
                        mol_type = protein
                        organism = Glycine max
SEQUENCE: 208
GRNVVIEQSF GAPK                                                   14

SEQ ID NO: 209          moltype = AA  length = 10
FEATURE                 Location/Qualifiers
source                  1..10
                        mol_type = protein
                        organism = Glycine max
SEQUENCE: 209
GVEELADAVK                                                        10

SEQ ID NO: 210          moltype = AA  length = 12
FEATURE                 Location/Qualifiers
source                  1..12
                        mol_type = protein
                        organism = Glycine max
SEQUENCE: 210
IGGASEAEVG EK                                                     12

SEQ ID NO: 211          moltype = AA  length = 11
FEATURE                 Location/Qualifiers
source                  1..11
                        mol_type = protein
                        organism = Glycine max
SEQUENCE: 211
IGVQIIQNAL K                                                      11

SEQ ID NO: 212          moltype = AA  length = 9
FEATURE                 Location/Qualifiers
source                  1..9
                        mol_type = protein
                        organism = Glycine max
SEQUENCE: 212
ISSINAIVK                                                         9

SEQ ID NO: 213          moltype = AA  length = 15
FEATURE                 Location/Qualifiers
source                  1..15
                        mol_type = protein
                        organism = Glycine max
SEQUENCE: 213
LLEQNDPDLG YDAAK                                                  15

SEQ ID NO: 214          moltype = AA  length = 9
FEATURE                 Location/Qualifiers
source                  1..9
                        mol_type = protein
                        organism = Glycine max
SEQUENCE: 214
LQTANFDQK                                                         9

SEQ ID NO: 215          moltype = AA  length = 9
FEATURE                 Location/Qualifiers
source                  1..9
```

```
                         mol_type = protein
                         organism = Glycine max
SEQUENCE: 215
LSGGVAVLK                                                                  9

SEQ ID NO: 216           moltype = AA  length = 8
FEATURE                  Location/Qualifiers
source                   1..8
                         mol_type = protein
                         organism = Glycine max
SEQUENCE: 216
NIGASLVK                                                                   8

SEQ ID NO: 217           moltype = AA  length = 8
FEATURE                  Location/Qualifiers
source                   1..8
                         mol_type = protein
                         organism = Glycine max
SEQUENCE: 217
TGIIDPLK                                                                   8

SEQ ID NO: 218           moltype = AA  length = 20
FEATURE                  Location/Qualifiers
source                   1..20
                         mol_type = protein
                         organism = Glycine max
SEQUENCE: 218
TPVHTIASNA GVEGAVVVGK                                                      20

SEQ ID NO: 219           moltype = DNA  length = 1725
FEATURE                  Location/Qualifiers
source                   1..1725
                         mol_type = other DNA
                         organism = Glycine max
CDS                      1..1725
SEQUENCE: 219
atgtatcgct ttgcttctaa cctcgcttcc aaagcaagga ttgctaggag tagcagccac  60
cagattggaa gtaggctgag ttcgagcaga aactatgcgg ctaaagacat tagatttggt  120
gtggaggctc gggcactgat gcttaagggt gttgaagagc tagctgatgc tgtcaaagta  180
accatgggtc ccaaggggcg taatgttgtg attgagcaaa gttttggtgc ccctaaagta  240
accaaagatg gagtaactgt tgcaaagagc attgaattca aggataaagt taagaatgtt  300
ggtgccagtc ttgtaaagca ggttgcaaat gctactaatg atgtggctgg tgatggaacc  360
acgtgcgcta cagtccttac acgagcaata tttactgaag gctgcaaatc agttgcggct  420
ggaatgaatg caatggacct gaggcgtggt ataagtatgg ctgtcgatgc tgtggtgaca  480
aacttgaaaa gcagagcaag gatgattagc acatctgaag aaatagcaca ggtagggaca  540
atatctgcta acggagagag agaaattggt gagttgattg caaaagctat ggagaaagtt  600
ggcaaagagg gagtaatcac aatttcagat ggcaaaacct tatataatga gttggaagtt  660
gttgaaggaa tgaagctcga caggggctac atatctcctt atttcattac aaatgataag  720
aaccagaaat gtgaacttga agatcccctc attctaattc atgagaagaa aatctcgagt  780
ataaatgcta tagttaaagt cttagagttg gctttgaaga gacaaagatc tttattgatt  840
attgccgagg atgtggaaag tgatgcactt gcaactctta ttctaaataa gcttcgggct  900
ggaattaagg tatgtgctat taaagcccct ggttttggcg aaaataggaa agccaatctt  960
caagatcttg cagttctcac aggaggagca cttattactg aagagcttgg cttgaagctt  1020
gaaaaagtgg atttggatat gcttggcacc tgtaaaaaaa taacagtttc taaggatgac  1080
actgtcattc ttgacggagc aggtgacaag aaagcacttg aggaaagatg cgagcagatt  1140
aggtctgcaa ttgaaaacag cacctcagat tatgacaagg aaaagttaca ggaaagatta  1200
gccaagcttt ctggtggtgt tgccgtgctt aagattggag gagccagtga agctgaagtt  1260
ggtgagaaga aggatagagt gacagatgcc ttaaatgcaa ctaaggctgc tgtagaggaa  1320
ggcattgtat caggtggtgg tgttgctctt ctatatgcgt caaaagagtt ggataaactt  1380
caaactgcta actttgatca gaagattggt gtccagatta tccaaaatgc tttaaagaca  1440
cctgtgctca caattgcatc aaatgcgggt gttgagggtg cagttgttgt tggcaaacta  1500
ttggaacagg agaatcatga tctaggatat gatgcagcca aaggtgaata tgttgatatg  1560
gttaaagctg gaatcataga ccctttgaag gtgattagga cagcccttggt tgatgcagcc  1620
agtgtatcat ctttgatgac aacaactgaa gctgttgtgt ctgaacttcc aaacgatgat  1680
aaagatactc cagctatggc tggtggcatg ggtggcatgg gttat                  1725

SEQ ID NO: 220           moltype = AA  length = 575
FEATURE                  Location/Qualifiers
source                   1..575
                         mol_type = protein
                         organism = Glycine max
SEQUENCE: 220
MYRFASNLAS KARIARSSSH QIGSRLSSSR NYAAKDIRFG VEARALMLKG VEELADAVKV  60
TMGPKGRNVV IEQSFGAPKV TKDGVTVAKS IEFKDKVKNV GASLVKQVAN ATNDVAGDGT  120
TCATVLTRAI FTEGCKSVAA GMNAMDLRRG ISMAVDAVVT NLKSRARMIS TSEEIAQVGT  180
ISANGEREIG ELIAKAMEKV GKEGVITISD GKTLYNELEV VEGMKLDRGY ISPYFITNDK  240
NQKCELEDPL ILIHEKKISS INAIVKVLEL ALKRQRSLLI IAEDVESDAL ATLILNKLRA  300
GIKVCAIKAP GFGENRKANL QDLAVLTGGA LITEELGLKL EKVDLDMLGT CKKITVSKDD  360
TVILDGAGDK KALEERCEQI RSAIENSTSD YDKEKLQERL AKLSGGVAVL KIGGASEAEV  420
```

```
GEKKDRVTDA LNATKAAVEE GIVSGGGVAL LYASKELDKL QTANFDQKIG VQIIQNALKT  480
PVLTIASNAG VEGAVVVGKL LEQENHDLGY DAAKGEYVDM VKAGIIDPLK VIRTALVDAA  540
SVSSLMTTTE AVVSELPNDD KDTPAMAGGM GGMGY                             575

SEQ ID NO: 221         moltype = AA  length = 8
FEATURE                Location/Qualifiers
source                 1..8
                       mol_type = protein
                       organism = Glycine max
SEQUENCE: 221
AGIIDPLK                                                           8

SEQ ID NO: 222         moltype = AA  length = 11
FEATURE                Location/Qualifiers
source                 1..11
                       mol_type = protein
                       organism = Glycine max
SEQUENCE: 222
DRVTDALNAT K                                                       11

SEQ ID NO: 223         moltype = AA  length = 10
FEATURE                Location/Qualifiers
source                 1..10
                       mol_type = protein
                       organism = Glycine max
SEQUENCE: 223
EGVITISDGK                                                         10

SEQ ID NO: 224         moltype = AA  length = 14
FEATURE                Location/Qualifiers
source                 1..14
                       mol_type = protein
                       organism = Glycine max
SEQUENCE: 224
GRNVVIEQSF GAPK                                                    14

SEQ ID NO: 225         moltype = AA  length = 10
FEATURE                Location/Qualifiers
source                 1..10
                       mol_type = protein
                       organism = Glycine max
SEQUENCE: 225
GVEELADAVK                                                         10

SEQ ID NO: 226         moltype = AA  length = 12
FEATURE                Location/Qualifiers
source                 1..12
                       mol_type = protein
                       organism = Glycine max
SEQUENCE: 226
IGGASEAEVG EK                                                      12

SEQ ID NO: 227         moltype = AA  length = 11
FEATURE                Location/Qualifiers
source                 1..11
                       mol_type = protein
                       organism = Glycine max
SEQUENCE: 227
IGVQIIQNAL K                                                       11

SEQ ID NO: 228         moltype = AA  length = 9
FEATURE                Location/Qualifiers
source                 1..9
                       mol_type = protein
                       organism = Glycine max
SEQUENCE: 228
ISSINAIVK                                                          9

SEQ ID NO: 229         moltype = AA  length = 15
FEATURE                Location/Qualifiers
source                 1..15
                       mol_type = protein
                       organism = Glycine max
SEQUENCE: 229
LLEQENHDLG YDAAK                                                   15

SEQ ID NO: 230         moltype = AA  length = 9
FEATURE                Location/Qualifiers
source                 1..9
```

```
                        mol_type = protein
                        organism = Glycine max
SEQUENCE: 230
LQTANFDQK                                                   9

SEQ ID NO: 231          moltype = AA  length = 9
FEATURE                 Location/Qualifiers
source                  1..9
                        mol_type = protein
                        organism = Glycine max
SEQUENCE: 231
LSGGVAVLK                                                   9

SEQ ID NO: 232          moltype = DNA  length = 1869
FEATURE                 Location/Qualifiers
source                  1..1869
                        mol_type = other DNA
                        organism = Glycine max
CDS                     1..1869
SEQUENCE: 232
atggctcaag ttcttgagaa ccccaccatt gacgcggcgg cttccggcgc gaacccctcg  60
ctgacgacca tctcgttgta cgtcggggat cttcaccacg acgtcaacga tccgcagctg  120
tatgatctct tcaaccaggt tgcccaagtc gtttccgttc gaatttgcag ggacgtggcc  180
acccaacaat cccttggtta cggctacgtc aatttcagca acgctcacga tgccgcaaaa  240
gcaattgatg tgctgaattt cactccactg aacggcaaaa tcattaggat aatgtactct  300
attcgggacc ctagtgctcg gaagagtggt gcagctaatg ttttcataaa gaatttggac  360
aaggcgattg atcacaaggc tttgtacgat acattttcgg cttttgggaa tattctatct  420
tgcaaggttg cgacagatgc ttctggccag tctaaaggcc atggttttgt gcagtttgag  480
agtgaagaat ctgcacaaaa tgcaattgac aagttaaacg gcatgctgat caatgataag  540
caggtctttg tgggtccttt cctgcggaag caggatagag agagtgctct cagtggcaca  600
aagtttaata acgttttcgt gaaaaacctg ttggattcaa tgactgaggc tgacttggag  660
agaatttttg gagaatatgg agctattact agcgctgtag tgatgagaga tgtagatggt  720
aaatcaaaag gttttggttt tgtcaatttt gcaaatgtag acgatgctgc taaagctgtg  780
gaggctctta atggaaagaa ttttgatggt aaggagtggt atgttggaaa agcccagaaa  840
aagtctgaaa gggagcttga actgaaaggg caacatgaac agattacaaa ggagactgtt  900
gataaatatc atggtacaaa cttgtatatc aagaacttgg atgatagtgt tggtgatgaa  960
gaactcatgg aactgttctc tgagtttggt acgataacct catgcaaggt tatgcgagat  1020
ccaaatggaa ttagtagagg atctggattt gtttcatttt caattgctga gggagcaact  1080
cgggctcttg gtgagatgaa tggtaaaatg gttgctggca aacctctcta tgttgccctt  1140
gcacagagaa aagaagatag aagagcaagg ttacaggcac aattttcaca atcgaggcct  1200
gctgcaataa cccctaatgt ttcacctcga atgcctctat accctctagg ggctcctgcg  1260
ataggacaac aatttttgta tggcaagca gctccagcca cgatacctca acattttgtt  1320
cctggaatga ggccaggtgg tgctccaaac ttctatgttc cactggttca gcagggtcaa  1380
cagggacagc gcccaggagg acaccgagga tcaggtccta tgcaacagct ccagcagcca  1440
ttgccattga tgcaccaaca gatgcttcca aggggacatg tctatcgata tccttctggc  1500
tccaatatgc aaaatattca actggcagga gtacctggag gaatggtcac ttatggcatt  1560
ggtcaacaaa tgcccacgca ggccctggcc tcggcccttg ccaatgctac tcctgaacag  1620
cagaggacta tgcttggtga agctttatac ccgttagtag ataagctgga gcatgaagca  1680
gcagcaaagg ttactggtat gctcttagag atggatcagc ctgaggtatt acatctgatt  1740
gagtcaccgg atgctctcaa ggctaaagtt gttgaggcca tggatgtgtt gaagaaagtt  1800
acacagcagc aatcaaacag cccagccgat caactggctt cactctctct gaatgataat  1860
gtcgagtct                                                   1869

SEQ ID NO: 233          moltype = AA  length = 623
FEATURE                 Location/Qualifiers
source                  1..623
                        mol_type = protein
                        organism = Glycine max
SEQUENCE: 233
MAQVLENPTI DAAASGANPS LTTISLYVGD LHHDVNDPQL YDLFNQVAQV VSVRICRDVA  60
TQQSLGYGYV NFSNAHDAAK AIDVLNFTPL NGKIIRIMYS IRDPSARKSG AANVFIKNLD  120
KAIDHKALYD TFSAFGNILS CKVATDASGQ SKGHGFVQFE SEESAQNAID KLNGMLINDK  180
QVFVGPFLRK QDRESALSGT KFNNVFVKNL LDSMTEADLE RIFGEYGAIT SAVVMRDVDG  240
KSKGFGFVNF ANVDDAAKAV EALNGKNFDG KEWYVGKAQK KSERELELKG QHEQITKETV  300
DKYHGTNLYI KNLDDSVGDE ELMELFSEFG TITSCKVMRD PNGISRGSGF VSFSIAEGAT  360
RALGEMNGKM VAGKPLYVAL AQRKEDRRAR LQAQFSQSRP AAITPNVSPR MPLYPLGAPA  420
IGQQFLYGQA APATIPQHFV PGMRPGGAPN FYVPLVQQGQ QGQRPGGHRG SGPMQQLQQP  480
LPLMHQQMLP RGHVYRYPSG SNMQNIQLAG VPGGMVTYGI GQQMPTQALA SALANATPEQ  540
QRTMLGEALY PLVDKLEHEA AAKVTGMLLE MDQPEVLHLI ESPDALKAKV VEAMDVLKKV  600
TQQQSNSPAD QLASLSLNDN VES                                   623

SEQ ID NO: 234          moltype = AA  length = 13
FEATURE                 Location/Qualifiers
source                  1..13
                        mol_type = protein
                        organism = Glycine max
SEQUENCE: 234
AIDVLNFTPL NGK                                              13
```

```
SEQ ID NO: 235          moltype = AA  length = 7
FEATURE                 Location/Qualifiers
source                  1..7
                        mol_type = protein
                        organism = Glycine max
SEQUENCE: 235
FNNVFVK                                                            7

SEQ ID NO: 236          moltype = AA  length = 15
FEATURE                 Location/Qualifiers
source                  1..15
                        mol_type = protein
                        organism = Glycine max
SEQUENCE: 236
GFGFVNFANV DDAAK                                                   15

SEQ ID NO: 237          moltype = AA  length = 9
FEATURE                 Location/Qualifiers
source                  1..9
                        mol_type = protein
                        organism = Glycine max
SEQUENCE: 237
SGAANVFIK                                                          9

SEQ ID NO: 238          moltype = DNA  length = 1851
FEATURE                 Location/Qualifiers
source                  1..1851
                        mol_type = other DNA
                        organism = Glycine max
CDS                     1..1851
SEQUENCE: 238
atggattctg attatggtat tcccagggaa ctctcagatc ttcaaaagat tcggtctttg  60
taccagccag agctccctcc ttgtctccag ggaaccactg tgagggttga atttggtgac  120
gcaaccacca ctgctgaccc cactgatgca ctcaccgtct gcagggcttt tcctaacact  180
tatggacacc ctttggctca ctttctcagg gccactgcca aagtccctga tgctcagatc  240
ataactgagt tccctcctat tagggtgggg attgtctttt gtgggagaca atctcctgga  300
gggcataatg tcatttgggg tatccacaat gctctcaaaa ttcacaatcc caacagtgtt  360
ttgcttggat ttcttggtgg ttcagaaggt ctatttgccc agaaaactct ggagataact  420
gacgatattc tttcgacgta caaaaatcaa ggtggttatg atttgcttgg gcggacgaag  480
gatcaaatta ggaccacaga acaagttaat gctgcacttg ctgcatgcaa caatttgaaa  540
cttgatggcc ttgtcataat cggaggggtg acatcaaaca cagatgctgc acagcttgct  600
gaaacatttg ttgtagcaaa atgccccaca aaggtggttg gtgttcctgt cactctgaat  660
ggagatctta aaaaccagtt tgtagaaact aatgttggtt ttgatacaat ttgtaaggtt  720
aattctcagc tcatcagcaa tgtctgcact gatgctctct ctgcagagaa gtattattat  780
ttcatccgtc ttatgggacg caaggcatca cacgttgctt tggaatgcac cctccagtcc  840
catccaaata tggtaattct tggtgaggag gttgctgcat caaagcttac cctttctgaa  900
attgcaaaac agattactga tgcaattcag gctagagcag agcaagacaa ataccatgga  960
gtcattctcc ttccagaagg gctgatagag agtattcctg aagtgtatgc cctcttgaag  1020
gaaattcatg gtttactcag acaaggtgtt gaagttgaca agatatcttc tcagctaaca  1080
ccatgggcat ctgctttatt tgaatttctg ccacccttta ttaggagaca gttgctcctt  1140
taccctgaat ccgacgactc agcacagtta tcacagattg aaactgagaa attactagca  1200
tatcttgtgg aagtcgagat taacaagcgt ctgaaagaag gcacatacaa ggggaagaaa  1260
ttcaatgcca tttgccactt ttttggttat caagctcgtg gatctctgcc atcaaaattt  1320
gactgtgatt acgcatatgt ccttgggcac atctgctacc atatactggc cgctggtcta  1380
aatggataca tggcaacttt aactaacctg aagaatccag taaacaagtg gaaatgtggg  1440
gctgctccaa ttgcatctat gatgactgta aagcgctggt ctccaaatcc aggagctaca  1500
tcaattggaa aacctgctat tcatccagct actgtggact tgagaggcaa agcatatgag  1560
ctgttgagac aaaaggcaca aagctttctt atggatgaca tctacagaaa tccaggtcca  1620
cttcagtttg atggtcccgg cgcagatgcc aaggttataa ctctttctgt tgaagaccag  1680
gactacatgg gccgcattaa gaaacttcag gagtaccttg aacaggttcg aaccattgtc  1740
aagccaggat gccctcagga ggttttgaaa gctgctctaa gcgtcatggc gtcggttacc  1800
gaagttctag ctgcaatgtc aacatcttat accaacaccc tggcatccct g           1851

SEQ ID NO: 239          moltype = AA  length = 617
FEATURE                 Location/Qualifiers
source                  1..617
                        mol_type = protein
                        organism = Glycine max
SEQUENCE: 239
MDSDYGIPRE LSDLQKIRSL YQPELPPCLQ GTTVRVEFGD ATTTADPTDA LTVCRAFPNT  60
YGHPLAHFLR ATAKVPDAQI ITEFPPIRVG IVFCGRQSPG GHNVIWGIHN ALKIHNPNSV  120
LLGFLGGSEG LFAQKTLEIT DDILSTYKNQ GGYDLLGRTK DQIRTTEQVN AALAACNNLK  180
LDGLVIIGGV TSNTDAAQLA ETFVVAKCPT KVVGVPVTLN GDLKNQFVET NVGFDTICKV  240
NSQLISNVCT DALSAEKYYY FIRLMGRKAS HVALECTLQS HPNMVILGEE VAASKLTLSE  300
IAKQITDAIQ ARAEQDKYHG VILLPEGLIE SIPEVYALLK EIHGLLRQGV EVDKISSQLT  360
PWASALFEFL PPFIRRQLLL YPESDDSAQL SQIETEKLLA YLVEVEINKR LKEGTYKGKK  420
FNAICHFFGY QARGSLPSKF DCDYAYVLGH ICYHILAAGL NGYMATLTNL KNPVNKWKCG  480
AAPIASMMTV KRWSPNPGAT SIGKPAIHPA TVDLRGKAYE LLRQKAQSFL MDDIYRNPGP  540
LQFDGPGADA KVITLSVEDQ DYMGRIKKLQ EYLEQVRTIV KPGCPQEVLK AALSVMASVT  600
```

```
EVLAAMSTSY TNTLASL                                                617

SEQ ID NO: 240         moltype = AA  length = 13
FEATURE                Location/Qualifiers
source                 1..13
                       mol_type = protein
                       organism = Glycine max
SEQUENCE: 240
VVGVPVTLNG DLK                                                    13

SEQ ID NO: 241         moltype = DNA  length = 1575
FEATURE                Location/Qualifiers
source                 1..1575
                       mol_type = other DNA
                       organism = Glycine max
CDS                    1..1575
SEQUENCE: 241
atgcccaaat tttttcatag cattttcaga ggaacaatgg cgggtagggt ttcgacgtgc  60
ttcttcttcg tgtttgctct ttctctcctt cttccttttc agatctccgc tgaggaatca  120
tcggagaaag agttcgtact cacattggat cactctaact ttcacgacac tgtcagcaag  180
cacgatttca tcgtcgtcga gttctacgct ccatggtgtg gccactgtaa gaagcttgct  240
cccgagtatg agaaagctgc ttctatcttg agtagtcatg atcctccggt tgttttggct  300
aaaattgatg ccaatgagga gaagaacaaa gaccttgcat ctcaatatga tgttagggga  360
tacccaacaa ttaagattct gagaaatggg ggaaagaatg ttcaggaata caaaggtccc  420
cgtgaagcag atggcatcgt tgactatttg aagaaacaaa gtggtcctgc ttcaactgaa  480
attaaatctg ctgatgaagc tactgctttc attggtgaaa ataaagttgc tattgttgga  540
gttttcccga aatttctgg agaggagttt gacaactttt ctgccttagc agagaagttg  600
cgttctgact atgacttcgg tcacactctg aatgccaaac accttccaag aggagagtca  660
tcagtttctg gtcccgtagt taggttgttc aagccattcg atgaactttt tgttgacttc  720
caggatttca atgtggaagc tctagagaaa tttgttgagg aatctagtac ccctgttgtt  780
actgtcttta acaatgatcc gagcaatcac cctttcgttg ccaaattctt caacagtccc  840
aatgcaaagg caatgttgtt catcaacttc actgccgaag gtgctgaatc tttcaaatca  900
aaataccgtg aagctgctga gcaacataaa caacagggtg taagcttttt ggtgggagat  960
gttgagtcta gtcaaggtgc tttccagtat tttggactga aagaagaaca agtacctcta  1020
attatcattc aacacaatga cgggaaaaag tttttttaaac ccaatttgga agctgatcac  1080
attccaactt ggttgaaggc gtacaaggat ggtaatgttg caccatttgt gaagtctgaa  1140
cccattcctg aagctaacga tgaacctgtt aaagtggtag ttgggaacag tcttgaggac  1200
attgttttca aatctgggaa gaatgttctg ctggagtttt atgctccctg gtgtggtcat  1260
tgcaaacagt tggctccaat attggacgaa gttgctatct catatcaaag tgatgctgat  1320
gttgttattg caaaactgga tgcaactgcc aacgatatcc caagtgaaac ctttgatgtc  1380
caaggttatc caaccgtgta cttcaggtca gcaagtggaa agttatcaca atacgaaggg  1440
ggtaggacca aggaagacat catagaattc atcgaaaaga accgggacaa acctgctcag  1500
caagaacaag gacaagataa acctgctcag caagaacaag gacaagatga gcaagaaaaa  1560
ggaaaagatg agctt                                                  1575

SEQ ID NO: 242         moltype = AA  length = 525
FEATURE                Location/Qualifiers
source                 1..525
                       mol_type = protein
                       organism = Glycine max
SEQUENCE: 242
MPKFFHSIFR GTMAGRVSTC FFFVFALSLL LPFQISAEES SEKEFVLTLD HSNFHDTVSK  60
HDFIVVEFYA PWCGHCKKLA PEYEKAASIL SSHDPPVVLA KIDANEEKNK DLASQYDVRG  120
YPTIKILRNG GKNVQEYKGP READGIVDYL KKQSGPASTE IKSADEATAF IGENKVAIVG  180
VFPKFSGEEF DNFSALAEKL RSDYDFGHTL NAKHLPRGES SVSGPVVRLF KPFDELFVDF  240
QDFNVEALEK FVEESSTPVV TVFNNDPSNH PFVAKFFNSP NAKAMLFINF TAEGAESFKS  300
KYREAAEQHK QQGVSFLVGD VESSQGAFQY FGLKEEQVPL IIIQHNDGKK FFKPNLEADH  360
IPTWLKAYKD GNVAPFVKSE PIPEANDEPV KVVVGNSLED IVFKSGKNVL LEFYAPWCGH  420
CKQLAPILDE VAISYQSDAD VVIAKLDATA NDIPSETFDV QGYPTVYFRS ASGKLSQYEG  480
GRTKEDIIEF IEKNRDKPAQ QEQGQDKPAQ QEQGQDEQEK GKDEL                 525

SEQ ID NO: 243         moltype = AA  length = 16
FEATURE                Location/Qualifiers
source                 1..16
                       mol_type = protein
                       organism = Glycine max
SEQUENCE: 243
AASILSSHDP PVVLAK                                                 16

SEQ ID NO: 244         moltype = AA  length = 9
FEATURE                Location/Qualifiers
source                 1..9
                       mol_type = protein
                       organism = Glycine max
SEQUENCE: 244
DGNVAPFVK                                                         9

SEQ ID NO: 245         moltype = AA  length = 15
FEATURE                Location/Qualifiers
```

```
source                  1..15
                        mol_type = protein
                        organism = Glycine max
SEQUENCE: 245
DLASQYDVRG YPTIK                                                15

SEQ ID NO: 246          moltype = AA  length = 9
FEATURE                 Location/Qualifiers
source                  1..9
                        mol_type = protein
                        organism = Glycine max
SEQUENCE: 246
EDIIEFIEK                                                       9

SEQ ID NO: 247          moltype = AA  length = 15
FEATURE                 Location/Qualifiers
source                  1..15
                        mol_type = protein
                        organism = Glycine max
SEQUENCE: 247
EEQVPLIIIQ HNDGK                                                15

SEQ ID NO: 248          moltype = AA  length = 17
FEATURE                 Location/Qualifiers
source                  1..17
                        mol_type = protein
                        organism = Glycine max
SEQUENCE: 248
EFVLTLDHSN FHDTVSK                                              17

SEQ ID NO: 249          moltype = AA  length = 16
FEATURE                 Location/Qualifiers
source                  1..16
                        mol_type = protein
                        organism = Glycine max
SEQUENCE: 249
FFKPNLEADH IPTWLK                                               16

SEQ ID NO: 250          moltype = AA  length = 8
FEATURE                 Location/Qualifiers
source                  1..8
                        mol_type = protein
                        organism = Glycine max
SEQUENCE: 250
FFNSPNAK                                                        8

SEQ ID NO: 251          moltype = AA  length = 15
FEATURE                 Location/Qualifiers
source                  1..15
                        mol_type = protein
                        organism = Glycine max
SEQUENCE: 251
FSGEEFDNFS ALAEK                                                15

SEQ ID NO: 252          moltype = AA  length = 25
FEATURE                 Location/Qualifiers
source                  1..25
                        mol_type = protein
                        organism = Glycine max
SEQUENCE: 252
FVEESSTPVV TVFNNDPSNH PFVAK                                     25

SEQ ID NO: 253          moltype = DNA  length = 1509
FEATURE                 Location/Qualifiers
source                  1..1509
                        mol_type = other DNA
                        organism = Glycine max
CDS                     1..1509
SEQUENCE: 253
atggcgggta cggtttcgac ttgtttcttc ttcgtgtttc ttctttctct ccttcttcct  60
tttcagatct ccgctgagga atcctcggag aaggagttcg tactcacatt ggatcactct  120
aactttcacg acactgtcag caagcacgat ttcatcgtcg tcgagttcta cgccccatgg  180
tgtggtcact gtaagaagct tgctccggag tatgagaaag ctgcttctat cttgagtagt  240
catgatcctc ctattgtttt ggctaaagta gatgccaatg aggagaagaa caaagacctt  300
gcatcacaat atgatgttaa gggattccca acaattaata ttctgagaaa tgggggaaag  360
aatgttcagg aatacaaagg tccccgtgaa gcagatggca tcgttgacta tttgaagaaa  420
caaagtggtc ctgcttcaac tgaaattaaa tctgctgatg aagctactgc ttttattggt  480
gaaaataaag ttgctattgt tggagttttc ccgaaatttt ctggagagga gtttgacaac  540
ttttctgcct tagcagagaa gttgcgttct gattatgact ttggtcacac tctgaatgcc  600
```

```
aaactccttc caagaggaga gtcatcagtt tctgggcccg tagttaggct gttcaagcca  660
ttcgatgaac tttttgttga cttccaggat ttcaatgtgg aagctctaga gaagtttgtt  720
gaggaatcta gtacccctgt tgttactgtc tttaacaatg aaccgagcaa tcacccctttc  780
gttgtcaaat tcttcaacag tcccaacgca aaggcaatgt tgttcatcaa cttcactgcc  840
gaaggtgctg aagctatcaa atcaaaatac cgtgaagctg ctgagcaata taaacaacag  900
ggtgtcagct tttggtggg agatgttgag tctagtcaag gtgctttcca gtattttgga  960
ctgaaagaag agcaagtacc tctaattatc attcaacata atgatgggaa aaagtttttt  1020
aaacccaatt tggaagctga tcacattcca acctggttga aggcatacaa ggatggtcat  1080
gttgcaccat ttgttaagtc tgaacccatt cccgagacta acgatgaacc tgttaaagtg  1140
gtagttgggg ccagtcttga ggacattgtt ttcaaatctg ggaagaatgt tctgctggag  1200
ttttatgctc cctggtgtgg tcattgcaaa cagttggctc caatattgga tgaagttgct  1260
atctcatatc aaaatgaagc tgatgttgtt attgcaaaac tggatgcaac tgccaacgat  1320
atcccaagtg aaacctttga tgtccaaggt tatcctaccg tgtacttcag gtcagcaagt  1380
ggaaagttat cacaatacga cggcggtagg accaaggaag acatcataga attcatcgaa  1440
aagaaccggg ataaacctgc tcagcaagaa caaggaaaag atgagcaaga acaaggaaaa  1500
gatgagctt                                                          1509

SEQ ID NO: 254         moltype = AA  length = 503
FEATURE                Location/Qualifiers
source                 1..503
                       mol_type = protein
                       organism = Glycine max
SEQUENCE: 254
MAGTVSTCFF FVFLLSLLLP FQISAEESSE KEFVLTLDHS NFHDTVSKHD FIVVEFYAPW  60
CGHCKKLAPE YEKAASILSS HDPPIVLAKV DANEEKNKDL ASQYDVKGFP TINILRNGGK  120
NVQEYKGPRE ADGIVDYLKK QSGPASTEIK SADEATAFIG ENKVAIVGVF PKFSGEEFDN  180
FSALAEKLRS DYDFGHTLNA KLLPRGESSV SGPVVRLFKP FDELFVDFQD FNVEALEKFV  240
EESSTPVVTV FNNEPSNHPF VVKFFNSPNA KAMLFINFTA EGAEAIKSKY REAAEQYKQQ  300
GVSFLVGDVE SSQGAFQYFG LKEEQVPLII IQHNDGKKFF KPNLEADHIP TWLKAYKDGH  360
VAPFVKSEPI PETNDEPVKV VVGASLEDIV FKSGKNVLLE FYAPWCGHCK QLAPILDEVA  420
ISYQNEADVV IAKLDATAND IPSETFDVQG YPTVYFRSAS GKLSQYDGGR TKEDIIEFIE  480
KNRDKPAQQE QGKDEQEQGK DEL                                          503

SEQ ID NO: 255         moltype = AA  length = 16
FEATURE                Location/Qualifiers
source                 1..16
                       mol_type = protein
                       organism = Glycine max
SEQUENCE: 255
AASILSSHDP PIVLAK                                                  16

SEQ ID NO: 256         moltype = AA  length = 9
FEATURE                Location/Qualifiers
source                 1..9
                       mol_type = protein
                       organism = Glycine max
SEQUENCE: 256
DGHVAPFVK                                                          9

SEQ ID NO: 257         moltype = AA  length = 9
FEATURE                Location/Qualifiers
source                 1..9
                       mol_type = protein
                       organism = Glycine max
SEQUENCE: 257
DLASQYDVK                                                          9

SEQ ID NO: 258         moltype = AA  length = 9
FEATURE                Location/Qualifiers
source                 1..9
                       mol_type = protein
                       organism = Glycine max
SEQUENCE: 258
EDIIEFIEK                                                          9

SEQ ID NO: 259         moltype = AA  length = 15
FEATURE                Location/Qualifiers
source                 1..15
                       mol_type = protein
                       organism = Glycine max
SEQUENCE: 259
EEQVPLIIIQ HNDGK                                                   15

SEQ ID NO: 260         moltype = AA  length = 17
FEATURE                Location/Qualifiers
source                 1..17
                       mol_type = protein
                       organism = Glycine max
SEQUENCE: 260
```

```
EFVLTLDHSN FHDTVSK                                                   17

SEQ ID NO: 261          moltype = AA  length = 16
FEATURE                 Location/Qualifiers
source                  1..16
                        mol_type = protein
                        organism = Glycine max
SEQUENCE: 261
FFKPNLEADH IPTWLK                                                    16

SEQ ID NO: 262          moltype = AA  length = 8
FEATURE                 Location/Qualifiers
source                  1..8
                        mol_type = protein
                        organism = Glycine max
SEQUENCE: 262
FFNSPNAK                                                             8

SEQ ID NO: 263          moltype = AA  length = 15
FEATURE                 Location/Qualifiers
source                  1..15
                        mol_type = protein
                        organism = Glycine max
SEQUENCE: 263
FSGEEFDNFS ALAEK                                                     15

SEQ ID NO: 264          moltype = AA  length = 25
FEATURE                 Location/Qualifiers
source                  1..25
                        mol_type = protein
                        organism = Glycine max
SEQUENCE: 264
FVEESSTPVV TVFNNEPSNH PFVVK                                          25

SEQ ID NO: 265          moltype = AA  length = 13
FEATURE                 Location/Qualifiers
source                  1..13
                        mol_type = protein
                        organism = Glycine max
SEQUENCE: 265
GFPTINILRN GGK                                                       13

SEQ ID NO: 266          moltype = AA  length = 13
FEATURE                 Location/Qualifiers
source                  1..13
                        mol_type = protein
                        organism = Glycine max
SEQUENCE: 266
GPREADGIVD YLK                                                       13

SEQ ID NO: 267          moltype = AA  length = 7
FEATURE                 Location/Qualifiers
source                  1..7
                        mol_type = protein
                        organism = Glycine max
SEQUENCE: 267
LAPEYEK                                                              7

SEQ ID NO: 268          moltype = AA  length = 29
FEATURE                 Location/Qualifiers
source                  1..29
                        mol_type = protein
                        organism = Glycine max
SEQUENCE: 268
LDATANDIPS ETFDVQGYPT VYFRSASGK                                      29

SEQ ID NO: 269          moltype = AA  length = 14
FEATURE                 Location/Qualifiers
source                  1..14
                        mol_type = protein
                        organism = Glycine max
SEQUENCE: 269
LRSDYDFGHT LNAK                                                      14

SEQ ID NO: 270          moltype = AA  length = 10
FEATURE                 Location/Qualifiers
source                  1..10
                        mol_type = protein
                        organism = Glycine max
```

```
SEQUENCE: 270
LSQYDGGRTK                                                  10

SEQ ID NO: 271          moltype = AA  length = 23
FEATURE                 Location/Qualifiers
source                  1..23
                        mol_type = protein
                        organism = Glycine max
SEQUENCE: 271
QLAPILDEVA ISYQNEADVV IAK                                   23

SEQ ID NO: 272          moltype = AA  length = 24
FEATURE                 Location/Qualifiers
source                  1..24
                        mol_type = protein
                        organism = Glycine max
SEQUENCE: 272
QQGVSFLVGD VESSQGAFQY FGLK                                  24

SEQ ID NO: 273          moltype = AA  length = 10
FEATURE                 Location/Qualifiers
source                  1..10
                        mol_type = protein
                        organism = Glycine max
SEQUENCE: 273
QSGPASTEIK                                                  10

SEQ ID NO: 274          moltype = AA  length = 13
FEATURE                 Location/Qualifiers
source                  1..13
                        mol_type = protein
                        organism = Glycine max
SEQUENCE: 274
SADEATAFIG ENK                                              13

SEQ ID NO: 275          moltype = AA  length = 13
FEATURE                 Location/Qualifiers
source                  1..13
                        mol_type = protein
                        organism = Glycine max
SEQUENCE: 275
SEPIPETNDE PVK                                              13

SEQ ID NO: 276          moltype = AA  length = 9
FEATURE                 Location/Qualifiers
source                  1..9
                        mol_type = protein
                        organism = Glycine max
SEQUENCE: 276
VAIVGVFPK                                                   9

SEQ ID NO: 277          moltype = AA  length = 13
FEATURE                 Location/Qualifiers
source                  1..13
                        mol_type = protein
                        organism = Glycine max
SEQUENCE: 277
VVVGASLEDI VFK                                              13

SEQ ID NO: 278          moltype = AA  length = 9
FEATURE                 Location/Qualifiers
source                  1..9
                        mol_type = protein
                        organism = Glycine max
SEQUENCE: 278
YREAAEQYK                                                   9

SEQ ID NO: 279          moltype = DNA  length = 1467
FEATURE                 Location/Qualifiers
source                  1..1467
                        mol_type = other DNA
                        organism = Glycine max
CDS                     1..1467
SEQUENCE: 279
atgggtgtgg ctcaaaacat tcccgatgcg gaggagggaa ccttggagat tggaatggaa  60
tacagaactg tttctggagt tgctgggcca ttggtcattc ttgataaagt taagggaccc  120
aagtttcaag agattgttaa cattcgctta ggagatggta ctactcggcg tggacaagtg  180
ctagaagttg atggtgaaaa ggctgttgtt caggtctttg agggtacatc tgggattgac  240
aataaattta caactgtgca atttactgga gaggtgttaa aaactccagt atcattggac  300
```

```
atgcttggcc gcatattcaa tggttctgga aaaccaattg ataatggtcc acccatttta  360
cctgaggctt acttggacat atcaggaagt tccatcaacc ctagtgagag aacctatcca  420
gaggagatga tacagacagg aatatctacc attgatgtca tgaattctat tgctagaggt  480
caaaagatcc ctctattctc agctgctggt ctcccccata atgaaattgc tgcacagata  540
tgccgtcagg ctggcttagt caagcgacta gaaaagtctg ataatcttct cgagggtgga  600
ggagaagagg acaattttgc cattgtgttt gcagctatgg gagttaacat ggagactgca  660
cagtttttca aacgtgactt tgaggaaaat ggctcgatgg agagagtgac ccttttcctt  720
aatctggcaa atgatcctac gattgagcgt atcatcactc ctcgtattgc tcttactact  780
gctgaatatt tggcatatga atgtggcaag catgttcttg tgatactaac tgatatgagt  840
tcttatgctg atgctcttcg tgaggtatct gctgcccgag aagaagtacc tggtagacgt  900
gggtatcccg gctacatgta tacagatctt gcaacaatat acgaacgtgc tggaagaatt  960
gaggggcgaa aaggctctat tacacaaatt ccaattctaa ccatgcctaa tgatgatatt  1020
acgcatccaa ctcctgatct tacaggatat attactgagg gacagatata tatcgacaga  1080
cagttgtata acaggcagat atatcctcca atcaatgtcc ttccatcatt gtctcgtttg  1140
atgaagagtg ccattggtga gggaatgaca cgaaaggatc attctgatgt gtccaaccag  1200
ctctatgcaa attatgccat tggaaaggat gtccaggcaa tgaaagccgt ggtcggagaa  1260
gaagcacttt catctgagga cctgctgtat ttggaatttt tggagaagtt tgagaggaag  1320
tttgttgccc aaggagcata cgatacacgc aatatcttcc agtcactaga tcttgcatgg  1380
actttgcttc ggattttccc tcgcgagctt ctccaccgta ttcctgcaaa gactcttgat  1440
cagttctaca gccgagatgc cagtaac                                      1467

SEQ ID NO: 280         moltype = AA  length = 489
FEATURE                Location/Qualifiers
source                 1..489
                       mol_type = protein
                       organism = Glycine max
SEQUENCE: 280
MGVAQNIPDA EEGTLEIGME YRTVSGVAGP LVILDKVKGP KFQEIVNIRL GDGTTRRGQV  60
LEVDGEKAVV QVFEGTSGID NKFTTVQFTG EVLKTPVSLD MLGRIFNGSG KPIDNGPPIL  120
PEAYLDISGS SINPSERTYP EEMIQTGIST IDVMNSIARG QKIPLFSAAG LPHNEIAAQI  180
CRQAGLVKRL EKSDNLLEGG GEEDNFAIVF AAMGVNMETA QFFKRDFEEN GSMERVTLFL  240
NLANDPTIER IITPRIALTT AEYLAYECGK HVLVILTDMS SYADALREVS AAREEVPGRR  300
GYPGYMYTDL ATIYERAGRI EGRKGSITQI PILTMPNDDI THPTPDLTGY ITEGQIYIDR  360
QLYNRQIYPP INVLPSLSRL MKSAIGEGMT RKDHSDVSNQ LYANYAIGKD VQAMKAVVGE  420
EALSSEDLLY LEFLEKFERK FVAQGAYDTR NIFQSLDLAW TLLRIFPREL LHRIPAKTLD  480
QFYSRDASN                                                          489

SEQ ID NO: 281         moltype = AA  length = 17
FEATURE                Location/Qualifiers
source                 1..17
                       mol_type = protein
                       organism = Glycine max
SEQUENCE: 281
DHSDVSNQLY ANYAIGK                                                 17

SEQ ID NO: 282         moltype = AA  length = 26
FEATURE                Location/Qualifiers
source                 1..26
                       mol_type = protein
                       organism = Glycine max
SEQUENCE: 282
FQEIVNIRLG DGTTRRGQVL EVDGEK                                       26

SEQ ID NO: 283         moltype = AA  length = 12
FEATURE                Location/Qualifiers
source                 1..12
                       mol_type = protein
                       organism = Glycine max
SEQUENCE: 283
FTTVQFTGEV LK                                                      12

SEQ ID NO: 284         moltype = AA  length = 12
FEATURE                Location/Qualifiers
source                 1..12
                       mol_type = protein
                       organism = Glycine max
SEQUENCE: 284
TLDQFYSRDA SN                                                      12

SEQ ID NO: 285         moltype = DNA  length = 1464
FEATURE                Location/Qualifiers
source                 1..1464
                       mol_type = other DNA
                       organism = Glycine max
CDS                    1..1464
SEQUENCE: 285
atgggtgtgg ctgagaacat tcccgatatg gaggagggta ccttggagat tggaatggaa  60
tacagaactg tatctggagt tgctggacca ttggtcattc ttgacaaagt taagggaccc  120
aaatttcaag agattgttaa tattcgttta ggagatggaa ctactcggcg tggacaagtt  180
```

```
ctagaggttg atggcgaaaa ggctgttgtt caggtatttg aaggcacatc tgggatcgac  240
aataagttta caactgtgca atttactgga gaggtgttaa aaactcctgt ctcactggac  300
atgcttggac gcatatttaa tggttctgga aaaccaattg ataatggtcc accaatttta  360
cctgaggctt acctggatat ttctggaagt tccatcaatc ctagtgagag aacctatcct  420
gaggagatga tacagacagg aatatctaca attgatgtca tgaattctat tgctagaggt  480
caaaagatcc ctctattctc agcagctggt ctcccccata atgaaattgc tgcacagatc  540
tgtcgtcagg ctggcttagt caagcgacta gagaaatctg ataatcttct tgagggtgga  600
gaagaggaca attttgctat tgtgtttgca gctatgggag ttaacatgga gactgcacag  660
tttttcaagc gtgactttga ggagaatgga tcaatggaga gagtgactct tttccttaat  720
ttggcaaatg atcctacaat tgagcgtatt atcactcctc gtattgctct tactactgct  780
gaatatttgg cttatgaatg tggcaagcac gttcttgtga tactcacaga catgagttct  840
tatgctgatg ctcttcgtga ggtatctgct gcccgagaag aagtgccggg tagacgtggt  900
tatcctggat atatgtatac agatcttgca acaatttatg aacgagctgg gagaattgag  960
gggcgtaaag gctctattac acaaattcca attctaacca tgcccaatga tgatattacg  1020
cacccaactc ctgatctaac aggatatatc actgaggggc agatatacat cgacaggcag  1080
ctgtataata gacagatata cccaccaatc aacgtcctcc catcactatc tcggttgatg  1140
aagagtgcta ttggtgaggg aatgactaga agggatcatt ctgatgtgtc caaccagctc  1200
tatgcaaatt atgctattgg aaaggatgtc caggcaatga aagcagtggt tggagaagaa  1260
gcactttcat ctgaggacct gctgtatctg gaatttttgg agaagtttga gaggaagttt  1320
gttgcccagg gagcctatga cacccgcaat atattccagt cacttgatct tgcatggact  1380
ttactccgga ttttccctcg tgaacttctt catcgtatac cagccaagac tcttgaccag  1440
ttttacagca gagatgctgg taat                                        1464

SEQ ID NO: 286         moltype = AA  length = 488
FEATURE                Location/Qualifiers
source                 1..488
                       mol_type = protein
                       organism = Glycine max
SEQUENCE: 286
MGVAENIPDM EEGTLEIGME YRTVSGVAGP LVILDKVKGP KFQEIVNIRL GDGTTRRGQV  60
LEVDGEKAVV QVFEGTSGID NKFTTVQFTG EVLKTPVSLD MLGRIFNGSG KPIDNGPPIL  120
PEAYLDISGS SINPSERTYP EEMIQTGIST IDVMNSIARG QKIPLFSAAG LPHNEIAAQI  180
CRQAGLVKRL EKSDNLLEGG EEDNFAIVFA AMGVNMETAQ FFKRDFEENG SMERVTLFLN  240
LANDPTIERI ITPRIALTTA EYLAYECGKH VLVILTDMSS YADALREVSA AREEVPGRRG  300
YPGYMYTDLA TIYERAGRIE GRKGSITQIP ILTMPNDDIT HPTPDLTGYI TEGQIYIDRQ  360
LYNRQIYPPI NVLPSLSRLM KSAIGEGMTR RDHSDVSNQL YANYAIGKDV QAMKAVVGEE  420
ALSSEDLLYL EFLEKFERKF VAQGAYDTRN IFQSLDLAWT LLRIFPRELL HRIPAKTLDQ  480
FYSRDAGN                                                          488

SEQ ID NO: 287         moltype = AA  length = 26
FEATURE                Location/Qualifiers
source                 1..26
                       mol_type = protein
                       organism = Glycine max
SEQUENCE: 287
FQEIVNIRLG DGTTRRGQVL EVDGEK                                      26

SEQ ID NO: 288         moltype = AA  length = 12
FEATURE                Location/Qualifiers
source                 1..12
                       mol_type = protein
                       organism = Glycine max
SEQUENCE: 288
FTTVQFTGEV LK                                                     12

SEQ ID NO: 289         moltype = AA  length = 12
FEATURE                Location/Qualifiers
source                 1..12
                       mol_type = protein
                       organism = Glycine max
SEQUENCE: 289
TLDQFYSRDA GN                                                     12

SEQ ID NO: 290         moltype = DNA  length = 1407
FEATURE                Location/Qualifiers
source                 1..1407
                       mol_type = other DNA
                       organism = Glycine max
CDS                    1..1407
SEQUENCE: 290
atggccaccg ctgccgagaa actctccgct ctcaaatccg ccgtcgccgg attgaacgaa  60
atcagtgaga atgagaagaa cggattcatc agcctcgtcg gccgctatct cagtggcgaa  120
gcgcagcatg tggaatggag caagatccag acgcctacgg acgaagtggt tgtgccttac  180
gacactttgg cgccaactcc tgaaggttct tcggaggtga agaatctatt ggacaagctt  240
gtggtgttga agctaaatgg aggcttggga acaactatgg gttgcactgg tcctaaatct  300
gtaattgaag ttcgtgatgg gttgacattt ctagatttaa ttgtcatcca aattgagaat  360
ctcaattcca aatatggaag caatgttcct ttgcttttga tgaattcatt caacactcat  420
gatgacactc aaaagattgt tgaaaaatac caaaactcaa atattgagat tcatactttt  480
aaccagagcc agtatcctcg attggttgtt gaggactttt tgccattgcc ttccaaaggg  540
```

-continued

```
catactgaca aggatggatg gtaccctcct ggccatggtg atgtcttccc atcattattg  600
aacagtggca aacttgatgc actattgtca cagggtaaag agtatgtgtt tgttgccaat  660
tcggataact tgggagctat agttgacttg aaaatcttga atcatttgat ccagaacaag  720
aatgaatact gtatggaggt gactcccaaa acattggctg atgtaaaggg tggcactttg  780
atttcttacg aaggaagggt tcagctcctg gaaattgcac aagtccccga tgaacatgtc  840
aatgagttca agtcaataga gaagttcaaa attttcaaca caaataattt gtgggtgaac  900
ttaaacgcag ttaaaaggct tgttgaagct gatgctctta agatggaaat tattcccaat  960
ccaaaggaag ttgacggaat aaaagttctt cagctggaaa ctgcagctgg tgctgcaata  1020
aggttctttg acaaggctat tgggattaat gttcctcgat cacgattcct tcctgtgaag  1080
gcaacttcag atttgcttct tgtccagtct gacctctaca ctttggaaga cggatttgtc  1140
attcggaaca aagctaggga aaatcctgaa aacccttcta ttgaactggg accagaattt  1200
aagaaggtta gcaacttctt gggccgcttc aagtcaattc ctagtatcgt tgagcttgac  1260
agtctaaaag tggctggtga tgtatggttt ggagctggtg ttatcctcaa ggggaaagtc  1320
agcattgtat caaagcccgg tgtaaagctg gaagttcccg acggtgttgc cattgtagac  1380
aaggaaatta atggcccaga ggacctg                                      1407

SEQ ID NO: 291          moltype = AA  length = 469
FEATURE                 Location/Qualifiers
source                  1..469
                        mol_type = protein
                        organism = Glycine max
SEQUENCE: 291
MATAAEKLSA LKSAVAGLNE ISENEKNGFI SLVGRYLSGE AQHVEWSKIQ TPTDEVVVPY  60
DTLAPTPEGS SEVKNLLDKL VVLKLNGGLG TTMGCTGPKS VIEVRDGLTF LDLIVIQIEN  120
LNSKYGSNVP LLLMNSFNTH DDTQKIVEKY QNSNIEIHTF NQSQYPRLVV EDFLPLPSKG  180
HTDKDGWYPP GHGDVFPSLL NSGKLDALLS QGKEYVFVAN SDNLGAIVDL KILNHLIQNK  240
NEYCMEVTPK TLADVKGGTL ISYEGRVQLL EIAQVPDEHV NEFKSIEKFK IFNTNNLWVN  300
LNAVKRLVEA DALKMEIIPN PKEVDGIKVL QLETAAGAAI RFFDKAIGIN VPRSRFLPVK  360
ATSDLLLVQS DLYTLEDGFV IRNKARENPE NPSIELGPEF KKVSNFLGRF KSIPSIVELD  420
SLKVAGDVWF GAGVILKGKV SIVSKPGVKL EVPDGVAIVD KEINGPEDL             469

SEQ ID NO: 292          moltype = AA  length = 15
FEATURE                 Location/Qualifiers
source                  1..15
                        mol_type = protein
                        organism = Glycine max
SEQUENCE: 292
AIGINVPRSR FLPVK                                                   15

SEQ ID NO: 293          moltype = AA  length = 17
FEATURE                 Location/Qualifiers
source                  1..17
                        mol_type = protein
                        organism = Glycine max
SEQUENCE: 293
ARENPENPSI ELGPEFK                                                 17

SEQ ID NO: 294          moltype = AA  length = 24
FEATURE                 Location/Qualifiers
source                  1..24
                        mol_type = protein
                        organism = Glycine max
SEQUENCE: 294
ATSDLLLVQS DLYTLEDGFV IRNK                                         24

SEQ ID NO: 295          moltype = AA  length = 8
FEATURE                 Location/Qualifiers
source                  1..8
                        mol_type = protein
                        organism = Glycine max
SEQUENCE: 295
EINGPEDL                                                           8

SEQ ID NO: 296          moltype = AA  length = 18
FEATURE                 Location/Qualifiers
source                  1..18
                        mol_type = protein
                        organism = Glycine max
SEQUENCE: 296
EYVFVANSDN LGAIVDLK                                                18

SEQ ID NO: 297          moltype = AA  length = 9
FEATURE                 Location/Qualifiers
source                  1..9
                        mol_type = protein
                        organism = Glycine max
SEQUENCE: 297
ILNHLIQNK                                                          9
```

```
SEQ ID NO: 298          moltype = AA  length = 26
FEATURE                 Location/Qualifiers
source                  1..26
                        mol_type = protein
                        organism = Glycine max
SEQUENCE: 298
IQTPTDEVVV PYDTLAPTPE GSSEVK                                   26

SEQ ID NO: 299          moltype = AA  length = 9
FEATURE                 Location/Qualifiers
source                  1..9
                        mol_type = protein
                        organism = Glycine max
SEQUENCE: 299
LDALLSQGK                                                      9

SEQ ID NO: 300          moltype = AA  length = 9
FEATURE                 Location/Qualifiers
source                  1..9
                        mol_type = protein
                        organism = Glycine max
SEQUENCE: 300
RLVEADALK                                                      9

SEQ ID NO: 301          moltype = AA  length = 14
FEATURE                 Location/Qualifiers
source                  1..14
                        mol_type = protein
                        organism = Glycine max
SEQUENCE: 301
SAVAGLNEIS ENEK                                                14

SEQ ID NO: 302          moltype = AA  length = 12
FEATURE                 Location/Qualifiers
source                  1..12
                        mol_type = protein
                        organism = Glycine max
SEQUENCE: 302
SIPSIVELDS LK                                                  12

SEQ ID NO: 303          moltype = AA  length = 17
FEATURE                 Location/Qualifiers
source                  1..17
                        mol_type = protein
                        organism = Glycine max
SEQUENCE: 303
VLQLETAAGA AIRFFDK                                             17

SEQ ID NO: 304          moltype = AA  length = 9
FEATURE                 Location/Qualifiers
source                  1..9
                        mol_type = protein
                        organism = Glycine max
SEQUENCE: 304
VSNFLGRFK                                                      9

SEQ ID NO: 305          moltype = DNA  length = 1353
FEATURE                 Location/Qualifiers
source                  1..1353
                        mol_type = other DNA
                        organism = Glycine max
CDS                     1..1353
SEQUENCE: 305
atgaccaccg ccaccgagaa gctctccgct ctcaaatccg ccgtcgccgg attgaacgaa  60
atcagtgaga gtgagaagaa cggattcatc agcctcgtca gccgctatct cagtggcgaa  120
gcgcagcatg tggaatggag caagatccag acgcctacgg acgaagtggt tgtgccttac  180
gacactttgg cgccaactcc tgatggttct tcggacgtga agaatctatt ggacaagctt  240
gtggtgttga agctaaatgg aggcttgggc acaactatgg gttgcactgg tcctaaatct  300
gtaattgaag ttcgtgatgg gttgacattt ctagatttaa ttgtgatcca gattgagaat  360
ctcaattcca aatatggaag caatgttcct ttgcttttga tgaattcatt caacactcat  420
gatgacactc aaaagattgt tgaaaaatac caaaactcca atattgagat tcatactttt  480
aaccagggca tactgacaag gatggatggt accctcctgg cccatggaga tgtctttcca  540
tcattattga acagtggcaa acttgatgca ctattgtcac agggtaaaga gtatgtattt  600
gttgccaatt cagataactt gggagctata gttgacttga aaatcttaaa tcatttgatc  660
cagaacaaga atgaatactg tatggaggtg actcccaaaa cattggctga tgtaaagggt  720
ggcactttga tttcttacga aggaaggctt ttggaaattg cacaagtccc agatgaacat  780
gtcaatgagt tcaagtcaat agagaagttc aaaattttca acacaaataa tttgtgggtg  840
aacttaaatg cagttaaaag gcttgttgaa gctgatgctc ttaagatgga aattattccc  900
aatccaaagg aagttgatgg aataaaagtt cttcagctgg aaactgcagc tggtgctgca  960
```

```
ataaggttct ttgacaaggc tattgggatt aatgttcctc gatcacgatt ccttcctgtg  1020
aaggcaactt cagatttgct tcttgtccag tctgacctct acactttgga agatggattt  1080
gtcattcgga acaaagctag ggcaaatcct gaaaaccctt ctattgaact tgggccagaa  1140
tttaagaagg ttagcaactt cttgggccgc ttcaagtcaa ttcccagtat tgttgagctt  1200
gacagtctaa aagtggctgg caatgtatgg tttggagctg gtgttatcct caagggaaaa  1260
atcagtatcg tggccaatcc tggtgttaag ctggaagttc ccgatggtgc tgtcatttcg  1320
gataaggaaa ttaatggccc agaggacctc ctg                                1353

SEQ ID NO: 306          moltype = AA  length = 451
FEATURE                 Location/Qualifiers
source                  1..451
                        mol_type = protein
                        organism = Glycine max
SEQUENCE: 306
MTTATEKLSA LKSAVAGLNE ISESEKNGFI SLVSRYLSGE AQHVEWSKIQ TPTDEVVVPY  60
DTLAPTPDGS SDVKNLLDKL VVLKLNGGLG TTMGCTGPKS VIEVRDGLTF LDLIVIQIEN  120
LNSKYGSNVP LLLMNSFNTH DDTQKIVEKY QNSNIEIHTF NQGILTRMDG TLLAHGDVFP  180
SLLNSGKLDA LLSQGKEYVF VANSDNLGAI VDLKILNHLI QNKNEYCMEV TPKTLADVKG  240
GTLISYEGRL LEIAQVPDEH VNEFKSIEKF KIFNTNNLWV NLNAVKRLVE ADALKMEIIP  300
NPKEVDGIKV LQLETAAGAA IRFFDKAIGI NVPRSRFLPV KATSDLLLVQ SDLYTLEDGF  360
VIRNKARANP ENPSIELGPE FKKVSNFLGR FKSIPSIVEL DSLKVAGNVW FGAGVILKGK  420
ISIVANPGVK LEVPDGAVIS DKEINGPEDL L                                 451

SEQ ID NO: 307          moltype = AA  length = 15
FEATURE                 Location/Qualifiers
source                  1..15
                        mol_type = protein
                        organism = Glycine max
SEQUENCE: 307
AIGINVPRSR FLPVK                                                    15

SEQ ID NO: 308          moltype = AA  length = 24
FEATURE                 Location/Qualifiers
source                  1..24
                        mol_type = protein
                        organism = Glycine max
SEQUENCE: 308
ATSDLLLVQS DLYTLEDGFV IRNK                                          24

SEQ ID NO: 309          moltype = AA  length = 18
FEATURE                 Location/Qualifiers
source                  1..18
                        mol_type = protein
                        organism = Glycine max
SEQUENCE: 309
EYVFVANSDN LGAIVDLK                                                 18

SEQ ID NO: 310          moltype = AA  length = 9
FEATURE                 Location/Qualifiers
source                  1..9
                        mol_type = protein
                        organism = Glycine max
SEQUENCE: 310
ILNHLIQNK                                                           9

SEQ ID NO: 311          moltype = AA  length = 26
FEATURE                 Location/Qualifiers
source                  1..26
                        mol_type = protein
                        organism = Glycine max
SEQUENCE: 311
IQTPTDEVVV PYDTLAPTPD GSSDVK                                        26

SEQ ID NO: 312          moltype = AA  length = 9
FEATURE                 Location/Qualifiers
source                  1..9
                        mol_type = protein
                        organism = Glycine max
SEQUENCE: 312
LDALLSQGK                                                           9

SEQ ID NO: 313          moltype = AA  length = 12
FEATURE                 Location/Qualifiers
source                  1..12
                        mol_type = protein
                        organism = Glycine max
SEQUENCE: 313
LEVPDGAVIS DK                                                       12
```

```
SEQ ID NO: 314          moltype = AA  length = 9
FEATURE                 Location/Qualifiers
source                  1..9
                        mol_type = protein
                        organism = Glycine max
SEQUENCE: 314
RLVEADALK                                                          9

SEQ ID NO: 315          moltype = AA  length = 14
FEATURE                 Location/Qualifiers
source                  1..14
                        mol_type = protein
                        organism = Glycine max
SEQUENCE: 315
SAVAGLNEIS ESEK                                                    14

SEQ ID NO: 316          moltype = AA  length = 12
FEATURE                 Location/Qualifiers
source                  1..12
                        mol_type = protein
                        organism = Glycine max
SEQUENCE: 316
SIPSIVELDS LK                                                      12

SEQ ID NO: 317          moltype = AA  length = 17
FEATURE                 Location/Qualifiers
source                  1..17
                        mol_type = protein
                        organism = Glycine max
SEQUENCE: 317
VLQLETAAGA AIRFFDK                                                 17

SEQ ID NO: 318          moltype = AA  length = 9
FEATURE                 Location/Qualifiers
source                  1..9
                        mol_type = protein
                        organism = Glycine max
SEQUENCE: 318
VSNFLGRFK                                                          9

SEQ ID NO: 319          moltype = DNA  length = 1332
FEATURE                 Location/Qualifiers
source                  1..1332
                        mol_type = other DNA
                        organism = Glycine max
CDS                     1..1332
SEQUENCE: 319
atggatgagg agtacgatgt gatcgtgttg ggcacgggtc tcaaggagtg cattctcagc  60
ggtcttctct ccgtcgatgg cctcaaggtt ctgcacatgg acaggaatga ctattacgga  120
ggagaatcca cttcgctcaa tcttattcag ctttggaaga gattcagggg agatgacaag  180
cctcctccac atttgggagc tagcagggac tataacatcg atatgaaccc taagtttatt  240
atggctaatg gcaatttggt gcgggttctc atacatactg atgttactaa gtatctctct  300
ttcaaagctg tggatgggag ctttgtgttt aataaaggaa aggttcataa ggtgcccgca  360
aatgacatgg aggccttgaa gtctccactt atggggctat ttgaaaaacg ccgagcacgc  420
aagtttttca tttatgtgca aaattacaat gagagtgatc ccaagaccca tgaagggatg  480
gacttgacaa gagtgactac taaagagttg atagcaaaat acggtcttga tgataacact  540
atagacttca ttggtcatgc tttggcgctt catagtgatg atcgctactt ggctgagcca  600
gcactggaca ctgtgaagag aatgaagtta tatgcagagt ctcttgcacg ctttcaagga  660
gggtcacctt acatatatcc tttgtatggt ttaggagagc ttccccaggc atttgcacgg  720
cttagtgctg tttatggtgg gacatatatg ttgaataagc ctgagtgcaa ggtagaattt  780
gatgaggaag gaaaggttgt tggtgtcaca tctgaagggg aaactgcaaa gtgcaaaaaa  840
gttgtttgtg atccatcata tttgcccggc aaggtgagga aggttggtag ggttgcaaga  900
gcaatagcca taatgagtca cccaatcccc agcactgatg attcccattc ggtgcaaatt  960
attttaccac agaaacagtt gggtcggaag tcagacatgt acctattttg ttgttcatat  1020
actcacaatg ttgctccaaa gggaaaattt attgcatttg tatcaaccga ggcagagaca  1080
gatcagccag caattgaact aaaacctgga attgaccttc taggacctgt tgatgagata  1140
ttttttgata tctatgacag atatgaaccg gtcaatgaac ccactttgga caactgcttt  1200
gtatcaacaa gttatgatgc tactactcac tttgagtcga ccgtggatga tgttctcaac  1260
atgtatacat tgataactgg aaaggttatt gacctgagtg tggatcttag tgctgctagt  1320
gctgcagaag ag                                                      1332

SEQ ID NO: 320          moltype = AA  length = 444
FEATURE                 Location/Qualifiers
source                  1..444
                        mol_type = protein
                        organism = Glycine max
SEQUENCE: 320
MDEEYDVIVL GTGLKECILS GLLSVDGLKV LHMDRNDYYG GESTSLNLIQ LWKRFRGDDK  60
PPPHLGASRD YNIDMNPKFI MANGNLVRVL IHTDVTKYLS FKAVDGSFVF NKGKVHKVPA  120
```

```
NDMEALKSPL MGLFEKRRAR KFFIYVQNYN ESDPKTHEGM DLTRVTTKEL IAKYGLDDNT  180
IDFIGHALAL HSDDRYLAEP ALDTVKRMKL YAESLARFQG GSPYIYPLYG LGELPQAFAR  240
LSAVYGGTYM LNKPECKVEF DEEGKVVGVT SEGETAKCKK VVCDPSYLPG KVRKVGRVAR  300
AIAIMSHPIP STDDSHSVQI ILPQKQLGRK SDMYLFCCSY THNVAPKGKF IAFVSTEAET  360
DQPAIELKPG IDLLGPVDEI FFDIYDRYEP VNEPTLDNCF VSTSYDATTH FESTVDDVLN  420
MYTLITGKVI DLSVDLSAAS AAEE                                        444

SEQ ID NO: 321          moltype = AA  length = 10
FEATURE                 Location/Qualifiers
source                  1..10
                        mol_type = protein
                        organism = Glycine max
SEQUENCE: 321
AVDGSFVFNK                                                        10

SEQ ID NO: 322          moltype = AA  length = 14
FEATURE                 Location/Qualifiers
source                  1..14
                        mol_type = protein
                        organism = Glycine max
SEQUENCE: 322
FFIYVQNYNE SDPK                                                   14

SEQ ID NO: 323          moltype = AA  length = 8
FEATURE                 Location/Qualifiers
source                  1..8
                        mol_type = protein
                        organism = Glycine max
SEQUENCE: 323
VEFDEEGK                                                          8

SEQ ID NO: 324          moltype = AA  length = 16
FEATURE                 Location/Qualifiers
source                  1..16
                        mol_type = protein
                        organism = Glycine max
SEQUENCE: 324
VIDLSVDLSA ASAAEE                                                 16

SEQ ID NO: 325          moltype = AA  length = 12
FEATURE                 Location/Qualifiers
source                  1..12
                        mol_type = protein
                        organism = Glycine max
SEQUENCE: 325
VVGVTSEGET AK                                                     12

SEQ ID NO: 326          moltype = DNA  length = 1332
FEATURE                 Location/Qualifiers
source                  1..1332
                        mol_type = other DNA
                        organism = Glycine max
CDS                     1..1332
SEQUENCE: 326
atggatgagg agtacgatgt gatcgtgttg ggcacgggtc tcaaggagtg cattctcagc  60
ggtcttctct ccgtcgatgg cctcaaggtt ctgcatatgg ataggaacga ctattacgga  120
ggagaatcca cttcgctcaa tcttattcag ctttggaaga gattcagggg agatgacaag  180
cctcctccac atttgggcgc tagcagggac tacaacatcg atatgaaccc caagtttatt  240
atggctaatg gcaatttggt gcgggttctc atacataccg atgttacaaa gtatctctat  300
ttcaaagctg tggatgggag ctatgtgttt aataaaggaa aggttcataa ggtgcctgca  360
aacgacatgg aggccttgaa gtccccactt atggggctat ttgaaaaacg ccgggcacgc  420
aagtttttca tttatgtgca aaactacaac gagagcgatc ccaagaccca cgaggggatg  480
gacttgacaa gagtgactac taaagagttg atagcaaaat acggccttga tgacaacact  540
atagacttca ttggtcatgc tttggcgctt catagcgatg atcgctactt ggctgagcca  600
gcactggaca ccgtgaagag aatgaagtta tatgcagagt ctcttgcacg ctttcaagga  660
gggtcacctt acatatatcc tttgtatggt ttaggagagc ttccccaggc atttgcacgg  720
cttagtgctg tttatggtgg aacatatatg ttgaataagc ctgagtgcaa ggtagaattt  780
gatgaggaag gaaaggttgt tggtgttaca tctgaagggg aaactgcaaa gtgtaaaaaa  840
gttgtttgtg atccatcata tttgcctggc aaggtgagga aggttggtag ggttgcaagg  900
gcgatagcca tcatgagcca cccaatcccc agcactgatg attcccattc agtgcaaatt  960
attttaccac agaaacagtt gggtcggaag tcagacatgt acctattttg ttgttcgtat  1020
actcacaatg ttgctccaaa gggaaaattt attgcatttg tatcaactga ggcagagaca  1080
gatcagccgg caattggact gaaacctgga attgaccttc taggacctgt tgatgagata  1140
ttttttgata tctatgacag atatgaacca gtcaacgaac ccactttgga caactgcttt  1200
atatcaacaa gttatgatgc tactactcac tttgagtcga ctgtggatga cgttctcaac  1260
atgtatacat tgataactgg aaaggttatt gacctcagtg tggatcttag tgctgctagt  1320
gctgcagaag ag                                                     1332

SEQ ID NO: 327          moltype = AA  length = 444
```

```
FEATURE                Location/Qualifiers
source                 1..444
                       mol_type = protein
                       organism = Glycine max
SEQUENCE: 327
MDEEYDVIVL GTGLKECILS GLLSVDGLKV LHMDRNDYYG GESTSLNLIQ LWKRFRGDDK  60
PPPHLGASRD YNIDMNPKFI MANGNLVRVL IHTDVTKYLY FKAVDGSYVF NKGKVHKVPA  120
NDMEALKSPL MGLFEKRRAR KFFIYVQNYN ESDPKTHEGM DLTRVTTKEL IAKYGLDDNT  180
IDFIGHALAL HSDDRYLAEP ALDTVKRMKL YAESLARFQG GSPYIYPLYG LGELPQAFAR  240
LSAVYGGTYM LNKPECKVEF DEEGKVVGVT SEGETAKCKK VVCDPSYLPG KVRKVGRVAR  300
AIAIMSHPIP STDDSHSVQI ILPQKQLGRK SDMYLFCCSY THNVAPKGKF IAFVSTEAET  360
DQPAIGLKPG IDLLGPVDEI FFDIYDRYEP VNEPTLDNCF ISTSYDATTH FESTVDDVLN  420
MYTLITGKVI DLSVDLSAAS AAEE                                        444

SEQ ID NO: 328         moltype = AA  length = 10
FEATURE                Location/Qualifiers
source                 1..10
                       mol_type = protein
                       organism = Glycine max
SEQUENCE: 328
AVDGSYVFNK                                                        10

SEQ ID NO: 329         moltype = AA  length = 14
FEATURE                Location/Qualifiers
source                 1..14
                       mol_type = protein
                       organism = Glycine max
SEQUENCE: 329
FFIYVQNYNE SDPK                                                   14

SEQ ID NO: 330         moltype = AA  length = 8
FEATURE                Location/Qualifiers
source                 1..8
                       mol_type = protein
                       organism = Glycine max
SEQUENCE: 330
VEFDEEGK                                                          8

SEQ ID NO: 331         moltype = AA  length = 16
FEATURE                Location/Qualifiers
source                 1..16
                       mol_type = protein
                       organism = Glycine max
SEQUENCE: 331
VIDLSVDLSA ASAAEE                                                 16

SEQ ID NO: 332         moltype = AA  length = 12
FEATURE                Location/Qualifiers
source                 1..12
                       mol_type = protein
                       organism = Glycine max
SEQUENCE: 332
VVGVTSEGET AK                                                     12

SEQ ID NO: 333         moltype = DNA  length = 1512
FEATURE                Location/Qualifiers
source                 1..1512
                       mol_type = other DNA
                       organism = Glycine max
CDS                    1..1512
SEQUENCE: 333
atggcgatga gaaccaaact ttctttagct atctttttct tttttctttt agccttattt  60
tcaaacctag cctttggcaa atgtaaagaa accgaggtag aagaagaaga ccctgagctc  120
gtaacatgca aacaccaatg ccaacagcca cagcaataca ctgagggtga caagcgggta  180
tgcttgcaaa gatgtgacag gtatcatcgt atgaagcaag agcgagagaa acaaatccaa  240
gaggaaactc gtgagaagaa agaggaggaa agccgtgaaa gggaagaaga acaacaagag  300
cagcatgagg aacaagatga aaatccctac atttttgagg aagataagga ttttgagacc  360
agagtcgaaa ctgaaggtgg cagaattcgg gttctcaaga agttcactga aaaatccaag  420
cttcttcagg gcattgagaa cttccgtttg gccattttgg aagctagagc acacacgttc  480
gtgtctcctc gccactttga ttccgaggtt gttttttca acatcaaggg gcgagccgta  540
cttgggttgg tgagtgaaag tgaaacagaa aaaatcaccc ttgaacctgg ggacatgata  600
cacataccag ctggcacccc actgtacatc gttaacagag atgagaatga taagctcttc  660
cttgccatgc tccatatacc tgtctctgtc tctactcctg gaaaatttga ggaatttttc  720
gggcctggag gacgagaccc agaatcggtc ctctcagcat tcagctggaa tgtgctgcaa  780
gctgcgctcc aaaccccaaa aggaaagtta gaaaagcttt ttgatcaaca gaacgaggga  840
agtattttcg caataagcag agaacaggtg cgtgcgttgg cccctaccaa gaaaagctct  900
tggtggccat tcggtggcga atccaagcct caattcaata ttttcagcaa gcgtcccact  960
atctccaacg gatatggtcg tttaactgaa gttggtcctg acgatgatga aaagagttgg  1020
cttcaaagac tcaatctcat gcttaccttt accaacatca cccagagatc tatgagtact  1080
```

```
attcactaca actcacatgc aacgaagata gcactggtga tcgatggcag agggcatctt  1140
caaatatcat gtccacacat gtcatcaagg tcgtcacact cgaagcatga taagagtagc  1200
ccttcatacc atagaatcag ttccgatttg aagcctggaa tggtgtttgt tgtccctccc  1260
ggtcatccct tcgtcaccat agcttccaat aaagagaatc tcctcatgat ttgcttcgag  1320
gttaacgctc gagacaacaa gaagtttaca tttgcaggga aggacaacat tgtgagttct  1380
ctggacaacg ttgctaagga gcttgccttt aactatcctt ctgagatggt gaacggagta  1440
ttcgaccgaa aggagagttt ctttttccct tttgagttgc cgagagagga gcgtggtcgt  1500
cgcgctgatg cg                                                      1512

SEQ ID NO: 334         moltype = AA  length = 504
FEATURE                Location/Qualifiers
source                 1..504
                       mol_type = protein
                       organism = Glycine max
SEQUENCE: 334
MAMRTKLSLA IFFFFLLALF SNLAFGKCKE TEVEEEDPEL VTCKHQCQQP QQYTEGDKRV  60
CLQRCDRYHR MKQEREKQIQ EETREKKEEE SREREEEQQE QHEEQDENPY IFEEDKDFET  120
RVETEGGRIR VLKKFTEKSK LLQGIENFRL AILEARAHTF VSPRHFDSEV VFFNIKGRAV  180
LGLVSESETE KITLEPGDMI HIPAGTPLYI VNRDENDKLF LAMLHIPVSV STPGKFEEFF  240
GPGGRDPESV LSAFSWNVLQ AALQTPKGKL EKLFDQQNEG SIFAISREQV RALAPTKKSS  300
WWPFGGESKP QFNIFSKRPT ISNGYGRLTE VGPDDDEKSW LQRLNLMLTF TNITQRSMST  360
IHYNSHATKI ALVIDGRGHL QISCPHMSSR SSHSKHDKSS PSYHRISSDL KPGMVFVVPP  420
GHPFVTIASN KENLLMICFE VNARDNKKFT FAGKDNIVSS LDNVAKELAF NYPSEMVNGV  480
FDRKESFFFP FELPREERGR RADA                                         504

SEQ ID NO: 335         moltype = AA  length = 17
FEATURE                Location/Qualifiers
source                 1..17
                       mol_type = protein
                       organism = Glycine max
SEQUENCE: 335
DFETRVETEG GRIRVLK                                                 17

SEQ ID NO: 336         moltype = AA  length = 12
FEATURE                Location/Qualifiers
source                 1..12
                       mol_type = protein
                       organism = Glycine max
SEQUENCE: 336
DNIVSSLDNV AK                                                      12

SEQ ID NO: 337         moltype = AA  length = 15
FEATURE                Location/Qualifiers
source                 1..15
                       mol_type = protein
                       organism = Glycine max
SEQUENCE: 337
GRAVLGLVSE SETEK                                                   15

SEQ ID NO: 338         moltype = AA  length = 25
FEATURE                Location/Qualifiers
source                 1..25
                       mol_type = protein
                       organism = Glycine max
SEQUENCE: 338
LFDQQNEGSI FAISREQVRA LAPTK                                        25

SEQ ID NO: 339         moltype = AA  length = 21
FEATURE                Location/Qualifiers
source                 1..21
                       mol_type = protein
                       organism = Glycine max
SEQUENCE: 339
RPTISNGYGR LTEVGPDDDE K                                            21

SEQ ID NO: 340         moltype = DNA  length = 1467
FEATURE                Location/Qualifiers
source                 1..1467
                       mol_type = other DNA
                       organism = Glycine max
CDS                    1..1467
SEQUENCE: 340
atggcgacca gagccaagct ttctttagct atcttccttt tctttctttt agccttgatt  60
tcaaacctag ccttgggcaa acttaaagaa accgaggtcg aagaagatcc cgagctcgta  120
acatgcaaac accagtgcca acagcaacgg caatacactg agagtgacaa gcgaacatgc  180
ttgcaacaat gtgacagtat gaagcaagag cgagagaaac aagtcgaaga ggaaactcgc  240
gagaaggaag aagaacatca agagcagcat gaggaggagc aagaccaaaa tccctacgtt  300
tttgaagaag ataaggattt ttcgaccaga gtcgaaacag aaggtggcag cattcgggtt  360
ctcaagaagt tcactgagaa atccaagctt cttcaaggca atgagaattt ccgtttggcc  420
```

```
atcttagaag ctagagcaca cacgttcgtg tccccacgcc actttgattc cgaggttgtc  480
ttgttcaaca ttaaggggag agccgtactt gggttggtga gggaaagtga aacagaaaaa  540
atcaccctag aacctggaga catgatacac ataccagcag gcacaccact gtacatcgtt  600
aacagagatg agaatgagaa gctcctcctt gccatgctcc atatacctgt ctctactcct  660
ggaaaatttg aggaattttt cgggcctgga ggacgagacc cagaatcggt cctctcagca  720
ttcagctgga atgtgctgca agctgcgctc caaaccccaa aaggaaagtt agaaaggctt  780
tttaatcaac agaacgaggg aagtattttc aaaataagca gagaacgggt gcgtgcgttg  840
gcccccacca agaaaagctc ttggtggcca ttcggcggcg aatccaaggc tcaattcaat  900
attttcagca agcgtcccac tttctccaac ggatatggcc gtttaactga agttggtcct  960
gatgatgaaa agagttggct tcaaagactc aacctcatgc ttacctttac caacatcacc  1020
cagagatcta tgagtactat tcactacaac tcacatgcaa cgaagatagc actggtgatg  1080
gatggtagag ggcatcttca aatatcatgt ccacacatgt catcaaggtc agactcaaag  1140
catgataaga gtagcccctc ataccataga atcagtgcgg acttgaagcc tggaatggtg  1200
tttgttgtcc ctcctggtca tcccttcgtc actatagctt ccaataaaga gaatctcctc  1260
ataatttgct tcgaggttaa cgttcgagac aacaagaagt ttacgtttgc agggaaggac  1320
aacattgtga gctctctgga caacgtagct aaggagctgg cctttaacta tccttctgag  1380
atggtgaacg gagtcttcga aagaaaggag agtctctttt tcccccttcga gttgccgagc  1440
gaggagcgtg gtcgtcgcgc tgttgcg                                      1467

SEQ ID NO: 341          moltype = AA  length = 489
FEATURE                 Location/Qualifiers
source                  1..489
                        mol_type = protein
                        organism = Glycine max
SEQUENCE: 341
MATRAKLSLA IFLFFLLALI SNLALGKLKE TEVEEDPELV TCKHQCQQQR QYTESDKRTC  60
LQQCDSMKQE REKQVEEETR EKEEEHQEQH EEEQDQNPYV FEEDKDFSTR VETEGGSIRV  120
LKKFTEKSKL LQGNENFRLA ILEARAHTFV SPRHFDSEVV LFNIKGRAVL GLVRESETEK  180
ITLEPGDMIH IPAGTPLYIV NRDENEKLLL AMLHIPVSTP GKFEEFFGPG GRDPESVLSA  240
FSWNVLQAAL QTPKGKLERL FNQQNEGSIF KISRERVRAL APTKKSSWWP FGGESKAQFN  300
IFSKRPTFSN GYGRLTEVGP DDEKSWLQRL NLMLTFTNIT QRSMSTIHYN SHATKIALVM  360
DGRGHLQISC PHMSSRSDSK HDKSSPSYHR ISADLKPGMV FVVPPGHPFV TIASNKENLL  420
IICFEVNVRD NKKFTFAGKD NIVSSLDNVA KELAFNYPSE MVNGVFERKE SLFFPFELPS  480
EERGRRAVA                                                          489

SEQ ID NO: 342          moltype = AA  length = 8
FEATURE                 Location/Qualifiers
source                  1..8
                        mol_type = protein
                        organism = Glycine max
SEQUENCE: 342
AQFNIFSK                                                           8

SEQ ID NO: 343          moltype = AA  length = 17
FEATURE                 Location/Qualifiers
source                  1..17
                        mol_type = protein
                        organism = Glycine max
SEQUENCE: 343
DFSTRVETEG GSIRVLK                                                 17

SEQ ID NO: 344          moltype = AA  length = 12
FEATURE                 Location/Qualifiers
source                  1..12
                        mol_type = protein
                        organism = Glycine max
SEQUENCE: 344
DNIVSSLDNV AK                                                      12

SEQ ID NO: 345          moltype = AA  length = 15
FEATURE                 Location/Qualifiers
source                  1..15
                        mol_type = protein
                        organism = Glycine max
SEQUENCE: 345
GRAVLGLVRE SETEK                                                   15

SEQ ID NO: 346          moltype = AA  length = 20
FEATURE                 Location/Qualifiers
source                  1..20
                        mol_type = protein
                        organism = Glycine max
SEQUENCE: 346
RPTFSNGYGR LTEVGPDDEK                                              20

SEQ ID NO: 347          moltype = DNA  length = 1266
FEATURE                 Location/Qualifiers
source                  1..1266
                        mol_type = other DNA
```

```
                        organism = Glycine max
CDS                     1..1266
SEQUENCE: 347
atggtgagag gattgctcaa caagctcgtc tctcgctccc tctcggtcgc cggaaaatgg  60
cagcacaatc aactccgccg cctcaacatc cacgagtacc agggtgctga attgatgagc  120
aaacacggag tcaacgttcc gagaggcgtg gctgtttcct ctgttgaaga ggccagaaag  180
gtcatcaagg accttttccc taatgaaaat gagttggtgg ttaagagtca aattttagcc  240
ggcggacgag gtttgggaac tttcaaaagc ggccttaagg gaggagtgca cattgttaag  300
actgaccagg ttgaagacat agctgggaag atgcttggac agatactagt taccaaacag  360
actggtcctc agggaaaaat agttagcaag gtttacttgt gtgaaaagct gtcacttgta  420
aatgagatgt actttgctat aacactggat cgtacgagtg ctggtccaat tataattgct  480
tgtagtaagg gaggaaccag cattgaagac cttgcagaga aatttccgga catgattata  540
aaggtacctg ttgatgtttt tgaaggtatt actgatgaag gtgctgcaaa ggttgttgat  600
ggtttggctc tcaaagtggc tgatagaaat aagtcgattg aacaagtgaa gaatttgtat  660
aaactttttg ttgattgtga ctgcactctt ttggaaatca atcccatagc ggagacagct  720
gataaccaat tggtggctgc tgatgctaag ttgaattttg atgataatgc tgcatatcgc  780
cagaaagaga tattttctct ccgtgataca acacaagagg accctcgaga ggtgactgct  840
gcaaaggcag atttaaatta tattgggtta gatggagaaa ttggctgcat ggtgaatgga  900
gcagggttag caatggccac aatggatata attaaattgc atgggggtac tcctgccaat  960
tttctggatg taggtggcaa tgcctctgaa aaccaggttg ttgaggcatt taaaatattg  1020
actgctgatg acaaagtgaa ggcaattttg gttaacattt ttggtggtat aatgaagtgt  1080
gatgttatag caagtggaat agtgaatgct gcaaaagagg ttgcactgaa agtaccagtt  1140
gtagttcgtc tggaaggcac caatgttgat caaggaaaaa gaatattgaa ggaaagtggt  1200
atggcattaa taacggctga agatttagat gatgcagctc agaaagcagt gaaagctgct  1260
tacaaa                                                             1266

SEQ ID NO: 348          moltype = AA  length = 422
FEATURE                 Location/Qualifiers
source                  1..422
                        mol_type = protein
                        organism = Glycine max
SEQUENCE: 348
MVRGLLNKLV SRSLSVAGKW QHNQLRRLNI HEYQGAELMS KHGVNVPRGV AVSSVEEARK  60
VIKDLFPNEN ELVVKSQILA GGRGLGTFKS GLKGGVHIVK TDQVEDIAGK MLGQILVTKQ  120
TGPQGKIVSK VYLCEKLSLV NEMYFAITLD RTSAGPIIIA CSKGGTSIED LAEKFPDMII  180
KVPVDVFEGI TDEGAAKVVD GLALKVADRN KSIEQVKNLY KLFVDCDCTL LEINPIAETA  240
DNQLVAADAK LNFDDNAAYR QKEIFSLRDT TQEDPREVTA AKADLNYIGL DGEIGCMVNG  300
AGLAMATMDI IKLHGGTPAN FLDVGGNASE NQVVEAFKIL TADDKVKAIL VNIFGGIMKC  360
DVIASGIVNA AKEVALKVPV VVRLEGTNVD QGKRILKESG MALITAEDLD DAAQKAVKAA  420
YK                                                                 422

SEQ ID NO: 349          moltype = AA  length = 12
FEATURE                 Location/Qualifiers
source                  1..12
                        mol_type = protein
                        organism = Glycine max
SEQUENCE: 349
DLFPNENELV VK                                                      12

SEQ ID NO: 350          moltype = AA  length = 20
FEATURE                 Location/Qualifiers
source                  1..20
                        mol_type = protein
                        organism = Glycine max
SEQUENCE: 350
EIFSLRDTTQ EDPREVTAAK                                              20

SEQ ID NO: 351          moltype = AA  length = 26
FEATURE                 Location/Qualifiers
source                  1..26
                        mol_type = protein
                        organism = Glycine max
SEQUENCE: 351
LHGGTPANFL DVGGNASENQ VVEAFK                                       26

SEQ ID NO: 352          moltype = AA  length = 12
FEATURE                 Location/Qualifiers
source                  1..12
                        mol_type = protein
                        organism = Glycine max
SEQUENCE: 352
LNFDDNAAYR QK                                                      12

SEQ ID NO: 353          moltype = AA  length = 14
FEATURE                 Location/Qualifiers
source                  1..14
                        mol_type = protein
                        organism = Glycine max
SEQUENCE: 353
```

```
SQILAGGRGL GTFK                                                    14

SEQ ID NO: 354          moltype = AA  length = 10
FEATURE                 Location/Qualifiers
source                  1..10
                        mol_type = protein
                        organism = Glycine max
SEQUENCE: 354
TDQVEDIAGK                                                         10

SEQ ID NO: 355          moltype = AA  length = 16
FEATURE                 Location/Qualifiers
source                  1..16
                        mol_type = protein
                        organism = Glycine max
SEQUENCE: 355
VPVVVRLEGT NVDQGK                                                  16

SEQ ID NO: 356          moltype = AA  length = 8
FEATURE                 Location/Qualifiers
source                  1..8
                        mol_type = protein
                        organism = Glycine max
SEQUENCE: 356
VVDGLALK                                                           8

SEQ ID NO: 357          moltype = DNA  length = 1266
FEATURE                 Location/Qualifiers
source                  1..1266
                        mol_type = other DNA
                        organism = Glycine max
CDS                     1..1266
SEQUENCE: 357
atggtgaggg gattgctcaa caagctcgtc tctcgctccc tctccgtcgc cggaaaatgg  60
cagcacaacc aactccgccg cctcaacatc cacgagtacc agggcgctga attgatgagc  120
aaacacggag ttaatgttcc gagaggcgtg gctgtttcct ctgttgaaga ggtcagaaag  180
gccatcaagg acctttttccc taatgaaaat gagttggtgg ttaagagtca aattttagcc  240
ggtggaagag gtttgggaac tttcaaaagc ggccttaagg gaggagtgca cattgttaag  300
actgaccagg ttgaagacat agctgggaag atgcttgggc agatactagt taccaaacag  360
actggtcctc agggaaaaat agttagcaag gtttacttgt gtgaaaagct gtcactagta  420
aatgagatgt actttgctat aacactggat cgtacgagtg ctggtccaat tataattgct  480
tgtagtaagg gaggaaccag cattgaagac ctagcagaga aatttccgga catgattata  540
aaggtacctg ttgatgtttt tgaaggaatt actgatgaag atgctgcaaa ggttgttgat  600
ggtttggctc tcaaagtggc tgatagaaat aagtcgattg aacaagtgaa gaatttgtat  660
aaactttttg ttgattgtga ctgcaccctt ttggaaatca atcccattgc ggagacagct  720
gataaccaat tggtggctgc tgatgctaag ttgaattttg acgataatgc tgcatatcgc  780
cagaaagaga tatttgctct ccgtgataca acacaagagg accctcgaga ggtgactgct  840
gcaaaggcag acttaaatta tattgggtta gatggagaaa taggctgcat ggtgaatgga  900
gcagggttag caatggccac aatggatata attaaattgc atgggggtac tcctgccaat  960
tttttggatg taggtggcaa tgcctctgaa ggccaggtgg ttgaggcatt taaaatattg  1020
actgctgatg acaaagtgaa ggcaattttg gttaacattt ttgggggtat aatgaagtgt  1080
gatgttatag caagtggaat agtgaatgct gcaaaagagg ttgcactgaa agtacccgta  1140
gtagttcgtc tggaaggcac caatgttgat catggaaaaa gaattttgaa ggaaagtggt  1200
atggcgttga taacggctga agatttagat gatgctgctc agaaagcagt gaaagctgct  1260
tacaaa                                                             1266

SEQ ID NO: 358          moltype = AA  length = 422
FEATURE                 Location/Qualifiers
source                  1..422
                        mol_type = protein
                        organism = Glycine max
SEQUENCE: 358
MVRGLLNKLV SRSLSVAGKW QHNQLRRLNI HEYQGAELMS KHGVNVPRGV AVSSVEEVRK  60
AIKDLFPNEN ELVVKSQILA GGRGLGTFKS GLKGGVHIVK TDQVEDIAGK MLGQILVTKQ  120
TGPQGKIVSK VYLCEKLSLV NEMYFAITLD RTSAGPIIIA CSKGGTSIED LAEKFPDMII  180
KVPVDVFEGI TDEDAAKVVD GLALKVADRN KSIEQVKNLY KLFVDCDCTL LEINPIAETA  240
DNQLVAADAK LNFDDNAAYR QKEIFALRDT TQEDPREVTA AKADLNYIGL DGEIGCMVNG  300
AGLAMATMDI IKLHGGTPAN FLDVGGNASE GQVVEAFKIL TADDKVKAIL VNIFGGIMKC  360
DVIASGIVNA AKEVALKVPV VVRLEGTNVD HGKRILKESG MALITAEDLD DAAQKAVKAA  420
YK                                                                 422

SEQ ID NO: 359          moltype = AA  length = 12
FEATURE                 Location/Qualifiers
source                  1..12
                        mol_type = protein
                        organism = Glycine max
SEQUENCE: 359
DLFPNENELV VK                                                      12
```

```
SEQ ID NO: 360          moltype = AA  length = 20
FEATURE                 Location/Qualifiers
source                  1..20
                        mol_type = protein
                        organism = Glycine max
SEQUENCE: 360
EIFALRDTTQ EDPREVTAAK                                                   20

SEQ ID NO: 361          moltype = AA  length = 26
FEATURE                 Location/Qualifiers
source                  1..26
                        mol_type = protein
                        organism = Glycine max
SEQUENCE: 361
LHGGTPANFL DVGGNASEGQ VVEAFK                                            26

SEQ ID NO: 362          moltype = AA  length = 12
FEATURE                 Location/Qualifiers
source                  1..12
                        mol_type = protein
                        organism = Glycine max
SEQUENCE: 362
LNFDDNAAYR QK                                                           12

SEQ ID NO: 363          moltype = AA  length = 14
FEATURE                 Location/Qualifiers
source                  1..14
                        mol_type = protein
                        organism = Glycine max
SEQUENCE: 363
SQILAGGRGL GTFK                                                         14

SEQ ID NO: 364          moltype = AA  length = 10
FEATURE                 Location/Qualifiers
source                  1..10
                        mol_type = protein
                        organism = Glycine max
SEQUENCE: 364
TDQVEDIAGK                                                              10

SEQ ID NO: 365          moltype = AA  length = 8
FEATURE                 Location/Qualifiers
source                  1..8
                        mol_type = protein
                        organism = Glycine max
SEQUENCE: 365
VVDGLALK                                                                8

SEQ ID NO: 366          moltype = DNA  length = 1203
FEATURE                 Location/Qualifiers
source                  1..1203
                        mol_type = other DNA
                        organism = Glycine max
CDS                     1..1203
SEQUENCE: 366
atggcgacta agaggagcgt gggaacgttg aaggagggtg atttgaaggg gaagagggta  60
ttcgtgaggg tcgatctgaa cgtgcctttg gatgacaacc ttaacatcac cgatgacact  120
agagtccgtg ctgctgttcc caccatcaag tacttgactg gttatggtgc taaagtgatc  180
ctttctagcc atttgggacg tccaaaaggt gtaacaccta aatacagttt gaagcctctt  240
gtgccaaggc tgtctcaact tcttggaatt gaggttacga tggccaatga ctctattggg  300
gaggaagttg aaaagttggt tacacaactt ccagaaggtg gtgttttgct tctagagaat  360
gtgaggttct acaaggagga agagaagaat gatcctgaat ttgcaaagaa gttggcttct  420
ctagctgatc tctatgtgaa tgatgcattt ggcactgccc acagagctca tgcttctaca  480
gaaggagttg ccaaatactt gaagccctct gttgcaggat tcctaatgca gaaggagctt  540
gattatctag ttggggctgt gtcaaacccc aagagaccat ttgctgctat tgtcggtgga  600
tcgaaggtgt cttccaagat tggagttatt gaatccttgt tggagaaagt taatgttctc  660
ttgcttggtg gaggaatgat ctttaccttt tacaaggctc agggttattc agttgggtca  720
tctcttgtgg aggaagacaa gcttagcctt gcaactacac ttcttgaaaa ggccaaggct  780
aaaggggttt ctttgttgct tccaactgat gttgtcatag cagacaagtt tgctgctgat  840
gctaacagca agactgtgcc ggcatcaagc atcccagatg ggtggatggg gttggatatt  900
ggtcctgatt ccatcaagac atttggtgaa gcattggata cgactcagac cattatttgg  960
aatggaccaa tgggtgtttt tgagtttgat aagtttgcca caggaacaga ggctatagcc  1020
aagaaactgg cagagctgag tgggaaggga gtgacaacca tcattggagg aggtgactcc  1080
gttgccgctg tggagaaggt tggacttgca gacaagatga gccacatctc cactggtggt  1140
ggtgccagct tagagcttct tgagggaaag caactccctg gtgtccttgc tcttgatgat  1200
gct                                                                1203

SEQ ID NO: 367          moltype = AA  length = 401
FEATURE                 Location/Qualifiers
```

```
source                  1..401
                        mol_type = protein
                        organism = Glycine max
SEQUENCE: 367
MATKRSVGTL KEGDLKGKRV FVRVDLNVPL DDNLNITDDT RVRAAVPTIK YLTGYGAKVI  60
LSSHLGRPKG VTPKYSLKPL VPRLSQLLGI EVTMANDSIG EEVEKLVTQL PEGGVLLLEN  120
VRFYKEEEKN DPEFAKKLAS LADLYVNDAF GTAHRAHAST EGVAKYLKPS VAGFLMQKEL  180
DYLVGAVSNP KRPFAAIVGG SKVSSKIGVI ESLLEKVNVL LLGGGMIFTF YKAQGYSVGS  240
SLVEEDKLSL ATTLLEKAKA KGVSLLLPTD VVIADKFAAD ANSKTVPASS IPDGWMGLDI  300
GPDSIKTFGE ALDTTQTIIW NGPMGVFEFD KFATGTEAIA KKLAELSGKG VTTIIGGGDS  360
VAAVEKVGLA DKMSHISTGG GASLELLEGK QLPGVLALDD A                    401

SEQ ID NO: 368          moltype = AA  length = 15
FEATURE                 Location/Qualifiers
source                  1..15
                        mol_type = protein
                        organism = Glycine max
SEQUENCE: 368
AQGYSVGSSL VEEDK                                                  15

SEQ ID NO: 369          moltype = AA  length = 13
FEATURE                 Location/Qualifiers
source                  1..13
                        mol_type = protein
                        organism = Glycine max
SEQUENCE: 369
ELDYLVGAVS NPK                                                    13

SEQ ID NO: 370          moltype = AA  length = 8
FEATURE                 Location/Qualifiers
source                  1..8
                        mol_type = protein
                        organism = Glycine max
SEQUENCE: 370
FAADANSK                                                          8

SEQ ID NO: 371          moltype = AA  length = 10
FEATURE                 Location/Qualifiers
source                  1..10
                        mol_type = protein
                        organism = Glycine max
SEQUENCE: 371
FATGTEAIAK                                                        10

SEQ ID NO: 372          moltype = AA  length = 15
FEATURE                 Location/Qualifiers
source                  1..15
                        mol_type = protein
                        organism = Glycine max
SEQUENCE: 372
GVSLLLPTDV VIADK                                                  15

SEQ ID NO: 373          moltype = AA  length = 17
FEATURE                 Location/Qualifiers
source                  1..17
                        mol_type = protein
                        organism = Glycine max
SEQUENCE: 373
GVTTIIGGGD SVAAVEK                                                17

SEQ ID NO: 374          moltype = AA  length = 10
FEATURE                 Location/Qualifiers
source                  1..10
                        mol_type = protein
                        organism = Glycine max
SEQUENCE: 374
IGVIESLLEK                                                        10

SEQ ID NO: 375          moltype = AA  length = 28
FEATURE                 Location/Qualifiers
source                  1..28
                        mol_type = protein
                        organism = Glycine max
SEQUENCE: 375
LASLADLYVN DAFGTAHRAH ASTEGVAK                                    28

SEQ ID NO: 376          moltype = AA  length = 10
FEATURE                 Location/Qualifiers
source                  1..10
```

```
                        mol_type = protein
                        organism = Glycine max
SEQUENCE: 376
LSLATTLLEK                                                     10

SEQ ID NO: 377          moltype = AA  length = 20
FEATURE                 Location/Qualifiers
source                  1..20
                        mol_type = protein
                        organism = Glycine max
SEQUENCE: 377
LVTQLPEGGV LLLENVRFYK                                          20

SEQ ID NO: 378          moltype = AA  length = 7
FEATURE                 Location/Qualifiers
source                  1..7
                        mol_type = protein
                        organism = Glycine max
SEQUENCE: 378
NDPEFAK                                                        7

SEQ ID NO: 379          moltype = AA  length = 11
FEATURE                 Location/Qualifiers
source                  1..11
                        mol_type = protein
                        organism = Glycine max
SEQUENCE: 379
QLPGVLALDD A                                                   11

SEQ ID NO: 380          moltype = AA  length = 11
FEATURE                 Location/Qualifiers
source                  1..11
                        mol_type = protein
                        organism = Glycine max
SEQUENCE: 380
RPFAAIVGGS K                                                   11

SEQ ID NO: 381          moltype = AA  length = 11
FEATURE                 Location/Qualifiers
source                  1..11
                        mol_type = protein
                        organism = Glycine max
SEQUENCE: 381
VILSSHLGRP K                                                   11

SEQ ID NO: 382          moltype = AA  length = 8
FEATURE                 Location/Qualifiers
source                  1..8
                        mol_type = protein
                        organism = Glycine max
SEQUENCE: 382
YLTGYGAK                                                       8

SEQ ID NO: 383          moltype = DNA  length = 1455
FEATURE                 Location/Qualifiers
source                  1..1455
                        mol_type = other DNA
                        organism = Glycine max
CDS                     1..1455
SEQUENCE: 383
atggcctcag ccgcatcccc caccactttc tctctcctcc actccgccac cccttcctcc  60
tcctccaccg ccacctccgc ctccccctcc ccctcgcgcg tgcagctcac ctcctccctc  120
cgcgcccgcc cgctgcgccg cctgggcttc gccgcggcgg acccgctgct cgcggcgagt  180
gtagcggcgc gcgtggcggc ggtgagagga ggaggaaagg gcgcgagggg ggtggtgtcg  240
atggcgaaga agagcgtggg ggacctgagc gcggcggacc tgaaggggaa gaaggtcttc  300
gtcagggccg acctcaacgt cccgctcgac gacaaccaga acatcaccga cgacaccaga  360
atccgcgccg ccattcccac catcaaacat ctcatccaaa acggcgccaa agtcattctc  420
tccagccact tggggcggcc gaagggtgtc actcccaaat acagcttggc gcctcttgta  480
ccccggcttt ctgagctcat tggtatccag attgtcaagg ccgaggacag tattggtcca  540
gaagtagaaa agttggtggc ttctcttcca gatggaggtg ttctccttct agaaaatgtg  600
aggttttaca aggaggaaga aaagaatgac cccgagcatg caaaaaagct tgcctctctg  660
gcagatctgt atgtgaatga tgcatttggt actgctcaca gggcacatgc atcaacagag  720
ggtgttacta aatacctgaa gccatctgtt gctggttttc ttttgcaaaa ggaacttgat  780
taccttgttg gggcagtatc aaaccccaaa aggccatttg ctgccattgt tggtggttcc  840
aaagtctcat ctaaaattgg agtgattgag tcacttttag aaaaagttga catccttctt  900
cttggtggag gaatgatctt cacattttac aaggcacaag gtctttcagt gggttcatcc  960
cttgtagaag aagataagtt ggatcttgct acatcactac ttgcaaaagc caaggaaaag  1020
ggggtgtctc tcttgttacc aagtgatgtg gtgattgcag acaaatttgc tcctgatgct  1080
aatagcaagg tcgtgccagc atctgccatc cctgatggct ggatgggatt ggatattggt  1140
```

```
ccagattctg ttaaatcatt cagtgaagca ttggatacta cccaaaccat catatggaat  1200
ggaccaatgg gagtgtttga gtttgacaag tttgctgttg gtacagaggc tattgcaaag  1260
aagctggctg acctcagtgg aaaggggggtg accacaatta ttggaggagg agattctgtt  1320
gcagctgtgg agaaagtagg agttgctagt gtcatgagcc acatatctac tggtggtggt  1380
gccagtttgg agttattgga aggcaaagag cttccaggag tccttgctct tgatgaagcc  1440
gtcccagtcg ctgtg                                                   1455

SEQ ID NO: 384         moltype = AA  length = 485
FEATURE                Location/Qualifiers
source                 1..485
                       mol_type = protein
                       organism = Glycine max
SEQUENCE: 384
MASAASPTTF SLLHSATPSS SSTATSASPS PSRVQLTSSL RARPLRRLGF AAADPLLAAS  60
VAARVAAVRG GGKGARGVVS MAKKSVGDLS AADLKGKKVF VRADLNVPLD DNQNITDDTR  120
IRAAIPTIKH LIQNGAKVIL SSHLGRPKGV TPKYSLAPLV PRLSELIGIQ IVKAEDSIGP  180
EVEKLVASLP DGGVLLLENV RFYKEEEKND PEHAKKLASL ADLYVNDAFG TAHRAHASTE  240
GVTKYLKPSV AGFLLQKELD YLVGAVSNPK RPFAAIVGGS KVSSKIGVIE SLLEKVDILL  300
LGGGMIFTFY KAQGLSVGSS LVEEDKLDLA TSLLAKAKEK GVSLLLPSDV VIADKFAPDA  360
NSKVVPASAI PDGWMGLDIG PDSVKSFSEA LDTTQTIIWN GPMGVFEFDK FAVGTEAIAK  420
KLADLSGKGV TTIIGGGDSV AAVEKVGVAS VMSHISTGGG ASLELLEGKE LPGVLALDEA  480
VPVAV                                                              485

SEQ ID NO: 385         moltype = AA  length = 13
FEATURE                Location/Qualifiers
source                 1..13
                       mol_type = protein
                       organism = Glycine max
SEQUENCE: 385
ELDYLVGAVS NPK                                                     13

SEQ ID NO: 386         moltype = AA  length = 16
FEATURE                Location/Qualifiers
source                 1..16
                       mol_type = protein
                       organism = Glycine max
SEQUENCE: 386
ELPGVLALDE AVPVAV                                                  16

SEQ ID NO: 387         moltype = AA  length = 10
FEATURE                Location/Qualifiers
source                 1..10
                       mol_type = protein
                       organism = Glycine max
SEQUENCE: 387
FAVGTEAIAK                                                         10

SEQ ID NO: 388         moltype = AA  length = 15
FEATURE                Location/Qualifiers
source                 1..15
                       mol_type = protein
                       organism = Glycine max
SEQUENCE: 388
GVSLLLPSDV VIADK                                                   15

SEQ ID NO: 389         moltype = AA  length = 17
FEATURE                Location/Qualifiers
source                 1..17
                       mol_type = protein
                       organism = Glycine max
SEQUENCE: 389
GVTTIIGGGD SVAAVEK                                                 17

SEQ ID NO: 390         moltype = AA  length = 10
FEATURE                Location/Qualifiers
source                 1..10
                       mol_type = protein
                       organism = Glycine max
SEQUENCE: 390
IGVIESLLEK                                                         10

SEQ ID NO: 391         moltype = AA  length = 11
FEATURE                Location/Qualifiers
source                 1..11
                       mol_type = protein
                       organism = Glycine max
SEQUENCE: 391
RPFAAIVGGS K                                                       11
```

```
SEQ ID NO: 392          moltype = AA  length = 11
FEATURE                 Location/Qualifiers
source                  1..11
                        mol_type = protein
                        organism = Glycine max
SEQUENCE: 392
VILSSHLGRP K                                                       11

SEQ ID NO: 393          moltype = DNA  length = 1203
FEATURE                 Location/Qualifiers
source                  1..1203
                        mol_type = other DNA
                        organism = Glycine max
CDS                     1..1203
SEQUENCE: 393
atggcgacta agaggagcgt gggaacgttg aaggagggtg atttgaaagg gaagagggtg  60
ttcgtgaggg tcgatctgaa cgtgcctttg gatgacaacc ttaacatcac cgatgacact  120
agagtccgtg ctgctgttcc caccatcaag tacttaactg gtcatggagc caaagtgatc  180
ctttctagcc acttgggacg tcctaaaggt gtaacaccta aatacagttt gaagcctctt  240
gtgccaaggc tgtctcaact tctcggaatt gaggttacga tggcaaatga ctctattggg  300
gaggaagttg agaagttggt tgcacaactt ccagaaggtg gtgttttgct tctagagaat  360
gtgaggttct ataaggagga agagaagaat gaccctgagt ttgcaaagaa gttggcttct  420
cttgctgatc tctacgtgaa tgatgctttc ggcactgccc acagagctca tgcttctaca  480
gaaggagtgg ccaaatactt gaagccctct gttgcaggat tccttatgca gaaggaactt  540
gactatctag ttggagctgt gtcaaacccc aagagaccat ttgctgctat cgttggtggg  600
tcaaaggtgt cttccaagat tggagttatt gagtccttgt tggagaaagt taacgttctc  660
ttgcttggtg gaggaatgat ctttaccttt tacaaggctc agggttattc agttggttca  720
tctcttgtgg aggaagacaa gcttagcctt gcaactacac ttctcgaaaa ggccaaggct  780
aaaggggttt ctttgttgct tccaactgat gtggtcatag cagacaagtt tgctgctgat  840
gctaacagca agactgtgcc agcatcaagc atcccagacg ggtggatggg attagatatt  900
ggtcccgatt ccatcaagac atttggtgaa gcattggata agacccagac cgtcatttgg  960
aatggaccaa tgggtgtttt tgagtttgat aagtttgcca caggaacaga ggccatagcc  1020
aagaaactgg cagagctgag tgggaaggga gtaacgacca tcattggagg aggtgactct  1080
gttgccgctg tggagaaggt tggtcttgca gacaagatga gccacatctc cactggtggt  1140
ggtgccagct tagagcttct tgaggggaag caactccctg gtgtccttgc ccttgatgat  1200
gct                                                                1203

SEQ ID NO: 394          moltype = AA  length = 401
FEATURE                 Location/Qualifiers
source                  1..401
                        mol_type = protein
                        organism = Glycine max
SEQUENCE: 394
MATKRSVGTL KEGDLKGKRV FVRVDLNVPL DDNLNITDDT RVRAAVPTIK YLTGHGAKVI  60
LSSHLGRPKG VTPKYSLKPL VPRLSQLLGI EVTMANDSIG EEVEKLVAQL PEGGVLLLEN  120
VRFYKEEEKN DPEFAKKLAS LADLYVNDAF GTAHRAHAST EGVAKYLKPS VAGFLMQKEL  180
DYLVGAVSNP KRPFAAIVGG SKVSSKIGVI ESLLEKVNVL LLGGGMIFTF YKAQGYSVGS  240
SLVEEDKLSL ATTLLEKAKA KGVSLLLPTD VVIADKFAAD ANSKTVPASS IPDGWMGLDI  300
GPDSIKTFGE ALDKTQTVIW NGPMGVFEFD KFATGTEAIA KKLAELSGKG VTTIIGGGDS  360
VAAVEKVGLA DKMSHISTGG GASLELLEGK QLPGVLALDD A                      401

SEQ ID NO: 395          moltype = AA  length = 15
FEATURE                 Location/Qualifiers
source                  1..15
                        mol_type = protein
                        organism = Glycine max
SEQUENCE: 395
AQGYSVGSSL VEEDK                                                   15

SEQ ID NO: 396          moltype = AA  length = 13
FEATURE                 Location/Qualifiers
source                  1..13
                        mol_type = protein
                        organism = Glycine max
SEQUENCE: 396
ELDYLVGAVS NPK                                                     13

SEQ ID NO: 397          moltype = AA  length = 8
FEATURE                 Location/Qualifiers
source                  1..8
                        mol_type = protein
                        organism = Glycine max
SEQUENCE: 397
FAADANSK                                                           8

SEQ ID NO: 398          moltype = AA  length = 10
FEATURE                 Location/Qualifiers
source                  1..10
                        mol_type = protein
```

```
                        organism = Glycine max
SEQUENCE: 398
FATGTEAIAK                                                      10

SEQ ID NO: 399          moltype = AA  length = 15
FEATURE                 Location/Qualifiers
source                  1..15
                        mol_type = protein
                        organism = Glycine max
SEQUENCE: 399
GVSLLLPTDV VIADK                                                15

SEQ ID NO: 400          moltype = AA  length = 17
FEATURE                 Location/Qualifiers
source                  1..17
                        mol_type = protein
                        organism = Glycine max
SEQUENCE: 400
GVTTIIGGGD SVAAVEK                                              17

SEQ ID NO: 401          moltype = AA  length = 10
FEATURE                 Location/Qualifiers
source                  1..10
                        mol_type = protein
                        organism = Glycine max
SEQUENCE: 401
IGVIESLLEK                                                      10

SEQ ID NO: 402          moltype = AA  length = 28
FEATURE                 Location/Qualifiers
source                  1..28
                        mol_type = protein
                        organism = Glycine max
SEQUENCE: 402
LASLADLYVN DAFGTAHRAH ASTEGVAK                                  28

SEQ ID NO: 403          moltype = AA  length = 10
FEATURE                 Location/Qualifiers
source                  1..10
                        mol_type = protein
                        organism = Glycine max
SEQUENCE: 403
LSLATTLLEK                                                      10

SEQ ID NO: 404          moltype = AA  length = 20
FEATURE                 Location/Qualifiers
source                  1..20
                        mol_type = protein
                        organism = Glycine max
SEQUENCE: 404
LVAQLPEGGV LLLENVRFYK                                           20

SEQ ID NO: 405          moltype = AA  length = 7
FEATURE                 Location/Qualifiers
source                  1..7
                        mol_type = protein
                        organism = Glycine max
SEQUENCE: 405
NDPEFAK                                                         7

SEQ ID NO: 406          moltype = AA  length = 11
FEATURE                 Location/Qualifiers
source                  1..11
                        mol_type = protein
                        organism = Glycine max
SEQUENCE: 406
QLPGVLALDD A                                                    11

SEQ ID NO: 407          moltype = AA  length = 11
FEATURE                 Location/Qualifiers
source                  1..11
                        mol_type = protein
                        organism = Glycine max
SEQUENCE: 407
RPFAAIVGGS K                                                    11

SEQ ID NO: 408          moltype = AA  length = 8
FEATURE                 Location/Qualifiers
source                  1..8
```

```
                        mol_type = protein
                        organism = Glycine max
SEQUENCE: 408
TFGEALDK                                                                8

SEQ ID NO: 409          moltype = AA  length = 11
FEATURE                 Location/Qualifiers
source                  1..11
                        mol_type = protein
                        organism = Glycine max
SEQUENCE: 409
VILSSHLGRP K                                                            11

SEQ ID NO: 410          moltype = DNA  length = 1143
FEATURE                 Location/Qualifiers
source                  1..1143
                        mol_type = other DNA
                        organism = Glycine max
CDS                     1..1143
SEQUENCE: 410
atgtcgtcga gcacagttgg tcaagtcatc aaatgcaaag ctgcggtttc atgggaggca  60
gggaagccac ttgtgattga agaagtagag gtggcaccac cacaagctgg tgaagtgcgt  120
ttgaagatcc tctacacctc tctttgccac actgatgttt acttctggga agccaagggc  180
caaactccat tgtttcctcg tatatttggt catgaagctg gagggattgt ggagagcgta  240
ggtgagggtg tgactcatct caaaccaggg gaccatgccc tcccagtgtt taccggggag  300
tgtggagaat gccctcattg caagtcagag gagagcaaca tgtgtgatct tctcaggatc  360
aacactgata ggggtgtcat gatccatgac agccaaacaa gattttctat taagggacaa  420
cctatttacc attttgttgg tacctccaca ttcagtgaat acactgttgt tcatgccgga  480
tgtgttgcca aagtcaaccc tgctgcccca cttgacaaaa tttgtgttct cagttgtgga  540
atttgcacag gtcttggggc tactatcaat gttgcaaaac caaaacctgg ttcttctgtt  600
gccatttttg gacttggagc tgttggcctt gctgctgctg aaggggcaag gatttctggt  660
gcatcaagaa ttattggggt tgatttagtt tctagcagat ttgaagaagc taagaagttt  720
ggggtcaatg aatttgtgaa cccaaaagac catgacaagc ctgtacaaga ggtgattgct  780
gcaatgacga atgggggtgt ggatcgtgct gttgaatgta ctggcagcat ccaagccatg  840
atctcggcat tcgaatgcgt ccacgatggt tggggtgttg ctgtacttgt tggagtgcca  900
aacaaagatg atgcattcaa aactcatcca gtgaatttct tgaacgagag aactctaaag  960
ggtaccttct acggaaacta caaaccccgc actgatcttc cttctgttgt ggagaagtac  1020
atgaatgggg aattggaact ggagaaattc atcactcaca cagttccatt ctcagagatt  1080
aacaaggctt ttgattacat gctgaaaggg gagtccatca gatgcatcat tcgaatgggg  1140
gag                                                                     1143

SEQ ID NO: 411          moltype = AA  length = 381
FEATURE                 Location/Qualifiers
source                  1..381
                        mol_type = protein
                        organism = Glycine max
SEQUENCE: 411
MSSSTVGQVI KCKAAVSWEA GKPLVIEEVE VAPPQAGEVR LKILYTSLCH TDVYFWEAKG  60
QTPLFPRIFG HEAGGIVESV GEGVTHLKPG DHALPVFTGE CGECPHCKSE ESNMCDLLRI  120
NTDRGVMIHD SQTRFSIKGQ PIYHFVGTST FSEYTVVHAG CVAKVNPAAP LDKICVLSCG  180
ICTGLGATIN VAKPKPGSSV AIFGLGAVGL AAAEGARISG ASRIIGVDLV SSRFEEAKKF  240
GVNEFVNPKD HDKPVQEVIA AMTNGGVDRA VECTGSIQAM ISAFECVHDG WGVAVLVGVP  300
NKDDAFKTHP VNFLNERTLK GTFYGNYKPR TDLPSVVEKY MNGELELEKF ITHTVPFSEI  360
NKAFDYMLKG ESIRCIIRMG E                                                 381

SEQ ID NO: 412          moltype = AA  length = 10
FEATURE                 Location/Qualifiers
source                  1..10
                        mol_type = protein
                        organism = Glycine max
SEQUENCE: 412
FGVNEFVNPK                                                              10

SEQ ID NO: 413          moltype = AA  length = 13
FEATURE                 Location/Qualifiers
source                  1..13
                        mol_type = protein
                        organism = Glycine max
SEQUENCE: 413
FITHTVPFSE INK                                                          13

SEQ ID NO: 414          moltype = AA  length = 19
FEATURE                 Location/Qualifiers
source                  1..19
                        mol_type = protein
                        organism = Glycine max
SEQUENCE: 414
GTFYGNYKPR TDLPSVVEK                                                    19
```

```
SEQ ID NO: 415         moltype = AA  length = 13
FEATURE                Location/Qualifiers
source                 1..13
                       mol_type = protein
                       organism = Glycine max
SEQUENCE: 415
THPVNFLNER TLK                                                      13

SEQ ID NO: 416         moltype = AA  length = 9
FEATURE                Location/Qualifiers
source                 1..9
                       mol_type = protein
                       organism = Glycine max
SEQUENCE: 416
VNPAAPLDK                                                           9

SEQ ID NO: 417         moltype = DNA  length = 1113
FEATURE                Location/Qualifiers
source                 1..1113
                       mol_type = other DNA
                       organism = Glycine max
CDS                    1..1113
SEQUENCE: 417
atgcgtgcag ctgcggtggc atgggaagca gggaagccac tgtcaataga aaccatagaa  60
gtggcaccac cccagaaagg tgaagtgcgt ttgaggatcc tcttcaactc cctttgccgt  120
agtgatgttt attggtggga tgctaaggac cagactcctc tgtttcctcg tatcttaggc  180
cacgaagctt cagggattgt ggagagcgtg ggcgagggtg tgacacatct gaaaccaggt  240
gaccatgcac tcccaatatt cactggggag tgtggtgaat gcacttattg taagtctgaa  300
gagagcaacc tgtgtgagct actcaggatc aacactgaca ggggtgttat gctgagtgat  360
ggaaaaacaa ggttctccaa aaatggccaa cccatttacc acttcgttgg aacctccact  420
ttcagtgaat acactgttct ccatgaagga tgtgtagcca agattaaccc taatgcccca  480
cttgacaaag ttgctattgt cagctgtgga ttctgcacag gttttggggc tactgtgaat  540
gttgcaaaac caaagcctaa taatactgtt gctgtctttg gcttaggagc tgttggtctt  600
gctgcctgtg aaggggcaag ggtttctggt gcatctagaa tcatcggggt tgatttactt  660
cccaatcgat ttgaacaagc caaaaaattt ggggtcactg attttgtaaa cccgaaagat  720
cacaacaaac cagtccaaga ggtcattgct gaaatgacta atggaggagt agatcgtgct  780
attgaatgca ctggaagcat ccaagcttca atctcagcat ttgaatgcac tcatgatggt  840
tggggtactg ctgtccttgt tggtgtgcca aagaaggatg ttgaattcaa aactaatcct  900
atgaagttca tggaagggag aactcttaag ggtaccttct atggtcacta cagaccccgc  960
actgacattc ctggtgttgt ggagaagtac ctcaacaagg agttggaact agacaaattt  1020
atcactcact ctgtgccatt ctcaaagatc aacactgcat ttgatcttat gctgaaaggg  1080
gagggcataa ggtgcctcat ctgcatggaa gag                              1113

SEQ ID NO: 418         moltype = AA  length = 371
FEATURE                Location/Qualifiers
source                 1..371
                       mol_type = protein
                       organism = Glycine max
SEQUENCE: 418
MRAAAVAWEA GKPLSIETIE VAPPQKGEVR LRILFNSLCR SDVYWWDAKD QTPLFPRILG  60
HEASGIVESV GEGVTHLKPG DHALPIFTGE CGECTYCKSE ESNLCELLRI NTDRGVMLSD  120
GKTRFSKNGQ PIYHFVGTST FSEYTVLHEG CVAKINPNAP LDKVAIVSCG FCTGFGATVN  180
VAKPKPNNTV AVFGLGAVGL AACEGARVSG ASRIIGVDLL PNRFEQAKKF GVTDFVNPKD  240
HNKPVQEVIA EMTNGGVDRA IECTGSIQAS ISAFECTHDG WGTAVLVGVP KKDVEFKTNP  300
MKFMEGRTLK GTFYGHYRPR TDIPGVVEKY LNKELELDKF ITHSVPFSKI NTAFDLMLKG  360
EGIRCLICME E                                                        371

SEQ ID NO: 419         moltype = AA  length = 19
FEATURE                Location/Qualifiers
source                 1..19
                       mol_type = protein
                       organism = Glycine max
SEQUENCE: 419
GTFYGHYRPR TDIPGVVEK                                                19

SEQ ID NO: 420         moltype = AA  length = 9
FEATURE                Location/Qualifiers
source                 1..9
                       mol_type = protein
                       organism = Glycine max
SEQUENCE: 420
INPNAPLDK                                                           9

SEQ ID NO: 421         moltype = DNA  length = 1140
FEATURE                Location/Qualifiers
source                 1..1140
                       mol_type = other DNA
                       organism = Glycine max
CDS                    1..1140
```

```
SEQUENCE: 421
atgtctagca ccgttggcca gaccatcaag tgcaaagctg cgattgcatg ggaggctggg  60
aagccgctgg tgattgaaga agtggaggtt gcgccaccgc aagccggtga agtccgtttg  120
aagatcctct acacctctct ttgccacact gatgtttact tctgggatgc gaagggccag  180
actccattgt ttcctcgcat ttttggccat gaagcttcgg ggattgtgga gagcgtaggc  240
gagggtgtga ctcatctgaa accaggtgac catgccctcc ctgtgttcac aggagagtgt  300
ggagattgcg cccattgcaa gtcagaggag agcaacatgt gtgagctact caggatcaac  360
accgataggg gtgtcatgat ccatgatggc caatcaaggt tctctaagaa tggacaaccc  420
atacaccatt tcttgggaac ctctacattc agtgaataca ctgttgtcca tgctggatgt  480
gttgcaaaga tcaaccctgc tgctccactt gacaaagttt gtgttctcag ttgtggaatt  540
tgcacaggtt ttggtgctac tgtaaatgta gcaaaaccaa aacctggttc ctctgttgcc  600
atatttggac ttggagctgt tggccttgcg gctgctgaag gtgcaagagt ttcaggtgct  660
tcaagaatca ttggagttga tttagtttct gcccgatttg aagaagctaa gaagtttggg  720
gttaatgagt ttgtgaaccc aaaggatcat gataaacctg tgcaacaggt aattgctgaa  780
atgaccaatg gaggtgtgga tcgggctgtt gaatgtactg gcagcatcca agccatggtc  840
tcagcattcg aatgcgtcca cgatggttgg ggtcttgctg tacttgttgg tgtgcctagt  900
aaagatgatg cattcaaaac tgctcctatt aatttcctga acgagaggac tcttaagggc  960
acctttatg gcaactacaa accacgcacc gatcttccat ctgttgtcga gaagtacatg  1020
agtggggagc tagaagtgga caaattcatc actcacacag ttccattctc agagatcaac  1080
aaagcttttg atttaatgct gaagggacag tccattaggt gtatcatccg catgcaagag  1140

SEQ ID NO: 422          moltype = AA  length = 380
FEATURE                 Location/Qualifiers
source                  1..380
                        mol_type = protein
                        organism = Glycine max
SEQUENCE: 422
MSSTVGQTIK CKAAIAWEAG KPLVIEEVEV APPQAGEVRL KILYTSLCHT DVYFWDAKGQ  60
TPLFPRIFGH EASGIVESVG EGVTHLKPGD HALPVFTGEC GDCAHCKSEE SNMCELLRIN  120
TDRGVMIHDG QSRFSKNGQP IHHFLGTSTF SEYTVVHAGC VAKINPAAPL DKVCVLSCGI  180
CTGFGATVNV AKPKPGSSVA IFGLGAVGLA AAEGARVSGA SRIIGVDLVS ARFEEAKKFG  240
VNEFVNPKDH DKPVQQVIAE MTNGGVDRAV ECTGSIQAMV SAFECVHDGW GLAVLVGVPS  300
KDDAFKTAPI NFLNERTLKG TFYGNYKPRT DLPSVVEKYM SGELEVDKFI THTVPFSEIN  360
KAFDLMLKGQ SIRCIIRMQE                                           380

SEQ ID NO: 423          moltype = AA  length = 10
FEATURE                 Location/Qualifiers
source                  1..10
                        mol_type = protein
                        organism = Glycine max
SEQUENCE: 423
FGVNEFVNPK                                                      10

SEQ ID NO: 424          moltype = AA  length = 13
FEATURE                 Location/Qualifiers
source                  1..13
                        mol_type = protein
                        organism = Glycine max
SEQUENCE: 424
FITHTVPFSE INK                                                  13

SEQ ID NO: 425          moltype = AA  length = 19
FEATURE                 Location/Qualifiers
source                  1..19
                        mol_type = protein
                        organism = Glycine max
SEQUENCE: 425
GTFYGNYKPR TDLPSVVEK                                            19

SEQ ID NO: 426          moltype = AA  length = 9
FEATURE                 Location/Qualifiers
source                  1..9
                        mol_type = protein
                        organism = Glycine max
SEQUENCE: 426
INPAAPLDK                                                       9

SEQ ID NO: 427          moltype = AA  length = 13
FEATURE                 Location/Qualifiers
source                  1..13
                        mol_type = protein
                        organism = Glycine max
SEQUENCE: 427
TAPINFLNER TLK                                                  13

SEQ ID NO: 428          moltype = DNA  length = 927
FEATURE                 Location/Qualifiers
source                  1..927
                        mol_type = other DNA
```

```
                        organism = Glycine max
CDS                     1..927
SEQUENCE: 428
atggcgtcaa gacagcaatt caaggaagac agagccgagg cagctgcaaa actcgcagcg  60
aaagacatcg gcgacatcaa cagaacaaac gagcgcgacg aggggtacga cttgcacgac  120
gaagccaact tcaagcaagc acgagctgaa gcagctgcaa agctggcggc caaggatctg  180
gaggacgcta acagattaag agacaacact ttcaacacat ggaaagagca acatcagcat  240
gatgagaaca aacccggtgt gatagggtcc atgtttagag ccgccaagga agccgtggtt  300
gggaagcctc accacgagga agtttatgca aaggaaacaa agatgggtga atattcagat  360
tatgcgactc agaaggcgag ggaaacgaag cagaaggctg gggagtatac agactatgcg  420
gctcagaaag caaaagaaac caaagactat gctgctgaga aggctaagaa tgctaaagat  480
accactgtgc agaaagctgg agagtacaag gattataccg ctgagaaggc taagaatgct  540
aaagatacca ctgtgcagaa agctggagaa tacaaggatt ataccgctga gaaggcaatt  600
gaagggaagg acagtgcagt ggggaagctt ggggagctaa aggaatctgc tgctgatgct  660
gctaaaaggg ctatgggttt cttcaccggt ggcaacaaag accaaactag agaggaggag  720
gaggaaacga ggcggagtat gcaggaggtg agggtgcaag ataaggagta tggaacggga  780
cgtggtactg gagagaagtt ggtgataaaa atggaagagt cgcggccagg agcggtggcg  840
gatgcgctca aagcagcgaa tagggccatg gacggcgata tggaggagga aggcgtgctt  900
catgtggagc gtcgtaggga gaaaatg                                      927

SEQ ID NO: 429          moltype = AA  length = 309
FEATURE                 Location/Qualifiers
source                  1..309
                        mol_type = protein
                        organism = Glycine max
SEQUENCE: 429
MASRQQFKED RAEAAAKLAA KDIGDINRTN ERDEGYDLHD EANFKQARAE AAAKLAAKDL  60
EDANRLRDNT FNTWKEQHQH DENKPGVIGS MFRAAKEAVV GKPHHEEVYA KETKMGEYSD  120
YATQKARETK QKAGEYTDYA AQKAKETKDY AAEKAKNAKD TTVQKAGEYK DYTAEKAKNA  180
KDTTVQKAGE YKDYTAEKAI EGKDSAVGKL GELKESAADA AKRAMGFFTG GNKDQTREEE  240
EETRRSMQEV RVQDKEYGTG RGTGEKLVIK MEESRPGAVA DALKAANRAM DGDMEEEGVL  300
HVERRREKM                                                          309

SEQ ID NO: 430          moltype = AA  length = 11
FEATURE                 Location/Qualifiers
source                  1..11
                        mol_type = protein
                        organism = Glycine max
SEQUENCE: 430
AGEYTDYAAQ K                                                       11

SEQ ID NO: 431          moltype = AA  length = 24
FEATURE                 Location/Qualifiers
source                  1..24
                        mol_type = protein
                        organism = Glycine max
SEQUENCE: 431
DIGDINRTNE RDEGYDLHDE ANFK                                         24

SEQ ID NO: 432          moltype = AA  length = 17
FEATURE                 Location/Qualifiers
source                  1..17
                        mol_type = protein
                        organism = Glycine max
SEQUENCE: 432
DLEDANRLRD NTFNTWK                                                 17

SEQ ID NO: 433          moltype = AA  length = 15
FEATURE                 Location/Qualifiers
source                  1..15
                        mol_type = protein
                        organism = Glycine max
SEQUENCE: 433
EAVVGKPHHE EVYAK                                                   15

SEQ ID NO: 434          moltype = DNA  length = 1104
FEATURE                 Location/Qualifiers
source                  1..1104
                        mol_type = other DNA
                        organism = Glycine max
CDS                     1..1104
SEQUENCE: 434
atgggcaagg tcaagatcgg aatcaacgga tttggaagaa ttggccgttt ggtagccaga  60
gtggctctgc agagagacga tgttgaactc gttgccgtta acgacccttt catcaccacc  120
gattacatga catacatgtt taaatacgac agtgttcatg gacactggaa gcatcacgat  180
gtcaccgtta aggacgagaa gacccttctc ttcggtgaca agccagtcac tatttttgga  240
cacaggtttt tatttttcac tttaattttt cttactgttt atgattgttg tgtcctgcat  300
gtaaacgttg agtgttgttt tctctgtgaa ctcagaaacc ctgaagagat cccatggggg  360
tcaactggag ctgacatcat tgttgagtcc accggagttt tcaccgataa ggacaaggcc  420
```

```
gccgcacatt tgaagggtgg tgcaaagaag gttattattt ctgcccccag taaggatgcc  480
cccatgtttg ttgttggtgt caacgagcac gagtacaagc cagagcttga tattatttcc  540
aatgctagct gcacaaccaa ctgccttgcc ccacttgcca aggttatcaa tgacaggttt  600
ggcattgttg agggtttgat gaccactgtt cattccatca ccgctaccca gaagactgtt  660
gatggaccat cagccaagga ctggagaggt ggaagagctg cttcatttaa catcattcct  720
agcagcactg gagctgccaa ggctgttggg aaagtcctcc ctgctttgaa tggaaaattg  780
actggtatgg cattccgtgt tcccaccgtg gatgtctctg ttgttgacct cacagtgagg  840
ctggagaaag aagcttccta cgatgaaatt aaaaatgcta tcaaggagga atcagagggc  900
aagttgaagg gaattcttgg ttacactgaa gatgatgtgg tctccactga ctttatcggc  960
gatagcagat caagtatttt tgatgcaaag gctggaattg cattgaataa gaactttgtg  1020
aagcttgttt cttggtacga caacgagtgg ggatacagct cacgtgtcat tgatcttctt  1080
gtattcgttg ccaagaagtc tctt                                        1104

SEQ ID NO: 435          moltype = AA  length = 368
FEATURE                 Location/Qualifiers
source                  1..368
                        mol_type = protein
                        organism = Glycine max
SEQUENCE: 435
MGKVKIGING FGRIGRLVAR VALQRDDVEL VAVNDPFITT DYMTYMFKYD SVHGHWKHHD  60
VTVKDEKTLL FGDKPVTIFG HRFLFFTLIF LTVYDCCVLH VNVECCFLCE LRNPEEIPWG  120
STGADIIVES TGVFTDKDKA AAHLKGGAKK VIISAPSKDA PMFVVGVNEH EYKPELDIIS  180
NASCTTNCLA PLAKVINDRF GIVEGLMTTV HSITATQKTV DGPSAKDWRG GRAASFNIIP  240
SSTGAAKAVG KVLPALNGKL TGMAFRVPTV DVSVVDLTVR LEKEASYDEI KNAIKEESEG  300
KLKGILGYTE DDVVSTDFIG DSRSSIFDAK AGIALNKNFV KLVSWYDNEW GYSSRVIDLL  360
VFVAKKSL                                                          368

SEQ ID NO: 436          moltype = AA  length = 8
FEATURE                 Location/Qualifiers
source                  1..8
                        mol_type = protein
                        organism = Glycine max
SEQUENCE: 436
EASYDEIK                                                          8

SEQ ID NO: 437          moltype = AA  length = 27
FEATURE                 Location/Qualifiers
source                  1..27
                        mol_type = protein
                        organism = Glycine max
SEQUENCE: 437
GILGYTEDDV VSTDFIGDSR SSIFDAK                                     27

SEQ ID NO: 438          moltype = AA  length = 8
FEATURE                 Location/Qualifiers
source                  1..8
                        mol_type = protein
                        organism = Glycine max
SEQUENCE: 438
VIISAPSK                                                          8

SEQ ID NO: 439          moltype = AA  length = 8
FEATURE                 Location/Qualifiers
source                  1..8
                        mol_type = protein
                        organism = Glycine max
SEQUENCE: 439
VLPALNGK                                                          8

SEQ ID NO: 440          moltype = DNA  length = 1014
FEATURE                 Location/Qualifiers
source                  1..1014
                        mol_type = other DNA
                        organism = Glycine max
CDS                     1..1014
SEQUENCE: 440
atgggcaagg tcaagatcgg aatcaacgga tttggaagaa ttggccgttt ggttgccaga  60
gtcgctctgc aaagagacga tgtggagctc gttgccgtta acgacccttt cattaccacc  120
gattacatga catacatgtt taaatacgac agtgttcacg gacactggaa gcatcacgat  180
gtcaccgtta aggacgagaa gacccttctc ttcggtgaca agccagtcac tgtttttgga  240
cacaggaacc ctgaagagat cccatggggg tcaactggag ctgatatcat tgttgagtcc  300
accggagttt tcaccgataa ggacaaggcc gccgcacatt tgaagggtgg tgcgaagaag  360
gttattattt ctgcccccag taaggatgcc cccatgtttg ttgttggtgt taacgagcac  420
gagtacaagc cagagcttga tattatttcc aatgctagct gcacaaccaa ctgccttgct  480
ccacttgcta aggttattaa tgacaggttt ggcattgttg agggtttgat gaccactgtt  540
cattccatca ctgccaccca gaagactgtt gatgggccat cagccaaaga ctggagaggt  600
ggaagagctg cttcatttaa catcattcct agcagcactg gagctgccaa ggctgttgga  660
aaagtccttc ctgctttgaa cggaaaattg actggtatgg cattccgtgt tcccaccgtg  720
gatgtctctg ttgttgacct cacagtgagg ctggagaagg aagcctccta cgatgaaatt  780
```

```
aaaaatgcta tcaaggagga atcagagggc aagttgaagg gaattcttgg ttacactgaa  840
gatgatgtgg tctccaccga ctttgtgggc gatagcagat caagtatttt tgatgcaaag  900
gctggaattg cattgaataa gaactttgtg aagcttgtct cttggtatga caacgagtgg  960
ggatacagct cacgtgtcat tgacctgctt gtattcgttg ccaagaagtc tttt        1014

SEQ ID NO: 441         moltype = AA  length = 338
FEATURE                Location/Qualifiers
source                 1..338
                       mol_type = protein
                       organism = Glycine max
SEQUENCE: 441
MGKVKIGING FGRIGRLVAR VALQRDDVEL VAVNDPFITT DYMTYMFKYD SVHGHWKHHD  60
VTVKDEKTLL FGDKPVTVFG HRNPEEIPWG STGADIIVES TGVFTDKDKA AAHLKGGAKK  120
VIISAPSKDA PMFVVGVNEH EYKPELDIIS NASCTTNCLA PLAKVINDRF GIVEGLMTTV  180
HSITATQKTV DGPSAKDWRG GRAASFNIIP SSTGAAKAVG KVLPALNGKL TGMAFRVPTV  240
DVSVVDLTVR LEKEASYDEI KNAIKEESEG KLKGILGYTE DDVVSTDFVG DSRSSIFDAK  300
AGIALNKNFV KLVSWYDNEW GYSSRVIDLL VFVAKKSF                          338

SEQ ID NO: 442         moltype = AA  length = 8
FEATURE                Location/Qualifiers
source                 1..8
                       mol_type = protein
                       organism = Glycine max
SEQUENCE: 442
EASYDEIK                                                           8

SEQ ID NO: 443         moltype = AA  length = 27
FEATURE                Location/Qualifiers
source                 1..27
                       mol_type = protein
                       organism = Glycine max
SEQUENCE: 443
GILGYTEDDV VSTDFVGDSR SSIFDAK                                      27

SEQ ID NO: 444         moltype = AA  length = 8
FEATURE                Location/Qualifiers
source                 1..8
                       mol_type = protein
                       organism = Glycine max
SEQUENCE: 444
VIISAPSK                                                           8

SEQ ID NO: 445         moltype = AA  length = 8
FEATURE                Location/Qualifiers
source                 1..8
                       mol_type = protein
                       organism = Glycine max
SEQUENCE: 445
VLPALNGK                                                           8

SEQ ID NO: 446         moltype = DNA  length = 1020
FEATURE                Location/Qualifiers
source                 1..1020
                       mol_type = other DNA
                       organism = Glycine max
CDS                    1..1020
SEQUENCE: 446
atggcatcag ataagaagat taggatcggc atcaacggat ttggaaggat tggccgtttg  60
gtggccaggg ttgcccttca aaggaatgat gttgaacttg ttgctgtcaa cgatcctttc  120
atcaccactg attacatgac atacatgttc aagtacgaca ccgttcatgg ccagtggaag  180
cattttgatg tgaaggtgaa ggactctaag acccttctct ttggtgagaa gcccgtcacc  240
gtttttggaa tcaggaaccc tgaggaaatt ccatggggtg aggttggtgc tgattatgtt  300
gttgagtcaa ctggtgtatt cactgacaag gacaaggctg ctgctcactt gaagggtggt  360
gccaagaagg ttgtcatctc tgccccaagc aaagatgcac ccatgtttgt tgttggtgtt  420
aacgagaagg agtacaagcc agagcttgac attgtttcca atgctagctg cactaccaat  480
tgtcttgctc ccctcgccaa ggttatcaac gaccgatttg gaattgtgga gggtcttatg  540
accactgttc atgccatcac agctactcag aagactgttg atggtccatc aaacaaggac  600
tggagggggtg gaagagctgc ttccttcaat ataattccca gcagcactgg agctgctaag  660
gctgtaggaa aagttcttcc agcactgaat ggtaaattga ctggcatgtc cttccgagtc  720
cccactgtag atgtttcagt tgttgacctc actgtcaggc tagagaagcc agcaacctat  780
gagcaaatca aatctgctat caaggaggaa tcagagggca aattgaaggg tattttgggt  840
tacaccgaag atgatgttgt gtctactgat tttgttggtg ataacaggtc tagcatattt  900
gacgccaagg ccggaatttc tttgaacgac aactttgtaa aacttgtttc ctggtatgac  960
aacgaatggg gttacagttc ccgtgtgatt gatttgattg tccacattgc atccgtggct  1020

SEQ ID NO: 447         moltype = AA  length = 340
FEATURE                Location/Qualifiers
source                 1..340
                       mol_type = protein
```

```
                          organism = Glycine max
SEQUENCE: 447
MASDKKIRIG INGFGRIGRL VARVALQRND VELVAVNDPF ITTDYMTYMF KYDTVHGQWK  60
HFDVKVKDSK TLLFGEKPVT VFGIRNPEEI PWGEVGADYV VESTGVFTDK DKAAAHLKGG  120
AKKVVISAPS KDAPMFVVGV NEKEYKPELD IVSNASCTTN CLAPLAKVIN DRFGIVEGLM  180
TTVHAITATQ KTVDGPSNKD WRGGRAASFN IIPSSTGAAK AVGKVLPALN GKLTGMSFRV  240
PTVDVSVVDL TVRLEKPATY EQIKSAIKEE SEGKLKGILG YTEDDVVSTD FVGDNRSSIF  300
DAKAGISLND NFVKLVSWYD NEWGYSSRVI DLIVHIASVA                        340

SEQ ID NO: 448          moltype = AA  length = 11
FEATURE                 Location/Qualifiers
source                  1..11
                        mol_type = protein
                        organism = Glycine max
SEQUENCE: 448
AGISLNDNFV K                                                       11

SEQ ID NO: 449          moltype = AA  length = 27
FEATURE                 Location/Qualifiers
source                  1..27
                        mol_type = protein
                        organism = Glycine max
SEQUENCE: 449
GILGYTEDDV VSTDFVGDNR SSIFDAK                                      27

SEQ ID NO: 450          moltype = AA  length = 8
FEATURE                 Location/Qualifiers
source                  1..8
                        mol_type = protein
                        organism = Glycine max
SEQUENCE: 450
VLPALNGK                                                           8

SEQ ID NO: 451          moltype = AA  length = 8
FEATURE                 Location/Qualifiers
source                  1..8
                        mol_type = protein
                        organism = Glycine max
SEQUENCE: 451
VVISAPSK                                                           8

SEQ ID NO: 452          moltype = DNA  length = 1050
FEATURE                 Location/Qualifiers
source                  1..1050
                        mol_type = other DNA
                        organism = Glycine max
CDS                     1..1050
SEQUENCE: 452
atggtgacct cgtcgcaaaa gattctggtt accggcggtg ccggtttcat aggcacccac  60
accgtggtcc agcttctcaa aggaggcttc agtgtttcaa taatcgacaa tttcgataac  120
tccgtcgtgg aagcagtgga ccgcgtccgc caagtggtgg gccctcagct ttctcagaac  180
ctggaattca cccagggcga tctcaggaat agggatgact tggagaaact cttctccaga  240
acaacttttg atgccgtgat ccactttgct ggcctgaaag cggttgctga aagcgtttcc  300
aagccccgtc gctattttga ttttaatttg gtcggcacca tcaacctcta ccaagttatg  360
gcaaagtata attgcagaaa gatggttttc tcatcatctg caaccgttta tggccaacct  420
gaaaagatac cgtgtgagga ggatttcagg ttacaagcta tgaatcccta tggacggacc  480
aagcttttcc tggaagaaat tgcccgagat attcagaaag ctgaaccaga atggaagatc  540
atattactga ggtacttcaa tccggttggg gctcatgaaa gtggtaaact cggtgaagat  600
cccaagggca tcccaaataa cctcatgcct tacattcagc aagtagccgt tggaagattg  660
ccggaactca atgtatatgg gcatgattat ccccacaaggg atggctctgc gatccgggac  720
tatatccatg tgatggactt agcagatggt catattgctg ccttgcgaaa gctcttcaca  780
acagagaaca taggttgtac tgcttacaac ctgggaactg gtcgtggaac atccgtgctt  840
gaaatggtta cagcatttga aaaggcgtct ggcaagaaaa ttccagtaaa attatgtcca  900
agaagaccgg gagatgctac tgaggtttat gcatctacag agagagctga gaaagaactt  960
ggatggaaag caaaatatgg tgtggatgag atgtgcaggg accaatggaa ttgggcaaag  1020
aacaatcccc agggttacac ggggaagcct                                   1050

SEQ ID NO: 453          moltype = AA  length = 350
FEATURE                 Location/Qualifiers
source                  1..350
                        mol_type = protein
                        organism = Glycine max
SEQUENCE: 453
MVTSSQKILV TGGAGFIGTH TVVQLLKGGF SVSIIDNFDN SVVEAVDRVR QVVGPQLSQN  60
LEFTQGDLRN RDDLEKLFSR TTFDAVIHFA GLKAVAESVS KPRRYFDFNL VGTINLYQVM  120
AKYNCRKMVF SSSATVYGQP EKIPCEEDFR LQAMNPYGRT KLFLEEIARD IQKAEPEWKI  180
ILLRYFNPVG AHESGKLGED PKGIPNNLMP YIQQVAVGRL PELNVYGHDY PTRDGSAIRD  240
YIHVMDLADG HIAALRKLFT TENIGCTAYN LGTGRGTSVL EMVTAFEKAS GKKIPVKLCP  300
RRPGDATEVY ASTERAEKEL GWKAKYGVDE MCRDQWNWAK NNPQGYTGKP             350
```

```
SEQ ID NO: 454          moltype = AA  length = 12
FEATURE                 Location/Qualifiers
source                  1..12
                        mol_type = protein
                        organism = Glycine max
SEQUENCE: 454
LFLEEIARDI QK                                                              12

SEQ ID NO: 455          moltype = DNA  length = 1050
FEATURE                 Location/Qualifiers
source                  1..1050
                        mol_type = other DNA
                        organism = Glycine max
CDS                     1..1050
SEQUENCE: 455
atggtgtctt cctcccaaca cattctggtc accggtggtg ccggtttcat tggcacccac  60
accgtcgttc agcttctcaa agctggcttc agcgtttcaa taatcgacaa tttcgataac  120
tccgtcatgg aagcagtgga ccgcgtccgc caagtggttg gccctctgct ttctcagaac  180
ctccaattca cccagggcga tctccggaat agggatgact tggagaaact cttctccaaa  240
acaacatttg atgccgtgat ccactttgct ggcttgaaag cggttgctga aagcgttgcg  300
aagccccgtc gctattttga ttttaatttg gttggcacca tcaacctcta cgaatttatg  360
gcaaagtata attgcaaaaa gatggttttc tcatcatctg caaccgttta tggccaacct  420
gaaaagatac cgtgtgagga ggatttcaag ttacaagcta tgaatcccta tggacggacc  480
aagcttttcc tggaagaaat tgcccgagat attcagaaag ctgaaccaga atggaagatc  540
atattactga gatacttcaa tccagttggg gctcatgaaa gtggcaaact cggtgaagat  600
cccaagggca tcccaaataa cctcatgcct tacattcagc aagtagctgt tggaagattg  660
actgaactca atgtatacgg tcatgattat ccaacgaggg atggctctgc gatccgggac  720
tatatccatg tgatggactt ggcagatggc catattgctg ccctgcgaaa gctcttcaca  780
acggagaaca taggttgtac tgcttacaac ctgggaactg gtcgtggaac atctgtgctt  840
gaaatggttg cagcatttga aaaggcttct ggcaagaaaa ttccagtaaa attatgtcca  900
agaagaccgg gagatgcgac tgaggtttat gcatctacag agagagctga gaaagaactt  960
ggttggaagg caaactatgg tgtggaggag atgtgcaggg accaatggaa ttgggcaaag  1020
aacaatccct ggggttacgc ggggaagcct                                  1050

SEQ ID NO: 456          moltype = AA  length = 350
FEATURE                 Location/Qualifiers
source                  1..350
                        mol_type = protein
                        organism = Glycine max
SEQUENCE: 456
MVSSSQHILV TGGAGFIGTH TVVQLLKAGF SVSIIDNFDN SVMEAVDRVR QVVGPLLSQN  60
LQFTQGDLRN RDDLEKLFSK TTFDAVIHFA GLKAVAESVA KPRRYFDFNL VGTINLYEFM  120
AKYNCKKMVF SSSATVYGQP EKIPCEEDFK LQAMNPYGRT KLFLEEIARD IQKAEPEWKI  180
ILLRYFNPVG AHESGKLGED PKGIPNNLMP YIQQVAVGRL TELNVYGHDY PTRDGSAIRD  240
YIHVMDLADG HIAALRKLFT TENIGCTAYN LGTGRGTSVL EMVAAFEKAS GKKIPVKLCP  300
RRPGDATEVY ASTERAEKEL GWKANYGVEE MCRDQWNWAK NNPWGYAGKP              350

SEQ ID NO: 457          moltype = AA  length = 12
FEATURE                 Location/Qualifiers
source                  1..12
                        mol_type = protein
                        organism = Glycine max
SEQUENCE: 457
LFLEEIARDI QK                                                              12

SEQ ID NO: 458          moltype = AA  length = 13
FEATURE                 Location/Qualifiers
source                  1..13
                        mol_type = protein
                        organism = Glycine max
SEQUENCE: 458
TTFDAVIHFA GLK                                                             13

SEQ ID NO: 459          moltype = DNA  length = 1341
FEATURE                 Location/Qualifiers
source                  1..1341
                        mol_type = other DNA
                        organism = Glycine max
CDS                     1..1341
SEQUENCE: 459
atgggtaagg aaaagactca catcaacatt gtcgtcattg gacatgtcga ctctgggaag  60
tcaactacca ctggtcattt gatctacaag cttggaggta ttgacaagcg tgtgattgag  120
aggttcgaga aggaggctgc tgagatgaac aagaggtcat tcaagtatgc ctgggtgctt  180
gacaagctca aggctgagcg cgaaagagga attaccattg atattgcttt gtggaagttt  240
gaaaccacca agtactactg cacagtcatc gatgcccccg gacatcgtga ctttatcaag  300
aacatgatta ctggtacctc ccaggctgat tgtgctgtcc ttatcattga ctccaccact  360
ggtggttttg aagctggtat ttctaaggat ggacagactc gtgagcatgc tcttcttgct  420
ttcacccttg gtgtgaagca gatgatctgc tgctgtaaca agatggatgc cactaccccg  480
```

```
aagtactcta aggctaggta tgatgaaatt gtgaaggaag tctcttccta cttgaagaag  540
gttggttaca acccagacaa gattccattt gtgcccatct ctggtttcga gggtgacaac  600
atgattgaga ggtccaccaa ccttgactgg tacaagggac caactctcct tgaggctctt  660
gaccaaatca atgagcccaa gaggccctca gacaagccac tcaggcttcc attgcaggat  720
gtctacaaaa ttggtggtat tggtaccgtg ccagtgggac gtgttgagac tggtgtcgtg  780
aagcccggta tggtggtgac ttttggtccc actgggctga caactgaggt taagtctgtt  840
gagatgcacc atgaggctct cacagaggct cttccaggtg acaatgttgg ctttaatgtg  900
aagaatgttg cagtcaagga tctcaagcgt ggttttgttg catccaactc caaggatgac  960
cctgccaagg aagctgccaa cttcacatct caagtcatta tcatgaacca ccctggccag  1020
attggaaatg gatacgcacc ggtgcttgat tgccacactt ctcacattgc tgtcaagttt  1080
tctgaaatct tgaccaagat tgacaggcga tctggtaagg agcttgagaa ggagcccaaa  1140
tttttgaaga atggtgatgc aggtatggtt aagatgattc caaccaagcc catggtggtt  1200
gaaactttct ctgagtatcc tccccttggt cgttttgctg tgagggacat gcgtcaaact  1260
gtggctgtcg gagtcatcaa gagtgttgag aagaaagacc ccaccggagc caaggtcacc  1320
aaggccgctg ccaagaagaa g                                           1341

SEQ ID NO: 460         moltype = AA  length = 447
FEATURE                Location/Qualifiers
source                 1..447
                       mol_type = protein
                       organism = Glycine max
SEQUENCE: 460
MGKEKTHINI VVIGHVDSGK STTTGHLIYK LGGIDKRVIE RFEKEAAEMN KRSFKYAWVL  60
DKLKAERERG ITIDIALWKF ETTKYYCTVI DAPGHRDFIK NMITGTSQAD CAVLIIDSTT  120
GGFEAGISKD GQTREHALLA FTLGVKQMIC CCNKMDATTP KYSKARYDEI VKEVSSYLKK  180
VGYNPDKIPF VPISGFEGDN MIERSTNLDW YKGPTLLEAL DQINEPKRPS DKPLRLPLQD  240
VYKIGGIGTV PVGRVETGVV KPGMVVTFGP TGLTTEVKSV EMHHEALTEA LPGDNVGFNV  300
KNVAVKDLKR GFVASNSKDD PAKEAANFTS QVIIMNHPGQ IGNGYAPVLD CHTSHIAVKF  360
SEILTKIDRR SGKELEKEPK FLKNGDAGMV KMIPTKPMVV ETFSEYPPLG RFAVRDMRQT  420
VAVGVIKSVE KKDPTGAKVT KAAAKKK                                     447

SEQ ID NO: 461         moltype = AA  length = 8
FEATURE                Location/Qualifiers
source                 1..8
                       mol_type = protein
                       organism = Glycine max
SEQUENCE: 461
ARYDEIVK                                                          8

SEQ ID NO: 462         moltype = AA  length = 17
FEATURE                Location/Qualifiers
source                 1..17
                       mol_type = protein
                       organism = Glycine max
SEQUENCE: 462
DGQTREHALL AFTLGVK                                                17

SEQ ID NO: 463         moltype = AA  length = 7
FEATURE                Location/Qualifiers
source                 1..7
                       mol_type = protein
                       organism = Glycine max
SEQUENCE: 463
EVSSYLK                                                           7

SEQ ID NO: 464         moltype = AA  length = 7
FEATURE                Location/Qualifiers
source                 1..7
                       mol_type = protein
                       organism = Glycine max
SEQUENCE: 464
FSEILTK                                                           7

SEQ ID NO: 465         moltype = AA  length = 10
FEATURE                Location/Qualifiers
source                 1..10
                       mol_type = protein
                       organism = Glycine max
SEQUENCE: 465
STTTGHLIYK                                                        10

SEQ ID NO: 466         moltype = AA  length = 15
FEATURE                Location/Qualifiers
source                 1..15
                       mol_type = protein
                       organism = Glycine max
SEQUENCE: 466
THINIVVIGH VDSGK                                                  15
```

```
SEQ ID NO: 467          moltype = DNA  length = 1341
FEATURE                 Location/Qualifiers
source                  1..1341
                        mol_type = other DNA
                        organism = Glycine max
CDS                     1..1341
SEQUENCE: 467
atgggtaaag agaaggttca cattaacatt gtggtcattg gccatgttga ctctgggaag  60
tcaaccacca ctggccactt gatttacaag cttggaggta ttgacaagcg tgttattgag  120
aggtttgaga aagaagctgc tgagatgaac aagaggtcat tcaaatacgc ctgggtgctt  180
gacaagctta aggctgagcg tgagagagga attaccattg atattgcatt atggaagttt  240
gagaccacca aatactactg cactgttatt gatgctccag gacatcgtga tttcatcaag  300
aacatgatta ctggaacttc ccaggctgat tgtgctgtcc ttatcattga ttccacaact  360
ggtggttttg aagctggtat ttccaaagat ggacagactc gcgagcatgc tctacttgcc  420
ttcacccttg gtgtcaagca aatgatctgt tgctgtaaca agatggatgc cactacccca  480
aagtactcta aggccaggta tgaagaaatt gtgaaggaag tttcttccta cttgaagaag  540
gtaggttaca acccagacaa gattccattt gttcccatct caggttttga gggtgacaac  600
atgattgaga ggtccaccaa tcttgattgg tacaagggac caacccttct cgaggctctt  660
gaccagatca atgagcccaa gagaccctca gacaagcctt tgaggcttcc cttgcaggat  720
gtctacaaga ttggtggtat tggaacagtg ccagtgggac gagttgaaac tggtgtcttg  780
aagcccggta tggtggtgac ttttgctccc actggcctga caactgaagt taagtctgtg  840
gagatgcacc atgaagctct ccaggaggcc cttccaggtg acaacgtagg atttaatgtg  900
aagaatgttg cagtcaagga tctcaagcgt ggttttgttg cctcaaactc taaggatgat  960
cctgccaagg aggctgccaa cttcacatcc caagtcatta taatgaacca tcctggccaa  1020
attggaaatg gttatgctcc tgtgcttgac tgccacactt ctcacattgc cgtcaagttt  1080
gccgaacttg tgaccaagat tgacaggcga tctggtaagg agattgagaa ggagcccaaa  1140
ttcttgaaaa atggagatgc aggttatgtt aagatgattc ccaccaagcc tatggtggtc  1200
gaaactttct ccgagtatcc tcctcttggt cgttttgccg tgagggacat gcgacaaact  1260
gtggctgttg gagtcatcaa gagtgtggag aagaaggacc caactggagc caaggtcacc  1320
aaggctgcac agaagaagaa g                                          1341

SEQ ID NO: 468          moltype = AA  length = 447
FEATURE                 Location/Qualifiers
source                  1..447
                        mol_type = protein
                        organism = Glycine max
SEQUENCE: 468
MGKEKVHINI VVIGHVDSGK STTTGHLIYK LGGIDKRVIE RFEKEAAEMN KRSFKYAWVL  60
DKLKAERERG ITIDIALWKF ETTKYYCTVI DAPGHRDFIK NMITGTSQAD CAVLIIDSTT  120
GGFEAGISKD GQTREHALLA FTLGVKQMIC CCNKMDATTP KYSKARYEEI VKEVSSYLKK  180
VGYNPDKIPF VPISGFEGDN MIERSTNLDW YKGPTLLEAL DQINEPKRPS DKPLRLPLQD  240
VYKIGGIGTV PVGRVETGVL KPGMVVTFAP TGLTTEVKSV EMHHEALQEA LPGDNVGFNV  300
KNVAVKDLKR GFVASNSKDD PAKEAANFTS QVIIMNHPGQ IGNGYAPVLD CHTSHIAVKF  360
AELVTKIDRR SGKEIEKEPK FLKNGDAGYV KMIPTKPMVV ETFSEYPPLG RFAVRDMRQT  420
VAVGVIKSVE KKDPTGAKVT KAAQKKK                                    447

SEQ ID NO: 469          moltype = AA  length = 17
FEATURE                 Location/Qualifiers
source                  1..17
                        mol_type = protein
                        organism = Glycine max
SEQUENCE: 469
DGQTREHALL AFTLGVK                                               17

SEQ ID NO: 470          moltype = AA  length = 7
FEATURE                 Location/Qualifiers
source                  1..7
                        mol_type = protein
                        organism = Glycine max
SEQUENCE: 470
EVSSYLK                                                          7

SEQ ID NO: 471          moltype = AA  length = 10
FEATURE                 Location/Qualifiers
source                  1..10
                        mol_type = protein
                        organism = Glycine max
SEQUENCE: 471
STTTGHLIYK                                                       10

SEQ ID NO: 472          moltype = DNA  length = 1344
FEATURE                 Location/Qualifiers
source                  1..1344
                        mol_type = other DNA
                        organism = Glycine max
CDS                     1..1344
SEQUENCE: 472
atgggtaagg aaaaggttca catcagtatt gtggtcattg gccatgtcga ctctgggaaa  60
tccactacca ctggtcacct gatttacaag cttggaggca ttgacaagcg tgttattgag  120
```

```
aggtttgaga aggaagctgc tgagatgaac aagaggtctt tcaagtatgc ctgggtgctg  180
gacaaactta aggctgagcg tgaaagagga atcaccattg atattgcttt gtggaagttt  240
gaaacaacaa agtattattg cacagttatt gatgcgcctg gacataggga tttcattaag  300
aatatgatta ctgggacatc ccaagctgac tgtgctgttc ttatcattga ttcgaccact  360
ggtggttttg aagctggtat ttccaaggat ggacagactc gtgaacatgc tctgctttca  420
ttcacccttg gtgtgaaaca gatgatttgc tgctgtaaca aaatggatgc tactacaccc  480
aagtattcca aggccaggta tgatgaaatt gtgaaggaag tctcttccta cttgaagaaa  540
gtaggataca accctgacaa gattcctttt gttcctatct ctggttttga gggagacaac  600
atgattgaga ggtccacaaa ccttgactgg tacaagggtc caactctgct tgatgcactt  660
gaccagatta gtgagcccaa gaggccctct gacaagcccc tcaggcttcc ccttcaggat  720
gtgtacaaga ttggaggtat tggaactgtg ccagtgggac gtgttgagac cggtgtcttg  780
aagcctggaa tggtggtgac ttttgcacca actggactga caactgaagt caagtctgtg  840
gagatgcacc atgaatctct tacagaggca catcctggtg acaatgtggg attcaatgtt  900
aagaatgttg ctgttaagga tttgaagcgt ggttatgttg cctcaaactc aaaggatgac  960
cctgcaaagg aggctgctaa cttcacagcc caagtcatca tcatgaacca ccctggtcag  1020
attggaaatg gctatgcccc tgtcctcgac tgccacactt ctcacattgc tgtcaagttt  1080
gctgaactca tgaccaagat tgacaggcga tccggcaaag agcttgagaa ggagcccaag  1140
tttttgaaga acggtgatgc tggttttgtt aagatgattc caaccaaacc catggttgtt  1200
gaaactttct ccgagtatcc tccacttggt aggtttgctg ttagggacat gcgtcaaact  1260
gttgctgtgg gagtcatcaa gaacgttgag aagaaggatc ctaccggagc caaggtcacc  1320
aaggctgccc agaagaagaa gtga                                        1344

SEQ ID NO: 473          moltype = AA  length = 447
FEATURE                 Location/Qualifiers
source                  1..447
                        mol_type = protein
                        organism = Glycine max
SEQUENCE: 473
MGKEKVHISI VVIGHVDSGK STTTGHLIYK LGGIDKRVIE RFEKEAAEMN KRSFKYAWVL  60
DKLKAERERG ITIDIALWKF ETTKYYCTVI DAPGHRDFIK NMITGTSQAD CAVLIIDSTT  120
GGFEAGISKD GQTREHALLS FTLGVKQMIC CCNKMDATTP KYSKARYDEI VKEVSSYLKK  180
VGYNPDKIPF VPISGFEGDN MIERSTNLDW YKGPTLLDAL DQISEPKRPS DKPLRLPLQD  240
VYKIGGIGTV PVGRVETGVL KPGMVVTFAP TGLTTEVKSV EMHHESLTEA HPGDNVGFNV  300
KNVAVKDLKR GYVASNSKDD PAKEAANFTA QVIIMNHPGQ IGNGYAPVLD CHTSHIAVKF  360
AELMTKIDRR SGKELEKEPK FLKNGDAGFV KMIPTKPMVV ETFSEYPPLG RFAVRDMRQT  420
VAVGVIKNVE KKDPTGAKVT KAAQKKK                                     447

SEQ ID NO: 474          moltype = AA  length = 8
FEATURE                 Location/Qualifiers
source                  1..8
                        mol_type = protein
                        organism = Glycine max
SEQUENCE: 474
ARYDEIVK                                                          8

SEQ ID NO: 475          moltype = AA  length = 17
FEATURE                 Location/Qualifiers
source                  1..17
                        mol_type = protein
                        organism = Glycine max
SEQUENCE: 475
DGQTREHALL SFTLGVK                                                17

SEQ ID NO: 476          moltype = AA  length = 7
FEATURE                 Location/Qualifiers
source                  1..7
                        mol_type = protein
                        organism = Glycine max
SEQUENCE: 476
EVSSYLK                                                           7

SEQ ID NO: 477          moltype = AA  length = 10
FEATURE                 Location/Qualifiers
source                  1..10
                        mol_type = protein
                        organism = Glycine max
SEQUENCE: 477
STTTGHLIYK                                                        10

SEQ ID NO: 478          moltype = DNA  length = 882
FEATURE                 Location/Qualifiers
source                  1..882
                        mol_type = other DNA
                        organism = Glycine max
CDS                     1..882
SEQUENCE: 478
atggcttccg gtgaacagaa attccctcct caacaacaac aaacacagcc tgggaaggag  60
catgctatga ctccagtacc ccaattcact agccctgact acaagccttc aaataaactt  120
caagggaaga ttgcattagt cactgggggt gattctggga ttggacgagc ggtgtgtaac  180
```

```
ttgtttgcct tagaaggtgc taccgtggcc ttcacgtatg tgaaggggca tgaggacaag  240
gacgcgaggg acacattgga aatgatcaag agagcaaaga cttcggatgc caaggatcca  300
atggcaatag catctgattt gggttacgat gagaactgca agagggtggt tgatgaggtc  360
gtgagtgctt atggttgtat tgacattctg gtcaacaatg cagctgagca gtacgagtgt  420
ggaaccgtgg aggacataga cgagcctagg cttgagaggg tctttcgtac aaatatcttc  480
tcctatttct tcatggcgag gcatgccttg aagcacatga aggaaggaag cagcattatc  540
aacacgacat cagtgaatgc atacaaggga catgcgaaac tattggacta cacgtccacc  600
aagggggcaa ttgtggccta tacaaggggt cttgcccttc agctggtgag taagggaatt  660
cgggttaatg ggtggctccc agggcccatt tggacccctt tgataccagc ctctttcaag  720
gaggaagaaa cggcccaatt tggagcgcag gtcccaatga agagagctgg tcaacctatt  780
gaggttgctc cttcctatgt ttttcttgct tccaaccaat gctcctctta cataactgga  840
caagtccttc accccaatgg tggaaccgtt gtgaatggtt aa                       882

SEQ ID NO: 479          moltype = AA  length = 293
FEATURE                 Location/Qualifiers
source                  1..293
                        mol_type = protein
                        organism = Glycine max
SEQUENCE: 479
MASGEQKFPP QQQQTQPGKE HAMTPVPQFT SPDYKPSNKL QGKIALVTGG DSGIGRAVCN  60
LFALEGATVA FTYVKGHEDK DARDTLEMIK RAKTSDAKDP MAIASDLGYD ENCKRVVDEV  120
VSAYGCIDIL VNNAAEQYEC GTVEDIDEPR LERVFRTNIF SYFFMARHAL KHMKEGSSII  180
NTTSVNAYKG HAKLLDYTST KGAIVAYTRG LALQLVSKGI RVNGVAPGPI WTPLIPASFK  240
EEETAQFGAQ VPMKRAGQPI EVAPSYVFLA SNQCSSYITG QVLHPNGGTV VNG          293

SEQ ID NO: 480          moltype = AA  length = 15
FEATURE                 Location/Qualifiers
source                  1..15
                        mol_type = protein
                        organism = Glycine max
SEQUENCE: 480
EGSSIINTTS VNAYK                                                    15

SEQ ID NO: 481          moltype = AA  length = 12
FEATURE                 Location/Qualifiers
source                  1..12
                        mol_type = protein
                        organism = Glycine max
SEQUENCE: 481
FPPQQQQTQP GK                                                       12

SEQ ID NO: 482          moltype = AA  length = 17
FEATURE                 Location/Qualifiers
source                  1..17
                        mol_type = protein
                        organism = Glycine max
SEQUENCE: 482
GAIVAYTRGL ALQLVSK                                                  17

SEQ ID NO: 483          moltype = AA  length = 8
FEATURE                 Location/Qualifiers
source                  1..8
                        mol_type = protein
                        organism = Glycine max
SEQUENCE: 483
LLDYTSTK                                                            8

SEQ ID NO: 484          moltype = DNA  length = 882
FEATURE                 Location/Qualifiers
source                  1..882
                        mol_type = other DNA
                        organism = Glycine max
CDS                     1..882
SEQUENCE: 484
atggcaagca ataaggagtc taagttccca gcacagagcc agaaaactca gccaggaaaa  60
gaacatgtaa tgaatccact cccacaagcc acaaatcctg atcacaaggc cgccaataaa  120
ctccagggaa aggtggcgtt ggtgacagga ggtgactcag gaattggcag agcggtttgc  180
ctgtgtttcg caaaagaggg tgcaaccgtg gcctttacat acgtaaaggg ccatgaggac  240
agggataaag atgatactct gaagatgctg cttgaagcta agacaagtgg tgcagacaat  300
ccattggcaa tagcagcgga tattggcttt gatgagaact gcaaacaggt cattgacctt  360
gttgtcaaag aatatggccg ccttgatgtt ctggtcaaca atgcagctga gcagcatttg  420
acaaactctg ttgaggaaat cacacaacag cagcttgaga gagtcttcgg aaccaacatc  480
ttttctcagt tctttttggt caagcatgct ctgaagcaca tgaaagaagg gagctgcatc  540
ataaactcta cttcagttaa tgcatacaat gggaatccag aagcgttgga ctacactgct  600
accaagggag caattgtggc cttcaccaga ggtctttctc agcagctagc gagtagggga  660
attagggtga atggtgtggc acctggccca gtttggacgc caatacaacc agcttcaaag  720
cctgctgaga tgattcagaa cttggggtgt gaggtgccaa tgaaccgcgt ggctcagcct  780
tgtgagattg caccatgtta tttgttcttg gcaacttgtc aggactcttc ctactttact  840
ggccaagtcc tccatccaaa tggtgggatg gtcgtcaacg ct                       882
```

```
SEQ ID NO: 485          moltype = AA  length = 294
FEATURE                 Location/Qualifiers
source                  1..294
                        mol_type = protein
                        organism = Glycine max
SEQUENCE: 485
MASNKESKFP AQSQKTQPGK EHVMNPLPQA TNPDHKAANK LQGKVALVTG GDSGIGRAVC  60
LCFAKEGATV AFTYVKGHED RDKDDTLKML LEAKTSGADN PLAIAADIGF DENCKQVIDL  120
VVKEYGRLDV LVNNAAEQHL TNSVEEITQQ QLERVFGTNI FSQFFLVKHA LKHMKEGSCI  180
INSTSVNAYN GNPEALDYTA TKGAIVAFTR GLSQQLASRG IRVNGVAPGP VWTPIQPASK  240
PAEMIQNLGC EVPMNRVAQP CEIAPCYLFL ATCQDSSYFT GQVLHPNGGM VVNA        294

SEQ ID NO: 486          moltype = AA  length = 11
FEATURE                 Location/Qualifiers
source                  1..11
                        mol_type = protein
                        organism = Glycine max
SEQUENCE: 486
EGATVAFTYV K                                                       11

SEQ ID NO: 487          moltype = AA  length = 8
FEATURE                 Location/Qualifiers
source                  1..8
                        mol_type = protein
                        organism = Glycine max
SEQUENCE: 487
QVIDLVVK                                                           8

SEQ ID NO: 488          moltype = DNA  length = 879
FEATURE                 Location/Qualifiers
source                  1..879
                        mol_type = other DNA
                        organism = Glycine max
CDS                     1..879
SEQUENCE: 488
atggcttcgg gtgaaaagaa attcccacct caacaacaac aaacacagcc tgggaaggag  60
catgctatga atccagtacc ccaattcact agccctgact acaagccttc aaataaactt  120
caaggaaaga tagcattagt gactgggggt gactctggga ttggacgagc ggtgtgtaac  180
ttgtttgcct tagaaggtgc taccgtgggc ttcacatatg tgaaggggca tgaggacaag  240
gacgcgaggg acacgttgga aatgatcaag agggcaaaga cttcggatgc taaagatcca  300
atggcggtac cagctgattt gggttacgac gagaattgca agagagtggt tgatgaggtc  360
gtgaatgctt atggttgtat tgacattctg gtcaacaatg cagctgagca atacgagtgt  420
ggaacagtgg aggacattga tgagcctagg cttgagaggg tctttcgtac aaatatcttc  480
tcctatttct tcatgaccag gcatgccttg aagcacatga aggaaggaag cagcattatc  540
aacacgacat cggtgaatgc atacaaggga aatgcgaaac tattggacta cacgtccacg  600
aagggagcaa ttgtggccta tacaagggga cttgctcttc agttggtgag taagggaatt  660
cgggttaatg ggtggctcc tgggcctatt tggaccccat tgataccctc ctctttcaag  720
gaggaagaaa cggctcaatt tggtgcccag gtgccaatga agagagctgg ccagcctatt  780
gaggttgctc cgtcttatgt ttttcttgct tgcaaccaat gctcctctta cataactgga  840
caagtccttc accccaatgg tggaaccgtt gtcaatggt                         879

SEQ ID NO: 489          moltype = AA  length = 293
FEATURE                 Location/Qualifiers
source                  1..293
                        mol_type = protein
                        organism = Glycine max
SEQUENCE: 489
MASGEKKFPP QQQQTQPGKE HAMNPVPQFT SPDYKPSNKL QGKIALVTGG DSGIGRAVCN  60
LFALEGATVG FTYVKGHEDK DARDTLEMIK RAKTSDAKDP MAVPADLGYD ENCKRVVDEV  120
VNAYGCIDIL VNNAAEQYEC GTVEDIDEPR LERVFRTNIF SYFFMTRHAL KHMKEGSSII  180
NTTSVNAYKG NAKLLDYTST KGAIVAYTRG LALQLVSKGI RVNGVAPGPI WTPLIPSSFK  240
EEETAQFGAQ VPMKRAGQPI EVAPSYVFLA CNQCSSYITG QVLHPNGGTV VNG         293

SEQ ID NO: 490          moltype = AA  length = 15
FEATURE                 Location/Qualifiers
source                  1..15
                        mol_type = protein
                        organism = Glycine max
SEQUENCE: 490
EGSSIINTTS VNAYK                                                   15

SEQ ID NO: 491          moltype = AA  length = 12
FEATURE                 Location/Qualifiers
source                  1..12
                        mol_type = protein
                        organism = Glycine max
SEQUENCE: 491
FPPQQQQTQP GK                                                      12
```

```
SEQ ID NO: 492          moltype = AA  length = 17
FEATURE                 Location/Qualifiers
source                  1..17
                        mol_type = protein
                        organism = Glycine max
SEQUENCE: 492
GAIVAYTRGL ALQLVSK                                                 17

SEQ ID NO: 493          moltype = AA  length = 8
FEATURE                 Location/Qualifiers
source                  1..8
                        mol_type = protein
                        organism = Glycine max
SEQUENCE: 493
LLDYTSTK                                                           8

SEQ ID NO: 494          moltype = DNA  length = 3207
FEATURE                 Location/Qualifiers
source                  1..3207
                        mol_type = other DNA
                        organism = Glycine max
CDS                     1..3207
SEQUENCE: 494
atggcttctg agcaaatgcc tcgcagagag aacaacagca atagggtgat agagagagag  60
gttcacgttg agacacacag aaaagagtcc ctccctgata agggaagggt tgtgatagag  120
agtgagaaga aggagaaaga gagagagttg gcttctgata gagccaggtc tggaaatata  180
gttaaggagg acaaagaggt tgaagaagga agaagaggaa aagaaagtgg tggtggtggt  240
ggtgttcagc atgagaggaa gtttgaaacg aaagttgaag agaagaaggg ttttggggaa  300
aaggctgaac tcgagggaat aacaagagtg gtggtgggaa gagagtgcag caaagaggag  360
aaacaaggaa gaacaagaga gaaagtagag gcagagaaag caagatcaat ggagaaaact  420
agagatgaag ctaaaggaag agaacaagct gaaaccaaag gtcaaaccaa gaagggtggt  480
ggtgaggaac agggaagaag aagagaagaa ataggagaag aaaataaaca atccagcctc  540
gaagagattt ctaaatgcag agctgaagct gaagagaaag ttaaggagag aaaggagaga  600
tcaaaacaag cagcaagtaa tgaagctgcc aaagagagaa acaagcaggc aaataaggag  660
gcaacaaagg caaaagatgt cacaagagag aagggtcaac aaggcaatct taaaacagga  720
aatgagacac aagacattgg ccaaaagggt tatggtggag caaaggatac cattggtaga  780
gtggacaaca ttactacacc acttgctaaa aaggctcaag ttgctggtag caccactgtt  840
cagtatgctg gagagaaatc agcacaagcc aaagatgcta cggtaggatc aatggagaaa  900
actacaaagg atgctaaagg aagagaaaaa gcaggaacca aaggtcaaac aaagaagggt  960
ggtggtgagg aacaaggaaa aagaagagaa gaaacaggag aagaaaaaca atccagcctg  1020
gaggagattt ctaagcacag agctgaagct caacaaaaag caatgagttc aattgaaggt  1080
gctaaggaga gatacgagag agcaaaacaa gaagcaagta aagcttccaa agagagaaac  1140
attcaagcaa ataagagggc tgaagaagaa agaagaaaag cagaaagtgg taggggtgtt  1200
catgtggata agtttgaaga gaagaaggat tcagttgctga aagcagaact cgagagaaga  1260
acaagagagg tagagggaag agagtggaac aaagaggaga aacaaagaag ttgtccaaga  1320
gggaaagtag aggcagagaa agcaagacca atggaagaaa caaaactgga agctaaagga  1380
agagaaaaag ctgaaaccaa agagggtggt ggtgaggaaa aaggaatgag aagagaagaa  1440
ataggagaag aaaataaaca atccagcctg gaagagattt ttaagtacag agctgaagct  1500
caacagaaag ttaaggagag aaacgagaga gcaaaacaag cagcagaagc tgccaaagag  1560
agaaacaagc aggcaaataa agggaatgaa gaaggcagaa gagaaagaga aagtggtggg  1620
ggtgttcatc atgaggctaa gtttgaaact aaaggtgaaa aaaagaagga tttagtggga  1680
agagagcgga acaaagagga gaaacaaaga agcagtccaa gaggaaaagt agaggcagag  1740
aaagcaagac caatggaaga aacaaaggtg gaagctaaag gaagagaaaa agatgtaacc  1800
aaagagggtg gtgttgagga acaaggaaga ggaagaaaag aaaatgaaca atctagcttg  1860
aaagacattt ccaagtacag agctgaagct caacaaaatt cattcaatgc tactgaagct  1920
gctaaggaaa gatacgagag ggcaaaccaa gcgacaagtg aagctgccaa agagagaaac  1980
aagcaggcaa ataaggaggc aacaaaggca aaagatgtca caagagaaat ggatcaacaa  2040
ggcaatctta aaacagaaaa tgagacacag gacaatgacc agaagggtta tggtggagca  2100
aagtacacca ttggtagtgt ggaccacatt actacaccat ttattgtaga ggccaatctt  2160
aaatcagaaa atcagataca agacaatggc caaaagggtt atggtggagc aaaggacaca  2220
attggtagtg tagaccacat tactacacca cttgctgaaa aggccaaagc tgctggtagc  2280
accactgctc agtatgttgg ggagaaagca gcacaagcca aagatgctac tgtgcaaact  2340
ggcaagagtg ctgcaaaagt tgcctcagat ttgagggaca aggctttggc cacagggtgg  2400
agtgctgcac attattctac tgagataact gtggagggaa ccaaggctgc aacaaatgtt  2460
gttaagggag ttgctgagta tgcaggacag aaggcttctg agcttgcagc tatgtcagtg  2520
gatactgcga aaggtttagc tgctgctgca gctggggaga atgccaagga gtacactgca  2580
aggaagaagg tggaagctga gatggatttg gaggccaaaa gggaagctca aaatcaggaa  2640
tcgaaggagt ggccatcagc aaaatccacc actgagagca ttcaaagagg acaaggacaa  2700
caagaacagc atgagcaagg agaaaaatgg gaacatggtg cacaaaggac taataagcca  2760
catgaaagca acattgtgga aacctttgag gaaaacctag gtgggattgg ggaaaaaagg  2820
gaacaaaaac cacttggaag catcattgga gagagctttc aaggagttca agaaaaaggg  2880
agtgaagtga tggcaagcat tggtgaaaaa ctgggaagtg ctgcacatac attagtgaag  2940
aagccattgg ataaggccac tgagggaggg agagaggtgt tgggagctgt aggtgaaact  3000
gtggttgaga ttggtgaaaa catggtgaaa aaaccagcac agaaagtgca gcagcatcaa  3060
ggtgaaggtg gaggaggggt gctgaatgcc attggtgaaa ccatagcaga gatagcagag  3120
acaactaagg tgattgttgc tggagaggga gaaaaggaga taatagtaaa aacacatgaa  3180
tttgaatatg gagacttgaa acttgat                                      3207
```

```
SEQ ID NO: 495          moltype = AA  length = 1069
FEATURE                 Location/Qualifiers
source                  1..1069
                        mol_type = protein
                        organism = Glycine max
SEQUENCE: 495
MASEQMPRRE NNSNRVIERE VHVETHRKES LPDKGRVVIE SEKKEKEREL ASDRARSGNI  60
VKEDKEVEEG RRGKESGGGG GVQHERKFET KVEEKKGFGE KAELEGITRV VVGRECSKEE  120
KQGRTREKVE AEKARSMEKT RDEAKGREQA ETKGQTKKGG GEEQGRRREE IGEENKQSSL  180
EEISKCRAEA EEKVKERKER SKQAASNEAA KERNKQANKE ATKAKDVTRE KGQQGNLKTG  240
NETQDIGQKG YGGAKDTIGR VDNITTPLAK KAQVAGSTTV QYAGEKSAQA KDATVGSMEK  300
TTKDAKGREK AGTKGQTKKG GGEEQGKRRE ETGEEKQSSL EEISKHRAEA QQKAMSSIEG  360
AKERYERAKQ EASKASKERN IQANKRAEEE RRKAESGRGV HVDKFEEKKD SVLKAELERR  420
TREVEGREWN KEEKQRSCPR GKVEAEKARP MEETKLEAKG REKAETKEGG GEEKGMRREE  480
IGEENKQSSL EEIFKYRAEA QQKVKERNER AKQAAEAAKE RNKQANKGNE EGRRERESGG  540
GVHHEAKFET KGEKKKDLVG RERNKEEKQR SSPRGKVEAE KARPMEETKV EAKGREKDVT  600
KEGGVEEQGR GRKENEQSSL KDISKYRAEA QQNSFNATEA AKERYERANQ ATSEAAKERN  660
KQANKEATKA KDVTREMDQQ GNLKTENETQ DNDQKGYGGA KYTIGSVDHI TTPFIVEANL  720
KSENQIQDNG QKGYGGAKDT IGSVDHITTP LAEKAKAAGS TTAQYVGEKA AQAKDATVQT  780
GKSAAKVASD LRDKALATGW SAAHYSTEIT VEGTKAATNV VKGVAEYAGQ KASELAAMSV  840
DTAKGLAAAA AGENAKEYTA RKKVEAEMDL EAKREAQNQE SKEWPSAKST TESIQRGQGQ  900
QEQHEQGEKW EHGAQRTNKP HESNIVETFE ENLGGIGEKR EQKPLGSIIG ESFQGVQEKG  960
SEVMASIGEK LGSAAHTLVK KPLDKATEGG REVLGAVGET VVEIGENMVK KPAQKVQQHQ  1020
GEGGGGVLNA IGETIAEIAE TTKVIVAGEG EKEIIVKTHE FEYGDLKLD             1069

SEQ ID NO: 496          moltype = AA  length = 13
FEATURE                 Location/Qualifiers
source                  1..13
                        mol_type = protein
                        organism = Glycine max
SEQUENCE: 496
AAGSTTAQYV GEK                                                    13

SEQ ID NO: 497          moltype = AA  length = 21
FEATURE                 Location/Qualifiers
source                  1..21
                        mol_type = protein
                        organism = Glycine max
SEQUENCE: 497
ALATGWSAAH YSTEITVEGT K                                           21

SEQ ID NO: 498          moltype = AA  length = 15
FEATURE                 Location/Qualifiers
source                  1..15
                        mol_type = protein
                        organism = Glycine max
SEQUENCE: 498
AQVAGSTTVQ YAGEK                                                  15

SEQ ID NO: 499          moltype = AA  length = 15
FEATURE                 Location/Qualifiers
source                  1..15
                        mol_type = protein
                        organism = Glycine max
SEQUENCE: 499
DTIGRVDNIT TPLAK                                                  15

SEQ ID NO: 500          moltype = AA  length = 16
FEATURE                 Location/Qualifiers
source                  1..16
                        mol_type = protein
                        organism = Glycine max
SEQUENCE: 500
DTIGSVDHIT TPLAEK                                                 16

SEQ ID NO: 501          moltype = AA  length = 16
FEATURE                 Location/Qualifiers
source                  1..16
                        mol_type = protein
                        organism = Glycine max
SEQUENCE: 501
ERELASDRAR SGNIVK                                                 16

SEQ ID NO: 502          moltype = AA  length = 15
FEATURE                 Location/Qualifiers
source                  1..15
                        mol_type = protein
                        organism = Glycine max
SEQUENCE: 502
```

```
ERYERANQAT SEAAK                                                    15

SEQ ID NO: 503          moltype = AA  length = 18
FEATURE                 Location/Qualifiers
source                  1..18
                        mol_type = protein
                        organism = Glycine max
SEQUENCE: 503
GGGEEQGRRR EEIGEENK                                                 18

SEQ ID NO: 504          moltype = AA  length = 12
FEATURE                 Location/Qualifiers
source                  1..12
                        mol_type = protein
                        organism = Glycine max
SEQUENCE: 504
GLAAAAAGEN AK                                                       12

SEQ ID NO: 505          moltype = AA  length = 9
FEATURE                 Location/Qualifiers
source                  1..9
                        mol_type = protein
                        organism = Glycine max
SEQUENCE: 505
GRVVIESEK                                                           9

SEQ ID NO: 506          moltype = AA  length = 9
FEATURE                 Location/Qualifiers
source                  1..9
                        mol_type = protein
                        organism = Glycine max
SEQUENCE: 506
GVAEYAGQK                                                           9

SEQ ID NO: 507          moltype = AA  length = 10
FEATURE                 Location/Qualifiers
source                  1..10
                        mol_type = protein
                        organism = Glycine max
SEQUENCE: 507
LGSAAHTLVK                                                          10

SEQ ID NO: 508          moltype = AA  length = 9
FEATURE                 Location/Qualifiers
source                  1..9
                        mol_type = protein
                        organism = Glycine max
SEQUENCE: 508
QSSLEEIFK                                                           9

SEQ ID NO: 509          moltype = AA  length = 9
FEATURE                 Location/Qualifiers
source                  1..9
                        mol_type = protein
                        organism = Glycine max
SEQUENCE: 509
QSSLEEISK                                                           9

SEQ ID NO: 510          moltype = AA  length = 20
FEATURE                 Location/Qualifiers
source                  1..20
                        mol_type = protein
                        organism = Glycine max
SEQUENCE: 510
REQKPLGSII GESFQGVQEK                                               20

SEQ ID NO: 511          moltype = AA  length = 11
FEATURE                 Location/Qualifiers
source                  1..11
                        mol_type = protein
                        organism = Glycine max
SEQUENCE: 511
TGNETQDIGQ K                                                        11

SEQ ID NO: 512          moltype = AA  length = 9
FEATURE                 Location/Qualifiers
source                  1..9
                        mol_type = protein
                        organism = Glycine max
```

```
SEQUENCE: 512
VIVAGEGEK                                                         9

SEQ ID NO: 513          moltype = AA  length = 28
FEATURE                 Location/Qualifiers
source                  1..28
                        mol_type = protein
                        organism = Glycine max
SEQUENCE: 513
VQQHQGEGGG GVLNAIGETI AEIAETTK                                    28

SEQ ID NO: 514          moltype = DNA  length = 735
FEATURE                 Location/Qualifiers
source                  1..735
                        mol_type = other DNA
                        organism = Glycine max
CDS                     1..735
SEQUENCE: 514
atggcactgt gcaaccgcgt cagatcggga atctctctct tcaccaaatc cacgttcctc  60
acttcccagc gatccactct ccaacgatcc ctcgttgccc ctttcatttc cctcgcctcc  120
agaaattacg ccaacgtgcc ggggcaaaag gaaaccaaag ttaaggtccc tctggctttg  180
tttggaggtt caggaaacta tgcctctgct ttgtatattg catctgtgaa agccaatgca  240
gtggaaaagg ttgagactga gcttctgcaa tttgttgagg cagtaaagaa tagtcccata  300
ttttcacagt ttataaggga cttgtctgtg gctaaggatg ttagagttaa agttatccag  360
gatatttgtg gggaagccaa gttttcggat gttacaaaga acttccttgt tattgttgct  420
gagaatggaa ggcttaaaaa catagacacc attgcaaaga ggtttgcaca gttgtcaatg  480
gcatataagg gagaagtgca agcgactgtg accactgttg ttcctcttcc ccctgaagag  540
gaaaaggcat tgaaggagac tcttcaggaa ataataggtt ctggagcgaa ggttcatctt  600
gaacagaaga ttgatccaag catacttggt gggcttgtgc ttgaatttag ccagaaggtc  660
tttgacatgt caattaagac cagggcacaa cagatggaga ggatcctccg agagcccgtg  720
tccattgcca acatc                                                  735

SEQ ID NO: 515          moltype = AA  length = 245
FEATURE                 Location/Qualifiers
source                  1..245
                        mol_type = protein
                        organism = Glycine max
SEQUENCE: 515
MALCNRVRSG ISLFTKSTFL TSQRSTLQRS LVAPFISLAS RNYANVPGQK ETKVKVPLAL  60
FGGSGNYASA LYIASVKANA VEKVETELLQ FVEAVKNSPI FSQFIRDLSV AKDVRVKVIQ  120
DICGEAKFSD VTKNFLVIVA ENGRLKNIDT IAKRFAQLSM AYKGEVQATV TTVVPLPPEE  180
EKALKETLQE IIGSGAKVHL EQKIDPSILG GLVLEFSQKV FDMSIKTRAQ QMERILREPV  240
SIANI                                                             245

SEQ ID NO: 516          moltype = AA  length = 12
FEATURE                 Location/Qualifiers
source                  1..12
                        mol_type = protein
                        organism = Glycine max
SEQUENCE: 516
ETLQEIIGSG AK                                                     12

SEQ ID NO: 517          moltype = DNA  length = 678
FEATURE                 Location/Qualifiers
source                  1..678
                        mol_type = other DNA
                        organism = Glycine max
CDS                     1..678
SEQUENCE: 517
atgaccacac aagtaccacc acacagtgtc caagtccaca caacaacaca ccgctacgaa  60
gctggcgtcg tcccccccgg agcccgtttc gaaccgccgc gttatgaagc cggcgtcaaa  120
gcgccctcca tttaccattc cgagagaggt ccaacgactt cccaggtcct cgccgtcctc  180
gccggcctcc cggtcggtgg catcctgctc ctcctggcgg gattgaccct ggcaggaacc  240
ctcaccggac tggcagttgc cacgccgctc ttcgtcctct tcagcccggt gctggttcca  300
gccacggtcg ccatcggcct ggccgtggcc gggttcctga cgtcgggggc cttcgggctc  360
acggcgctgt cttccttctc ctggatcctg aactacatcc gggagaccca gccagcctcg  420
gagaacctcg ccgccgccgc gaagcatcac ctcgccgagg cggcggagta cgtggggcag  480
aagacgaagg aagtggggca gaagaccaag gaggttgggc aggatattca gagcaaggca  540
caggatacaa gggaggcagc tgcaagggat gcaagggagg cagctgcaag ggatgcaagg  600
gaagctgctg caagggatgc aaaggtggag gcaagggatg taaagagaac aacagtgaca  660
gcaacaaccg caaccgca                                               678

SEQ ID NO: 518          moltype = AA  length = 226
FEATURE                 Location/Qualifiers
source                  1..226
                        mol_type = protein
                        organism = Glycine max
SEQUENCE: 518
MTTQVPPHSV QVHTTTHRYE AGVVPPGARF EPPRYEAGVK APSIYHSERG PTTSQVLAVL  60
```

```
AGLPVGGILL LLAGLTLAGT LTGLAVATPL FVLFSPVLVP ATVAIGLAVA GFLTSGAFGL  120
TALSSFSWIL NYIRETQPAS ENLAAAAKHH LAEAAEYVGQ KTKEVGQKTK EVGQDIQSKA  180
QDTREAAARD AREAAARDAR EAAARDAKVE ARDVKRTTVT ATTATA                 226

SEQ ID NO: 519         moltype = AA  length = 9
FEATURE                Location/Qualifiers
source                 1..9
                       mol_type = protein
                       organism = Glycine max
SEQUENCE: 519
EVGQDIQSK                                                          9

SEQ ID NO: 520         moltype = AA  length = 11
FEATURE                Location/Qualifiers
source                 1..11
                       mol_type = protein
                       organism = Glycine max
SEQUENCE: 520
RTTVTATTAT A                                                       11

SEQ ID NO: 521         moltype = DNA  length = 627
FEATURE                Location/Qualifiers
source                 1..627
                       mol_type = other DNA
                       organism = Glycine max
CDS                    1..627
SEQUENCE: 521
atgacaagga aacaagcaag ttccacgaga cgtggcggtc tttcaggagt cttgcattcc  60
aaatccaaat cttctcctct actctccata tcccttgtcc tatttgtagc catccttctc  120
atcctttatg cttgtatcgg gtcaggtata ttgggaggaa gaaaggatgt gattagcatg  180
gctgaagatg atttttcatg cacttttgaa gttccaagtg caattcctgt tttgaagaat  240
gcatatggtg gcagcatgaa aaatgttttg cacgtaggcc ctgagagttg ttcggtggtc  300
tccaaatttt taagagaagg ggaaactgaa gcatggggtg tggagccata tgacttagac  360
gatgctgata ggaactgcaa ggctcttgtg cagaaaggca ttatacgtgt tgcagatata  420
aaattccctt taccatacag ggtgaagtct ttttctcatg ttatagtgtc agatgctttg  480
gattacctgt ctccaaaata tataaacaaa actcttcctg agctagcaag ggtatcttct  540
gatggtatta ttattttcac aggttaccca ggtcaaccga gagctaaaat agcaccatta  600
tccaaatttg gccgtccaca taggtgc                                      627

SEQ ID NO: 522         moltype = AA  length = 209
FEATURE                Location/Qualifiers
source                 1..209
                       mol_type = protein
                       organism = Glycine max
SEQUENCE: 522
MTRKQASSTR RGGLSGVLHS KSKSSPLLSI SLVLFVAILL ILYACIGSGI LGGRKDVISM  60
AEDDFSCTFE VPSAIPVLKN AYGGSMKNVL HVGPESCSVV SKFLREGETE AWGVEPYDLD  120
DADRNCKALV QKGIIRVADI KFPLPYRVKS FSHVIVSDAL DYLSPKYINK TLPELARVSS  180
DGIIIFTGYP GQPRAKIAPL SKFGRPHRC                                    209

SEQ ID NO: 523         moltype = AA  length = 8
FEATURE                Location/Qualifiers
source                 1..8
                       mol_type = protein
                       organism = Glycine max
SEQUENCE: 523
NAYGGSMK                                                           8

SEQ ID NO: 524         moltype = DNA  length = 723
FEATURE                Location/Qualifiers
source                 1..723
                       mol_type = other DNA
                       organism = Glycine max
CDS                    1..723
SEQUENCE: 524
atggccgcgc gagctctgtt gaccagaaaa accctagcca ccgtgctccg caacgacgcg  60
aagcccataa tcggagttgg cataacagca gcggctactc attcacgcgg gttgcacgtg  120
tacacgctac ccgatctgga ttacgactat ggcgcactgg agccagccat cagcggcgac  180
atcatgcagc tgcaccacca gaagcaccac cagacttaca tcaccaacta caacaaggcc  240
ctcgagcagc tccaagacgc catcgccaag aaagattcct ccgccgtcgt taagctccag  300
ggcgccatca agttcaacgg cggaggtcat gtcaaccatt ctattttctg gaaaaatcta  360
gctcctgttc gtgaaggagg tggtgaacca cccaagggtt cactgggatg ggctattgac  420
acacattttg gttcttttga agcattaata caaaaagtta acgcagaagg tgctgcacta  480
caggggtctg gatgggtgtg gcttggtctg gacaaagagt tgaagaggct tgtagttgaa  540
accactgcca accaggaccc actggttact aagggaccaa atttggttcc attgattggt  600
attgatgttt gggagcatgc gtactactta cagtacaaga atgttagacc agactatctg  660
aagaacattt ggaaagttat taattggaaa tatgccagtg aagtgtatga gaaagagagc  720
tct                                                                723
```

```
SEQ ID NO: 525          moltype = AA  length = 241
FEATURE                 Location/Qualifiers
source                  1..241
                        mol_type = protein
                        organism = Glycine max
SEQUENCE: 525
MAARALLTRK TLATVLRNDA KPIIGVGITA AATHSRGLHV YTLPDLDYDY GALEPAISGD  60
IMQLHHQKHH QTYITNYNKA LEQLQDAIAK KDSSAVVKLQ GAIKFNGGGH VNHSIFWKNL  120
APVREGGGEP PKGSLGWAID THFGSFEALI QKVNAEGAAL QGSGWVWLGL DKELKRLVVE  180
TTANQDPLVT KGPNLVPLIG IDVWEHAYYL QYKNVRPDYL KNIWKVINWK YASEVYEKES  240
S                                                                  241

SEQ ID NO: 526          moltype = AA  length = 11
FEATURE                 Location/Qualifiers
source                  1..11
                        mol_type = protein
                        organism = Glycine max
SEQUENCE: 526
ALEQLQDAIA K                                                       11

SEQ ID NO: 527          moltype = AA  length = 11
FEATURE                 Location/Qualifiers
source                  1..11
                        mol_type = protein
                        organism = Glycine max
SEQUENCE: 527
HHQTYITNYN K                                                       11

SEQ ID NO: 528          moltype = AA  length = 14
FEATURE                 Location/Qualifiers
source                  1..14
                        mol_type = protein
                        organism = Glycine max
SEQUENCE: 528
NLAPVREGGG EPPK                                                    14

SEQ ID NO: 529          moltype = AA  length = 8
FEATURE                 Location/Qualifiers
source                  1..8
                        mol_type = protein
                        organism = Glycine max
SEQUENCE: 529
NVRPDYLK                                                           8

SEQ ID NO: 530          moltype = AA  length = 16
FEATURE                 Location/Qualifiers
source                  1..16
                        mol_type = protein
                        organism = Glycine max
SEQUENCE: 530
RLVVETTANQ DPLVTK                                                  16

SEQ ID NO: 531          moltype = AA  length = 8
FEATURE                 Location/Qualifiers
source                  1..8
                        mol_type = protein
                        organism = Glycine max
SEQUENCE: 531
YASEVYEK                                                           8

SEQ ID NO: 532          moltype = DNA  length = 720
FEATURE                 Location/Qualifiers
source                  1..720
                        mol_type = other DNA
                        organism = Glycine max
CDS                     1..720
SEQUENCE: 532
atggccgcgc gagccctgtt gaccagaaaa accctagcca ccgttctccg caacgacgcg  60
aagcccataa tcggagctgg catagctgca gctactcatt ctcgtgggtt gcacgtgtac  120
acgctccccg atctggatta cgactatggc gctctggagc cagccatcag cggcgaaatc  180
atgcagctgc accaccagaa gcaccaccag acttacatca ccaacttcaa caaggccctc  240
gagcagctcc aagacgccgt cgccaagaaa gattcctccg ccgtcgttaa gctccagggc  300
gccatcaagt tcaacggcgg aggtcacgtc aaccattcta ttttctggaa aaatctagct  360
cctgttcgtg aaggaggtgg tgaaccaccc aagggttcac tgggatgggc cattgacaca  420
cattttggct cttttgaagc attagtacaa aaagttaatg cagaaggtgc tgcactacag  480
gggtctggat gggtgtggct tggtctggac aaagagttga agaggcttgt agttgaaacc  540
actgccaacc aggacccact ggttactaag ggaccaaatt tggttccatt gcttggtatt  600
gatgtttggg agcatgcgta ctacttacag tacaagaatg ttagaccaga ctatctgaag  660
aacatttgga aagttattaa ttggaaatat gccagtgaag tgtatgagaa agagagctct  720
```

```
SEQ ID NO: 533          moltype = AA  length = 240
FEATURE                 Location/Qualifiers
source                  1..240
                        mol_type = protein
                        organism = Glycine max
SEQUENCE: 533
MAARALLTRK TLATVLRNDA KPIIGAGIAA ATHSRGLHVY TLPDLDYDYG ALEPAISGEI  60
MQLHHQKHHQ TYITNFNKAL EQLQDAVAKK DSSAVVKLQG AIKFNGGGHV NHSIFWKNLA  120
PVREGGGEPP KGSLGWAIDT HFGSFEALVQ KVNAEGAALQ GSGWVWLGLD KELKRLVVET  180
TANQDPLVTK GPNLVPLLGI DVWEHAYYLQ YKNVRPDYLK NIWKVINWKY ASEVYEKESS  240

SEQ ID NO: 534          moltype = AA  length = 11
FEATURE                 Location/Qualifiers
source                  1..11
                        mol_type = protein
                        organism = Glycine max
SEQUENCE: 534
ALEQLQDAVA K                                                        11

SEQ ID NO: 535          moltype = AA  length = 11
FEATURE                 Location/Qualifiers
source                  1..11
                        mol_type = protein
                        organism = Glycine max
SEQUENCE: 535
HHQTYITNFN K                                                        11

SEQ ID NO: 536          moltype = AA  length = 14
FEATURE                 Location/Qualifiers
source                  1..14
                        mol_type = protein
                        organism = Glycine max
SEQUENCE: 536
NLAPVREGGG EPPK                                                     14

SEQ ID NO: 537          moltype = AA  length = 8
FEATURE                 Location/Qualifiers
source                  1..8
                        mol_type = protein
                        organism = Glycine max
SEQUENCE: 537
NVRPDYLK                                                            8

SEQ ID NO: 538          moltype = AA  length = 16
FEATURE                 Location/Qualifiers
source                  1..16
                        mol_type = protein
                        organism = Glycine max
SEQUENCE: 538
RLVVETTANQ DPLVTK                                                   16

SEQ ID NO: 539          moltype = AA  length = 8
FEATURE                 Location/Qualifiers
source                  1..8
                        mol_type = protein
                        organism = Glycine max
SEQUENCE: 539
YASEVYEK                                                            8

SEQ ID NO: 540          moltype = DNA  length = 486
FEATURE                 Location/Qualifiers
source                  1..486
                        mol_type = other DNA
                        organism = Glycine max
CDS                     1..486
SEQUENCE: 540
atggctccaa ttgcagtggg agatgtcatt ccagacggca ttttggctta cttggatgaa  60
gaaaacaaac cccaaactgt ctctattcac tctctcgccg ccggcaagaa agtcatcatc  120
tttggggttc ccggtgcctt cactcctaca tgcagcttga agcacgtgcc tggcttcatt  180
gagagagcag aagagctgaa aggaaagggt gtggacgaaa taatctgtat cagcgtgaat  240
gatccctttg tgatgaactc atgggccaaa acgttcccag agaacaagca tgttaagttc  300
cttgctgatg gtgcagccaa atacaccaat gccctcggtc ttgagcttga cctcaccgac  360
aagggtctcg gcgtccgctc aaagaggttt gctttgctgg tggaagacct caaggtgaag  420
gttgcaaatg ttgaaagtgg aggagagttc accatctcca gtgctgaaga gatcatcaag  480
gccctc                                                              486

SEQ ID NO: 541          moltype = AA  length = 162
FEATURE                 Location/Qualifiers
```

```
source                  1..162
                        mol_type = protein
                        organism = Glycine max
SEQUENCE: 541
MAPIAVGDVI PDGILAYLDE ENKPQTVSIH SLAAGKKVII FGVPGAFTPT CSLKHVPGFI  60
ERAEELKGKG VDEIICISVN DPFVMNSWAK TFPENKHVKF LADGAAKYTN ALGLELDLTD  120
KGLGVRSKRF ALLVEDLKVK VANVESGGEF TISSAEEIIK AL                    162

SEQ ID NO: 542          moltype = AA  length = 13
FEATURE                 Location/Qualifiers
source                  1..13
                        mol_type = protein
                        organism = Glycine max
SEQUENCE: 542
HVPGFIERAE ELK                                                    13

SEQ ID NO: 543          moltype = AA  length = 10
FEATURE                 Location/Qualifiers
source                  1..10
                        mol_type = protein
                        organism = Glycine max
SEQUENCE: 543
RFALLVEDLK                                                        10

SEQ ID NO: 544          moltype = AA  length = 20
FEATURE                 Location/Qualifiers
source                  1..20
                        mol_type = protein
                        organism = Glycine max
SEQUENCE: 544
VANVESGGEF TISSAEEIIK                                             20

SEQ ID NO: 545          moltype = AA  length = 14
FEATURE                 Location/Qualifiers
source                  1..14
                        mol_type = protein
                        organism = Glycine max
SEQUENCE: 545
YTNALGLELD LTDK                                                   14

SEQ ID NO: 546          moltype = DNA  length = 486
FEATURE                 Location/Qualifiers
source                  1..486
                        mol_type = other DNA
                        organism = Glycine max
CDS                     1..486
SEQUENCE: 546
atggctccaa ttgcagtggg aaacgtgatt ccagacggca ttttggctta cttggatgaa  60
gaaaacaaac cccaaactgt ctccattcac tctctcgcca ccggcaagaa agtcatcatc  120
tttggggttc ccggtgcctt cactcctact tgcagcttga agcacgttcc tggcttcatt  180
gagagagcag aagagctgaa agggaagggt gtggacgaaa taatctgtat cagtgtgaat  240
gatccatttg tgatgaactc atgggccaaa acattcccag agaacaagca tgttaagttc  300
cttgctgatg gtgcagccaa atacaccaat gcccttggtc ttgagcttga cctcactgac  360
aagggtctcg gcgtccgctc aaagaggttt gctctgctgg tggaagacct caaggtgaag  420
gttgcgaatg ttgaaagtgg aggagagttc accatctcca gtgctgaaga gatcatcaag  480
gccctt                                                            486

SEQ ID NO: 547          moltype = AA  length = 162
FEATURE                 Location/Qualifiers
source                  1..162
                        mol_type = protein
                        organism = Glycine max
SEQUENCE: 547
MAPIAVGNVI PDGILAYLDE ENKPQTVSIH SLATGKKVII FGVPGAFTPT CSLKHVPGFI  60
ERAEELKGKG VDEIICISVN DPFVMNSWAK TFPENKHVKF LADGAAKYTN ALGLELDLTD  120
KGLGVRSKRF ALLVEDLKVK VANVESGGEF TISSAEEIIK AL                    162

SEQ ID NO: 548          moltype = AA  length = 13
FEATURE                 Location/Qualifiers
source                  1..13
                        mol_type = protein
                        organism = Glycine max
SEQUENCE: 548
HVPGFIERAE ELK                                                    13

SEQ ID NO: 549          moltype = AA  length = 10
FEATURE                 Location/Qualifiers
source                  1..10
                        mol_type = protein
```

```
                        organism = Glycine max
SEQUENCE: 549
RFALLVEDLK                                                         10

SEQ ID NO: 550          moltype = AA  length = 20
FEATURE                 Location/Qualifiers
source                  1..20
                        mol_type = protein
                        organism = Glycine max
SEQUENCE: 550
VANVESGGEF TISSAEEIIK                                              20

SEQ ID NO: 551          moltype = AA  length = 14
FEATURE                 Location/Qualifiers
source                  1..14
                        mol_type = protein
                        organism = Glycine max
SEQUENCE: 551
YTNALGLELD LTDK                                                    14

SEQ ID NO: 552          moltype = DNA  length = 456
FEATURE                 Location/Qualifiers
source                  1..456
                        mol_type = other DNA
                        organism = Glycine max
CDS                     1..456
SEQUENCE: 552
atgtcgcagt tgctggataa agccaagaac ttcgtgtcgg agaaggtaaa tgatatggcc  60
aagccggagg cgagtgtcac tgacgtggac ttcaagcgcg tgagcaaaga taatgtcgag  120
tacttggcca aggtctctgt tcgtaaccct tattcaactt ccatacccat ttgtgagatc  180
aactactctt tcaaaagcgc atccagggag atagcatcag ggaaaattcc agacccagga  240
tcgttgaagg caaaggacac aacaatggtg gatgtgccag ttaaggttcc atacagcata  300
ttgatgagct tggcaaagga cattggtgct gactgggaca tagactatca attggatctt  360
ggtctggtta ttgatgttcc tgtcattggc atcttcacca ttcctctctc tcagaaagga  420
gagatcaagc taccaaccct ctctaccatg ttcgcc                            456

SEQ ID NO: 553          moltype = AA  length = 152
FEATURE                 Location/Qualifiers
source                  1..152
                        mol_type = protein
                        organism = Glycine max
SEQUENCE: 553
MSQLLDKAKN FVSEKVNDMA KPEASVTDVD FKRVSKDNVE YLAKVSVRNP YSTSIPICEI  60
NYSFKSASRE IASGKIPDPG SLKAKDTTMV DVPVKVPYSI LMSLAKDIGA DWDIDYQLDL  120
GLVIDVPVIG IFTIPLSQKG EIKLPTLSTM FA                                152

SEQ ID NO: 554          moltype = AA  length = 8
FEATURE                 Location/Qualifiers
source                  1..8
                        mol_type = protein
                        organism = Glycine max
SEQUENCE: 554
DNVEYLAK                                                           8

SEQ ID NO: 555          moltype = DNA  length = 480
FEATURE                 Location/Qualifiers
source                  1..480
                        mol_type = other DNA
                        organism = Glycine max
CDS                     1..480
SEQUENCE: 555
atgtcggacg aagagcacca tttcgagtcc aaggcagacg ccggtgcctc caaaacctac  60
cctcagcaag ccggtaccat tcgcaagaac ggctacatcg tcatcaaagg acgcccctgc  120
aaggttgtgg aagtttcgac ttccaaaact ggaaagcacg gtcacgccaa gtgccacttt  180
gttggaattg atattttcac tgccaagaaa cttgaggata ttgtgccctc ttctcacaac  240
tgtgatgttc ctcatgtgaa tcgtactgat taccagctca ttgatattgc tgaggatgga  300
tttttgagtc tgcttactga aaatgggaac accaaggatg acctcaagct tcccactgat  360
gagagtctgc tcactcagat aaaggatgga tttgctgagg gcaaggatct tgttgtgtct  420
gtcatgtctg ctatgggtga ggaacagatt tgcgccctga aggatattgg gccaaagaac  480

SEQ ID NO: 556          moltype = AA  length = 160
FEATURE                 Location/Qualifiers
source                  1..160
                        mol_type = protein
                        organism = Glycine max
SEQUENCE: 556
MSDEEHHFES KADAGASKTY PQQAGTIRKN GYIVIKGRPC KVVEVSTSKT GKHGHAKCHF  60
VGIDIFTAKK LEDIVPSSHN CDVPHVNRTD YQLIDIAEDG FLSLLTENGN TKDDLKLPTD  120
ESLLTQIKDG FAEGKDLVVS VMSAMGEEQI CALKDIGPKN                        160
```

```
SEQ ID NO: 557          moltype = AA  length = 12
FEATURE                 Location/Qualifiers
source                  1..12
                        mol_type = protein
                        organism = Glycine max
SEQUENCE: 557
LPTDESLLTQ IK                                                      12

SEQ ID NO: 558          moltype = AA  length = 7
FEATURE                 Location/Qualifiers
source                  1..7
                        mol_type = protein
                        organism = Glycine max
SEQUENCE: 558
NGYIVIK                                                            7

SEQ ID NO: 559          moltype = DNA  length = 480
FEATURE                 Location/Qualifiers
source                  1..480
                        mol_type = other DNA
                        organism = Glycine max
CDS                     1..480
SEQUENCE: 559
atgtcggacg aagagcatca cttcgattct caggcggatg cgggagcgtc caagacgtat  60
cctcagcagg ctggtaccat tcgcaagaat ggctacatcg tcatcaaatc caggccttgc  120
aaggttgtag aggtctctac gtcaaagaca ggcaaacatg gacatgcaaa gtgtcacttt  180
gctgcaattg atatttttaa tgggaaaaag cttgaagata ttgttccatc atcccacaac  240
tgtgatgttc cacatgtgaa tcgcactgac tatcagctta ttgatatctc tgaagacggc  300
tttgtgagtc tgttgactga taatggaaat accaaggatg atctgaagct tcctactgat  360
gaggcattgc ttgctcagat taaagatgga ttttctgaag gaaaagacct tgtggtttct  420
gttatgtctg caatgggaga agaacagatc tgttcactga aggacatcgg tcccaaaaat  480

SEQ ID NO: 560          moltype = AA  length = 160
FEATURE                 Location/Qualifiers
source                  1..160
                        mol_type = protein
                        organism = Glycine max
SEQUENCE: 560
MSDEEHHFDS QADAGASKTY PQQAGTIRKN GYIVIKSRPC KVVEVSTSKT GKHGHAKCHF  60
AAIDIFNGKK LEDIVPSSHN CDVPHVNRTD YQLIDISEDG FVSLLTDNGN TKDDLKLPTD  120
EALLAQIKDG FSEGKDLVVS VMSAMGEEQI CSLKDIGPKN                        160

SEQ ID NO: 561          moltype = AA  length = 7
FEATURE                 Location/Qualifiers
source                  1..7
                        mol_type = protein
                        organism = Glycine max
SEQUENCE: 561
NGYIVIK                                                            7

SEQ ID NO: 562          moltype = AA  length = 11
FEATURE                 Location/Qualifiers
source                  1..11
                        mol_type = protein
                        organism = Glycine max
SEQUENCE: 562
TYPQQAGTIR K                                                       11

SEQ ID NO: 563          moltype = AA  length = 8
FEATURE                 Location/Qualifiers
source                  1..8
                        mol_type = protein
                        organism = Glycine max
SEQUENCE: 563
VVEVSTSK                                                           8

SEQ ID NO: 564          moltype = DNA  length = 501
FEATURE                 Location/Qualifiers
source                  1..501
                        mol_type = other DNA
                        organism = Glycine max
CDS                     1..501
SEQUENCE: 564
atggctagcc aatcaaacac taaatcagtt cacgatttca cagttaaaga tgccagggga  60
aataatgtta atctcgccga ttacaaagga aaggtccttc tcattgtcaa tgttgcctca  120
caatgcggct tgactaattc aaactacaca gagcttaacc aattgtatga gaaatacaaa  180
gggaaaggac ttgaaattct ggcattccca tgcaatcagt ttggggctca ggagccagga  240
actaatgaag agattgtgga gtttgcttgt actcgcttca aagctgagtt tcccattttc  300
```

```
gacaaggtgg atgtgaatgg tgacaatgct gctccactgt acaagtttct gaaatcaagc  360
aaaggtggac tctttgggga tagtatcaaa tggaacttct ccaaattcct tgttgataag  420
gatgggaatg tcgttgaccg ttatgcaccc acaacttctc ctctcagcat tgagaaagac  480
ataaagaagc tgctagatgc a                                            501

SEQ ID NO: 565          moltype = AA  length = 167
FEATURE                 Location/Qualifiers
source                  1..167
                        mol_type = protein
                        organism = Glycine max
SEQUENCE: 565
MASQSNTKSV HDFTVKDARG NNVNLADYKG KVLLIVNVAS QCGLTNSNYT ELNQLYEKYK  60
GKGLEILAFP CNQFGAQEPG TNEEIVEFAC TRFKAEFPIF DKVDVNGDNA APLYKFLKSS  120
KGGLFGDSIK WNFSKFLVDK DGNVVDRYAP TTSPLSIEKD IKKLLDA                167

SEQ ID NO: 566          moltype = AA  length = 8
FEATURE                 Location/Qualifiers
source                  1..8
                        mol_type = protein
                        organism = Glycine max
SEQUENCE: 566
AEFPIFDK                                                           8

SEQ ID NO: 567          moltype = AA  length = 13
FEATURE                 Location/Qualifiers
source                  1..13
                        mol_type = protein
                        organism = Glycine max
SEQUENCE: 567
DARGNNVNLA DYK                                                     13

SEQ ID NO: 568          moltype = AA  length = 19
FEATURE                 Location/Qualifiers
source                  1..19
                        mol_type = protein
                        organism = Glycine max
SEQUENCE: 568
DGNVVDRYAP TTSPLSIEK                                               19

SEQ ID NO: 569          moltype = AA  length = 9
FEATURE                 Location/Qualifiers
source                  1..9
                        mol_type = protein
                        organism = Glycine max
SEQUENCE: 569
GGLFGDSIK                                                          9

SEQ ID NO: 570          moltype = AA  length = 13
FEATURE                 Location/Qualifiers
source                  1..13
                        mol_type = protein
                        organism = Glycine max
SEQUENCE: 570
VDVNGDNAAP LYK                                                     13

SEQ ID NO: 571          moltype = DNA  length = 357
FEATURE                 Location/Qualifiers
source                  1..357
                        mol_type = other DNA
                        organism = Glycine max
CDS                     1..357
SEQUENCE: 571
atggcttccg aagaatccca gaacaagccc cccagcgagc agtccactac cgaactcatc  60
acgagcgcga agctggtggc ggaggcggcg cagtcggctc tgaagagcga cagcgacaaa  120
gtggacaagg ccaaggtggc tgacgctgcc ggcgatcttc tcgacgcggc ggggaagtat  180
ggaaaacttg atgacaaaca aggcataggg caatatgttg acaaggctgc tgattatctg  240
cataattacc agggtgataa taccactgct ccttcacagc ctgcagagtc taaaggtgaa  300
gaaagtggtg gtgggttagg tggtcttgca aacttggctg gaggcttctt caaaaag     357

SEQ ID NO: 572          moltype = AA  length = 119
FEATURE                 Location/Qualifiers
source                  1..119
                        mol_type = protein
                        organism = Glycine max
SEQUENCE: 572
MASEESQNKP PSEQSTTELI TSAKLVAEAA QSALKSDSDK VDKAKVADAA GDLLDAAGKY  60
GKLDDKQGIG QYVDKAADYL HNYQGDNTTA PSQPAESKGE ESGGGLGGLA NLAGGFFKK   119

SEQ ID NO: 573          moltype = AA  length = 23
```

```
FEATURE                 Location/Qualifiers
source                  1..23
                        mol_type = protein
                        organism = Glycine max
SEQUENCE: 573
AADYLHNYQG DNTTAPSQPA ESK                                           23

SEQ ID NO: 574          moltype = AA  length = 11
FEATURE                 Location/Qualifiers
source                  1..11
                        mol_type = protein
                        organism = Glycine max
SEQUENCE: 574
LVAEAAQSAL K                                                        11

SEQ ID NO: 575          moltype = AA  length = 9
FEATURE                 Location/Qualifiers
source                  1..9
                        mol_type = protein
                        organism = Glycine max
SEQUENCE: 575
QGIGQYVDK                                                           9

SEQ ID NO: 576          moltype = AA  length = 14
FEATURE                 Location/Qualifiers
source                  1..14
                        mol_type = protein
                        organism = Glycine max
SEQUENCE: 576
VADAAGDLLD AAGK                                                     14

SEQ ID NO: 577          moltype = DNA  length = 777
FEATURE                 Location/Qualifiers
source                  1..777
                        mol_type = other DNA
                        organism = Glycine max
CDS                     1..777
SEQUENCE: 577
atggcggccg ctccctcgcc tcgcgaagag aacgtctaca tggcgaagct cgccgagcag  60
gccgagcgct acgaagagat ggtggagttc atggagaagg tctccgccgc cgccgacaac  120
gaggaactta ccgtggagga gaggaacctc ctctccgtcg cctacaagaa cgtgatcgga  180
gcgcgccgcg cctcgtggcg catcatctcc tcgatcgagc agaaggagga gagccgcggc  240
aacgaggatc acgtctccgt catccgcgac taccgatcca agatcgagtc cgagctctcc  300
aacatctgcg acggtatcct caagctcctc gactctcgcc tcattccatc cgcttcctcc  360
ggcgattcca aggtcttcta cctcaagatg aagggagatt accacagata ccttgccgag  420
ttcaagaccg gcgccgagcg taaggaggct gccgagagca ctctctctgc atacaaagcc  480
gcacaggaca ttgcgaatgc cgaactgcct cctactcatc caattaggct tggccttgct  540
cttaactttt ctgtatttta ctacgaaatc cttaattctc cggatcgtgc ctgcaacctt  600
gcaaaacagg cttttgatga agctattgct gaattggata cactgggaga ggagtcatac  660
aaggatagca ctttgatcat gcaactcctt cgtgataacc tcacactttg gacctctgac  720
atgcaggacg atggagcaga tgaaattaaa gaagcagcac cgaaaccgga tgaccag     777

SEQ ID NO: 578          moltype = AA  length = 259
FEATURE                 Location/Qualifiers
source                  1..259
                        mol_type = protein
                        organism = Glycine max
SEQUENCE: 578
MAAAPSPREE NVYMAKLAEQ AERYEEMVEF MEKVSAAADN EELTVEERNL LSVAYKNVIG  60
ARRASWRIIS SIEQKEESRG NEDHVSVIRD YRSKIESELS NICDGILKLL DSRLIPSASS  120
GDSKVFYLKM KGDYHRYLAE FKTGAERKEA AESTLSAYKA AQDIANAELP PTHPIRLGLA  180
LNFSVFYYEI LNSPDRACNL AKQAFDEAIA ELDTLGEESY KDSTLIMQLL RDNLTLWTSD  240
MQDDGADEIK EAAPKPDDQ                                                259

SEQ ID NO: 579          moltype = AA  length = 11
FEATURE                 Location/Qualifiers
source                  1..11
                        mol_type = protein
                        organism = Glycine max
SEQUENCE: 579
EAAESTLSAY K                                                        11

SEQ ID NO: 580          moltype = AA  length = 16
FEATURE                 Location/Qualifiers
source                  1..16
                        mol_type = protein
                        organism = Glycine max
SEQUENCE: 580
LLDSRLIPSA SSGDSK                                                   16
```

```
SEQ ID NO: 581          moltype = AA  length = 19
FEATURE                 Location/Qualifiers
source                  1..19
                        mol_type = protein
                        organism = Glycine max
SEQUENCE: 581
QAFDEAIAEL DTLGEESYK                                          19

SEQ ID NO: 582          moltype = AA  length = 23
FEATURE                 Location/Qualifiers
source                  1..23
                        mol_type = protein
                        organism = Glycine max
SEQUENCE: 582
VSAAADNEEL TVEERNLLSV AYK                                     23

SEQ ID NO: 583          moltype = DNA  length = 993
FEATURE                 Location/Qualifiers
source                  1..993
                        mol_type = other DNA
                        organism = Glycine max
CDS                     1..993
SEQUENCE: 583
atggcgttga acaatggcgt ccccgccacc ggcaccggcc tcatcgtcag cttcggtgag  60
atgctcatcg acttcgtccc caccgtctct ggcgtgtccc tggccgaggc ccctggcttc  120
ctcaaggccc ccggcggcgc ccccgctaac gtcgccatcg ccgtgtcgcg cctcggcggc  180
aaagccgcct tcgtcggcaa gctcggcgac gacgagttcg gccacatgct cgccggaatc  240
ctcaaggaaa acggcgttcg cgccgacggc atcaactttg accagggcgc acgcaccgcc  300
ctggccttcg tgaccctacg cgccgacggg gagcgtgagt tcatgttcta cagaaacccc  360
agcgccgaca tgctcctcaa gcccgaagaa ctcaatctcg aactcatcag atctgcaaaa  420
gttttccatt acggatcaat cagtttgatc gtggagccat gcagatcagc acacttgaag  480
gcaatggaag tagccaagga atctgggtgc ttgctctcct atgaccccaa ccttcgtcta  540
cctttgtggc cttcggctga ggaagctcgt aagcaaatac tgagcatttg ggagaaggct  600
gatttgatca aggtcagtga tgcggagctt gagttcctca caggaagtga caagattgat  660
gatgaatctg ctttgtcatt gtggcacccc aatttgaagt tgctccttgt cactcttggg  720
gaacatggtt ccagatacta caccaagagt ttcaaaggat cggtagatgc tttccatgtc  780
aatacagttg atacaactgg tgccggtgat tcctttgttg gtgctttatt ggccaagatt  840
gtcgatgatc agtccatact tgaagatgaa ccaaggttaa gagaagtact aaagtttgca  900
aatgcatgtg gagctattac aactacccaa aagggagcaa ttccggccct tcccaaagag  960
gaggctgcac tgaaactgat caaagggggg tca                          993

SEQ ID NO: 584          moltype = AA  length = 331
FEATURE                 Location/Qualifiers
source                  1..331
                        mol_type = protein
                        organism = Glycine max
SEQUENCE: 584
MALNNGVPAT GTGLIVSFGE MLIDFVPTVS GVSLAEAPGF LKAPGGAPAN VAIAVSRLGG  60
KAAFVGKLGD DEFGHMLAGI LKENGVRADG INFDQGARTA LAFVTLRADG EREFMFYRNP  120
SADMLLKPEE LNLELIRSAK VFHYGSISLI VEPCRSAHLK AMEVAKESGC LLSYDPNLRL  180
PLWPSAEEAR KQILSIWEKA DLIKVSDAEL EFLTGSDKID DESALSLWHP NLKLLLVTLG  240
EHGSRYYTKS FKGSVDAFHV NTVDTTGAGD SFVGALLAKI VDDQSILEDE PRLREVLKFA  300
NACGAITTTQ KGAIPALPKE EAALKLIKGG S                            331

SEQ ID NO: 585          moltype = AA  length = 19
FEATURE                 Location/Qualifiers
source                  1..19
                        mol_type = protein
                        organism = Glycine max
SEQUENCE: 585
APGGAPANVA IAVSRLGGK                                          19

SEQ ID NO: 586          moltype = AA  length = 27
FEATURE                 Location/Qualifiers
source                  1..27
                        mol_type = protein
                        organism = Glycine max
SEQUENCE: 586
GSVDAFHVNT VDTTGAGDSF VGALLAK                                 27

SEQ ID NO: 587          moltype = AA  length = 19
FEATURE                 Location/Qualifiers
source                  1..19
                        mol_type = protein
                        organism = Glycine max
SEQUENCE: 587
IVDDQSILED EPRLREVLK                                          19
```

```
SEQ ID NO: 588          moltype = AA  length = 14
FEATURE                 Location/Qualifiers
source                  1..14
                        mol_type = protein
                        organism = Glycine max
SEQUENCE: 588
VSDAELEFLT GSDK                                                    14

SEQ ID NO: 589          moltype = DNA  length = 759
FEATURE                 Location/Qualifiers
source                  1..759
                        mol_type = other DNA
                        organism = Glycine max
CDS                     1..759
SEQUENCE: 589
atgggcagaa agttcttcgt tggtggcaac tggaaatgca atgggaccac tgaggaggtg  60
aagaagattg ttactacttt aaatgaagct aaagtccctg gagaagatgt tgtagaagtt  120
gttgtgagcc ctccttttgt gttccttcct tttgtaaaaa gtttgctgcg ccctgatttc  180
catgtctcgg cccaaaattg ttgggttcgc aaaggtggtg cttatactgg agaggttagt  240
gctgaaatgc ttgttaattt gggaattcct tgggttatta ttggtcactc tgaacggagg  300
cagcttttga atgaatcaaa tgagtttgtg ggagataaag ttgcctatgc acttcaacaa  360
ggtctgaaag ttatagcatg cattggggaa actcttgaac agcgtgaagc tggtacaaca  420
acggctgttg ttgctgagca aacaaaagca attgcagcta aaatatcaaa ttgggacaat  480
gtcgttttgg cctatgagcc agtttgggcc attggaacag gaaaggttgc aactcctgct  540
caggctcaag aggttcatgc tgatttaagg aaatgggttc atgacaatgt gagtgctgaa  600
gttgctgcat ctgtaagaat tatctatgga ggctctgtaa atggaggaaa ctgcaaagaa  660
ttggcagcac agcccgatgt tgatggattt ttggttggtg gtgcatccct caaggcggaa  720
tttgtggaca tcataaacgc tgccactgtg aagaagaat                         759

SEQ ID NO: 590          moltype = AA  length = 253
FEATURE                 Location/Qualifiers
source                  1..253
                        mol_type = protein
                        organism = Glycine max
SEQUENCE: 590
MGRKFFVGGN WKCNGTTEEV KKIVTTLNEA KVPGEDVVEV VVSPPFVFLP FVKSLLRPDF  60
HVSAQNCWVR KGGAYTGEVS AEMLVNLGIP WVIIGHSERR QLLNESNEFV GDKVAYALQQ  120
GLKVIACIGE TLEQREAGTT TAVVAEQTKA IAAKISNWDN VVLAYEPVWA IGTGKVATPA  180
QAQEVHADLR KWVHDNVSAE VAASVRIIYG GSVNGGNCKE LAAQPDVDGF LVGGASLKAE  240
FVDIINAATV KKN                                                     253

SEQ ID NO: 591          moltype = AA  length = 13
FEATURE                 Location/Qualifiers
source                  1..13
                        mol_type = protein
                        organism = Glycine max
SEQUENCE: 591
AEFVDIINAA TVK                                                     13

SEQ ID NO: 592          moltype = AA  length = 19
FEATURE                 Location/Qualifiers
source                  1..19
                        mol_type = protein
                        organism = Glycine max
SEQUENCE: 592
ELAAQPDVDG FLVGGASLK                                               19

SEQ ID NO: 593          moltype = AA  length = 8
FEATURE                 Location/Qualifiers
source                  1..8
                        mol_type = protein
                        organism = Glycine max
SEQUENCE: 593
FFVGGNWK                                                           8

SEQ ID NO: 594          moltype = AA  length = 9
FEATURE                 Location/Qualifiers
source                  1..9
                        mol_type = protein
                        organism = Glycine max
SEQUENCE: 594
IVTTLNEAK                                                          9

SEQ ID NO: 595          moltype = AA  length = 16
FEATURE                 Location/Qualifiers
source                  1..16
                        mol_type = protein
                        organism = Glycine max
SEQUENCE: 595
```

-continued

```
VATPAQAQEV HADLRK                                              16

SEQ ID NO: 596          moltype = AA  length = 10
FEATURE                 Location/Qualifiers
source                  1..10
                        mol_type = protein
                        organism = Glycine max
SEQUENCE: 596
VAYALQQGLK                                                     10

SEQ ID NO: 597          moltype = AA  length = 22
FEATURE                 Location/Qualifiers
source                  1..22
                        mol_type = protein
                        organism = Glycine max
SEQUENCE: 597
VPGEDVVEVV VSPPFVFLPF VK                                       22

SEQ ID NO: 598          moltype = DNA  length = 759
FEATURE                 Location/Qualifiers
source                  1..759
                        mol_type = other DNA
                        organism = Glycine max
CDS                     1..759
SEQUENCE: 598
atgggcagaa aattcttcgt tggtggcaac tggaaatgca atgggaccac tgaggaggta  60
aagaagattg ttactacttt gaatgaggct aaagtccctg gagaagatgt cgtagaagtt  120
gttgtgagcc ctccttttgt gttccttcct gttgtaaaaa gtttgctgcg ccctgatttc  180
catgtttcgg cacaaaactg ttgggttcgc aaaggtggtg cttataccgg tgaggttagt  240
gctgaaatgc ttgttaattt gggaattcct tgggttatta ttggtcactc tgaacggagg  300
cagcttttaa atgaatcaaa tgagtttgtg ggagataaag ttgcctatgc acttcaacaa  360
ggtctaaaag ttattgcatg cattggggag actctcgaac agcgtgaagc tggtacaaca  420
acggctgttg tttctgagca aacaaaagca attgcagcta aaatatcaaa ttgggacaat  480
gtcgttttgg cctacgagcc agtttgggcc attggaacag gaaaggttgc tactcctgct  540
caggctcaag aggtccatgc tgatttgagg aaatgggttc atgacaatgt gagtgctgaa  600
gttgctgcat ctgtaagaat tatctatgga ggttctgtaa atggaggaaa ctgcaaagaa  660
ttggccgcac agcccgatgt tgatggattt ttggttggtg gtgcctccct gaagccggag  720
ttcgtggaca tcataaatgc tgccactgtg aagaagaat                        759

SEQ ID NO: 599          moltype = AA  length = 253
FEATURE                 Location/Qualifiers
source                  1..253
                        mol_type = protein
                        organism = Glycine max
SEQUENCE: 599
MGRKFFVGGN WKCNGTTEEV KKIVTTLNEA KVPGEDVVEV VVSPPFVFLP VVKSLLRPDF  60
HVSAQNCWVR KGGAYTGEVS AEMLVNLGIP WVIIGHSERR QLLNESNEFV GDKVAYALQQ  120
GLKVIACIGE TLEQREAGTT TAVVSEQTKA IAAKISNWDN VVLAYEPVWA IGTGKVATPA  180
QAQEVHADLR KWVHDNVSAE VAASVRIIYG GSVNGGNCKE LAAQPDVDGF LVGGASLKPE  240
FVDIINAATV KKN                                                 253

SEQ ID NO: 600          moltype = AA  length = 32
FEATURE                 Location/Qualifiers
source                  1..32
                        mol_type = protein
                        organism = Glycine max
SEQUENCE: 600
ELAAQPDVDG FLVGGASLKP EFVDIINAAT VK                            32

SEQ ID NO: 601          moltype = AA  length = 8
FEATURE                 Location/Qualifiers
source                  1..8
                        mol_type = protein
                        organism = Glycine max
SEQUENCE: 601
FFVGGNWK                                                       8

SEQ ID NO: 602          moltype = AA  length = 9
FEATURE                 Location/Qualifiers
source                  1..9
                        mol_type = protein
                        organism = Glycine max
SEQUENCE: 602
IVTTLNEAK                                                      9

SEQ ID NO: 603          moltype = AA  length = 16
FEATURE                 Location/Qualifiers
source                  1..16
                        mol_type = protein
```

```
                        organism = Glycine max
SEQUENCE: 603
VATPAQAQEV HADLRK                                                   16

SEQ ID NO: 604          moltype = AA  length = 10
FEATURE                 Location/Qualifiers
source                  1..10
                        mol_type = protein
                        organism = Glycine max
SEQUENCE: 604
VAYALQQGLK                                                          10

SEQ ID NO: 605          moltype = DNA  length = 765
FEATURE                 Location/Qualifiers
source                  1..765
                        mol_type = other DNA
                        organism = Glycine max
CDS                     1..765
SEQUENCE: 605
atggcctcat tgggtgggtt acaaaatgtg agcggcatca attttcttat caaagagaaa  60
ggatgttgta tgctgcaggg tccaaaagtc aatgcaaagt tcgagctgaa gccgccacca  120
tatccactga atggtttgga gccggtgatg agccagcaga cacttgagtt tcactggggg  180
aagcaccaca agacttatgt ggaaaatctg aaaaaacaag ttgttgggac agagcttgat  240
gggaagtcac tagaagagat tattgtcaca tcatacaata agggtgacat tcttccagct  300
ttcaacaatg cagcacaggt atggaaccat gacttcttct gggagtgcat gaaaccaggt  360
ggaggtggaa agccatccgg ggagcttcta gaactgattg aaagagactt tggttcattt  420
gtaaaattcc ttgatgagtt caaggctgct gctgcaacac aatttggttc agggtgggct  480
tggctagcat atagagcaag aaaatttgat ggggaaaatg tagcaaatcc tccttcaccc  540
gatgaggaca acaagctagt ggtgctcaag agtcccaatg ctgtgaaccc ccttgtttgg  600
ggaggttact acccacttct taccattgat gtttgggagc atgcttacta ccttgatttt  660
cagaaccggc gtcctgatta tatatcagtg ttcatggata agcttgtttc ctgggatgca  720
gtgagctcta gacttgaaca agctaaggct ttaattacca gtgca                   765

SEQ ID NO: 606          moltype = AA  length = 255
FEATURE                 Location/Qualifiers
source                  1..255
                        mol_type = protein
                        organism = Glycine max
SEQUENCE: 606
MASLGGLQNV SGINFLIKEK GCCMLQGPKV NAKFELKPPP YPLNGLEPVM SQQTLEFHWG  60
KHHKTYVENL KKQVVGTELD GKSLEEIIVT SYNKGDILPA FNNAAQVWNH DFFWECMKPG  120
GGGKPSGELL ELIERDFGSF VKFLDEFKAA AATQFGSGWA WLAYRARKFD GENVANPPSP  180
DEDNKLVVLK SPNAVNPLVW GGYYPLLTID VWEHAYYLDF QNRRPDYISV FMDKLVSWDA  240
VSSRLEQAKA LITSA                                                    255

SEQ ID NO: 607          moltype = AA  length = 17
FEATURE                 Location/Qualifiers
source                  1..17
                        mol_type = protein
                        organism = Glycine max
SEQUENCE: 607
FDGENVANPP SPDEDNK                                                  17

SEQ ID NO: 608          moltype = AA  length = 15
FEATURE                 Location/Qualifiers
source                  1..15
                        mol_type = protein
                        organism = Glycine max
SEQUENCE: 608
LVSWDAVSSR LEQAK                                                    15

SEQ ID NO: 609          moltype = AA  length = 10
FEATURE                 Location/Qualifiers
source                  1..10
                        mol_type = protein
                        organism = Glycine max
SEQUENCE: 609
QVVGTELDGK                                                          10

SEQ ID NO: 610          moltype = AA  length = 12
FEATURE                 Location/Qualifiers
source                  1..12
                        mol_type = protein
                        organism = Glycine max
SEQUENCE: 610
SLEEIIVTSY NK                                                       12

SEQ ID NO: 611          moltype = AA  length = 7
FEATURE                 Location/Qualifiers
```

```
source                  1..7
                        mol_type = protein
                        organism = Glycine max
SEQUENCE: 611
TYVENLK                                                            7

SEQ ID NO: 612          moltype = DNA  length = 732
FEATURE                 Location/Qualifiers
source                  1..732
                        mol_type = other DNA
                        organism = Glycine max
CDS                     1..732
SEQUENCE: 612
atggcctcat tgggtgggtt acaaaatcta agcggcatca attttcttat caaaaaagag  60
ggtccaaaag tcaatgcgaa gttcgagctg aagccgccac catatccact gaatggtttg  120
gagccggtga tgagccagca gacacttgag tttcattggg ggaaacacca caagacatat  180
gtggaaaatc tgaaaaaaca aattgttggg acagagcttg atgggaaatc actagaagag  240
attatagtga catcatataa taagggtgac attcttccag ctttcaacaa tgcagcacag  300
gtatggaacc atgacttctt ctgggagtgc atgaaaccag gtggaggtgg aaagccatcc  360
ggggagcttc tagaactgat tgaaagagac tttggctcat ttgaaaaatt ccttgatgag  420
tttaaggctg ctgctgcaac acaatttggt tcaggatggg cttggcttgc atatagagca  480
agcaaatttg atggggaaaa tgcagcaaat cctccttcac cagatgagga caacaagcta  540
gtggtgctca agagtcccaa tgctgtgaac ccccttgttt ggggaggcta ttatccactt  600
cttaccattg atgtttggga gcatgcttac aaccttgatt ttcagaaccg gcgccctgat  660
tatatatcag tgttcatgga taagcttgtt tcctgggatg cagtgagttc tagacttgaa  720
caagcaaggc tt                                                      732

SEQ ID NO: 613          moltype = AA  length = 244
FEATURE                 Location/Qualifiers
source                  1..244
                        mol_type = protein
                        organism = Glycine max
SEQUENCE: 613
MASLGGLQNL SGINFLIKKE GPKVNAKFEL KPPPYPLNGL EPVMSQQTLE FHWGKHHKTY  60
VENLKKQIVG TELDGKSLEE IIVTSYNKGD ILPAFNNAAQ VWNHDFFWEC MKPGGGGKPS  120
GELLELIERD FGSFEKFLDE FKAAAATQFG SGWAWLAYRA SKFDGENAAN PPSPDEDNKL  180
VVLKSPNAVN PLVWGGYYPL LTIDVWEHAY NLDFQNRRPD YISVFMDKLV SWDAVSSRLE  240
QARL                                                               244

SEQ ID NO: 614          moltype = AA  length = 10
FEATURE                 Location/Qualifiers
source                  1..10
                        mol_type = protein
                        organism = Glycine max
SEQUENCE: 614
QIVGTELDGK                                                         10

SEQ ID NO: 615          moltype = AA  length = 12
FEATURE                 Location/Qualifiers
source                  1..12
                        mol_type = protein
                        organism = Glycine max
SEQUENCE: 615
SLEEIIVTSY NK                                                      12

SEQ ID NO: 616          moltype = AA  length = 7
FEATURE                 Location/Qualifiers
source                  1..7
                        mol_type = protein
                        organism = Glycine max
SEQUENCE: 616
TYVENLK                                                            7

SEQ ID NO: 617          moltype = DNA  length = 1419
FEATURE                 Location/Qualifiers
source                  1..1419
                        mol_type = other DNA
                        organism = Glycine max
CDS                     1..1419
SEQUENCE: 617
atggcttcta aggtggtttc ggttttggtt atagcgatga tgttgtttgc catgaactgt  60
aactgcacta gtgttggcca catgccttca accaaagagg aaggtcacga ttttcaggag  120
tctaaagcca agaccacaca aactgcgaac aaggccatgg aaactggtaa agagggacaa  180
gaagccgcag agtcatggac agaatgggct aaagagaaac tcagtgaagg tcttggcttc  240
aaacatgatc aggaatccaa agaatccacc actaacaaag tctctgatta tgccactgac  300
actgcacaga aatccaagga ttatgcaact gacactgctc agaaatcaaa ggactatgca  360
ggtgatgctg ctcagaaatc aaaggactac gcaggtgatg ctgctcagaa aaccaaagac  420
tatgccagtg acactgcaca gacatcaaag gactatgctg gtgatgctgc tcagaaatca  480
aagggctatg ttggtgatgc tgcacaaaag accaaagaat atgttggtga tgcagcacag  540
```

-continued

```
aagacaaagg attatgccac tgacgcagca cagaagacca aagattatgc tactcagaag  600
accaaggact atgcaagtga tgcaactgat gctgcaaaga agactaaaga ttatgctgct  660
cagaagacta aggactatgc aagtgaagct agtgatgttg cacagaacac aaaagattat  720
gctgctcaga agaccaagga ctatgccagc ggtggtgcgc agaagaccaa ggattatgcc  780
agcggtggtg cgcagaagac caaggactat gcaagtgatg ctgcgcagaa gaccaaggac  840
tatgcaagtg atggtgctca aaagagcaaa gaatatgcgg gtgatgtagc actgaatgcc  900
aaagattatg ctcaaaaaag caaagattac gcaggtgatg ctgcacagaa tgtcaaagat  960
tatgcaagtg atgcagtgca gaagagaaaa gagtattctg gtgatgcttc tcacaagagc  1020
aaagaggctt ctgattatgc cagtgagacg gctaagaaga ccaaagatta tgtcggtgat  1080
gctgctcaga gaagcaaagg ggctgctgaa tatgctagtg atgcggctca gaggaccaaa  1140
gagtatgctg gtgatgctac caagagaagc aaagaggctt ctaatgatca tgccaatgac  1200
atggctcaga agaccaaaga ctacgccagt gacactgctc agagaaccaa ggaaaaactc  1260
caagacattg catctgaagc tggtcaatac agtgcagaga aagctagaga aatgaaggat  1320
gcagcagcag agaaggcaag tgacatagca aaggctgcaa agcaaaaatc acaagaggtg  1380
aaagagaaat taggtggaca acaccgggat gccgagctt                        1419
```

```
SEQ ID NO: 618          moltype = AA  length = 473
FEATURE                 Location/Qualifiers
source                  1..473
                        mol_type = protein
                        organism = Glycine max
SEQUENCE: 618
MASKVVSVLV IAMMLFAMNC NCTSVGHMPS TKEEGHDFQE SKAKTTQTAN KAMETGKEGQ  60
EAAESWTEWA KEKLSEGLGF KHDQESKEST TNKVSDYATD TAQKSKDYAT DTAQKSKDYA  120
GDAAQKSKDY AGDAAQKTKD YASDTAQTSK DYAGDAAQKS KGYVGDAAQK TKEYVGDAAQ  180
KTKDYATDAA QKTKDYATQK TKDYASDATD AAKKTKDYAA QKTKDYASEA SDVAQNTKDY  240
AAQKTKDYAS GGAQKTKDYA SGGAQKTKDY ASDAAQKTKD YASDGAQKSK EYAGDVALNA  300
KDYAQKSKDY AGDAAQNVKD YASDAVQKRK EYSGDASHKS KEASDYASET AKKTKDYVGD  360
AAQRSKGAAE YASDAAQRTK EYAGDATKRS KEASNDHAND MAQKTKDYAS DTAQRTKEKL  420
QDIASEAGQY SAEKAREMKD AAAEKASDIA KAAKQKSQEV KEKLGGQHRD AEL        473

SEQ ID NO: 619          moltype = AA  length = 11
FEATURE                 Location/Qualifiers
source                  1..11
                        mol_type = protein
                        organism = Glycine max
SEQUENCE: 619
DYAGDAAQNV K                                                      11

SEQ ID NO: 620          moltype = AA  length = 9
FEATURE                 Location/Qualifiers
source                  1..9
                        mol_type = protein
                        organism = Glycine max
SEQUENCE: 620
DYASDAAQK                                                         9

SEQ ID NO: 621          moltype = AA  length = 11
FEATURE                 Location/Qualifiers
source                  1..11
                        mol_type = protein
                        organism = Glycine max
SEQUENCE: 621
DYASDATDAA K                                                      11

SEQ ID NO: 622          moltype = AA  length = 9
FEATURE                 Location/Qualifiers
source                  1..9
                        mol_type = protein
                        organism = Glycine max
SEQUENCE: 622
DYASDAVQK                                                         9

SEQ ID NO: 623          moltype = AA  length = 11
FEATURE                 Location/Qualifiers
source                  1..11
                        mol_type = protein
                        organism = Glycine max
SEQUENCE: 623
DYASDTAQRT K                                                      11

SEQ ID NO: 624          moltype = AA  length = 11
FEATURE                 Location/Qualifiers
source                  1..11
                        mol_type = protein
                        organism = Glycine max
SEQUENCE: 624
DYASDTAQTS K                                                      11
```

```
SEQ ID NO: 625          moltype = AA  length = 14
FEATURE                 Location/Qualifiers
source                  1..14
                        mol_type = protein
                        organism = Glycine max
SEQUENCE: 625
DYASEASDVA QNTK                                                    14

SEQ ID NO: 626          moltype = AA  length = 9
FEATURE                 Location/Qualifiers
source                  1..9
                        mol_type = protein
                        organism = Glycine max
SEQUENCE: 626
DYATDAAQK                                                          9

SEQ ID NO: 627          moltype = AA  length = 11
FEATURE                 Location/Qualifiers
source                  1..11
                        mol_type = protein
                        organism = Glycine max
SEQUENCE: 627
DYVGDAAQRS K                                                       11

SEQ ID NO: 628          moltype = AA  length = 11
FEATURE                 Location/Qualifiers
source                  1..11
                        mol_type = protein
                        organism = Glycine max
SEQUENCE: 628
EASDYASETA K                                                       11

SEQ ID NO: 629          moltype = AA  length = 11
FEATURE                 Location/Qualifiers
source                  1..11
                        mol_type = protein
                        organism = Glycine max
SEQUENCE: 629
EYAGDVALNA K                                                       11

SEQ ID NO: 630          moltype = AA  length = 9
FEATURE                 Location/Qualifiers
source                  1..9
                        mol_type = protein
                        organism = Glycine max
SEQUENCE: 630
EYVGDAAQK                                                          9

SEQ ID NO: 631          moltype = AA  length = 14
FEATURE                 Location/Qualifiers
source                  1..14
                        mol_type = protein
                        organism = Glycine max
SEQUENCE: 631
GAAEYASDAA QRTK                                                    14

SEQ ID NO: 632          moltype = AA  length = 9
FEATURE                 Location/Qualifiers
source                  1..9
                        mol_type = protein
                        organism = Glycine max
SEQUENCE: 632
GYVGDAAQK                                                          9

SEQ ID NO: 633          moltype = AA  length = 15
FEATURE                 Location/Qualifiers
source                  1..15
                        mol_type = protein
                        organism = Glycine max
SEQUENCE: 633
LQDIASEAGQ YSAEK                                                   15

SEQ ID NO: 634          moltype = AA  length = 8
FEATURE                 Location/Qualifiers
source                  1..8
                        mol_type = protein
                        organism = Glycine max
SEQUENCE: 634
LSEGLGFK                                                           8
```

```
SEQ ID NO: 635          moltype = AA  length = 11
FEATURE                 Location/Qualifiers
source                  1..11
                        mol_type = protein
                        organism = Glycine max
SEQUENCE: 635
VSDYATDTAQ K                                                        11

SEQ ID NO: 636          moltype = DNA  length = 1374
FEATURE                 Location/Qualifiers
source                  1..1374
                        mol_type = other DNA
                        organism = Glycine max
CDS                     1..1374
SEQUENCE: 636
atggcttcga gggtggtttc ggttttggtg atagcgatga tgttgtttgc catgaactgt  60
aactgcacta gtgttggcca catgccttca accaaagagg aaggtcacga ttttcaggag  120
gctaaagcca agacaacaca aactgcgaac aaggccatgg aaactggtaa agatgggaaa  180
gaagccgcag agtcatggac agaatgggct aaagagaaac tcactgaagg tcttggcttc  240
aaacatgatc aagaatccac cactaagaaa gtctctgact atgccggtga tgctgctcag  300
aaatcaaagg actatgccgg tgacactgct cagaaaacca aggactatgc cggtgacact  360
gctcagaaaa ccaaggacta tgccggtgac actgcacaga catcaaagga ctatgccggt  420
gatgctgctc agaaatcaaa gggctatgtc ggtgatgctg cacaaaagac caaagaatat  480
gttggtgatg ctgctcagaa gaccatggat tatgccactg atgcagcaca gaagaccaaa  540
gattatgcta ctcagaagac taaggactat gcaagtgatg caactgatgc tgcaaaaaag  600
actaaagatt atgctgctca gaagaccaag gattatgcaa gtgatgcaac tgatgctgca  660
aaaaagacta aggattatgc tgcgcagaag accaaggact atgccagtgg tggtgcgcag  720
aagaccaagg actatgccag tggtgctgcg cagaagacca aggactatgc aagtgatgct  780
gcgcagagga ccaaggacca tgcaagtgat ggtgctcaaa agagcaaaga atatgcgggt  840
gatgtagcac agaatgccaa agattatgct caaaagagca aagattatgc gggtgatgct  900
gtacagaata tcaaagatta tgcaaatgat gcagcgcaca agagcaaaga ttatgctggt  960
gatgcttctc acaagagcaa agaagcttct gattatgcca gtgagacggc tcagaagacc  1020
aaagactatg ttggtgatgc tgctcagaaa agcaaagagg cttctgaata tgctagtgat  1080
gcggctcaga ggaccaaaga gtatgctggt gatgccacca agagaagcaa agaggcttct  1140
gatcatgcca atgacatggc tcggaagacc aaagactacg ccagtgacac tgctcagaga  1200
accaaggaaa aactccaaga cattgcatct gaggctggtc aatacagtac agagaaggcc  1260
agagaaatga aggatgcagc agcagagaag gctagtgaca ttgcaaaggc tgcaaagcaa  1320
aaatcacaag agctgaaaga caaattaggt ggacaacacc gggatgctga gctt        1374

SEQ ID NO: 637          moltype = AA  length = 458
FEATURE                 Location/Qualifiers
source                  1..458
                        mol_type = protein
                        organism = Glycine max
SEQUENCE: 637
MASRVVSVLV IAMMLFAMNC NCTSVGHMPS TKEEGHDFQE AKAKTTQTAN KAMETGKDGK  60
EAAESWTEWA KEKLTEGLGF KHDQESTTKK VSDYAGDAAQ KSKDYAGDTA QKTKDYAGDT  120
AQKTKDYAGD TAQTSKDYAG DAAQKSKGYV GDAAQKTKEY VGDAAQKTMD YATDAAQKTK  180
DYATQKTKDY ASDATDAAKK TKDYAAQKTK DYASDATDAA KKTKDYAAQK TKDYASGGAQ  240
KTKDYASGAA QKTKDYASDA AQRTKDHASD GAQKSKEYAG DVAQNAKDYA QKSKDYAGDA  300
VQNIKDYAND AAHKSKDYAG DASHKSKEAS DYASETAQKT KDYVGDAAQK SKEASEYASD  360
AAQRTKEYAG DATKRSKEAS DHANDMARKT KDYASDTAQR TKEKLQDIAS EAGQYSTEKA  420
REMKDAAAEK ASDIAKAAKQ KSQELKDKLG GQHRDAEL                           458

SEQ ID NO: 638          moltype = AA  length = 11
FEATURE                 Location/Qualifiers
source                  1..11
                        mol_type = protein
                        organism = Glycine max
SEQUENCE: 638
DYAGDAVQNI K                                                        11

SEQ ID NO: 639          moltype = AA  length = 11
FEATURE                 Location/Qualifiers
source                  1..11
                        mol_type = protein
                        organism = Glycine max
SEQUENCE: 639
DYASDAAQRT K                                                        11

SEQ ID NO: 640          moltype = AA  length = 11
FEATURE                 Location/Qualifiers
source                  1..11
                        mol_type = protein
                        organism = Glycine max
SEQUENCE: 640
DYASDATDAA K                                                        11
```

```
SEQ ID NO: 641          moltype = AA  length = 11
FEATURE                 Location/Qualifiers
source                  1..11
                        mol_type = protein
                        organism = Glycine max
SEQUENCE: 641
DYASDTAQRT K                                                      11

SEQ ID NO: 642          moltype = AA  length = 9
FEATURE                 Location/Qualifiers
source                  1..9
                        mol_type = protein
                        organism = Glycine max
SEQUENCE: 642
DYVGDAAQK                                                         9

SEQ ID NO: 643          moltype = AA  length = 12
FEATURE                 Location/Qualifiers
source                  1..12
                        mol_type = protein
                        organism = Glycine max
SEQUENCE: 643
EASDYASETA QK                                                     12

SEQ ID NO: 644          moltype = AA  length = 14
FEATURE                 Location/Qualifiers
source                  1..14
                        mol_type = protein
                        organism = Glycine max
SEQUENCE: 644
EASEYASDAA QRTK                                                   14

SEQ ID NO: 645          moltype = AA  length = 11
FEATURE                 Location/Qualifiers
source                  1..11
                        mol_type = protein
                        organism = Glycine max
SEQUENCE: 645
EYAGDVAQNA K                                                      11

SEQ ID NO: 646          moltype = AA  length = 9
FEATURE                 Location/Qualifiers
source                  1..9
                        mol_type = protein
                        organism = Glycine max
SEQUENCE: 646
GYVGDAAQK                                                         9

SEQ ID NO: 647          moltype = AA  length = 15
FEATURE                 Location/Qualifiers
source                  1..15
                        mol_type = protein
                        organism = Glycine max
SEQUENCE: 647
LQDIASEAGQ YSTEK                                                  15

SEQ ID NO: 648          moltype = AA  length = 8
FEATURE                 Location/Qualifiers
source                  1..8
                        mol_type = protein
                        organism = Glycine max
SEQUENCE: 648
LTEGLGFK                                                          8

SEQ ID NO: 649          moltype = AA  length = 11
FEATURE                 Location/Qualifiers
source                  1..11
                        mol_type = protein
                        organism = Glycine max
SEQUENCE: 649
VSDYAGDAAQ K                                                      11
```

SOYBEAN ALLERGY ANTIGEN

CROSS-REFERENCE TO RELATED APPLICATIONS

This application is a divisional application of U.S. patent application Ser. No. 16/081,302, filed on Aug. 30, 2018, which is a U.S. national stage filing, under 35 U.S.C. § 371(c), of International Application No. PCT/JP2017/008593, filed on Mar. 3, 2017, which claims priority to Japanese Patent Application No. 2016-041547, filed on Mar. 3, 2016. The entire contents of each of the aforementioned applications are incorporated herein by reference.

REFERENCE TO SEQUENCE LISTING

The instant application contains a Sequence Listing XML file which has been submitted electronically in XML format and is hereby incorporated by reference in its entirety. Said XML file, created on Aug. 30, 2023, is named Seq_Listing_129249_00203.XML and is 702,767 bytes in size.

TECHNICAL FIELD

The present invention relates to a novel antigen of an allergy to soybean. The present invention also relates to a kit, a composition, and a method for diagnosing allergy to soybean. The present invention also relates to a pharmaceutical composition comprising such an antigen and soybean or processed products of soybean in which such an antigen is eliminated or reduced. The present invention further relates to a tester for determining the presence or absence of a soybean antigen in an object of interest.

BACKGROUND ART

In serum and tissues of allergic patients, IgE antibodies specific to particular antigens are produced. Physiological consequences caused by interaction between such IgE antibodies and such particular antigens elicit allergic reactions.

In the process of production of conventional allergy testing agents, antigen reagents are commonly prepared simply by grinding a candidate allergenic food, material or the like (Patent Literature 1). As seen above, conventional antigen reagents do not necessarily contain only a particular antigenic protein inducing an allergic reaction (allergen component), and rather contain different types of protein components. Thus, conventional antigen reagents contain varied amounts of allergen components. For this reason, the only case where conventional allergy tests have permitted detection of a positive allergic reaction is when in a conventional antigen reagent containing many types of proteins, a particular protein acting as an allergen component is present in an amount exceeding a threshold that allows determination of a positive reaction for binding to an IgE antibody. However, no determination of a positive reaction was possible and diagnosis efficiency was not sufficiently high when using a conventional allergy testing agent in patients possessing an IgE antibody binding to an allergen component present in small amounts in an allergen such as food.

The severity and symptoms of an allergic reaction do not necessarily correlate with the content of an allergen component. Even when a patient's IgE antibody reacts with an allergen component present in trace amounts in a candidate allergic food, material or the like, the allergic reaction may develop allergic symptoms or may affect the severity of those symptoms.

An attempt to increase the diagnostic efficiency is being made by examining IgE antibodies to components composing a crude antigen to distinguish sensitization that directly contributes to a diagnosis from sensitization based on cross-antigenicity by a pan-allergen or the like. 8 soybean allergens are currently registered to the World Health Organization/International Union of Immunological Societies (WHO/IUIS).

However, while it is necessary to exhaustively identify allergen components in candidate allergic foods and materials in order to enhance the reliability of allergy tests, the patient detection rate by the measurement of such allergenic components is far insufficient. Identification of novel allergens in soybean is very important not only for increasing the precision of diagnosis, but also for determining targets of therapeutic agents and low allergenic foods.

Meanwhile, in the field of protein separation and purification, various efforts have conventionally been made to develop methods for separating and purifying a protein or nucleic acid of interest from cell extracts or the like. Such methods may well be exemplified by dialysis based on salt concentration, and centrifugal separation.

Other efforts have been made to develop many purification methods based on electric charges of protein or nucleic acid residues or on the difference in molecular weight. Electric charge-based purification methods can be exemplified by column chromatography using ion exchange resins, and isoelectric focusing.

Purifications based on molecular weight difference can be exemplified by centrifugal separation, molecular-sieve column chromatography, and SDS-PAGE (sodium dodecyl sulfate-polyacrylamide gel electrophoresis).

In recent years, a method for separating and purifying many different proteins from a small amount of sample has been used, which is more specifically a two-dimensional electrophoresis consisting of isoelectric focusing in the first dimension, followed by SDS-PAGE in the second dimension. The present applicant has conventionally developed some 2D electrophoresis methods with high separation ability (Patent Literature 2-5).

CITATION LIST

Patent Literature

PTL1: Japanese Patent Application Publication No. JP 2002-286716
PTL2: Japanese Patent Application Publication No. JP 2011-33544
PTL3: Japanese Patent Application Publication No. JP 2011-33546
PTL4: Japanese Patent Application Publication No. JP 2011-33547
PTL5: Japanese Patent Application Publication No. JP 2011-33548

SUMMARY OF INVENTION

Technical Problem

The present invention provides novel antigens of an allergy to soybean. The present invention also provides methods and kits for diagnosing allergy to soybean. The present invention also provides pharmaceutical compositions comprising such an antigen and soybean or processed products of soybean in which such an antigen is eliminated or reduced. The present invention further provides testers for determining the presence or absence of a soybean antigen in an object of interest.

Solution to Problem

In order to solve the aforementioned problems, the present inventors had made intensive studies to identify causative antigens of an allergy to soybean. As a result, the inventors succeeded in identifying novel antigens to which an IgE antibody in the serum of a soybean-allergic patient specifically binds. The present invention has been completed based on this finding.

Thus, in one embodiment, the present invention can be as defined below.

[1] A kit for diagnosing an allergy to a soybean, the kit comprising, as an antigen, at least one of proteins defined below in any of the following (1) to (8):

(1) (1A) Bowman-Birk type proteinase inhibitor D-II or a variant thereof, which is defined below in any of (1A-a) to (1A-e):
 (1A-a) a protein comprising an amino acid sequence with deletion, substitution, insertion or addition of one or several amino acids in SEQ ID NO: 2;
 (1A-b) a protein comprising an amino acid sequence having at least 70% identity to the amino acid sequence of SEQ ID NO: 2;
 (1A-c) a protein comprising an amino acid sequence encoded by a nucleotide sequence with deletion, substitution, insertion or addition of one or several nucleotides in SEQ ID NO: 1;
 (1A-d) a protein comprising an amino acid sequence encoded by a nucleotide sequence having at least 70% identity to the nucleotide sequence of SEQ ID NO: 1; or
 (1A-e) a protein comprising an amino acid sequence encoded by a nucleic acid that hybridizes under stringent conditions with a nucleic acid having a nucleotide sequence complementary to the nucleotide sequence of SEQ ID NO: 1; or
 (1B) a protein comprising at least one amino acid sequence selected from the group consisting of SEQ ID NOs: 17-20;

(2) (2A) Ribulose bisphosphate carboxylase large chain or a variant thereof, which is defined below in any of (2A-a) to (2A-e):
 (2A-a) a protein comprising an amino acid sequence with deletion, substitution, insertion or addition of one or several amino acids in SEQ ID NO: 4;
 (2A-b) a protein comprising an amino acid sequence having at least 70% identity to the amino acid sequence of SEQ ID NO: 4;
 (2A-c) a protein comprising an amino acid sequence encoded by a nucleotide sequence with deletion, substitution, insertion or addition of one or several nucleotides in SEQ ID NO: 3;
 (2A-d) a protein comprising an amino acid sequence encoded by a nucleotide sequence having at least 70% identity to the nucleotide sequence of SEQ ID NO: 3; or
 (2A-e) a protein comprising an amino acid sequence encoded by a nucleic acid that hybridizes under stringent conditions with a nucleic acid having a nucleotide sequence complementary to the nucleotide sequence of SEQ ID NO: 3; or
 (2B) a protein comprising at least one amino acid sequence selected from the group consisting of SEQ ID NOs: 21-28;

(3) (3A) Gamma-glutamyl hydrolase or a variant thereof, which is defined below in any of (3A-a) to (3A-e):
 (3A-a) a protein comprising an amino acid sequence with deletion, substitution, insertion or addition of one or several amino acids in SEQ ID NO: 6;
 (3A-b) a protein comprising an amino acid sequence having at least 70% identity to the amino acid sequence of SEQ ID NO: 6;
 (3A-c) a protein comprising an amino acid sequence encoded by a nucleotide sequence with deletion, substitution, insertion or addition of one or several nucleotides in SEQ ID NO: 5;
 (3A-d) a protein comprising an amino acid sequence encoded by a nucleotide sequence having at least 70% identity to the nucleotide sequence of SEQ ID NO: 5; or
 (3A-e) a protein comprising an amino acid sequence encoded by a nucleic acid that hybridizes under stringent conditions with a nucleic acid having a nucleotide sequence complementary to the nucleotide sequence of SEQ ID NO: 5; or
 (3B) a protein comprising an amino acid sequence of SEQ ID NO: 29 or 30;

(4) (4A) Guanine nucleotide-binding protein subunit beta-like protein or a variant thereof, which is defined below in any of (4A-a) to (4A-e):
 (4A-a) a protein comprising an amino acid sequence with deletion, substitution, insertion or addition of one or several amino acids in SEQ ID NO: 8;
 (4A-b) a protein comprising an amino acid sequence having at least 70% identity to the amino acid sequence of SEQ ID NO: 8;
 (4A-c) a protein comprising an amino acid sequence encoded by a nucleotide sequence with deletion, substitution, insertion or addition of one or several nucleotides in SEQ ID NO: 7;
 (4A-d) a protein comprising an amino acid sequence encoded by a nucleotide sequence having at least 70% identity to the nucleotide sequence of SEQ ID NO: 7; or
 (4A-e) a protein comprising an amino acid sequence encoded by a nucleic acid that hybridizes under stringent conditions with a nucleic acid having a nucleotide sequence complementary to the nucleotide sequence of SEQ ID NO: 7; or
 (4B) a protein comprising an amino acid sequence of SEQ ID NO: 31 or 32;

(5) (5A) Protein SLE3 or a variant thereof, which is defined below in any of (5A-a) to (5A-e):
 (5A-a) a protein comprising an amino acid sequence with deletion, substitution, insertion or addition of one or several amino acids in SEQ ID NO: 10;
 (5A-b) a protein comprising an amino acid sequence having at least 70% identity to the amino acid sequence of SEQ ID NO: 10;
 (5A-c) a protein comprising an amino acid sequence encoded by a nucleotide sequence with deletion, substitution, insertion or addition of one or several nucleotides in SEQ ID NO: 9;
 (5A-d) a protein comprising an amino acid sequence encoded by a nucleotide sequence having at least 70% identity to the nucleotide sequence of SEQ ID NO: 9; or (5A-e) a protein comprising an amino acid sequence encoded by a nucleic acid that hybridizes under stringent conditions with a nucleic acid having a nucleotide sequence complementary to the nucleotide sequence of SEQ ID NO: 9; or (5B) a protein comprising an amino acid sequence of SEQ ID NO: 33 or 34;

(6) (6A) Seed biotin-containing protein SBP65 or a variant thereof, which is defined below in any of (6A-a) to (6A-e):

(6A-a) a protein comprising an amino acid sequence with deletion, substitution, insertion or addition of one or several amino acids in SEQ ID NO: 12;

(6A-b) a protein comprising an amino acid sequence having at least 70% identity to the amino acid sequence of SEQ ID NO: 12;

(6A-c) a protein comprising an amino acid sequence encoded by a nucleotide sequence with deletion, substitution, insertion or addition of one or several nucleotides in SEQ ID NO: 11;

(6A-d) a protein comprising an amino acid sequence encoded by a nucleotide sequence having at least 70% identity to the nucleotide sequence of SEQ ID NO: 11; or (6A-e) a protein comprising an amino acid sequence encoded by a nucleic acid that hybridizes under stringent conditions with a nucleic acid having a nucleotide sequence complementary to the nucleotide sequence of SEQ ID NO: 11; or (6B) a protein comprising at least one amino acid sequence selected from the group consisting of SEQ ID NOs: 35-53;

(7) (7A) Ferritin-2 or a variant thereof, which is defined below in any of (7A-a) to (7A-e):

(7A-a) a protein comprising an amino acid sequence with deletion, substitution, insertion or addition of one or several amino acids in SEQ ID NO: 14;

(7A-b) a protein comprising an amino acid sequence having at least 70% identity to the amino acid sequence of SEQ ID NO: 14;

(7A-c) a protein comprising an amino acid sequence encoded by a nucleotide sequence with deletion, substitution, insertion or addition of one or several nucleotides in SEQ ID NO: 13;

(7A-d) a protein comprising an amino acid sequence encoded by a nucleotide sequence having at least 70% identity to the nucleotide sequence of SEQ ID NO: 13; or (7A-e) a protein comprising an amino acid sequence encoded by a nucleic acid that hybridizes under stringent conditions with a nucleic acid having a nucleotide sequence complementary to the nucleotide sequence of SEQ ID NO: 13; or (7B) a protein comprising at least one amino acid sequence selected from the group consisting of SEQ ID NOs: 54-61;

(8) (8A) Cell division cycle protein 48 homolog or a variant thereof, which is defined below in any of (8A-a) to (8A-e):

(8A-a) a protein comprising an amino acid sequence with deletion, substitution, insertion or addition of one or several amino acids in SEQ ID NO: 16;

(8A-b) a protein comprising an amino acid sequence having at least 70% identity to the amino acid sequence of SEQ ID NO: 16;

(8A-c) a protein comprising an amino acid sequence encoded by a nucleotide sequence with deletion, substitution, insertion or addition of one or several nucleotides in SEQ ID NO: 15;

(8A-d) a protein comprising an amino acid sequence encoded by a nucleotide sequence having at least 70% identity to the nucleotide sequence of SEQ ID NO: 15; or (8A-e) a protein comprising an amino acid sequence encoded by a nucleic acid that hybridizes under stringent conditions with a nucleic acid having a nucleotide sequence complementary to the nucleotide sequence of SEQ ID NO: 15; or (8B) a protein comprising at least one amino acid sequence selected from the group consisting of SEQ ID NOs: 62-68.

[2] A composition for diagnosing an allergy to a soybean, comprising, as an antigen, at least one of proteins as defined above in any of (1) to (8) of [1].

[3] A method for providing an indicator for diagnosing an allergy to a soybean in a subject, the method comprising the steps of:

(i) contacting a sample obtained from the subject with an antigen, wherein the sample is a solution comprising an Ig antibody;

(ii) detecting binding between the IgE antibody present in the sample from the subject and the antigen; and (iii) when the binding between the IgE antibody in the subject and the antigen is detected, an indicator of the fact that the subject is allergic to a soybean is provided;

wherein the antigen is at least one of proteins as defined above in any of (1) to (8) of [1].

[4] A pharmaceutical composition comprising at least one of proteins as defined above in any of (1) to (8) of [1].

[5] The pharmaceutical composition as set forth in [4], wherein the pharmaceutical composition is intended for the treatment of an allergy to a soybean.

[6] A soybean or processed product of soybean, in which an antigen is eliminated or reduced, wherein antigen is at least one of proteins as defined above in any of (1) to (8) of [1].

[7] A tester for determining the presence or absence of a soybean antigen in an object of interest, comprising an antibody that binds to at least one of proteins as defined above in any of (1) to (8) of [1].

[8] A soybean-derived antigen which is at least one of proteins as defined above in any of (1) to (8) of [1] and is causative of an allergy to soybean.

[9] A kit for diagnosing an allergy to a soybean, the kit comprising, as an antigen, at least one of proteins defined below in any one of (1a) to (55a):

(1α) (1αA1) endoplasmin homolog isoform X2 or a variant thereof, which is defined below in any of (1αA1-a) to (1αA1-e):

(1αA1-a) a protein comprising an amino acid sequence with deletion, substitution, insertion or addition of one or several amino acids in SEQ ID NO: 70;

(1αA1-b) a protein comprising an amino acid sequence having at least 70% identity to the amino acid sequence of SEQ ID NO: 70;

(1αA1-c) a protein comprising an amino acid sequence encoded by a nucleotide sequence with deletion, substitution, insertion or addition of one or several nucleotides in SEQ ID NO: 69;

(1αA1-d) a protein comprising an amino acid sequence encoded by a nucleotide sequence having at least 70% identity to the nucleotide sequence of SEQ ID NO: 69; or (1αA1-e) a protein comprising an amino acid sequence encoded by a nucleic acid that hybridizes under stringent conditions with a nucleic acid having a nucleotide sequence complementary to the nucleotide sequence of SEQ ID NO: 69;

(1αB1) a protein comprising at least one amino acid sequence selected from the group consisting of SEQ ID NOs: 71-87, (1αA2) endoplasmin homolog isoform X2 or a variant thereof, which is defined below in any of (1αA2-a) to (1αA2-e):

(1αA2-a) a protein comprising an amino acid sequence with deletion, substitution, insertion or addition of one or several amino acids in SEQ ID NO: 89;

(1αA2-b) a protein comprising an amino acid sequence having at least 70% identity to the amino acid sequence of SEQ ID NO: 89;

(1αA2-c) a protein comprising an amino acid sequence encoded by a nucleotide sequence with deletion, substitution, insertion or addition of one or several nucleotides in SEQ ID NO: 88;

(1αA2-d) a protein comprising an amino acid sequence encoded by a nucleotide sequence having at least 70% identity to the nucleotide sequence of SEQ ID NO: 88; or (1αA2-e) a protein comprising an amino acid sequence encoded by a nucleic acid that hybridizes under stringent conditions with a nucleic acid having a nucleotide sequence complementary to the nucleotide sequence of SEQ ID NO: 88; or (1αB2) a protein comprising at least one amino acid sequence selected from the group consisting of SEQ ID NOs: 90-104;

(2α) (2αA1) heat shock cognate protein 80 or a variant thereof, which is defined below in any of (2αA1-a) to (2αA1-e):

(2αA1-a) a protein comprising an amino acid sequence with deletion, substitution, insertion or addition of one or several amino acids in SEQ ID NO: 106;

(2αA1-b) a protein comprising an amino acid sequence having at least 70% identity to the amino acid sequence of SEQ ID NO: 106;

(2αA1-c) a protein comprising an amino acid sequence encoded by a nucleotide sequence with deletion, substitution, insertion or addition of one or several nucleotides in SEQ ID NO: 105;

(2αA1-d) a protein comprising an amino acid sequence encoded by a nucleotide sequence having at least 70% identity to the nucleotide sequence of SEQ ID NO: 105; or (2αA1-e) a protein comprising an amino acid sequence encoded by a nucleic acid that hybridizes under stringent conditions with a nucleic acid having a nucleotide sequence complementary to the nucleotide sequence of SEQ ID NO: 105; or (2αB1) a protein comprising at least one amino acid sequence selected from the group consisting of SEQ ID NOs: 107-120;

(2αA2) heat shock protein 90-1 or a variant thereof, which is defined below in any of (2αA2-a) to (2αA2-e):

(2αA2-a) a protein comprising an amino acid sequence with deletion, substitution, insertion or addition of one or several amino acids in SEQ ID NO: 122;

(2αA2-b) a protein comprising an amino acid sequence having at least 70% identity to the amino acid sequence of SEQ ID NO: 122;

(2αA2-c) a protein comprising an amino acid sequence encoded by a nucleotide sequence with deletion, substitution, insertion or addition of one or several nucleotides in SEQ ID NO: 121;

(2αA2-d) a protein comprising an amino acid sequence encoded by a nucleotide sequence having at least 70% identity to the nucleotide sequence of SEQ ID NO: 121; or (2αA2-e) a protein comprising an amino acid sequence encoded by a nucleic acid that hybridizes under stringent conditions with a nucleic acid having a nucleotide sequence complementary to the nucleotide sequence of SEQ ID NO: 121; or (2αB2) a protein comprising at least one amino acid sequence selected from the group consisting of SEQ ID NOs: 123-137;

(2αA3) hypothetical protein GLYMA_02G302500 or a variant thereof, which is defined below in any of (2αA3-a) to (2αA3-e):

(2αA3-a) a protein comprising an amino acid sequence with deletion, substitution, insertion or addition of one or several amino acids in SEQ ID NO: 139;

(2αA3-b) a protein comprising an amino acid sequence having at least 70% identity to the amino acid sequence of SEQ ID NO: 139;

(2αA3-c) a protein comprising an amino acid sequence encoded by a nucleotide sequence with deletion, substitution, insertion or addition of one or several nucleotides in SEQ ID NO: 138;

(2αA3-d) a protein comprising an amino acid sequence encoded by a nucleotide sequence having at least 70% identity to the nucleotide sequence of SEQ ID NO: 138; or (2αA3-e) a protein comprising an amino acid sequence encoded by a nucleic acid that hybridizes under stringent conditions with a nucleic acid having a nucleotide sequence complementary to the nucleotide sequence of SEQ ID NO: 138; or (2αB3) a protein comprising at least one amino acid sequence selected from the group consisting of SEQ ID NOs: 140-153;

(4α) (4αA) embryo-specific urease isoform X1 or a variant thereof, which is defined below in any of (4αA-a) to (4αA-e):

(4αA-a) a protein comprising an amino acid sequence with deletion, substitution, insertion or addition of one or several amino acids in SEQ ID NO: 155;

(4αA-b) a protein comprising an amino acid sequence having at least 70% identity to the amino acid sequence of SEQ ID NO: 155;

(4αA-c) a protein comprising an amino acid sequence encoded by a nucleotide sequence with deletion, substitution, insertion or addition of one or several nucleotides in SEQ ID NO: 154;

(4αA-d) a protein comprising an amino acid sequence encoded by a nucleotide sequence having at least 70% identity to the nucleotide sequence of SEQ ID NO: 154; or (4αA-e) a protein comprising an amino acid sequence encoded by a nucleic acid that hybridizes under stringent conditions with a nucleic acid having a nucleotide sequence complementary to the nucleotide sequence of SEQ ID NO: 154; or (4αB) a protein comprising at least one amino acid sequence selected from the group consisting of SEQ ID NOs: 156 and 157;

(5α) (5αA) alpha-1,4 glucan phosphorylase L isozyme, chloroplastic/amyloplastic or a variant thereof, which is defined below in any of (5αA-a) to (5αA-e):
(5αA-a) a protein comprising an amino acid sequence with deletion, substitution, insertion or addition of one or several amino acids in SEQ ID NO: 159;
(5αA-b) a protein comprising an amino acid sequence having at least 70% identity to the amino acid sequence of SEQ ID NO: 159;
(5αA-c) a protein comprising an amino acid sequence encoded by a nucleotide sequence with deletion, substitution, insertion or addition of one or several nucleotides in SEQ ID NO: 158;
(5αA-d) a protein comprising an amino acid sequence encoded by a nucleotide sequence having at least 70% identity to the nucleotide sequence of SEQ ID NO: 158; or
(5αA-e) a protein comprising an amino acid sequence encoded by a nucleic acid that hybridizes under stringent conditions with a nucleic acid having a nucleotide sequence complementary to the nucleotide sequence of SEQ ID NO: 158; or
(5αB) a protein comprising at least one amino acid sequence selected from the group consisting of SEQ ID NOs: 160 and 161;
(6α) (6αA1) aconitate hydratase 1 or a variant thereof, which is defined below in any of (6αA1-a) to (6αA1-e):
(6αA1-a) a protein comprising an amino acid sequence with deletion, substitution, insertion or addition of one or several amino acids in SEQ ID NO: 163;
(6αA1-b) a protein comprising an amino acid sequence having at least 70% identity to the amino acid sequence of SEQ ID NO: 163;
(6αA1-c) a protein comprising an amino acid sequence encoded by a nucleotide sequence with deletion, substitution, insertion or addition of one or several nucleotides in SEQ ID NO: 162;
(6αA1-d) a protein comprising an amino acid sequence encoded by a nucleotide sequence having at least 70% identity to the nucleotide sequence of SEQ ID NO: 162; or
(6αA1-e) a protein comprising an amino acid sequence encoded by a nucleic acid that hybridizes under stringent conditions with a nucleic acid having a nucleotide sequence complementary to the nucleotide sequence of SEQ ID NO: 162;
(6αB1) a protein comprising at least one amino acid sequence selected from the group consisting of SEQ ID NOs: 164-167; or
(6αA2) aconitate hydratase 1 or a variant thereof, which is defined below in any of (6αA2-a) to (6αA2-e):
(6αA2-a) a protein comprising an amino acid sequence with deletion, substitution, insertion or addition of one or several amino acids in SEQ ID NO: 169;
(6αA2-b) a protein comprising an amino acid sequence having at least 70% identity to the amino acid sequence of SEQ ID NO: 169;
(6αA2-c) a protein comprising an amino acid sequence encoded by a nucleotide sequence with deletion, substitution, insertion or addition of one or several nucleotides in SEQ ID NO: 168;
(6αA2-d) a protein comprising an amino acid sequence encoded by a nucleotide sequence having at least 70% identity to the nucleotide sequence of SEQ ID NO: 168; or
(6αA2-e) a protein comprising an amino acid sequence encoded by a nucleic acid that hybridizes under stringent conditions with a nucleic acid having a nucleotide sequence complementary to the nucleotide sequence of SEQ ID NO: 168; or
(6αB2) a protein comprising at least one amino acid sequence selected from the group consisting of SEQ ID NOs: 170-172;
(7α) (7αA) methionine synthase or a variant thereof, which is defined below in any of (7αA-a) to (7αA-e):
(7αA-a) a protein comprising an amino acid sequence with deletion, substitution, insertion or addition of one or several amino acids in SEQ ID NO: 174;
(7αA-b) a protein comprising an amino acid sequence having at least 70% identity to the amino acid sequence of SEQ ID NO: 174;
(7αA-c) a protein comprising an amino acid sequence encoded by a nucleotide sequence with deletion, substitution, insertion or addition of one or several nucleotides in SEQ ID NO: 173;
(7αA-d) a protein comprising an amino acid sequence encoded by a nucleotide sequence having at least 70% identity to the nucleotide sequence of SEQ ID NO: 173; or
(7αA-e) a protein comprising an amino acid sequence encoded by a nucleic acid that hybridizes under stringent conditions with a nucleic acid having a nucleotide sequence complementary to the nucleotide sequence of SEQ ID NO: 173; or
(7αB) a protein comprising at least one amino acid sequence selected from the group consisting of SEQ ID NOs: 175-187;
(8α) (8αA) transketolase, chloroplastic or a variant thereof, which is defined below in any of (8αA-a) to (8αA-e):
(8αA-a) a protein comprising an amino acid sequence with deletion, substitution, insertion or addition of one or several amino acids in SEQ ID NO: 189;
(8αA-b) a protein comprising an amino acid sequence having at least 70% identity to the amino acid sequence of SEQ ID NO: 189;
(8αA-c) a protein comprising an amino acid sequence encoded by a nucleotide sequence with deletion, substitution, insertion or addition of one or several nucleotides in SEQ ID NO: 188;
(8αA-d) a protein comprising an amino acid sequence encoded by a nucleotide sequence having at least 70% identity to the nucleotide sequence of SEQ ID NO: 188; or
(8αA-e) a protein comprising an amino acid sequence encoded by a nucleic acid that hybridizes under stringent conditions with a nucleic acid having a nucleotide sequence complementary to the nucleotide sequence of SEQ ID NO: 188; or
(8αB) a protein comprising at least one amino acid sequence selected from the group consisting of SEQ ID NOs: 190-199;
(9α) (9αA) lysine-tRNA ligase, cytoplasmic-like isoform X2 or a variant thereof, which is defined below in any of (9αA-a) to (9αA-e):
(9αA-a) a protein comprising an amino acid sequence with deletion, substitution, insertion or addition of one or several amino acids in SEQ ID NO: 201;
(9αA-b) a protein comprising an amino acid sequence having at least 70% identity to the amino acid sequence of SEQ ID NO: 201;

(9αA-c) a protein comprising an amino acid sequence encoded by a nucleotide sequence with deletion, substitution, insertion or addition of one or several nucleotides in SEQ ID NO: 200;

(9αA-d) a protein comprising an amino acid sequence encoded by a nucleotide sequence having at least 70% identity to the nucleotide sequence of SEQ ID NO: 200; or (9αA-e) a protein comprising an amino acid sequence encoded by a nucleic acid that hybridizes under stringent conditions with a nucleic acid having a nucleotide sequence complementary to the nucleotide sequence of SEQ ID NO: 200; or (9αB) a protein comprising an amino acid sequence of SEQ ID NO: 202;

(10α) (10αA1) chaperonin CPN60-2, mitochondrial or a variant thereof, which is defined below in any of (10αA1-a) to (10αA1-e):

(10αA1-a) a protein comprising an amino acid sequence with deletion, substitution, insertion or addition of one or several amino acids in SEQ ID NO: 204;

(10αA1-b) a protein comprising an amino acid sequence having at least 70% identity to the amino acid sequence of SEQ ID NO: 204;

(10αA1-c) a protein comprising an amino acid sequence encoded by a nucleotide sequence with deletion, substitution, insertion or addition of one or several nucleotides in SEQ ID NO: 203;

(10αA1-d) a protein comprising an amino acid sequence encoded by a nucleotide sequence having at least 70% identity to the nucleotide sequence of SEQ ID NO: 203; or (10αA1-e) a protein comprising an amino acid sequence encoded by a nucleic acid that hybridizes under stringent conditions with a nucleic acid having a nucleotide sequence complementary to the nucleotide sequence of SEQ ID NO: 203;

(10αB1) a protein comprising at least one amino acid sequence selected from the group consisting of SEQ ID NOs: 205-218;

(10αA2) chaperonin CPN60-2, mitochondrial-like isoform X1 or a variant thereof, which is defined below in any of (10αA2-a) to (10αA2-e):

(10αA2-a) a protein comprising an amino acid sequence with deletion, substitution, insertion or addition of one or several amino acids in SEQ ID NO: 220;

(10αA2-b) a protein comprising an amino acid sequence having at least 70% identity to the amino acid sequence of SEQ ID NO: 220;

(10αA2-c) a protein comprising an amino acid sequence encoded by a nucleotide sequence with deletion, substitution, insertion or addition of one or several nucleotides in SEQ ID NO: 219;

(10αA2-d) a protein comprising an amino acid sequence encoded by a nucleotide sequence having at least 70% identity to the nucleotide sequence of SEQ ID NO: 219; or (10αA2-e) a protein comprising an amino acid sequence encoded by a nucleic acid that hybridizes under stringent conditions with a nucleic acid having a nucleotide sequence complementary to the nucleotide sequence of SEQ ID NO: 219; or (10αB2) a protein comprising at least one amino acid sequence selected from the group consisting of SEQ ID NOs: 221-231;

(11α) (11αA) polyadenylate-binding protein 8 isoform X3 or a variant thereof, which is defined below in any of (11αA-a) to (11αA-e):

(11αA-a) a protein comprising an amino acid sequence with deletion, substitution, insertion or addition of one or several amino acids in SEQ ID NO: 233;

(11αA-b) a protein comprising an amino acid sequence having at least 70% identity to the amino acid sequence of SEQ ID NO: 233;

(11αA-c) a protein comprising an amino acid sequence encoded by a nucleotide sequence with deletion, substitution, insertion or addition of one or several nucleotides in SEQ ID NO: 232;

(11αA-d) a protein comprising an amino acid sequence encoded by a nucleotide sequence having at least 70% identity to the nucleotide sequence of SEQ ID NO: 232; or (11αA-e) a protein comprising an amino acid sequence encoded by a nucleic acid that hybridizes under stringent conditions with a nucleic acid having a nucleotide sequence complementary to the nucleotide sequence of SEQ ID NO: 232; or (11αB) a protein comprising at least one amino acid sequence selected from the group consisting of SEQ ID NOs: 234-237;

(12α) (12αA) pyrophosphate-fructose 6-phosphate 1-phosphotransferase subunit alpha-like or a variant thereof, which is defined below in any of (12αA-a) to (12αA-e):

(12αA-a) a protein comprising an amino acid sequence with deletion, substitution, insertion or addition of one or several amino acids in SEQ ID NO: 239;

(12αA-b) a protein comprising an amino acid sequence having at least 70% identity to the amino acid sequence of SEQ ID NO: 239;

(12αA-c) a protein comprising an amino acid sequence encoded by a nucleotide sequence with deletion, substitution, insertion or addition of one or several nucleotides in SEQ ID NO: 238;

(12αA-d) a protein comprising an amino acid sequence encoded by a nucleotide sequence having at least 70% identity to the nucleotide sequence of SEQ ID NO: 238; or (12αA-e) a protein comprising an amino acid sequence encoded by a nucleic acid that hybridizes under stringent conditions with a nucleic acid having a nucleotide sequence complementary to the nucleotide sequence of SEQ ID NO: 238; or (12αB) a protein comprising an amino acid sequence of SEQ ID NO: 240;

(13α) (13αA1) protein disulfide isomerase-like protein precursor or a variant thereof, which is defined below in any of (13αA1-a) to (13αA1-e):

(13αA1-a) a protein comprising an amino acid sequence with deletion, substitution, insertion or addition of one or several amino acids in SEQ ID NO: 242;

(13αA1-b) a protein comprising an amino acid sequence having at least 70% identity to the amino acid sequence of SEQ ID NO: 242;

(13αA1-c) a protein comprising an amino acid sequence encoded by a nucleotide sequence with deletion, substitution, insertion or addition of one or several nucleotides in SEQ ID NO: 241;

(13αA1-d) a protein comprising an amino acid sequence encoded by a nucleotide sequence having at least 70% identity to the nucleotide sequence of SEQ ID NO: 241; or (13αA1-e) a protein comprising an amino acid sequence encoded by a nucleic acid that hybridizes under stringent conditions with a nucleic acid having a nucleotide sequence complementary to the nucleotide sequence of SEQ ID NO: 241;

(13αB1) a protein comprising at least one amino acid sequence selected from the group consisting of SEQ ID NOs: 243-252;

(13αA2) protein disulfide-isomerase or a variant thereof, which is defined below in any of (13αA2-a) to (13αA2-e):

(13αA2-a) a protein comprising an amino acid sequence with deletion, substitution, insertion or addition of one or several amino acids in SEQ ID NO: 254;

(13αA2-b) a protein comprising an amino acid sequence having at least 70% identity to the amino acid sequence of SEQ ID NO: 254;

(13αA2-c) a protein comprising an amino acid sequence encoded by a nucleotide sequence with deletion, substitution, insertion or addition of one or several nucleotides in SEQ ID NO: 253;

(13αA2-d) a protein comprising an amino acid sequence encoded by a nucleotide sequence having at least 70% identity to the nucleotide sequence of SEQ ID NO: 253; or (13αA2-e) a protein comprising an amino acid sequence encoded by a nucleic acid that hybridizes under stringent conditions with a nucleic acid having a nucleotide sequence complementary to the nucleotide sequence of SEQ ID NO: 253; or (13αB2) a protein comprising at least one amino acid sequence selected from the group consisting of SEQ ID NOs: 255-278;

(14α) (14αA1) V-type proton ATPase subunit B 2 or a variant thereof, which is defined below in any of (14αA1-a) to (14αA1-e):

(14αA1-a) a protein comprising an amino acid sequence with deletion, substitution, insertion or addition of one or several amino acids in SEQ ID NO: 280;

(14αA1-b) a protein comprising an amino acid sequence having at least 70% identity to the amino acid sequence of SEQ ID NO: 280;

(14αA1-c) a protein comprising an amino acid sequence encoded by a nucleotide sequence with deletion, substitution, insertion or addition of one or several nucleotides in SEQ ID NO: 279;

(14αA1-d) a protein comprising an amino acid sequence encoded by a nucleotide sequence having at least 70% identity to the nucleotide sequence of SEQ ID NO: 279; or (14αA1-e) a protein comprising an amino acid sequence encoded by a nucleic acid that hybridizes under stringent conditions with a nucleic acid having a nucleotide sequence complementary to the nucleotide sequence of SEQ ID NO: 279;

(14αB1) a protein comprising at least one amino acid sequence selected from the group consisting of SEQ ID NOs: 281-284;

(14αA2) V-type proton ATPase subunit B 2 or a variant thereof, which is defined below in any of (14αA2-a) to (14αA2-e):

(14αA2-a) a protein comprising an amino acid sequence with deletion, substitution, insertion or addition of one or several amino acids in SEQ ID NO: 286;

(14αA2-b) a protein comprising an amino acid sequence having at least 70% identity to the amino acid sequence of SEQ ID NO: 286;

(14αA2-c) a protein comprising an amino acid sequence encoded by a nucleotide sequence with deletion, substitution, insertion or addition of one or several nucleotides in SEQ ID NO: 285;

(14αA2-d) a protein comprising an amino acid sequence encoded by a nucleotide sequence having at least 70% identity to the nucleotide sequence of SEQ ID NO: 285; or (14αA2-e) a protein comprising an amino acid sequence encoded by a nucleic acid that hybridizes under stringent conditions with a nucleic acid having a nucleotide sequence complementary to the nucleotide sequence of SEQ ID NO: 285; or (14αB2) a protein comprising at least one amino acid sequence selected from the group consisting of SEQ ID NOs: 287-289;

(15, 16α) (15, 16αA1) UTP-glucose-1-phosphate uridylyltransferase or a variant thereof, which is defined below in any of (15, 16αA1-a) to (15, 16αA1-e):

(15, 16αA1-a) a protein comprising an amino acid sequence with deletion, substitution, insertion or addition of one or several amino acids in SEQ ID NO: 291;

(15, 16αA1-b) a protein comprising an amino acid sequence having at least 70% identity to the amino acid sequence of SEQ ID NO: 291;

(15, 16αA1-c) a protein comprising an amino acid sequence encoded by a nucleotide sequence with deletion, substitution, insertion or addition of one or several nucleotides in SEQ ID NO: 290;

(15, 16αA1-d) a protein comprising an amino acid sequence encoded by a nucleotide sequence having at least 70% identity to the nucleotide sequence of SEQ ID NO: 290; or (15, 16αA1-e) a protein comprising an amino acid sequence encoded by a nucleic acid that hybridizes under stringent conditions with a nucleic acid having a nucleotide sequence complementary to the nucleotide sequence of SEQ ID NO: 290;

(15, 16αB1) a protein comprising at least one amino acid sequence selected from the group consisting of SEQ ID NOs: 292-304;

(15, 16αA2) hypothetical protein GLYMA_02G241100 or a variant thereof, which is defined below in any of (15, 16αA2-a) to (15, 16αA2-e):

(15, 16αA2-a) a protein comprising an amino acid sequence with deletion, substitution, insertion or addition of one or several amino acids in SEQ ID NO: 306;

(15, 16αA2-b) a protein comprising an amino acid sequence having at least 70% identity to the amino acid sequence of SEQ ID NO: 306;

(15, 16αA2-c) a protein comprising an amino acid sequence encoded by a nucleotide sequence with deletion, substitution, insertion or addition of one or several nucleotides in SEQ ID NO: 305;

(15, 16αA2-d) a protein comprising an amino acid sequence encoded by a nucleotide sequence having at least 70% identity to the nucleotide sequence of SEQ ID NO: 305; or (15, 16αA2-e) a protein comprising an amino acid sequence encoded by a nucleic acid that hybridizes under stringent conditions with a nucleic acid having a nucleotide sequence complementary to the nucleotide sequence of SEQ ID NO: 305; or (15, 16αB2) a protein comprising at least one amino acid sequence selected from the group consisting of SEQ ID NOs: 307-318;

(17α) (17αA1) guanosine nucleotide diphosphate dissociation inhibitor 2 or a variant thereof, which is defined below in any of (17αA1-a) to (17αA1-e):

(17αA1-a) a protein comprising an amino acid sequence with deletion, substitution, insertion or addition of one or several amino acids in SEQ ID NO: 320;

(17αA1-b) a protein comprising an amino acid sequence having at least 70% identity to the amino acid sequence of SEQ ID NO: 320;

(17αA1-c) a protein comprising an amino acid sequence encoded by a nucleotide sequence with deletion, substitution, insertion or addition of one or several nucleotides in SEQ ID NO: 319;

(17αA1-d) a protein comprising an amino acid sequence encoded by a nucleotide sequence having at least 70% identity to the nucleotide sequence of SEQ ID NO: 319; or (17αA1-e) a protein comprising an amino acid sequence encoded by a nucleic acid that hybridizes under stringent conditions with a nucleic acid having a nucleotide sequence complementary to the nucleotide sequence of SEQ ID NO: 319;

(17αB1) a protein comprising at least one amino acid sequence selected from the group consisting of SEQ ID NOs: 321-325;

(17αA2) rab GDP dissociation inhibitor alpha-like or a variant thereof, which is defined below in any of (17αA2-a) to (17αA2-e):

(17αA2-a) a protein comprising an amino acid sequence with deletion, substitution, insertion or addition of one or several amino acids in SEQ ID NO: 327;

(17αA2-b) a protein comprising an amino acid sequence having at least 70% identity to the amino acid sequence of SEQ ID NO: 327;

(17αA2-c) a protein comprising an amino acid sequence encoded by a nucleotide sequence with deletion, substitution, insertion or addition of one or several nucleotides in SEQ ID NO: 326;

(17αA2-d) a protein comprising an amino acid sequence encoded by a nucleotide sequence having at least 70% identity to the nucleotide sequence of SEQ ID NO: 326; or (17αA2-e) a protein comprising an amino acid sequence encoded by a nucleic acid that hybridizes under stringent conditions with a nucleic acid having a nucleotide sequence complementary to the nucleotide sequence of SEQ ID NO: 326; or (17αB2) a protein comprising at least one amino acid sequence selected from the group consisting of SEQ ID NOs: 328-332;

(18α) (18αA) hypothetical protein GLYMA_10G028300 or a variant thereof, which is defined below in any of (18αA-a) to (18αA-e):

(18αA-a) a protein comprising an amino acid sequence with deletion, substitution, insertion or addition of one or several amino acids in SEQ ID NO: 334;

(18αA-b) a protein comprising an amino acid sequence having at least 70% identity to the amino acid sequence of SEQ ID NO: 334;

(18αA-c) a protein comprising an amino acid sequence encoded by a nucleotide sequence with deletion, substitution, insertion or addition of one or several nucleotides in SEQ ID NO: 333;

(18αA-d) a protein comprising an amino acid sequence encoded by a nucleotide sequence having at least 70% identity to the nucleotide sequence of SEQ ID NO: 333; or (18αA-e) a protein comprising an amino acid sequence encoded by a nucleic acid that hybridizes under stringent conditions with a nucleic acid having a nucleotide sequence complementary to the nucleotide sequence of SEQ ID NO: 333; or (18αB) a protein comprising at least one amino acid sequence selected from the group consisting of SEQ ID NOs: 335-339;

(19α) (19αA) sucrose binding protein homolog S-64 or a variant thereof, which is defined below in any of (19αA-a) to (19αA-e):

(19αA-a) a protein comprising an amino acid sequence with deletion, substitution, insertion or addition of one or several amino acids in SEQ ID NO: 341;

(19αA-b) a protein comprising an amino acid sequence having at least 70% identity to the amino acid sequence of SEQ ID NO: 341;

(19αA-c) a protein comprising an amino acid sequence encoded by a nucleotide sequence with deletion, substitution, insertion or addition of one or several nucleotides in SEQ ID NO: 340;

(19αA-d) a protein comprising an amino acid sequence encoded by a nucleotide sequence having at least 70% identity to the nucleotide sequence of SEQ ID NO: 340; or (19αA-e) a protein comprising an amino acid sequence encoded by a nucleic acid that hybridizes under stringent conditions with a nucleic acid having a nucleotide sequence complementary to the nucleotide sequence of SEQ ID NO: 340; or (19αB) a protein comprising at least one amino acid sequence selected from the group consisting of SEQ ID NOs: 342-346;

(25α) (25αA1) succinyl-CoA ligase [ADP-forming] subunit beta, mitochondrial or a variant thereof, which is defined below in any of (25αA1-a) to (25αA1-e):

(25αA1-a) a protein comprising an amino acid sequence with deletion, substitution, insertion or addition of one or several amino acids in SEQ ID NO: 348;

(25αA1-b) a protein comprising an amino acid sequence having at least 70% identity to the amino acid sequence of SEQ ID NO: 348;

(25αA1-c) a protein comprising an amino acid sequence encoded by a nucleotide sequence with deletion, substitution, insertion or addition of one or several nucleotides in SEQ ID NO: 347;

(25αA1-d) a protein comprising an amino acid sequence encoded by a nucleotide sequence having at least 70% identity to the nucleotide sequence of SEQ ID NO: 347; or (25αA1-e) a protein comprising an amino acid sequence encoded by a nucleic acid that hybridizes under stringent conditions with a nucleic acid having a nucleotide sequence complementary to the nucleotide sequence of SEQ ID NO: 347;

(25αB1) a protein comprising at least one amino acid sequence selected from the group consisting of SEQ ID NOs: 349-356;

(25αA2) succinyl-CoA ligase [ADP-forming] subunit beta, mitochondrial or a variant thereof, which is defined below in any of (25αA2-a) to (25αA2-e):

(25αA2-a) a protein comprising an amino acid sequence with deletion, substitution, insertion or addition of one or several amino acids in SEQ ID NO: 358;

(25αA2-b) a protein comprising an amino acid sequence having at least 70% identity to the amino acid sequence of SEQ ID NO: 358;

(25αA2-c) a protein comprising an amino acid sequence encoded by a nucleotide sequence with deletion, substitution, insertion or addition of one or several nucleotides in SEQ ID NO: 357;

(25αA2-d) a protein comprising an amino acid sequence encoded by a nucleotide sequence having at least 70% identity to the nucleotide sequence of SEQ ID NO: 357; or (25αA2-e) a protein comprising an amino acid sequence encoded by a nucleic acid that hybridizes under stringent conditions with a nucleic acid having a nucleotide sequence complementary to the nucleotide sequence of SEQ ID NO: 357; or (25αB2) a protein comprising at least one amino acid sequence selected from the group consisting of SEQ ID NOs: 359-365;

(26α) (26αA1) phosphoglycerate kinase, cytosolic or a variant thereof, which is defined below in any of (26αA1-a) to (26αA1-e):

(26αA1-a) a protein comprising an amino acid sequence with deletion, substitution, insertion or addition of one or several amino acids in SEQ ID NO: 367;

(26αA1-b) a protein comprising an amino acid sequence having at least 70% identity to the amino acid sequence of SEQ ID NO: 367;

(26αA1-c) a protein comprising an amino acid sequence encoded by a nucleotide sequence with deletion, substitution, insertion or addition of one or several nucleotides in SEQ ID NO: 366;

(26αA1-d) a protein comprising an amino acid sequence encoded by a nucleotide sequence having at least 70% identity to the nucleotide sequence of SEQ ID NO: 366; or (26αA1-e) a protein comprising an amino acid sequence encoded by a nucleic acid that hybridizes under stringent conditions with a nucleic acid having a nucleotide sequence complementary to the nucleotide sequence of SEQ ID NO: 366;

(26αB1) a protein comprising at least one amino acid sequence selected from the group consisting of SEQ ID NOs: 368-382;

(26αA2) phosphoglycerate kinase, cytosolic or a variant thereof, which is defined below in any of (26αA2-a) to (26αA2-e):

(26αA2-a) a protein comprising an amino acid sequence with deletion, substitution, insertion or addition of one or several amino acids in SEQ ID NO: 384;

(26αA2-b) a protein comprising an amino acid sequence having at least 70% identity to the amino acid sequence of SEQ ID NO: 384;

(26αA2-c) a protein comprising an amino acid sequence encoded by a nucleotide sequence with deletion, substitution, insertion or addition of one or several nucleotides in SEQ ID NO: 383;

(26αA2-d) a protein comprising an amino acid sequence encoded by a nucleotide sequence having at least 70% identity to the nucleotide sequence of SEQ ID NO: 383; or (26αA2-e) a protein comprising an amino acid sequence encoded by a nucleic acid that hybridizes under stringent conditions with a nucleic acid having a nucleotide sequence complementary to the nucleotide sequence of SEQ ID NO: 383;

(26αB2) a protein comprising at least one amino acid sequence selected from the group consisting of SEQ ID NOs: 385-392;

(26αA3) phosphoglycerate kinase, cytosolic or a variant thereof, which is defined below in any of (26αA3-a) to (26αA3-e):

(26αA3-a) a protein comprising an amino acid sequence with deletion, substitution, insertion or addition of one or several amino acids in SEQ ID NO: 394;

(26αA3-b) a protein comprising an amino acid sequence having at least 70% identity to the amino acid sequence of SEQ ID NO: 394;

(26αA3-c) a protein comprising an amino acid sequence encoded by a nucleotide sequence with deletion, substitution, insertion or addition of one or several nucleotides in SEQ ID NO: 393;

(26αA3-d) a protein comprising an amino acid sequence encoded by a nucleotide sequence having at least 70% identity to the nucleotide sequence of SEQ ID NO: 393; or (26αA3-e) a protein comprising an amino acid sequence encoded by a nucleic acid that hybridizes under stringent conditions with a nucleic acid having a nucleotide sequence complementary to the nucleotide sequence of SEQ ID NO: 393; or (26αB3) a protein comprising at least one amino acid sequence selected from the group consisting of SEQ ID NOs: 395-409;

(27α) (27αA1) alcohol dehydrogenase 1 or a variant thereof, which is defined below in any of (27αA1-a) to (27αA1-e):

(27αA1-a) a protein comprising an amino acid sequence with deletion, substitution, insertion or addition of one or several amino acids in SEQ ID NO: 411;

(27αA1-b) a protein comprising an amino acid sequence having at least 70% identity to the amino acid sequence of SEQ ID NO: 411;

(27αA1-c) a protein comprising an amino acid sequence encoded by a nucleotide sequence with deletion, substitution, insertion or addition of one or several nucleotides in SEQ ID NO: 410;

(27αA1-d) a protein comprising an amino acid sequence encoded by a nucleotide sequence having at least 70% identity to the nucleotide sequence of SEQ ID NO: 410; or (27αA1-e) a protein comprising an amino acid sequence encoded by a nucleic acid that hybridizes under stringent conditions with a nucleic acid having a nucleotide sequence complementary to the nucleotide sequence of SEQ ID NO: 410;

(27αB1) a protein comprising at least one amino acid sequence selected from the group consisting of SEQ ID NOs: 412-416;

(27αA2) alcohol dehydrogenase 1 or a variant thereof, which is defined below in any of (27αA2-a) to (27αA2-e):

(27αA2-a) a protein comprising an amino acid sequence with deletion, substitution, insertion or addition of one or several amino acids in SEQ ID NO: 418;

(27αA2-b) a protein comprising an amino acid sequence having at least 70% identity to the amino acid sequence of SEQ ID NO: 418;

(27αA2-c) a protein comprising an amino acid sequence encoded by a nucleotide sequence with deletion, substitution, insertion or addition of one or several nucleotides in SEQ ID NO: 417;

(27αA2-d) a protein comprising an amino acid sequence encoded by a nucleotide sequence having at least 70% identity to the nucleotide sequence of SEQ ID NO: 417; or (27αA2-e) a protein comprising an amino acid sequence encoded by a nucleic acid that hybridizes under stringent conditions with a nucleic acid having a nucleotide sequence complementary to the nucleotide sequence of SEQ ID NO: 417;

(27αB2) a protein comprising at least one amino acid sequence selected from the group consisting of SEQ ID NOs: 419 and 420;

(27αA3) alcohol dehydrogenase 1-like or a variant thereof, which is defined below in any of (27αA3-a) to (27αA3-e):

(27αA3-a) a protein comprising an amino acid sequence with deletion, substitution, insertion or addition of one or several amino acids in SEQ ID NO: 422;

(27αA3-b) a protein comprising an amino acid sequence having at least 70% identity to the amino acid sequence of SEQ ID NO: 422;

(27αA3-c) a protein comprising an amino acid sequence encoded by a nucleotide sequence with deletion, substitution, insertion or addition of one or several nucleotides in SEQ ID NO: 421;

(27αA3-d) a protein comprising an amino acid sequence encoded by a nucleotide sequence having at least 70% identity to the nucleotide sequence of SEQ ID NO: 421; or (27αA3-e) a protein comprising an amino acid sequence encoded by a nucleic acid that hybridizes under stringent conditions with a nucleic acid having a nucleotide sequence complementary to the nucleotide sequence of SEQ ID NO: 421; or (27αB3) a protein comprising at least one amino acid sequence selected from the group consisting of SEQ ID NOs: 423-427;

(28α) (28αA) 35 kDa seed maturation protein isoform X1 or a variant thereof, which is defined below in any of (28αA-a) to (28αA-e):

(28αA-a) a protein comprising an amino acid sequence with deletion, substitution, insertion or addition of one or several amino acids in SEQ ID NO: 429;

(28αA-b) a protein comprising an amino acid sequence having at least 70% identity to the amino acid sequence of SEQ ID NO: 429;

(28αA-c) a protein comprising an amino acid sequence encoded by a nucleotide sequence with deletion, substitution, insertion or addition of one or several nucleotides in SEQ ID NO: 428;

(28αA-d) a protein comprising an amino acid sequence encoded by a nucleotide sequence having at least 70% identity to the nucleotide sequence of SEQ ID NO: 428; or (28αA-e) a protein comprising an amino acid sequence encoded by a nucleic acid that hybridizes under stringent conditions with a nucleic acid having a nucleotide sequence complementary to the nucleotide sequence of SEQ ID NO: 428; or (28αB) a protein comprising at least one amino acid sequence selected from the group consisting of SEQ ID NOs: 430-433;

(29-33α) (29-33αA1) glyceraldehyde-3-phosphate dehydrogenase isoform X1 or a variant thereof, which is defined below in any of (29-33αA1-a) to (29-33αA1-e):

(29-33αA1-a) a protein comprising an amino acid sequence with deletion, substitution, insertion or addition of one or several amino acids in SEQ ID NO: 435;

(29-33αA1-b) a protein comprising an amino acid sequence having at least 70% identity to the amino acid sequence of SEQ ID NO: 435;

(29-33αA1-c) a protein comprising an amino acid sequence encoded by a nucleotide sequence with deletion, substitution, insertion or addition of one or several nucleotides in SEQ ID NO: 434;

(29-33αA1-d) a protein comprising an amino acid sequence encoded by a nucleotide sequence having at least 70% identity to the nucleotide sequence of SEQ ID NO: 434; or (29-33αA1-e) a protein comprising an amino acid sequence encoded by a nucleic acid that hybridizes under stringent conditions with a nucleic acid having a nucleotide sequence complementary to the nucleotide sequence of SEQ ID NO: 434;

(29-33αB1) a protein comprising at least one amino acid sequence selected from the group consisting of SEQ ID NOs: 436-439;

(29-33αA2) glyceraldehyde-3-phosphate dehydrogenase, cytosolic or a variant thereof, which is defined below in any of (29-33αA2-a) to (29-33αA2-e):

(29-33αA2-a) a protein comprising an amino acid sequence with deletion, substitution, insertion or addition of one or several amino acids in SEQ ID NO: 441;

(29-33αA2-b) a protein comprising an amino acid sequence having at least 70% identity to the amino acid sequence of SEQ ID NO: 441;

(29-33αA2-c) a protein comprising an amino acid sequence encoded by a nucleotide sequence with deletion, substitution, insertion or addition of one or several nucleotides in SEQ ID NO: 440;

(29-33αA2-d) a protein comprising an amino acid sequence encoded by a nucleotide sequence having at least 70% identity to the nucleotide sequence of SEQ ID NO: 440; or (29-33αA2-e) a protein comprising an amino acid sequence encoded by a nucleic acid that hybridizes under stringent conditions with a nucleic acid having a nucleotide sequence complementary to the nucleotide sequence of SEQ ID NO: 440;

(29-33αB2) a protein comprising at least one amino acid sequence selected from the group consisting of SEQ ID NOs: 442-445;

(29-33αA3) uncharacterized protein LOC100782924 or a variant thereof, which is defined below in any of (29-33αA3-a) to (29-33αA3-e):

(29-33αA3-a) a protein comprising an amino acid sequence with deletion, substitution, insertion or addition of one or several amino acids in SEQ ID NO: 447;

(29-33αA3-b) a protein comprising an amino acid sequence having at least 70% identity to the amino acid sequence of SEQ ID NO: 447;

(29-33αA3-c) a protein comprising an amino acid sequence encoded by a nucleotide sequence with deletion, substitution, insertion or addition of one or several nucleotides in SEQ ID NO: 446;

(29-33αA3-d) a protein comprising an amino acid sequence encoded by a nucleotide sequence having at least 70% identity to the nucleotide sequence of SEQ ID NO: 446; or (29-33αA3-e) a protein comprising an amino acid sequence encoded by a nucleic acid that hybridizes under stringent conditions with a nucleic acid having a nucleotide sequence complementary to the nucleotide sequence of SEQ ID NO: 446; or (29-33αB3) a protein comprising at least one amino acid sequence selected from the group consisting of SEQ ID NOs: 448-451, (34α) (34αA1) bifunctional UDP-glucose 4-epimerase and UDP-xylose 4-epimerase 1-like or a variant thereof, which is defined below in any of (34αA1-a) to (34αA1-e):

(34αA1-a) a protein comprising an amino acid sequence with deletion, substitution, insertion or addition of one or several amino acids in SEQ ID NO: 453;

(34αA1-b) a protein comprising an amino acid sequence having at least 70% identity to the amino acid sequence of SEQ ID NO: 453;

(34αA1-c) a protein comprising an amino acid sequence encoded by a nucleotide sequence with deletion, substitution, insertion or addition of one or several nucleotides in SEQ ID NO: 452;

(34αA1-d) a protein comprising an amino acid sequence encoded by a nucleotide sequence having at least 70% identity to the nucleotide sequence of SEQ ID NO: 452; or (34αA1-e) a protein comprising an amino acid sequence encoded by a nucleic acid that hybridizes under stringent conditions with a nucleic acid having a nucleotide sequence complementary to the nucleotide sequence of SEQ ID NO: 452;

(34αB1) a protein comprising an amino acid sequence of SEQ ID NO: 454;

(34αA2) uncharacterized protein LOC100803483 or a variant thereof, which is defined below in any of (34αA2-a) to (34αA2-e):

(34αA2-a) a protein comprising an amino acid sequence with deletion, substitution, insertion or addition of one or several amino acids in SEQ ID NO: 456;

(34αA2-b) a protein comprising an amino acid sequence having at least 70% identity to the amino acid sequence of SEQ ID NO: 456;

(34αA2-c) a protein comprising an amino acid sequence encoded by a nucleotide sequence with deletion, substitution, insertion or addition of one or several nucleotides in SEQ ID NO: 455;

(34αA2-d) a protein comprising an amino acid sequence encoded by a nucleotide sequence having at least 70% identity to the nucleotide sequence of SEQ ID NO: 455; or (34αA2-e) a protein comprising an amino acid sequence encoded by a nucleic acid that hybridizes under stringent conditions with a nucleic acid having a nucleotide sequence complementary to the nucleotide sequence of SEQ ID NO: 455; or (34αB2) a protein comprising at least one amino acid sequence selected from the group consisting of SEQ ID NOs: 457 and 458;

(35α) (35αA1) elongation factor 1-alpha or a variant thereof, which is defined below in any of (35αA1-a) to (35αA1-e):

(35αA1-a) a protein comprising an amino acid sequence with deletion, substitution, insertion or addition of one or several amino acids in SEQ ID NO: 460;

(35αA1-b) a protein comprising an amino acid sequence having at least 70% identity to the amino acid sequence of SEQ ID NO: 460;

(35αA1-c) a protein comprising an amino acid sequence encoded by a nucleotide sequence with deletion, substitution, insertion or addition of one or several nucleotides in SEQ ID NO: 459;

(35αA1-d) a protein comprising an amino acid sequence encoded by a nucleotide sequence having at least 70% identity to the nucleotide sequence of SEQ ID NO: 459; or (35αA1-e) a protein comprising an amino acid sequence encoded by a nucleic acid that hybridizes under stringent conditions with a nucleic acid having a nucleotide sequence complementary to the nucleotide sequence of SEQ ID NO: 459;

(35αB1) a protein comprising at least one amino acid sequence selected from the group consisting of SEQ ID NOs: 461-466;

(35αA2) elongation factor 1-alpha or a variant thereof, which is defined below in any of (35αA2-a) to (35αA2-e):

(35αA2-a) a protein comprising an amino acid sequence with deletion, substitution, insertion or addition of one or several amino acids in SEQ ID NO: 468;

(35αA2-b) a protein comprising an amino acid sequence having at least 70% identity to the amino acid sequence of SEQ ID NO: 468;

(35αA2-c) a protein comprising an amino acid sequence encoded by a nucleotide sequence with deletion, substitution, insertion or addition of one or several nucleotides in SEQ ID NO: 467;

(35αA2-d) a protein comprising an amino acid sequence encoded by a nucleotide sequence having at least 70% identity to the nucleotide sequence of SEQ ID NO: 467; or (35αA2-e) a protein comprising an amino acid sequence encoded by a nucleic acid that hybridizes under stringent conditions with a nucleic acid having a nucleotide sequence complementary to the nucleotide sequence of SEQ ID NO: 467;

(35αB2) a protein comprising at least one amino acid sequence selected from the group consisting of SEQ ID NOs: 469-471;

(35αA3) elongation factor-1A isoform X1 or a variant thereof, which is defined below in any of (35αA3-a) to (35αA3-e):

(35αA3-a) a protein comprising an amino acid sequence with deletion, substitution, insertion or addition of one or several amino acids in SEQ ID NO: 473;

(35αA3-b) a protein comprising an amino acid sequence having at least 70% identity to the amino acid sequence of SEQ ID NO: 473;

(35αA3-c) a protein comprising an amino acid sequence encoded by a nucleotide sequence with deletion, substitution, insertion or addition of one or several nucleotides in SEQ ID NO: 472;

(35αA3-d) a protein comprising an amino acid sequence encoded by a nucleotide sequence having at least 70% identity to the nucleotide sequence of SEQ ID NO: 472; or (35αA3-e) a protein comprising an amino acid sequence encoded by a nucleic acid that hybridizes under stringent conditions with a nucleic acid having a nucleotide sequence complementary to the nucleotide sequence of SEQ ID NO: 472; or (35αB3) a protein comprising at least one amino acid sequence selected from the group consisting of SEQ ID NOs: 474-477;

(36, 37α) (36, 37αA1) seed maturation protein PM34 or a variant thereof, which is defined below in any of (36, 37αA1-a) to (36, 37αA1-e):

(36, 37αA1-a) a protein comprising an amino acid sequence with deletion, substitution, insertion or addition of one or several amino acids in SEQ ID NO: 479;

(36, 37αA1-b) a protein comprising an amino acid sequence having at least 70% identity to the amino acid sequence of SEQ ID NO: 479;

(36, 37αA1-c) a protein comprising an amino acid sequence encoded by a nucleotide sequence with deletion, substitution, insertion or addition of one or several nucleotides in SEQ ID NO: 478;

(36, 37αA1-d) a protein comprising an amino acid sequence encoded by a nucleotide sequence having at least 70% identity to the nucleotide sequence of SEQ ID NO: 478; or (36, 37αA1-e) a protein comprising an amino acid sequence encoded by a nucleic acid that hybridizes under stringent conditions with a nucleic acid having a nucleotide sequence complementary to the nucleotide sequence of SEQ ID NO: 478;

(36, 37αB1) a protein comprising at least one amino acid sequence selected from the group consisting of SEQ ID NOs: 480-483;

(36, 37αA2) uncharacterized protein LOC100809384 or a variant thereof, which is defined below in any of (36, 37αA2-a) to (36, 37αA2-e):

(36, 37αA2-a) a protein comprising an amino acid sequence with deletion, substitution, insertion or addition of one or several amino acids in SEQ ID NO: 485;

(36, 37αA2-b) a protein comprising an amino acid sequence having at least 70% identity to the amino acid sequence of SEQ ID NO: 485;

(36, 37αA2-c) a protein comprising an amino acid sequence encoded by a nucleotide sequence with deletion, substitution, insertion or addition of one or several nucleotides in SEQ ID NO: 484;

(36, 37αA2-d) a protein comprising an amino acid sequence encoded by a nucleotide sequence having at least 70% identity to the nucleotide sequence of SEQ ID NO: 484; or (36, 37αA2-e) a protein comprising an amino acid sequence encoded by a nucleic acid that hybridizes under stringent conditions with a nucleic acid having a nucleotide sequence complementary to the nucleotide sequence of SEQ ID NO: 484;

(36, 37αB2) a protein comprising at least one amino acid sequence selected from the group consisting of SEQ ID NOs: 486 and 487;

(36, 37αA3) hypothetical protein GLYMA_10G155300 or a variant thereof, which is defined below in any of (36, 37αA3-a) to (36, 37αA3-e):

(36, 37αA3-a) a protein comprising an amino acid sequence with deletion, substitution, insertion or addition of one or several amino acids in SEQ ID NO: 489;

(36, 37αA3-b) a protein comprising an amino acid sequence having at least 70% identity to the amino acid sequence of SEQ ID NO: 489;

(36, 37αA3-c) a protein comprising an amino acid sequence encoded by a nucleotide sequence with deletion, substitution, insertion or addition of one or several nucleotides in SEQ ID NO: 488;

(36, 37αA3-d) a protein comprising an amino acid sequence encoded by a nucleotide sequence having at least 70% identity to the nucleotide sequence of SEQ ID NO: 488; or (36, 37αA3-e) a protein comprising an amino acid sequence encoded by a nucleic acid that hybridizes under stringent conditions with a nucleic acid having a nucleotide sequence complementary to the nucleotide sequence of SEQ ID NO: 488; or (36, 37αB3) a protein comprising at least one amino acid sequence selected from the group consisting of SEQ ID NOs: 490-493;

(38α) (38αA) seed biotin-containing protein SBP65-like isoform X1 or a variant thereof, which is defined below in any of (38αA-a) to (38αA-e):

(38αA-a) a protein comprising an amino acid sequence with deletion, substitution, insertion or addition of one or several amino acids in SEQ ID NO: 495;

(38αA-b) a protein comprising an amino acid sequence having at least 70% identity to the amino acid sequence of SEQ ID NO: 495;

(38αA-c) a protein comprising an amino acid sequence encoded by a nucleotide sequence with deletion, substitution, insertion or addition of one or several nucleotides in SEQ ID NO: 494;

(38αA-d) a protein comprising an amino acid sequence encoded by a nucleotide sequence having at least 70% identity to the nucleotide sequence of SEQ ID NO: 494; or (38αA-e) a protein comprising an amino acid sequence encoded by a nucleic acid that hybridizes under stringent conditions with a nucleic acid having a nucleotide sequence complementary to the nucleotide sequence of SEQ ID NO: 494; or (38αB) a protein comprising at least one amino acid sequence selected from the group consisting of SEQ ID NOs: 496-513;

(39α) (39αA) ATP synthase subunit 0, mitochondrial-like or a variant thereof, which is defined below in any of (39αA-a) to (39αA-e):

(39αA-a) a protein comprising an amino acid sequence with deletion, substitution, insertion or addition of one or several amino acids in SEQ ID NO: 515;

(39αA-b) a protein comprising an amino acid sequence having at least 70% identity to the amino acid sequence of SEQ ID NO: 515;

(39αA-c) a protein comprising an amino acid sequence encoded by a nucleotide sequence with deletion, substitution, insertion or addition of one or several nucleotides in SEQ ID NO: 514;

(39αA-d) a protein comprising an amino acid sequence encoded by a nucleotide sequence having at least 70% identity to the nucleotide sequence of SEQ ID NO: 514; or (39αA-e) a protein comprising an amino acid sequence encoded by a nucleic acid that hybridizes under stringent conditions with a nucleic acid having a nucleotide sequence complementary to the nucleotide sequence of SEQ ID NO: 514; or (39αB) a protein comprising an amino acid sequence of SEQ ID NO: 516;

(40, 56α) (40, 56αA) P24 oleosin isoform A or a variant thereof, which is defined below in any of (40, 56αA-a) to (40, 56αA-e):

(40, 56αA-a) a protein comprising an amino acid sequence with deletion, substitution, insertion or addition of one or several amino acids in SEQ ID NO: 518;

(40, 56αA-b) a protein comprising an amino acid sequence having at least 70% identity to the amino acid sequence of SEQ ID NO: 518;

(40, 56αA-c) a protein comprising an amino acid sequence encoded by a nucleotide sequence with deletion, substitution, insertion or addition of one or several nucleotides in SEQ ID NO: 517;

(40, 56αA-d) a protein comprising an amino acid sequence encoded by a nucleotide sequence having at least 70% identity to the nucleotide sequence of SEQ ID NO: 517; or (40, 56αA-e) a protein comprising an amino acid sequence encoded by a nucleic acid that hybridizes under stringent conditions with a nucleic acid having a nucleotide sequence complementary to the nucleotide sequence of SEQ ID NO: 517; or (40, 56αB) a protein comprising at least one amino acid sequence selected from the group consisting of SEQ ID NOs: 519 and 520;

(41α) (41αA) uncharacterized protein At3g49720-like isoform X2 or a variant thereof, which is defined below in any of (41αA-a) to (41αA-e):

(41αA-a) a protein comprising an amino acid sequence with deletion, substitution, insertion or addition of one or several amino acids in SEQ ID NO: 522;

(41αA-b) a protein comprising an amino acid sequence having at least 70% identity to the amino acid sequence of SEQ ID NO: 522;

(41αA-c) a protein comprising an amino acid sequence encoded by a nucleotide sequence with deletion, substitution, insertion or addition of one or several nucleotides in SEQ ID NO: 521;

(41αA-d) a protein comprising an amino acid sequence encoded by a nucleotide sequence having at least 70% identity to the nucleotide sequence of SEQ ID NO: 521; or (41αA-e) a protein comprising an amino acid sequence encoded by a nucleic acid that hybridizes under stringent conditions with a nucleic acid having a nucleotide sequence complementary to the nucleotide sequence of SEQ ID NO: 521; or (41αB) a protein comprising an amino acid sequence of SEQ ID NO: 523;

(42, 43α) (42, 43αA1) superoxide dismutase [Mn], mitochondrial or a variant thereof, which is defined below in any of (42, 43αA1-a) to (42, 43αA1-e):

(42, 43αA1-a) a protein comprising an amino acid sequence with deletion, substitution, insertion or addition of one or several amino acids in SEQ ID NO: 525;

(42, 43αA1-b) a protein comprising an amino acid sequence having at least 70% identity to the amino acid sequence of SEQ ID NO: 525;

(42, 43αA1-c) a protein comprising an amino acid sequence encoded by a nucleotide sequence with deletion, substitution, insertion or addition of one or several nucleotides in SEQ ID NO: 524;

(42, 43αA1-d) a protein comprising an amino acid sequence encoded by a nucleotide sequence having at least 70% identity to the nucleotide sequence of SEQ ID NO: 524; or (42, 43αA1-e) a protein comprising an amino acid sequence encoded by a nucleic acid that hybridizes under stringent conditions with a nucleic acid having a nucleotide sequence complementary to the nucleotide sequence of SEQ ID NO: 524;

(42, 43αB1) a protein comprising at least one amino acid sequence selected from the group consisting of SEQ ID NOs: 526-531;

(42, 43αA2) hypothetical protein GLYMA_04G221300 or a variant thereof, which is defined below in any of (42, 43αA2-a) to (42, 43αA2-e):

(42, 43αA2-a) a protein comprising an amino acid sequence with deletion, substitution, insertion or addition of one or several amino acids in SEQ ID NO: 533;

(42, 43αA2-b) a protein comprising an amino acid sequence having at least 70% identity to the amino acid sequence of SEQ ID NO: 533;

(42, 43αA2-c) a protein comprising an amino acid sequence encoded by a nucleotide sequence with deletion, substitution, insertion or addition of one or several nucleotides in SEQ ID NO: 532;

(42, 43αA2-d) a protein comprising an amino acid sequence encoded by a nucleotide sequence having at least 70% identity to the nucleotide sequence of SEQ ID NO: 532; or (42, 43αA2-e) a protein comprising an amino acid sequence encoded by a nucleic acid that hybridizes under stringent conditions with a nucleic acid having a nucleotide sequence complementary to the nucleotide sequence of SEQ ID NO: 532; or (42, 43αB2) a protein comprising at least one amino acid sequence selected from the group consisting of SEQ ID NOs: 534-539;

(45α) (45αA1) uncharacterized protein LOC100499771 or a variant thereof, which is defined below in any of (45αA1-a) to (45αA1-e):

(45αA1-a) a protein comprising an amino acid sequence with deletion, substitution, insertion or addition of one or several amino acids in SEQ ID NO: 541;

(45αA1-b) a protein comprising an amino acid sequence having at least 70% identity to the amino acid sequence of SEQ ID NO: 541;

(45αA1-c) a protein comprising an amino acid sequence encoded by a nucleotide sequence with deletion, substitution, insertion or addition of one or several nucleotides in SEQ ID NO: 540;

(45αA1-d) a protein comprising an amino acid sequence encoded by a nucleotide sequence having at least 70% identity to the nucleotide sequence of SEQ ID NO: 540; or (45αA1-e) a protein comprising an amino acid sequence encoded by a nucleic acid that hybridizes under stringent conditions with a nucleic acid having a nucleotide sequence complementary to the nucleotide sequence of SEQ ID NO: 540;

(45αB1) a protein comprising at least one amino acid sequence selected from the group consisting of SEQ ID NOs: 542-545;

(45αA2) hypothetical protein GLYMA_09G192800 or a variant thereof, which is defined below in any of (45αA2-a) to (45αA2-e):

(45αA2-a) a protein comprising an amino acid sequence with deletion, substitution, insertion or addition of one or several amino acids in SEQ ID NO: 547;

(45αA2-b) a protein comprising an amino acid sequence having at least 70% identity to the amino acid sequence of SEQ ID NO: 547;

(45αA2-c) a protein comprising an amino acid sequence encoded by a nucleotide sequence with deletion, substitution, insertion or addition of one or several nucleotides in SEQ ID NO: 546;

(45αA2-d) a protein comprising an amino acid sequence encoded by a nucleotide sequence having at least 70% identity to the nucleotide sequence of SEQ ID NO: 546; or (45αA2-e) a protein comprising an amino acid sequence encoded by a nucleic acid that hybridizes under stringent conditions with a nucleic acid having a nucleotide sequence complementary to the nucleotide sequence of SEQ ID NO: 546; or (45αB2) a protein comprising at least one amino acid sequence selected from the group consisting of SEQ ID NOs: 548-551;

(46α) (46αA) seed maturation protein PM22 or a variant thereof, which is defined below in any of (46αA-a) to (46αA-e):

(46αA-a) a protein comprising an amino acid sequence with deletion, substitution, insertion or addition of one or several amino acids in SEQ ID NO: 553;

(46αA-b) a protein comprising an amino acid sequence having at least 70% identity to the amino acid sequence of SEQ ID NO: 553;

(46αA-c) a protein comprising an amino acid sequence encoded by a nucleotide sequence with deletion, substitution, insertion or addition of one or several nucleotides in SEQ ID NO: 552;

(46αA-d) a protein comprising an amino acid sequence encoded by a nucleotide sequence having at least 70% identity to the nucleotide sequence of SEQ ID NO: 552; or (46αA-e) a protein comprising an amino acid sequence encoded by a nucleic acid that hybridizes under stringent conditions with a nucleic acid having a nucleotide sequence complementary to the nucleotide sequence of SEQ ID NO: 552; or (46αB) a protein comprising an amino acid sequence of SEQ ID NO: 554;

(47α) (47αA1) eukaryotic translation initiation factor 5A-2 or a variant thereof, which is defined below in any of (47αA1-a) to (47αA1-e):

(47αA1-a) a protein comprising an amino acid sequence with deletion, substitution, insertion or addition of one or several amino acids in SEQ ID NO: 556;

(47αA1-b) a protein comprising an amino acid sequence having at least 70% identity to the amino acid sequence of SEQ ID NO: 556;

(47αA1-c) a protein comprising an amino acid sequence encoded by a nucleotide sequence with deletion, substitution, insertion or addition of one or several nucleotides in SEQ ID NO: 555;

(47αA1-d) a protein comprising an amino acid sequence encoded by a nucleotide sequence having at least 70% identity to the nucleotide sequence of SEQ ID NO: 555; or (47αA1-e) a protein comprising an amino acid sequence encoded by a nucleic acid that hybridizes under stringent conditions with a nucleic acid having a nucleotide sequence complementary to the nucleotide sequence of SEQ ID NO: 555;

(47αB1) a protein comprising at least one amino acid sequence selected from the group consisting of SEQ ID NOs: 557 and 558;

(47αA2) uncharacterized protein LOC100305510 or a variant thereof, which is defined below in any of (47αA2-a) to (47αA2-e):

(47αA2-a) a protein comprising an amino acid sequence with deletion, substitution, insertion or addition of one or several amino acids in SEQ ID NO: 560;

(47αA2-b) a protein comprising an amino acid sequence having at least 70% identity to the amino acid sequence of SEQ ID NO: 560;

(47αA2-c) a protein comprising an amino acid sequence encoded by a nucleotide sequence with deletion, substitution, insertion or addition of one or several nucleotides in SEQ ID NO: 559;

(47αA2-d) a protein comprising an amino acid sequence encoded by a nucleotide sequence having at least 70% identity to the nucleotide sequence of SEQ ID NO: 559; or (47αA2-e) a protein comprising an amino acid sequence encoded by a nucleic acid that hybridizes under stringent conditions with a nucleic acid having a nucleotide sequence complementary to the nucleotide sequence of SEQ ID NO: 559; or (47αB2) a protein comprising at least one amino acid sequence selected from the group consisting of SEQ ID NOs: 561-563;

(48α) (48αA) uncharacterized protein LOC100306570 or a variant thereof, which is defined below in any of (48αA-a) to (48αA-e):

(48αA-a) a protein comprising an amino acid sequence with deletion, substitution, insertion or addition of one or several amino acids in SEQ ID NO: 565;

(48αA-b) a protein comprising an amino acid sequence having at least 70% identity to the amino acid sequence of SEQ ID NO: 565;

(48αA-c) a protein comprising an amino acid sequence encoded by a nucleotide sequence with deletion, substitution, insertion or addition of one or several nucleotides in SEQ ID NO: 564;

(48αA-d) a protein comprising an amino acid sequence encoded by a nucleotide sequence having at least 70% identity to the nucleotide sequence of SEQ ID NO: 564; or (48αA-e) a protein comprising an amino acid sequence encoded by a nucleic acid that hybridizes under stringent conditions with a nucleic acid having a nucleotide sequence complementary to the nucleotide sequence of SEQ ID NO: 564; or (48αB) a protein comprising at least one amino acid sequence selected from the group consisting of SEQ ID NOs: 566-570;

(50α) (50αA) uncharacterized protein LOC100813859 or a variant thereof, which is defined below in any of (50αA-a) to (50αA-e):

(50αA-a) a protein comprising an amino acid sequence with deletion, substitution, insertion or addition of one or several amino acids in SEQ ID NO: 572;

(50αA-b) a protein comprising an amino acid sequence having at least 70% identity to the amino acid sequence of SEQ ID NO: 572;

(50αA-c) a protein comprising an amino acid sequence encoded by a nucleotide sequence with deletion, substitution, insertion or addition of one or several nucleotides in SEQ ID NO: 571;

(50αA-d) a protein comprising an amino acid sequence encoded by a nucleotide sequence having at least 70% identity to the nucleotide sequence of SEQ ID NO: 571; or (50αA-e) a protein comprising an amino acid sequence encoded by a nucleic acid that hybridizes under stringent conditions with a nucleic acid having a nucleotide sequence complementary to the nucleotide sequence of SEQ ID NO: 571; or (50αB) a protein comprising at least one amino acid sequence selected from the group consisting of SEQ ID NOs: 573-576;

(51α) (51αA) 14-3-3-like protein or a variant thereof, which is defined below in any of (51αA-a) to (51αA-e):

(51αA-a) a protein comprising an amino acid sequence with deletion, substitution, insertion or addition of one or several amino acids in SEQ ID NO: 578;

(51αA-b) a protein comprising an amino acid sequence having at least 70% identity to the amino acid sequence of SEQ ID NO: 578;

(51αA-c) a protein comprising an amino acid sequence encoded by a nucleotide sequence with deletion, substitution, insertion or addition of one or several nucleotides in SEQ ID NO: 577;

(51αA-d) a protein comprising an amino acid sequence encoded by a nucleotide sequence having at least 70% identity to the nucleotide sequence of SEQ ID NO: 577; or (51αA-e) a protein comprising an amino acid sequence encoded by a nucleic acid that hybridizes under stringent conditions with a nucleic acid having a nucleotide sequence complementary to the nucleotide sequence of SEQ ID NO: 577; or (51αB) a protein comprising at least one amino acid sequence selected from the group consisting of SEQ ID NOs: 579-582;

(52α) (52αA) probable fructokinase-4 or a variant thereof, which is defined below in any of (52αA-a) to (52αA-e):

(52αA-a) a protein comprising an amino acid sequence with deletion, substitution, insertion or addition of one or several amino acids in SEQ ID NO: 584;

(52αA-b) a protein comprising an amino acid sequence having at least 70% identity to the amino acid sequence of SEQ ID NO: 584;

(52αA-c) a protein comprising an amino acid sequence encoded by a nucleotide sequence with deletion, substitution, insertion or addition of one or several nucleotides in SEQ ID NO: 583;

(52αA-d) a protein comprising an amino acid sequence encoded by a nucleotide sequence having at least 70% identity to the nucleotide sequence of SEQ ID NO: 583; or (52αA-e) a protein comprising an amino acid sequence encoded by a nucleic acid that hybridizes under stringent conditions with a nucleic acid having a nucleotide sequence complementary to the nucleotide sequence of SEQ ID NO: 583; or (52αB) a protein comprising at least one amino acid sequence selected from the group consisting of SEQ ID NOs: 585-588;

(53α) (53αA1) triosephosphate isomerase isoform X1 or a variant thereof, which is defined below in any of (53αA1-a) to (53αA1-e):

(53αA1-a) a protein comprising an amino acid sequence with deletion, substitution, insertion or addition of one or several amino acids in SEQ ID NO: 590;

(53αA1-b) a protein comprising an amino acid sequence having at least 70% identity to the amino acid sequence of SEQ ID NO: 590;

(53αA1-c) a protein comprising an amino acid sequence encoded by a nucleotide sequence with deletion, substitution, insertion or addition of one or several nucleotides in SEQ ID NO: 589;

(53αA1-d) a protein comprising an amino acid sequence encoded by a nucleotide sequence having at least 70% identity to the nucleotide sequence of SEQ ID NO: 589; or (53αA1-e) a protein comprising an amino acid sequence encoded by a nucleic acid that hybridizes under stringent conditions with a nucleic acid having a nucleotide sequence complementary to the nucleotide sequence of SEQ ID NO: 589;

(53αB1) a protein comprising at least one amino acid sequence selected from the group consisting of SEQ ID NOs: 591-597;

(53αA2) triosephosphate isomerase, cytosolic or a variant thereof, which is defined below in any of (53αA2-a) to (53αA2-e):

(53αA2-a) a protein comprising an amino acid sequence with deletion, substitution, insertion or addition of one or several amino acids in SEQ ID NO: 599;

(53αA2-b) a protein comprising an amino acid sequence having at least 70% identity to the amino acid sequence of SEQ ID NO: 599;

(53αA2-c) a protein comprising an amino acid sequence encoded by a nucleotide sequence with deletion, substitution, insertion or addition of one or several nucleotides in SEQ ID NO: 598;

(53αA2-d) a protein comprising an amino acid sequence encoded by a nucleotide sequence having at least 70% identity to the nucleotide sequence of SEQ ID NO: 598; or (53αA2-e) a protein comprising an amino acid sequence encoded by a nucleic acid that hybridizes under stringent conditions with a nucleic acid having a nucleotide sequence complementary to the nucleotide sequence of SEQ ID NO: 598; or (53αB2) a protein comprising at least one amino acid sequence selected from the group consisting of SEQ ID NOs: 600-604;

(54α) (54αA1) superoxide dismutase [Fe], chloroplastic isoform X1 or a variant thereof, which is defined below in any of (54αA1-a) to (54αA1-e):

(54αA1-a) a protein comprising an amino acid sequence with deletion, substitution, insertion or addition of one or several amino acids in SEQ ID NO: 606;

(54αA1-b) a protein comprising an amino acid sequence having at least 70% identity to the amino acid sequence of SEQ ID NO: 606;

(53αA1-c) a protein comprising an amino acid sequence encoded by a nucleotide sequence with deletion, substitution, insertion or addition of one or several nucleotides in SEQ ID NO: 605;

(54αA1-d) a protein comprising an amino acid sequence encoded by a nucleotide sequence having at least 70% identity to the nucleotide sequence of SEQ ID NO: 605; or (54αA1-e) a protein comprising an amino acid sequence encoded by a nucleic acid that hybridizes under stringent conditions with a nucleic acid having a nucleotide sequence complementary to the nucleotide sequence of SEQ ID NO: 605;

(54αB1) a protein comprising at least one amino acid sequence selected from the group consisting of SEQ ID NOs: 607-611;

(54αA2) iron-superoxide dismutase or a variant thereof, which is defined below in any of (54αA2-a) to (54αA2-e):

(54αA2-a) a protein comprising an amino acid sequence with deletion, substitution, insertion or addition of one or several amino acids in SEQ ID NO: 613;

(54αA2-b) a protein comprising an amino acid sequence having at least 70% identity to the amino acid sequence of SEQ ID NO: 613;

(54αA2-c) a protein comprising an amino acid sequence encoded by a nucleotide sequence with deletion, substitution, insertion or addition of one or several nucleotides in SEQ ID NO: 612;

(54αA2-d) a protein comprising an amino acid sequence encoded by a nucleotide sequence having at least 70% identity to the nucleotide sequence of SEQ ID NO: 612; or (54αA2-e) a protein comprising an amino acid sequence encoded by a nucleic acid that hybridizes under stringent conditions with a nucleic acid having a nucleotide sequence complementary to the nucleotide sequence of SEQ ID NO: 612; or (54αB2) a protein comprising at least one amino acid sequence selected from the group consisting of SEQ ID NOs: 614-616; or (55α) (55αA1) 51 kDa seed maturation protein precursor or a variant thereof, which is defined below in any of (55αA1-a) to (55αA1-e):

(55αA1-a) a protein comprising an amino acid sequence with deletion, substitution, insertion or addition of one or several amino acids in SEQ ID NO: 618;

(55αA1-b) a protein comprising an amino acid sequence having at least 70% identity to the amino acid sequence of SEQ ID NO: 618;

(55αA1-c) a protein comprising an amino acid sequence encoded by a nucleotide sequence with deletion, substitution, insertion or addition of one or several nucleotides in SEQ ID NO: 617;

(55αA1-d) a protein comprising an amino acid sequence encoded by a nucleotide sequence having at least 70% identity to the nucleotide sequence of SEQ ID NO: 617; or (55αA1-e) a protein comprising an amino acid sequence encoded by a nucleic acid that hybridizes under stringent conditions with a nucleic acid having a nucleotide sequence complementary to the nucleotide sequence of SEQ ID NO: 617;

(55αB1) a protein comprising at least one amino acid sequence selected from the group consisting of SEQ ID NOs: 619-635;

(55αA2) Lea protein precursor or a variant thereof, which is defined below in any of (55αA2-a) to (55αA2-e):

(55αA2-a) a protein comprising an amino acid sequence with deletion, substitution, insertion or addition of one or several amino acids in SEQ ID NO: 637;

(55αA2-b) a protein comprising an amino acid sequence having at least 70% identity to the amino acid sequence of SEQ ID NO: 637;

(55αA2-c) a protein comprising an amino acid sequence encoded by a nucleotide sequence with deletion, substitution, insertion or addition of one or several nucleotides in SEQ ID NO: 636;

(55αA2-d) a protein comprising an amino acid sequence encoded by a nucleotide sequence having at least 70% identity to the nucleotide sequence of SEQ ID NO: 636; or (55αA2-e) a protein comprising an amino acid sequence encoded by a nucleic acid that hybridizes under stringent conditions with a nucleic acid having a nucleotide sequence complementary to the nucleotide sequence of SEQ ID NO: 636; or (55αB2) a protein comprising at least one amino acid sequence selected from the group consisting of SEQ ID NOs: 638-649.

[10] A composition for diagnosing an allergy to a soybean, comprising, as an antigen, at least one of proteins as defined above in any of (1a) to (55a) of [9].

[11] A method for providing an indicator for diagnosing an allergy to a soybean in a subject, the method comprising the steps of:

(i) contacting a sample obtained from the subject with an antigen, wherein the sample is a solution comprising an Ig antibody;

(ii) detecting binding between the IgE antibody present in the sample from the subject and the antigen; and (iii) when the binding between the IgE antibody in the subject and the antigen is detected, an indicator of the fact that the subject is allergic to a soybean is provided;

wherein the antigen is at least one of proteins as defined above in any of (1a) to (55a) of [9].

[12] A pharmaceutical composition comprising at least one of proteins as defined above in any of (1a) to (55a) of [9].

[13] The pharmaceutical composition as set forth in [12], wherein the pharmaceutical composition is intended for the treatment of an allergy to a soybean.

[14] A soybean or processed products of soybean in which an antigen is eliminated or reduced, wherein the antigen is at least one of proteins as defined above in any of (1a) to (55a) of [9].

[15] A tester for determining the presence or absence of a soybean antigen in an object of interest, comprising an antibody that binds to at least one of proteins as defined above in any of (1a) to (55a) of [9].

[16] A soybean-derived antigen which is at least one of proteins as defined above in any of (1a) to (55a) of [9] and is causative of an allergy to soybean.

Advantageous Effects of Invention

The present invention can provide novel antigens of an allergy to soybean. Since the novel antigens (allergen components) that trigger a soybean allergy were identified according to this invention, this invention can provide highly sensitive methods and kits for diagnosing an allergy to soybean, pharmaceutical compositions comprising such an antigen, soybean or processed products of soybean in which such an antigen is eliminated or reduced.

DESCRIPTION OF EMBODIMENTS

Figure 1:
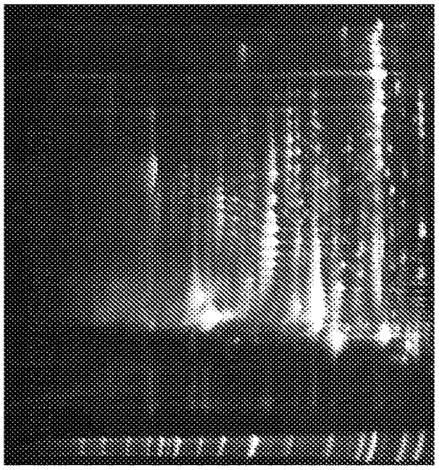
FIG. 1 is a photograph of a gel showing a protein electrophoretic pattern in two-dimensional electrophoresis of proteins contained in soybean. The bands at the left of the photograph are bands of molecular weight markers.

The present invention will be described in detail below, but the present invention is not limited to them.

Unless otherwise defined herein, all scientific and technical terms used in relation to the present invention shall have meanings commonly understood by those skilled in the art.

Amino acid sequences herein are represented by one-letter amino acid symbols well known to those skilled in the art and the left end corresponds to the amino terminal and the right end corresponds to the carboxy terminal.

As referred to herein, the "allergy" refers to the state in which, when a certain antigen enters the body of a living individual sensitized to said antigen, the living individual shows a hypersensitive reaction detrimental to him/her. In blood and tissues of individuals with many food-allergic diseases, IgE antibodies specific to antigens are produced. IgE antibodies bind to mast cells or basophils. When an antigen specific to such an IgE antibody enters again the body of a patient with an allergic disease, said antigen combines with the IgE antibody bound to mast cells or basophils, and the IgE antibody crosslinks said antigen on the cell surface, resulting in physiological effects of IgE antibody-antigen interaction. Examples of such physiological effects include release of histamine, serotonin, heparin, eosinophil chemotactic factors, leucotrienes, or the like. These released substances provoke an allergic reaction resulting from the combination of an IgE antibody with particular antigens. Such allergic reactions caused by particular antigens occur through the aforementioned pathway.

As referred to herein, the "allergy to soybean" refers to the state in which an individual has an allergic reaction caused by proteins, etc. present in soybean which act as an antigen. The allergy to soybean can produce an allergic reaction upon contact with, or consumption of, an antigen present in soybean. In general, allergic reactions caused by consumption of foods are particularly referred to as "food allergies". The allergy to soybean may be a food allergy.

As referred to herein, the "antigen" refers to a substance that provokes an allergic reaction, and is also referred to as an "allergen component". The antigen is preferably a protein.

As referred to herein, the "protein" refers to a molecule having a structure in which naturally occurring amino acids are joined together by peptide bond. The number of amino acids present in a protein is not particularly limited, but proteins having about 2 to 50 amino acids joined together by peptide bond are in some cases called "peptides". In the case where amino acids can form different enantiomers, the amino acids are understood to form an L-enantiomer, unless otherwise indicated. The amino acid sequences of proteins or peptides as used herein are represented by one-letter symbols of amino acids in accordance with standard usage and the notational convention commonly used in the art. The leftward direction represents the amino-terminal direction, and the rightward direction represents the carboxy-terminal direction.

Identification of Antigens

Proteins contained in soybean were analyzed by the aforementioned technique to identify causative antigens of an allergy to soybean. To be specific, soybean proteins were subjected to two-dimensional electrophoresis under the conditions described below.

The electrophoresis in the first dimension was isoelectric focusing, which was performed using isoelectric focusing gels with a gel-strip length of 5 to 10 cm and a gel pH range of 3 to 10. The pH gradient of the gels in the direction of electrophoresis was as follows: with the total gel-strip length being taken as 1, the gel-strip length up to pH 5 was "a=0.15 to 0.3", the gel-strip length from pH 5 to 7 was "b=0.4 to 0.7", and the gel-strip length above pH 7 was "c=0.15 to 0.3". More specifically, the isoelectric focusing was performed using the IPG gels, Immobiline Drystrip (pH3-10NL), produced by GE Healthcare Bio-Sciences Corporation (hereinafter abbreviated as "GE"). The electrophoresis system used was IPGphor produced by GE. The maximum current of the electrophoresis system was limited to 75 μA per gel strip. The voltage program adopted to perform the first-dimensional isoelectric focusing was as follows: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

The electrophoresis in the second dimension was SDS-PAGE, which was performed using polyacrylamide gels whose gel concentration at the distal end in the direction of electrophoresis was set to 3 to 6% and whose gel concentration at the proximal end was set to a higher value than that at the distal end. More specifically, the SDS-PAGE was performed using NuPAGE 4-12% Bris-Tris Gels (IPG well, Mini, 1 mm) produced by Life Technologies. The electrophoresis system used was XCell SureLock Mini-Cell produced by Life Technologies. The electrophoresis was run at a constant voltage of 200 V for about 45 minutes using an electrophoresis buffer composed of 50 mM MOPS, 50 mM Tris base, 0.1% (w/v) SDS and 1 mM EDTA.

As a result, the following spots in a two-dimensional electrophoresis gel run under the conditions described above for proteins in soybean have been revealed to exhibit specific binding to IgE antibodies from soybean-allergic patients.

Spot 1: Molecular weight 1 to 30 kDa, pl 3.0 to 7.0
Spot 2: Molecular weight 30 to 75 kDa, pl 4.0 to 8.5
Spot 3: Molecular weight 20 to 50 kDa, pl 7.0 to 12.0
Spot 4: Molecular weight 20 to 50 kDa, pl 6.0 to 10.0
Spot 5: Molecular weight 2 to 30 kDa, pl 4.0 to 9.0
Spot 6: Molecular weight 50 to 100 kDa, pl 5.0 to 10.0
Spot 7: Molecular weight 5 to 37 kDa, pl 3.0 to 7.0
Spot 8: Molecular weight 75 to 200 kDa, pl 4.0 to 6.0
Spot 1α: Molecular weight 70 to 120 kDa, pl 2.5 to 6.5
Spot 2α: Molecular weight 50 to 120 kDa, pl 2.5 to 6.5
Spot 4α: Molecular weight 70 to 120 kDa, pl 3.5 to 7.5
Spot 5α: Molecular weight 70 to 170 kDa, pl 3.5 to 7.5
Spot 6α: Molecular weight 70 to 120 kDa, pl 3.5 to 7.5
Spot 7α: Molecular weight 50 to 120 kDa, pl 3.5 to 7.5
Spot 8α: Molecular weight 50 to 120 kDa, pl 3.5 to 8.5
Spot 9α: Molecular weight 50 to 120 kDa, pl 3.5 to 8.5
Spot 10α: Molecular weight 30 to 90 kDa, pl 3.5 to 7.5
Spot 11α: Molecular weight 30 to 90 kDa, pl 3.5 to 8.5
Spot 12α: Molecular weight 30 to 90 kDa, pl 3.5 to 8.5
Spot 13α: Molecular weight 30 to 90 kDa, pl 3.5 to 7.5
Spot 14α: Molecular weight 30 to 90 kDa, pl 2.5 to 6.5
Spot 15α, 16α: Molecular weight 20 to 90 kDa, pl 3.5 to 7.5
Spot 17α: Molecular weight 20 to 90 kDa, pl 3.5 to 7.5
Spot 18α: Molecular weight 30 to 90 kDa, pl 3.5 to 8.5
Spot 19α: Molecular weight 30 to 90 kDa, pl 3.5 to 8.5
Spot 25α: Molecular weight 20 to 90 kDa, pl 3.5 to 7.5
Spot 26α: Molecular weight 20 to 90 kDa, pl 3.5 to 7.5
Spot 27α: Molecular weight 20 to 90 kDa, pl 3.5 to 7.5
Spot 28α Molecular weight 10 to 70 kDa, pl 3.5 to 7.5
Spot 29α, 30α, 31α, 32α, 33α: Molecular weight 10 to 70 kDa, pl 3.5 to 8.5
Spot 34α: Molecular weight 10 to 70 kDa, pl 5.5 to 10.5
Spot 35α: Molecular weight 20 to 90 kDa, pl 5.5 to 10.5
Spot 36α, 37α: Molecular weight 10 to 70 kDa, pl 3.5 to 8.5
Spot 38α: Molecular weight 70 to 170 kDa, pl 5.5 to 10.5
Spot 39α: Molecular weight 5 to 60 kDa, pl 5.5 to 10.5
Spot 40α, 56α: Molecular weight 5 to 60 kDa, pl 5.5 to 10.5

Spot 4α: Molecular weight 5 to 60 kDa, pl 5.5 to 10.5
Spot 42α, 43α: Molecular weight to 60 kDa, pl 5.5 to 10.5
Spot 45α: Molecular weight 2 to 50 kDa, pl 3.5 to 7.5
Spot 46α: Molecular weight 2 to 50 kDa, pl 3.5 to 7.5
Spot 47α: Molecular weight 2 to 50 kDa, pl 3.5 to 7.5
Spot 48α: Molecular weight 2 to 50 kDa, pl 3.5 to 8.5
Spot 50α: Molecular weight 2 to 50 kDa, pl 2.5 to 6.5
Spot 51α: Molecular weight 1 to 60 kDa, pl 2.5 to 6.5
Spot 52α: Molecular weight 10 to 70 kDa, pl 3.5 to 7.5
Spot 53α: Molecular weight 5 to 60 kDa, pl 3.5 to 8.5
Spot 54α: Molecular weight 3 to 60 kDa, pl 3.5 to 8.5
Spot 55α: Molecular weight 30 to 90 kDa, pl 5.5 to 10.5

Antigen (1) Antigen in Spot 1

As the result of sequence identification of the antigen in spot 1 by mass spectroscopy, the following amino acid sequences were detected.

```
                                (SEQ ID NO: 17)
DQSSSYDDDEYSK

                                (SEQ ID NO: 18)
KSDQSSSYDDDEYSK

                                (SEQ ID NO: 19)
SDQSSSYDDDEYSK

                                (SEQ ID NO: 20)
SYDDDEYSK
```

Also, the mass spectroscopic data obtained for spot 1 on a mass spectrometer was analyzed by comparing the data against the Uniprot protein data, and as a result, the antigen in question was identified as Bowman-Birk type proteinase inhibitor D-II (amino acid sequence: SEQ ID NO: 2, encoding nucleotide sequence: SEQ ID NO: 1).

Accordingly, in the present invention, the antigen in spot 1 can be any of (1A-a) to (1A-e) and (1B) as defined below:

(1A-a) a protein comprising an amino acid sequence with deletion, substitution, insertion or addition of one or several amino acids in SEQ ID NO: 2;

(1A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 2;

(1A-c) a protein comprising an amino acid sequence encoded by a nucleotide sequence with deletion, substitution, insertion or addition of one or several nucleotides in SEQ ID NO: 1;

(1A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 1;

(1A-e) a protein comprising an amino acid sequence encoded by a nucleic acid that hybridizes under stringent conditions with a nucleic acid having a nucleotide sequence complementary to the nucleotide sequence of SEQ ID NO: 1;

(1B) a protein comprising at least one amino acid sequence selected from the group consisting of SEQ ID NOs: 17-20, preferably a protein comprising at least 2 or 3 or all sequences of the amino acid sequences; more preferably a protein comprising at least one amino acid sequence selected from the group consisting of SEQ ID NOs: 17-19, preferably a protein comprising at least 2 or all sequences of the amino acid sequences. As referred to above, the amino acid sequence of any of SEQ ID NOs: 17-20 may be an amino acid sequence derived therefrom by deletion, substitution, insertion or addition of one or several amino acids.

The proteins of (1A-a) to (1A-e) and (1B) as defined above also include those proteins whose amino acid residues are modified by phosphorylation, sugar chain modification, aminoacylation, ring-opening, deamination or the like.

The proteins of (1A-a) to (1A-e) and (1B) as defined above can be proteins that are found in a protein spot with a molecular weight of around 1 to 30 kDa, preferably around 2 to 25 kDa, more preferably around 5 to 20 kDa and an isoelectric point of 3.0 to 7.0, preferably 4.0 to 6.0 on gels used in the two-dimensional electrophoresis performed under the conditions described above in the subsection titled "Identification of antigens".

Preferably, a protein that is an antigen in spot 1 has activity equivalent to that of the protein having the amino acid sequence of SEQ ID NO: 2 (Bowman-Birk type proteinase inhibitor D-II) or causative of an allergy to soybean.

(2) Antigen in Spot 2

As the result of sequence identification of the antigen in spot 2 by mass spectroscopy, the following amino acid sequences were detected.

```
                                (SEQ ID NO: 21)
ALRALRLEDLRIPTAYIK

                                (SEQ ID NO: 22)
ALRLSGGDHVHAGTVVGK

                                (SEQ ID NO: 23)
LEGEREITLGFVDLLRDDFVEK

                                (SEQ ID NO: 24)
LRLEDLRIPTAYIK

                                (SEQ ID NO: 25)
LTYYTPDYETK

                                (SEQ ID NO: 26)
TDGLTSLDRYK

                                (SEQ ID NO: 27)
TFQGPPHGIQVERD

                                (SEQ ID NO: 28)
TFQGPPHGIQVERDK
```

Also, the mass spectroscopic data obtained for spot 2 on a mass spectrometer was analyzed by comparing the data against the Uniprot protein data, and as a result, the antigen in question was identified as Ribulose bisphosphate carboxylase large chain (amino acid sequence: SEQ ID NO: 4, encoding nucleotide sequence: SEQ ID NO: 3).

Accordingly, in the present invention, the antigen in spot 2 can be any of (2A-a) to (2A-e) and (2B) as defined below:

(2A-a) a protein comprising an amino acid sequence with deletion, substitution, insertion or addition of one or several amino acids in SEQ ID NO: 4;

(2A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 4;

(2A-c) a protein comprising an amino acid sequence encoded by a nucleotide sequence with deletion, substitution, insertion or addition of one or several nucleotides in SEQ ID NO: 3;

(2A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 3;

(2A-e) a protein comprising an amino acid sequence encoded by a nucleic acid that hybridizes under stringent conditions with a nucleic acid having a nucleotide sequence complementary to the nucleotide sequence of SEQ ID NO: 3;

(2B) a protein comprising at least one amino acid sequence selected from the group consisting of SEQ ID NOs: 21-28, preferably a protein comprising at least 2, 3, 4, 5, 6 or 7 or all sequences of the amino acid sequences. As referred to above, the amino acid sequence of any of SEQ ID NOs: 21-28 may be an amino acid sequence derived therefrom by deletion, substitution, insertion or addition of one or several amino acids.

The proteins of (2A-a) to (2A-e) and (2B) as defined above also include those proteins whose amino acid residues are modified by phosphorylation, sugar chain modification, aminoacylation, ring-opening, deamination or the like.

The proteins of (2A-a) to (2A-e) and (2B) as defined above can be proteins that are found in a protein spot with a molecular weight of around 30 to 75 kDa, preferably around 37 to 70 kDa, more preferably around 40 to 60 kDa and an isoelectric point of 4.0 to 8.5, preferably 5.5 to 7.5 on gels used in the two-dimensional electrophoresis performed under the conditions described above in the subsection titled "Identification of antigens".

Preferably, a protein that is an antigen in spot 2 has activity equivalent to that of the protein having the amino acid sequence of SEQ ID NO: 4 (Ribulose bisphosphate carboxylase large chain) or causative of an allergy to soybean.

(3) Antigen in Spot 3

As the result of sequence identification of the antigen in spot 3 by mass spectroscopy, the following amino acid sequences were detected.

```
                    (SEQ ID NO: 29)
APHTEDAIRVTQSTANFFISEARK

                    (SEQ ID NO: 30)
FVESGGARVIPLIYNESPENLNK
```

Also, the mass spectroscopic data obtained for spot 3 on a mass spectrometer was analyzed by comparing the data against the Uniprot protein data, and as a result, the antigen in question was identified as Gamma-glutamyl hydrolase (amino acid sequence: SEQ ID NO: 6, encoding nucleotide sequence: SEQ ID NO: 5).

Accordingly, in the present invention, the antigen in spot 3 can be any of (3A-a) to (3A-e) and (3B) as defined below:

(3A-a) a protein comprising an amino acid sequence with deletion, substitution, insertion or addition of one or several amino acids in SEQ ID NO: 6;

(3A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 6;

(3A-c) a protein comprising an amino acid sequence encoded by a nucleotide sequence with deletion, substitution, insertion or addition of one or several nucleotides in SEQ ID NO: 5;

(3A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 5.

(3A-e) a protein comprising an amino acid sequence encoded by a nucleic acid that hybridizes under stringent conditions with a nucleic acid having a nucleotide sequence complementary to the nucleotide sequence of SEQ ID NO: 5;

(3B) a protein comprising an amino acid sequence of SEQ ID NO: 29 or 30, preferably a protein comprising the amino acid sequences of SEQ ID NO: 29 and 30. As referred to above, the amino acid sequence(s) of SEQ ID NOs: 29 and/or 30 may be an amino acid sequence(s) derived therefrom by deletion, substitution, insertion or addition of one or several amino acids.

The proteins of (3A-a) to (3A-e) and (3B) as defined above also include those proteins whose amino acid residues are modified by phosphorylation, sugar chain modification, aminoacylation, ring-opening, deamination or the like.

The proteins of (3A-a) to (3A-e) and (3B) as defined above can be proteins that are found in a protein spot with a molecular weight of around 20 to 50 kDa, preferably around 25 to 40 kDa, more preferably around 25 to 37 kDa and an isoelectric point of 7.0 to 12.0, preferably 8.0 to 10.0 on gels used in the two-dimensional electrophoresis performed under the conditions described above in the subsection titled "Identification of antigens".

Preferably, a protein that is an antigen in spot 3 has activity equivalent to that of the protein having the amino acid sequence of SEQ ID NO: 6 (Gamma-glutamyl hydrolase) or causative of an allergy to soybean.

(4) Antigen in Spot 4

As the result of sequence identification of the antigen in spot 4 by mass spectroscopy, the following amino acid sequences were detected.

```
                    (SEQ ID NO: 31)
IWDLESK

                    (SEQ ID NO: 32)
SIVEDLK
```

Also, the mass spectroscopic data obtained for spot 4 on a mass spectrometer was analyzed by comparing the data against the Uniprot protein data, and as a result, the antigen in question was identified as Guanine nucleotide-binding protein subunit beta-like protein (amino acid sequence: SEQ ID NO: 8, encoding nucleotide sequence: SEQ ID NO: 7).

Accordingly, in the present invention, the antigen in spot 4 can be any of (4-a) to (4-e) and (4B) as defined below:

(4-a) a protein comprising an amino acid sequence with deletion, substitution, insertion or addition of one or several amino acids in SEQ ID NO: 8;

(4-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 8;

(4-c) a protein comprising an amino acid sequence encoded by a nucleotide sequence with deletion, substitution, insertion or addition of one or several nucleotides in SEQ ID NO: 7;

(4A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 7;

(4A-e) a protein comprising an amino acid sequence encoded by a nucleic acid that hybridizes under stringent conditions with a nucleic acid having a nucleotide sequence complementary to the nucleotide sequence of SEQ ID NO: 7;

(4B) a protein comprising an amino acid sequence of SEQ ID NO: 31 or 32, preferably a protein comprising the amino acid sequences of SEQ ID NO: 31 and 32. As referred to above, the amino acid sequence(s) of SEQ ID NOs: 31 and/or 32 may be an amino acid sequence (s) derived therefrom by deletion, substitution, insertion or addition of one or several amino acids.

The proteins of (4A-a) to (4A-e) and (4B) as defined above also include those proteins whose amino acid residues are modified by phosphorylation, sugar chain modification, aminoacylation, ring-opening, deamination or the like.

The proteins of (4A-a) to (4A-e) and (4B) as defined above can be proteins that are found in a protein spot with a molecular weight of around 20 to 50 kDa, preferably around 25 to 40 kDa, more preferably around 25 to 37 kDa and an isoelectric point of 6.0 to 10.0, preferably 7.0 to 9.0 on gels used in the two-dimensional electrophoresis performed under the conditions described above in the subsection titled "Identification of antigens".

Preferably, a protein that is an antigen in spot 4 has activity equivalent to that of the protein having the amino acid sequence of SEQ ID NO: 8 (Guanine nucleotide-binding protein subunit beta-like protein) or causative of an allergy to soybean.

(5) Antigen in Spot 5

As the result of sequence identification of the antigen in spot 5 by mass spectroscopy, the following amino acid sequences were detected.

```
                                   (SEQ ID NO: 33)
QELDERARQGETVVPGGTGGK

                                   (SEQ ID NO: 34)
SGEERAQEEAIDIDESK
```

Also, the mass spectroscopic data obtained for spot 5 on a mass spectrometer was analyzed by comparing the data against the Uniprot protein data, and as a result, the antigen in question was identified as Protein SLE3 (amino acid sequence: SEQ ID NO: 10, encoding nucleotide sequence: SEQ ID NO: 9).

Accordingly, in the present invention, the antigen in spot 5 can be any of (5A-a) to (5A-e) and (5B) as defined below:

(5A-a) a protein comprising an amino acid sequence with deletion, substitution, insertion or addition of one or several amino acids in SEQ ID NO: 10;

(5A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 10;

(5A-c) a protein comprising an amino acid sequence encoded by a nucleotide sequence with deletion, substitution, insertion or addition of one or several nucleotides in SEQ ID NO: 9;

(5A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 9;

(5A-e) a protein comprising an amino acid sequence encoded by a nucleic acid that hybridizes under stringent conditions with a nucleic acid having a nucleotide sequence complementary to the nucleotide sequence of SEQ ID NO: 9;

(5B) a protein comprising an amino acid sequence of SEQ ID NO: 33 or 34, preferably a protein comprising the amino acid sequences of SEQ ID NO: 33 and 34. As referred to above, the amino acid sequence(s) of SEQ ID NOs: 33 and/or 34 may be an amino acid sequence(s) derived therefrom by deletion, substitution, insertion or addition of one or several amino acids.

The proteins of (5A-a) to (5A-e) and (5B) as defined above also include those proteins whose amino acid residues are modified by phosphorylation, sugar chain modification, aminoacylation, ring-opening, deamination or the like.

The proteins of (5A-a) to (5A-e) and (5B) as defined above can be proteins that are found in a protein spot with a molecular weight of around 2 to 30 kDa, preferably around 3 to 25 kDa, more preferably around 5 to 20 kDa and an isoelectric point of 4.0 to 9.0, preferably 5.0 to 7.0 on gels used in the two-dimensional electrophoresis performed under the conditions described above in the subsection titled "Identification of antigens".

Preferably, a protein that is an antigen in spot 5 has activity equivalent to that of the protein having the amino acid sequence of SEQ ID NO: 10 (Protein SLE3) or causative of an allergy to soybean.

(6) Antigen in Spot 6

As the result of sequence identification of the antigen in spot 6 by mass spectroscopy, the following amino acid sequences were detected.

```
                                   (SEQ ID NO: 35)
AAAHVVEGAAGYAGHK

                                   (SEQ ID NO: 36)
AKDYTLQAAEK

                                   (SEQ ID NO: 37)
ARETHELGAHFESLADK

                                   (SEQ ID NO: 38)
ATAVGWAAAHFSAEK

                                   (SEQ ID NO: 39)
DTPQGSIEALQAGERVK

                                   (SEQ ID NO: 40)
DYTLQAAEK

                                   (SEQ ID NO: 41)
EEAQRELEAK

                                   (SEQ ID NO: 42)
EGTGSIVFTAIGETVSSAGEK

                                   (SEQ ID NO: 43)
ERGRESGGQVVAEK

                                   (SEQ ID NO: 44)
GLAASAGETAK

                                   (SEQ ID NO: 45)
GQQGYAVTK

                                   (SEQ ID NO: 46)
KPSQPQEAEERPSEGIGETVRQYAQK
```

-continued (SEQ ID NO: 47)
PAEIVQER (SEQ ID NO: 48)
PQGSIEALQAGERVK (SEQ ID NO: 49)
QAASETLNTTTQTAQEK (SEQ ID NO: 50)
SAGGTTASYVGEK (SEQ ID NO: 51)
SLTSIGEK (SEQ ID NO: 52)
TPQGSIEALQAGERVK (SEQ ID NO: 53)
VTDHAAANVVGNK Also, the mass spectroscopic data obtained for spot 6 on a mass spectrometer was analyzed by comparing the data against the Uniprot protein data, and as a result, the antigen in question was identified as Seed biotin-containing protein SBP65 (amino acid sequence: SEQ ID NO: 12, encoding nucleotide sequence: SEQ ID NO: 11).

Accordingly, in the present invention, the antigen in spot 6 can be any of (6A-a) to (6A-e) and (6B) as defined below:

(6A-a) a protein comprising an amino acid sequence with deletion, substitution, insertion or addition of one or several amino acids in SEQ ID NO: 12;

(6A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 12;

(6A-c) a protein comprising an amino acid sequence encoded by a nucleotide sequence with deletion, substitution, insertion or addition of one or several nucleotides in SEQ ID NO: 11;

(6A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 11;

(6A-e) a protein comprising an amino acid sequence encoded by a nucleic acid that hybridizes under stringent conditions with a nucleic acid having a nucleotide sequence complementary to the nucleotide sequence of SEQ ID NO: 11;

(6B) a protein comprising at least one amino acid sequence selected from the group consisting of SEQ ID NOs: 35-53, preferably a protein comprising at least 2, 3, 4, 5, 6, 7, 8, 9, 10, 11, 12, 13, 14, 15, 16, 17 or 18 or all sequences of the amino acid sequences; more preferably a protein comprising at least one amino acid sequence selected from the group consisting of SEQ ID NOs: 35-39, 41-44, 46, 48-50, 52 and 53, preferably a protein comprising at least 2, 3, 4, 5, 6, 7, 8, 9, 10, 11, 12, 13 or 14 or all sequences of the amino acid sequences. As referred to above, the amino acid sequence of any of SEQ ID NOs: 35-53 may be an amino acid sequence derived therefrom by deletion, substitution, insertion or addition of one or several amino acids.

The proteins of (6A-a) to (6A-e) and (6B) as defined above also include those proteins whose amino acid residues are modified by phosphorylation, sugar chain modification, aminoacylation, ring-opening, deamination or the like.

The proteins of (6A-a) to (6A-e) and (6B) as defined above can be proteins that are found in a protein spot with a molecular weight of around 50 to 100 kDa, preferably around 55 to 90 kDa, more preferably around 60 to 75 kDa and an isoelectric point of 5.0 to 10.0, preferably 6.0 to 8.0 on gels used in the two-dimensional electrophoresis performed under the conditions described above in the subsection titled “Identification of antigens”.

Preferably, a protein that is an antigen in spot 6 has activity equivalent to that of the protein having the amino acid sequence of SEQ ID NO: 12 (Seed biotin-containing protein SBP65) or causative of an allergy to soybean.

(7) Antigen in Spot 7

As the result of sequence identification of the antigen in spot 7 by mass spectroscopy, the following amino acid sequences were detected.

(SEQ ID NO: 54)
AASNAPAPLAGVIFEPFQELKK (SEQ ID NO: 55)
ASNAPAPLAGVIFEPFQELKK (SEQ ID NO: 56)
FFKESSEEEREHAEQLIK (SEQ ID NO: 57)
GHGVWHFDQK (SEQ ID NO: 58)
IAEYVAQLRLVGK (SEQ ID NO: 59)
KIAEYVAQLRLVGK (SEQ ID NO: 60)
LLHDEDHV (SEQ ID NO: 61)
SNAPAPLAGVIFEPFQELKK

Also, the mass spectroscopic data obtained for spot 7 on a mass spectrometer was analyzed by comparing the data against the Uniprot protein data, and as a result, the antigen in question was identified as Ferritin-2 (amino acid sequence: SEQ ID NO: 14, encoding nucleotide sequence: SEQ ID NO: 13).

Accordingly, in the present invention, the antigen in spot 7 can be any of (7A-a) to (7A-e) and (7B) as defined below:

(7A-a) a protein comprising an amino acid sequence with deletion, substitution, insertion or addition of one or several amino acids in SEQ ID NO: 14;

(7A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 14;

(7A-c) a protein comprising an amino acid sequence encoded by a nucleotide sequence with deletion, substitution, insertion or addition of one or several nucleotides in SEQ ID NO: 13;

(7A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 13;

(7A-e) a protein comprising an amino acid sequence encoded by a nucleic acid that hybridizes under stringent conditions with a nucleic acid having a nucleotide sequence complementary to the nucleotide sequence of SEQ ID NO: 13;

(7B) a protein comprising at least one amino acid sequence selected from the group consisting of SEQ ID NOs: 54-61, preferably a protein comprising at least 2, 3, 4, 5, 6 or 7 or all sequences of the amino acid sequences; more preferably a protein comprising at least one amino acid sequence selected from the group consisting of SEQ ID NOs: 54-59 and 61, preferably a protein comprising at least 2, 3, 4, 5 or 6 or all sequences of the amino acid sequences. As referred to above, the amino acid sequence of any of SEQ ID NOs: 54-61 may be an amino acid sequence derived therefrom by deletion, substitution, insertion or addition of one or several amino acids.

The proteins of (7A-a) to (7A-e) and (7B) as defined above also include those proteins whose amino acid residues are modified by phosphorylation, sugar chain modification, aminoacylation, ring-opening, deamination or the like.

The proteins of (7A-a) to (7A-e) and (7B) as defined above can be proteins that are found in a protein spot with a molecular weight of around 5 to 37 kDa, preferably around 10 to 30 kDa, more preferably around 15 to 25 kDa and an isoelectric point of 3.0 to 7.0, preferably 4.0 to 6.0 on gels used in the two-dimensional electrophoresis performed under the conditions described above in the subsection titled "Identification of antigens".

Preferably, a protein that is an antigen in spot 7 has activity equivalent to that of the protein having the amino acid sequence of SEQ ID NO: 14 (Ferritin-2) or causative of an allergy to soybean.

(8) Antigen in Spot 8

As the result of sequence identification of the antigen in spot 8 by mass spectroscopy, the following amino acid sequences were detected.

```
                                        (SEQ ID NO: 62)
AGESESNLRK

                                        (SEQ ID NO: 63)
GESEANVREIFDK

                                        (SEQ ID NO: 64)
GILLYGPPGSGK

                                        (SEQ ID NO: 65)
LAGESESNLRK

                                        (SEQ ID NO: 66)
LSDDVDLERIAK

                                        (SEQ ID NO: 67)
RELQETVQYPVEHPEK

                                        (SEQ ID NO: 68)
TVFIIGATNRPDIID
```

Also, the mass spectroscopic data obtained for spot 8 on a mass spectrometer was analyzed by comparing the data against the Uniprot protein data, and as a result, the antigen in question was identified as Cell division cycle protein 48 homolog (amino acid sequence: SEQ ID NO: 16, encoding nucleotide sequence: SEQ ID NO: 15).

Accordingly, in the present invention, the antigen in spot 8 can be any of (8A-a) to (8A-e) and (8B) as defined below:

(8A-a) a protein comprising an amino acid sequence with deletion, substitution, insertion or addition of one or several amino acids in SEQ ID NO: 16;

(8A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 16;

(8A-c) a protein comprising an amino acid sequence encoded by a nucleotide sequence with deletion, substitution, insertion or addition of one or several nucleotides in SEQ ID NO: 15;

(8A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 15;

(8A-e) a protein comprising an amino acid sequence encoded by a nucleic acid that hybridizes under stringent conditions with a nucleic acid having a nucleotide sequence complementary to the nucleotide sequence of SEQ ID NO: 15;

(8B) a protein comprising at least one amino acid sequence selected from the group consisting of SEQ ID NOs: 62-68, preferably a protein comprising at least 2, 3, 4, 5 or 6 or all sequences of the amino acid sequences. As referred to above, the amino acid sequence of any of SEQ ID NOs: 62-68 may be an amino acid sequence derived therefrom by deletion, substitution, insertion or addition of one or several amino acids.

The proteins of (8A-a) to (8A-e) and (8B) as defined above also include those proteins whose amino acid residues are modified by phosphorylation, sugar chain modification, aminoacylation, ring-opening, deamination or the like.

The proteins of (8A-a) to (8A-e) and (8B) as defined above can be proteins that are found in a protein spot with a molecular weight of around 75 to 200 kDa, preferably around 100 to 170 kDa, more preferably around 100 to 150 kDa and an isoelectric point of 3.0 to 7.0, preferably 4.0 to 6.0 on gels used in the two-dimensional electrophoresis performed under the conditions described above in the subsection titled "Identification of antigens".

Preferably, a protein that is an antigen in spot 8 has activity equivalent to that of the protein having the amino acid sequence of SEQ ID NO: 16 (Cell division cycle protein 48 homolog) or causative of an allergy to soybean.

(1α) Antigen in Spot 1α As the result of sequence identification of the antigen in spot 1α by mass spectroscopy, the following amino acid sequences were detected.

```
                                        (SEQ ID NO: 71)
APQDLYESYYNANK

                                        (SEQ ID NO: 72)
AVLFVPPK

                                        (SEQ ID NO: 73)
DFASRIYDSVK

                                        (SEQ ID NO: 74)
DIFLRELISNASDALDK

                                        (SEQ ID NO: 75)
DIFYITGTSK

                                        (SEQ ID NO: 76)
DNVDDVK

                                        (SEQ ID NO: 77)
EDSKPETDAVNDDNDVK
```

-continued (SEQ ID NO: 78)
EEAGEYLEESK (SEQ ID NO: 79)
EQLENSPFLERLK (SEQ ID NO: 80)
EVLGEGDNTK (SEQ ID NO: 81)
EVTEEEYTK (SEQ ID NO: 82)
FYHSLAK (SEQ ID NO: 83)
IGAVPHGLSTDSDVVK (SEQ ID NO: 84)
LGIIEDATNRNRLAK (SEQ ID NO: 85)
NPEDEGVK (SEQ ID NO: 86)
SGTSAFVEK (SEQ ID NO: 87)
TSLDISPEATVEEEDDTEVEAESDAK (SEQ ID NO: 90)
APQDLYESYYNANK (SEQ ID NO: 91)
AVLFVPPK (SEQ ID NO: 92)
DFASRIYDSVK (SEQ ID NO: 93)
DIFLRELISNASDALDK (SEQ ID NO: 94)
DIFYITGTSK (SEQ ID NO: 95)
DNVDDVK (SEQ ID NO: 96)
DVLGEGDNTK (SEQ ID NO: 97)
EEAGEYLQESK (SEQ ID NO: 98)
EQLENSPFLERLK (SEQ ID NO: 99)
EVTEEEYTK (SEQ ID NO: 100)
FYHSLAK (SEQ ID NO: 101)
IGAVPHGLSTDSDVVK (SEQ ID NO: 102)
LGIIEDATNRNRLAK (SEQ ID NO: 103)
NPEDEGVK (SEQ ID NO: 104)
SGTSAFVEK Also, the mass spectroscopic data obtained for spot 1α on a mass spectrometer was analyzed by comparing the data against the NCBI protein data, and as a result, endoplasmin homolog isoform X2 (amino acid sequence: SEQ ID NO: 70, encoding nucleotide sequence: SEQ ID NO: 69) was identified as a protein comprising any of SEQ ID NOs: 71 to 87 and endoplasmin homolog isoform X2 (amino acid sequence: SEQ ID NO: 89, encoding nucleotide sequence: SEQ ID NO: 88) was identified as a protein comprising any of SEQ ID NOs: 90 to 104.

Accordingly, the antigen in spot 1α in the present invention can be any of proteins selected from the group consisting of the proteins as defined below in (1αA1-a) to (1αA1-e), (1αB1), (1αA2-a) to (1αA2-e), and (1αB2):

(1αA1-a) a protein comprising an amino acid sequence with deletion, substitution, insertion or addition of one or several amino acids in SEQ ID NO: 70;

(1αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 70;

(1αA1-c) a protein comprising an amino acid sequence encoded by a nucleotide sequence with deletion, substitution, insertion or addition of one or several nucleotides in SEQ ID NO: 69;

(1αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 69;

(1αA1-e) a protein comprising an amino acid sequence encoded by a nucleic acid that hybridizes under stringent conditions with a nucleic acid having a nucleotide sequence complementary to the nucleotide sequence of SEQ ID NO: 69;

(1αB1) a protein comprising at least one amino acid sequence selected from the group consisting of SEQ ID NOs: 71-87, preferably a protein comprising at least 2, 3, 4, 5, 6, 7, 8, 9, 10, 11, 12, 13, 14, 15, or 16 or all sequences of the amino acid sequences. As referred to above, the amino acid sequence of any of SEQ ID NOs: 71 to 87 may be an amino acid sequence derived therefrom by deletion, substitution, insertion or addition of one or several amino acids;

(1αA2-a) a protein comprising an amino acid sequence with deletion, substitution, insertion or addition of one or several amino acids in SEQ ID NO: 89;

(1αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 89;

(1αA2-c) a protein comprising an amino acid sequence encoded by a nucleotide sequence with deletion, substitution, insertion or addition of one or several nucleotides in SEQ ID NO: 88;

(1αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 88;

(1αA2-e) a protein comprising an amino acid sequence encoded by a nucleic acid that hybridizes under stringent conditions with a nucleic acid having a nucleotide sequence complementary to the nucleotide sequence of SEQ ID NO: 88;

(1αB2) a protein comprising at least one amino acid sequence selected from the group consisting of SEQ ID NOs: 90-104, preferably a protein comprising at least 2, 3, 4, 5, 6, 7, 8, 9, 10, 11, 12, 13, or 14 or all sequences of the amino acid sequences. As referred to above, the amino acid sequence of any of SEQ ID NOs: 90-104 may be an amino acid sequence derived therefrom by deletion, substitution, insertion or addition of one or several amino acids.

The protein selected from the group consisting of the proteins as defined above in (1αA1-a) to (1αA1-e), (1αB1), (1αA2-a) to (1αA2-e), and (1αB2) also include those proteins whose amino acid residues are modified by phosphorylation, sugar chain modification, aminoacylation, ring-opening, deamination or the like.

The protein selected from the group consisting of the proteins as defined above in (1αA1-a) to (1αA1-e), (1αB1), (1αA2-a) to (1αA2-e), and (1αB2) can be proteins that are found in a protein spot with a molecular weight of around 70 to 120 kDa, preferably around 80 to 110 kDa, and an isoelectric point of 2.5 to 6.5, preferably 3.0 to 6.0 on gels used in the two-dimensional electrophoresis performed under the conditions described above in the subsection titled “Identification of antigens”.

Preferably, a protein that is an antigen in spot 1α has activity equivalent to that of the protein having the amino acid sequence of SEQ ID NO: 70 or 89 (endoplasmin homolog isoform X2) or causative of an allergy to soybean.

(2α) Antigen in Spot 2α

As the result of sequence identification of the antigen in spot 2α by mass spectroscopy, the following amino acid sequences were detected.

(SEQ ID NO: 107)
ADLVNNLGTIARSGTK (SEQ ID NO: 108)
AVENSPFLEK (SEQ ID NO: 109)
EDQLEYLEERRLK (SEQ ID NO: 110)
EEYAAFYK (SEQ ID NO: 111)
EGQNDIYYITGESK (SEQ ID NO: 112)
EIFLRELISNASDALDK (SEQ ID NO: 113)
FYEAFSK (SEQ ID NO: 114)
HFSVEGQLEFK (SEQ ID NO: 115)
IRFESLTDK (SEQ ID NO: 116)
LAELLRYHSTK (SEQ ID NO: 117)
LDESEDEK (SEQ ID NO: 118)
LGIHEDSQNK (SEQ ID NO: 119)
RAPFDLFDTRK (SEQ ID NO: 120)
VEDVDEDK

-continued (SEQ ID NO: 123)
ADLVNNLGTIARSGTK (SEQ ID NO: 124)
AVENSPFLEK (SEQ ID NO: 125)
EDQLEYLEERRLK (SEQ ID NO: 126)
EEYSAFYK (SEQ ID NO: 127)
EGQSDIYYITGESK (SEQ ID NO: 128)
EIFLRELISNASDALDK (SEQ ID NO: 129)
FYEAFSK (SEQ ID NO: 130)
HFSVEGQLEFK (SEQ ID NO: 131)
IAELLRYHSTK (SEQ ID NO: 132)
IRFESLTDK (SEQ ID NO: 133)
LDESEDEK (SEQ ID NO: 134)
LGIHEDSQNK (SEQ ID NO: 135)
RAPFDLFDTRK (SEQ ID NO: 136)
SGDELTSLK (SEQ ID NO: 137)
VEDVDEEK (SEQ ID NO: 140)
ADLVNNLGTIARSGTK (SEQ ID NO: 141)
AVENSPFLEK (SEQ ID NO: 142)
EDQLEYLEERRLK (SEQ ID NO: 143)
EEYAAFYK (SEQ ID NO: 144)
EGQNDIYYITGESK (SEQ ID NO: 145)
EIFLRELISNASDALDK (SEQ ID NO: 146)
FYEAFSK (SEQ ID NO: 147)
HFSVEGQLEFK (SEQ ID NO: 148)
IRFESLTDK (SEQ ID NO: 149)
LAELLRYHSTK (SEQ ID NO: 150)
LDESEDEK -continued (SEQ ID NO: 151)

LGIHEDSQNK (SEQ ID NO: 152)

RAPFDLFDTK (SEQ ID NO: 153)

VEDVDEDK

Also, the mass spectroscopic data obtained for spot 2α on a mass spectrometer was analyzed by comparing the data against the NCBI protein data, and as a result, heat shock cognate protein 80 (amino acid sequence: SEQ ID NO: 106, encoding nucleotide sequence: SEQ ID NO: 105) was identified as a protein comprising any of SEQ ID NOs: 107 to 120, heat shock protein 90-1 (amino acid sequence: SEQ ID NO: 122, encoding nucleotide sequence: SEQ ID NO: 121) was identified as a protein comprising any of SEQ ID NOs: 123 to 137, and hypothetical protein GLYMA_02G302500 was identified as a protein comprising any of SEQ ID NOs: 140 to 153.

Accordingly, the antigen in spot 2α in the present invention can be any of proteins selected from the group consisting of the proteins as defined below in (2αA1-a) to (2αA1-e), (2αB1), (2αA2-a) to (2αA2-e), (2αB2), (2αA3-a) to (2αA3-e), and (2αB3):

(2αA1-a) a protein comprising an amino acid sequence with deletion, substitution, insertion or addition of one or several amino acids in SEQ ID NO: 106;

(2αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 106;

(2αA1-c) a protein comprising an amino acid sequence encoded by a nucleotide sequence with deletion, substitution, insertion or addition of one or several nucleotides in SEQ ID NO: 105;

(2αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 105;

(2αA1-e) a protein comprising an amino acid sequence encoded by a nucleic acid that hybridizes under stringent conditions with a nucleic acid having a nucleotide sequence complementary to the nucleotide sequence of SEQ ID NO: 105;

(2αB1) a protein comprising at least one amino acid sequence selected from the group consisting of SEQ ID NOs: 107-120, preferably a protein comprising at least 2, 3, 4, 5, 6, 7, 8, 9, 10, 11, 12, or 13 or all sequences of the amino acid sequences. As referred to above, the amino acid sequence of any of SEQ ID NOs: 107 to 120 may be an amino acid sequence derived therefrom by deletion, substitution, insertion or addition of one or several amino acids;

(2αA2-a) a protein comprising an amino acid sequence with deletion, substitution, insertion or addition of one or several amino acids in SEQ ID NO: 122;

(2αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 122;

(2αA2-c) a protein comprising an amino acid sequence encoded by a nucleotide sequence with deletion, substitution, insertion or addition of one or several nucleotides in SEQ ID NO: 121;

(2αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 121;

(2αA2-e) a protein comprising an amino acid sequence encoded by a nucleic acid that hybridizes under stringent conditions with a nucleic acid having a nucleotide sequence complementary to the nucleotide sequence of SEQ ID NO: 121;

(2αB2) a protein comprising at least one amino acid sequence selected from the group consisting of SEQ ID NOs: 123-137, preferably a protein comprising at least 2, 3, 4, 5, 6, 7, 8, 9, 10, 11, 12, 13, or 14 or all sequences of the amino acid sequences. As referred to above, the amino acid sequence of any of SEQ ID NOs: 123 to 137 may be an amino acid sequence derived therefrom by deletion, substitution, insertion or addition of one or several amino acids.

(2αA3-a) a protein comprising an amino acid sequence with deletion, substitution, insertion or addition of one or several amino acids in SEQ ID NO: 139;

(2αA3-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 139;

(2αA3-c) a protein comprising an amino acid sequence encoded by a nucleotide sequence with deletion, substitution, insertion or addition of one or several nucleotides in SEQ ID NO: 138;

(2αA3-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 138;

(2αA3-e) a protein comprising an amino acid sequence encoded by a nucleic acid that hybridizes under stringent conditions with a nucleic acid having a nucleotide sequence complementary to the nucleotide sequence of SEQ ID NO: 138;

(2αB3) a protein comprising at least one amino acid sequence selected from the group consisting of SEQ ID NOs: 140-153, preferably a protein comprising at least 2, 3, 4, 5, 6, 7, 8, 9, 10, 11, 12, or 13 or all sequences of the amino acid sequences. As referred to above, the amino acid sequence of any of SEQ ID NOs: 140 to 153 may be an amino acid sequence derived therefrom by deletion, substitution, insertion or addition of one or several amino acids.

The protein selected from the group consisting of the proteins as defined above in (2αA1-a) to (2αA1-e), (2αB1), (2αA2-a) to (2αA2-e), (2αB2), (2αA3-a) to (2αA3-e), and (2αB3) also include those proteins whose amino acid residues are modified by phosphorylation, sugar chain modification, aminoacylation, ring-opening, deamination or the like.

The protein selected from the group consisting of the proteins as defined above in (2αA1-a) to (2αA1-e), (2αB1), (2αA2-a) to (2αA2-e), (2αB2), (2αA3-a) to (2αA3-e), and (2αB3) can be proteins that are found in a protein spot with a molecular weight of around 50 to 120 kDa, preferably around 60 to 110 kDa, and an isoelectric point of 2.5 to 6.5, preferably 3.0 to 6.0 on gels used in the two-dimensional electrophoresis performed under the conditions described above in the subsection titled "Identification of antigens".

Preferably, a protein that is an antigen in spot 2α has activity equivalent to that of the protein having the amino acid sequence of SEQ ID NO: 106 (heat shock cognate protein 80), the protein having the amino acid sequence of SEQ ID NO: 122 (heat shock protein 90-1), or the protein having the amino acid sequence of SEQ ID NO: 139 (hypothetical protein GLYMA_02G302500), or causative of an allergy to soybean.

(4α) Antigen in Spot 4α

As the result of sequence identification of the antigen in spot 4α by mass spectroscopy, the following amino acid sequences were detected.

```
                                        (SEQ ID NO: 156)
AGGALSIAFVSK

                                        (SEQ ID NO: 157)
DGLIVSIGK
```

Also, the mass spectroscopic data obtained for spot 4α on a mass spectrometer was analyzed by comparing the data against the NCBI protein data, and as a result, embryo-specific urease isoform X1 (amino acid sequence: SEQ ID NO: 155, encoding nucleotide sequence: SEQ ID NO: 154) was identified as a protein comprising SEQ ID NO: 156 or 157.

Accordingly, the antigens in spot 4α in the present invention can be any protein selected from the group consisting of the proteins as defined below in (4αA-a) to (4αA-e) and (4αB):

(4αA-a) a protein comprising an amino acid sequence with deletion, substitution, insertion or addition of one or several amino acids in SEQ ID NO: 155;

(4αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 155;

(4αA-c) a protein comprising an amino acid sequence encoded by a nucleotide sequence with deletion, substitution, insertion or addition of one or several nucleotides in SEQ ID NO: 154;

(4αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 154;

(4αA-e) a protein comprising an amino acid sequence encoded by a nucleic acid that hybridizes under stringent conditions with a nucleic acid having a nucleotide sequence complementary to the nucleotide sequence of SEQ ID NO: 154;

(4αB) a protein comprising at least one amino acid sequence selected from the group consisting of SEQ ID NOs: 156 and 157, preferably a protein comprising both the amino acid sequences. As referred to above, the amino acid sequence of any of SEQ ID NOs: 156 and 157 may be an amino acid sequence derived therefrom by deletion, substitution, insertion or addition of one or several amino acids.

The proteins selected from the group consisting of (4αA-a) to (4αA-e) and (4αB) as defined above also include those proteins whose amino acid residues are modified by phosphorylation, sugar chain modification, aminoacylation, ring-opening, deamination or the like.

The proteins selected from the group consisting of (4αA-a) to (4αA-e) and (4αB) as defined above can be proteins that are found in a protein spot with a molecular weight of around 70 to 120 kDa, preferably around 80 to 110 kDa and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 4α has activity equivalent to that of the protein having the amino acid sequence of SEQ ID NO: 155 (embryo-specific urease isoform X1) or causative of an allergy to soybean.

(5α) Antigen in Spot 5α

As the result of sequence identification of the antigen in spot 5α by mass spectroscopy, the following amino acid sequences were detected.

```
                                        (SEQ ID NO: 160)
AFATYVQAK

                                        (SEQ ID NO: 161)
QQEATTSLSSFTPDASSIASSIK
```

Also, the mass spectroscopic data obtained for spot 5α on a mass spectrometer was analyzed by comparing the data against the NCBI protein data, and as a result, alpha-1,4 glucan phosphorylase L isozyme, chloroplastic/amyloplastic (amino acid sequence: SEQ ID NO: 159, encoding nucleotide sequence: SEQ ID NO: 158) was identified as a protein comprising SEQ ID NO: 160 or 161.

Accordingly, the antigens in spot 5α in the present invention can be any protein selected from the group consisting of the proteins as defined below in (5αA-a) to (5αA-e) and (5αB):

(5αA-a) a protein comprising an amino acid sequence with deletion, substitution, insertion or addition of one or several amino acids in SEQ ID NO: 159;

(5αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 159;

(5αA-c) a protein comprising an amino acid sequence encoded by a nucleotide sequence with deletion, substitution, insertion or addition of one or several nucleotides in SEQ ID NO: 158;

(5αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 158;

(5αA-e) a protein comprising an amino acid sequence encoded by a nucleic acid that hybridizes under stringent conditions with a nucleic acid having a nucleotide sequence complementary to the nucleotide sequence of SEQ ID NO: 158;

(5αB) a protein comprising at least one amino acid sequence selected from the group consisting of SEQ ID NOs: 160 and 161, preferably a protein comprising both the amino acid sequences. As referred to above, the amino acid sequence of any of SEQ ID NOs: 160 and 161 may be an amino acid sequence derived therefrom by deletion, substitution, insertion or addition of one or several amino acids.

The proteins selected from the group consisting of (5αA-a) to (5αA-e) and (5αB) as defined above also include those proteins whose amino acid residues are modified by phosphorylation, sugar chain modification, aminoacylation, ring-opening, deamination or the like.

The proteins selected from the group consisting of (5αA-a) to (5αA-e) and (5αB) as defined above can be proteins that are found in a protein spot with a molecular weight of around 70 to 170 kDa, preferably around 80 to 160 kDa and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 5α has activity equivalent to that of the protein having the amino acid sequence of SEQ ID NO: 159 (alpha-1,4 glucan phosphorylase L isozyme, chloroplastic/amyloplastic) or causative of an allergy to soybean.

(6α) Antigen in Spot 6α

As the result of sequence identification of the antigen in spot 6α by mass spectroscopy, the following amino acid sequences were detected.

```
                                  (SEQ ID NO: 164)
FLNGEVGPK

                                  (SEQ ID NO: 165)
LSVFDAAEK

                                  (SEQ ID NO: 166)
LSVFDVAEK

                                  (SEQ ID NO: 167)
TSLAPGSGVVTK

                                  (SEQ ID NO: 170)
FLNGEVGPK

                                  (SEQ ID NO: 171)
LSVFDVAEK

                                  (SEQ ID NO: 172)
TSLAPGSGVVTK
```

Also, the mass spectroscopic data obtained for spot 6α on a mass spectrometer was analyzed by comparing the data against the NCBI protein data, and as a result, aconitate hydratase 1 (amino acid sequence: SEQ ID NO: 163, encoding nucleotide sequence: SEQ ID NO: 162) was identified as a protein comprising any of SEQ ID NOs: 164 to 167 and aconitate hydratase 1 (amino acid sequence: SEQ ID NO: 169, encoding nucleotide sequence: SEQ ID NO: 168) was identified as a protein comprising any of SEQ ID NOs: 170 to 172.

Accordingly, the antigen in spot 6α in the present invention can be any of proteins selected from the group consisting of the proteins as defined below in (6αA1-a) to (6αA1-e), (6αB1), (6αA2-a) to (6αA2-e), and (6αB2):

(6αA1-a) a protein comprising an amino acid sequence with deletion, substitution, insertion or addition of one or several amino acids in SEQ ID NO: 163;

(6αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 163;

(6αA1-c) a protein comprising an amino acid sequence encoded by a nucleotide sequence with deletion, substitution, insertion or addition of one or several nucleotides in SEQ ID NO: 162;

(6αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 162;

(6αA1-e) a protein comprising an amino acid sequence encoded by a nucleic acid that hybridizes under stringent conditions with a nucleic acid having a nucleotide sequence complementary to the nucleotide sequence of SEQ ID NO: 162;

(6αB1) a protein comprising at least one amino acid sequence selected from the group consisting of SEQ ID NOs: 164-167, preferably a protein comprising at least 2, 3, or all sequences of the amino acid sequences. As referred to above, the amino acid sequence of any of SEQ ID NOs: 164 to 167 may be an amino acid sequence derived therefrom by deletion, substitution, insertion or addition of one or several amino acids;

(6αA2-a) a protein comprising an amino acid sequence with deletion, substitution, insertion or addition of one or several amino acids in SEQ ID NO: 169;

(6αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 169;

(6αA2-c) a protein comprising an amino acid sequence encoded by a nucleotide sequence with deletion, substitution, insertion or addition of one or several nucleotides in SEQ ID NO: 168;

(6αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 168;

(6αA2-e) a protein comprising an amino acid sequence encoded by a nucleic acid that hybridizes under stringent conditions with a nucleic acid having a nucleotide sequence complementary to the nucleotide sequence of SEQ ID NO: 168;

(6αB2) a protein comprising at least one amino acid sequence selected from the group consisting of SEQ ID NOs: 170-172, preferably a protein comprising at least 2, or all sequences of the amino acid sequences. As referred to above, the amino acid sequence of any of SEQ ID NOs: 170 to 172 may be an amino acid sequence derived therefrom by deletion, substitution, insertion or addition of one or several amino acids.

The protein selected from the group consisting of the proteins as defined above in (6αA1-a) to (6αA1-e), (6αB1), (6αA2-a) to (6αA2-e), and (6αB2) also include those proteins whose amino acid residues are modified by phosphorylation, sugar chain modification, aminoacylation, ring-opening, deamination or the like.

The protein selected from the group consisting of the proteins as defined above in (6αA1-a) to (6αA1-e), (6αB1), (6αA2-a) to (6αA2-e), and (6αB2) can be proteins that are found in a protein spot with a molecular weight of around 70 to 120 kDa, preferably around 80 to 110 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 6α has activity equivalent to that of the protein having the amino acid sequence of SEQ ID NO: 163 or 169 (aconitate hydratase 1) or causative of an allergy to soybean.

(7α) Antigen in Spot 7α

As the result of sequence identification of the antigen in spot 7a by mass spectroscopy, the following amino acid sequences were detected.

```
                                        (SEQ ID NO: 175)
AGITVIQIDEAALREGLPLRK

                                        (SEQ ID NO: 176)
ALGVDTVPVLVGPVTYLLLSKPAK

                                        (SEQ ID NO: 177)
DEAFFSGNAAALASRK

                                        (SEQ ID NO: 178)
DEVEDLEK

                                        (SEQ ID NO: 179)
ISEEEYVK

                                        (SEQ ID NO: 180)
IVEVNALAK

                                        (SEQ ID NO: 181)
LIRNELAK

                                        (SEQ ID NO: 182)
LLSVFREGVK

                                        (SEQ ID NO: 183)
LVVSTSSSLLHTAVDLVNETK

                                        (SEQ ID NO: 184)
SFSLLSLLPK

                                        (SEQ ID NO: 185)
SSPRVTNEAVQK

                                        (SEQ ID NO: 186)
TLTSLNGVTAYGFDLVRGTNTLDLIK

                                        (SEQ ID NO: 187)
YGAGIGPGVYDIHSPRIPPTEEIADRINK
```

Also, the mass spectroscopic data obtained for spot 7a on a mass spectrometer was analyzed by comparing the data against the NCBI protein data, and as a result, methionine synthase (amino acid sequence: SEQ ID NO: 174, encoding nucleotide sequence: SEQ ID NO: 173) was identified as a protein comprising any of SEQ ID NOs: 175 to 187.

Accordingly, the antigens in spot 7a in the present invention can be any protein selected from the group consisting of the proteins as defined below in (7αA-a) to (7αA-e) and (7αB):

(7αA-a) a protein comprising an amino acid sequence with deletion, substitution, insertion or addition of one or several amino acids in SEQ ID NO: 174;

(7αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 174;

(7αA-c) a protein comprising an amino acid sequence encoded by a nucleotide sequence with deletion, substitution, insertion or addition of one or several nucleotides in SEQ ID NO: 173;

(7αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 173;

(7αA-e) a protein comprising an amino acid sequence encoded by a nucleic acid that hybridizes under stringent conditions with a nucleic acid having a nucleotide sequence complementary to the nucleotide sequence of SEQ ID NO: 173;

(7αB) a protein comprising at least one amino acid sequence selected from the group consisting of SEQ ID NOs: 175-187, preferably a protein comprising at least 2, 3, 4, 5, 6, 7, 8, 9, 10, 11 or 12 or all sequences of the amino acid sequences. As referred to above, the amino acid sequence of any of SEQ ID NOs: 175-187 may be an amino acid sequence derived therefrom by deletion, substitution, insertion or addition of one or several amino acids.

The proteins selected from the group consisting of (7αA-a) to (7αA-e) and (7αB) as defined above also include those proteins whose amino acid residues are modified by phosphorylation, sugar chain modification, aminoacylation, ring-opening, deamination or the like.

The proteins selected from the group consisting of (7αA-a) to (7αA-e) and (7αB) as defined above can be proteins that are found in a protein spot with a molecular weight of around 50 to 120 kDa, preferably around 60 to 110 kDa and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 7a has activity equivalent to that of the protein having the amino acid sequence of SEQ ID NO: 174 (methionine synthase) or causative of an allergy to soybean.

(8α) Antigen in Spot 8α

As the result of sequence identification of the antigen in spot 8α by mass spectroscopy, the following amino acid sequences were detected.

```
                                        (SEQ ID NO: 190)
AIGIDRFGASAPAGRIYK

                                        (SEQ ID NO: 191)
ALPTYTPESPADATRNLSQTNLNALAK

                                        (SEQ ID NO: 192)
ANSYSVHGSALGAK

                                        (SEQ ID NO: 193)
ATADAALVEK

                                        (SEQ ID NO: 194)
DKPTLIK

                                        (SEQ ID NO: 195)
GGYTISDNSTGNKPDVILIGTGSELEIAAK

                                        (SEQ ID NO: 196)
LPQLPGTSIEGVEK

                                        (SEQ ID NO: 197)
NGNNGYDDIRAAIK
```

-continued (SEQ ID NO: 198)
SVNTIRFLAIDAVEK (SEQ ID NO: 199)
VTTTIGYGSPNK

Also, the mass spectroscopic data obtained for spot 8α on a mass spectrometer was analyzed by comparing the data against the NCBI protein data, and as a result, transketolase, chloroplastic (amino acid sequence: SEQ ID NO: 189, encoding nucleotide sequence: SEQ ID NO: 188) was identified as a protein comprising any of SEQ ID NOs: 190 to 199.

Accordingly, the antigens in spot 8α in the present invention can be any protein selected from the group consisting of the proteins as defined below in (8αA-a) to (8αA-e) and (8αB):

(8αA-a) a protein comprising an amino acid sequence with deletion, substitution, insertion or addition of one or several amino acids in SEQ ID NO: 189;

(8αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 189;

(8αA-c) a protein comprising an amino acid sequence encoded by a nucleotide sequence with deletion, substitution, insertion or addition of one or several nucleotides in SEQ ID NO: 188;

(8αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 188;

(8αA-e) a protein comprising an amino acid sequence encoded by a nucleic acid that hybridizes under stringent conditions with a nucleic acid having a nucleotide sequence complementary to the nucleotide sequence of SEQ ID NO: 188;

(8αB) a protein comprising at least one amino acid sequence selected from the group consisting of SEQ ID NOs: 190-199, preferably a protein comprising at least 2, 3, 4, 5, 6, 7, 8 or 9 or all sequences of the amino acid sequences. As referred to above, the amino acid sequence of any of SEQ ID NOs: 190-199 may be an amino acid sequence derived therefrom by deletion, substitution, insertion or addition of one or several amino acids.

The proteins selected from the group consisting of (8αA-a) to (8αA-e) and (8αB) as defined above also include those proteins whose amino acid residues are modified by phosphorylation, sugar chain modification, aminoacylation, ring-opening, deamination or the like.

The proteins selected from the group consisting of (8αA-a) to (8αA-e) and (8αB) as defined above can be proteins that are found in a protein spot with a molecular weight of around 50 to 120 kDa, preferably around 60 to 110 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 8α has activity equivalent to that of the protein having the amino acid sequence of SEQ ID NO: 189 (transketolase, chloroplastic) or causative of an allergy to soybean.

(9α) Antigen in Spot 9α

As the result of sequence identification of the antigen in spot 9α by mass spectroscopy, the following amino acid sequences were detected.

(SEQ ID NO: 202)
DLSSEEANQYLK

Also, the mass spectroscopic data obtained for spot 9α on a mass spectrometer was analyzed by comparing the data against the NCBI protein data, and as a result, lysine-tRNA ligase, cytoplasmic-like isoform X2 (amino acid sequence: SEQ ID NO: 201, encoding nucleotide sequence: SEQ ID NO: 200) was identified as a protein comprising SEQ ID NO: 202.

Accordingly, the antigens in spot 9α in the present invention can be any protein selected from the group consisting of the proteins as defined below in (9αA-a) to (9αA-e) and (9αB):

(9αA-a) a protein comprising an amino acid sequence with deletion, substitution, insertion or addition of one or several amino acids in SEQ ID NO: 201;

(9αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 201;

(9αA-c) a protein comprising an amino acid sequence encoded by a nucleotide sequence with deletion, substitution, insertion or addition of one or several nucleotides in SEQ ID NO: 200;

(9αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 200;

(9αA-e) a protein comprising an amino acid sequence encoded by a nucleic acid that hybridizes under stringent conditions with a nucleic acid having a nucleotide sequence complementary to the nucleotide sequence of SEQ ID NO: 200;

(9αB) a protein comprising an amino acid sequence of SEQ ID NO: 202. As referred to above, the amino acid sequence(s) of SEQ ID NO: 202 may be an amino acid sequence(s) derived therefrom by deletion, substitution, insertion or addition of one or several amino acids.

The proteins selected from the group consisting of (9αA-a) to (9αA-e) and (9αB) as defined above also include those proteins whose amino acid residues are modified by phosphorylation, sugar chain modification, aminoacylation, ring-opening, deamination or the like.

The proteins selected from the group consisting of (9αA-a) to (9αA-e) and (9αB) as defined above can be proteins that are found in a protein spot with a molecular weight of around 50 to 120 kDa, preferably around 60 to 110 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 9α has activity equivalent to that of the protein having the amino acid sequence of SEQ ID NO: 201 (lysine-tRNA ligase, cytoplasmic-like isoform X2) or causative of an allergy to soybean.

(10α) Antigen in Spot 10α

As the result of sequence identification of the antigen in spot 10α by mass spectroscopy, the following amino acid sequences were detected.

(SEQ ID NO: 205)
AAVEEGIVPGGGVALLYASSELDK (SEQ ID NO: 206)
DRVTDALNATK (SEQ ID NO: 207)
EGVITISDGK (SEQ ID NO: 208)
GRNVVIEQSFGAPK (SEQ ID NO: 209)
GVEELADAVK (SEQ ID NO: 210)
IGGASEAEVGEK (SEQ ID NO: 211)
IGVQIIQNALK (SEQ ID NO: 212)
ISSINAIVK (SEQ ID NO: 213)
LLEQNDPDLGYDAAK (SEQ ID NO: 214)
LQTANFDQK (SEQ ID NO: 215)
LSGGVAVLK (SEQ ID NO: 216)
NIGASLVK (SEQ ID NO: 217)
TGIIDPLK (SEQ ID NO: 218)
TPVHTIASNAGVEGAVVVGK (SEQ ID NO: 221)
AGIIDPLK (SEQ ID NO: 222)
DRVTDALNATK (SEQ ID NO: 223)
EGVITISDGK (SEQ ID NO: 224)
GRNVVIEQSFGAPK (SEQ ID NO: 225)
GVEELADAVK (SEQ ID NO: 226)
IGGASEAEVGEK (SEQ ID NO: 227)
IGVQIIQNALK (SEQ ID NO: 228)
ISSINAIVK (SEQ ID NO: 229)
LLEQENHDLGYDAAK (SEQ ID NO: 230)
LQTANFDQK (SEQ ID NO: 231)
LSGGVAVLK

Also, the mass spectroscopic data obtained for spot 10α on a mass spectrometer was analyzed by comparing the data against the NCBI protein data, and as a result, chaperonin CPN60-2, mitochondrial (amino acid sequence: SEQ ID NO: 204, encoding nucleotide sequence: SEQ ID NO: 203) was identified as a protein comprising any of SEQ ID NOs: 205 to 218 and chaperonin CPN60-2, mitochondrial-like isoform X1 (amino acid sequence: SEQ ID NO: 220, encoding nucleotide sequence: SEQ ID NO: 219) was identified as a protein comprising any of SEQ ID NOs: 221 to 231.

Accordingly, the antigen in spot 10α in the present invention can be any of proteins selected from the group consisting of the proteins as defined below in (10αA1-a) to (10αA1-e), (10αB1), (10αA2-a) to (10αA2-e), and (10αB2):

(10αA1-a) a protein comprising an amino acid sequence with deletion, substitution, insertion or addition of one or several amino acids in SEQ ID NO: 204;

(10αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 204;

(10αA1-c) a protein comprising an amino acid sequence encoded by a nucleotide sequence with deletion, substitution, insertion or addition of one or several nucleotides in SEQ ID NO: 203;

(10αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 203;

(10αA1-e) a protein comprising an amino acid sequence encoded by a nucleic acid that hybridizes under stringent conditions with a nucleic acid having a nucleotide sequence complementary to the nucleotide sequence of SEQ ID NO: 203;

(10αB1) a protein comprising at least one amino acid sequence selected from the group consisting of SEQ ID NOs: 205-218, preferably a protein comprising at least 2, 3, 4, 5, 6, 7, 8, 9, 10, 11, 12, or 13 or all sequences of the amino acid sequences. As referred to above, the amino acid sequence of any of SEQ ID NOs: 205 to 218 may be an amino acid sequence derived therefrom by deletion, substitution, insertion or addition of one or several amino acids;

(10αA2-a) a protein comprising an amino acid sequence with deletion, substitution, insertion or addition of one or several amino acids in SEQ ID NO: 220;

(10αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 220;

(10αA2-c) a protein comprising an amino acid sequence encoded by a nucleotide sequence with deletion, substitution, insertion or addition of one or several nucleotides in SEQ ID NO: 219;

(10αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 219;

(10αA2-e) a protein comprising an amino acid sequence encoded by a nucleic acid that hybridizes under stringent conditions with a nucleic acid having a nucleotide sequence complementary to the nucleotide sequence of SEQ ID NO: 219;

(10αB2) a protein comprising at least one amino acid sequence selected from the group consisting of SEQ ID NOs: 221-231, preferably a protein comprising at least 2, 3, 4, 5, 6, 7, 8, 9, or 10, or all sequences of the amino acid sequences. As referred to above, the amino acid sequence of any of SEQ ID NOs: 221 to 231 may be an amino acid sequence derived therefrom by deletion, substitution, insertion or addition of one or several amino acids.

The protein selected from the group consisting of the proteins as defined above in (10αA1-a) to (10αA1-e), (10αB1), (10αA2-a) to (10αA2-e), and (10αB2) also include those proteins whose amino acid residues are modified by phosphorylation, sugar chain modification, aminoacylation, ring-opening, deamination or the like.

The protein selected from the group consisting of the proteins as defined above in (10αA1-a) to (10αA1-e), (10αB1), (10αA2-a) to (10αA2-e), and (10αB2) can be proteins that are found in a protein spot with a molecular weight of around 30 to 90 kDa, preferably around 40 to 80 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 10α has activity equivalent to that of the protein having the amino acid sequence of SEQ ID NO: 204 (chaperonin CPN60-2, mitochondrial) or the protein having the amino acid sequence of SEQ ID NO: 220 (chaperonin CPN60-2, mitochondrial-like isoform X1) or causative of an allergy to soybean.

(11α) Antigen in Spot 11α

As the result of sequence identification of the antigen in spot 11α by mass spectroscopy, the following amino acid sequences were detected.

```
                                        (SEQ ID NO: 234)
AIDVLNFTPLNGK

                                        (SEQ ID NO: 235)
FNNVFVK

                                        (SEQ ID NO: 236)
GFGFVNFANVDDAAK

                                        (SEQ ID NO: 237)
SGAANVFIK
```

Also, the mass spectroscopic data obtained for spot 11α on a mass spectrometer was analyzed by comparing the data against the NCBI protein data, and as a result, polyadenylate-binding protein 8 isoform X3 (amino acid sequence: SEQ ID NO: 233, encoding nucleotide sequence: SEQ ID NO: 232) was identified as a protein comprising any of SEQ ID NOs: 234 to 237.

Accordingly, the antigens in spot 11α in the present invention can be any protein selected from the group consisting of the proteins as defined below in (11αA-a) to (11αA-e) and (11αB):

(11αA-a) a protein comprising an amino acid sequence with deletion, substitution, insertion or addition of one or several amino acids in SEQ ID NO: 233;

(11αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 233;

(11αA-c) a protein comprising an amino acid sequence encoded by a nucleotide sequence with deletion, substitution, insertion or addition of one or several nucleotides in SEQ ID NO: 232;

(11αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 232;

(11αA-e) a protein comprising an amino acid sequence encoded by a nucleic acid that hybridizes under stringent conditions with a nucleic acid having a nucleotide sequence complementary to the nucleotide sequence of SEQ ID NO: 232;

(11αB) a protein comprising at least one amino acid sequence selected from the group consisting of SEQ ID NOs: 234-237, preferably a protein comprising at least 2 or 3 or all sequences of the amino acid sequences. As referred to above, the amino acid sequence of any of SEQ ID NOs: 234-237 may be an amino acid sequence derived therefrom by deletion, substitution, insertion or addition of one or several amino acids.

The proteins selected from the group consisting of (11αA-a) to (11αA-e) and (11αB) as defined above also include those proteins whose amino acid residues are modified by phosphorylation, sugar chain modification, aminoacylation, ring-opening, deamination or the like.

The proteins selected from the group consisting of (11αA-a) to (11αA-e) and (11αB) as defined above can be proteins that are found in a protein spot with a molecular weight of around 30 to 90 kDa, preferably around 40 to 80 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 11α has activity equivalent to that of the protein having the amino acid sequence of SEQ ID NO: 233 (polyadenylate-binding protein 8 isoform X3) or causative of an allergy to soybean.

(12α) Antigen in Spot 12α

As the result of sequence identification of the antigen in spot 12α by mass spectroscopy, the following amino acid sequences were detected.

```
                                        (SEQ ID NO: 240)
                              VVGVPVTLNGDLK
```

Also, the mass spectroscopic data obtained for spot 12α on a mass spectrometer was analyzed by comparing the data against the NCBI protein data, and as a result, pyrophosphate-fructose 6-phosphate 1-phosphotransferase subunit alpha-like (amino acid sequence: SEQ ID NO: 239, encoding nucleotide sequence: SEQ ID NO: 238) was identified as a protein comprising SEQ ID NO: 240.

Accordingly, the antigens in spot 12α in the present invention can be any protein selected from the group consisting of the proteins as defined below in (12αA-a) to (12αA-e) and (12αB):

(12αA-a) a protein comprising an amino acid sequence with deletion, substitution, insertion or addition of one or several amino acids in SEQ ID NO: 239;

(12αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 239;

(12αA-c) a protein comprising an amino acid sequence encoded by a nucleotide sequence with deletion, substitution, insertion or addition of one or several nucleotides in SEQ ID NO: 238;

(12αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 238;

(12αA-e) a protein comprising an amino acid sequence encoded by a nucleic acid that hybridizes under stringent conditions with a nucleic acid having a nucleotide sequence complementary to the nucleotide sequence of SEQ ID NO: 238;

(12αB) a protein comprising an amino acid sequence of SEQ ID NO: 240. As referred to above, the amino acid sequence(s) of SEQ ID NO: 240 may be an amino acid sequence(s) derived therefrom by deletion, substitution, insertion or addition of one or several amino acids.

The proteins selected from the group consisting of (12αA-a) to (12αA-e) and (12αB) as defined above also include those proteins whose amino acid residues are modified by phosphorylation, sugar chain modification, aminoacylation, ring-opening, deamination or the like.

The proteins selected from the group consisting of (12αA-a) to (12αA-e) and (12αB) as defined above can be proteins that are found in a protein spot with a molecular weight of around 30 to 90 kDa, preferably around 40 to 80 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 12α has activity equivalent to that of the protein having the amino acid sequence of SEQ ID NO: 239 (pyrophosphate-fructose 6-phosphate 1-phosphotransferase subunit alpha-like) or causative of an allergy to soybean.

(13α) Antigen in Spot 13α

As the result of sequence identification of the antigen in spot 13α by mass spectroscopy, the following amino acid sequences were detected.

```
(SEQ ID NO: 243)
AASILSSHDPPVVLAK

(SEQ ID NO: 244)
DGNVAPFVK

(SEQ ID NO: 245)
DLASQYDVRGYPTIK

(SEQ ID NO: 246)
EDIIEFIEK

(SEQ ID NO: 247)
EEQVPLIIIQHNDGK

(SEQ ID NO: 248)
EFVLTLDHSNFHDTVSK

(SEQ ID NO: 249)
FFKPNLEADHIPTWLK

(SEQ ID NO: 250)
FFNSPNAK
```

-continued

```
(SEQ ID NO: 251)
FSGEEFDNFSALAEK

(SEQ ID NO: 252)
FVEESSTPVVTVFNNDPSNHPFVAK

(SEQ ID NO: 255)
AASILSSHDPPIVLAK

(SEQ ID NO: 256)
DGHVAPFVK

(SEQ ID NO: 257)
DLASQYDVK

(SEQ ID NO: 258)
EDIIEFIEK

(SEQ ID NO: 259)
EEQVPLIIIQHNDGK

(SEQ ID NO: 260)
EFVLTLDHSNFHDTVSK

(SEQ ID NO: 261)
FFKPNLEADHIPTWLK

(SEQ ID NO: 262)
FFNSPNAK

(SEQ ID NO: 263)
FSGEEFDNFSALAEK

(SEQ ID NO: 264)
FVEESSTPVVTVFNNEPSNHPFVVK

(SEQ ID NO: 265)
GFPTINILRNGGK

(SEQ ID NO: 266)
GPREADGIVDYLK

(SEQ ID NO: 267)
LAPEYEK

(SEQ ID NO: 268)
LDATANDIPSETFDVQGYPTVYFRSASGK

(SEQ ID NO: 269)
LRSDYDFGHTLNAK

(SEQ ID NO: 270)
LSQYDGGRTK

(SEQ ID NO: 271)
QLAPILDEVAISYQNEADVVIAK

(SEQ ID NO: 272)
QQGVSFLVGDVESSQGAFQYFGLK

(SEQ ID NO: 273)
QSGPASTEIK

(SEQ ID NO: 274)
SADEATAFIGENK

(SEQ ID NO: 275)
SEPIPETNDEPVK

(SEQ ID NO: 276)
VAIVGVFPK

(SEQ ID NO: 277)
VVVGASLEDIVFK

(SEQ ID NO: 278)
YREAAEQYK
```

Also, the mass spectroscopic data obtained for spot 13α on a mass spectrometer was analyzed by comparing the data against the NCBI protein data, and as a result, protein disulfide isomerase-like protein precursor (amino acid sequence: SEQ ID NO: 242, encoding nucleotide sequence: SEQ ID NO: 241) was identified as a protein comprising any of SEQ ID NOs: 243 to 252 and protein disulfide-isomerase (amino acid sequence: SEQ ID NO: 254, encoding nucleotide sequence: SEQ ID NO: 253) was identified as a protein comprising any of SEQ ID NOs: 255 to 278.

Accordingly, the antigen in spot 13α in the present invention can be any of proteins selected from the group consisting of the proteins as defined below in (13αA1-a) to (13αA1-e), (13αB1), (13αA2-a) to (13αA2-e), and (13αB2):

(13αA1-a) a protein comprising an amino acid sequence with deletion, substitution, insertion or addition of one or several amino acids in SEQ ID NO: 242;

(13αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 242;

(13αA1-c) a protein comprising an amino acid sequence encoded by a nucleotide sequence with deletion, substitution, insertion or addition of one or several nucleotides in SEQ ID NO: 241;

(13αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 241;

(13αA1-e) a protein comprising an amino acid sequence encoded by a nucleic acid that hybridizes under stringent conditions with a nucleic acid having a nucleotide sequence complementary to the nucleotide sequence of SEQ ID NO: 241;

(13αB1) a protein comprising at least one amino acid sequence selected from the group consisting of SEQ ID NOs: 243-252, preferably a protein comprising at least 2, 3, 4, 5, 6, 7, 8, or 9, or all sequences of the amino acid sequences. As referred to above, the amino acid sequence of any of SEQ ID NOs: 243-252 may be an amino acid sequence derived therefrom by deletion, substitution, insertion or addition of one or several amino acids;

(13αA2-a) a protein comprising an amino acid sequence with deletion, substitution, insertion or addition of one or several amino acids in SEQ ID NO: 254;

(13αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 254;

(13αA2-c) a protein comprising an amino acid sequence encoded by a nucleotide sequence with deletion, substitution, insertion or addition of one or several nucleotides in SEQ ID NO: 253;

(13αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 253;

(13αA2-e) a protein comprising an amino acid sequence encoded by a nucleic acid that hybridizes under stringent conditions with a nucleic acid having a nucleotide sequence complementary to the nucleotide sequence of SEQ ID NO: 253;

(13αB2) a protein comprising at least one amino acid sequence selected from the group consisting of SEQ ID NOs: 255-278, preferably a protein comprising at least 2, 3, 4, 5, 6, 7, 8, 9, 10, 11, 12, 13, 14, 15, 16, 17, 18, 19, 20, 21, 22, or 23, or all sequences of the amino acid sequences. As referred to above, the amino acid sequence of any of SEQ ID NOs: 255-278 may be an amino acid sequence derived therefrom by deletion, substitution, insertion or addition of one or several amino acids.

The protein selected from the group consisting of the proteins as defined above in (13αA1-a) to (13αA1-e), (13αB1), (13αA2-a) to (13αA2-e), and (13αB2) also include those proteins whose amino acid residues are modified by phosphorylation, sugar chain modification, aminoacylation, ring-opening, deamination or the like.

The protein selected from the group consisting of the proteins as defined above in (13αA1-a) to (13αA1-e), (13αB1), (13αA2-a) to (13αA2-e), and (13αB2) can be proteins that are found in a protein spot with a molecular weight of around 30 to 90 kDa, preferably around 40 to 80 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 13α has activity equivalent to that of the protein having the amino acid sequence of SEQ ID NO: 242 (protein disulfide isomerase-like protein precursor) or the protein having the amino acid sequence of SEQ ID NO: 254 (protein disulfide-isomerase) or causative of an allergy to soybean.

(14α) Antigen in Spot 14α

As the result of sequence identification of the antigen in spot 14α by mass spectroscopy, the following amino acid sequences were detected.

```
                         (SEQ ID NO: 281)
DHSDVSNQLYANYAIGK

                         (SEQ ID NO: 282)
FQEIVNIRLGDGTTRRGQVLEVDGEK

                         (SEQ ID NO: 283)
FTTVQFTGEVLK

                         (SEQ ID NO: 284)
TLDQFYSRDASN

                         (SEQ ID NO: 287)
FQEIVNIRLGDGTTRRGQVLEVDGEK

                         (SEQ ID NO: 288)
FTTVQFTGEVLK

                         (SEQ ID NO: 289)
TLDQFYSRDAGN
```

Also, the mass spectroscopic data obtained for spot 14α on a mass spectrometer was analyzed by comparing the data against the NCBI protein data, and as a result, V-type proton ATPase subunit B2 (amino acid sequence: SEQ ID NO: 280, encoding nucleotide sequence: SEQ ID NO: 279) was identified as a protein comprising any of SEQ ID NOs: 281 to 284 and V-type proton ATPase subunit B2 (amino acid sequence: SEQ ID NO: 286, encoding nucleotide sequence: SEQ ID NO: 285) was identified as a protein comprising any of SEQ ID NOs: 287 to 289.

Accordingly, the antigen in spot 14α in the present invention can be any of proteins selected from the group consisting of the proteins as defined below in (14αA1-a) to (14αA1-e), (14αB1), (14αA2-a) to (14αA2-e), and (14αB2):

(14αA1-a) a protein comprising an amino acid sequence with deletion, substitution, insertion or addition of one or several amino acids in SEQ ID NO: 280;

(14αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 280;

(14αA1-c) a protein comprising an amino acid sequence encoded by a nucleotide sequence with deletion, substitution, insertion or addition of one or several nucleotides in SEQ ID NO: 279;

(14αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 279;

(14αA1-e) a protein comprising an amino acid sequence encoded by a nucleic acid that hybridizes under stringent conditions with a nucleic acid having a nucleotide sequence complementary to the nucleotide sequence of SEQ ID NO: 279;

(14αB1) a protein comprising at least one amino acid sequence selected from the group consisting of SEQ ID NOs: 281-284, preferably a protein comprising at least 2, 3, or all sequences of the amino acid sequences. As referred to above, the amino acid sequence of any of SEQ ID NOs: 281 to 284 may be an amino acid sequence derived therefrom by deletion, substitution, insertion or addition of one or several amino acids;

(14αA2-a) a protein comprising an amino acid sequence with deletion, substitution, insertion or addition of one or several amino acids in SEQ ID NO: 286;

(14αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 286;

(14αA2-c) a protein comprising an amino acid sequence encoded by a nucleotide sequence with deletion, substitution, insertion or addition of one or several nucleotides in SEQ ID NO: 285;

(14αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 285;

(14αA2-e) a protein comprising an amino acid sequence encoded by a nucleic acid that hybridizes under stringent conditions with a nucleic acid having a nucleotide sequence complementary to the nucleotide sequence of SEQ ID NO: 285;

(14αB2) a protein comprising at least one amino acid sequence selected from the group consisting of SEQ ID NOs: 287-289, preferably a protein comprising at least 2, or all sequences of the amino acid sequences. As referred to above, the amino acid sequence of any of SEQ ID NOs: 287 to 289 may be an amino acid sequence derived therefrom by deletion, substitution, insertion or addition of one or several amino acids.

The protein selected from the group consisting of the proteins as defined above in (14αA1-a) to (14αA1-e), (14B1), (14αA2-a) to (14αA2-e), and (14αB2) also include those proteins whose amino acid residues are modified by phosphorylation, sugar chain modification, aminoacylation, ring-opening, deamination or the like.

The protein selected from the group consisting of the proteins as defined above in (14αA1-a) to (14αA1-e), (14αB1), (14αA2-a) to (14αA2-e), and (14αB2) can be proteins that are found in a protein spot with a molecular weight of around 30 to 90 kDa, preferably around 40 to 80 kDa, and an isoelectric point of 2.5 to 6.5, preferably 3.0 to 6.0 on gels used in the two-dimensional electrophoresis performed under the conditions described above in the subsection titled "Identification of antigens".

Preferably, a protein that is an antigen in spot 14α has activity equivalent to that of the protein having the amino acid sequence of SEQ ID NO: 280 or 286 (V-type proton ATPase subunit B2) or causative of an allergy to soybean.

(15a, 16α) Antigens in Spots 15α, 16α

As the result of sequence identification of the antigens in spots 15α and 16α by mass spectroscopy, the following amino acid sequences were detected.

(SEQ ID NO: 292)
AIGINVPRSRFLPVK (SEQ ID NO: 293)
ARENPENPSIELGPEFK (SEQ ID NO: 294)
ATSDLLLVQSDLYTLEDGFVIRNK (SEQ ID NO: 295)
EINGPEDL (SEQ ID NO: 296)
EYVFVANSDNLGAIVDLK (SEQ ID NO: 297)
ILNHLIQNK (SEQ ID NO: 298)
IQTPTDEVVVPYDTLAPTPEGSSEVK (SEQ ID NO: 299)
LDALLSQGK (SEQ ID NO: 300)
RLVEADALK (SEQ ID NO: 301)
SAVAGLNEISENEK (SEQ ID NO: 302)
SIPSIVELDSLK (SEQ ID NO: 303)
VLQLETAAGAAIRFFDK (SEQ ID NO: 304)
VSNFLGRFK (SEQ ID NO: 307)
AIGINVPRSRFLPVK (SEQ ID NO: 308)
ATSDLLLVQSDLYTLEDGFVIRNK (SEQ ID NO: 309)
EYVFVANSDNLGAIVDLK (SEQ ID NO: 310)
ILNHLIQNK (SEQ ID NO: 311)
IQTPTDEVVVPYDTLAPTPDGSSDVK

-continued

```
                        (SEQ ID NO: 312)
LDALLSQGK

                        (SEQ ID NO: 313)
LEVPDGAVISDK

                        (SEQ ID NO: 314)
RLVEADALK

                        (SEQ ID NO: 315)
SAVAGLNEISESEK

                        (SEQ ID NO: 316)
SIPSIVELDSLK

                        (SEQ ID NO: 317)
VLQLETAAGAAIRFFDK

                        (SEQ ID NO: 318)
VSNFLGRFK
```

Also, the mass spectroscopic data obtained for spots 15α, 16a on a mass spectrometer was analyzed by comparing the data against the NCBI protein data, and as a result, UTP-glucose-1-phosphate uridylyltransferase (amino acid sequence: SEQ ID NO: 291, encoding nucleotide sequence: SEQ ID NO: 290) was identified as a protein comprising any of SEQ ID NOs: 292 to 304 and the hypothetical protein GLYMA_02G241100 (amino acid sequence: SEQ ID NO: 306, encoding nucleotide sequence: SEQ ID NO: 305) was identified as a protein comprising any of SEQ ID NOs: 307 to 318.

Accordingly, the antigen in spot 15α, 16α in the present invention can be any of proteins selected from the group consisting of the proteins as defined below in (15, 16αA1-a) to (15, 16αA1-e), (15, 16αB1), (15, 16αA2-a) to (15, 16αA2-e), and (15, 16αB2):

(15, 16αA1-a) a protein comprising an amino acid sequence with deletion, substitution, insertion or addition of one or several amino acids in SEQ ID NO: 291;

(15, 16αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 291;

(15, 16αA1-c) a protein comprising an amino acid sequence encoded by a nucleotide sequence with deletion, substitution, insertion or addition of one or several nucleotides in SEQ ID NO: 290;

(15, 16αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 290;

(15, 16αA1-e) a protein comprising an amino acid sequence encoded by a nucleic acid that hybridizes under stringent conditions with a nucleic acid having a nucleotide sequence complementary to the nucleotide sequence of SEQ ID NO: 290;

(15, 16αB1) a protein comprising at least one amino acid sequence selected from the group consisting of SEQ ID NOs: 292-304, preferably a protein comprising at least 2, 3, 4, 5, 6, 7, 8, 9, 10, 11, or 12 or all sequences of the amino acid sequences. As referred to above, the amino acid sequence of any of SEQ ID NOs: 292 to 304 may be an amino acid sequence derived therefrom by deletion, substitution, insertion or addition of one or several amino acids;

(15, 16αA2-a) a protein comprising an amino acid sequence with deletion, substitution, insertion or addition of one or several amino acids in SEQ ID NO: 306;

(15, 16αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 306;

(15, 16αA2-c) a protein comprising an amino acid sequence encoded by a nucleotide sequence with deletion, substitution, insertion or addition of one or several nucleotides in SEQ ID NO: 305;

(15, 16αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 305;

(15, 16αA2-e) a protein comprising an amino acid sequence encoded by a nucleic acid that hybridizes under stringent conditions with a nucleic acid having a nucleotide sequence complementary to the nucleotide sequence of SEQ ID NO: 305;

(15, 16αB2) a protein comprising at least one amino acid sequence selected from the group consisting of SEQ ID NOs: 307-318, preferably a protein comprising at least 2, 3, 4, 5, 6, 7, 8, 9, 10, or 11 or all sequences of the amino acid sequences. As referred to above, the amino acid sequence of any of SEQ ID NOs: 307 to 318 may be an amino acid sequence derived therefrom by deletion, substitution, insertion or addition of one or several amino acids.

The protein selected from the group consisting of the proteins as defined above in (15, 16αA1-a) to (15, 16αA1-e), (15, 16αB1), (15, 16αA2-a) to (15, 16αA2-e), and (15, 16αB2) also include those proteins whose amino acid residues are modified by phosphorylation, sugar chain modification, aminoacylation, ring-opening, deamination or the like.

The protein selected from the group consisting of the proteins as defined above in (15, 16αA1-a) to (15, 16αA1-e), (15, 16αB1), (15, 16αA2-a) to (15, 16αA2-e), and (15, 16αB2) can be proteins that are found in a protein spot with a molecular weight of around 20 to 90 kDa, preferably around 30 to 80 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 15α or 16α has activity equivalent to that of the protein having the amino acid sequence of SEQ ID NO: 291 (UTP-glucose-1-phosphate uridylyltransferase) or the protein having the amino acid sequence of SEQ ID NO: 306 (hypothetical protein GLYMA_02G241100) or causative of an allergy to soybean.

(17α) Antigen in Spot 17α

As the result of sequence identification of the antigen in spot 17α by mass spectroscopy, the following amino acid sequences were detected.

```
                        (SEQ ID NO: 321)
AVDGSFVFNK

                        (SEQ ID NO: 322)
FFIYVQNYNESDPK
```

-continued (SEQ ID NO: 323)
VEFDEEGK (SEQ ID NO: 324)
VIDLSVDLSAASAAEE (SEQ ID NO: 325)
VVGVTSEGETAK (SEQ ID NO: 328)
AVDGSYVFNK (SEQ ID NO: 329)
FFIYVQNYNESDPK (SEQ ID NO: 330)
VEFDEEGK (SEQ ID NO: 331)
VIDLSVDLSAASAAEE (SEQ ID NO: 332)
VVGVTSEGETAK Also, the mass spectroscopic data obtained for spot 17α on a mass spectrometer was analyzed by comparing the data against the NCBI protein data, and as a result, guanosine nucleotide diphosphate dissociation inhibitor 2 (amino acid sequence: SEQ ID NO: 320, encoding nucleotide sequence: SEQ ID NO: 319) was identified as a protein comprising any of SEQ ID NOs: 321 to 325 and rab GDP dissociation inhibitor alpha-like (amino acid sequence: SEQ ID NO: 327, encoding nucleotide sequence: SEQ ID NO: 326) was identified as a protein comprising any of SEQ ID NOs: 328 to 332.

Accordingly, the antigen in spot 17α in the present invention can be any of proteins selected from the group consisting of the proteins as defined below in (17αA1-a) to (17αA1-e), (17αB1), (17αA2-a) to (17αA2-e), and (17αB2):

(17αA1-a) a protein comprising an amino acid sequence with deletion, substitution, insertion or addition of one or several amino acids in SEQ ID NO: 320;

(17αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 320;

(17αA1-c) a protein comprising an amino acid sequence encoded by a nucleotide sequence with deletion, substitution, insertion or addition of one or several nucleotides in SEQ ID NO: 319;

(17αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 319;

(17αA1-e) a protein comprising an amino acid sequence encoded by a nucleic acid that hybridizes under stringent conditions with a nucleic acid having a nucleotide sequence complementary to the nucleotide sequence of SEQ ID NO: 319;

(17αB1) a protein comprising at least one amino acid sequence selected from the group consisting of SEQ ID NOs: 321-325, preferably a protein comprising at least 2, 3, or 4 or all sequences of the amino acid sequences. As referred to above, the amino acid sequence of any of SEQ ID NOs: 321 to 325 may be an amino acid sequence derived therefrom by deletion, substitution, insertion or addition of one or several amino acids.

(17αA2-a) a protein comprising an amino acid sequence with deletion, substitution, insertion or addition of one or several amino acids in SEQ ID NO: 327;

(17αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 327;

(17αA2-c) a protein comprising an amino acid sequence encoded by a nucleotide sequence with deletion, substitution, insertion or addition of one or several nucleotides in SEQ ID NO: 326;

(17αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 326;

(17αA2-e) a protein comprising an amino acid sequence encoded by a nucleic acid that hybridizes under stringent conditions with a nucleic acid having a nucleotide sequence complementary to the nucleotide sequence of SEQ ID NO: 326;

(17αB2) a protein comprising at least one amino acid sequence selected from the group consisting of SEQ ID NOs: 328-332, preferably a protein comprising at least 2, 3, or 4 or all sequences of the amino acid sequences. As referred to above, the amino acid sequence of any of SEQ ID NOs: 328 to 332 may be an amino acid sequence derived therefrom by deletion, substitution, insertion or addition of one or several amino acids;

The protein selected from the group consisting of the proteins as defined above in (17αA1-a) to (17αA1-e), (17αB1), (17αA2-a) to (17αA2-e), and (17αB2) also include those proteins whose amino acid residues are modified by phosphorylation, sugar chain modification, aminoacylation, ring-opening, deamination or the like.

The protein selected from the group consisting of the proteins as defined above in (17αA1-a) to (17αA1-e), (17αB1), (17αA2-a) to (17αA2-e), and (17αB2) can be proteins that are found in a protein spot with a molecular weight of around 20 to 90 kDa, preferably around 30 to 80 kDa, and an isoelectric point of 3.5 to 7.5, preferably 4.0 to 7.0 on gels used in the two-dimensional electrophoresis performed under the conditions described above in the subsection titled “Identification of antigens”.

Preferably, a protein that is an antigen in spot 17α has activity equivalent to that of the protein having the amino acid sequence of SEQ ID NO: 320 (guanosine nucleotide diphosphate dissociation inhibitor 2) or the protein having the amino acid sequence of SEQ ID NO: 327 (rab GDP dissociation inhibitor alpha-like) or causative of an allergy to soybean.

(18α) Antigen in Spot 18α

As the result of sequence identification of the antigen in spot 18α by mass spectroscopy, the following amino acid sequences were detected.

(SEQ ID NO: 335)
DFETRVETEGGRIRVLK (SEQ ID NO: 336)
DNIVSSLDNVAK

-continued (SEQ ID NO: 337)
GRAVLGLVSESETEK (SEQ ID NO: 338)
LFDQQNEGSIFAISREQVRALAPTK (SEQ ID NO: 339)
RPTISNGYGRLTEVGPDDDEK Also, the mass spectroscopic data obtained for spot 18α on a mass spectrometer was analyzed by comparing the data against the NCBI protein data, and as a result, hypothetical protein GLYMA_10G028300 (amino acid sequence: SEQ ID NO: 334, encoding nucleotide sequence: SEQ ID NO: 333) was identified as a protein comprising any of SEQ ID NOs: 335 to 339.

Accordingly, the antigens in spot 18α in the present invention can be any protein selected from the group consisting of the proteins as defined below in (18αA-a) to (18αA-e) and (18αB):

(18αA-a) a protein comprising an amino acid sequence with deletion, substitution, insertion or addition of one or several amino acids in SEQ ID NO: 334;

(18αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 334;

(18αA-c) a protein comprising an amino acid sequence encoded by a nucleotide sequence with deletion, substitution, insertion or addition of one or several nucleotides in SEQ ID NO: 333;

(18αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 333;

(18αA-e) a protein comprising an amino acid sequence encoded by a nucleic acid that hybridizes under stringent conditions with a nucleic acid having a nucleotide sequence complementary to the nucleotide sequence of SEQ ID NO: 333;

(18αB) a protein comprising at least one amino acid sequence selected from the group consisting of SEQ ID NOs: 335-339, preferably a protein comprising at least 2, 3 or 4 or all sequences of the amino acid sequences. As referred to above, the amino acid sequence of any of SEQ ID NOs: 335-339 may be an amino acid sequence derived therefrom by deletion, substitution, insertion or addition of one or several amino acids.

The proteins selected from the group consisting of (18αA-a) to (18αA-e) and (18αB) as defined above also include those proteins whose amino acid residues are modified by phosphorylation, sugar chain modification, aminoacylation, ring-opening, deamination or the like.

The proteins selected from the group consisting of (18αA-a) to (18αA-e) and (18αB) as defined above can be proteins that are found in a protein spot with a molecular weight of around 30 to 90 kDa, preferably around 40 to 80 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 18α has activity equivalent to that of the protein having the amino acid sequence of SEQ ID NO: 334 (hypothetical protein GLYMA_10G028300) or causative of an allergy to soybean.

(19α) Antigen in Spot 19α

As the result of sequence identification of the antigen in spot 19α by mass spectroscopy, the following amino acid sequences were detected.

(SEQ ID NO: 342)
AQFNIFSK (SEQ ID NO: 343)
DFSTRVETEGGSIRVLK (SEQ ID NO: 344)
DNIVSSLDNVAK (SEQ ID NO: 345)
GRAVLGLVRESETEK (SEQ ID NO: 346)
RPTFSNGYGRLTEVGPDDEK

Also, the mass spectroscopic data obtained for spot 19α on a mass spectrometer was analyzed by comparing the data against the NCBI protein data, and as a result, sucrose binding protein homolog S-64 (amino acid sequence: SEQ ID NO: 341, encoding nucleotide sequence: SEQ ID NO: 340) was identified as a protein comprising any of SEQ ID NOs: 342 to 346.

Accordingly, the antigens in spot 19α in the present invention can be any protein selected from the group consisting of the proteins as defined below in (19αA-a) to (19αA-e) and (19αB):

(19αA-a) a protein comprising an amino acid sequence with deletion, substitution, insertion or addition of one or several amino acids in SEQ ID NO: 341;

(19αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 341;

(19αA-c) a protein comprising an amino acid sequence encoded by a nucleotide sequence with deletion, substitution, insertion or addition of one or several nucleotides in SEQ ID NO: 340;

(19αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 340;

(19αA-e) a protein comprising an amino acid sequence encoded by a nucleic acid that hybridizes under stringent conditions with a nucleic acid having a nucleotide sequence complementary to the nucleotide sequence of SEQ ID NO: 340;

(19αB) a protein comprising at least one amino acid sequence selected from the group consisting of SEQ ID NOs: 342-346, preferably a protein comprising at least 2, 3 or 4 or all sequences of the amino acid sequences. As referred to above, the amino acid sequence of any of SEQ ID NOs: 342-346 may be an amino acid sequence derived therefrom by deletion, substitution, insertion or addition of one or several amino acids.

The proteins selected from the group consisting of (19αA-a) to (19αA-e) and (19αB) as defined above also include those proteins whose amino acid residues are modified by phosphorylation, sugar chain modification, aminoacylation, ring-opening, deamination or the like.

The proteins selected from the group consisting of (19αA-a) to (19αA-e) and (19αB) as defined above can be proteins that are found in a protein spot with a molecular weight of around 30 to 90 kDa, preferably around 40 to 80 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 19α has activity equivalent to that of the protein having the amino acid sequence of SEQ ID NO: 341 (sucrose binding protein homolog S-64) or causative of an allergy to soybean.

(25α) Antigen in Spot 25α

As the result of sequence identification of the antigen in spot 25α by mass spectroscopy, the following amino acid sequences were detected.

```
                                  (SEQ ID NO: 349)
DLFPNENELVVK

                                  (SEQ ID NO: 350)
EIFSLRDTTQEDPREVTAAK

                                  (SEQ ID NO: 351)
LHGGTPANFLDVGGNASENQVVEAFK

                                  (SEQ ID NO: 352)
LNFDDNAAYRQK

                                  (SEQ ID NO: 353)
SQILAGGRGLGTFK

                                  (SEQ ID NO: 354)
TDQVEDIAGK

                                  (SEQ ID NO: 355)
VPVVVRLEGTNVDQGK

                                  (SEQ ID NO: 356)
VVDGLALK

                                  (SEQ ID NO: 359)
DLFPNENELVVK

                                  (SEQ ID NO: 360)
EIFALRDTTQEDPREVTAAK

                                  (SEQ ID NO: 361)
LHGGTPANFLDVGGNASEGQVVEAFK

                                  (SEQ ID NO: 362)
LNFDDNAAYRQK

                                  (SEQ ID NO: 363)
SQILAGGRGLGTFK

                                  (SEQ ID NO: 364)
TDQVEDIAGK

                                  (SEQ ID NO: 365)
VVDGLALK
```

Also, the mass spectroscopic data obtained for spot 25α on a mass spectrometer was analyzed by comparing the data against the NCBI protein data, and as a result, succinyl-CoA ligase [ADP-forming] subunit beta, mitochondrial (amino acid sequence: SEQ ID NO: 348, encoding nucleotide sequence: SEQ ID NO: 347) was identified as a protein comprising any of SEQ ID NOs: 349 to 356 and succinyl-CoA ligase [ADP-forming]subunit beta, mitochondrial (amino acid sequence: SEQ ID NO: 358, encoding nucleotide sequence: SEQ ID NO: 357) was identified as a protein comprising any of SEQ ID NOs: 359 to 365.

Accordingly, the antigen in spot 25α in the present invention can be any of proteins selected from the group consisting of the proteins as defined below in (25αA1-a) to (25αA1-e), (25αB1), (25αA2-a) to (25αA2-e), and (25αB2):

(25αA1-a) a protein comprising an amino acid sequence with deletion, substitution, insertion or addition of one or several amino acids in SEQ ID NO: 348;

(25αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 348;

(25αA1-c) a protein comprising an amino acid sequence encoded by a nucleotide sequence with deletion, substitution, insertion or addition of one or several nucleotides in SEQ ID NO: 347;

(25αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 347;

(25αA1-e) a protein comprising an amino acid sequence encoded by a nucleic acid that hybridizes under stringent conditions with a nucleic acid having a nucleotide sequence complementary to the nucleotide sequence of SEQ ID NO: 347;

(25αB1) a protein comprising at least one amino acid sequence selected from the group consisting of SEQ ID NOs: 349-356, preferably a protein comprising at least 2, 3, 4, 5, 6, or 7 or all sequences of the amino acid sequences. As referred to above, the amino acid sequence of any of SEQ ID NOs: 349 to 356 may be an amino acid sequence derived therefrom by deletion, substitution, insertion or addition of one or several amino acids;

(25αA2-a) a protein comprising an amino acid sequence with deletion, substitution, insertion or addition of one or several amino acids in SEQ ID NO: 358;

(25αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 358;

(25αA2-c) a protein comprising an amino acid sequence encoded by a nucleotide sequence with deletion, substitution, insertion or addition of one or several nucleotides in SEQ ID NO: 357;

(25αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 357;

(25αA2-e) a protein comprising an amino acid sequence encoded by a nucleic acid that hybridizes under stringent conditions with a nucleic acid having a nucleotide sequence complementary to the nucleotide sequence of SEQ ID NO: 357;

(25αB2) a protein comprising at least one amino acid sequence selected from the group consisting of SEQ ID NOs: 359-365, preferably a protein comprising at least 2, 3, 4, 5, or 6 or all sequences of the amino acid sequences. As referred to above, the amino acid sequence of any of SEQ ID NOs: 359 to 365 may be an amino acid sequence derived therefrom by deletion, substitution, insertion or addition of one or several amino acids.

The protein selected from the group consisting of the proteins as defined above in (25αA1-a) to (25αA1-e), (25αB1), (25αA2-a) to (25αA2-e), and (25αB2) also include those proteins whose amino acid residues are modified by phosphorylation, sugar chain modification, aminoacylation, ring-opening, deamination or the like.

The protein selected from the group consisting of the proteins as defined above in (25αA1-a) to (25αA1-e), (25αB1), (25αA2-a) to (25αA2-e), and (25αB2) can be proteins that are found in a protein spot with a molecular weight of around 20 to 90 kDa, preferably around 30 to 80 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 25α has activity equivalent to that of the protein having the amino acid sequence of SEQ ID NO: 348 or 358 (succinyl-CoA ligase [ADP-forming] subunit beta, mitochondrial) or causative of an allergy to soybean.

(26α) Antigen in Spot 26α

As the result of sequence identification of the antigen in spot 26α by mass spectroscopy, the following amino acid sequences were detected.

(SEQ ID NO: 368)
AQGYSVGSSLVEEDK (SEQ ID NO: 369)
ELDYLVGAVSNPK (SEQ ID NO: 370)
FAADANSK (SEQ ID NO: 371)
FATGTEAIAK (SEQ ID NO: 372)
GVSLLLPTDVVIADK (SEQ ID NO: 373)
GVTTIIGGGDSVAAVEK (SEQ ID NO: 374)
IGVIESLLEK (SEQ ID NO: 375)
LASLADLYVNDAFGTAHRAHASTEGVAK (SEQ ID NO: 376)
LSLATTLLEK (SEQ ID NO: 377)
LVTQLPEGGVLLLENVRFYK (SEQ ID NO: 378)
NDPEFAK (SEQ ID NO: 379)
QLPGVLALDDA (SEQ ID NO: 380)
RPFAAIVGGSK (SEQ ID NO: 381)
VILSSHLGRPK (SEQ ID NO: 382)
YLTGYGAK (SEQ ID NO: 385)
ELDYLVGAVSNPK (SEQ ID NO: 386)
ELPGVLALDEAVPVAV

-continued (SEQ ID NO: 387)
FAVGTEAIAK (SEQ ID NO: 388)
GVSLLLPSDVVIADK (SEQ ID NO: 389)
GVTTIIGGGDSVAAVEK (SEQ ID NO: 390)
IGVIESLLEK (SEQ ID NO: 391)
RPFAAIVGGSK (SEQ ID NO: 392)
VILSSHLGRPK (SEQ ID NO: 395)
AQGYSVGSSLVEEDK (SEQ ID NO: 396)
ELDYLVGAVSNPK (SEQ ID NO: 397)
FAADANSK (SEQ ID NO: 398)
FATGTEAIAK (SEQ ID NO: 399)
GVSLLLPTDVVIADK (SEQ ID NO: 400)
GVTTIIGGGDSVAAVEK (SEQ ID NO: 401)
IGVIESLLEK (SEQ ID NO: 402)
LASLADLYVNDAFGTAHRAHASTEGVAK (SEQ ID NO: 403)
LSLATTLLEK (SEQ ID NO: 404)
LVAQLPEGGVLLLENVRFYK (SEQ ID NO: 405)
NDPEFAK (SEQ ID NO: 406)
QLPGVLALDDA (SEQ ID NO: 407)
RPFAAIVGGSK (SEQ ID NO: 408)
TFGEALDK (SEQ ID NO: 409)
VILSSHLGRPK Also, the mass spectroscopic data obtained for spot 26a on a mass spectrometer was analyzed by comparing the data against the NCBI protein data, and as a result, phosphoglycerate kinase, cytosolic (amino acid sequence: SEQ ID NO: 367, encoding nucleotide sequence: SEQ ID NO: 366) was identified as a protein comprising any of SEQ ID NOs: 368 to 382, phosphoglycerate kinase, cytosolic (amino acid sequence: SEQ ID NO: 384, encoding nucleotide sequence: SEQ ID NO: 383) was identified as a protein comprising any of SEQ ID NOs: 385 to 392, and phosphoglycerate kinase, cytosolic (amino acid sequence: SEQ ID NO: 394, encoding nucleotide sequence: SEQ ID NO: 393) was identified as a protein comprising any of SEQ ID NOs: 395 to 409.

Accordingly, the antigen in spot 26a in the present invention can be any of proteins selected from the group consisting of the proteins as defined below in (26αA1-a) to (26αA1-e), (26αB1), (26αA2-a) to (26αA2-e), (26αB2), (26αA3-a) to (26αA3-e), and (26αB3):

(26αA1-a) a protein comprising an amino acid sequence with deletion, substitution, insertion or addition of one or several amino acids in SEQ ID NO: 367;

(26αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 367;

(26αA1-c) a protein comprising an amino acid sequence encoded by a nucleotide sequence with deletion, substitution, insertion or addition of one or several nucleotides in SEQ ID NO: 366;

(26αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 366;

(26αA1-e) a protein comprising an amino acid sequence encoded by a nucleic acid that hybridizes under stringent conditions with a nucleic acid having a nucleotide sequence complementary to the nucleotide sequence of SEQ ID NO: 366;

(26αB1) a protein comprising at least one amino acid sequence selected from the group consisting of SEQ ID NOs: 368-382, preferably a protein comprising at least 2, 3, 4, 5, 6, 7, 8, 9, 10, 11, 12, 13, or 14 or all sequences of the amino acid sequences. As referred to above, the amino acid sequence of any of SEQ ID NOs: 368 to 382 may be an amino acid sequence derived therefrom by deletion, substitution, insertion or addition of one or several amino acids;

(26αA2-a) a protein comprising an amino acid sequence with deletion, substitution, insertion or addition of one or several amino acids in SEQ ID NO: 384;

(26αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 384;

(26αA2-c) a protein comprising an amino acid sequence encoded by a nucleotide sequence with deletion, substitution, insertion or addition of one or several nucleotides in SEQ ID NO: 383;

(26αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 383;

(26αA2-e) a protein comprising an amino acid sequence encoded by a nucleic acid that hybridizes under stringent conditions with a nucleic acid having a nucleotide sequence complementary to the nucleotide sequence of SEQ ID NO: 383;

(26αB2) a protein comprising at least one amino acid sequence selected from the group consisting of SEQ ID NOs: 385-392, preferably a protein comprising at least 2, 3, 4, 5, 6, or 7 or all sequences of the amino acid sequences. As referred to above, the amino acid sequence of any of SEQ ID NOs: 385 to 392 may be an amino acid sequence derived therefrom by deletion, substitution, insertion or addition of one or several amino acids.

(26αA3-a) a protein comprising an amino acid sequence with deletion, substitution, insertion or addition of one or several amino acids in SEQ ID NO: 394;

(26αA3-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 394;

(26αA3-c) a protein comprising an amino acid sequence encoded by a nucleotide sequence with deletion, substitution, insertion or addition of one or several nucleotides in SEQ ID NO: 393;

(26αA3-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 393;

(26αA3-e) a protein comprising an amino acid sequence encoded by a nucleic acid that hybridizes under stringent conditions with a nucleic acid having a nucleotide sequence complementary to the nucleotide sequence of SEQ ID NO: 393;

(26αB3) a protein comprising at least one amino acid sequence selected from the group consisting of SEQ ID NOs: 395-409, preferably a protein comprising at least 2, 3, 4, 5, 6, 7, 8, 9, 10, 11, 12, 13, or 14 or all sequences of the amino acid sequences. As referred to above, the amino acid sequence of any of SEQ ID NOs: 395 to 409 may be an amino acid sequence derived therefrom by deletion, substitution, insertion or addition of one or several amino acids.

The protein selected from the group consisting of the proteins as defined above in (26αA1-a) to (26αA1-e), (26αB1), (26αA2-a) to (26αA2-e), (26αB2), (26αA3-a) to (26αA3-e), and (26αB3) also include those proteins whose amino acid residues are modified by phosphorylation, sugar chain modification, aminoacylation, ring-opening, deamination or the like.

The protein selected from the group consisting of the proteins as defined above in (26αA1-a) to (26αA1-e), (26αB1), (26αA2-a) to (26αA2-e), (26αB2), (26αA3-a) to (26αA3-e), and (26αB3) can be proteins that are found in a protein spot with a molecular weight of around 20 to 90 kDa, preferably around 30 to 80 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 25α has activity equivalent to that of the protein having the amino acid sequence of SEQ ID NO: 367, 384, or 394 (phosphoglycerate kinase, cytosolic) or causative of an allergy to soybean.

(27α) Antigen in Spot 27α

As the result of sequence identification of the antigen in spot 27α by mass spectroscopy, the following amino acid sequences were detected.

```
(SEQ ID NO: 412)
FGVNEFVNPK

(SEQ ID NO: 413)
FITHTVPFSEINK
```

-continued

```
                          (SEQ ID NO: 414)
GTFYGNYKPRTDLPSVVEK

                          (SEQ ID NO: 415)
THPVNFLNERTLK

                          (SEQ ID NO: 416)
VNPAAPLDK

                          (SEQ ID NO: 419)
GTFYGHYRPRTDIPGVVEK

                          (SEQ ID NO: 420)
INPNAPLDK

                          (SEQ ID NO: 423)
FGVNEFVNPK

                          (SEQ ID NO: 424)
FITHTVPFSEINK

                          (SEQ ID NO: 425)
GTFYGNYKPRTDLPSVVEK

                          (SEQ ID NO: 426)
INPAAPLDK

                          (SEQ ID NO: 427)
TAPINFLNERTLK
```

Also, the mass spectroscopic data obtained for spot 27a on a mass spectrometer was analyzed by comparing the data against the NCBI protein data, and as a result, alcohol dehydrogenase 1 (amino acid sequence: SEQ ID NO: 411, encoding nucleotide sequence: SEQ ID NO: 410) was identified as a protein comprising any of SEQ ID NOs: 412 to 416, alcohol dehydrogenase 1 (amino acid sequence: SEQ ID NO: 418, encoding nucleotide sequence: SEQ ID NO: 417) was identified as a protein comprising any of SEQ ID NOs: 419 and 420, and alcohol dehydrogenase 1-like (amino acid sequence: SEQ ID NO: 422, encoding nucleotide sequence: SEQ ID NO: 421) was identified as a protein comprising any of SEQ ID NOs: 423 to 427.

Accordingly, the antigen in spot 27a in the present invention can be any of proteins selected from the group consisting of the proteins as defined below in (27αA1-a) to (27αA1-e), (27αB1), (27αA2-a) to (27αA2-e), (27αB2), (27αA3-a) to (27αA3-e), and (27αB3):

(27αA1-a) a protein comprising an amino acid sequence with deletion, substitution, insertion or addition of one or several amino acids in SEQ ID NO: 411;

(27αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 411;

(27αA1-c) a protein comprising an amino acid sequence encoded by a nucleotide sequence with deletion, substitution, insertion or addition of one or several nucleotides in SEQ ID NO: 410;

(27αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 410;

(27αA1-e) a protein comprising an amino acid sequence encoded by a nucleic acid that hybridizes under stringent conditions with a nucleic acid having a nucleotide sequence complementary to the nucleotide sequence of SEQ ID NO: 410;

(27αB1) a protein comprising at least one amino acid sequence selected from the group consisting of SEQ ID NOs: 412-416, preferably a protein comprising at least 2, 3, or 4 or all sequences of the amino acid sequences. As referred to above, the amino acid sequence of any of SEQ ID NOs: 412 to 416 may be an amino acid sequence derived therefrom by deletion, substitution, insertion or addition of one or several amino acids;

(27αA2-a) a protein comprising an amino acid sequence with deletion, substitution, insertion or addition of one or several amino acids in SEQ ID NO: 418;

(27αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 418;

(27αA2-c) a protein comprising an amino acid sequence encoded by a nucleotide sequence with deletion, substitution, insertion or addition of one or several nucleotides in SEQ ID NO: 417;

(27αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 417;

(27αA2-e) a protein comprising an amino acid sequence encoded by a nucleic acid that hybridizes under stringent conditions with a nucleic acid having a nucleotide sequence complementary to the nucleotide sequence of SEQ ID NO: 417;

(27αB2) a protein comprising at least one amino acid sequence selected from the group consisting of SEQ ID NOs: 419 and 420, preferably a protein comprising both the amino acid sequences. As referred to above, the amino acid sequence of any of SEQ ID NOs: 419, 420 may be an amino acid sequence derived therefrom by deletion, substitution, insertion or addition of one or several amino acids.

(27αA3-a) a protein comprising an amino acid sequence with deletion, substitution, insertion or addition of one or several amino acids in SEQ ID NO: 422;

(27αA3-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 422;

(27αA3-c) a protein comprising an amino acid sequence encoded by a nucleotide sequence with deletion, substitution, insertion or addition of one or several nucleotides in SEQ ID NO: 421;

(27αA3-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 421;

(27αA3-e) a protein comprising an amino acid sequence encoded by a nucleic acid that hybridizes under stringent conditions with a nucleic acid having a nucleotide sequence complementary to the nucleotide sequence of SEQ ID NO: 421;

(27αB3) a protein comprising at least one amino acid sequence selected from the group consisting of SEQ ID NOs: 423-427, preferably a protein comprising at least 2, 3, or 4 or all sequences of the amino acid sequences. As referred to above, the amino acid sequence of any of SEQ ID NOs: 423 to 427 may be an amino acid sequence derived therefrom by deletion, substitution, insertion or addition of one or several amino acids.

The protein selected from the group consisting of the proteins as defined above in (27αA1-a) to (27αA1-e), (27αB1), (27αA2-a) to (27αA2-e), (27αB2), (27αA3-a) to (27αA3-e), and (27αB3) also include those proteins whose amino acid residues are modified by phosphorylation, sugar chain modification, aminoacylation, ring-opening, deamination or the like.

The protein selected from the group consisting of the proteins as defined above in (27αA1-a) to (27αA1-e), (27αB1), (27αA2-a) to (27αA2-e), (27αB2), (27αA3-a) to (27αA3-e), and (27αB3) can be proteins that are found in a protein spot with a molecular weight of around 20 to 90 kDa, preferably around 30 to 80 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 27a has activity equivalent to that of the protein having the amino acid sequence of SEQ ID NO: 411 or 418 (alcohol dehydrogenase 1) or the protein having the amino acid sequence of SEQ ID NO: 422 (alcohol dehydrogenase 1-like) or causative of an allergy to soybean.

(28α) Antigen in Spot 28α

As the result of sequence identification of the antigen in spot 28α by mass spectroscopy, the following amino acid sequences were detected.

```
                                   (SEQ ID NO: 430)
AGEYTDYAAQK

                                   (SEQ ID NO: 431)
DIGDINRTNERDEGYDLHDEANFK

                                   (SEQ ID NO: 432)
DLEDANRLRDNTFNTWK

                                   (SEQ ID NO: 433)
EAVVGKPHHEEVYAK
```

Also, the mass spectroscopic data obtained for spot 28α on a mass spectrometer was analyzed by comparing the data against the NCBI protein data, and as a result, 35 kDa seed maturation protein isoform X1 (amino acid sequence: SEQ ID NO: 429, encoding nucleotide sequence: SEQ ID NO: 428) was identified as a protein comprising any of SEQ ID NO: 430 to 433.

Accordingly, the antigens in spot 28α in the present invention can be any protein selected from the group consisting of the proteins as defined below in (28αA-a) to (28αA-e) and (28αB):

(28αA-a) a protein comprising an amino acid sequence with deletion, substitution, insertion or addition of one or several amino acids in SEQ ID NO: 429;

(28αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 429;

(28αA-c) a protein comprising an amino acid sequence encoded by a nucleotide sequence with deletion, substitution, insertion or addition of one or several nucleotides in SEQ ID NO: 428;

(28αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 428;

(28αA-e) a protein comprising an amino acid sequence encoded by a nucleic acid that hybridizes under stringent conditions with a nucleic acid having a nucleotide sequence complementary to the nucleotide sequence of SEQ ID NO: 428;

(28αB) a protein comprising at least one amino acid sequence selected from the group consisting of SEQ ID NOs: 430-433, preferably a protein comprising at least 2 or 3 or all sequences of the amino acid sequences. As referred to above, the amino acid sequence of any of SEQ ID NOs: 430-433 may be an amino acid sequence derived therefrom by deletion, substitution, insertion or addition of one or several amino acids.

The proteins selected from the group consisting of (28αA-a) to (28αA-e) and (28αB) as defined above also include those proteins whose amino acid residues are modified by phosphorylation, sugar chain modification, aminoacylation, ring-opening, deamination or the like.

The proteins selected from the group consisting of (28αA-a) to (28αA-e) and (28αB) as defined above can be proteins that are found in a protein spot with a molecular weight of around 10 to 70 kDa, preferably around 20 to 60 kDa and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 28α has activity equivalent to that of the protein having the amino acid sequence of SEQ ID NO: 422 (35 kDa seed maturation protein isoform X1) or causative of an allergy to soybean.

(29α, 30α, 31α, 32α, 33α) Antigens in spots 29α to 33α

As the result of sequence identification of the antigens in spots 29α to 33α by mass spectroscopy, the following amino acid sequences were detected.

```
                                   (SEQ ID NO: 436)
EASYDEIK

                                   (SEQ ID NO: 437)
GILGYTEDDVVSTDFIGDSRSSIFDAK

                                   (SEQ ID NO: 438)
VIISAPSK

                                   (SEQ ID NO: 439)
VLPALNGK

                                   (SEQ ID NO: 442)
EASYDEIK

                                   (SEQ ID NO: 443)
GILGYTEDDVVSTDFVGDSRSSIFDAK

                                   (SEQ ID NO: 444)
VIISAPSK

                                   (SEQ ID NO: 445)
VLPALNGK

                                   (SEQ ID NO: 448)
AGISLNDNFVK

                                   (SEQ ID NO: 449)
GILGYTEDDVVSTDFVGDNRSSIFDAK
```

-continued (SEQ ID NO: 450)
VLPALNGK (SEQ ID NO: 451)
VVISAPSK

Also, the mass spectroscopic data obtained for spots 29α to 33α on a mass spectrometer was analyzed by comparing the data against the NCBI protein data, and as a result, glyceraldehyde-3-phosphate dehydrogenase isoform X1 (amino acid sequence: SEQ ID NO: 435, encoding nucleotide sequence: SEQ ID NO: 434) was identified as a protein comprising any of SEQ ID NO: 436 to 439, glyceraldehyde-3-phosphate dehydrogenase, cytosolic (amino acid sequence: SEQ ID NO: 441, encoding nucleotide sequence: SEQ ID NO: 440) was identified as a protein comprising any of SEQ ID NO: 442 to 445, and uncharacterized protein LOC100782924 (amino acid sequence: SEQ ID NO: 447, encoding nucleotide sequence: SEQ ID NO: 446) was identified as a protein comprising any of SEQ ID NO: 448 to 451.

Accordingly, the antigen in spot 29α to 33α in the present invention can be any of proteins selected from the group consisting of the proteins as defined below in (29-33αA1-a) to (29-33αA1-e), (29-33αB1), (29-33αA2-a) to (29-33αA2-e), (29-33αB2), (29-33αA3-a) to (29-33αA3-e), and (29-33αB3):

(29-33αA1-a) a protein comprising an amino acid sequence with deletion, substitution, insertion or addition of one or several amino acids in SEQ ID NO: 435;

(29-33αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 435;

(29-33αA1-c) a protein comprising an amino acid sequence encoded by a nucleotide sequence with deletion, substitution, insertion or addition of one or several nucleotides in SEQ ID NO: 434;

(29-33αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 434;

(29-33αA1-e) a protein comprising an amino acid sequence encoded by a nucleic acid that hybridizes under stringent conditions with a nucleic acid having a nucleotide sequence complementary to the nucleotide sequence of SEQ ID NO: 434;

(29-33αB1) a protein comprising at least one amino acid sequence selected from the group consisting of SEQ ID NOs: 436-439, preferably a protein comprising at least 2, 3, or all sequences of the amino acid sequences. As referred to above, the amino acid sequence of any of SEQ ID NOs: 436 to 439 may be an amino acid sequence derived therefrom by deletion, substitution, insertion or addition of one or several amino acids;

(29-33αA2-a) a protein comprising an amino acid sequence with deletion, substitution, insertion or addition of one or several amino acids in SEQ ID NO: 441;

(29-33αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 441;

(29-33αA2-c) a protein comprising an amino acid sequence encoded by a nucleotide sequence with deletion, substitution, insertion or addition of one or several nucleotides in SEQ ID NO: 440;

(29-33αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 440;

(29-33αA2-e) a protein comprising an amino acid sequence encoded by a nucleic acid that hybridizes under stringent conditions with a nucleic acid having a nucleotide sequence complementary to the nucleotide sequence of SEQ ID NO: 440;

(29-33αB2) a protein comprising at least one amino acid sequence selected from the group consisting of SEQ ID NOs: 442-445, preferably a protein comprising at least 2, 3, or all sequences of the amino acid sequences. As referred to above, the amino acid sequence of any of SEQ ID NOs: 442 to 445 may be an amino acid sequence derived therefrom by deletion, substitution, insertion or addition of one or several amino acids.

(29-33αA3-a) a protein comprising an amino acid sequence with deletion, substitution, insertion or addition of one or several amino acids in SEQ ID NO: 447;

(29-33αA3-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 447;

(29-33αA3-c) a protein comprising an amino acid sequence encoded by a nucleotide sequence with deletion, substitution, insertion or addition of one or several nucleotides in SEQ ID NO: 446;

(29-33αA3-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 446;

(29-33αA3-e) a protein comprising an amino acid sequence encoded by a nucleic acid that hybridizes under stringent conditions with a nucleic acid having a nucleotide sequence complementary to the nucleotide sequence of SEQ ID NO: 446;

(29-33αB3) a protein comprising at least one amino acid sequence selected from the group consisting of SEQ ID NOs: 448-451, preferably a protein comprising at least 2, 3, or all sequences of the amino acid sequences. As referred to above, the amino acid sequence of any of SEQ ID NOs: 448 to 451 may be an amino acid sequence derived therefrom by deletion, substitution, insertion or addition of one or several amino acids.

The protein selected from the group consisting of the proteins as defined above in (29-33αA1-a) to (29-33αA1-e), (29-33αB1), (29-33αA2-a) to (29-33αA2-e), (29-33αB2), (29-33αA3-a) to (29-33αA3-e), and (29-33αB3) also include those proteins whose amino acid residues are modified by phosphorylation, sugar chain modification, aminoacylation, ring-opening, deamination or the like.

The protein selected from the group consisting of the proteins as defined above in (29-33αA1-a) to (29-33αA1-e), (29-33αB1), (29-33αA2-a) to (29-33αA2-e), (29-33αB2), (29-33αA3-a) to (29-33αA3-e), and (29-33αB3) can be proteins that are found in a protein spot with a molecular weight of around 10 to 70 kDa, preferably around 20 to 60 kDa, and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in any of spots 29α to 33α has activity equivalent to that of the protein having the amino acid sequence of SEQ ID NO: 435 (glyceraldehyde-3-phosphate dehydrogenase isoform X1), the protein having the amino acid sequence of SEQ ID NO: 441 (glyceraldehyde-3-phosphate dehydrogenase, cytosolic), or the protein having the amino acid sequence of SEQ ID NO: 447 (uncharacterized protein LOC100782924) or causative of an allergy to soybean.

(34α) Antigen in Spot 34α

As the result of sequence identification of the antigen in spot 34α by mass spectroscopy, the following amino acid sequences were detected.

```
                    (SEQ ID NO: 454)
LFLEEIARDIQK

                    (SEQ ID NO: 457)
LFLEEIARDIQK

                    (SEQ ID NO: 458)
TTFDAVIHFAGLK
```

Also, the mass spectroscopic data obtained for spot 34α on a mass spectrometer was analyzed by comparing the data against the NCBI protein data, and as a result, bifunctional UDP-glucose 4-epimerase and UDP-xylose 4-epimerase 1-like (amino acid sequence: SEQ ID NO: 453, encoding nucleotide sequence: SEQ ID NO: 452) was identified as a protein comprising SEQ ID NO: 454 and uncharacterized protein LOC100803483 (amino acid sequence: SEQ ID NO: 456, encoding nucleotide sequence: SEQ ID NO: 455) was identified as a protein comprising SEQ ID NO: 457 or 458.

Accordingly, the antigen in spot 34α in the present invention can be any of proteins selected from the group consisting of the proteins as defined below in (34αA1-a) to (34αA1-e), (34αB1), (34αA2-a) to (34αA2-e), and (34αB2):

(34αA1-a) a protein comprising an amino acid sequence with deletion, substitution, insertion or addition of one or several amino acids in SEQ ID NO: 453;

(34αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 453;

(34αA1-c) a protein comprising an amino acid sequence encoded by a nucleotide sequence with deletion, substitution, insertion or addition of one or several nucleotides in SEQ ID NO: 452;

(34αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 452;

(34αA1-e) a protein comprising an amino acid sequence encoded by a nucleic acid that hybridizes under stringent conditions with a nucleic acid having a nucleotide sequence complementary to the nucleotide sequence of SEQ ID NO: 452;

(34αB1) a protein comprising an amino acid sequence of SEQ ID NOs: 454. As referred to above, the amino acid sequence of any of SEQ ID NOs: 464 may be an amino acid sequence derived therefrom by deletion, substitution, insertion or addition of one or several amino acids;

(34αA2-a) a protein comprising an amino acid sequence with deletion, substitution, insertion or addition of one or several amino acids in SEQ ID NO: 456;

(34αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 456;

(34αA2-c) a protein comprising an amino acid sequence encoded by a nucleotide sequence with deletion, substitution, insertion or addition of one or several nucleotides in SEQ ID NO: 455;

(34αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 455;

(34αA2-e) a protein comprising an amino acid sequence encoded by a nucleic acid that hybridizes under stringent conditions with a nucleic acid having a nucleotide sequence complementary to the nucleotide sequence of SEQ ID NO: 455;

(34αB2) a protein comprising at least one amino acid sequence selected from the group consisting of SEQ ID NOs: 457 and 458, preferably a protein comprising both the amino acid sequences. As referred to above, the amino acid sequence of any of SEQ ID NOs: 457, 458 may be an amino acid sequence derived therefrom by deletion, substitution, insertion or addition of one or several amino acids.

The protein selected from the group consisting of the proteins as defined above in (34αA1-a) to (34αA1-e), (34αB1), (34αA2-a) to (34αA2-e), and (34αB2) also include those proteins whose amino acid residues are modified by phosphorylation, sugar chain modification, aminoacylation, ring-opening, deamination or the like.

The protein selected from the group consisting of the proteins as defined above in (34αA1-a) to (34αA1-e), (34αB1), (34αA2-a) to (34αA2-e), and (34αB2) can be proteins that are found in a protein spot with a molecular weight of around 10 to 70 kDa, preferably around 20 to 60 kDa, and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 34α has activity equivalent to that of the protein having the amino acid sequence of SEQ ID NO: 453 (bifunctional UDP-glucose 4-epimerase and UDP-xylose 4-epimerase 1-like) or the protein having the amino acid sequence of SEQ ID NO: 456 (uncharacterized protein LOC100803483) or causative of an allergy to soybean.

(35α) Antigen in Spot 35α

As the result of sequence identification of the antigen in spot 35α by mass spectroscopy, the following amino acid sequences were detected.

```
                    (SEQ ID NO: 461)
ARYDEIVK

                    (SEQ ID NO: 462)
DGQTREHALLAFTLGVK
```

-continued

```
                    (SEQ ID NO: 463)
EVSSYLK

                    (SEQ ID NO: 464)
FSEILTK

                    (SEQ ID NO: 465)
STTTGHLIYK

                    (SEQ ID NO: 466)
THINIVVIGHVDSGK

                    (SEQ ID NO: 469)
DGQTREHALLAFTLGVK

                    (SEQ ID NO: 470)
EVSSYLK

                    (SEQ ID NO: 471)
STTTGHLIYK

                    (SEQ ID NO: 474)
ARYDEIVK

                    (SEQ ID NO: 475)
DGQTREHALLSFTLGVK

                    (SEQ ID NO: 476)
EVSSYLK

                    (SEQ ID NO: 477)
STTTGHLIYK
```

Also, the mass spectroscopic data obtained for spot 35α on a mass spectrometer was analyzed by comparing the data against the NCBI protein data, and as a result, elongation factor 1-alpha (amino acid sequence: SEQ ID NO: 460, encoding nucleotide sequence: SEQ ID NO: 459) was identified as a protein comprising any of SEQ ID NOs: 461 to 466, elongation factor 1-alpha (amino acid sequence: SEQ ID NO: 468, encoding nucleotide sequence: SEQ ID NO: 467) was identified as a protein comprising any of SEQ ID NOs: 469 to 471, and elongation factor-1A isoform X1 (amino acid sequence: SEQ ID NO: 473, encoding nucleotide sequence: SEQ ID NO: 472) was identified as a protein comprising any of SEQ ID NOs: 474 to 477.

Accordingly, the antigen in spot 35α in the present invention can be any of proteins selected from the group consisting of the proteins as defined below in (35αA1-a) to (35αA1-e), (35αB1), (35αA2-a) to (35αA2-e), (35αB2), (35αA3-a) to (35αA3-e), and (35αB3):

(35αA1-a) a protein comprising an amino acid sequence with deletion, substitution, insertion or addition of one or several amino acids in SEQ ID NO: 460;

(35αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 460;

(35αA1-c) a protein comprising an amino acid sequence encoded by a nucleotide sequence with deletion, substitution, insertion or addition of one or several nucleotides in SEQ ID NO: 459;

(35αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 459;

(35αA1-e) a protein comprising an amino acid sequence encoded by a nucleic acid that hybridizes under stringent conditions with a nucleic acid having a nucleotide sequence complementary to the nucleotide sequence of SEQ ID NO: 459;

(35αB1) a protein comprising at least one amino acid sequence selected from the group consisting of SEQ ID NOs: 461-466, preferably a protein comprising at least 2, 3, 4, or 5 or all sequences of the amino acid sequences. As referred to above, the amino acid sequence of any of SEQ ID NOs: 461-466 may be an amino acid sequence derived therefrom by deletion, substitution, insertion or addition of one or several amino acids;

(35αA2-a) a protein comprising an amino acid sequence with deletion, substitution, insertion or addition of one or several amino acids in SEQ ID NO: 468;

(35αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 468;

(35αA2-c) a protein comprising an amino acid sequence encoded by a nucleotide sequence with deletion, substitution, insertion or addition of one or several nucleotides in SEQ ID NO: 467;

(35αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 467;

(35αA2-e) a protein comprising an amino acid sequence encoded by a nucleic acid that hybridizes under stringent conditions with a nucleic acid having a nucleotide sequence complementary to the nucleotide sequence of SEQ ID NO: 467;

(35αB2) a protein comprising at least one amino acid sequence selected from the group consisting of SEQ ID NOs: 469-471, preferably a protein comprising at least 2, or all sequences of the amino acid sequences. As referred to above, the amino acid sequence of any of SEQ ID NOs: 469 to 471 may be an amino acid sequence derived therefrom by deletion, substitution, insertion or addition of one or several amino acids.

(35αA3-a) a protein comprising an amino acid sequence with deletion, substitution, insertion or addition of one or several amino acids in SEQ ID NO: 473;

(35αA3-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 473;

(35αA3-c) a protein comprising an amino acid sequence encoded by a nucleotide sequence with deletion, substitution, insertion or addition of one or several nucleotides in SEQ ID NO: 472;

(35αA3-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 472;

(35αA3-e) a protein comprising an amino acid sequence encoded by a nucleic acid that hybridizes under stringent conditions with a nucleic acid having a nucleotide sequence complementary to the nucleotide sequence of SEQ ID NO: 472;

(35αB3) a protein comprising at least one amino acid sequence selected from the group consisting of SEQ ID NOs: 474-477, preferably a protein comprising at least 2, 3, or all sequences of the amino acid sequences. As referred to above, the amino acid sequence of any of SEQ ID NOs: 474 to 477 may be an amino acid sequence derived therefrom by deletion, substitution, insertion or addition of one or several amino acids.

The protein selected from the group consisting of the proteins as defined above in (35αA1-a) to (35αA1-e), (35αB1), (35αA2-a) to (35αA2-e), (35αB2), (35αA3-a) to (35αA3-e), and (35αB3) also include those proteins whose amino acid residues are modified by phosphorylation, sugar chain modification, aminoacylation, ring-opening, deamination or the like.

The protein selected from the group consisting of the proteins as defined above in (35αA1-a) to (35αA1-e), (35αB1), (35αA2-a) to (35αA2-e), (35αB2), (35αA3-a) to (35αA3-e), and (35αB3) can be proteins that are found in a protein spot with a molecular weight of around 20 to 90 kDa, preferably around 30 to 80 kDa, and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 35α has activity equivalent to that of the protein having the amino acid sequence of SEQ ID NO: 460 or 468 (elongation factor 1-alpha) or the protein having the amino acid sequence of SEQ ID NO: 473 (elongation factor-1A isoform X1) or causative of an allergy to soybean.

(36α, 37α) Antigens in Spots 36α, 37α

As the result of sequence identification of the antigens in spots 36α and 37α by mass spectroscopy, the following amino acid sequences were detected.

```
(SEQ ID NO: 480)
EGSSIINTTSVNAYK

(SEQ ID NO: 481)
FPPQQQQTQPGK

(SEQ ID NO: 482)
GAIVAYTRGLALQLVSK

(SEQ ID NO: 483)
LLDYTSTK

(SEQ ID NO: 486)
EGATVAFTYVK

(SEQ ID NO: 487)
QVIDLVVK

(SEQ ID NO: 490)
EGSSIINTTSVNAYK

(SEQ ID NO: 491)
FPPQQQQTQPGK

(SEQ ID NO: 492)
GAIVAYTRGLALQLVSK

(SEQ ID NO: 493)
LLDYTSTK
```

Also, the mass spectroscopic data obtained for spots 36a and 37a on a mass spectrometer was analyzed by comparing the data against the NCBI protein data, and as a result, seed maturation protein PM34 (amino acid sequence: SEQ ID NO: 479, encoding nucleotide sequence: SEQ ID NO: 478) was identified as a protein comprising any of SEQ ID NOs: 480 to 483, uncharacterized protein LOC100809384 (amino acid sequence: SEQ ID NO: 485, encoding nucleotide sequence: SEQ ID NO: 484) was identified as a protein comprising SEQ ID NO: 486 or 487, and hypothetical protein GLYMA_10G155300 (amino acid sequence: SEQ ID NO: 489, encoding nucleotide sequence: SEQ ID NO: 488) was identified as a protein comprising any of SEQ ID NOs: 490 to 493.

Accordingly, the antigen in spot 36a, 37a in the present invention can be any of proteins selected from the group consisting of the proteins as defined below in (36, 37αA1-a) to (36, 37αA1-e), (36, 37αB1), (36, 37αA2-a) to (36, 37αA2-e), (36, 37αB2), (36, 37αA3-a) to (36, 37αA3-e), and (36, 37αB3):

(36, 37αA1-a) a protein comprising an amino acid sequence with deletion, substitution, insertion or addition of one or several amino acids in SEQ ID NO: 479;

(36, 37αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 479;

(36, 37αA1-c) a protein comprising an amino acid sequence encoded by a nucleotide sequence with deletion, substitution, insertion or addition of one or several nucleotides in SEQ ID NO: 478;

(36, 37αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 478;

(36, 37αA1-e) a protein comprising an amino acid sequence encoded by a nucleic acid that hybridizes under stringent conditions with a nucleic acid having a nucleotide sequence complementary to the nucleotide sequence of SEQ ID NO: 478;

(36, 37αB1) a protein comprising at least one amino acid sequence selected from the group consisting of SEQ ID NOs: 480-483, preferably a protein comprising at least 2, 3, or all sequences of the amino acid sequences. As referred to above, the amino acid sequence of any of SEQ ID NOs: 480 to 483 may be an amino acid sequence derived therefrom by deletion, substitution, insertion or addition of one or several amino acids;

(36, 37αA2-a) a protein comprising an amino acid sequence with deletion, substitution, insertion or addition of one or several amino acids in SEQ ID NO: 485;

(36, 37αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 485;

(36, 37αA2-c) a protein comprising an amino acid sequence encoded by a nucleotide sequence with deletion, substitution, insertion or addition of one or several nucleotides in SEQ ID NO: 484;

(36, 37αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 484;

(36, 37αA2-e) a protein comprising an amino acid sequence encoded by a nucleic acid that hybridizes under stringent conditions with a nucleic acid having a nucleotide sequence complementary to the nucleotide sequence of SEQ ID NO: 484;

(36, 37αB2) a protein comprising at least one amino acid sequence selected from the group consisting of SEQ ID NOs: 486 and 487, preferably a protein comprising both the amino acid sequences. As referred to above, the amino acid sequence of any of SEQ ID NOs: 486, 487 may be an amino acid sequence derived therefrom by deletion, substitution, insertion or addition of one or several amino acids.

(36, 37αA3-a) a protein comprising an amino acid sequence with deletion, substitution, insertion or addition of one or several amino acids in SEQ ID NO: 489;

(36, 37αA3-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 489;

(36, 37αA3-c) a protein comprising an amino acid sequence encoded by a nucleotide sequence with deletion, substitution, insertion or addition of one or several nucleotides in SEQ ID NO: 488;

(36, 37αA3-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 488;

(36, 37αA3-e) a protein comprising an amino acid sequence encoded by a nucleic acid that hybridizes under stringent conditions with a nucleic acid having a nucleotide sequence complementary to the nucleotide sequence of SEQ ID NO: 488;

(36, 37αB3) a protein comprising at least one amino acid sequence selected from the group consisting of SEQ ID NOs: 490-493, preferably a protein comprising at least 2, 3, or all sequences of the amino acid sequences. As referred to above, the amino acid sequence of any of SEQ ID NOs: 490 to 493 may be an amino acid sequence derived therefrom by deletion, substitution, insertion or addition of one or several amino acids.

The protein selected from the group consisting of the proteins as defined above in (36, 37αA1-a) to (36, 37αA1-e), (36, 37αB1), (36, 37αA2-a) to (36, 37αA2-e), (36, 37αB2), (36, 37αA3-a) to (36, 37αA3-e), and (36, 37αB3) also include those proteins whose amino acid residues are modified by phosphorylation, sugar chain modification, aminoacylation, ring-opening, deamination or the like.

The protein selected from the group consisting of the proteins as defined above in (36, 37αA1-a) to (36, 37αA1-e), (36, 37αB1), (36, 37αA2-a) to (36, 37αA2-e), (36, 37αB2), (36, 37αA3-a) to (36, 37αA3-e), and (36, 37αB3) can be proteins that are found in a protein spot with a molecular weight of around 10 to 70 kDa, preferably around 20 to 60 kDa, and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 36a or 37a has activity equivalent to that of the protein having the amino acid sequence of SEQ ID NO: 479 (seed maturation protein PM34), the protein having the amino acid sequence of SEQ ID NO: 485 (uncharacterized protein LOC100809384), or the protein having the amino acid sequence of SEQ ID NO: 489 (hypothetical protein GLYMA_10G155300) or causative of an allergy to soybean.

(38α) Antigen in Spot 38α

As the result of sequence identification of the antigen in spot 38a by mass spectroscopy, the following amino acid sequences were detected.

```
                                        (SEQ ID NO: 496)
AAGSTTAQYVGEK

                                        (SEQ ID NO: 497)
ALATGWSAAHYSTEITVEGTK

                                        (SEQ ID NO: 498)
AQVAGSTTVQYAGEK

                                        (SEQ ID NO: 499)
DTIGRVDNITTPLAK

                                        (SEQ ID NO: 500)
DTIGSVDHITTPLAEK

                                        (SEQ ID NO: 501)
ERELASDRARSGNIVK

                                        (SEQ ID NO: 502)
ERYERANQATSEAAK

                                        (SEQ ID NO: 503)
GGGEEQGRRREEIGEENK

                                        (SEQ ID NO: 504)
GLAAAAAGENAK

                                        (SEQ ID NO: 505)
GRVVIESEK

                                        (SEQ ID NO: 506)
GVAEYAGQK

                                        (SEQ ID NO: 507)
LGSAAHTLVK

                                        (SEQ ID NO: 508)
QSSLEEIFK

                                        (SEQ ID NO: 509)
QSSLEEISK

                                        (SEQ ID NO: 510)
REQKPLGSIIGESFQGVQEK

                                        (SEQ ID NO: 511)
TGNETQDIGQK

                                        (SEQ ID NO: 512)
VIVAGEGEK

                                        (SEQ ID NO: 513)
VQQHQGEGGGGVLNAIGETIAEIAETTK
```

Also, the mass spectroscopic data obtained for spot 38a on a mass spectrometer was analyzed by comparing the data against the NCBI protein data, and as a result, seed biotin-containing protein SBP65-like isoform X1 (amino acid sequence: SEQ ID NO: 495, encoding nucleotide sequence: SEQ ID NO: 494) was identified as a protein comprising any of SEQ ID NOs: 496 to 513.

Accordingly, the antigens in spot 38a in the present invention can be any protein selected from the group consisting of the proteins as defined below in (38αA-a) to (38αA-e) and (38αB):

(38αA-a) a protein comprising an amino acid sequence with deletion, substitution, insertion or addition of one or several amino acids in SEQ ID NO: 495;

(38αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 495;

(38αA-c) a protein comprising an amino acid sequence encoded by a nucleotide sequence with deletion, substitution, insertion or addition of one or several nucleotides in SEQ ID NO: 494;

(38αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 494;

(38αA-e) a protein comprising an amino acid sequence encoded by a nucleic acid that hybridizes under stringent conditions with a nucleic acid having a nucleotide sequence complementary to the nucleotide sequence of SEQ ID NO: 494;

(38αB) a protein comprising at least one amino acid sequence selected from the group consisting of SEQ ID NOs: 496-513, preferably a protein comprising at least 2, 3, 4, 5, 6, 7, 8, 9, 10, 11, 12, 13, 14, 15, 16 or 17 or all sequences of the amino acid sequences. As referred to above, the amino acid sequence of any of SEQ ID NOs: 496-513 may be an amino acid sequence derived therefrom by deletion, substitution, insertion or addition of one or several amino acids.

The proteins selected from the group consisting of (38αA-a) to (38αA-e) and (38αB) as defined above also include those proteins whose amino acid residues are modified by phosphorylation, sugar chain modification, aminoacylation, ring-opening, deamination or the like.

The proteins selected from the group consisting of (38αA-a) to (38αA-e) and (38αB) as defined above can be proteins that are found in a protein spot with a molecular weight of around 70 to 170 kDa, preferably around 80 to 160 kDa and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 38a has activity equivalent to that of the protein having the amino acid sequence of SEQ ID NO: 495 (seed biotin-containing protein SBP65-like isoform X1) or causative of an allergy to soybean.

(39α) Antigen in Spot 39α

As the result of sequence identification of the antigen in spot 39α by mass spectroscopy, the following amino acid sequences were detected.

```
                                        (SEQ ID NO: 516)
ETLQEIIGSGAK
```

Also, the mass spectroscopic data obtained for spot 39α on a mass spectrometer was analyzed by comparing the data against the NCBI protein data, and as a result, ATP synthase subunit 0, mitochondrial-like (amino acid sequence: SEQ ID NO: 515, encoding nucleotide sequence: SEQ ID NO: 514) was identified as a protein comprising SEQ ID NO: 516.

Accordingly, the antigens in spot 39α in the present invention can be any protein selected from the group consisting of the proteins as defined below in (39αA-a) to (39αA-e) and (39αB):

(39αA-a) a protein comprising an amino acid sequence with deletion, substitution, insertion or addition of one or several amino acids in SEQ ID NO: 515;

(39αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 515;

(39αA-c) a protein comprising an amino acid sequence encoded by a nucleotide sequence with deletion, substitution, insertion or addition of one or several nucleotides in SEQ ID NO: 514;

(39αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 514;

(39αA-e) a protein comprising an amino acid sequence encoded by a nucleic acid that hybridizes under stringent conditions with a nucleic acid having a nucleotide sequence complementary to the nucleotide sequence of SEQ ID NO: 514;

(39αB) a protein comprising an amino acid sequence of SEQ ID NO: 516. As referred to above, the amino acid sequence(s) of SEQ ID NO: 516 may be an amino acid sequence(s) derived therefrom by deletion, substitution, insertion or addition of one or several amino acids.

The proteins selected from the group consisting of (39αA-a) to (39αA-e) and (39αB) as defined above also include those proteins whose amino acid residues are modified by phosphorylation, sugar chain modification, aminoacylation, ring-opening, deamination or the like.

The proteins selected from the group consisting of (39αA-a) to (39αA-e) and (39αB) as defined above can be proteins that are found in a protein spot with a molecular weight of around 5 to 60 kDa, preferably around 10 to 50 kDa and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 39α has activity equivalent to that of the protein having the amino acid sequence of SEQ ID NO: 515 (ATP synthase subunit 0, mitochondrial-like) or causative of an allergy to soybean.

(40α, 56α) Antigens in Spots 40α, 56α

As the result of sequence identification of the antigens in spots 40α and 56α by mass spectroscopy, the following amino acid sequences were detected.

```
                                        (SEQ ID NO: 519)
EVGQDIQSK

                                        (SEQ ID NO: 520)
RTTVTATTATA
```

Also, the mass spectroscopic data obtained for spots 40a and 56a on a mass spectrometer was analyzed by comparing the data against the NCBI protein data, and as a result, P24 oleosin isoform A (amino acid sequence: SEQ ID NO: 518, encoding nucleotide sequence: SEQ ID NO: 517) was identified as a protein comprising SEQ ID NO: 519 or 520.

Accordingly, the antigens in spot 40a, 56a in the present invention can be any protein selected from the group consisting of the proteins as defined below in (40, 56αA-a) to (40, 56αA-e) and (40, 56αB):

(40, 56αA-a) a protein comprising an amino acid sequence with deletion, substitution, insertion or addition of one or several amino acids in SEQ ID NO: 518;

(40, 56αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 518;

(40, 56αA-c) a protein comprising an amino acid sequence encoded by a nucleotide sequence with deletion, substitution, insertion or addition of one or several nucleotides in SEQ ID NO: 517;

(40, 56αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 517;

(40, 56αA-e) a protein comprising an amino acid sequence encoded by a nucleic acid that hybridizes under stringent conditions with a nucleic acid having a nucleotide sequence complementary to the nucleotide sequence of SEQ ID NO: 517;

(40, 56αB) a protein comprising at least one amino acid sequence selected from the group consisting of SEQ ID NOs: 519 and 520, preferably a protein comprising both the amino acid sequences. As referred to above, the amino acid sequence of any of SEQ ID NOs: 519 and 520 may be an amino acid sequence derived therefrom by deletion, substitution, insertion or addition of one or several amino acids.

The proteins selected from the group consisting of (40, 56αA-a) to (40, 56αA-e) and (40, 56αB) as defined above also include those proteins whose amino acid residues are modified by phosphorylation, sugar chain modification, aminoacylation, ring-opening, deamination or the like.

The proteins selected from the group consisting of (40, 56αA-a) to (40, 56αA-e) and (40, 56αB) as defined above can be proteins that are found in a protein spot with a molecular weight of around 5 to 60 kDa, preferably around 10 to 50 kDa and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 40a or 56a has activity equivalent to that of the protein having the amino acid sequence of SEQ ID NO: 518 (P24 oleosin isoform A) or causative of an allergy to soybean.

(41α) Antigen in Spot 41α

As the result of sequence identification of the antigen in spot 41α by mass spectroscopy, the following amino acid sequences were detected.

```
                                  (SEQ ID NO: 523)
NAYGGSMK
```

Also, the mass spectroscopic data obtained for spot 41a on a mass spectrometer was analyzed by comparing the data against the NCBI protein data, and as a result, uncharacterized protein At3g49720-like isoform X2 (amino acid sequence: SEQ ID NO: 522, encoding nucleotide sequence: SEQ ID NO: 521) was identified as a protein comprising SEQ ID NO: 523.

Accordingly, the antigens in spot 41a in the present invention can be any protein selected from the group consisting of the proteins as defined below in (41αA-a) to (41αA-e) and (41αB):

(41αA-a) a protein comprising an amino acid sequence with deletion, substitution, insertion or addition of one or several amino acids in SEQ ID NO: 522;

(41αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 522;

(41αA-c) a protein comprising an amino acid sequence encoded by a nucleotide sequence with deletion, substitution, insertion or addition of one or several nucleotides in SEQ ID NO: 521;

(41αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 521;

(41αA-e) a protein comprising an amino acid sequence encoded by a nucleic acid that hybridizes under stringent conditions with a nucleic acid having a nucleotide sequence complementary to the nucleotide sequence of SEQ ID NO: 521;

(41αB) a protein comprising an amino acid sequence of SEQ ID NO: 523. As referred to above, the amino acid sequence of SEQ ID NO: 523 may be an amino acid sequence derived therefrom by deletion, substitution, insertion or addition of one or several amino acids.

The proteins selected from the group consisting of (41αA-a) to (41αA-e) and (41αB) as defined above also include those proteins whose amino acid residues are modified by phosphorylation, sugar chain modification, aminoacylation, ring-opening, deamination or the like.

The proteins selected from the group consisting of (41αA-a) to (41αA-e) and (41αB) as defined above can be proteins that are found in a protein spot with a molecular weight of around 5 to 60 kDa, preferably around 10 to 50 kDa and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 41a has activity equivalent to that of the protein having the amino acid sequence of SEQ ID NO: 515 (ATP synthase subunit 0, mitochondrial-like) or causative of an allergy to soybean.

(42α, 43α) Antigen in Spots 42α, 43α

As the result of sequence identification of the antigens in spots 42α and 43α by mass spectroscopy, the following amino acid sequences were detected.

```
                                  (SEQ ID NO: 526)
ALEQLQDAIAK

                                  (SEQ ID NO: 527)
HHQTYITNYNK

                                  (SEQ ID NO: 528)
NLAPVREGGGEPPK

                                  (SEQ ID NO: 529)
NVRPDYLK

                                  (SEQ ID NO: 530)
RLVVETTANQDPLVTK

                                  (SEQ ID NO: 531)
YASEVYEK

                                  (SEQ ID NO: 534)
ALEQLQDAVAK

                                  (SEQ ID NO: 535)
HHQTYITNFNK
```

-continued (SEQ ID NO: 536)
NLAPVREGGGEPPK (SEQ ID NO: 537)
NVRPDYLK (SEQ ID NO: 538)
RLVVETTANQDPLVTK (SEQ ID NO: 539)
YASEVYEK Also, the mass spectroscopic data obtained for spots 42α and 43α on a mass spectrometer was analyzed by comparing the data against the NCBI protein data, and as a result, superoxide dismutase [Mn], mitochondrial (amino acid sequence: SEQ ID NO: 525, encoding nucleotide sequence: SEQ ID NO: 524) was identified as a protein comprising any of SEQ ID NOs: 526 to 531 and hypothetical protein GLYMA_04G221300 (amino acid sequence: SEQ ID NO: 533, encoding nucleotide sequence: SEQ ID NO: 532) was identified as a protein comprising any of SEQ ID NOs: 534 to 539.

Accordingly, the antigen in spot 42a, 43a in the present invention can be any of proteins selected from the group consisting of the proteins as defined below in (42, 43αA1-a) to (42, 43αA1-e), (42, 43αB1), (42, 43αA2-a) to (42, 43αA2-e), and (42, 43αB2):

(42, 43αA1-a) a protein comprising an amino acid sequence with deletion, substitution, insertion or addition of one or several amino acids in SEQ ID NO: 525;

(42, 43αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 525;

(42, 43αA1-c) a protein comprising an amino acid sequence encoded by a nucleotide sequence with deletion, substitution, insertion or addition of one or several nucleotides in SEQ ID NO: 524;

(42, 43αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 524;

(42, 43αA1-e) a protein comprising an amino acid sequence encoded by a nucleic acid that hybridizes under stringent conditions with a nucleic acid having a nucleotide sequence complementary to the nucleotide sequence of SEQ ID NO: 524;

(42, 43αB1) a protein comprising at least one amino acid sequence selected from the group consisting of SEQ ID NOs: 526-531, preferably a protein comprising at least 2, 3, 4, or 5 or all sequences of the amino acid sequences. As referred to above, the amino acid sequence of any of SEQ ID NOs: 526 to 531 may be an amino acid sequence derived therefrom by deletion, substitution, insertion or addition of one or several amino acids;

(42, 43αA2-a) a protein comprising an amino acid sequence with deletion, substitution, insertion or addition of one or several amino acids in SEQ ID NO: 533;

(42, 43αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 533;

(42, 43αA2-c) a protein comprising an amino acid sequence encoded by a nucleotide sequence with deletion, substitution, insertion or addition of one or several nucleotides in SEQ ID NO: 532;

(42, 43αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 532;

(42, 43αA2-e) a protein comprising an amino acid sequence encoded by a nucleic acid that hybridizes under stringent conditions with a nucleic acid having a nucleotide sequence complementary to the nucleotide sequence of SEQ ID NO: 532;

(42, 43αB2) a protein comprising at least one amino acid sequence selected from the group consisting of SEQ ID NOs: 534-539, preferably a protein comprising at least 2, 3, 4, or 5 or all sequences of the amino acid sequences. As referred to above, the amino acid sequence of any of SEQ ID NOs: 534 to 539 may be an amino acid sequence derived therefrom by deletion, substitution, insertion or addition of one or several amino acids.

The protein selected from the group consisting of the proteins as defined above in (42, 43αA1-a) to (42, 43αA1-e), (42, 43αB1), (42, 43αA2-a) to (42, 43αA2-e), and (42, 43αB2) also include those proteins whose amino acid residues are modified by phosphorylation, sugar chain modification, aminoacylation, ring-opening, deamination or the like.

The protein selected from the group consisting of the proteins as defined above in (42, 43αA1-a) to (42, 43αA1-e), (42, 43αB1), (42, 43αA2-a) to (42, 43αA2-e), and (42, 43αB2) can be proteins that are found in a protein spot with a molecular weight of around 5 to 60 kDa, preferably around 10 to 50 kDa, and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 42a or 43a has activity equivalent to that of the protein having the amino acid sequence of SEQ ID NO: 525 (superoxide dismutase [Mn], mitochondrial) or the protein having the amino acid sequence of SEQ ID NO: 533 (hypothetical protein GLYMA_04G221300) or causative of an allergy to soybean.

(45α) Antigen in Spot 45α

As the result of sequence identification of the antigen in spot 45α by mass spectroscopy, the following amino acid sequences were detected.

(SEQ ID NO: 542)
HVPGFIERAEELK (SEQ ID NO: 543)
RFALLVEDLK (SEQ ID NO: 544)
VANVESGGEFTISSAEEIIK (SEQ ID NO: 545)
YTNALGLELDLTDK

-continued (SEQ ID NO: 548)
HVPGFIERAEELK (SEQ ID NO: 549)
RFALLVEDLK (SEQ ID NO: 550)
VANVESGGEFTISSAEEIIK (SEQ ID NO: 551)
YTNALGLELDLTDK Also, the mass spectroscopic data obtained for spot 45α on a mass spectrometer was analyzed by comparing the data against the NCBI protein data, and as a result, uncharacterized protein LOC100499771 (amino acid sequence: SEQ ID NO: 541, encoding nucleotide sequence: SEQ ID NO: 540) was identified as a protein comprising any of SEQ ID NOs: 542 to 545 and hypothetical protein GLYMA_09G192800 (amino acid sequence: SEQ ID NO: 547, encoding nucleotide sequence: SEQ ID NO: 546) was identified as a protein comprising any of SEQ ID NOs: 548 to 551.

Accordingly, the antigen in spot 45α in the present invention can be any of proteins selected from the group consisting of the proteins as defined below in (45αA1-a) to (45αA1-e), (45αB1), (45αA2-a) to (45αA2e), and (45αB2):

(45αA1-a) a protein comprising an amino acid sequence with deletion, substitution, insertion or addition of one or several amino acids in SEQ ID NO: 541;

(45αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 541;

(45αA1-c) a protein comprising an amino acid sequence encoded by a nucleotide sequence with deletion, substitution, insertion or addition of one or several nucleotides in SEQ ID NO: 540;

(45αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 540;

(45αA1-e) a protein comprising an amino acid sequence encoded by a nucleic acid that hybridizes under stringent conditions with a nucleic acid having a nucleotide sequence complementary to the nucleotide sequence of SEQ ID NO: 540;

(45αB1) a protein comprising at least one amino acid sequence selected from the group consisting of SEQ ID NOs: 542-545, preferably a protein comprising at least 2, 3, or all sequences of the amino acid sequences. As referred to above, the amino acid sequence of any of SEQ ID NOs: 542 to 545 may be an amino acid sequence derived therefrom by deletion, substitution, insertion or addition of one or several amino acids;

(45αA2-a) a protein comprising an amino acid sequence with deletion, substitution, insertion or addition of one or several amino acids in SEQ ID NO: 547;

(45αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 547;

(45αA2-c) a protein comprising an amino acid sequence encoded by a nucleotide sequence with deletion, substitution, insertion or addition of one or several nucleotides in SEQ ID NO: 546;

(45αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 546;

(45αA2-e) a protein comprising an amino acid sequence encoded by a nucleic acid that hybridizes under stringent conditions with a nucleic acid having a nucleotide sequence complementary to the nucleotide sequence of SEQ ID NO: 546;

(45αB2) a protein comprising at least one amino acid sequence selected from the group consisting of SEQ ID NOs: 548-551, preferably a protein comprising at least 2, 3, or all sequences of the amino acid sequences. As referred to above, the amino acid sequence of any of SEQ ID NOs: 548 to 551 may be an amino acid sequence derived therefrom by deletion, substitution, insertion or addition of one or several amino acids.

The protein selected from the group consisting of the proteins as defined above in (45αA1-a) to (45αA1-e), (45αB1), (45αA2-a) to (45αA2-e), and (45αB2) also include those proteins whose amino acid residues are modified by phosphorylation, sugar chain modification, aminoacylation, ring-opening, deamination or the like.

The protein selected from the group consisting of the proteins as defined above in (45αA1-a) to (45αA1-e), (45αB1), (45αA2-a) to (45αA2-e), and (45αB2) can be proteins that are found in a protein spot with a molecular weight of around 2 to 50 kDa, preferably around 5 to 40 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 45α has activity equivalent to that of the protein having the amino acid sequence of SEQ ID NO: 541 (uncharacterized protein LOC100499771) or the protein having the amino acid sequence of SEQ ID NO: 547 (hypothetical protein GLYMA_09G192800) or causative of an allergy to soybean.

(46α) Antigen in Spot 46α

As the result of sequence identification of the antigen in spot 46α by mass spectroscopy, the following amino acid sequences were detected.

(SEQ ID NO: 554)
DNVEYLAK

Also, the mass spectroscopic data obtained for spot 46a on a mass spectrometer was analyzed by comparing the data against the NCBI protein data, and as a result, seed maturation protein PM22 (amino acid sequence: SEQ ID NO: 553, encoding nucleotide sequence: SEQ ID NO: 552) was identified as a protein comprising SEQ ID NO: 554.

Accordingly, the antigens in spot 46a in the present invention can be any protein selected from the group consisting of the proteins as defined below in (46αA-a) to (46αA-e) and (46αB):

(46αA-a) a protein comprising an amino acid sequence with deletion, substitution, insertion or addition of one or several amino acids in SEQ ID NO: 553;

(46αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 553;

(46αA-c) a protein comprising an amino acid sequence encoded by a nucleotide sequence with deletion, substitution, insertion or addition of one or several nucleotides in SEQ ID NO: 552;

(46αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 552;

(46αA-e) a protein comprising an amino acid sequence encoded by a nucleic acid that hybridizes under stringent conditions with a nucleic acid having a nucleotide sequence complementary to the nucleotide sequence of SEQ ID NO: 552;

(46αB) a protein comprising an amino acid sequence of SEQ ID NO: 554. As referred to above, the amino acid sequence(s) of SEQ ID NO: 554 may be an amino acid sequence(s) derived therefrom by deletion, substitution, insertion or addition of one or several amino acids.

The proteins selected from the group consisting of (46αA-a) to (46αA-e) and (46αB) as defined above also include those proteins whose amino acid residues are modified by phosphorylation, sugar chain modification, aminoacylation, ring-opening, deamination or the like.

The proteins selected from the group consisting of (46αA-a) to (46αA-e) and (46αB) as defined above can be proteins that are found in a protein spot with a molecular weight of around 2 to 50 kDa, preferably around 5 to 40 kDa and an isoelectric point of 3.5 to 7.5, preferably 4.0 to 7.0 on gels used in the two-dimensional electrophoresis performed under the conditions described above in the subsection titled “Identification of antigens”.

Preferably, a protein that is an antigen in spot 46a has activity equivalent to that of the protein having the amino acid sequence of SEQ ID NO: 553 (seed maturation protein PM22) or causative of an allergy to soybean.

(47α) Antigen in Spot 47α

As the result of sequence identification of the antigen in spot 47a by mass spectroscopy, the following amino acid sequences were detected.

```
                                    (SEQ ID NO: 557)
LPTDESLLTQIK

                                    (SEQ ID NO: 558)
NGYIVIK

                                    (SEQ ID NO: 561)
NGYIVIK

                                    (SEQ ID NO: 562)
TYPQQAGTIRK

                                    (SEQ ID NO: 563)
VVEVSTSK
```

Also, the mass spectroscopic data obtained for spot 47a on a mass spectrometer was analyzed by comparing the data against the NCBI protein data, and as a result, eukaryotic translation initiation factor 5A-2 (amino acid sequence: SEQ ID NO: 556, encoding nucleotide sequence: SEQ ID NO: 555) was identified as a protein comprising SEQ ID NO: 557 or 558 and uncharacterized protein LOC100305510 (amino acid sequence: SEQ ID NO: 560, encoding nucleotide sequence: SEQ ID NO: 559) was identified as a protein comprising any of SEQ ID NOs: 561 to 563.

Accordingly, the antigen in spot 47a in the present invention can be any of proteins selected from the group consisting of the proteins as defined below in (47αA1-a) to (47αA1-e), (47αB1), (47αA2-a) to (47αA2-e), and (47αB2):

(47αA1-a) a protein comprising an amino acid sequence with deletion, substitution, insertion or addition of one or several amino acids in SEQ ID NO: 556;

(47αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 556;

(47αA1-c) a protein comprising an amino acid sequence encoded by a nucleotide sequence with deletion, substitution, insertion or addition of one or several nucleotides in SEQ ID NO: 555;

(47αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 555;

(47αA1-e) a protein comprising an amino acid sequence encoded by a nucleic acid that hybridizes under stringent conditions with a nucleic acid having a nucleotide sequence complementary to the nucleotide sequence of SEQ ID NO: 555;

(47αB1) a protein comprising at least one amino acid sequence selected from the group consisting of SEQ ID NOs: 557 and 558, preferably a protein comprising both the amino acid sequences. As referred to above, the amino acid sequence of any of SEQ ID NOs: 557, 558 may be an amino acid sequence derived therefrom by deletion, substitution, insertion or addition of one or several amino acids;

(47αA2-a) a protein comprising an amino acid sequence with deletion, substitution, insertion or addition of one or several amino acids in SEQ ID NO: 560;

(47αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 560;

(47αA2-c) a protein comprising an amino acid sequence encoded by a nucleotide sequence with deletion, substitution, insertion or addition of one or several nucleotides in SEQ ID NO: 559;

(47αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 559;

(47αA2-e) a protein comprising an amino acid sequence encoded by a nucleic acid that hybridizes under stringent conditions with a nucleic acid having a nucleotide sequence complementary to the nucleotide sequence of SEQ ID NO: 559;

(47αB2) a protein comprising at least one amino acid sequence selected from the group consisting of SEQ ID NOs: 561-563, preferably a protein comprising at least 2, or all sequences of the amino acid sequences. As referred to above, the amino acid sequence of any of SEQ ID NOs: 561-563 may be an amino acid sequence derived therefrom by deletion, substitution, insertion or addition of one or several amino acids.

The protein selected from the group consisting of the proteins as defined above in (47αA1-a) to (47αA1-e), (47αB1), (47αA2-a) to (47αA2-e), and (47αB2) also include those proteins whose amino acid residues are modified by phosphorylation, sugar chain modification, aminoacylation, ring-opening, deamination or the like.

The protein selected from the group consisting of the proteins as defined above in (47αA1-a) to (47αA1-e), (47αB1), (47αA2-a) to (47αA2-e), and (47αB2) can be proteins that are found in a protein spot with a molecular weight of around 2 to 50 kDa, preferably around 5 to 40 kDa, and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 47a has activity equivalent to that of the protein having the amino acid sequence of SEQ ID NO: 556 (eukaryotic translation initiation factor 5A-2) or the protein having the amino acid sequence of SEQ ID NO: 560 (uncharacterized protein LOC100305510) or causative of an allergy to soybean.

(48α) Antigen in Spot 48α

As the result of sequence identification of the antigen in spot 48α by mass spectroscopy, the following amino acid sequences were detected.

```
                                        (SEQ ID NO: 566)
AEFPIFDK

                                        (SEQ ID NO: 567)
DARGNNVNLADYK

                                        (SEQ ID NO: 568)
DGNVVDRYAPTTSPLSIEK

                                        (SEQ ID NO: 569)
GGLFGDSIK

                                        (SEQ ID NO: 570)
VDVNGDNAAPLYK
```

Also, the mass spectroscopic data obtained for spot 48α on a mass spectrometer was analyzed by comparing the data against the NCBI protein data, and as a result, uncharacterized protein LOC100306570 (amino acid sequence: SEQ ID NO: 565, encoding nucleotide sequence: SEQ ID NO: 564) was identified as a protein comprising any of SEQ ID NOs: 566 to 570.

Accordingly, the antigens in spot 48α in the present invention can be any protein selected from the group consisting of the proteins as defined below in (48αA-a) to (48αA-e) and (48αB):

(48αA-a) a protein comprising an amino acid sequence with deletion, substitution, insertion or addition of one or several amino acids in SEQ ID NO: 565;

(48αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 565;

(48αA-c) a protein comprising an amino acid sequence encoded by a nucleotide sequence with deletion, substitution, insertion or addition of one or several nucleotides in SEQ ID NO: 564;

(48αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 564;

(48αA-e) a protein comprising an amino acid sequence encoded by a nucleic acid that hybridizes under stringent conditions with a nucleic acid having a nucleotide sequence complementary to the nucleotide sequence of SEQ ID NO: 564;

(48αB) a protein comprising at least one amino acid sequence selected from the group consisting of SEQ ID NOs: 566-570, preferably a protein comprising at least 2, 3 or 4 or all sequences of the amino acid sequences. As referred to above, the amino acid sequence of any of SEQ ID NOs: 566-570 may be an amino acid sequence derived therefrom by deletion, substitution, insertion or addition of one or several amino acids.

The proteins selected from the group consisting of (48αA-a) to (48αA-e) and (48αB) as defined above also include those proteins whose amino acid residues are modified by phosphorylation, sugar chain modification, aminoacylation, ring-opening, deamination or the like.

The proteins selected from the group consisting of (48αA-a) to (48αA-e) and (48αB) as defined above can be proteins that are found in a protein spot with a molecular weight of around 2 to 50 kDa, preferably around 5 to 40 kDa and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 48α has activity equivalent to that of the protein having the amino acid sequence of SEQ ID NO: 565 (uncharacterized protein LOC100306570) or causative of an allergy to soybean.

(50α) Antigen in Spot 50α

As the result of sequence identification of the antigen in spot 50α by mass spectroscopy, the following amino acid sequences were detected.

```
                                        (SEQ ID NO: 573)
AADYLHNYQGDNTTAPSQPAESK

                                        (SEQ ID NO: 574)
LVAEAAQSALK

                                        (SEQ ID NO: 575)
QGIGQYVDK

                                        (SEQ ID NO: 576)
VADAAGDLLDAAGK
```

Also, the mass spectroscopic data obtained for spot 50a on a mass spectrometer was analyzed by comparing the data against the NCBI protein data, and as a result, uncharacterized protein LOC100813859 (amino acid sequence: SEQ ID NO: 572, encoding nucleotide sequence: SEQ ID NO: 571) was identified as a protein comprising any of SEQ ID NOs: 573 to 576.

Accordingly, the antigens in spot 50a in the present invention can be any protein selected from the group consisting of the proteins as defined below in (50αA-a) to (50αA-e) and (50αB):

(50αA-a) a protein comprising an amino acid sequence with deletion, substitution, insertion or addition of one or several amino acids in SEQ ID NO: 572;

(50αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 572;

(50αA-c) a protein comprising an amino acid sequence encoded by a nucleotide sequence with deletion, substitution, insertion or addition of one or several nucleotides in SEQ ID NO: 571;

(50αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 571;

(50αA-e) a protein comprising an amino acid sequence encoded by a nucleic acid that hybridizes under stringent conditions with a nucleic acid having a nucleotide sequence complementary to the nucleotide sequence of SEQ ID NO: 571;

(50αB) a protein comprising at least one amino acid sequence selected from the group consisting of SEQ ID NOs: 573-576, preferably a protein comprising at least 2 or 3 or all sequences of the amino acid sequences. As referred to above, the amino acid sequence of any of SEQ ID NOs: 573-576 may be an amino acid sequence derived therefrom by deletion, substitution, insertion or addition of one or several amino acids.

The proteins selected from the group consisting of (50αA-a) to (50αA-e) and (50αB) as defined above also include those proteins whose amino acid residues are modified by phosphorylation, sugar chain modification, aminoacylation, ring-opening, deamination or the like.

The proteins selected from the group consisting of (50αA-a) to (50αA-e) and (50αB) as defined above can be proteins that are found in a protein spot with a molecular weight of around 2 to 50 kDa, preferably around 5 to 40 kDa and an isoelectric point of 2.5 to 6.5, preferably 3.0 to 6.0 on gels used in the two-dimensional electrophoresis performed under the conditions described above in the subsection titled "Identification of antigens".

Preferably, a protein that is an antigen in spot 50a has activity equivalent to that of the protein having the amino acid sequence of SEQ ID NO: 572 (uncharacterized protein LOC100813859) or causative of an allergy to soybean.

(51α) Antigen in Spot 51α

As the result of sequence identification of the antigen in spot 51α by mass spectroscopy, the following amino acid sequences were detected.

```
                                       (SEQ ID NO: 579)
EAAESTLSAYK

                                       (SEQ ID NO: 580)
LLDSRLIPSASSGDSK

                                       (SEQ ID NO: 581)
QAFDEAIAELDTLGEESYK

                                       (SEQ ID NO: 582)
VSAAADNEELTVEERNLLSVAYK
```

Also, the mass spectroscopic data obtained for spot 51α on a mass spectrometer was analyzed by comparing the data against the NCBI protein data, and as a result, 14-3-3-like protein (amino acid sequence: SEQ ID NO: 578, encoding nucleotide sequence: SEQ ID NO: 577) was identified as a protein comprising any of SEQ ID NOs: 579 to 582.

Accordingly, the antigens in spot 51α in the present invention can be any protein selected from the group consisting of the proteins as defined below in (51αA-a) to (51αA-e) and (51αB):

(51αA-a) a protein comprising an amino acid sequence with deletion, substitution, insertion or addition of one or several amino acids in SEQ ID NO: 578;

(51αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 578;

(51αA-c) a protein comprising an amino acid sequence encoded by a nucleotide sequence with deletion, substitution, insertion or addition of one or several nucleotides in SEQ ID NO: 577;

(51αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 577;

(51αA-e) a protein comprising an amino acid sequence encoded by a nucleic acid that hybridizes under stringent conditions with a nucleic acid having a nucleotide sequence complementary to the nucleotide sequence of SEQ ID NO: 577;

(51αB) a protein comprising at least one amino acid sequence selected from the group consisting of SEQ ID NOs: 579-582, preferably a protein comprising at least 2 or 3 or all sequences of the amino acid sequences. As referred to above, the amino acid sequence of any of SEQ ID NOs: 579-582 may be an amino acid sequence derived therefrom by deletion, substitution, insertion or addition of one or several amino acids.

The proteins selected from the group consisting of (51αA-a) to (51αA-e) and (51αB) as defined above also include those proteins whose amino acid residues are modified by phosphorylation, sugar chain modification, aminoacylation, ring-opening, deamination or the like.

The proteins selected from the group consisting of (51αA-a) to (51αA-e) and (51αB) as defined above can be proteins that are found in a protein spot with a molecular weight of around 5 to 60 kDa, preferably around 10 to 50 kDa and an isoelectric point of 2.5 to 6.5, preferably 3.0 to 6.0 on gels used in the two-dimensional electrophoresis performed under the conditions described above in the subsection titled "Identification of antigens".

Preferably, a protein that is an antigen in spot 51α has activity equivalent to that of the protein having the amino acid sequence of SEQ ID NO: 578 (14-3-3-like protein) or causative of an allergy to soybean.

(52α) Antigen in Spot 52α

As the result of sequence identification of the antigen in spot 52α by mass spectroscopy, the following amino acid sequences were detected.

```
                                       (SEQ ID NO: 585)
APGGAPANVAIAVSRLGGK

                                       (SEQ ID NO: 586)
GSVDAFHVNTVDTTGAGDSFVGALLAK

                                       (SEQ ID NO: 587)
IVDDQSILEDEPRLREVLK

                                       (SEQ ID NO: 588)
VSDAELEFLTGSDK
```

Also, the mass spectroscopic data obtained for spot 52α on a mass spectrometer was analyzed by comparing the data against the NCBI protein data, and as a result, probable fructokinase-4 (amino acid sequence: SEQ ID NO: 584, encoding nucleotide sequence: SEQ ID NO: 583) was identified as a protein comprising any of SEQ ID NOs: 585 to 588.

Accordingly, the antigens in spot 52α in the present invention can be any protein selected from the group consisting of the proteins as defined below in (52αA-a) to (52αA-e) and (52αB):

(52αA-a) a protein comprising an amino acid sequence with deletion, substitution, insertion or addition of one or several amino acids in SEQ ID NO: 584;

(52αA-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 584;

(52αA-c) a protein comprising an amino acid sequence encoded by a nucleotide sequence with deletion, substitution, insertion or addition of one or several nucleotides in SEQ ID NO: 583;

(52αA-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 583;

(52αA-e) a protein comprising an amino acid sequence encoded by a nucleic acid that hybridizes under stringent conditions with a nucleic acid having a nucleotide sequence complementary to the nucleotide sequence of SEQ ID NO: 583;

(52αB) a protein comprising at least one amino acid sequence selected from the group consisting of SEQ ID NOs: 585-588, preferably a protein comprising at least 2 or 3 or all sequences of the amino acid sequences. As referred to above, the amino acid sequence of any of SEQ ID NOs: 585-588 may be an amino acid sequence derived therefrom by deletion, substitution, insertion or addition of one or several amino acids.

The proteins selected from the group consisting of (52αA-a) to (52αA-e) and (52αB) as defined above also include those proteins whose amino acid residues are modified by phosphorylation, sugar chain modification, aminoacylation, ring-opening, deamination or the like.

The proteins selected from the group consisting of (52αA-a) to (52αA-e) and (52αB) as defined above can be proteins that are found in a protein spot with a molecular weight of around 5 to 60 kDa, preferably around 10 to 50 kDa and an isoelectric point of 3.5 to 7.5, preferably 4.0 to 7.0 on gels used in the two-dimensional electrophoresis performed under the conditions described above in the subsection titled "Identification of antigens".

Preferably, a protein that is an antigen in spot 52α has activity equivalent to that of the protein having the amino acid sequence of SEQ ID NO: 584 (probable fructokinase-4) or causative of an allergy to soybean.

(53α) Antigen in Spot 53α

As the result of sequence identification of the antigen in spot 53α by mass spectroscopy, the following amino acid sequences were detected.

```
                                    (SEQ ID NO: 591)
AEFVDIINAATVK

                                    (SEQ ID NO: 592)
ELAAQPDVDGFLVGGASLK
```

-continued

```
                                    (SEQ ID NO: 593)
FFVGGNWK

                                    (SEQ ID NO: 594)
IVTTLNEAK

                                    (SEQ ID NO: 595)
VATPAQAQEVHADLRK

                                    (SEQ ID NO: 596)
VAYALQQGLK

                                    (SEQ ID NO: 597)
VPGEDVVEVVVSPPFVFLPFVK

                                    (SEQ ID NO: 600)
ELAAQPDVDGFLVGGASLKPEFVDIINAATVK

                                    (SEQ ID NO: 601)
FFVGGNWK

                                    (SEQ ID NO: 602)
IVTTLNEAK

                                    (SEQ ID NO: 603)
VATPAQAQEVHADLRK

                                    (SEQ ID NO: 604)
VAYALQQGLK
```

Also, the mass spectroscopic data obtained for spot 53α on a mass spectrometer was analyzed by comparing the data against the NCBI protein data, and as a result, triosephosphate isomerase isoform X1 (amino acid sequence: SEQ ID NO: 590, encoding nucleotide sequence: SEQ ID NO: 589) was identified as a protein comprising any of SEQ ID NOs: 591 to 597 and triosephosphate isomerase, cytosolic (amino acid sequence: SEQ ID NO: 599, encoding nucleotide sequence: SEQ ID NO: 598) was identified as a protein comprising any of SEQ ID NOs: 600 to 604.

Accordingly, the antigen in spot 53α in the present invention can be any of proteins selected from the group consisting of the proteins as defined below in (53αA1-a) to (53αA1-e), (53αB1), (53αA2-a) to (53αA2-e), and (53αB2):

(53αA1-a) a protein comprising an amino acid sequence with deletion, substitution, insertion or addition of one or several amino acids in SEQ ID NO: 590;

(53αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 590;

(53αA1-c) a protein comprising an amino acid sequence encoded by a nucleotide sequence with deletion, substitution, insertion or addition of one or several nucleotides in SEQ ID NO: 589;

(53αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 589;

(53αA1-e) a protein comprising an amino acid sequence encoded by a nucleic acid that hybridizes under stringent conditions with a nucleic acid having a nucleotide sequence complementary to the nucleotide sequence of SEQ ID NO: 589;

(53αB1) a protein comprising at least one amino acid sequence selected from the group consisting of SEQ ID NOs: 591-597, preferably a protein comprising at least 2, 3, 4, 5, or 6 or all sequences of the amino acid sequences. As referred to above, the amino acid sequence of any of SEQ ID NOs: 591 to 597 may be an amino acid sequence derived therefrom by deletion, substitution, insertion or addition of one or several amino acids;

(53αA2-a) a protein comprising an amino acid sequence with deletion, substitution, insertion or addition of one or several amino acids in SEQ ID NO: 599;

(53αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 599;

(53αA2-c) a protein comprising an amino acid sequence encoded by a nucleotide sequence with deletion, substitution, insertion or addition of one or several nucleotides in SEQ ID NO: 598;

(53αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 598;

(53αA2-e) a protein comprising an amino acid sequence encoded by a nucleic acid that hybridizes under stringent conditions with a nucleic acid having a nucleotide sequence complementary to the nucleotide sequence of SEQ ID NO: 598;

(53αB2) a protein comprising at least one amino acid sequence selected from the group consisting of SEQ ID NOs: 600-604, preferably a protein comprising at least 2, 3, or 4 or all sequences of the amino acid sequences. As referred to above, the amino acid sequence of any of SEQ ID NOs: 600 to 604 may be an amino acid sequence derived therefrom by deletion, substitution, insertion or addition of one or several amino acids.

The protein selected from the group consisting of the proteins as defined above in (53αA1-a) to (53αA1-e), (53αB1), (53αA2-a) to (53αA2-e), and (53αB2) also include those proteins whose amino acid residues are modified by phosphorylation, sugar chain modification, aminoacylation, ring-opening, deamination or the like.

The protein selected from the group consisting of the proteins as defined above in (53αA1-a) to (53αA1-e), (53αB1), (53αA2-a) to (53αA2-e), and (53αB2) can be proteins that are found in a protein spot with a molecular weight of around 5 to 60 kDa, preferably around 10 to 50 kDa, and an isoelectric point of 3.5 to 8.5, preferably 4.0 to 8.0 on gels used in the two-dimensional electrophoresis performed under the conditions described above in the subsection titled "Identification of antigens".

Preferably, a protein that is an antigen in spot 53α has activity equivalent to that of the protein having the amino acid sequence of SEQ ID NO: 590 (triosephosphate isomerase isoform X1) or the protein having the amino acid sequence of SEQ ID NO: 599 (triosephosphate isomerase, cytosolic) or causative of an allergy to soybean.

(54α) Antigen in Spot 54α

As the result of sequence identification of the antigen in spot 54α by mass spectroscopy, the following amino acid sequences were detected.

```
                                     (SEQ ID NO: 607)
FDGENVANPPSPDEDNK

                                     (SEQ ID NO: 608)
LVSWDAVSSRLEQAK

                                     (SEQ ID NO: 609)
QVVGTELDGK

                                     (SEQ ID NO: 610)
SLEEIIVTSYNK

                                     (SEQ ID NO: 611)
TYVENLK

                                     (SEQ ID NO: 614)
QIVGTELDGK

                                     (SEQ ID NO: 615)
SLEEIIVTSYNK

                                     (SEQ ID NO: 616)
TYVENLK
```

Also, the mass spectroscopic data obtained for spot 54α on a mass spectrometer was analyzed by comparing the data against the NCBI protein data, and as a result, superoxide dismutase [Fe], chloroplastic isoform X1 (amino acid sequence: SEQ ID NO: 606, encoding nucleotide sequence: SEQ ID NO: 605) as a protein comprising any of SEQ ID NOs: 607 to 611 and iron-superoxide dismutase (amino acid sequence: SEQ ID NO: 613, encoding nucleotide sequence: SEQ ID NO: 612) was identified as a protein comprising any of SEQ ID NOs: 614 to 616.

Accordingly, the antigen in spot 54α in the present invention can be any of proteins selected from the group consisting of the proteins as defined below in (54αA1-a) to (54αA1-e), (54αB1), (54αA2-a) to (54αA2-e), and (54αB2):

(54αA1-a) a protein comprising an amino acid sequence with deletion, substitution, insertion or addition of one or several amino acids in SEQ ID NO: 606;

(54αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 606;

(54αA1-c) a protein comprising an amino acid sequence encoded by a nucleotide sequence with deletion, substitution, insertion or addition of one or several nucleotides in SEQ ID NO: 605;

(54αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 605;

(54αA1-e) a protein comprising an amino acid sequence encoded by a nucleic acid that hybridizes under stringent conditions with a nucleic acid having a nucleotide sequence complementary to the nucleotide sequence of SEQ ID NO: 605;

(54αB1) a protein comprising at least one amino acid sequence selected from the group consisting of SEQ ID NOs: 607-611, preferably a protein comprising at least 2, 3, or 4 or all sequences of the amino acid sequences. As referred to above, the amino acid sequence of any of SEQ ID NOs: 607-611 may be an amino acid sequence derived therefrom by deletion, substitution, insertion or addition of one or several amino acids;

(54αA2-a) a protein comprising an amino acid sequence with deletion, substitution, insertion or addition of one or several amino acids in SEQ ID NO: 613;

(54αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 613;

(54αA2-c) a protein comprising an amino acid sequence encoded by a nucleotide sequence with deletion, substitution, insertion or addition of one or several nucleotides in SEQ ID NO: 612;

(54αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 612;

(54αA2-e) a protein comprising an amino acid sequence encoded by a nucleic acid that hybridizes under stringent conditions with a nucleic acid having a nucleotide sequence complementary to the nucleotide sequence of SEQ ID NO: 612;

(54αB2) a protein comprising at least one amino acid sequence selected from the group consisting of SEQ ID NOs: 614-616, preferably a protein comprising at least 2, or all sequences of the amino acid sequences. As referred to above, the amino acid sequence of any of SEQ ID NOs: 614 to 616 may be an amino acid sequence derived therefrom by deletion, substitution, insertion or addition of one or several amino acids.

The protein selected from the group consisting of the proteins as defined above in (54αA1-a) to (54αA1-e), (54B1), (54αA2-a) to (54αA2-e), and (54αB2) also include those proteins whose amino acid residues are modified by phosphorylation, sugar chain modification, aminoacylation, ring-opening, deamination or the like.

The protein selected from the group consisting of the proteins as defined above in (54αA1-a) to (54αA1-e), (54B1), (54αA2-a) to (54αA2-e), and (54αB2) can be proteins that are found in a protein spot with a molecular weight of around 5 to 60 kDa, preferably around 10 to 50 kDa, and an isoelectric point of 3.5 to 8.5, preferably 4.0 to 8.0 on gels used in the two-dimensional electrophoresis performed under the conditions described above in the subsection titled “Identification of antigens”.

Preferably, a protein that is an antigen in spot 54α has activity equivalent to that of the protein having the amino acid sequence of SEQ ID NO: 606 (superoxide dismutase [Fe], chloroplastic isoform X1) or the protein having the amino acid sequence of SEQ ID NO: 613 (iron-superoxide dismutase) or causative of an allergy to soybean.

(55α) Antigen in Spot 55α

As the result of sequence identification of the antigen in spot 55α by mass spectroscopy, the following amino acid sequences were detected.

```
                                        (SEQ ID NO: 619)
DYAGDAAQNVK

                                        (SEQ ID NO: 620)
DYASDAAQK

                                        (SEQ ID NO: 621)
DYASDATDAAK

                                        (SEQ ID NO: 622)
DYASDAVQK
```

-continued

```
                                        (SEQ ID NO: 623)
DYASDTAQRTK

                                        (SEQ ID NO: 624)
DYASDTAQTSK

                                        (SEQ ID NO: 625)
DYASEASDVAQNTK

                                        (SEQ ID NO: 626)
DYATDAAQK

                                        (SEQ ID NO: 627)
DYVGDAAQRSK

                                        (SEQ ID NO: 628)
EASDYASETAK

                                        (SEQ ID NO: 629)
EYAGDVALNAK

                                        (SEQ ID NO: 630)
EYVGDAAQK

                                        (SEQ ID NO: 631)
GAAEYASDAAQRTK

                                        (SEQ ID NO: 632)
GYVGDAAQK

                                        (SEQ ID NO: 633)
LQDIASEAGQYSAEK

                                        (SEQ ID NO: 634)
LSEGLGFK

                                        (SEQ ID NO: 635)
VSDYATDTAQK

                                        (SEQ ID NO: 638)
DYAGDAVQNIK

                                        (SEQ ID NO: 639)
DYASDAAQRTK

                                        (SEQ ID NO: 640)
DYASDATDAAK

                                        (SEQ ID NO: 641)
DYASDTAQRTK

                                        (SEQ ID NO: 642)
DYVGDAAQK

                                        (SEQ ID NO: 643)
EASDYASETAQK

                                        (SEQ ID NO: 644)
EASEYASDAAQRTK

                                        (SEQ ID NO: 645)
EYAGDVAQNAK

                                        (SEQ ID NO: 646)
GYVGDAAQK

                                        (SEQ ID NO: 647)
LQDIASEAGQYSTEK

                                        (SEQ ID NO: 648)
LTEGLGFK

                                        (SEQ ID NO: 649)
VSDYAGDAAQK
```

Also, the mass spectroscopic data obtained for spot 55a on a mass spectrometer was analyzed by comparing the data against the NCBI protein data, and as a result, 51 kDa seed maturation protein precursor (amino acid sequence: SEQ ID NO: 618, encoding nucleotide sequence: SEQ ID NO: 617)

was identified as a protein comprising any of SEQ ID NOs: 619 to 635 and Lea protein precursor (amino acid sequence: SEQ ID NO: 637, encoding nucleotide sequence: SEQ ID NO: 636) was identified as a protein comprising any of SEQ ID NOs: 638 to 649.

Accordingly, the antigen in spot 55a in the present invention can be any of proteins selected from the group consisting of the proteins as defined below in (55αA1-a) to (55αA1-e), (55αB1), (55αA2-a) to (55αA2-e), and (55αB2):

(55αA1-a) a protein comprising an amino acid sequence with deletion, substitution, insertion or addition of one or several amino acids in SEQ ID NO: 618;

(55αA1-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 618;

(55αA1-c) a protein comprising an amino acid sequence encoded by a nucleotide sequence with deletion, substitution, insertion or addition of one or several nucleotides in SEQ ID NO: 617;

(55αA1-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 617;

(55αA1-e) a protein comprising an amino acid sequence encoded by a nucleic acid that hybridizes under stringent conditions with a nucleic acid having a nucleotide sequence complementary to the nucleotide sequence of SEQ ID NO: 617;

(55αB1) a protein comprising at least one amino acid sequence selected from the group consisting of SEQ ID NOs: 619-635, preferably a protein comprising at least 2, 3, 4, 5, 6, 7, 8, 9, 10, 11, 12, 13, 14, 15, or 16 or all sequences of the amino acid sequences. As referred to above, the amino acid sequence of any of SEQ ID NOs: 619 to 635 may be an amino acid sequence derived therefrom by deletion, substitution, insertion or addition of one or several amino acids;

(55αA2-a) a protein comprising an amino acid sequence with deletion, substitution, insertion or addition of one or several amino acids in SEQ ID NO: 637;

(55αA2-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 637;

(55αA2-c) a protein comprising an amino acid sequence encoded by a nucleotide sequence with deletion, substitution, insertion or addition of one or several nucleotides in SEQ ID NO: 636;

(55αA2-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 636;

(55αA2-e) a protein comprising an amino acid sequence encoded by a nucleic acid that hybridizes under stringent conditions with a nucleic acid having a nucleotide sequence complementary to the nucleotide sequence of SEQ ID NO: 636;

(55αB2) a protein comprising at least one amino acid sequence selected from the group consisting of SEQ ID NOs: 638-649, preferably a protein comprising at least 2, 3, 4, 5, 6, 7, 8, 9, 10, or 11 or all sequences of the amino acid sequences. As referred to above, the amino acid sequence of any of SEQ ID NOs: 638 to 649 may be an amino acid sequence derived therefrom by deletion, substitution, insertion or addition of one or several amino acids.

The protein selected from the group consisting of the proteins as defined above in (55αA1-a) to (55αA1-e), (55αB1), (55αA2-a) to (55αA2-e), and (55αB2) also include those proteins whose amino acid residues are modified by phosphorylation, sugar chain modification, aminoacylation, ring-opening, deamination or the like.

The protein selected from the group consisting of the proteins as defined above in (55αA1-a) to (55αA1-e), (55αB1), (55αA2-a) to (55αA2-e), and (55αB2) can be proteins that are found in a protein spot with a molecular weight of around 30 to 90 kDa, preferably around 40 to 80 kDa, and an isoelectric point of 5.5 to 10.5, preferably 6.0 to 10.0 on gels used in the two-dimensional electrophoresis performed under the conditions described above in the subsection titled "Identification of antigens".

Preferably, a protein that is an antigen in spot 55a has activity equivalent to that of the protein having the amino acid sequence of SEQ ID NO: 618 (51 kDa seed maturation protein precursor) or the protein having the amino acid sequence of SEQ ID NO: 637 (Lea protein precursor) or causative of an allergy to soybean.

By stating herein "deletion, substitution, insertion or addition of one or several amino acids" in relation to amino acid sequence, it is meant that in an amino acid sequence of interest, one or several amino acids (e.g., 30%, preferably 25%, 20%, 15%, 10%, 5%, 3%, 2%, or 1% of amino acids with respect to the total length of the amino acid sequence) are deleted, one or several amino acids are substituted by any other amino acids, any other amino acids are inserted, and/or any other amino acids are added.

Among the aforementioned modifications, substitution is preferably conservative substitution. The "conservative substitution" refers to the substitution of a certain amino acid residue by a different amino acid residue having similar physicochemical characteristics, and can be any type of substitution as long as it does not substantially change the characteristics of the structure of the original sequence for example, any type of substitution is acceptable as long as any substituted amino acids do not disrupt the helical structure of the original sequence or other secondary structures that characterize the original sequence. The following gives examples of separate groups of amino acid residues that are conservatively substitutable with each other, but substitutable amino acid residues are not limited to the examples given below.

Group A: leucine, isoleucine, valine, alanine, methionine
Group B: aspartic acid, glutamic acid
Group C: asparagine, glutamine
Group D: lysine, arginine
Group E: serine, threonine
Group F: phenylalanine, tyrosine In the case of non-conservative substitution, one member belonging to one of the aforementioned groups can be replaced with a member belong to any other group. For example, in order to eliminate the possibility of unwanted sugar-chain modification, amino acids of group B, D or E as listed above may be substituted by those of any other group. Also, cysteines may be deleted or substituted by any other amino acids to prevent them from being folded into a protein in its tertiary structure. Also, in order to maintain the balance between hydrophilicity and hydrophobicity or to increase hydrophilicity for the purpose of facilitating synthesis, any amino acids may be substituted in consideration of the hydropathy scales of amino acids, which are a measure of the hydrophilic and hydrophobic properties of amino acids (J. Kyte and R. Doolittle, J. Mol. Biol., Vol. 157, p. 105-132, 1982).

As referred to herein, the percent identity between two amino acid sequences can be determined by visual inspection and mathematical calculation. Alternatively, the percent identity can be determined using a computer program. Examples of such computer programs include BLAST FASTA (Altschul, et al., J. Mol. Biol., 215: 403-410 (1990)), and ClustalW. In particular, various conditions (parameters) for identity searches with the BLAST program are described in Altschul, et al. (Nucl. Acids. Res., 25, p. 3389-3402, 1997), and are publicly available on the websites of the National Center for Biotechnology Information (NCBI) and DNA Data Bank of Japan (DDBJ) (Altschul, et al., BLAST Handbook, Altschul, et al., NCB/NLM/NIH Bethesda, MD 20894). Also, the percent identity can be determined using a genetic information processing software program, such as GENETYX Ver.7 (Genetyx Corporation), DINASIS Pro (Hitachi Software Engineering Co., Ltd.), or Vector NTI (Infomax Inc.).

By stating herein "deletion, substitution, insertion or addition of one or several nucleotides" in relation to nucleotide sequence, it is meant that in a nucleotide sequence of interest, one or several nucleotides (e.g., 30%, preferably 25%, 20%, 15%, 10%, 5%, 3%, 2% or 1%, of nucleotides with respect to the total length of the nucleotide sequence) are deleted, one or several nucleotides are substituted by any other nucleotides, any other nucleotides are inserted, and/or any other nucleotides are added. It is preferable that such a nucleotide deletion, substitution, insertion or addition should not give rise to a frame shift in an amino acid coding sequence.

As referred to herein, the percent identity between two nucleotide sequences can be determined by visual inspection and mathematical calculation. Alternatively, the percent identity can be determined using a computer program. Examples of such sequence comparison computer programs include the BLASTN program, version 2.2.7, available on the website of the National Library of Medicine (http://www.ncbi.nlm.nih.gov/blast/bl2seq/bls.html) (Altschul, et al. (1990) J. Mol. Biol., 215: 403-10), or the WU-BLAST 2.0 algorithm. Standard default parameter settings for WU-BLAST 2.0 are found and available on the following website: http://blast.wustl.edu.

As referred to herein, "under stringent conditions" means that hybridization takes place under moderately or highly stringent conditions. To be specific, the moderately stringent conditions can be easily determined by those having ordinary skill in the art on the basis of, for example, the length of DNA. Basic conditions are described in Sambrook, et al., Molecular Cloning: A Laboratory Manual, 3rd ed., ch. 6-7, Cold Spring Harbor Laboratory Press, 2001. The moderately stringent conditions include hybridization under the conditions of preferably 1×SSC to 6×SSC at 42° C. to 55° C., more preferably 1×SSC to 3×SSC at 45° C. to 50° C., most preferably 2×SSC at 50° C. In the case of using a hybridization solution containing, for example, about 50% formamide, a temperature around 5 to 15° C. lower than the foregoing should be adopted. Washing is also carried out under the conditions of 0.5×SSC to 6×SSC at 40° C. to 60° C. In the process of hybridization and washing, generally 0.05% to 0.2% SDS, preferably about 0.1% SDS, may be added. Likewise, the highly stringent conditions can be easily determined by those having ordinary skill in the art on the basis of, for example, the length of DNA. Generally, the highly stringent (high stringent) conditions include hybridization and/or washing at a higher temperature and/or a lower salt concentration than those adopted under the moderately stringent conditions. For example, hybridization is carried out under the conditions of 0.1×SSC to 2×SSC at 55° C. to 65° C., more preferably 0.1×SSC to 1×SSC at 60° C. to 65° C., most preferably 0.2×SSC at 63° C. Washing is carried out under the conditions of 0.2×SSC to 2×SSC at 50° C. to 68° C., more preferably 0.2×SSC at 60 to 65° C.

Antigens may be obtained by separating and purifying them from soybean using a combination of protein purification methods well known to those skilled in the art. Also, antigens may be obtained by expressing them as recombinant proteins using a genetic recombination technique well known to those skilled in the art and by separating and purifying them using protein purification methods well known to those skilled in the art.

Exemplary protein purification methods include: solubility-based purification methods such as salt precipitation and solvent precipitation; purification methods based on molecular weight difference, such as dialysis, ultrafiltration, gel filtration and SDS-PAGE; charge-based purification methods such as ion exchange chromatography and hydroxylapatite chromatography; specific affinity-based purification methods such as affinity chromatography; purification methods based on hydrophobicity difference, such as reverse-phase high-performance liquid chromatography; and purification methods based on isoelectric point difference, such as isoelectric focusing.

Preparation of a protein by a genetic recombination technique is carried out by preparing an expression vector comprising an antigen-encoding nucleic acid, introducing the expression vector into appropriate host cells by gene transfer or genetic transformation, culturing the host cells under suitable conditions for expression of a recombinant protein, and recovering the recombinant protein expressed in the host cells.

The "vector" refers to a nucleic acid that can be used to introduce a nucleic acid attached thereto into host cells. The "expression vector" is a vector that can induce the expression of a protein encoded by a nucleic acid introduced therethrough. Exemplary vectors include plasmid vectors and viral vectors. Those skilled in the art can select an appropriate expression vector for the expression of a recombinant protein depending on the type of host cells to be used.

The "host cells" refers to cells that undergo gene transfer or genetic transformation by a vector. The host cells can be appropriately selected by those skilled in the art depending on the type of the vector to be used. The host cells can be derived from prokaryotes such as *E. coli*. When prokaryotic cells like *E coli.* are used as host cells, the antigen of the present invention may be designed to contain an N-terminal methionine residue in order to facilitate the expression of a recombinant protein in the prokaryotic cells. The N-terminal methionine can be cleaved from the recombinant protein after expression. Also, the host cells may be cells derived from eukaryotes, such as single-cell eukaryotes like yeast, plant cells and animal cells (e.g., human cells, monkey cells, hamster cells, rat cells, murine cells or insect cells) or silkworm.

Gene transfer or genetic transformation of an expression vector into host cells can be carried out as appropriate by following a technique known to those skilled in the art. Those skilled in the art can make possible the expression of a recombinant protein by selecting suitable conditions for the expression of the recombinant protein as appropriate depending on the type of host cells and culturing the host cells under the selected conditions. Then, those skilled in the art can homogenize the host cells having the expressed recombinant protein, and separate and purify an antigen expressed as the recombinant protein from the resulting homogenate by using an appropriate combination of such protein purification methods as mentioned above.

Diagnosis Kit and Method

The present invention provides a method for providing an indicator for diagnosing an allergy to a soybean in a subject, the method comprising the steps of:

(i) contacting a sample obtained from the subject with an antigen, wherein the sample is a solution comprising an Ig antibody;

(ii) detecting binding between an IgE antibody present in the sample from the subject and the antigen; and (iii) when the binding between the IgE antibody in the subject and the antigen is detected, an indicator of the fact that the subject is allergic to a soybean is provided;

wherein the antigen is at least one of proteins as defined above in any of (1) to (8) and (1α) to (55α).

The sample obtained from a subject is a solution containing an Ig antibody, preferably an IgE antibody, as collected from the subject. Examples of such solutions include blood, saliva, sputum, snivel, urine, sweat, and tear. The sample obtained from the subject may be subjected to pretreatment for increasing the concentration of an Ig antibody in the sample before being contacted with an antigen. The pretreatment of a sample may involve, for example, collection of the serum from the blood. In a particularly preferred mode, the step (i) mentioned above is carried out by contacting an IgE antibody present in the serum obtained from a subject with an antigen.

Detection of contact and binding between the sample obtained from a subject and an antigen can be carried out by using a known method. Examples of such methods that can be used include detection by ELISA (Enzyme-Linked Immunosorbent Assay), sandwich immunoassay, immunoblotting, or immunoprecipitation. These are all techniques for detecting binding between an antigen and an IgE antibody from a subject by contacting and binding the IgE antibody from a subject with the antigen, allowing an enzymatically labelled secondary antibody to act on the IgE antibody specifically bound to the antigen, and adding an enzyme substrate (generally, chromogenic or luminescent reagent) to detect an enzymatic reaction product. Also, a method for detecting a fluorescently labeled secondary antibody can be used. Furthermore, a method for detecting antigen-antibody binding as a refraction angle using surface plasmon resonance can be used.

The antigen may be provided as an isolated antigen in a state immobilized on a carrier. In this case, the steps (i) and (ii) mentioned above can be carried out using ELISA, sandwich immunoassay, or the like. Also, the step (i) mentioned above can be carried out by contacting the sample obtained from a subject with an antigen-immobilized surface. The isolated antigen may be obtained by separating and purifying it from soybean using a combination of protein purification methods well known to those skilled in the art, or by preparing it using a genetic recombination technique.

The antigen may be detected by immunoblotting in a state separated by two-dimensional electrophoresis. The two-dimensional electrophoresis is a technique for separating a protein sample by performing isoelectric focusing in the first dimension and performing SDS-PAGE (SDS-polyacrylamide gel electrophoresis) in the second dimension. The conditions for two-dimensional electrophoresis are not particularly limited as long as the conditions permit the separation of the antigen of the present invention. For example, the conditions for two-dimensional electrophoresis as described above in the subsection titled "Identification of antigens" can be adopted. Also, the electrophoresis conditions may be defined by reference to the descriptions in Patent Literatures 1 to 4 mentioned above. For example, two-dimensional electrophoresis can be carried out under the conditions that satisfy at least one selected from the group consisting of the following requirements:

(A) the isoelectric focusing gels used in the first dimension should have a gel-strip length of 5 to 10 cm and a gel pH range of 3 to 10, and the pH gradient of the gels in the direction of electrophoresis should be as follows: where the gel-strip length up to pH 5 is taken as "a", that length from pH 5 to 7 as "b", and that length above pH 7 as "c", the relations "a<b" and "b>c" are satisfied;

(B) in the case of (A), when the total gel-strip length is taken as 1, "a" should be in the range of 0.15 to 0.3, "b" should be in the range of 0.4 to 0.7, and "c" should be in the range of 0.15 to 0.3;

(C) in the first dimensional isoelectric focusing, a constant voltage step should be performed by applying a constant voltage ranging from 100 V to 600 V per gel strip containing a sample, and after the electrophoresis variation width during electrophoresis for 30 minutes falls within the range of 5 μA, a voltage-increasing step should be started at which the voltage is increased from the aforementioned constant voltage;

(D) in the case of (C), the final voltage at the voltage-increasing step should be in the range of 3000 V to 6000 V;

(E) the isoelectric focusing gels used in the first dimension should have a longitudinal gel-strip length of 5 to 10 cm, and the electrophoresis gels used in the second dimension should have a gel concentration at the distal end in the direction of electrophoresis, which is in the range of 3 to 6%; and (F) in the case of (E), the electrophoresis gels used in the second dimension should have a gel concentration at the proximal end in the direction of electrophoresis, which is set to a higher value than that at the distal end in the direction of electrophoresis.

The aforementioned antigens (1) to (8) and (1α) to (55α) are antigens that specifically bind to IgE antibodies from patients with allergy to soybean. Therefore, when binding between an IgE antibody from a subject and the antigen is detected, an indicator of the fact that the subject is allergic to soybean is provided.

The present invention further provides a kit for diagnosing an allergy to a soybean, comprising at least one of the aforementioned antigens (1) to (8) and (1α) to (55α). The diagnosis kit of this invention may be used in the aforementioned method for providing an indicator for diagnosing an allergy to a soybean or in a diagnosis method as described later. The diagnosis kit of this invention may comprise not only the at least one of the aforementioned antigens (1) to (8) and (1α) to (55α), but also an anti-IgE antibody labeled with an enzyme and a chromogenic or luminescent substrate serving as a substrate for the enzyme. Also, a fluorescent-labeled anti-IgE antibody may be used. In the diagnosis kit of this invention, the antigen may be provided in a state immobilized on a carrier. The diagnosis kit of this invention may also be provided together with instructions on the procedure for diagnosis or a package containing said instructions.

The present invention further provides a composition for diagnosing an allergy to a soybean, comprising at least one of the aforementioned antigens (1) to (8) and (1α) to (55α). The diagnosis composition of this invention can be used in a diagnosis method as described below. The diagnosis composition of this invention may further comprise a pharmaceutically acceptable carrier and/or additives commonly used with the antigen of this invention depending on the need.

In one mode, the present invention provides a method for diagnosing an allergy to a soybean in a subject, the method comprising:

(i) contacting a sample obtained from the subject with an antigen;

(ii) detecting binding between an IgE antibody present in the sample from the subject and the antigen; and (iii) when the binding between the IgE antibody in the subject and the antigen is detected, diagnosing the subject as being allergic to a soybean;

wherein the antigen is at least one of proteins as defined above in any of (1) to (8) and (1α) to (55α). In this method, the steps (i) and (ii) are performed as described above regarding the corresponding steps of the method for providing an indicator for diagnosing an allergy to a soybean.

In another mode, the present invention provides a method for diagnosing an allergy to a soybean in a subject, the method comprising administering to the subject at least one of the aforementioned antigens (1) to (8) and (1α) to (55α). This method may be performed in the form of a skin test characterized by applying the antigen onto the skin. Examples of the skin test include various forms of tests, such as: a prick test in which a diagnosis composition is applied onto the skin and then a tiny prick to such an extent as not to provoke bleeding is made in the skin to allow an antigen to penetrate the skin, thereby observing a skin reaction; a scratch test in which a diagnosis composition is applied onto the skin and then the skin is lightly scratched to observe a reaction; a patch test in which a diagnosis composition in the form of cream, ointment, etc. is applied onto the skin to observe a reaction; and an intracutaneous test in which an antigen is administered intracutaneously to observe a reaction. If a skin reaction such as swelling occurs in a skin portion to which the antigen has been applied, the subject of interest is diagnosed as having an allergy to a soybean. The amount of the antigen to be applied to the skin in such tests can be, for example, not more than 100 μg per dose.

In yet another mode, the present invention provides at least one of the aforementioned antigens (1) to (8) and (1α) to (55α), intended for use in the diagnosis of an allergy to a soybean.

In still another mode, the present invention provides use of at least one of the aforementioned antigens (1) to (8) and (1α) to (55α) for the production of a diagnostic agent for an allergy to a soybean.

Pharmaceutical Composition and Treatment Method

The present invention provides a pharmaceutical composition comprising at least one of the aforementioned antigens (1) to (8) and (1α) to (55α). In one mode, the aforementioned pharmaceutical composition is used for the treatment and diagnosis of an allergy to a soybean.

The present invention also provides a method for treating an allergy to a soybean, the method comprising administering at least one of the aforementioned antigens (1) to (8) and (1α) to (55α) to a patient in need of a treatment for an allergy to a soybean.

In another mode, the present invention provides at least one of the aforementioned antigens (1) to (8) and (1α) to (55α), intended for use in the treatment for an allergy to a soybean. In yet another mode, the present invention provides use of at least one of the aforementioned antigens (1) to (8) and (1α) to (55α) for the production of a therapeutic agent for an allergy to a soybean.

In the process of allergy treatment, a hyposensitization therapy aiming to induce immunological tolerance by administering an antigen to a patient is often adopted. The at least one of the aforementioned antigens (1) to (8) and (1α) to (55α) can be used as an active ingredient for a hyposensitization therapy or a load test for an allergy to a soybean. Here, the antigen protein to be used in the hyposensitization therapy and the load test may be a protein that has been expressed and purified and may be a protein that has been expressed in food such as rice, such as rice-based vaccine expressing pollen allergens.

The pharmaceutical composition of the present invention can be administered by common administration routes. Examples of common administration routes include oral, sublingual, percutaneous, intracutaneous, subcutaneous, intravascular, intranasal, intramuscular, and intraperitoneal administrations.

The pharmaceutical composition of the present invention can be used as a pharmaceutical composition to which a commonly used pharmaceutically acceptable adjuvant or excipient or any other additives (e.g., stabilizer, solubilizer, emulsifier, buffer, preservative, colorant) are added by a conventional method together with the antigen of this invention depending on the need. The dosage form of the pharmaceutical composition can be selected by those skilled in the art as appropriate depending on the administration route.

The pharmaceutical composition can be in the form of, for example, tablet, capsule, troche, sublingual tablet, parenteral injection, intranasal spray, poultice, solution, cream, or lotion. The administration dose, frequency and/or period of the pharmaceutical composition of this invention can be selected by a physician as appropriate depending on the administration route and the patient's condition and characteristics such as age and body weight. For example, the pharmaceutical composition may be administered to an adult patient at a dose of not more than 100 μg per dose. The administration interval can be, for example, once daily, once weekly, twice weekly, once per three months or so. The administration period can be, for example, several weeks to several years. The pharmaceutical composition may be administered in such a manner that the dose is increased in incremental steps over the administration period.

Tester

The present invention provides a tester comprising an antibody for at least one of the aforementioned antigens (1) to (8) and (1α) to (55α).

The antibody can be prepared by a conventional method. For example, the antibody may be prepared by immunizing a mammal such as rabbit with one of the aforementioned antigens (1) to (8) and (1α) to (55α). The antibody may be an Ig antibody, a polyclonal antibody, a monoclonal antibody, or an antigen-binding fragment thereof (e.g., Fab, $F(ab')_2$, Fab').

Further, in the aforementioned tester, the antibody may be provided in a form bound to a carrier. The type of the carrier is not particularly limited as long as it is usable for detection of binding between an antibody and an antigen. Any given carrier known to those skilled in the art can be used.

In one mode, the aforementioned tester is used to determine the presence or absence of an antigen in foods or in products of interest in a food production line. The tester may also be used for quality inspection of production lines and pre-shipment products by manufacturers, or may be used for self-checking of the presence or absence of an antigen in a food of interest by consumers.

Examples of a method for determining the presence or absence of an antigen include a method in which a prepared tester comprising an Ig antibody is contacted with a sample obtained from a food, etc., ELISA or the like method is used to detect whether there is a binding between the Ig antibody and an antigen in the sample, and if the binding between the Ig antibody and the antigen is detected, it is determined that the antibody remains in the food, etc. of interest.

Allergen-Free Food and the Like

The present invention provides a soybean or processed product of soybean in which at least one of the aforementioned antigens (1) to (8) and (1α) to (55α) is eliminated or reduced.

The method for eliminating or reducing the antigen of the present invention in a soybean or processed products of soybean is not limited. The elimination or reduction of the antigen may be conducted by any method, as long as the method permits the elimination or reduction of the antigen.

For example, the soybean of the present invention whose antigen is eliminated or reduced may be obtained by preparing a soybean in which the expression of the antigen of the present invention is knocked out, using a gene knock-out technique.

An antigen of the present invention may be the artefact that an antigen of the present invention assumed the removal or a reduced soybean raw material as for the removal or the reduced processed products of soybean. In the case of using an ordinary soybean as a source ingredient, a treatment for removing or reducing the antigen of this invention is performed before or after preparation of a processed product of soybean. The methods for removing or reducing the antigen of the present invention include a method to remove protein component in a high pressure treatment and food such as elution with the neutral salt solution or the high temperature steam with an antigen of the present invention in the processed products of soybean which assumed a normal soybean raw material.

EXAMPLES

The following describes examples of the present invention. The technical scope of this invention is not limited by these examples.

Example 1: Confirmation of a Protein Pattern

Proteins contained in soybean were investigated using a two-dimensional electrophoresis method described below.

Protein Extraction

Commercially available dry soybeans (several beans) were powdered. 500 μl of water was added to 50 mg of the powder and shaking extraction was conducted using a vortex mixer at 25° C. for 10 minutes. After the shaking extraction, a liquid protein extract was collected.

Thereafter, the precipitation procedure was repeated twice using a 2D-CleanUP Kit (produced by GE). In the first round of precipitation, the collected liquid protein extract was precipitated by adding TCA (trichloroacetic acid) thereto and the precipitated product produced by this procedure (TCA-precipitated product) was collected. In the second round of precipitation, the TCA-precipitated product collected above was further precipitated by adding acetone thereto and the precipitated product (sample) produced by this procedure was collected.

Preparation of a Sample Solution

Part of the collected sample (50 μg on a protein weight basis) was dissolved in 150 μL of a DeStreak Rehydration Solution (produced by GE), which is a swelling buffer for first-dimensional isoelectric focusing gels, thereby obtaining a sample solution for first-dimensional isoelectric focusing (sample solution for swelling). The constituents of the DeStreak Rehydration Solution are as mentioned below.

7M thiourea
2M urea
4% (w/v) of CHAPS (3-[(3-cholamidopropyl)dimethylammonio]propanesulfonate)
0.5% (v/v) IPG buffer; produced by GE Moderate Amount of BPB (Bromophenol Blue)

Penetration of the sample into first-dimensional isoelectric focusing gels First-dimensional isoelectric focusing gel strips (Immobiline Drystrip IPG gels (pH3-10NL); produced by GE) were immersed in 140 μL of the foregoing sample solution for first-dimensional isoelectric focusing (sample solution for swelling) and impregnated with the solution at room temperature overnight.

In this example, an IPGphor electrophoresis system produced by GE was used.

An electrophoresis tray was filled with silicone oil. Filter paper moisten with water was positioned at both ends of the gel strips impregnated with the sample, and the gel strips were set in the electrophoresis tray such that the gel strips were covered with silicone oil. Electrodes were placed on the gel strips with the filter paper intervening therebetween.

The maximum current of the isoelectric focusing system was set to 75 μA per gel strip, and the first-dimensional isoelectric focusing was carried out according to the following voltage program: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

SDS equilibration of isoelectric focusing gels After the aforementioned first-dimensional isoelectric focusing was done, the gel strips were taken out of the isoelectric focusing system, immersed in an equilibration buffer containing a reducing agent, and shaken at room temperature for 15 minutes. The constituents of the equilibration buffer containing the reducing agent are as mentioned below.

100 mM Tris-HCl (pH 8.0)
6M urea
30% (v/v) glycerol
2% (w/v) SDS
1% (w/v) DTT

Next, the equilibration buffer containing the reducing agent was removed, and then the gel strips were immersed in an equilibration buffer containing an alkylating agent and shaken at room temperature for 15 minutes to obtain SDS-equilibrated gels. The constituents of the equilibration buffer containing the alkylating agent are as mentioned below.

100 mM Tris-HCl (pH 8.0)
6M urea

30% (v/v) glycerol

2% (w/v) SDS 2.5% (w/v) iodoacetamide

Second-Dimensional SDS-PAGE

In this example, the XCell SureLock Mini-Cell electrophoresis system produced by Life Technologies was used. The second-dimensional electrophoresis gels used were NuPAGE 4-12% Bis-Tris Gels produced by Life Technologies. Also, an electrophoresis buffer composed of the following constituents was prepared and used.

50 mM MOPS 50 mM Tris base 0.1% (w/v) SDS 1 mM EDTA

Further, an agarose solution for gel adhesion was used in this example, which was prepared by dissolving 0.5% (w/v) Agarose S (produced by Nippon Gene Co., Ltd.) and a moderate amount of BPB (bromophenol blue) in the electrophoresis buffer.

SDS-PAGE wells were washed well with the electrophoresis buffer, and then the buffer used for the washing was removed. Next, the washed wells were charged with the fully dissolved agarose solution for gel adhesion. Next, the SDS-equilibrated gel strips were immersed in agarose and closely adhered to second-dimensional electrophoresis gels using tweezers. After it was confirmed that agarose was fully fixed with the gels being closely adhered to each other, electrophoresis was performed at a constant voltage of 200 V for about 45 minutes.

Fluorescent Staining of Gels

The gels were fluorescently stained with SYPRO Ruby (produced by Life Technologies).

First, an airtight container to be used was washed well in advance with 98% (v/v) ethanol. The electrophoresed second-dimensional electrophoresis gel strips were taken out of the SDS-PAGE system, placed onto the washed airtight container, and treated twice by immersion in 50% (v/v) methanol and 7% (v/v) aqueous solution containing acetic acid for 30 minutes. Then, a further immersion treatment was done for 10 minutes, with the solution being replaced by water. Next, the second-dimensional electrophoresis gel strips were immersed in 40 mL of SYPRO Ruby and shaken at room temperature overnight. Thereafter, the SYPRO Ruby was removed, and then the second-dimensional electrophoresis gel strips were washed with water and shaken in 10% (v/v) methanol and 7% (v/v) aqueous solution containing acetic acid for 30 minutes. Further shaking was done for at least 30 minutes, with the solution being replaced by water.

Analysis

The second-dimensional electrophoresis gels obtained through the foregoing series of treatments were subjected to fluorescent image scanning on Typhoon 9400 (produced by GE). The results of the two-dimensional electrophoresis are shown in FIG. 1. Molecular weight marker bands are found at the left of the panels. The positions of the bands denote particular molecular weights (in KDa).

Example 2: Identification of Antigens by Immunoblotting (1)

Identification of antigens by immunoblotting was carried out by taking all the steps up to the step of "Second-dimensional SDS-PAGE" as described above in Example 1, followed by the steps of "Transfer to membrane", "Immunoblotting" and "Analysis" as described below.

Transfer to membrane Transfer to membrane was done using the following transfer system and transfer buffer.

Transfer system: XCell SureLock Mini-Cell and XCell II Blot Module (produced by Life Technologies) Transfer buffer: NuPAGE Transfer Buffer (X20) (produced by Life Technologies), used in a form diluted 20-fold with milliQ water.

To be specific, proteins in the two-dimensional electrophoresis gels were transferred to a membrane (PVDF membrane) according to the following procedure.

(1) The PVDF membrane was immersed in 100% methanol followed by milliQ water, and then moved into the transfer buffer to hydrophilize the PVDF membrane.

(2) After sponge, filter paper, the gels treated by second-dimensional SDS-PAGE, the hydrophilized PVDF membrane, filter paper, and sponge were put in place in this order, the transfer system was energized at a constant voltage of 30 V for one hour.

Immunoblotting

Immunoblotting of the membrane was carried out using, as a primary antibody, a serum sample from a patient with a soybean allergy or a serum sample from a healthy subject.

Immunoblotting of the membrane was carried out according to the following procedure.

(1) The transferred membrane was shaken in a 5% skim milk/PBST solution (a PBS buffer containing 0.3% Tween 20 nonionic surfactant) at room temperature for one hour.

(2) The membrane was left to stand in a solution of 3% primary antibody serum in 5% skim milk/PBST at room temperature for one hour.

(3) The membrane was washed with a PBST solution (5 min.×3 times).

(4) The membrane was left to stand in a 1:2500 dilution of the secondary antibody, anti-human IgE-HRP (horseradish peroxidase), with a 3% skim milk/PBST solution at room temperature for one hour.

(5) The membrane was washed with a PBST solution (5 min.×3 times).

(6) The membrane was left to stand in Pierce Western Blotting Substrate Plus (produced by Thermo Fisher Scientific) for 5 minutes.

Analysis

The membrane obtained through the foregoing series of treatments was subjected to fluorescent image scanning on Typhoon 9400 (produced by GE).

Figure 2:
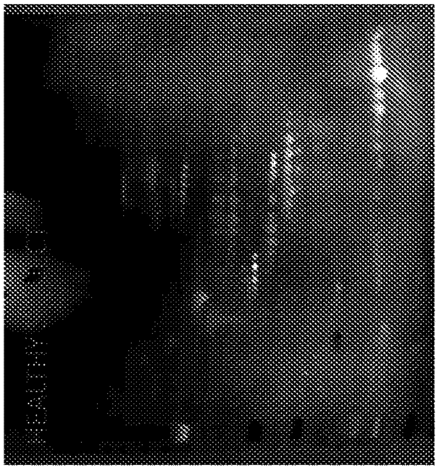
FIG. 2 is a photograph of an immunoblot of a two-dimensional electrophoretic pattern of proteins contained in soybean stained with serum of a healthy subject.
Figure 3A:
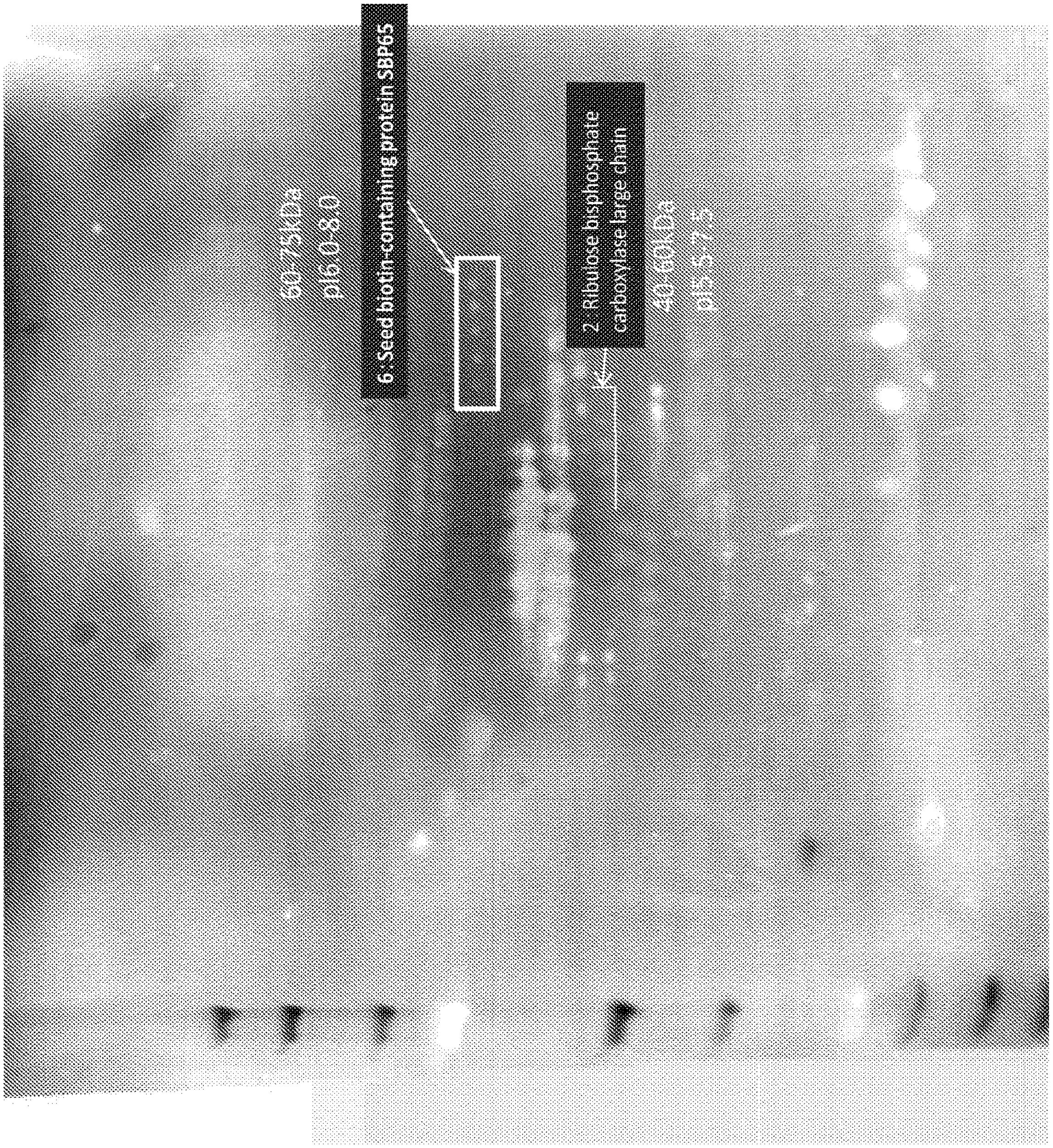
FIG. 3A is a photograph of an immunoblot of a two-dimensional electrophoretic pattern of proteins contained in soybean stained with serum of Soybean-allergic patient 1. The arrows indicate spots where the serum of the soybean-allergic patient specifically reacted.
Figure 3B:
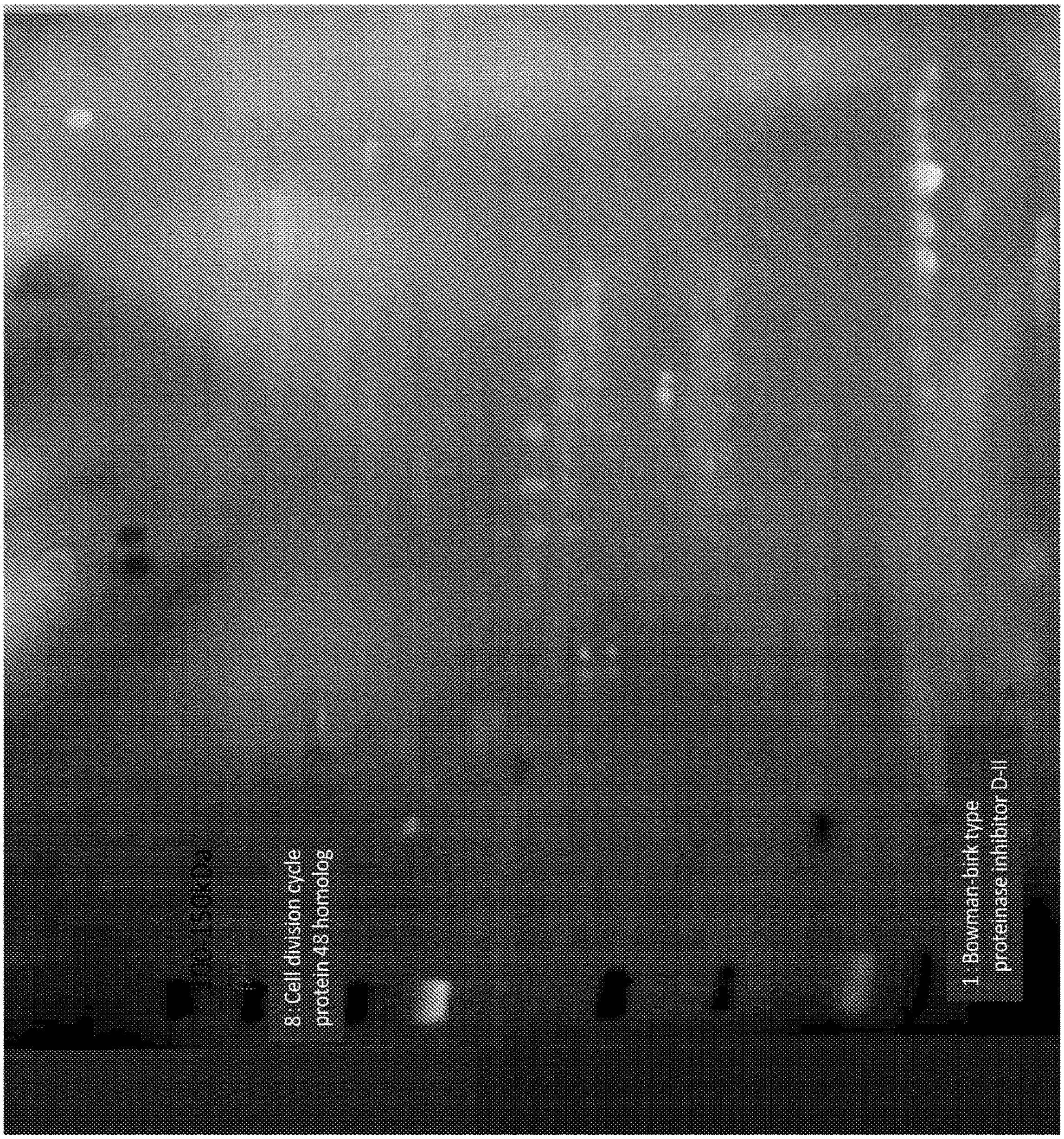
FIG. 3B is a photograph of an immunoblot of a two-dimensional electrophoretic pattern of proteins contained in soybean stained with serum of Soybean-allergic patient 2. The arrows indicate spots where the serum of the soybean-allergic patient specifically reacted.
Figure 3C:
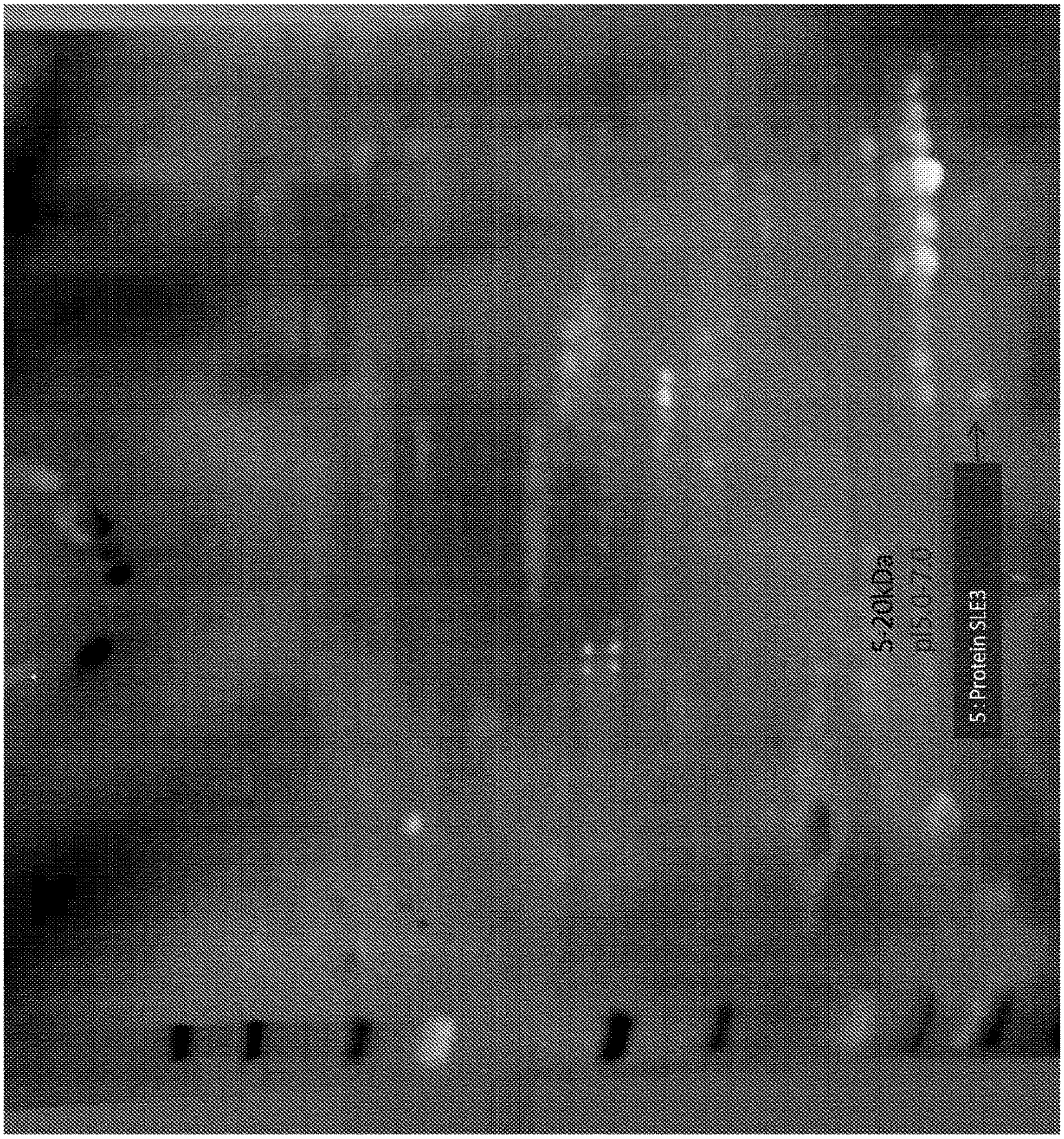
FIG. 3C is a photograph of an immunoblot of a two-dimensional electrophoretic pattern of proteins contained in soybean stained with serum of Soybean-allergic patient 3. The arrows indicate spots where the serum of the soybean-allergic patient specifically reacted.
Figure 3D:
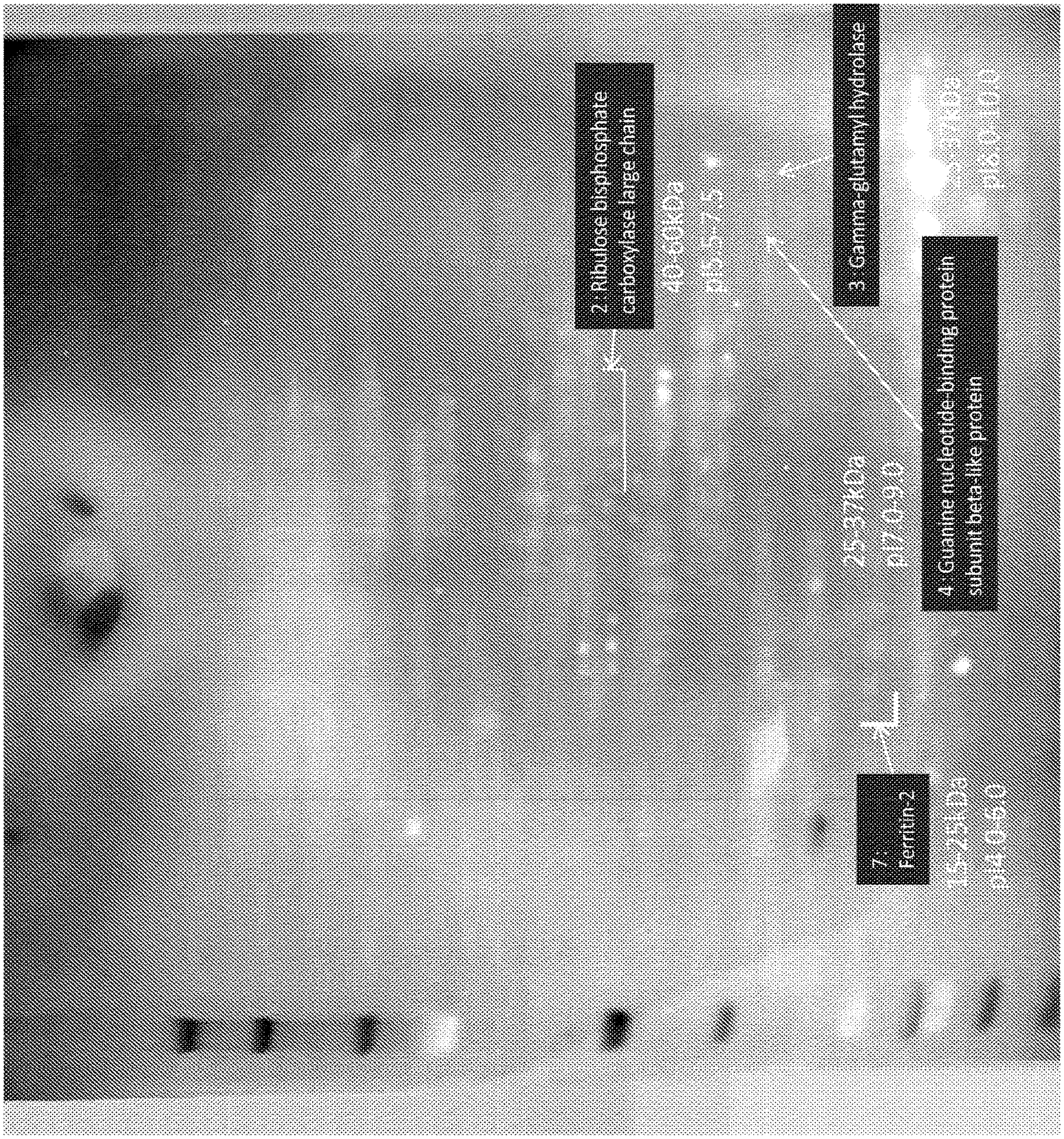
FIG. 3D is a photograph of an immunoblot of a two-dimensional electrophoretic pattern of proteins contained in soybean stained with serum of Soybean-allergic patient 4. The arrows indicate spots where the serum of the soybean-allergic patient specifically reacted.

The immunoblots obtained with the serum from the soybean-allergic patient were compared with those obtained with the control serum from the healthy subject. By immunoblotting using the serum from soybean-allergic Patient 1, Patient 2, Patient 3, and Patient 4, 8 spots were detected (FIGS. 3A to D), which are different from the spots detected when the serum of the healthy subject was used (FIG. 2) and different from those of the known soybean allergen proteins.

The molecular weights and isoelectric points of the 8 spots are as follows.

Spot 1: Molecular weight 5 to 20 kDa, pl 4.0 to 6.0

Spot 2: Molecular weight 40 to 60 kDa, pl 5.5 to 7.5

Spot 3: Molecular weight 25 to 37 kDa, pl 8.0 to 10.0

Spot 4: Molecular weight 25 to 37 kDa, pl 7.0 to 9.0

Spot 5: Molecular weight 5 to 20 kDa, pl 5.0 to 7.0

Spot 6: Molecular weight 60 to 75 kDa, pl 6.0 to 8.0

Spot 7: Molecular weight 15 to 25 kDa, pl 4.0 to 6.0

Spot 8: Molecular weight 100 to 150 kDa, pl 4.0 to 6.0

Example 3: Mass Spectrometry and Identification of Antigens (1)

The amino acid sequences of the antigens that form the above eight protein spots were identified by mass spectroscopy.

To be specific, protein extraction and mass spectroscopy were done by the following procedure.

(1) Soybeans were subjected to protein extraction, two-dimensional electrophoresis and transfer to membrane by following the procedures described in Example 1 and 2, and the resulting membrane was stained by shaking in a solution of 0.008% Direct blue in 40% ethanol and 10% acetic acid.

(2) Then, the membrane was decolorized by repeating a 5-minute treatment with 40% ethanol and 10% acetic acid three times, washed with water for 5 minutes, and then dried by air.

(3) A protein spot of interest was cut out with a clean cutter blade and put into a centrifugal tube. The cut membrane was subjected to hydrophilization with 50 μL of methanol, followed by washing with 100 μL of water twice and then centrifugal cleaning. Thereafter, 20 μL of 20 mM $NH_4HCO_3$ and 50% acetonitrile were added.

(4) 1 μL of 1 pmol/μL lysyl endopeptidase (produced by WAKO) was added, and the solution was left to stand at 37° C. for 60 minutes and then collected in a new centrifugal tube. After 20 μL of 20 mM $NH_4HCO_3$ and 70% acetonitrile were added to the membrane, the membrane was immersed therein at room temperature for 10 minutes, and the resulting solution was further collected. The solution was dissolved with 0.1% formic acid and L of 4% acetonitrile and transferred to a tube.

(5) The collected solution was dried under reduced pressure, dissolved with 15 μL of solution A (a 0.1% formic acid/4% acetonitrile solution), and analyzed by mass spectroscopy (ESI-TOF5600, produced by AB Sciex).

(6) Identification of proteins based on the MS data obtained with the mass spectrometer was done by searching the NCBI database.

Results

The mass spectrometry of the spots resulted in the detection of the following amino acid sequences.

Spot 1: the amino acid sequences set forth in SEQ ID NO: 17 to 20

Spot 2: the amino acid sequences set forth in SEQ ID NO: 21 to 28

Spot 3: the amino acid sequences set forth in SEQ ID NO: 29, 30

Spot 4: the amino acid sequences set forth in SEQ ID NO: 31, 32

Spot 5: the amino acid sequences set forth in SEQ ID NO: 33, 34

Spot 6: the amino acid sequences set forth in SEQ ID NO: 35 to 53

Spot 7: the amino acid sequences set forth in SEQ ID NO: 54 to 61

Spot 8: the amino acid sequences set forth in SEQ ID NO: 62 to 68

Furthermore, the spots were identified as the following proteins by the analysis of the mass data obtained from the mass spectrometer for the spots at NCBI.

Spot 1: Bowman-Birk type proteinase inhibitor D-II (UniProt accession number P01064, amino acid sequence: SEQ ID NO: 2, encoding nucleotide sequence: SEQ ID NO: 1)

Spot 2: Ribulose bisphosphate carboxylase large chain (UniProt accession number P27066, amino acid sequence: SEQ ID NO: 4, encoding nucleotide sequence: SEQ ID NO: 3)

Spot 3: Gamma-glutamyl hydrolase (UniProt accession number P93164, amino acid sequence: SEQ ID NO: 6, encoding nucleotide sequence: SEQ ID NO: 5)

Spot 4: Guanine nucleotide-binding protein subunit beta-like protein (UniProt accession number Q39836, amino acid sequence: SEQ ID NO: 8, encoding nucleotide sequence: SEQ ID NO: 7)

Spot 5: Protein SLE3 (UniProt accession number C6T0L2, amino acid sequence: SEQ ID NO: 10, encoding nucleotide sequence: SEQ ID NO: 9)

Spot 6: Seed biotin-containing protein SBP65 (UniProt accession number Q39846, amino acid sequence: SEQ ID NO: 12, encoding nucleotide sequence: SEQ ID NO: 11)

Spot 7: Ferritin-2 (UniProt accession number Q941C4, amino acid sequence: SEQ ID NO: 14, encoding nucleotide sequence: SEQ ID NO: 13)

Spot 8: Cell division cycle protein 48 homolog (UniProt accession number P54774, amino acid sequence: SEQ ID NO: 16, encoding nucleotide sequence: SEQ ID NO: 15)

Example 4: Identification of Antigens by Immunoblotting (2)

Figure 4:
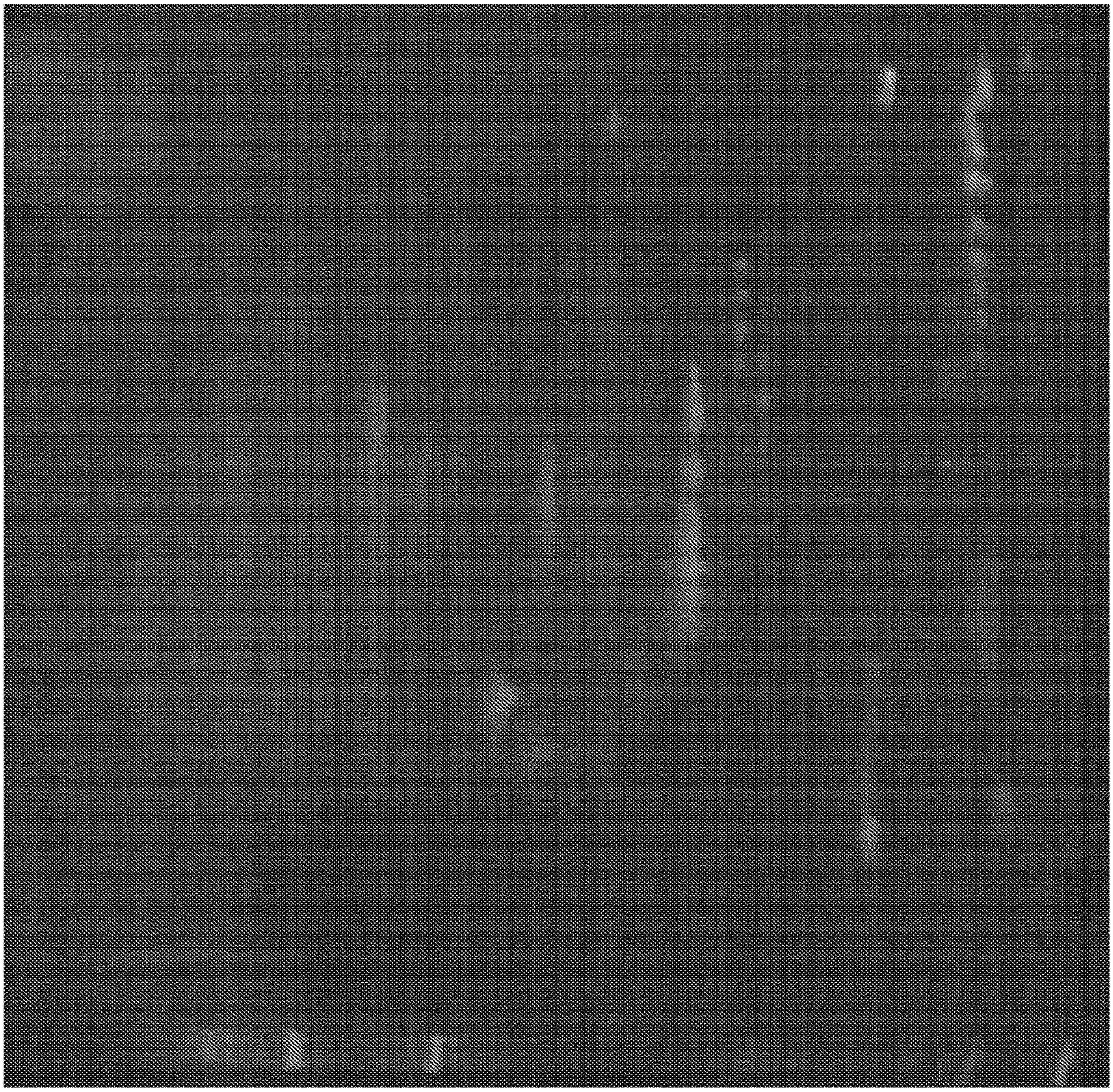
FIG. 4 is a photograph of an immunoblot of a two-dimensional electrophoretic pattern of proteins contained in soybean stained with serum of a healthy subject.
Figure 5A:
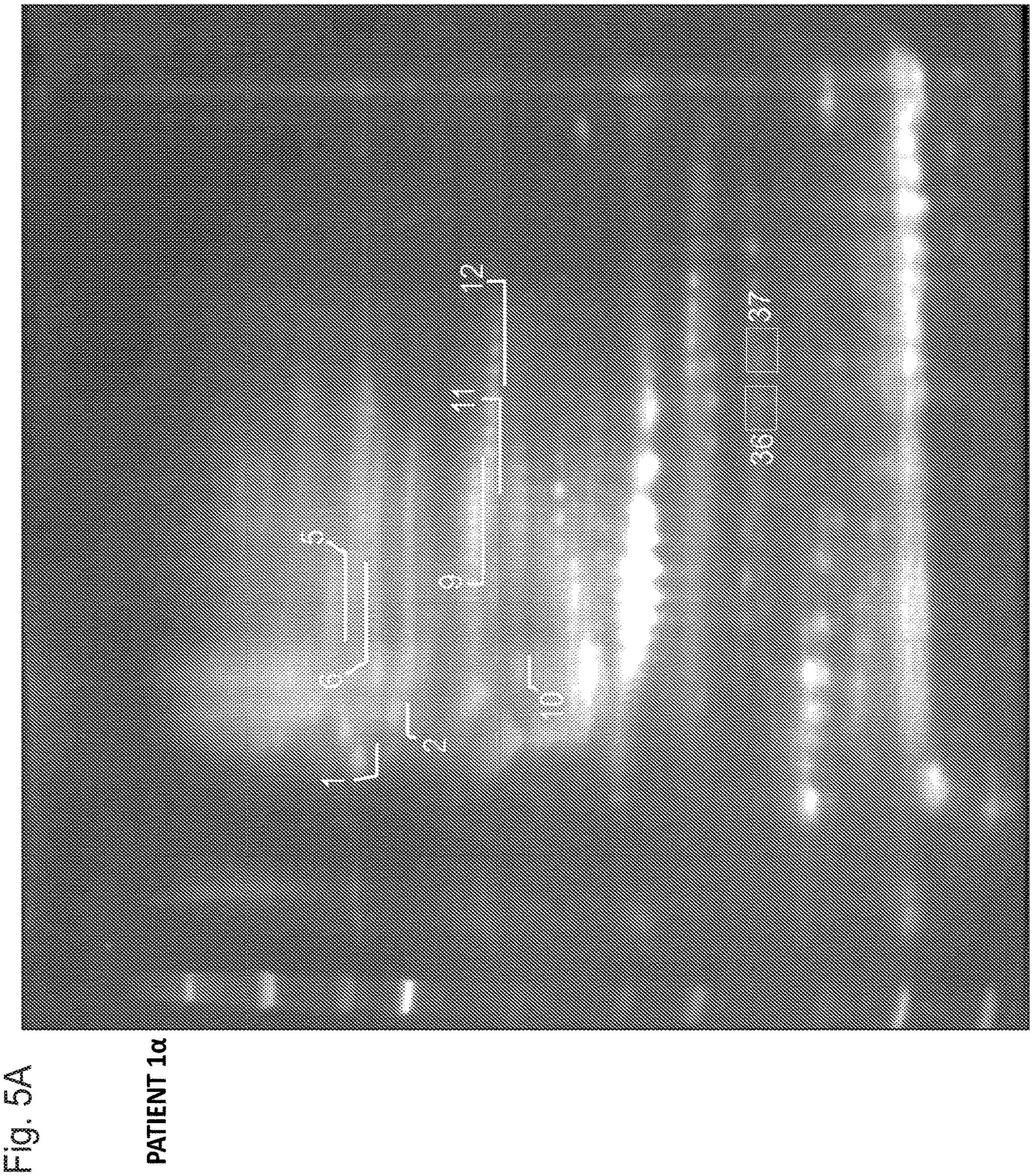
FIG. 5A is a photograph of an immunoblot of a two-dimensional electrophoretic pattern of proteins contained in soybean stained with serum of Soybean-allergic patient 1a. The spots indicated with a white line or enclosed in a square are spot where the serum of the soybean-allergic patient specifically reacted. The numbers (n) indicated are the numbers of the spots and correspond to the spots indicated with "na" herein.
Figure 5B:
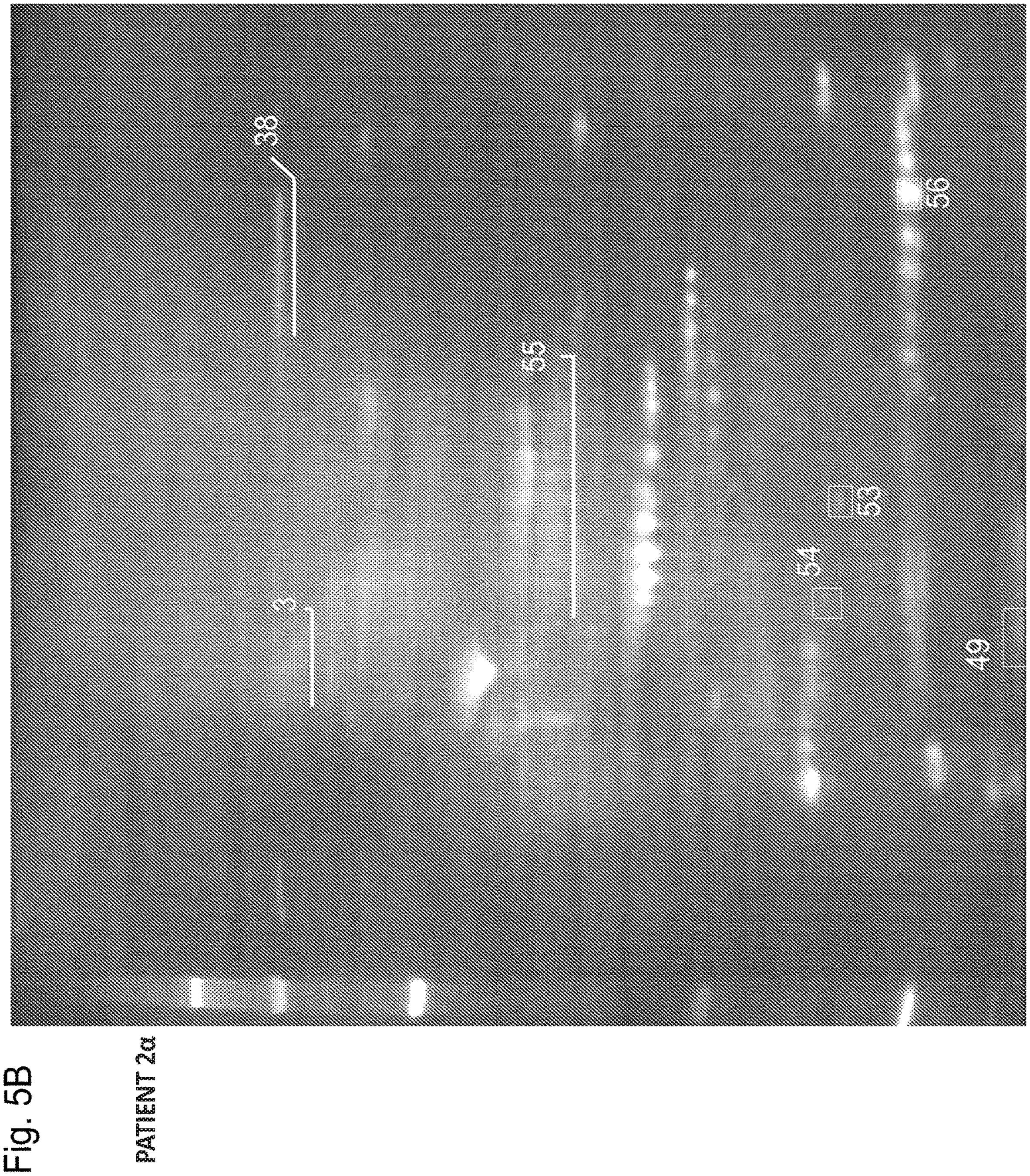
FIG. 5B is a photograph of an immunoblot of a two-dimensional electrophoretic pattern of proteins contained in soybean stained with serum of Soybean-allergic patient 2. The spots indicated with a white line or enclosed in a square are spot where the serum of the soybean-allergic patient specifically reacted. The numbers (n) indicated are the numbers of the spots and correspond to the spots indicated with "na" herein.
Figure 5C:
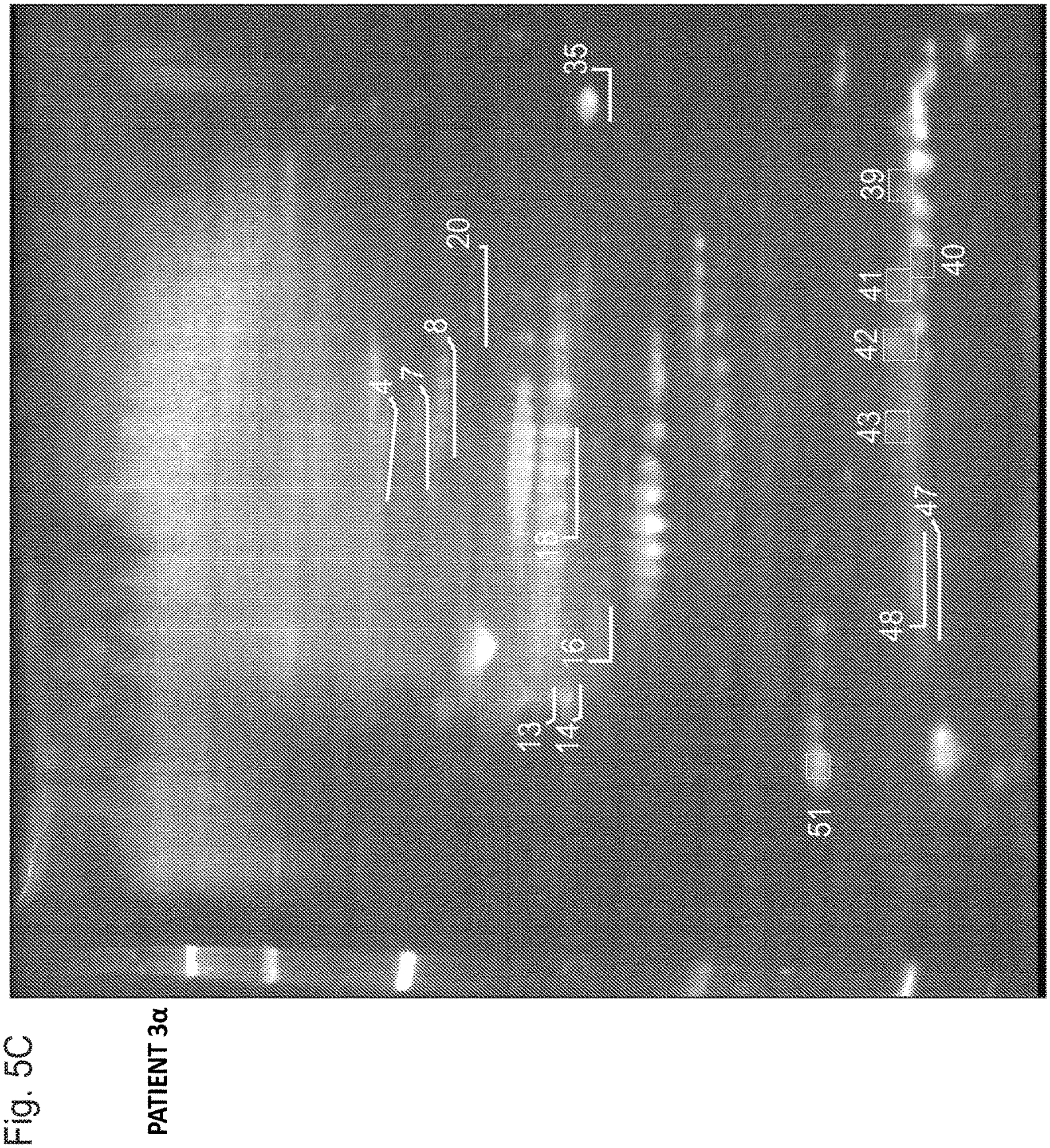
FIG. 5C is a photograph of an immunoblot of a two-dimensional electrophoretic pattern of proteins contained in soybean stained with serum of Soybean-allergic patient 3a. The spots indicated with a white line or enclosed in a square are spot where the serum of the soybean-allergic patient specifically reacted. The numbers (n) indicated are the numbers of the spots and correspond to the spots indicated with "na" herein.
Figure 5D:
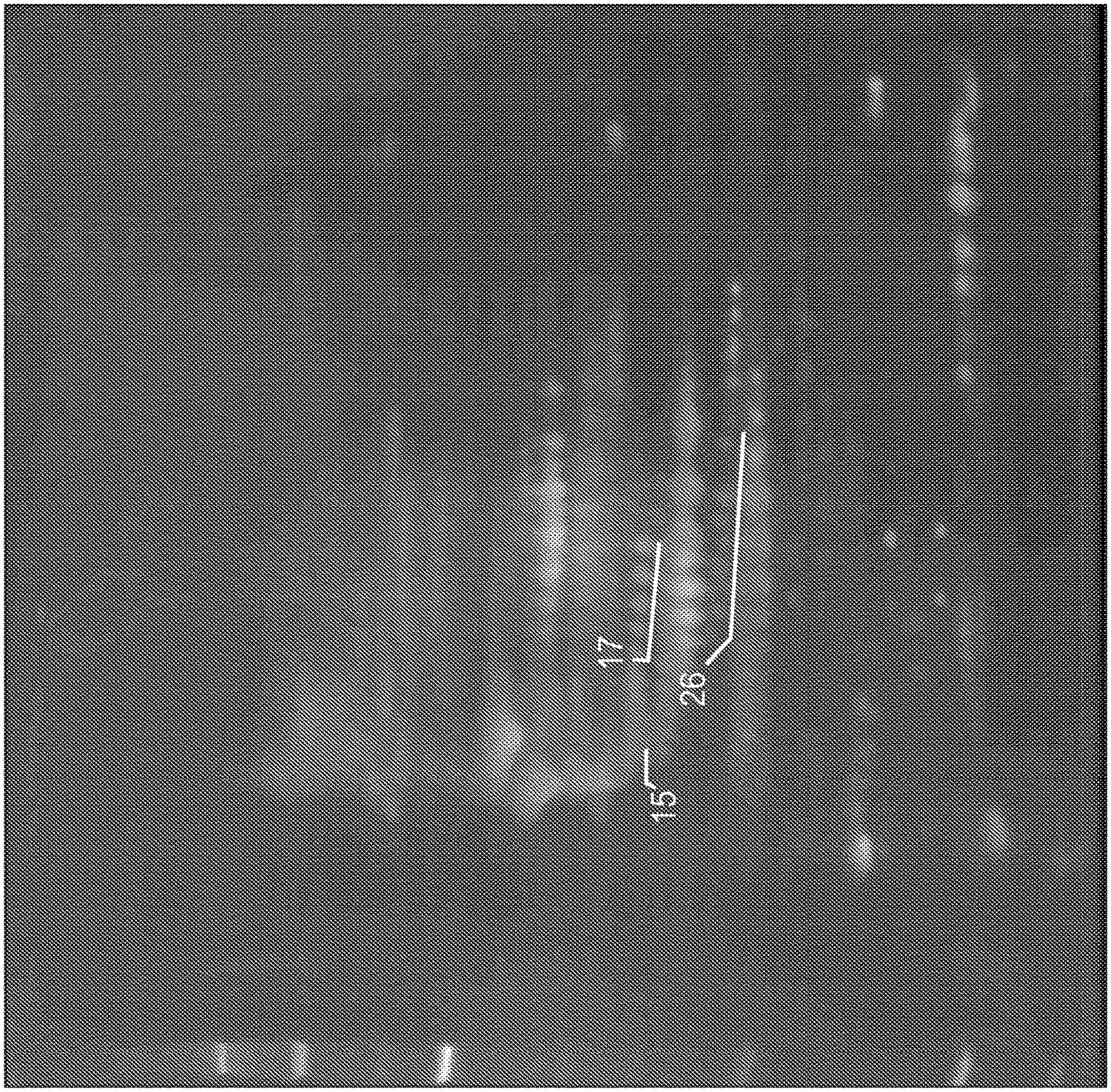
FIG. 5D is a photograph of an immunoblot of a two-dimensional electrophoretic pattern of proteins contained in soybean stained with serum of Soybean-allergic patient 4a. The spots indicated with a while line are spots where the serum of the soybean-allergic patient specifically reacted. The numbers (n) indicated are the numbers of the spots and correspond to the spots indicated with "na" herein.
Figure 5E:
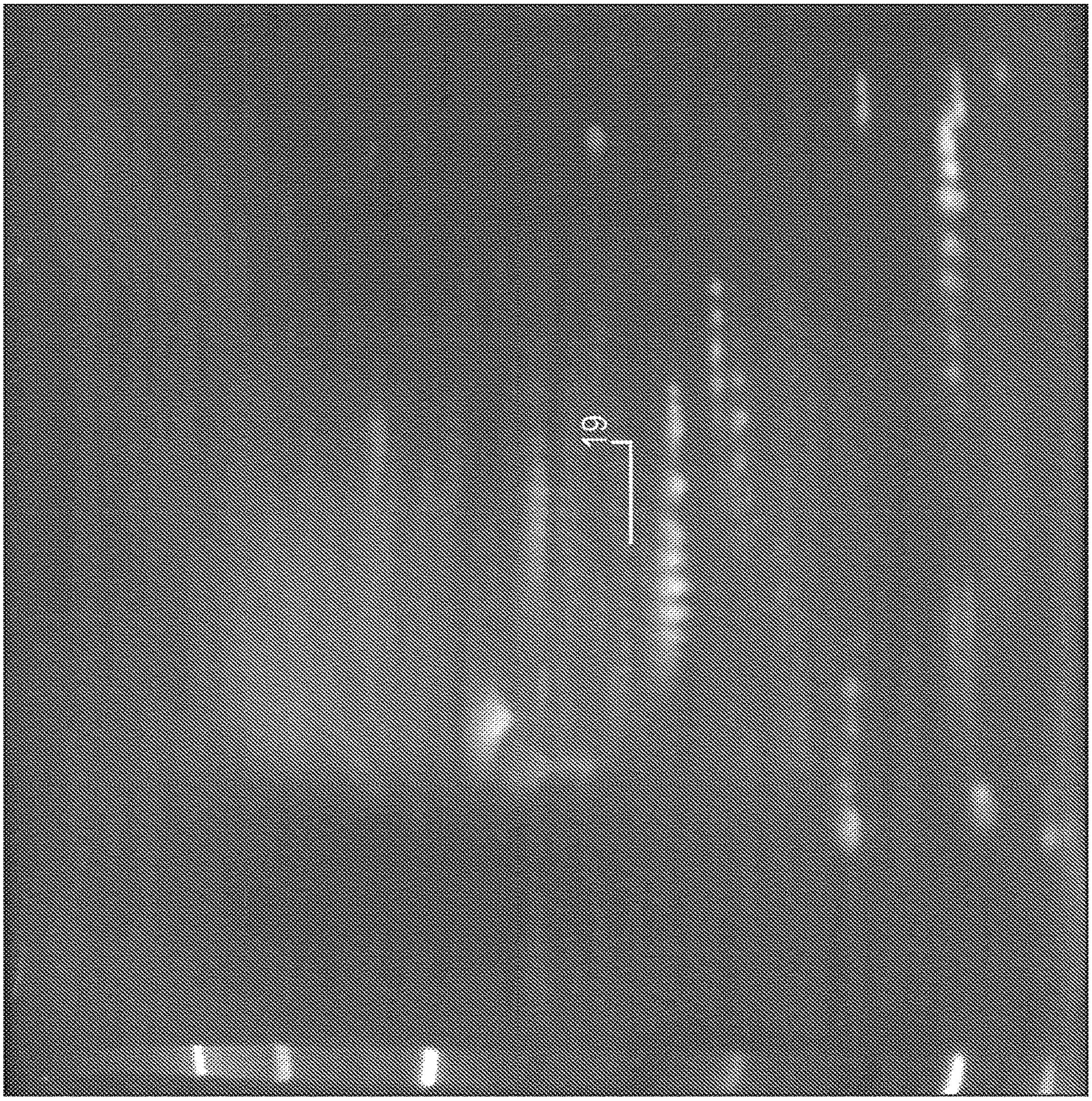
FIG. 5E is a photograph of an immunoblot of a two-dimensional electrophoretic pattern of proteins contained in soybean stained with serum of Soybean-allergic patient 5a. The spots indicated with a while line are spots where the serum of the soybean-allergic patient specifically reacted. The numbers (n) indicated are the numbers of the spots and correspond to the spots indicated with "na" herein.
Figure 5F:
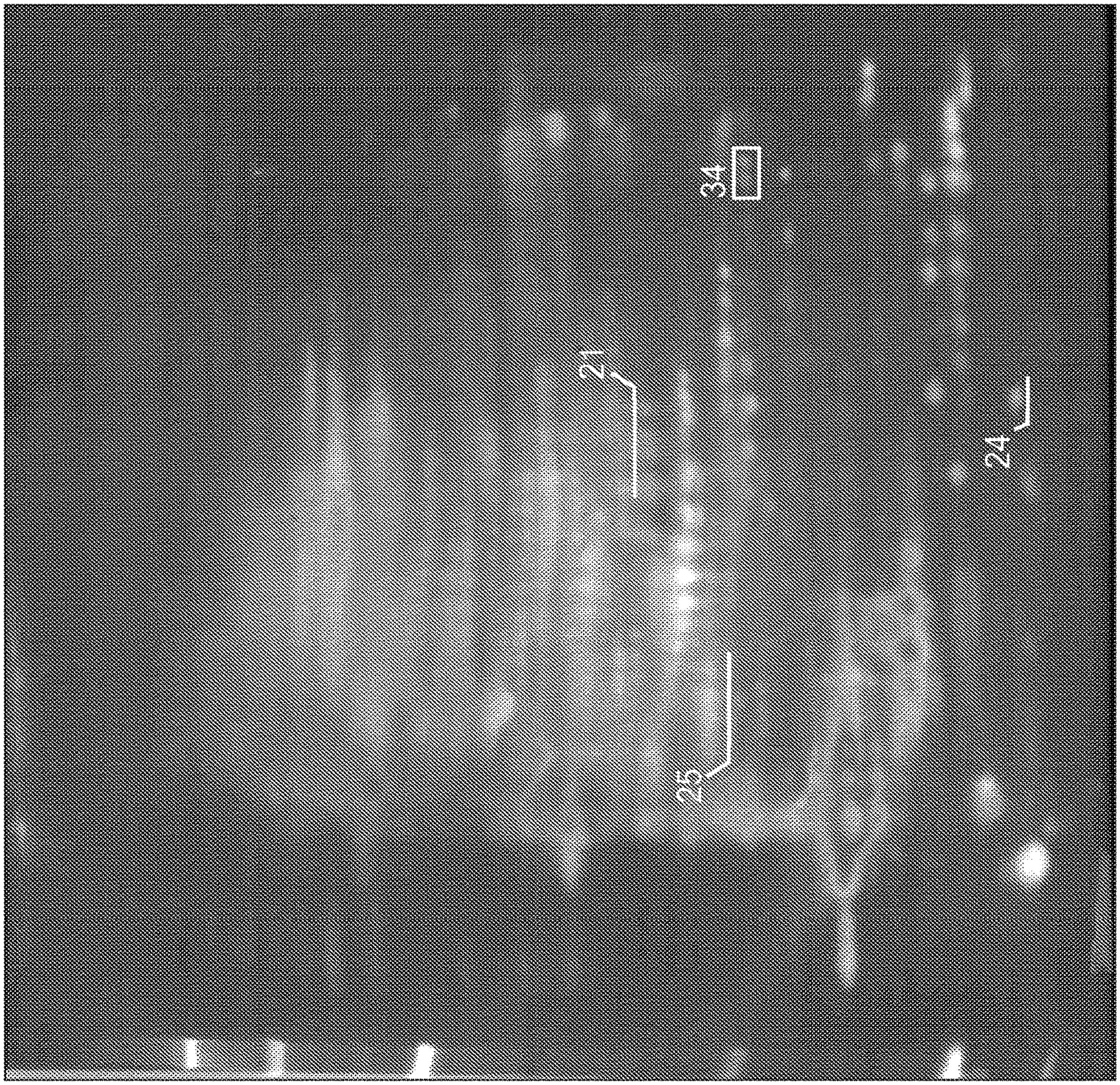
FIG. 5F is a photograph of an immunoblot of a two-dimensional electrophoretic pattern of proteins contained in soybean stained with serum of Soybean-allergic patient 6a. The spots indicated with a white line or enclosed in a square are spot where the serum of the soybean-allergic patient specifically reacted. The numbers (n) indicated are the numbers of the spots and correspond to the spots indicated with "na" herein.
Figure 5G:
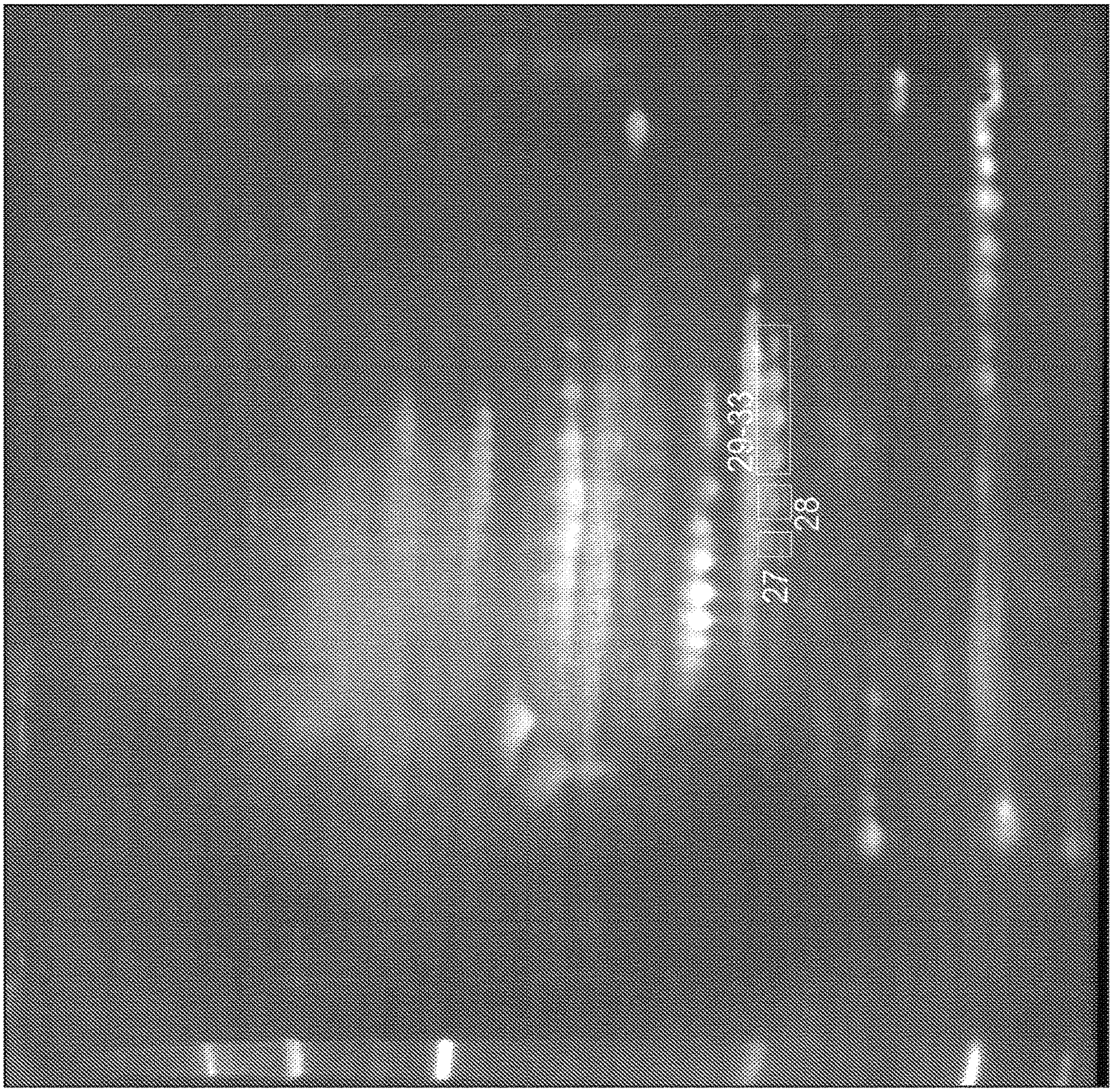
FIG. 5G is a photograph of an immunoblot of a two-dimensional electrophoretic pattern of proteins contained in soybean stained with serum of Soybean-allergic patient 7a. The spots enclosed in a square are spots where the serum of the soybean-allergic patient specifically reacted. The numbers (n) indicated are the numbers of the spots and correspond to the spots indicated with "na" herein.
Figure 5H:
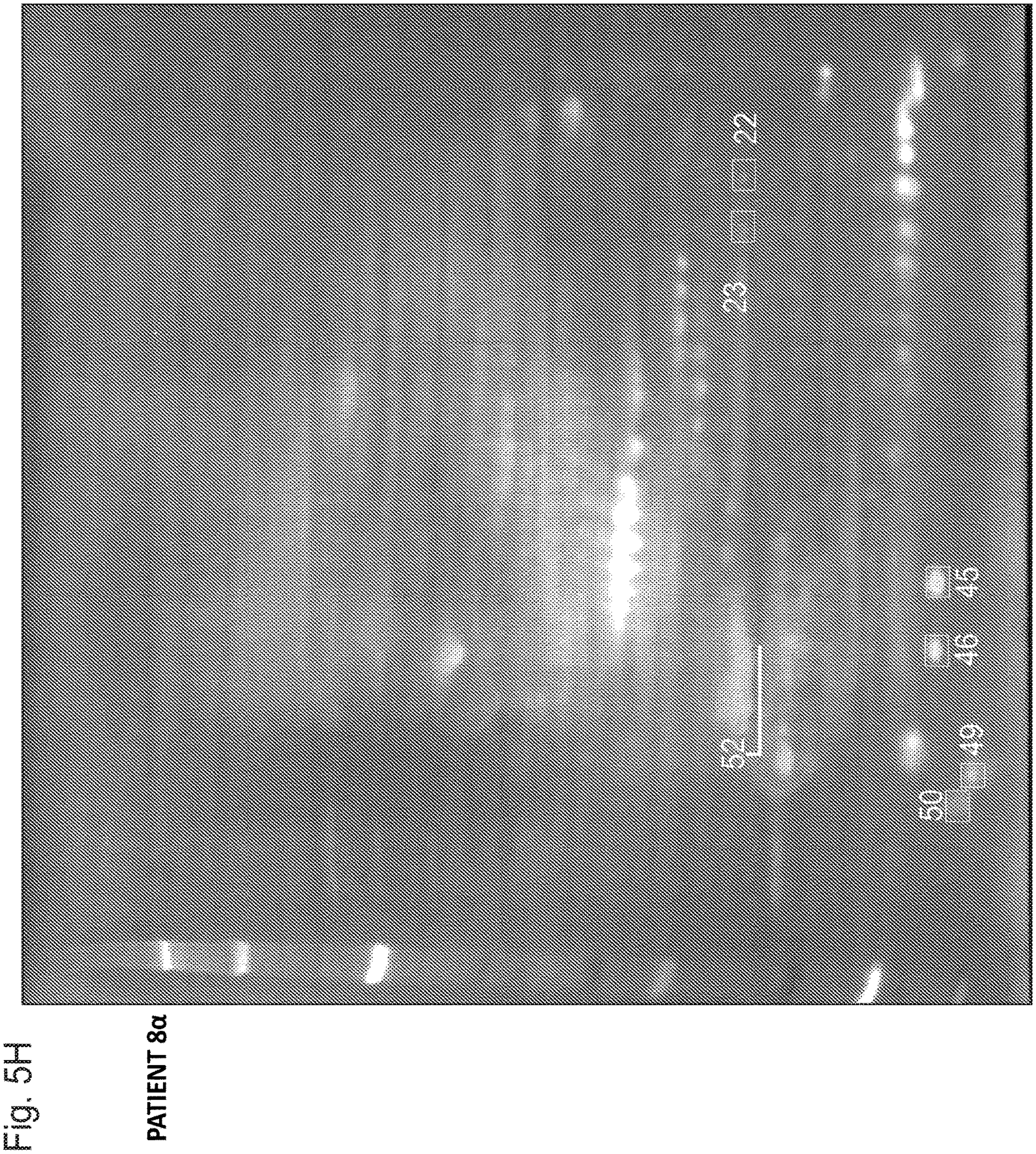
FIG. 5H is a photograph of an immunoblot of a two-dimensional electrophoretic pattern of proteins contained in soybean stained with serum of Soybean-allergic patient 8a. The spots indicated with a white line or enclosed in a square are spot where the serum of the soybean-allergic patient specifically reacted. The numbers (n) indicated are the numbers of the spots and correspond to the spots indicated with "na" herein.
Figure 5I:
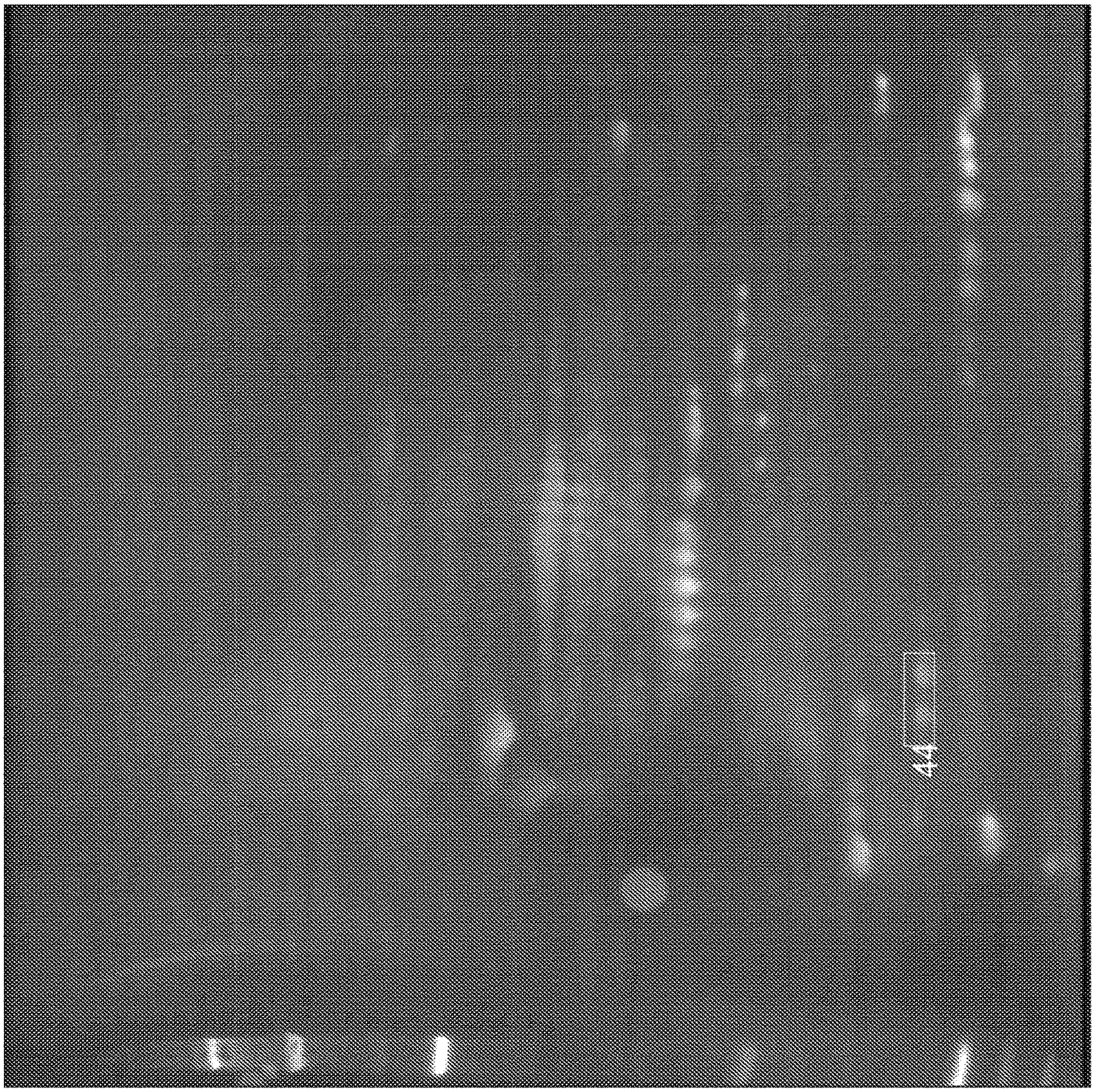
FIG. 5I is a photograph of an immunoblot of a two-dimensional electrophoretic pattern of proteins contained in soybean stained with serum of Soybean-allergic patient 9a. The spots indicated with a white line or enclosed in a square are spot where the serum of the soybean-allergic patient specifically reacted. The numbers (n) indicated are the numbers of the spots and correspond to the spots indicated with "na" herein.

The immunoblots obtained with the serum from the soybean-allergic patient were compared with those obtained with the control serum from the healthy subject, in the same manner as in Example 2. By immunoblotting using the serum from soybean-allergic Patient 1α, Patient 2α, Patient 3α, Patient 4α, Patient 5α, Patient 6α, Patient 7α, Patient 8α, and Patient 9α, 56 spots were detected (FIGS. 5A to I), which are different from the spots detected when the serum of the healthy subject was used (FIG. 4) and different from those of the known soybean allergen proteins.

The molecular weights and isoelectric points of the 56 spots are as follows.

Spot 1α: Molecular weight 80 to 110 kDa, pl 3.0 to 6.0
Spot 2α: Molecular weight 60 to 110 kDa, pl 3.0 to 6.0
Spot 3α: Molecular weight 100 to 150 kDa, pl 4.0 to 6.0
Spot 4α: Molecular weight 80 to 110 kDa, pl 4.0 to 7.0
Spot 5α: Molecular weight 80 to 160 kDa, pl 4.0 to 7.0
Spot 6α: Molecular weight 80 to 110 kDa, pl 4.0 to 7.0
Spot 7α: Molecular weight 60 to 110 kDa, pl 4.0 to 7.0
Spot 8α: Molecular weight 60 to 110 kDa, pl 4.0 to 8.0
Spot 9α: Molecular weight 60 to 110 kDa, pl 4.0 to 8.0
Spot 10α: Molecular weight 40 to 80 kDa, pl 4.0 to 7.0
Spot 11α: Molecular weight 40 to 80 kDa, pl 4.0 to 8.0
Spot 12α: Molecular weight 40 to 80 kDa, pl 4.0 to 8.0
Spot 13α: Molecular weight 40 to 80 kDa, pl 4.0 to 7.0
Spot 14α: Molecular weight 40 to 80 kDa, pl 3.0 to 6.0
Spot 15α, 16α: Molecular weight 30 to 80 kDa, pl 4.0 to 7.0
Spot 17α: Molecular weight 30 to 80 kDa, pl 4.0 to 7.0
Spot 18α: Molecular weight 40 to 80 kDa, pl 4.0 to 8.0
Spot 19α: Molecular weight 40 to 80 kDa, pl 4.0 to 8.0
Spot 20α: Molecular weight 60 to 75 kDa, pl 6.0 to 8.0
Spot 21α: Molecular weight 40 to 60 kDa, pl 5.0 to 8.0
Spot 22α: Molecular weight 25 to 37 kDa, pl 8.0 to 10.0
Spot 23α: Molecular weight 25 to 37 kDa, pl 7.0 to 9.0
Spot 24α: Molecular weight 5 to 20 kDa, pl 5.0 to 7.0
Spot 25α: Molecular weight 30 to 80 kDa, pl 4.0 to 7.0
Spot 26α: Molecular weight 30 to 80 kDa, pl 4.0 to 7.0

Spot 27α: Molecular weight 30 to 80 kDa, pl 4.0 to 7.0
Spot 28α: Molecular weight 20 to 60 kDa, pl 4.0 to 7.0
Spot 29α, 30a, 31a, 32a, 33a: Molecular weight 20 to 60 kDa, pl 4.0 to 8.0
Spot 34α: Molecular weight 20 to 60 kDa, pl 6.0 to 10.0
Spot 35α: Molecular weight 30 to 80 kDa, pl 6.0 to 10.0
Spot 36α, 37a: Molecular weight 20 to 60 kDa, pl 4.0 to 8.0
Spot 38α: Molecular weight 80 to 160 kDa, pl 6.0 to 10.0
Spot 39α: Molecular weight 10 to 50 kDa, pl 6.0 to 10.0
Spot 40α, 56α: Molecular weight 10 to 50 kDa, pl 6.0 to 10.0
Spot 41α: Molecular weight 10 to 50 kDa, pl 6.0 to 10.0
Spot 42α, 43a: Molecular weight 10 to 50 kDa, pl 6.0 to 10.0
Spot 44α: Molecular weight 10 to 50 kDa, pl 4.0 to 7.0
Spot 45α: Molecular weight 5 to 40 kDa, pl 4.0 to 7.0
Spot 46α: Molecular weight 5 to 40 kDa, pl 4.0 to 7.0
Spot 47α: Molecular weight 5 to 40 kDa, pl 4.0 to 7.0
Spot 48α: Molecular weight 5 to 40 kDa, pl 4.0 to 8.0
Spot 49α: Molecular weight 5 to 20 kDa, pl 4.0 to 7.0
Spot 50α: Molecular weight 5 to 40 kDa, pl 3.0 to 6.0
Spot 51α: Molecular weight 10 to 50 kDa, pl 3.0 to 6.0
Spot 52α: Molecular weight 20 to 60 kDa, pl 4.0 to 7.0
Spot 53α: Molecular weight 10 to 50 kDa, pl 4.0 to 8.0
Spot 54α: Molecular weight 10 to 50 kDa, pl 4.0 to 8.0
Spot 55α: Molecular weight 40 to 80 kDa, pl 6.0 to 10.0

Example 5: Mass Spectrometry and Identification of Antigens (2)

The amino acid sequences of the antigens that form the 56 protein spots were identified by mass spectroscopy, in the same manner as in Example 3.

The mass spectrometry of the spots resulted in the detection of the following amino acid sequences.

Furthermore, the spots were identified as the following proteins by the analysis of the mass data obtained from the mass spectrometer for the spots at NCBI.

Spot 1α:

The amino acid sequences set forth in SEQ ID NOs: 71 to 87 were detected by the mass spectrometry.

The protein identified from this mass data was endoplasmin homolog isoform X2 (NCBI accession number XP_006596543.1, amino acid sequence: SEQ ID NO: 70, encoding nucleotide sequence: SEQ ID NO: 69).

The amino acid sequences set forth in SEQ ID NOs: 90 to 104 were detected by the mass spectrometry. The protein identified from this mass data was endoplasmin homolog isoform X2 (NCBI accession number XP_006601356.1, amino acid sequence: SEQ ID NO: 89, encoding nucleotide sequence: SEQ ID NO: 88).

Spot 2α

The amino acid sequences set forth in SEQ ID NOs: 107 to 120 were detected by the mass spectrometry. The protein identified from this mass data was heat shock cognate protein 80 (NCBI accession number XP_003544594.1, amino acid sequence: SEQ ID NO: 106, encoding nucleotide sequence: SEQ ID NO: 105).

The amino acid sequences set forth in SEQ ID NOs: 123 to 137 were detected by the mass spectrometry. The protein identified from this mass data was heat shock protein 90-1 (NCBI accession number NP_001236612.1, amino acid sequence: SEQ ID NO: 122, encoding nucleotide sequence: SEQ ID NO: 121).

The amino acid sequences set forth in SEQ ID NOs: 140 to 153 were detected by the mass spectrometry. The protein identified from this mass data was hypothetical protein GLYMA_02G302500 (NCBI accession number KRH73936.1, amino acid sequence: SEQ ID NO: 139, encoding nucleotide sequence: SEQ ID NO: 138).

Spot 3α:

The amino acid sequences set forth in SEQ ID NOs: 62 to 68 were detected by the mass spectrometry, as in Spot 8 of Example 3. The protein identified from this mass data was Cell division cycle protein 48 homolog (UniProt accession number P54774, amino acid sequence: SEQ ID NO: 16, encoding nucleotide sequence: SEQ ID NO: 15).

Spot 4α:

The amino acid sequences set forth in SEQ ID NOs: 156, 157 were detected by the mass spectrometry. The protein identified from this mass data was embryo-specific urease isoform X1 (NCBI accession number XP_014630847.1, amino acid sequence: SEQ ID NO: 155, encoding nucleotide sequence: SEQ ID NO: 154).

Spot 5α:

The amino acid sequences set forth in SEQ ID NOs: 160, 161 were detected by the mass spectrometry. The protein identified from this mass data was alpha-1,4 glucan phosphorylase L isozyme, chloroplastic/amyloplastic (NCBI accession number XP_006603904.1, amino acid sequence: SEQ ID NO: 159, encoding nucleotide sequence: SEQ ID NO: 158).

Spot 6α:

The amino acid sequences set forth in SEQ ID NOs: 164 to 167 were detected by the mass spectrometry. The protein identified from this mass data was aconitate hydratase 1 (NCBI accession number XP_003537655.1, amino acid sequence: SEQ ID NO: 163, encoding nucleotide sequence: SEQ ID NO: 162).

The amino acid sequences set forth in SEQ ID NOs: 170 to 172 were detected by the mass spectrometry. The protein identified from this mass data was aconitate hydratase 1 (NCBI accession number XP_003517155.1, amino acid sequence: SEQ ID NO: 169, encoding nucleotide sequence: SEQ ID NO: 168).

Spot 7α:

The amino acid sequences set forth in SEQ ID NOs: 175 to 187 were detected by the mass spectrometry. The protein identified from this mass data was methionine synthase (NCBI accession number NP_001235794.1, amino acid sequence: SEQ ID NO: 174, encoding nucleotide sequence: SEQ ID NO: 173).

Spot 8α:

The amino acid sequences set forth in SEQ ID NOs: 190 to 199 were detected by the mass spectrometry. The protein identified from this mass data was transketolase, chloroplastic (NCBI accession number XP_003521870.1, amino acid sequence: SEQ ID NO: 189, encoding nucleotide sequence: SEQ ID NO: 188).

Spot 9α:

The amino acid sequence set forth in SEQ ID NO: 202 was detected by the mass spectrometry. The protein identified from this mass data was lysine-tRNA ligase, cytoplasmic-like isoform X2 (NCBI accession number XP_014625509.1, amino acid sequence: SEQ ID NO: 201, encoding nucleotide sequence: SEQ ID NO: 200).

Spot 10a

The amino acid sequences set forth in SEQ ID NOs: 205 to 218 were detected by the mass spectrometry. The protein identified from this mass data was chaperonin CPN60-2, mitochondrial (NCBI accession number XP_003556325.1, amino acid sequence: SEQ ID NO: 204, encoding nucleotide sequence: SEQ ID NO: 203).

The amino acid sequences set forth in SEQ ID NOs: 221 to 231 were detected by the mass spectrometry. The protein identified from this mass data was chaperonin CPN60-2, mitochondrial-like isoform X1 (NCBI accession number XP_003535967.1, amino acid sequence: SEQ ID NO: 220, encoding nucleotide sequence: SEQ ID NO: 219).

Spot 11α:

The amino acid sequences set forth in SEQ ID NOs: 234 to 237 were detected by the mass spectrometry. The protein identified from this mass data was polyadenylate-binding protein 8 isoform X3 (NCBI accession number XP_006578034.1, amino acid sequence: SEQ ID NO: 233, encoding nucleotide sequence: SEQ ID NO: 232).

Spot 12α:

The amino acid sequence set forth in SEQ ID NO: 240 was detected by the mass spectrometry. The protein identified from this mass data was pyrophosphate-fructose 6-phosphate 1-phosphotransferase subunit alpha-like (NCBI accession number XP_003555655.1, amino acid sequence: SEQ ID NO: 239, encoding nucleotide sequence: SEQ ID NO: 238).

Spot 13α:

The amino acid sequences set forth in SEQ ID NOs: 243 to 252 were detected by the mass spectrometry. The protein identified from this mass data was protein disulfide isomerase-like protein precursor (NCBI accession number NP_001238009.1, amino acid sequence: SEQ ID NO: 242, encoding nucleotide sequence: SEQ ID NO: 241).

The amino acid sequences set forth in SEQ ID NOs: 255 to 278 were detected by the mass spectrometry. The protein identified from this mass data was protein disulfide-isomerase (NCBI accession number XP_006581588.1, amino acid sequence: SEQ ID NO: 254, encoding nucleotide sequence: SEQ ID NO: 253).

Spot 14α:

The amino acid sequences set forth in SEQ ID NOs: 281 to 284 were detected by the mass spectrometry. The protein identified from this mass data was V-type proton ATPase subunit B 2 (NCBI accession number XP_003552473.1, amino acid sequence: SEQ ID NO: 280, encoding nucleotide sequence: SEQ ID NO: 279).

The amino acid sequences set forth in SEQ ID NOs: 287 to 289 were detected by the mass spectrometry. The protein identified from this mass data was V-type proton ATPase subunit B 2 (NCBI accession number XP_006605857.1, amino acid sequence: SEQ ID NO: 286, encoding nucleotide sequence: SEQ ID NO: 275).

Spots 15α, 16α:

The amino acid sequences set forth in SEQ ID NOs: 292 to 304 were detected by the mass spectrometry. The protein identified from this mass data was UTP-glucose-1-phosphate uridylyltransferase (NCBI accession number XP_003544964.1, amino acid sequence: SEQ ID NO: 291, encoding nucleotide sequence: SEQ ID NO: 290).

The amino acid sequences set forth in SEQ ID NOs: 307 to 318 were detected by the mass spectrometry. The protein identified from this mass data was hypothetical protein GLYMA_02G241100 (NCBI accession number KRH72929.1, amino acid sequence: SEQ ID NO: 306, encoding nucleotide sequence: SEQ ID NO: 305).

Spot 17α:

The amino acid sequences set forth in SEQ ID NOs: 321 to 325 were detected by the mass spectrometry. The protein identified from this mass data was guanosine nucleotide diphosphate dissociation inhibitor 2 (NCBI accession number XP_003531293.1, amino acid sequence: SEQ ID NO: 320, encoding nucleotide sequence: SEQ ID NO: 319).

The amino acid sequences set forth in SEQ ID NOs: 328 to 332 were detected by the mass spectrometry. The protein identified from this mass data was rab GDP dissociation inhibitor alpha-like (NCBI accession number NP_001276273.1, amino acid sequence: SEQ ID NO: 327, encoding nucleotide sequence: SEQ ID NO: 326).

Spot 18α:

The amino acid sequences set forth in SEQ ID NOs: 335 to 339 were detected by the mass spectrometry. The protein identified from this mass data was hypothetical protein GLYMA_10G028300 (NCBI accession number KRH32039.1, amino acid sequence: SEQ ID NO: 334, encoding nucleotide sequence: SEQ ID NO: 333).

Spot 19α:

The amino acid sequences set forth in SEQ ID NOs: 342 to 346 were detected by the mass spectrometry. The protein identified from this mass data was sucrose binding protein homolog S-64 (NCBI accession number AAF05723.1, amino acid sequence: SEQ ID NO: 341, encoding nucleotide sequence: SEQ ID NO: 340).

Spot 20α:

The amino acid sequences set forth in SEQ ID NOs: 35 to 53 were detected by the mass spectrometry, as in Spot 6 of Example 3. The protein identified from this mass data was Seed biotin-containing protein SBP65 (UniProt accession number Q39846, amino acid sequence: SEQ ID NO: 12, encoding nucleotide sequence: SEQ ID NO: 11).

Spot 21α:

The amino acid sequences set forth in SEQ ID NOs: 21 to 28 were detected by the mass spectrometry, as in Spot 2 of Example 3. The protein identified from this mass data was Ribulose bisphosphate carboxylase large chain (UniProt accession number P27066, amino acid sequence: SEQ ID NO: 4, encoding nucleotide sequence: SEQ ID NO: 3).

Spot 22α:

The amino acid sequences set forth in SEQ ID NOs: 29, 30 were detected by the mass spectrometry, as in Spot 3 of Example 3. The protein identified from this mass data was Gamma-glutamyl hydrolase (UniProt accession number P93164, amino acid sequence: SEQ ID NO: 6, encoding nucleotide sequence: SEQ ID NO: 5).

Spot 23α:

The amino acid sequences set forth in SEQ ID NOs: 31, 32 were detected by the mass spectrometry, as in Spot 4 of Example 3. The protein identified from this mass data was Guanine nucleotide-binding protein subunit beta-like protein (UniProt accession number Q39836, amino acid sequence: SEQ ID NO: 8, encoding nucleotide sequence: SEQ ID NO: 7).

Spot 24α:

The amino acid sequences set forth in SEQ ID NOs: 33, 34 were detected by the mass spectrometry, as in Spot 5 of Example 3. The protein identified from this mass data was Protein SLE3 (UniProt accession number C6T0L2, amino acid sequence: SEQ ID NO: 10, encoding nucleotide sequence: SEQ ID NO: 9).

Spot 25α:

The amino acid sequences set forth in SEQ ID NOs: 349 to 356 were detected by the mass spectrometry. The protein identified from this mass data was succinyl-CoA ligase [ADP-forming] subunit beta, mitochondrial (NCBI accession number XP_003537078.1, amino acid sequence: SEQ ID NO: 348, encoding nucleotide sequence: SEQ ID NO: 347).

The amino acid sequences set forth in SEQ ID NOs: 359 to 365 were detected by the mass spectrometry. The protein identified from this mass data was succinyl-CoA ligase

[ADP-forming] subunit beta, mitochondrial (NCBI accession number XP_003542431.1, amino acid sequence: SEQ ID NO: 358, encoding nucleotide sequence: SEQ ID NO: 357).

Spot 26α:

The amino acid sequences set forth in SEQ ID NOs: 368 to 382 were detected by the mass spectrometry. The protein identified from this mass data was phosphoglycerate kinase, cytosolic (NCBI accession number XP_003546821.1, amino acid sequence: SEQ ID NO: 367, encoding nucleotide sequence: SEQ ID NO: 366).

The amino acid sequences set forth in SEQ ID NOs: 385 to 392 were detected by the mass spectrometry. The protein identified from this mass data was phosphoglycerate kinase, cytosolic (NCBI accession number XP_003531482.1, amino acid sequence: SEQ ID NO: 384, encoding nucleotide sequence: SEQ ID NO: 383).

The amino acid sequences set forth in SEQ ID NOs: 395 to 409 were detected by the mass spectrometry. The protein identified from this mass data was phosphoglycerate kinase, cytosolic (NCBI accession number XP_003531483.1, amino acid sequence: SEQ ID NO: 394, encoding nucleotide sequence: SEQ ID NO: 393).

Spot 27α:

The amino acid sequences set forth in SEQ ID NOs: 412 to 416 were detected by the mass spectrometry. The protein identified from this mass data was alcohol dehydrogenase 1 (NCBI accession number XP_003526673.1, amino acid sequence: SEQ ID NO: 411, encoding nucleotide sequence: SEQ ID NO: 410).

The amino acid sequences set forth in SEQ ID NOs: 419, 420 were detected by the mass spectrometry. The protein identified from this mass data was alcohol dehydrogenase 1 (NCBI accession number XP_003545664.3, amino acid sequence: SEQ ID NO: 418, encoding nucleotide sequence: SEQ ID NO: 417).

The amino acid sequences set forth in SEQ ID NOs: 423 to 427 were detected by the mass spectrometry. The protein identified from this mass data was alcohol dehydrogenase 1-like (NCBI accession number XP_003544738.1, amino acid sequence: SEQ ID NO: 422, encoding nucleotide sequence: SEQ ID NO: 421).

Spot 28α:

The amino acid sequences set forth in SEQ ID NOs: 430 to 433 were detected by the mass spectrometry. The protein identified from this mass data was 35 kDa seed maturation protein isoform X1 (NCBI accession number XP_006576267.1, amino acid sequence: SEQ ID NO: 429, encoding nucleotide sequence: SEQ ID NO: 428).

Spots 29α, 30α, 31α, 32α, 33α:

The amino acid sequences set forth in SEQ ID NOs: 436 to 439 were detected by the mass spectrometry. The protein identified from this mass data was glyceraldehyde-3-phosphate dehydrogenase isoform X1 (NCBI accession number XP_014631598.1, amino acid sequence: SEQ ID NO: 435, encoding nucleotide sequence: SEQ ID NO: 434).

The amino acid sequences set forth in SEQ ID NOs: 442 to 445 were detected by the mass spectrometry. The protein identified from this mass data was glyceraldehyde-3-phosphate dehydrogenase, cytosolic (NCBI accession number XP_006578692.1, amino acid sequence: SEQ ID NO: 441, encoding nucleotide sequence: SEQ ID NO: 440).

The amino acid sequences set forth in SEQ ID NOs: 448 to 451 were detected by the mass spectrometry. The protein identified from this mass data was uncharacterized protein LOC100782924 (NCBI accession number NP_001240046.1, amino acid sequence: SEQ ID NO: 447, encoding nucleotide sequence: SEQ ID NO: 446).

Spot 34α:

The amino acid sequence set forth in SEQ ID NO: 454 was detected by the mass spectrometry. The protein identified from this mass data was bifunctional UDP-glucose 4-epimerase and UDP-xylose 4-epimerase 1-like (NCBI accession number XP_003532591.1, amino acid sequence: SEQ ID NO: 453, encoding nucleotide sequence: SEQ ID NO: 452).

The amino acid sequences set forth in SEQ ID NOs: 457, 458 were detected by the mass spectrometry. The protein identified from this mass data was uncharacterized protein LOC100803483 (NCBI accession number NP_001241075.1, amino acid sequence: SEQ ID NO: 456, encoding nucleotide sequence: SEQ ID NO: 455).

Spot 35α:

The amino acid sequences set forth in SEQ ID NOs: 461 to 466 were detected by the mass spectrometry. The protein identified from this mass data was elongation factor 1-alpha (NCBI accession number XP_003553292.1, amino acid sequence: SEQ ID NO: 460, encoding nucleotide sequence: SEQ ID NO: 459).

The amino acid sequences set forth in SEQ ID NOs: 469 to 471 were detected by the mass spectrometry. The protein identified from this mass data was elongation factor 1-alpha (NCBI accession number XP_003547695.1, amino acid sequence: SEQ ID NO: 468, encoding nucleotide sequence: SEQ ID NO: 467).

The amino acid sequences set forth in SEQ ID NOs: 474 to 477 were detected by the mass spectrometry. The protein identified from this mass data was elongation factor-1A isoform X1 (NCBI accession number XP_006600131.1, amino acid sequence: SEQ ID NO: 473, encoding nucleotide sequence: SEQ ID NO: 472).

Spots 36α, 37α:

The amino acid sequences set forth in SEQ ID NOs: 480 to 483 were detected by the mass spectrometry. The protein identified from this mass data was seed maturation protein PM34 (NCBI accession number NP_001238285.1, amino acid sequence: SEQ ID NO: 479, encoding nucleotide sequence: SEQ ID NO: 478).

The amino acid sequences set forth in SEQ ID NOs: 486, 487 were detected by the mass spectrometry. The protein identified from this mass data was uncharacterized protein LOC100809384 (NCBI accession number NP_001241158.1, amino acid sequence: SEQ ID NO: 485, encoding nucleotide sequence: SEQ ID NO: 484).

The amino acid sequences set forth in SEQ ID NOs: 490 to 493 were detected by the mass spectrometry. The protein identified from this mass data was hypothetical protein GLYMA_10G155300 (NCBI accession number KRH33956.1, amino acid sequence: SEQ ID NO: 489, encoding nucleotide sequence: SEQ ID NO: 488).

Spot 38α

The amino acid sequences set forth in SEQ ID NOs: 496 to 513 were detected by the mass spectrometry. The protein identified from this mass data was seed biotin-containing protein SBP65-like isoform X1 (NCBI accession number XP_003526237.1, amino acid sequence: SEQ ID NO: 495, encoding nucleotide sequence: SEQ ID NO: 494).

Spot 39α:

The amino acid sequence set forth in SEQ ID NO: 516 was detected by the mass spectrometry. The protein identified from this mass data was ATP synthase subunit 0, mitochondrial-like (NCBI accession number XP_003546884.1, amino acid sequence: SEQ ID NO: 515, encoding nucleotide sequence: SEQ ID NO: 514).

Spots 40α, 56α:

The amino acid sequences set forth in SEQ ID NOs: 519, 520 were detected by the mass spectrometry. The protein identified from this mass data was P24 oleosin isoform A (NCBI accession number XP_003553822.1, amino acid sequence: SEQ ID NO: 518, encoding nucleotide sequence: SEQ ID NO: 517).

Spot 41α:

The amino acid sequence set forth in SEQ ID NO: 523 was detected by the mass spectrometry. The protein identified from this mass data was uncharacterized protein At3g49720-like isoform X2 (NCBI accession number XP_006600908.1, amino acid sequence: SEQ ID NO: 522, encoding nucleotide sequence: SEQ ID NO: 521).

Spots 42α, 43α

The amino acid sequences set forth in SEQ ID NOs: 526 to 531 were detected by the mass spectrometry. The protein identified from this mass data was superoxide dismutase [Mn], mitochondrial (NCBI accession number XP_003526813.1, amino acid sequence: SEQ ID NO: 525, encoding nucleotide sequence: SEQ ID NO: 524).

The amino acid sequences set forth in SEQ ID NOs: 534 to 539 were detected by the mass spectrometry. The protein identified from this mass data was hypothetical protein GLYMA_04G221300 (NCBI accession number KRH64185.1, amino acid sequence: SEQ ID NO: 533, encoding nucleotide sequence: SEQ ID NO: 532).

Spot 44α:

The amino acid sequences set forth in SEQ ID NOs: 54 to 61 were detected by the mass spectrometry, as in Spot 7 of Example 3. The protein identified from this mass data was Ferritin-2 (UniProt accession number Q941C4, amino acid sequence: SEQ ID NO: 14, encoding nucleotide sequence: SEQ ID NO: 13).

Spot 45α:

The amino acid sequences set forth in SEQ ID NOs: 542 to 545 were detected by the mass spectrometry. The protein identified from this mass data was uncharacterized protein LOC100499771 (NCBI accession number NP_001235797.1, amino acid sequence: SEQ ID NO: 541, encoding nucleotide sequence: SEQ ID NO: 540).

The amino acid sequences set forth in SEQ ID NOs: 548 to 551 were detected by the mass spectrometry. The protein identified from this mass data was hypothetical protein GLYMA_09G192800 (NCBI accession number KRH39322.1, amino acid sequence: SEQ ID NO: 547, encoding nucleotide sequence: SEQ ID NO: 546).

Spot 46α:

The amino acid sequence set forth in SEQ ID NO: 554 was detected by the mass spectrometry. The protein identified from this mass data was seed maturation protein PM22 (NCBI accession number NP_001237935.1, amino acid sequence: SEQ ID NO: 553, encoding nucleotide sequence: SEQ ID NO: 552).

Spot 47α:

The amino acid sequences set forth in SEQ ID NOs: 557, 558 were detected by the mass spectrometry. The protein identified from this mass data was eukaryotic translation initiation factor 5A-2 (NCBI accession number XP_003549690.1, amino acid sequence: SEQ ID NO: 556, encoding nucleotide sequence: SEQ ID NO: 555).

The amino acid sequences set forth in SEQ ID NOs: 561 to 563 were detected by the mass spectrometry. The protein identified from this mass data was uncharacterized protein LOC100305510 (NCBI accession number NP_001236395.1, amino acid sequence: SEQ ID NO: 560, encoding nucleotide sequence: SEQ ID NO: 559).

Spot 48α:

The amino acid sequences set forth in SEQ ID NOs: 566 to 570 were detected by the mass spectrometry. The protein identified from this mass data was uncharacterized protein LOC100306570 (NCBI accession number NP_001236895.1, amino acid sequence: SEQ ID NO: 565, encoding nucleotide sequence: SEQ ID NO: 564).

Spot 49α:

The amino acid sequences set forth in SEQ ID NOs: 17 to 20 were detected by the mass spectrometry, as in Spot 1 of Example 3. The protein identified from this mass data was Bowman-Birk type proteinase inhibitor D-II (UniProt accession number P01064, amino acid sequence: SEQ ID NO: 2, encoding nucleotide sequence: SEQ ID NO: 1).

Spot 50α:

The amino acid sequences set forth in SEQ ID NOs: 573 to 576 were detected by the mass spectrometry. The protein identified from this mass data was uncharacterized protein LOC100813859 (NCBI accession number NP_001239816.1, amino acid sequence: SEQ ID NO: 572, encoding nucleotide sequence: SEQ ID NO: 571).

Spot 51α:

The amino acid sequences set forth in SEQ ID NOs: 579 to 582 were detected by the mass spectrometry. The protein identified from this mass data was 14-3-3-like protein (NCBI accession number XP_003526571.1, amino acid sequence: SEQ ID NO: 578, encoding nucleotide sequence: SEQ ID NO: 577).

Spot 52α:

The amino acid sequences set forth in SEQ ID NOs: 585 to 588 were detected by the mass spectrometry. The protein identified from this mass data was probable fructokinase-4 (NCBI accession number XP_003543564.1, amino acid sequence: SEQ ID NO: 584, encoding nucleotide sequence: SEQ ID NO: 583).

Spot 53α:

The amino acid sequences set forth in SEQ ID NOs: 591 to 597 were detected by the mass spectrometry. The protein identified from this mass data was triosephosphate isomerase isoform X1 (NCBI accession number XP_006593480.2, amino acid sequence: SEQ ID NO: 590, encoding nucleotide sequence: SEQ ID NO: 589).

The amino acid sequences set forth in SEQ ID NOs: 600 to 604 were detected by the mass spectrometry. The protein identified from this mass data was triosephosphate isomerase, cytosolic (NCBI accession number XP_003547334.1, amino acid sequence: SEQ ID NO: 599, encoding nucleotide sequence: SEQ ID NO: 598).

Spot 54α:

The amino acid sequences set forth in SEQ ID NOs: 607 to 611 were detected by the mass spectrometry. The protein identified from this mass data was superoxide dismutase [Fe], chloroplastic isoform X1 (NCBI accession number XP_014627751.1, amino acid sequence: SEQ ID NO: 606, encoding nucleotide sequence: SEQ ID NO: 605).

The amino acid sequences set forth in SEQ ID NOs: 614 to 616 were detected by the mass spectrometry. The protein identified from this mass data was iron-superoxide dismutase (NCBI accession number NP_001237901.1, amino acid sequence: SEQ ID NO: 613, encoding nucleotide sequence: SEQ ID NO: 612).

Spot 55α:

The amino acid sequences set forth in SEQ ID NOs: 619 to 635 were detected by the mass spectrometry. The protein identified from this mass data was 51 kDa seed maturation protein precursor (NCBI accession number NP_001238138.1, amino acid sequence: SEQ ID NO: 618, encoding nucleotide sequence: SEQ ID NO: 617).

The amino acid sequences set forth in SEQ ID NOs: 638 to 649 were detected by the mass spectrometry. The protein identified from this mass data was Lea protein precursor (NCBI accession number NP_001238201.1, amino acid sequence: SEQ ID NO: 637, encoding nucleotide sequence: SEQ ID NO: 636).

INDUSTRIAL APPLICABILITY

The present invention can provide novel antigens of an allergy to soybean, methods and kits for diagnosing an allergy to soybean, pharmaceutical compositions comprising such an antigen, and soybeans or processed products of soybean in which such an antigen is eliminated or reduced.

The invention claimed is:

1. A method for detecting binding between a soybean antigen and an antibody that specifically binds to the soybean antigen present in a sample, wherein the method uses a kit that comprises the soybean antigen, wherein the soybean antigen is a Bowman-Birk type proteinase inhibitor D-II antigen comprising the amino acid sequence of SEQ ID NO: 2, wherein the soybean antigen specifically binds to IgE antibody from a patient having allergy to soybean, wherein the soybean antigen is immobilized to a carrier or a surface, wherein the method comprises:

(i) contacting the antibody in the sample with the soybean antigen from the kit, and (ii) detecting binding between said soybean antigen and the antibody in the sample.

2. A method for detecting binding between a soybean antigen and an antibody that specifically binds to the soybean antigen present in a sample, wherein the method uses a kit that comprises the soybean antigen, wherein the soybean antigen is a Bowman-Birk type proteinase inhibitor D-II antigen comprising the amino acid sequence of SEQ ID NO: 2, wherein the soybean antigen specifically binds to IgE antibody from a patient having allergy to soybean, wherein the kit further comprises a reagent that detects binding between said soybean antigen and said antibody;

wherein the method comprises:

(i) contacting the antibody in the sample with the soybean antigen from the kit, and (ii) detecting binding between said soybean antigen and the antibody in the sample.

3. The method of claim 2, wherein the reagent comprises an enzymatically labelled secondary antibody against said antibody that specifically binds to said soybean antigen.

4. The method of claim 3, wherein the kit further comprises an enzyme substrate for an enzyme in the enzymatically labelled secondary antibody.

5. The method of claim 2, wherein the reagent comprises a fluorescently labelled secondary antibody against the antibody that specifically binds to said soybean antigen.

* * * * *